(12) United States Patent
Zhang et al.

(10) Patent No.: US 9,802,949 B2
(45) Date of Patent: Oct. 31, 2017

(54) FUSED RING COMPOUNDS AS HEPATITIS C VIRUS INHIBITORS, PHARMACEUTICAL COMPOSITIONS AND USES THEREOF

(71) Applicant: SUNSHINE LAKE PHARMA CO., LTD., Dongguan, Guangdong (CN)

(72) Inventors: Yingjun Zhang, Dongguan (CN); Jiancun Zhang, San Mateo, CA (US); Hongming Xie, Dongguan (CN); Qingyun Ren, Dongguan (CN); Shifeng Li, Dongguan (CN); Changping Fu, Dongguan (CN); Bailin Hu, Dongguan (CN); Xiwei Wu, Dongguan (CN); Changhua Tang, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 125 days.

(21) Appl. No.: 14/647,449

(22) PCT Filed: Nov. 28, 2013

(86) PCT No.: PCT/CN2013/001465
§ 371 (c)(1),
(2) Date: May 26, 2015

(87) PCT Pub. No.: WO2014/082380
PCT Pub. Date: Jun. 5, 2014

(65) Prior Publication Data
US 2015/0307509 A1    Oct. 29, 2015

(30) Foreign Application Priority Data

Nov. 29, 2012 (CN) .......................... 2012 1 0497565
Apr. 3, 2013 (CN) .......................... 2013 1 0116819

(51) Int. Cl.
| | | |
|---|---|---|
| A01N 43/54 | (2006.01) |
| A61K 31/517 | (2006.01) |
| C07D 491/107 | (2006.01) |
| A61K 31/4025 | (2006.01) |
| A61K 31/4178 | (2006.01) |
| A61K 31/4184 | (2006.01) |

(Continued)

(52) U.S. Cl.
CPC ...... *C07D 491/107* (2013.01); *A61K 31/4025* (2013.01); *A61K 31/4178* (2013.01); *A61K 31/4184* (2013.01); *A61K 31/423* (2013.01); *A61K 31/427* (2013.01); *A61K 31/438* (2013.01); *A61K 31/439* (2013.01); *A61K 31/4439* (2013.01); *A61K 31/454* (2013.01); *A61K 31/4545* (2013.01); *A61K 31/4709* (2013.01); *A61K 31/502* (2013.01); *A61K 31/517* (2013.01); *A61K 31/5377* (2013.01); *A61K 31/549* (2013.01); *A61K 38/212* (2013.01); *A61K 45/06* (2013.01); *C07D 401/14* (2013.01); *C07D 403/14* (2013.01); *C07D 409/14* (2013.01); *C07D 413/14* (2013.01); *C07D 417/14* (2013.01); *C07D 471/08* (2013.01); *C07D 491/113* (2013.01)

(58) Field of Classification Search
USPC ...................................................... 514/266.23
See application file for complete search history.

(56) References Cited

U.S. PATENT DOCUMENTS

| | | | |
|---|---|---|---|
| 7,659,270 B2 | 2/2010 | Bachand et al. |
| 7,704,992 B2 | 4/2010 | Bachand et al. |

(Continued)

FOREIGN PATENT DOCUMENTS

| | | |
|---|---|---|
| WO | WO2004002977 A1 | 1/2004 |
| WO | WO2010138790 A1 | 12/2010 |

(Continued)

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802).*

(Continued)

*Primary Examiner* — Marcos Sznaidman
(74) *Attorney, Agent, or Firm* — Kam W. Law; Squire Patton Boggs (US) LLP

(57) ABSTRACT

Provided are fused tricyclic compounds effective to inhibit the function of the NS5A protein of formula (I), wherein X, X', Y, Y', A, A', $Q^1$, $Q^2$, $R^1$-$R^4$, $X^4$, $R^{5a}$, f and W are defined as in the description. Also provided herein are pharmaceutical compositions thereof, and uses in the manufacture of a medicament for treating HCV infection or a HCV disorder thereof.

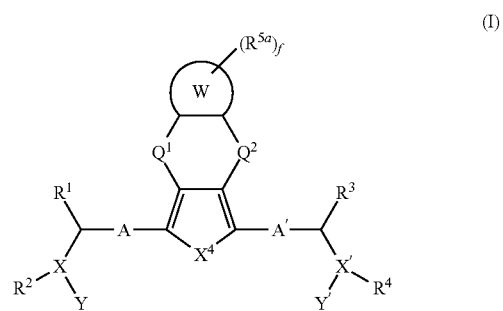

4 Claims, No Drawings

(51) Int. Cl.

| | | |
|---|---|---|
| A61K 31/423 | (2006.01) |
| A61K 31/427 | (2006.01) |
| A61K 31/439 | (2006.01) |
| A61K 31/4439 | (2006.01) |
| A61K 31/4545 | (2006.01) |
| A61K 31/502 | (2006.01) |
| A61K 31/5377 | (2006.01) |
| A61K 31/549 | (2006.01) |
| C07D 403/14 | (2006.01) |
| C07D 401/14 | (2006.01) |
| C07D 413/14 | (2006.01) |
| C07D 409/14 | (2006.01) |
| C07D 417/14 | (2006.01) |
| C07D 491/113 | (2006.01) |
| A61K 45/06 | (2006.01) |
| A61K 38/21 | (2006.01) |
| A61K 31/438 | (2006.01) |
| A61K 31/454 | (2006.01) |
| A61K 31/4709 | (2006.01) |
| C07D 471/08 | (2006.01) |

(56) References Cited

U.S. PATENT DOCUMENTS

| | | |
|---|---|---|
| 8,008,263 B2 | 8/2011 | Britt et al. |
| 8,143,414 B2 | 3/2012 | Lavoie et al. |
| 8,221,737 B2 | 7/2012 | Or et al. |
| 8,273,341 B2 | 9/2012 | Guo et al. |
| 8,303,944 B2 | 11/2012 | Bachand et al. |
| 8,314,135 B2 | 11/2012 | Qiu et al. |
| 8,354,419 B2 | 1/2013 | Henderson et al. |
| 8,362,068 B2 | 1/2013 | Dousson et al. |
| 2010/0226883 A1 | 9/2010 | Qiu |
| 2011/0112100 A1 | 5/2011 | Milbank et al. |
| 2011/0274648 A1 | 11/2011 | Lavoie et al. |
| 2011/0312996 A1 | 12/2011 | Buckman et al. |
| 2012/0028978 A1 | 2/2012 | Zhong et al. |
| 2012/0039847 A1 | 2/2012 | Zhao |
| 2012/0040962 A1 | 2/2012 | Li et al. |
| 2012/0083483 A1 | 4/2012 | Coburn et al. |
| 2012/0115841 A1 | 5/2012 | Bur et al. |
| 2012/0115855 A1 | 5/2012 | Li et al. |
| 2012/0115918 A1 | 5/2012 | DeGoey et al. |
| 2012/0122864 A1 | 5/2012 | Zhong et al. |
| 2012/0195857 A1 | 8/2012 | Belema et al. |
| 2012/0251491 A1 | 10/2012 | Rosenblum et al. |
| 2012/0258909 A1 | 10/2012 | Liepold et al. |
| 2012/0264780 A1 | 10/2012 | Kullmann et al. |
| 2012/0276047 A1 | 11/2012 | Rosenblum et al. |
| 2013/0072523 A1 | 3/2013 | Liu et al. |

FOREIGN PATENT DOCUMENTS

| | | |
|---|---|---|
| WO | WO201179327 A1 | 6/2011 |
| WO | WO2011087740 A1 | 7/2011 |
| WO | WO2011119853 A1 | 9/2011 |
| WO | WO2011119870 A1 | 9/2011 |
| WO | WO2011149856 A1 | 12/2011 |
| WO | WO2011156543 A2 | 12/2011 |
| WO | WO2012003642 A1 | 1/2012 |
| WO | WO2012013643 A1 | 2/2012 |
| WO | WO2012018534 A2 | 2/2012 |
| WO | WO2012040923 A1 | 4/2012 |
| WO | WO2012040924 A1 | 4/2012 |
| WO | WO2012041014 A1 | 4/2012 |
| WO | WO2012041227 A1 | 4/2012 |
| WO | WO2012050848 A1 | 4/2012 |
| WO | WO2012050918 A2 | 4/2012 |
| WO | WO2012083048 A2 | 6/2012 |
| WO | WO2012083053 A2 | 6/2012 |
| WO | WO2012122716 A1 | 9/2012 |
| WO | WO2012125926 A2 | 9/2012 |
| WO | WO2013021337 A1 | 2/2013 |
| WO | WO2013022810 A1 | 2/2013 |

OTHER PUBLICATIONS

International Search Report of PCT/CN2013/001465.
Written Opinion of PCT/CN2013/001465.

* cited by examiner

FUSED RING COMPOUNDS AS HEPATITIS C VIRUS INHIBITORS, PHARMACEUTICAL COMPOSITIONS AND USES THEREOF

CROSS-REFERENCE TO RELATED APPLICATIONS

This is a U.S. national stage application of the International Patent Application No. PCT/CN2013/001465, filed Nov. 28, 2013, which claims priorities to Chinese Patent Application No. 201210497565.6, filed Nov. 29, 2012, and No. 201310116819.X, filed Apr. 3, 2013, all of which are incorporated herein by reference in their entirety.

FIELD OF THE INVENTION

The present disclosure relates to a field of medicine, and more particularly to compounds for treating Hepatitis C virus (HCV) infection, compositions comprising such compounds, use of the compounds and the compositions thereof, and methods thereof.

BACKGROUND OF THE INVENTION

HCV is a major human pathogen, infecting an estimated 170 million persons worldwide roughly five times the number infected by human immunodeficiency virus type 1. A substantial fraction of these HCV infected individuals develop serious progressive liver disease, including cirrhosis and hepatocellular carcinoma. Chronic HCV infection is thus a major worldwide cause of liver-related premature mortality.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. The treatment has side effects in many patients, so they do not durably respond to treatment. Thus, new and effective methods of treating HCV infection are urgently needed.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame (ORF).

Considerable heterogeneity is found within nucleotide and encoded amino acid sequence throughout the HCV genome. At least seven major genotypes have been characterized, and more than 50 subtypes have been described. In HCV infected cells, viral RNA is translated into a polyprotein that is cleaved into ten individual proteins. At the amino terminus are structural proteins, follows E1 and E2. Additionally, there are six non-structural proteins, NS2, NS3, NS4A, NS4B, NS5A and NS5B, which play a function role in the HCV lifecycle (see, for example, Lindenbach et al., *Nature*, 2005, 436, 933-938).

The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A and NS5B) is effected by two viral proteases. The first one is believed to be a metalloprotease and cleaves at the NS2-NS3 junction; the second one is a serine protease within the N-terminal region of NS3 (also referred herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to herein as HCV polymerase) is a RNA-dependent RNA polymerase that is involved in the replication of HCV.

Compounds useful for treating HCV-infected patients are desired which selectively inhibit HCV viral replication. In particular, compounds which are effective to inhibit the function of the NS5A protein are desired. The HCV NS5A protein is described, for example, in Tan et al., *Virology*, 2001, 284, 1-12; and in Park et al., *J. Biol. Chem.*, 2003, 278, 30711-30718.

SUMMARY OF THE INVENTION

Provided herein are novel fused ring compounds and methods of their use to treat HCV infection. Specifically, it has been found that the fused ring compounds disclosed herein, and compositions thereof, are effective as inhibitors of HCV infection, especially the HCV NS5A protein.

In one aspect, provided herein are compounds having Formula (I):

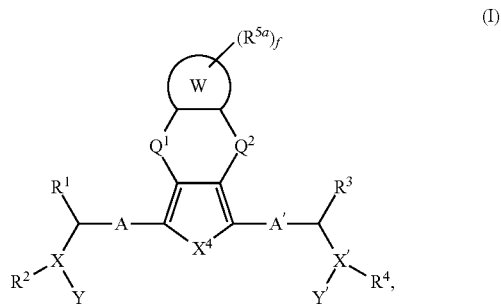

or a stereoisomer, a geometric isomer, a tautomer, an N-oxide, a hydrate, a solvate, a metabolite, a pharmaceutically acceptable salt or a prodrug thereof, wherein each of A and A' is independently a bond, alkylene, alkenylene, cycloalkylene, heterocycloalkylene, $-(CR^8R^{8a})_n-O-(CR^8R^{8a})_g-$, $-(CR^8R^{8a})_n-N(R^5)-(CR^8R^{8a})_p-$, $-(CR^8R^{8a})_n-S(=O)_r-N(R^5)-(CR^8$ $R^{8a})_p$—, —$(CR^8R^{8a})_n$—C(=O)—N($R^5$)—$(CR^8R^{8a})_p$—, —$(CR^8R^{8a})_n$—N($R^5$)—C(=O)—N($R^5$)—$(CR^8R^{8a})_p$—, —$(CR^8R^{8a})_n$—C(=O)—O—$(CR^8R^{8a})_p$—, —$(CR^8R^{8a})_n$—N($R^5$)—S(=O)$_r$—N($R^5$)—$(CR^8R^{8a})_p$—, —$(CR^8R^{8a})_n$—S(=O)$_r$—$(CR^8R^{8a})_p$—, —$(CR^8R^{8a})_n$—S(=O)$_r$—O—$(CR^8R^{8a})_p$—, —$(CR^8R^{8a})_n$—C(=O)—$(CR^8R^{8a})_p$—, —$(CR^8R^{8a})_n$—C(=S)—$(CR^8R^{8a})_p$—, or —$(CR^8R^{8a})_n$—N($R^5$)—C(=O)—O—$(CR^8R^{8a})_p$—, or each of A and A' is independently
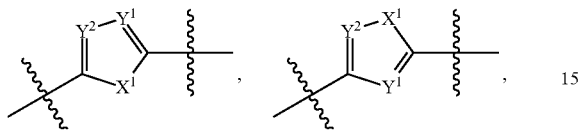,
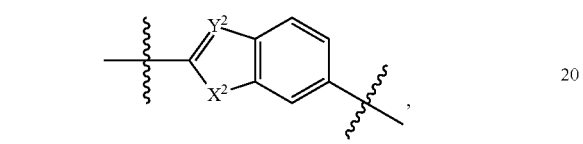,
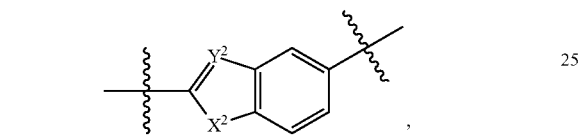,
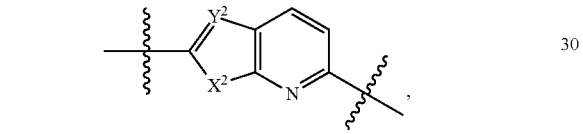,
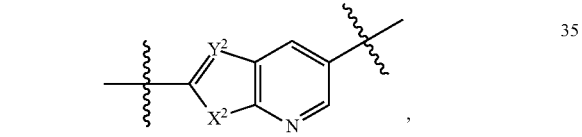,
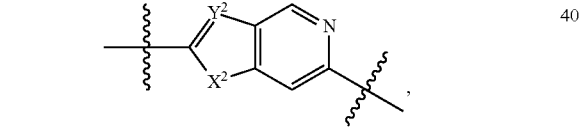,
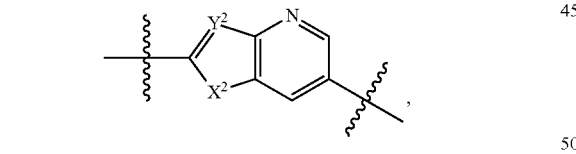,
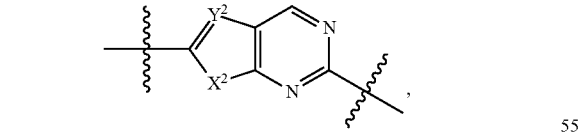,
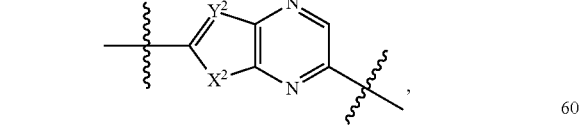,
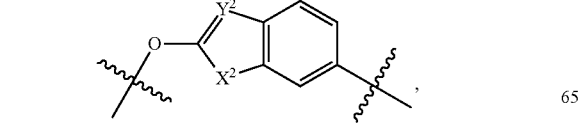,
-continued
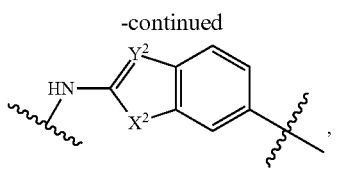,
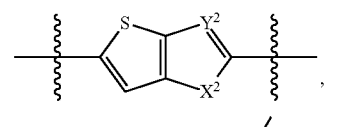,
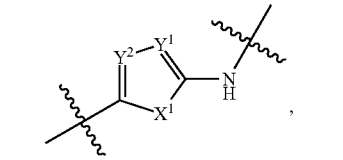,
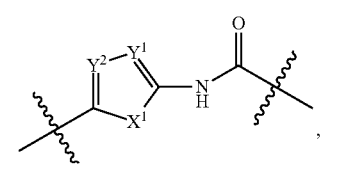,
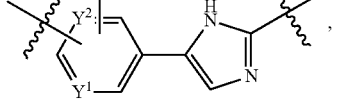,
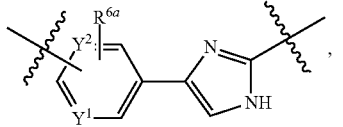,
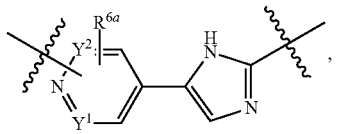,
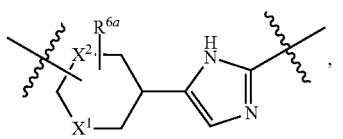,
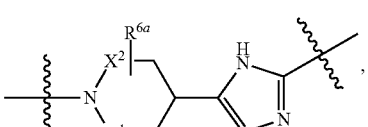,
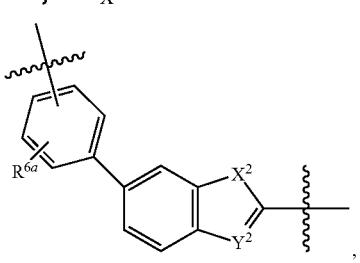,

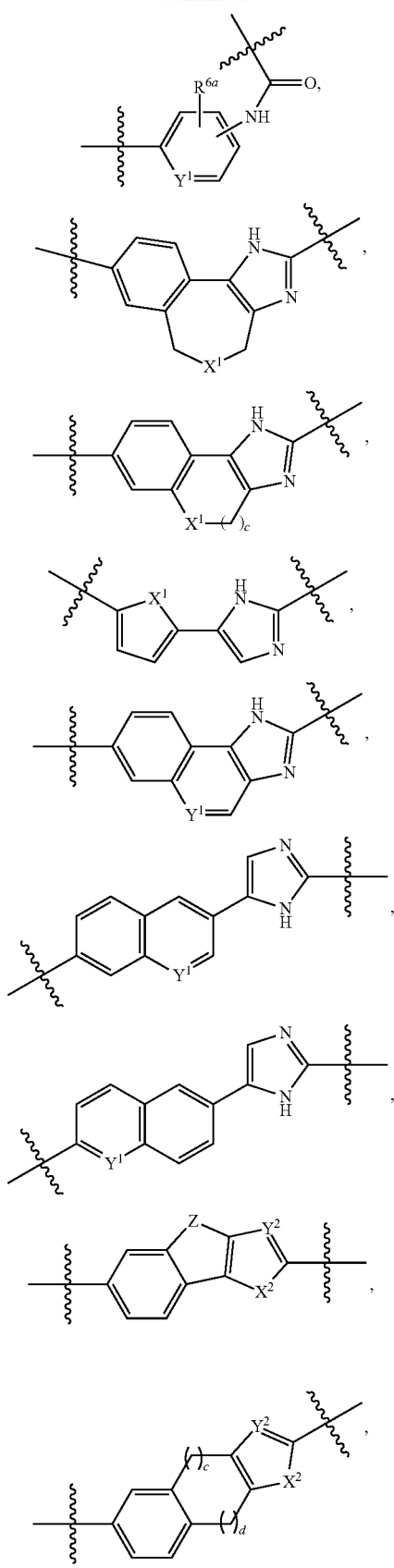
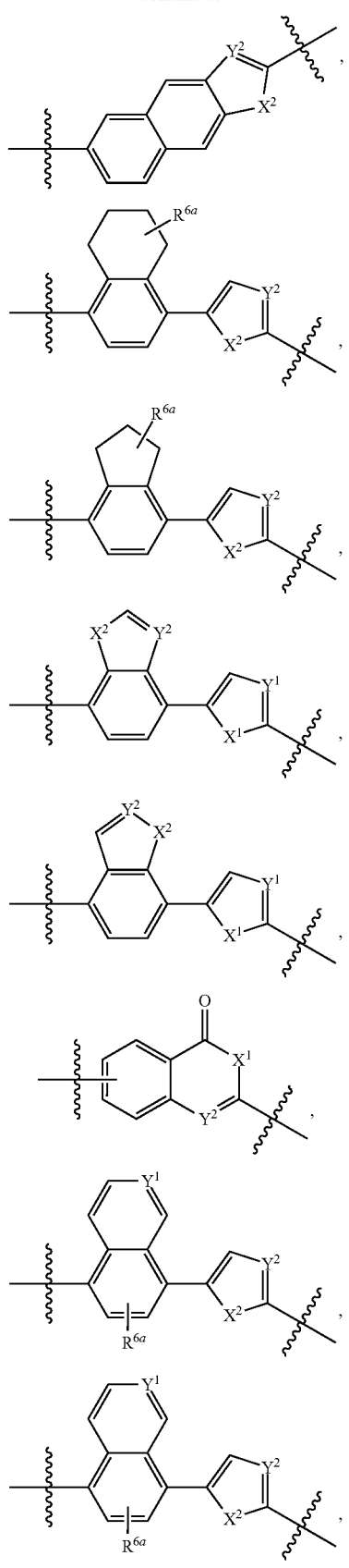

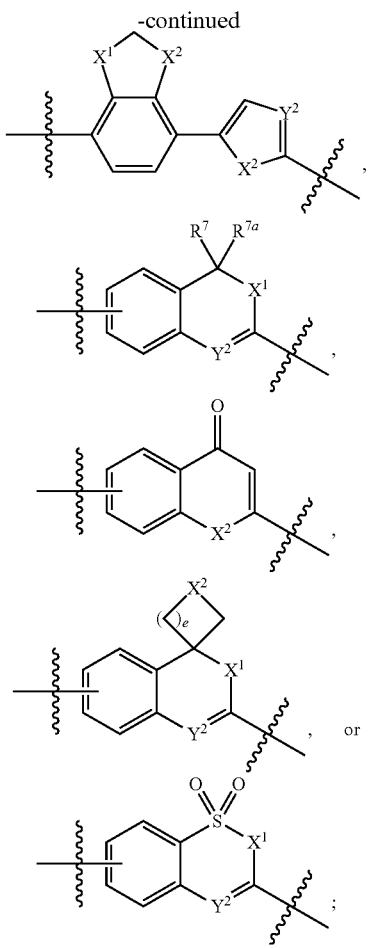

wherein each $X^1$ is independently O, S, $NR^6$, or $CR^7R^{7a}$;
each $X^2$ is independently $NR^6$, O or S;
$X^4$ is $(CR^7R^{7a})_n$, —$Y^1$=$Y^2$—, O, S or $NR^6$;
W is a carbocyclyl or heterocyclyl ring;
each $Y^1$ and $Y^2$ is independently N or $CR^7$;
Z is —$(CH_2)_a$—, —CH=CH—, —N=CH—, —$(CH_2)_a$—$N(R^5)$—$(CH_2)_b$—, or —$(CH_2)_a$—O—$(CH_2)_b$—;
each c and d is independently 1 or 2;
each a, b, n and p is independently 0, 1, 2 or 3;
each r is independently 0, 1 or 2;
each of $Q^1$ and $Q^2$ is independently a bond, $NR^6$, O, S, C(=O) or $(CR^7R^{7a})_e$;
each e and f is independently 0, 1, 2, 3 or 4;
each of X and X' is independently N or $CR^7$;
each of Y and Y' is independently H, deuterium, alkyl, heteroalkyl, cycloalkyl, heterocyclyl, aryl, heteroaryl, aralkyl, a monovalent group derived from an α-amino acid or an optically isomer thereof, or —[U—$(CR^9R^{9a})_t$—N$(R^{10})$—$(CR^9R^{9a})_t]_k$—U—$(CR^9R^{9a})_t$—N$(R^{11})$—$(CR^9R^{9a})_t$—$R^{12}$, —U—$(CR^9R^{9a})_t$—$R^{12}$ or —[U—$(CR^9R^{9a})_t$—N$(R^{10})$—$(CR^9R^{9a})_t]_k$—U—$(CR^9R^{9a})_t$—O—$(CR^9R^{9a})_t$—$R^{12}$;
each U is independently —C(=O)—, —C(=S)—, —S(=O)— or —S(=O)$_2$—;
each t is independently 0, 1, 2, 3 or 4;
each k is independently 0, 1 or 2;
each of $R^1$, $R^2$, $R^3$ and $R^4$ is independently H, deuterium, alkyl, heteroalkyl, aralkyl, cycloalkyl, heterocyclyl, heteroaryl or aryl; or $R^1$ and $R^2$, together with X—CH they are attached to, optionally form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle; or $R^3$ and $R^4$, together with X—CH they are attached to, optionally form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle;

each $R^5$ is independently H, deuterium, hydroxy, alkyl, heteroalkyl, cycloalkyl, heterocyclyl, aryl, heteroaryl, aralkyl, alkoxy, alkyl-OC(=O)—, alkyl-C(=O)—, carbamoyl, alkyl-OS(=O)$_r$—, alkyl-S(=O)$_r$O—, alkyl-S(=O)$_r$— or aminosulfonyl;

each $R^{5a}$ is independently H, deuterium, oxo(=O), hydroxy, amino, F, Cl, Br, I, cyano, $R^{13a}R^{13}N$—, —C(=O)$NR^{13}R^{13a}$, —OC(=O)$NR^{13}R^{13a}$, —OC(=O)$OR^{13}$, —N($R^{13}$)C(=O)$NR^{13}R^{13a}$, —N($R^{13}$)C(=O)$OR^{13a}$, —N($R^{13}$)C(=O)—$R^{13a}$, $R^{13}R^{13a}N$—S(=O)$_2$—, $R^{13}S$(=O)$_2$—, $R^{13}S$(=O)$_2N(R^{13a})$—, $R^{13a}R^{13}N$-alkyl, $R^{13}S$(=O)-alkyl, $R^{13}R^{13a}N$—C(=O)-alkyl, $R^{13a}R^{13}N$-alkoxy, $R^{13}S$(=O)-alkoxy, $R^{13}R^{13a}N$—C(=O)-alkoxy, aryl, heteroaryl, alkoxy, alkylamino, alkyl, haloalkyl, alkenyl, alkynyl, heterocyclyl, cycloalkyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, alkyacyl, alkylacyloxy, alkoxyacyl, alkylsulfonyl, alkoxysulfonyl, alkylsulfinyl, alkylsulfonyloxy, alkylsulfinyloxy, heterocyclylalkylamino or aryloxy;

each $R^6$ is independently H, deuterium, $R^{13}R^{13a}NC$(=O)—, $R^{13}OC$(=O)—, $R^{13}C$(=O)—, $R^{13}R^{13a}NS$(=O)—, $R^{13}OS$(=O)—, $R^{13}S$(=O)—, $R^{13}R^{13a}NS$(=O)$_2$—, $R^{13}OS$(=O)$_2$—, $R^{13}S$(=O)$_2$—, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl; wherein said aliphatic is alkyl;

each $R^{6a}$ is independently H, deuterium, hydroxy, amino, F, Cl, Br, I, cyano, oxo(=O), $R^{13a}R^{13}N$—, —C(=O)$NR^{13}R^{13a}$, —OC(=O)$NR^{13}R^{13a}$, —OC(=O)$OR^{13}$, —N($R^{13}$)C(=O)$NR^{13}R^{13a}$, —N($R^{13}$)C(=O)$OR^{13a}$, —N($R^{13}$)C(=O)—$R^{13a}$, $R^{13}R^{13a}N$—S(=O)$_2$—, $R^{13}S$(=O)$_2$—, $R^{13}S$(=O)$_2N(R^{13a})$—, $R^{13a}R^{13}N$-alkyl, $R^{13}S$(=O)-alkyl, $R^{13}R^{13a}N$—C(=O)-alkyl, $R^{13a}R^{13}N$-alkoxy, $R^{13}S$(=O)-alkoxy, $R^{13}R^{13a}N$—C(=O)-alkoxy, aryl, heteroaryl, alkoxy, alkylamino, alkyl, haloalkyl, alkenyl, alkynyl, heterocyclyl, cycloalkyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, alkyacyl, alkylacyloxy, alkoxyacyl, alkylsulfonyl, alkoxysulfonyl, alkylsulfinyl, alkylsulfonyloxy, alkylsulfinyloxy, heterocyclylalkylamino or aryloxy;

each $R^8$ and $R^{8a}$ is independently H, deuterium, F, Cl, Br, I, aliphatic, heteroalkyl, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl; wherein said aliphatic is alkyl;

each $R^8$ and $R^{8a}$ is independently H, deuterium, hydroxy, cyano, nitro, F, Cl, Br, I, alkyl, heteroalkyl, cycloalkyl, heterocyclyl, aryl, heteroaryl, aralkyl, alkoxy, alkyl-OC
(=O)—, alkyl-C(=O)—, carbamoyl, alkyl-OS(=O)$_r$—,
alkyl-S(=O)$_r$O—, alkyl-S(=O)$_r$— or aminosulfonyl;

each $R^9$, $R^{9a}$, $R^{10}$ and $R^{11}$ is independently H, deuterium, alkyl, heteroalkyl, cycloalkyl, heterocyclyl, aryl, heteroaryl, aralkyl, haloalkyl, hydroxyalkyl, heteroarylalkyl, heterocyclylalkyl or cycloalkylalkyl;

each $R^{12}$ is independently $R^{13a}R^{13}N$—, —C(=O)$R^{13}$, —C(=S)$R^{13}$, —C(=O)—O—$R^{13}$, —C(=O)N$R^{13}R^{13a}$, —OC(=O)N$R^{13}R^{13a}$, —OC(=O)O$R^{13}$, —N($R^{13}$)C(=O) N$R^{13}R^{13a}$, —N($R^{13}$)C(=O)O$R^{13a}$, —N($R^{13}$)C(=O)— $R^{13a}$, $R^{13}R^{13a}N$—S(=O)$_2$, $R^{13}S$(=O)$_2$—, $R^{13}S$(=O)$_2$N ($R^{13a}$)—, $R^{13}OS$(=O)$_2$—, alkyl, heteroalkyl, cycloalkyl, heterocyclyl, aryl, heteroaryl or aralkyl;

or $R^{11}$ and $R^{12}$ are optionally joined to form a 4-7 membered ring; and each $R^{13}$ and $R^{13a}$ is independently H, deuterium, alkyl, heteroalkyl, cycloalkyl, heterocyclyl, aryl, heteroaryl, or aralkyl; with the proviso that where $R^{13}$ and $R^{13a}$ are bonded to the same nitrogen atom, $R^{13}$ and $R^{13a}$, together with the nitrogen atom they are attached to, optionally form a substituted or unsubstituted 3-8 membered ring, or a substituted or unsubstituted spiro bicyclic ring or fused bicyclic ring, wherein each of alkylene, alkenylene, cycloalkylene, heterocycloalkylene, —(CR$^8$R$^{8a}$)$_n$—O—(CR$^8$R$^{8a}$)$_p$—, —(CR$^8$R$^{8a}$)$_n$—N(R$^5$)—(CR$^8$R$^{8a}$)$_p$—, —(CR$^8$R$^{8a}$)$_n$—S (=O)$_r$—N(R$^5$)—(CR$^8$R$^{8a}$)$_p$—, —(CR$^8$R$^{8a}$)$_n$—C(=O)—N (R$^5$)—(CR$^8$R$^{8a}$)$_p$—, —(CR$^8$R$^{8a}$)$_n$—N(R$^5$)—C(=O)—N (R$^5$)—(CR$^8$R$^{8a}$)$_p$—, —(CR$^8$R$^{8a}$)$_n$—C(=O)—O— (CR$^8$R$^{8a}$)$_p$—, —(CR$^8$R$^{8a}$)$_n$—N(R$^5$)—S(=O)$_r$—N(R$^5$)— (CR$^8$R$^{8a}$)$_p$—, —(CR$^8$R$^{8a}$)$_n$—S(=O)$_r$—(CR$^8$R$^{8a}$)$_p$—, —(CR$^8$R$^{8a}$)$_n$—S(=O)$_r$—O—(CR$^8$R$^{8a}$)$_p$—, —(CR$^8$R$^{8a}$)$_n$ —C(=O)—(CR$^8$R$^{8a}$)$_p$—, —(CR$^8$R$^{8a}$)$_n$—C(=S)— (CR$^8$R$^{8a}$)$_p$—, —(CR$^8$R$^{8a}$)$_n$—N(R$^5$)—C(=O)—O— (CR$^8$R$^{8a}$)$_p$—, —[U—(CR$^9$R$^{9a}$)$_t$—NR$^{10}$—(CR$^9$R$^{9a}$)$_t$]$_k$— U—(CR$^9$R$^{9a}$)$_t$—NR$^{11}$—(CR$^9$R$^{9a}$)$_t$—R$^{12}$, —U—(CR$^9$R$^{9a}$)$_t$ —R$^{12}$, —[U—(CR$^9$R$^{9a}$)$_t$—NR$^{10}$—(CR$^9$R$^{9a}$)$_t$]$_k$—U— (CR$^9$R$^{9a}$)$_t$—O—(CR$^9$R$^{9a}$)$_t$—R$^{12}$, NR$^6$, CR$^7$R$^{7a}$, CR$^7$, —(CH$_2$)$_a$—, —CH=CH—, —N=CH—, —(CH$_2$)$_a$—N (R$^5$)—(CH$_2$)$_b$—, —(CH$_2$)$_a$—O—(CH$_2$)$_b$—, R$^{13a}$R$^{13}$N—, —C(=O)R$^{13}$, —C(=S)R$^{13}$, —C(=O)—O—R$^{13}$, —C(=O)NR$^{13}$R$^{13a}$, —OC(=O)NR$^{13}$R$^{13a}$, —OC(=O) OR$^{13}$, —N(R$^{13}$)C(=O)NR$^{13}$R$^{13a}$, —N(R$^{13}$)C(=O)OR$^{13a}$, —N(R$^{13}$)C(=O)—R$^{13a}$, R$^{13}$R$^{13a}$N—S(=O)$_2$—, R$^{13}$S (=O)$_2$—, R$^{13}$S(=O)$_2$N(R$^{13a}$)—, R$^{13}$OS(=O)$_2$—, R$^{13a}$R$^{13}$N—, alkyl-OC(=O)—, alkyl-C(=O)—, alkyl-OS (=O)$_r$—, alkyl-S(=O)$_r$O—, alkyl-S(=O)$_r$—, R$^{13}$R$^{13a}$NS (=O)$_r$—, R$^{13}$OS(=O)—, R$^{13}$S(=O)—, R$^{13a}$R$^{13}$N-alkyl, R$^{13}$S(=O)-alkyl, R$^{13}$R$^{13a}$N—C(=O)-alkyl, R$^{13a}$R$^{13}$N-alkoxy, R$^{13}$S(=O)-alkoxy, R$^{13}$R$^{13a}$N—C(=O)-alkylamino, alkyl, heteroalkyl, carbocyclyl, cycloalkyl, heterocyclyl, aryl, heteroaryl, aralkyl, α-amino acid, C$_{5-12}$ fused bicycle, C$_{5-12}$ fused heterobicycle, C$_{5-12}$ spiro bicycle, C$_{5-12}$ spiro heterobicycle, alkoxy, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, haloalkyl, alkenyl, alkynyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino and aryloxy is optionally substituted with one or more substituents which independently selected from deuterium, hydroxy, amino, halo, cyano, aryl, heteroaryl, alkoxy, alkylamino, alkylthio, alkyl, alkenyl, alkynyl, heterocyclyl, mercapto, nitro, aryloxy, heteroaryloxy, oxo(=O), carboxy, hydroxy-substituted alkoxy, hydroxy-substituted alkyl-C(=O), alkyl-C(=O), alkyl-S(=O), alkyl-S(=O)$_2$—, hydroxy-substituted alkyl-S(=O), hydroy-substituted alkyl-S(=O)$_2$ or carboxy-substituted alkoxy.

In some embodiments, W is a C$_{3-8}$ carbocyclyl or C$_{2-10}$ heterocyclyl ring.

In some embodiments,

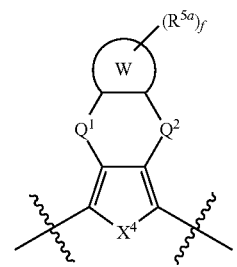

is

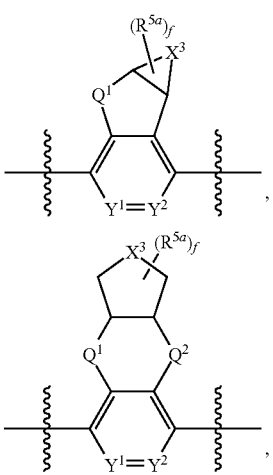
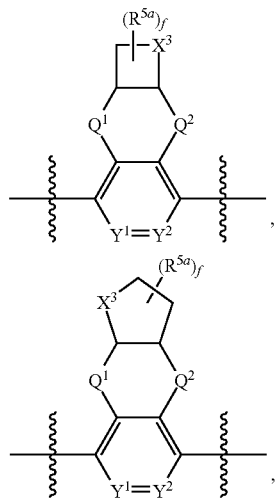
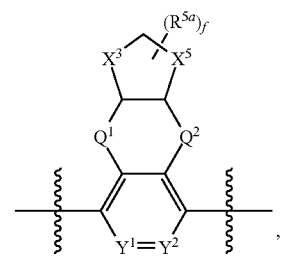
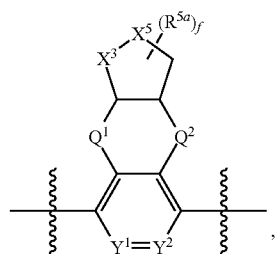
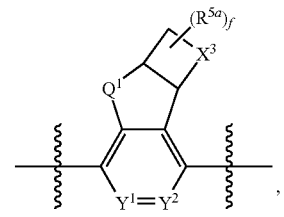
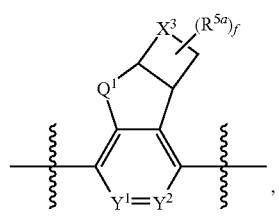

-continued
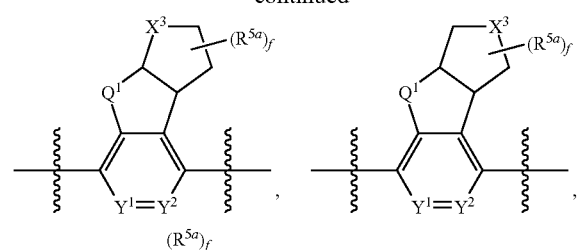
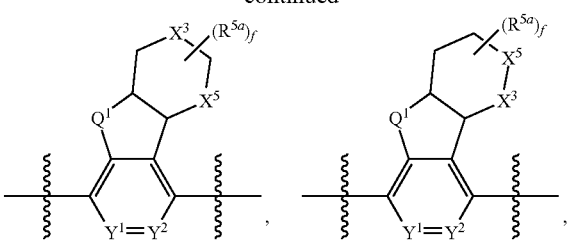
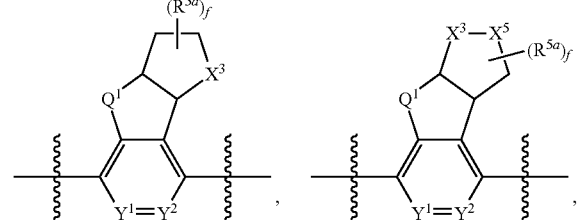
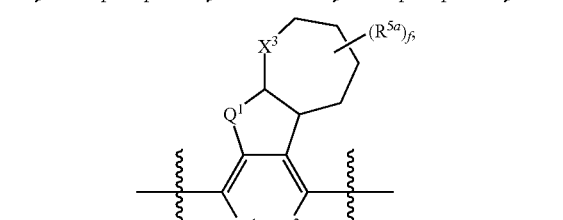
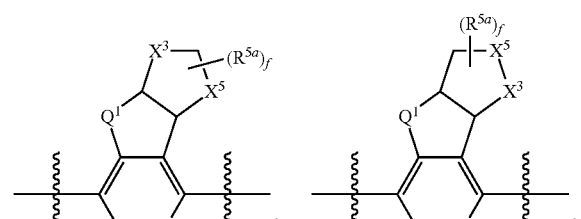
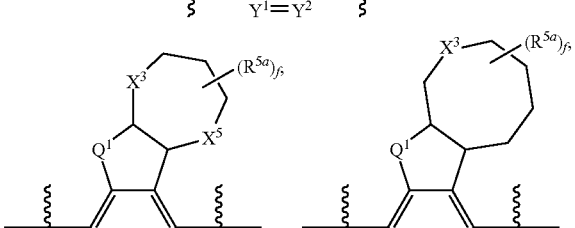
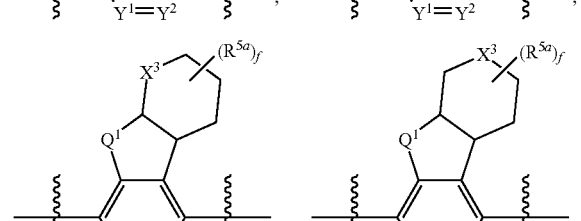
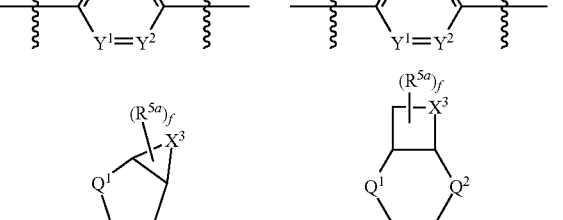
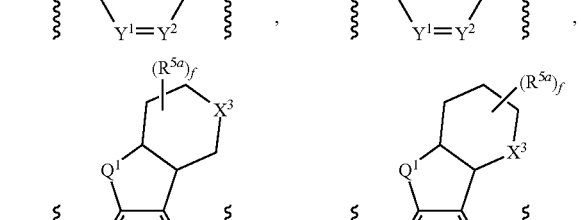
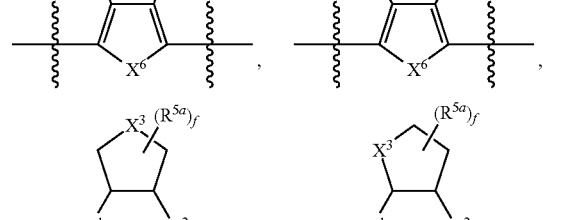
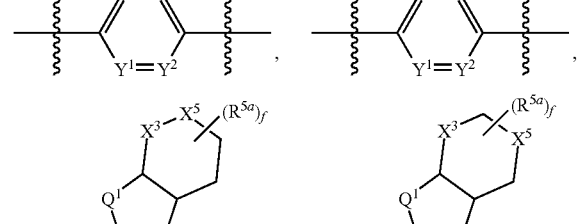
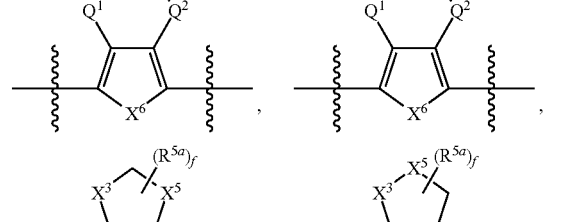
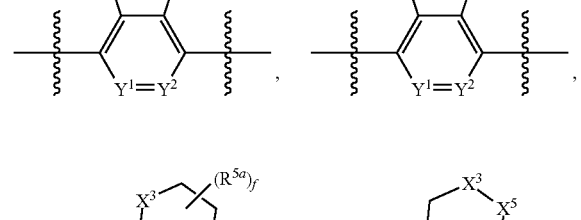
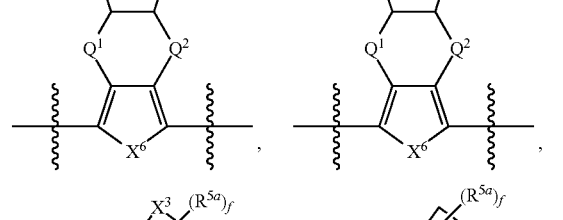
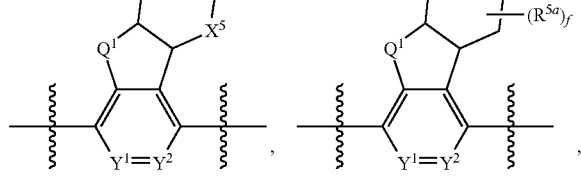
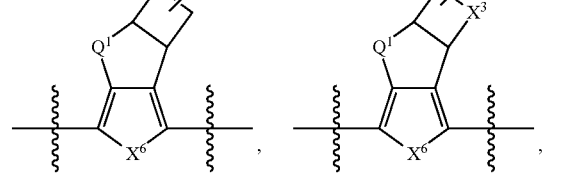

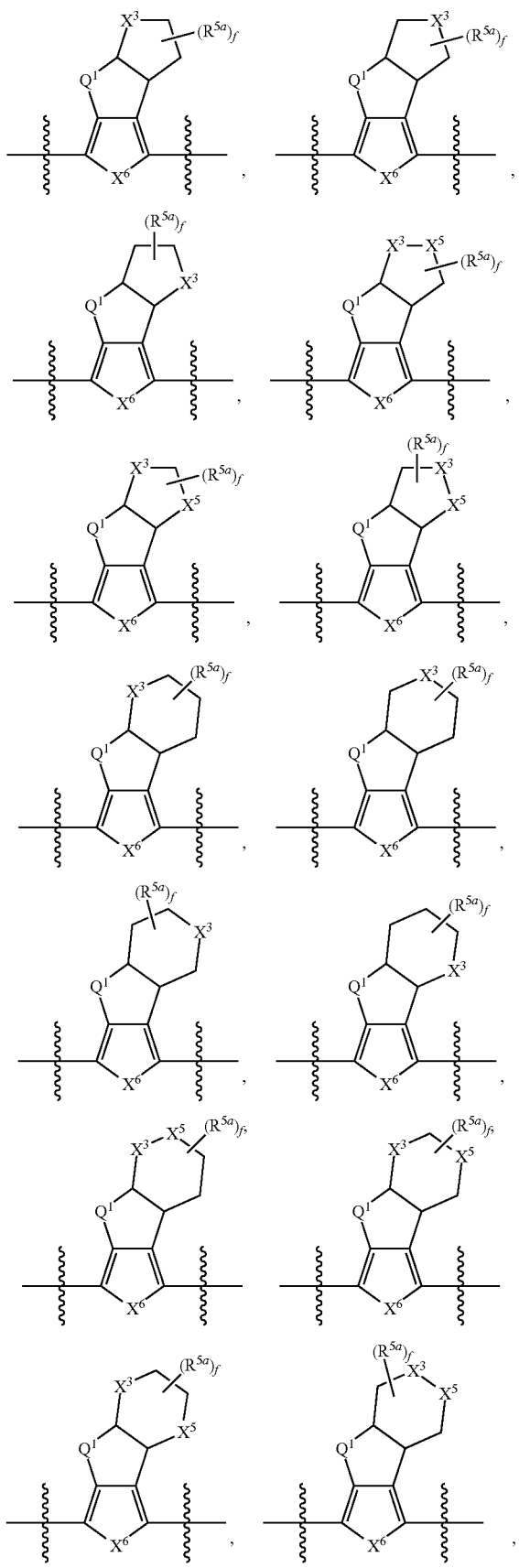

wherein each $X^6$ is independently $CR^7R^{7a}$, O, S or $NR^6$;
each $Y^1$ and $Y^2$ is independently N or $CR^7$;
each f is independently 0, 1, 2, 3 or 4;
each $X^3$ and $X^5$ is independently $NR^6$, O, S, C(=O) or $(CR^7R^{7a})_e$;
each $Q^1$ and $Q^2$ is independently a bond, $NR^6$, O, S, C(=O) or $(CR^7R^{7a})_e$;
each e is independently 0, 1, 2, 3 or 4;
each $R^{5a}$ is independently H, deuterium, oxo(=O), hydroxy, amino, F, Cl, Br, I, cyano, $R^{13a}R^{13}N-$, $-C(=O)NR^{13}R^{13a}$, $-OC(=O)NR^{13}R^{13a}$, $-OC(=O)OR^{13}$, $-N(R^{13})C(=O)NR^{13}R^{13a}$, $-N(R^{13})C(=O)OR^{13a}$, $-N(R^{13})C(=O)-R^{13a}$, $R^{13}R^{13a}N-S(=O)_2-$, $R^{13}S(=O)_2-$, $R^{13}S(=O)_2N(R^{13a})-$, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, $-CF_3$, $-OCF_3$, mercapto, nitro, $C_{1-6}$ alkylamino, $C_{3-10}$ cycloalkyl or $C_{6-10}$ aryloxy;
each $R^6$ is independently H, deuterium, $R^{13}R^{13a}NC(=O)-$, $R^{13}OC(=O)-$, $R^{13}C(=O)-$, $R^{13}R^{13a}NS(=O)-$, $R^{13}OS(=O)-$, $R^{13}S(=O)-$, $R^{13}R^{13a}NS(=O)_2-$, $R^{13}OS(=O)_2-$, $R^{13}S(=O)_2-$, $C_{1-6}$ alkyl, $C_{1-6}$ haloalkyl, $C_{1-6}$ hydroxyalkyl, $C_{1-6}$ aminoalkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryloxy-$C_{1-6}$-alkyl, $C_{2-10}$ heterocyclyloxy-$C_{1-6}$-alkyl, $C_{3-10}$ cycloalkyloxy-$C_{1-6}$-alkyl, $C_{6-10}$ arylamino-$C_{1-6}$-alkyl, $C_{2-10}$ heterocyclylamino-$C_{1-6}$-alkyl, $C_{3-10}$ cycloalkylamino-$C_{1-6}$-alkyl, $C_{6-10}$ aryl, $C_{1-9}$ heteroaryl, $C_{2-10}$ heterocyclyl or $C_{3-10}$ carbocyclyl;

each $R^7$ and $R^{7a}$ is independently H, deuterium, F, Cl, Br, I, $C_{1-6}$ alkyl, $C_{2-6}$ heteroalkyl, $C_{1-6}$ haloalkyl, $C_{1-6}$ hydroxyalkyl, $C_{1-6}$ aminoalkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryloxy-$C_{1-6}$-alkyl, $C_{2-10}$ heterocyclyloxy-$C_{1-6}$-alkyl, $C_{3-10}$ cycloalkyloxy-$C_{1-6}$-alkyl, $C_{6-10}$ arylamino-$C_{1-6}$-alkyl, $C_{2-10}$ heterocyclylamino-$C_{1-6}$-alkyl, $C_{3-10}$ cycloalkylamino-$C_{1-6}$-alkyl, $C_{6-10}$ aryl, $C_{1-9}$ heteroaryl, $C_{2-10}$ heterocyclyl or $C_{3-10}$ carbocyclyl; and each $R^{13}$ and $R^{13a}$ is independently H, deuterium, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; with the proviso that where $R^{13}$ and $R^{13a}$ are bonded to the same nitrogen atom, $R^{13}$ and $R^{13a}$, together with the nitrogen atom they are attached to, optionally form a substituted or unsubstituted 3-8 membered ring, or a substituted or unsubstituted spiro bicyclic ring or fused bicyclic ring.

In some embodiments,

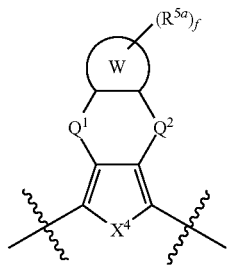

is

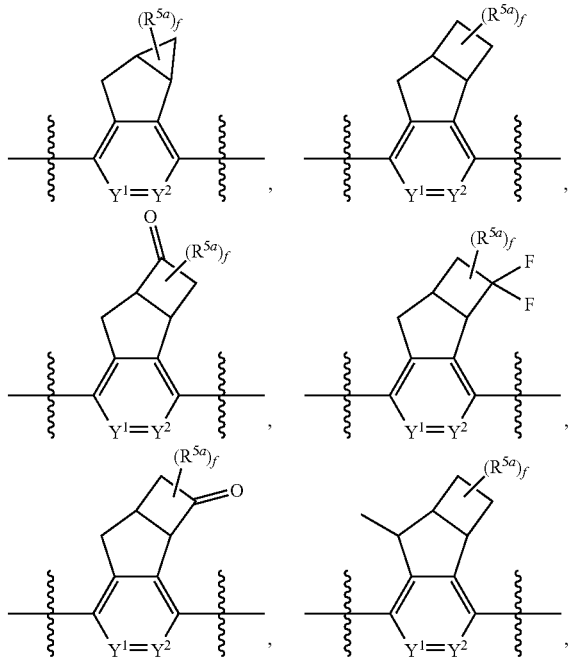

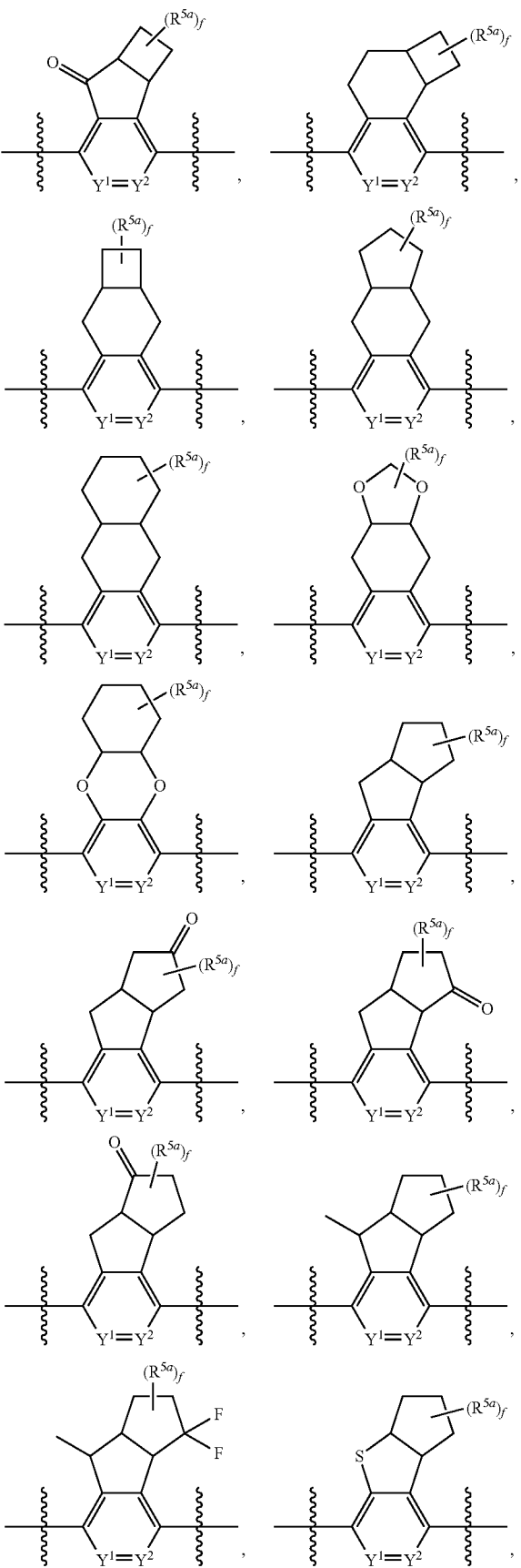

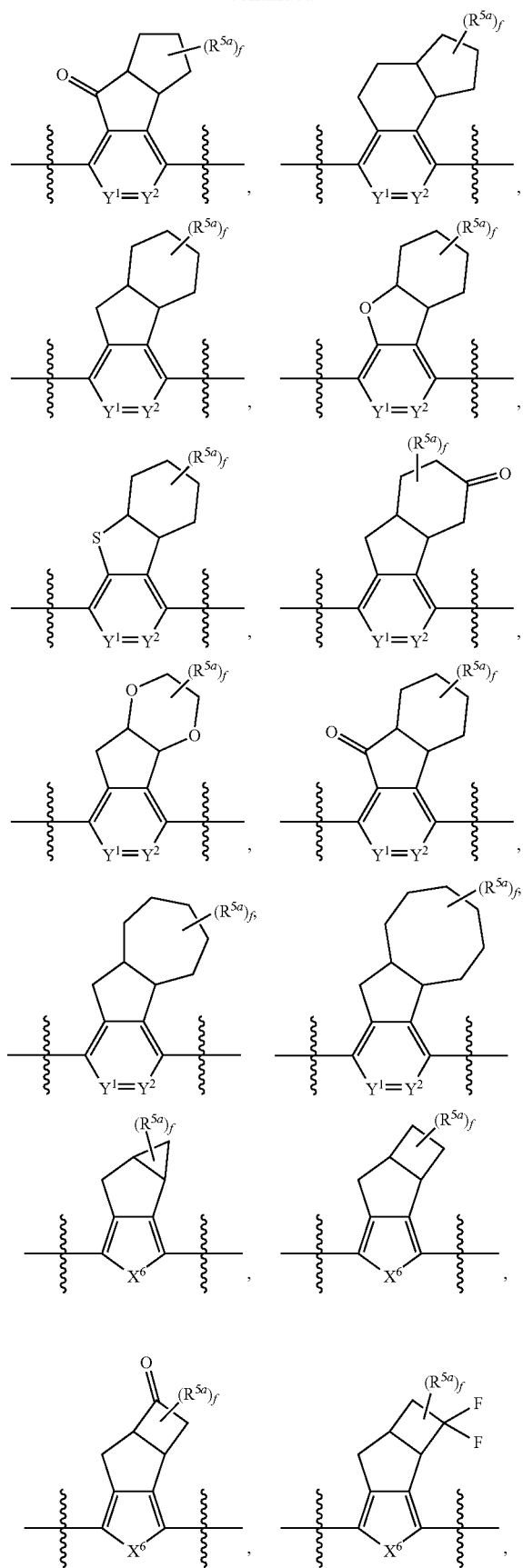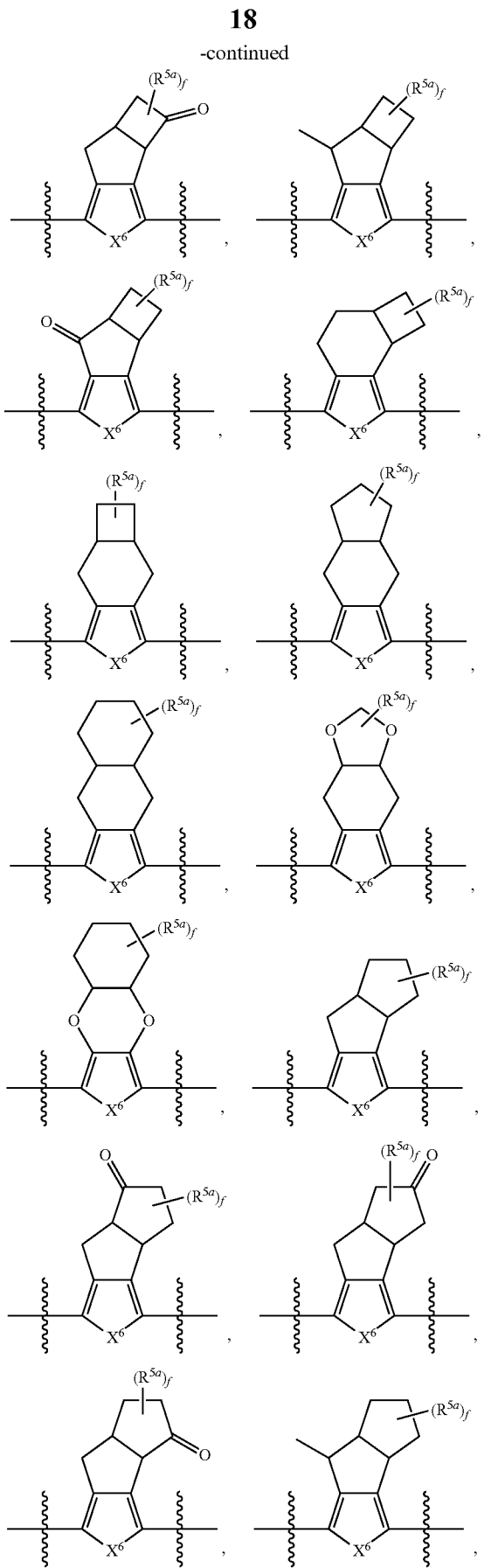

-continued

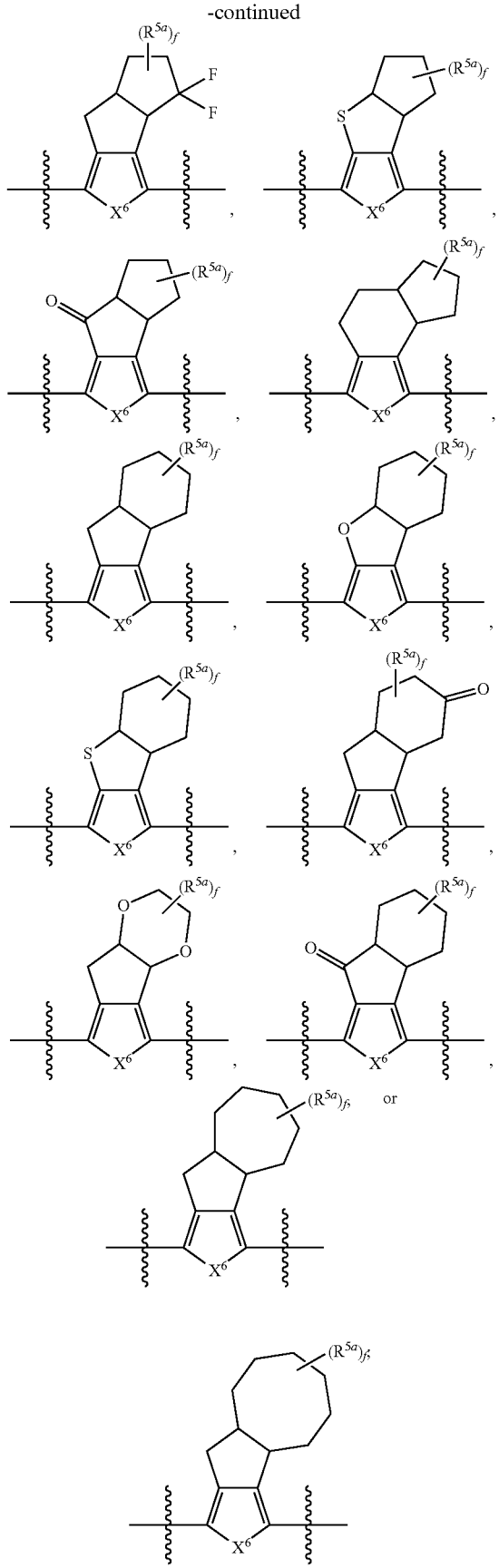

wherein each $Y^1$ and $Y^2$ is independently N or $CR^7$;
each $X^6$ is independently $CR^7R^{7a}$, O, S, or $NR^6$;
each f is independently 0, 1, 2, 3 or 4;
each $R^{5a}$ is independently H, deuterium, oxo(=O), hydroxy, amino, F, Cl, Br, I, cyano, $R^{13a}R^{13}N$—, —C(=O)$NR^{13}R^{13a}$, —OC(=O)$NR^{13}R^{13a}$, —OC(=O)$OR^{13}$, —N($R^{13}$)C(=O)$NR^{13}R^{13a}$, —N($R^{13}$)C(=O)$OR^{13a}$, —N($R^{13}$)C(=O)—$R^{13a}$, $R^{13}R^{13a}N$—S(=O)$_2$—, $R^{13}S$(=O)$_2$—, $R^{13}S$(=O)$_2N(R^{13a})$—, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, —$CF_3$, —$OCF_3$, mercapto, nitro or $C_{1-6}$ alkylamino;
each $R^6$ is independently H, deuterium, $C_{1-6}$ alkyl, $C_{1-6}$ haloalkyl, $C_{1-6}$ hydroxyalkyl, $C_{1-6}$ aminoalkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-16}$-alkyl, or $C_{3-8}$ cycloalkyl-$C_{1-6}$-alkyl;
each $R^7$ and $R^{7a}$ is independently H, deuterium, F, Cl, Br, I, $C_{1-6}$ alkyl, $C_{2-6}$ heteroalkyl, $C_{1-6}$ haloalkyl, $C_{1-6}$ hydroxyalkyl, $C_{1-6}$ aminoalkyl, $C_{1-6}$ alkoxy-$C_{1-16}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryloxy-$C_{1-6}$-alkyl, $C_{2-10}$ heterocyclyloxy-$C_{1-6}$-alkyl, $C_{3-10}$ cycloalkyloxy-$C_{1-6}$-alkyl, $C_{6-10}$ arylamino-$C_{6}$-alkyl, $C_{2-10}$ heterocyclylamino-$C_{1-6}$-alkyl, $C_{3-10}$ cycloalkylamino-$C_{1-6}$-alkyl, $C_{6-10}$ aryl, $C_{1-9}$ heteroaryl, $C_{2-10}$ heterocyclyl or $C_{3-8}$ carbocyclyl; and
each $R^{13}$ and $R^{13a}$ is independently H, deuterium, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; with the proviso that where $R^{13}$ and $R^{13a}$ are bonded to the same nitrogen atom, $R^{13}$ and $R^{13a}$, together with the nitrogen atom they are attached to, optionally form a substituted or unsubstituted 3-8 membered ring, or a substituted or unsubstituted spiro bicyclic ring or fused bicyclic ring.

In some embodiments, each of A and A' is independently a bond, $C_{1-6}$ alkylene, $C_{2-6}$ alkenylene, $C_{3-8}$ cycloalkylene, $C_{2-10}$ heterocycloalkylene, —$(CR^8R^{8a})_n$—O—$(CR^8R^{8a})_p$—, —$(CR^8R^{8a})_nN(R^5)$—$(CR^8R^{8a})_p$—, —$(CR^8R^{8a})_n$—S(=O)$_r$—N($R^5$)—$(CR^8R^{8a})_p$—, $(CR^8R^{8a})_n$—C(=)—N($R^5$)—$(CR^8R^{8a})_p$—, —$(CR^8R^{8a})_n$—N($R^5$)—C(=O)$_r$—N($R^5$)—$(CR^8R^{8a})_p$—, $(CR^8R^{8a})_n$—C(=O)—O—$(CR^8R^{8a})_p$—, —$(CR^8R^{8a})_n$—N($R^5$)—S(=O)$_r$—N($R^5$)—$(CR^8R^{8a})_p$—, —$(CR^8R^{8a})_n$—S(=O)$_r$—$(CR^8R^{8a})_p$—, —$(CR^8R^{8a})_n$—S(=O)$_r$—O—$(CR^8R^{8a})_n$C(=O)—$(CR^8R^{8a})_p$—, —$(CR^8R^{8a})_n$—C(=S)—$(CR^8R^{8a})_p$—, or —$(CR^8R^{8a})_n$—N($R^5$)—C(=O)—O—$(CR^8R^{8a})_p$—, or each of A and A' is independently

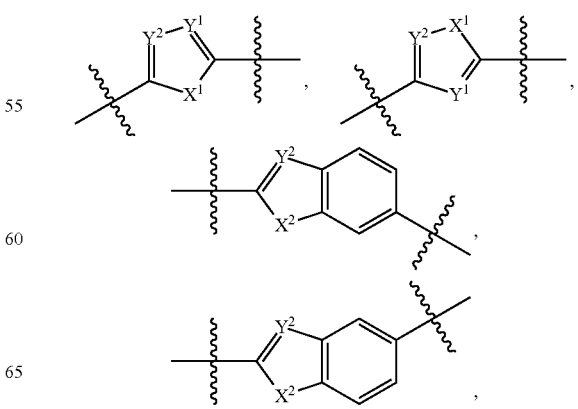

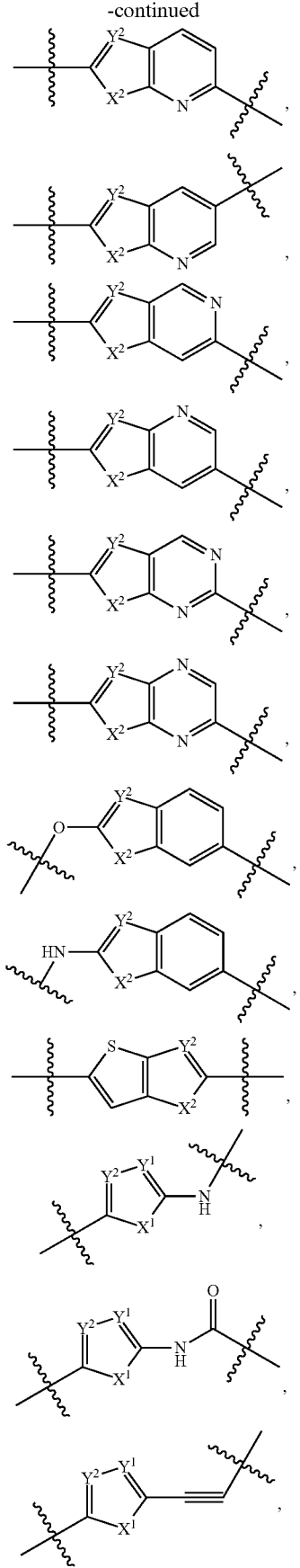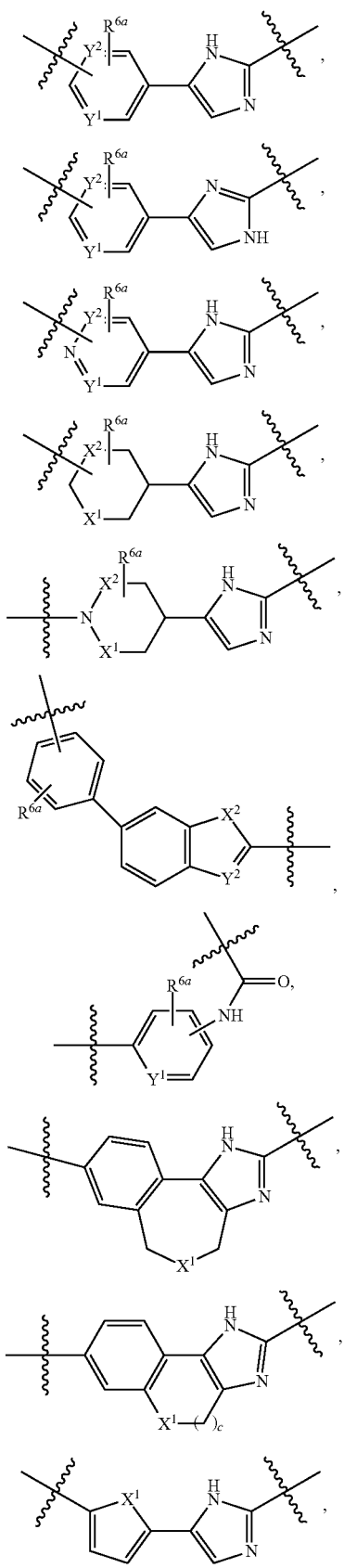

-continued
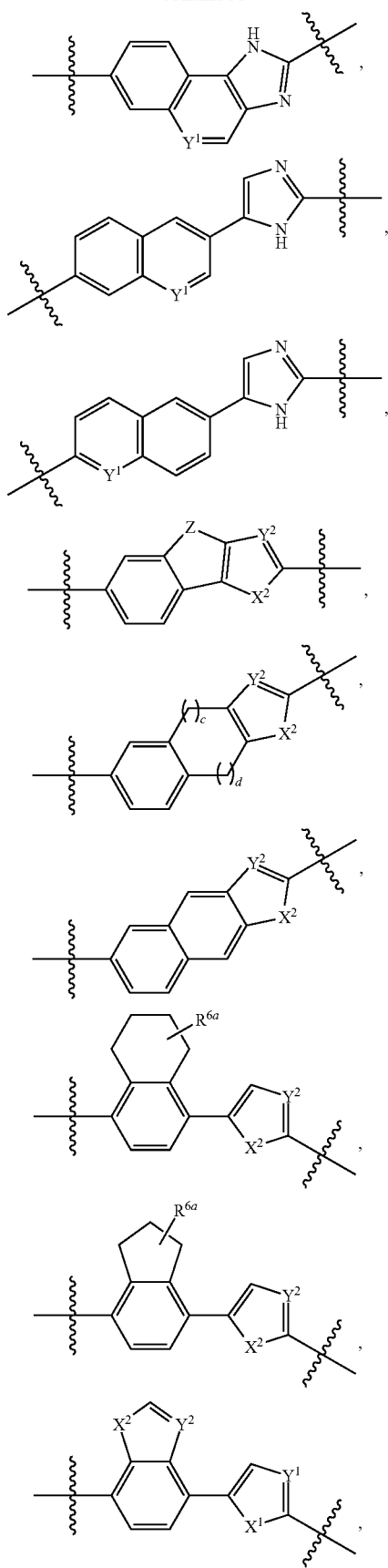
-continued
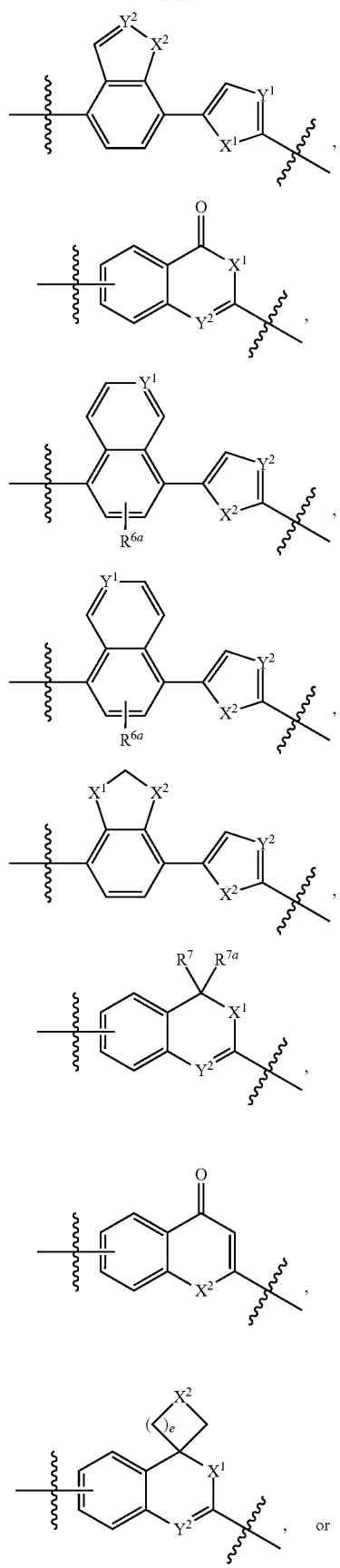

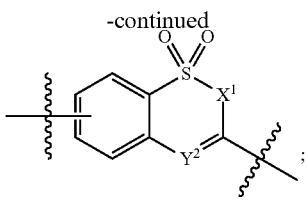

wherein each $X^1$ is independently O, S, $NR^6$, or $CR^7R^{7a}$;
each $X^2$ is independently $NR^6$, O or S;
each $Y^1$ and $Y^2$ is independently N or $CR^7$;
each e is independently 0, 1, 2, 3 or 4;
Z is $-(CH_2)_a-$, $-CH=CH-$, $-N=CH-$, $-(CH_2)_a-N(R^5)-(CH_2)_b-$ or $-(CH_2)_a-O-(CH_2)_b-$;
each c and d is independently 1 or 2;
each a, b, n and p is independently 0, 1, 2 or 3;
each r is independently 0, 1 or 2;
each $R^5$ is independently H, deuterium, hydroxy, $C_{1-6}$ alkyl, $C_{2-6}$ heteroalkyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;
each $R^6$ is independently H, deuterium, $R^{13}R^{13a}NC(=O)-$, $R^{13}OC(=O)-$, $R^{13}C(=O)-$, $R^{13}R^{13a}NS(=O)-$, $R^{13}OS(=O)-$, $R^{13}S(=O)-$, $R^{13}R^{13a}NS(=O)_2-$, $R^{13}OS(=O)_2-$, $R^{13}S(=O)_2-$, $C_{1-6}$ alkyl, $C_{1-6}$ haloalkyl, $C_{1-6}$ hydroxyalkyl, $C_{1-6}$ aminoalkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryloxy-$C_{1-6}$-alkyl, $C_{2-10}$ heterocyclyloxy-$C_{1-6}$-alkyl, $C_{3-10}$ cycloalkyloxy-$C_{1-6}$-alkyl, $C_{6-10}$ arylamino-$C_{1-6}$-alkyl, $C_{2-10}$ heterocyclylamino-$C_{1-6}$-alkyl, $C_{3-10}$ cycloalkylamino-$C_{1-6}$-alkyl, $C_{6-10}$ aryl, $C_{1-9}$ heteroaryl, $C_{2-10}$ heterocyclyl or $C_{3-10}$ carbocyclyl;
each $R^{6a}$ is independently H, deuterium, hydroxy, amino, F, Cl, Br, I, cyano, oxo(=O), $R^{13a}R^{13}N-$, $-C(=O)NR^{13}R^{13a}$, $-OC(=O)NR^{13}R^{13a}$, $-OC(=O)OR^{13}$, $-N(R^{13})C(=O)NR^{13}R^{13a}$, $-N(R^{13})C(=O)OR^{3a}$, $-N(R^{13})C(=O)-R^{13a}$, $R^{13}R^{13a}N-S(=O)_2-$, $R^{13}S(=O)_2-$, $R^{13}S(=O)_2N(R^{13a})-$, $R^{13a}R^{13}N-C_{1-6}$ alkyl, $R^{13}S(=O)-C_{1-6}$ alkyl, $R^{13}R^{13a}N-C(=O)-C_{1-6}$ alkyl, $R^{13a}R^{13}N-C_{1-6}$ alkoxy, $R^{13}S(=O)-C_{1-6}$ alkoxy, $R^{13}R^{13a}N-C(=O)-C_{1-6}$ alkoxy, $C_{6-10}$ aryl, $C_{1-9}$ heteroaryl, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, $C_{2-10}$ heterocyclyl, $C_{3-8}$ cycloalkyl, mercapto, nitro, $C_{6-10}$ aryl-$C_{1-6}$-alkyl, $C_{6-10}$ arylamino, $C_{1-9}$ heteroarylamino or $C_{6-10}$ aryloxy;
each $R^7$ and $R^{7a}$ is independently H, deuterium, F, Cl, Br, I, $C_{1-6}$ alkyl, $C_{2-6}$ heteroalkyl, $C_{1-6}$ haloalkyl, $C_{1-6}$ hydroxyalkyl, $C_{1-6}$ aminoalkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryloxy-$C_{1-6}$ alkyl, $C_{2-10}$ heterocyclyloxy-$C_{1-6}$-alkyl, $C_{3-10}$ cycloalkyloxy-$C_{1-6}$-alkyl, $C_{6-10}$ arylamino-$C_{1-6}$-alkyl, $C_{2-10}$ heterocyclylamino-$C_{1-6}$-alkyl, $C_{3-10}$ cycloalkylamino-$C_{1-6}$-alkyl, $C_{6-10}$ aryl, $C_{1-9}$ heteroaryl, $C_{2-10}$ heterocyclyl or $C_{3-8}$ carbocyclyl;
each $R^{13}$ and $R^{13a}$ is independently H, deuterium, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; with the proviso that where $R^{13}$ and $R^{13a}$ are bonded to the same nitrogen atom, $R^{13}$ and $R^{13a}$, together with the nitrogen atom they are attached to, optionally form a substituted or unsubstituted 3-8 membered ring, or a substituted or unsubstituted spiro bicyclic ring or fused bicyclic ring; and
each $R^8$ and $R^{8a}$ is independently H, deuterium, hydroxy, cyano, nitro, F, Cl, Br, I, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl.

In some embodiments, each of A and A' is independently a bond, $-CH_2-$, $-(CH_2)_2-$, $-CH=CH-$, $-CH=CH-CH_2-$, $-N(R^5)-$, $-C(=O)-$, $-C(=S)-$, $-C(=O)-O-$, $-C(=O)N(R^5)-$, $-OC(=O)N(R^5)-$, $-OC(=O)O-$, $-N(R^5)C(=O)N(R^5)-$, $-(R^5)N-S(=O)_2-$, $-S(=O)_2-$, $-OS(=O)_2-$, $-(R^5)N-S(=O)-$, $-S(=O)-$, $-OS(=O)-$, or each of A and A' is independently selected from

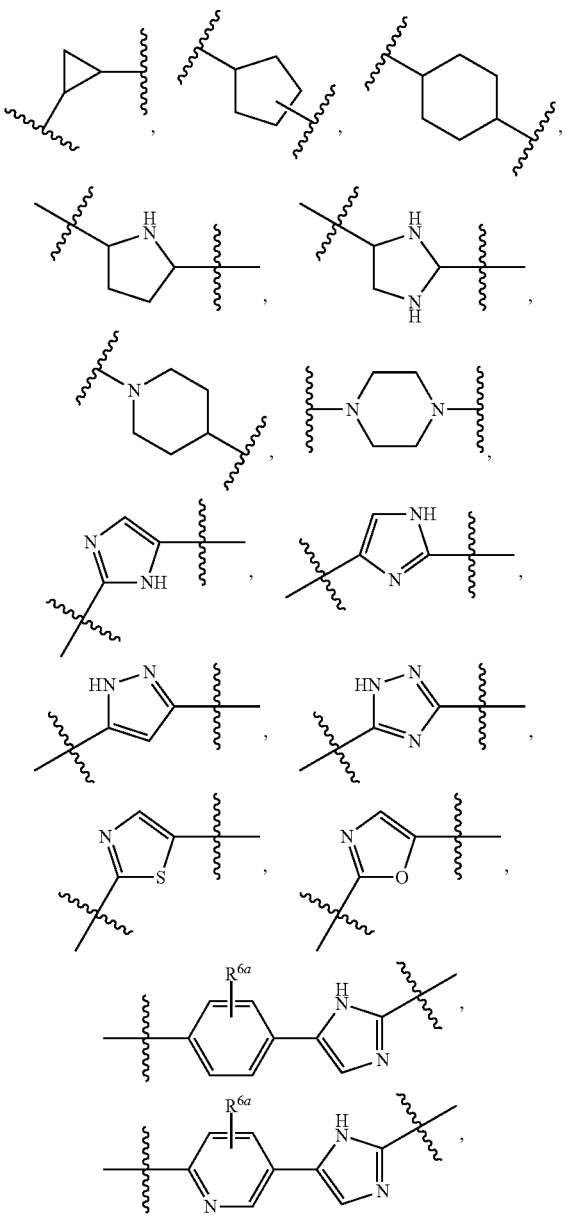

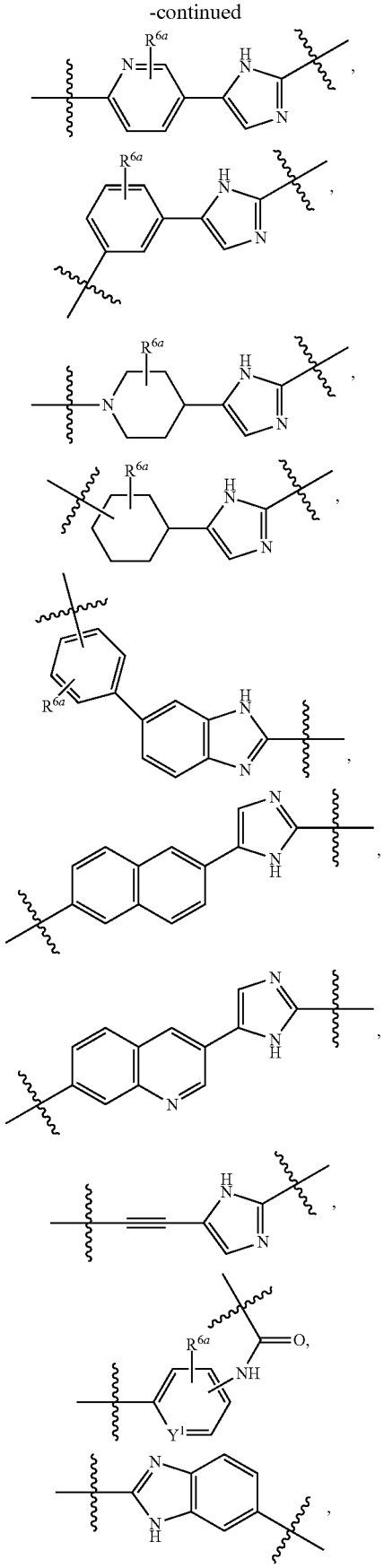
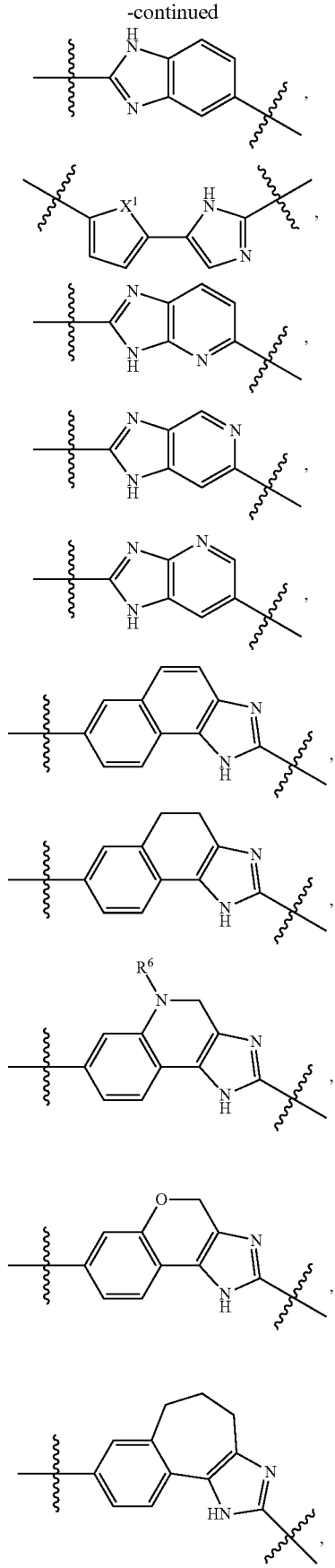

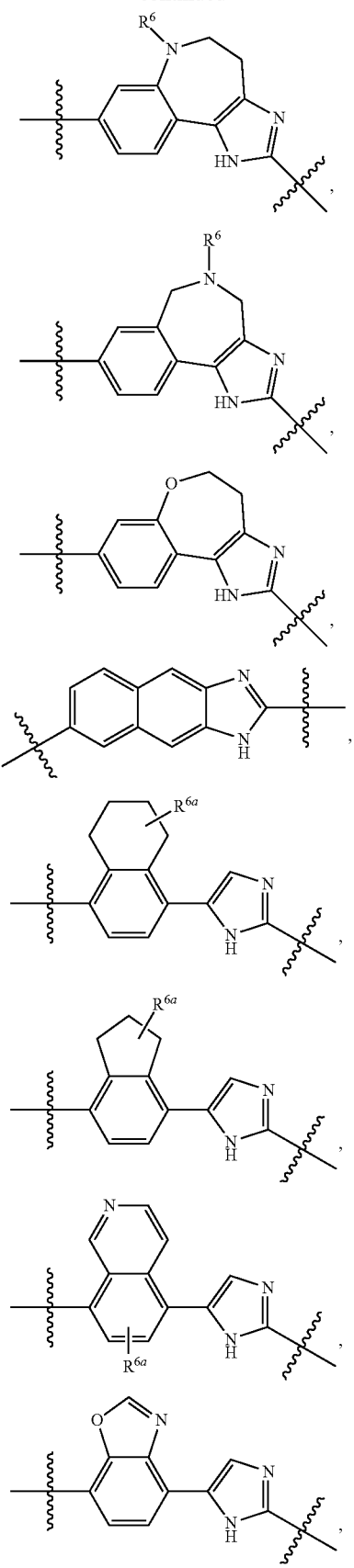
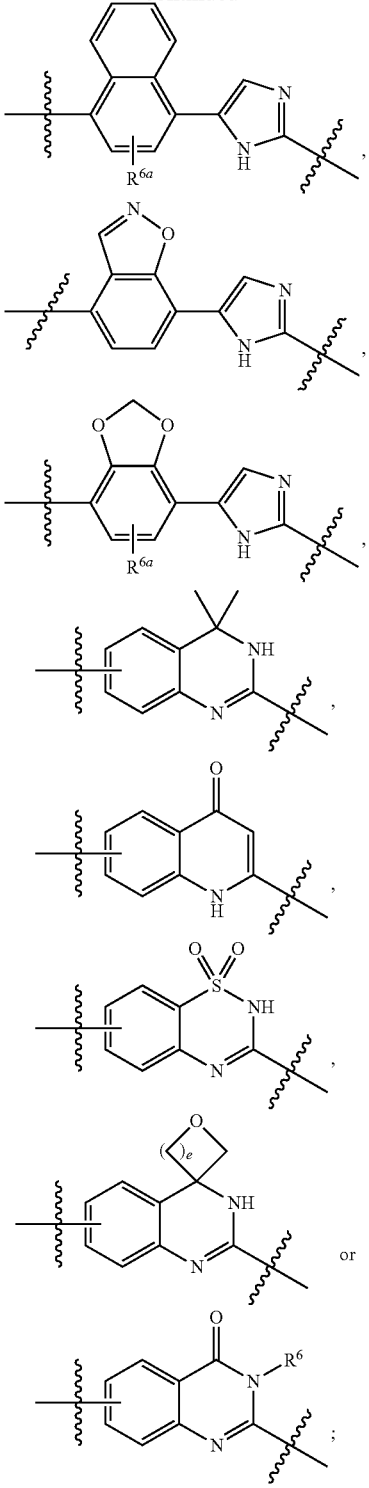
wherein $X^1$ is O or S;
each $Y^1$ is independently N or $CR^7$;
e is 0, 1, 2, 3 or 4;
each $Y^1$ is independently H, deuterium, hydroxy, $C_{1-6}$ alkyl, $C_{2-6}$ heteroalkyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;

each $R^6$ is independently H, deuterium, $C_{1-4}$ alkyl, $C_{1-6}$ haloalkyl, $C_{1-6}$ hydroxyalkyl, $C_{1-6}$ aminoalkyl, $C_{1-6}$alkoxy-$C_{1-4}$-alkyl, $C_{1-6}$ alkylamino-$C_{1-4}$-alkyl, $C_{1-6}$ alkylthio-$C_{1-4}$-alkyl, $C_{6-10}$ aryl-$C_{1-4}$-alkyl, $C_{1-9}$ heteroaryl, $C_{6-10}$ aryl, $C_{2-10}$ heterocyclyl or $C_{3-8}$ carbocyclyl;

each $R^{6a}$ is independently H, deuterium, oxo(=O), hydroxy, amino, F, Cl, Br, I, cyano, $R^{13a}R^{13}N—$, $—C(=O)NR^{13}R^{13a}$, $—OC(=O)NR^{13}R^{13a}$, $—OC(=O)OR^{13}$, $—N(R^{13})C(=O)NR^{13}R^{13a}$, $—N(R^{13})C(=O)OR^{13a}$, $—N(R^{13})C(=O)—R^{13a}$, $R^{13}R^{13a}N—S(=O)_2—$, $R^{13}S(=O)_2—$, $R^{13}S(=O)_2N(R^{13a})—$, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, mercapto or nitro;

each $R^7$ is independently H, deuterium, F, Cl, Br, I, $C_{1-6}$ alkyl, $C_{2-6}$ heteroalkyl, $C_{1-6}$ haloalkyl, $C_{1-6}$ hydroxyalkyl, $C_{1-6}$ aminoalkyl, $C_{1-6}$ alkoxy-$C_{1-16}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryloxy-$C_{1-6}$-alkyl, $C_{2-10}$ heterocyclyloxy-$C_{1-6}$-alkyl, $C_{3-10}$ cycloalkyloxy-$C_{1-6}$-alkyl, $C_{6-10}$ arylamino-$C_{1-6}$-alkyl, $C_{2-10}$ heterocyclylamino-$C_{1-6}$-alkyl, $C_{3-10}$ cycloalkylamino-$C_{1-6}$-alkyl, $C_{6-10}$ aryl, $C_{1-9}$ heteroaryl, $C_{2-10}$ heterocyclyl or $C_{3-8}$ carbocyclyl; and each of $R^{13}$ and $R^{13a}$ is independently H, deuterium, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; with the proviso that where $R^{13}$ and $R^{13a}$ are bonded to the same nitrogen atom, $R^{13}$ and $R^{13a}$, together with the nitrogen atom they are attached to, optionally form a substituted or unsubstituted 3-8 membered ring, or a substituted or unsubstituted spiro bicyclic ring or fused bicyclic ring.

In some embodiments, each of $R^1$, $R^2$, $R^3$ and $R^4$ is independently H, deuterium, $C_{1-8}$ alkyl, $C_{1-8}$ heteroalkyl, $C_{6-10}$ aryl-$C_{1-6}$-alkyl, $C_{3-10}$ cycloalkyl, $C_{2-10}$ heterocyclyl, $C_{1-9}$ heteroaryl or $C_{6-10}$ aryl; or $R^1$ and $R^2$, together with X—CH they are attached to, optionally form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle; or $R^3$ and $R^4$, together with X—CH they are attached to, optionally form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle.

In other embodiments, $R^1$ and $R^2$, together with X—CH they are attached to, or $R^3$ and $R^4$, together with X—CH they are attached to, optionally form a 3-8 membered heterocycle, $C_{5-12}$ fused bicycle, $C_{5-12}$ fused heterobicycle, $C_{5-12}$ spiro bicycle or $C_{5-12}$ spiro heterobicycle.

In other embodiments, $R^1$, $R^2$ and Y—X—CH together form one of the following monovalent groups:

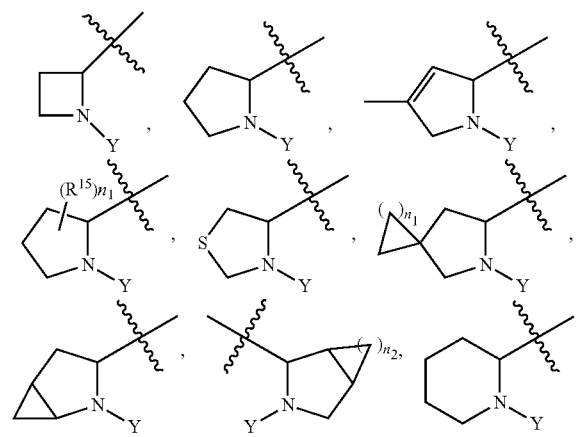

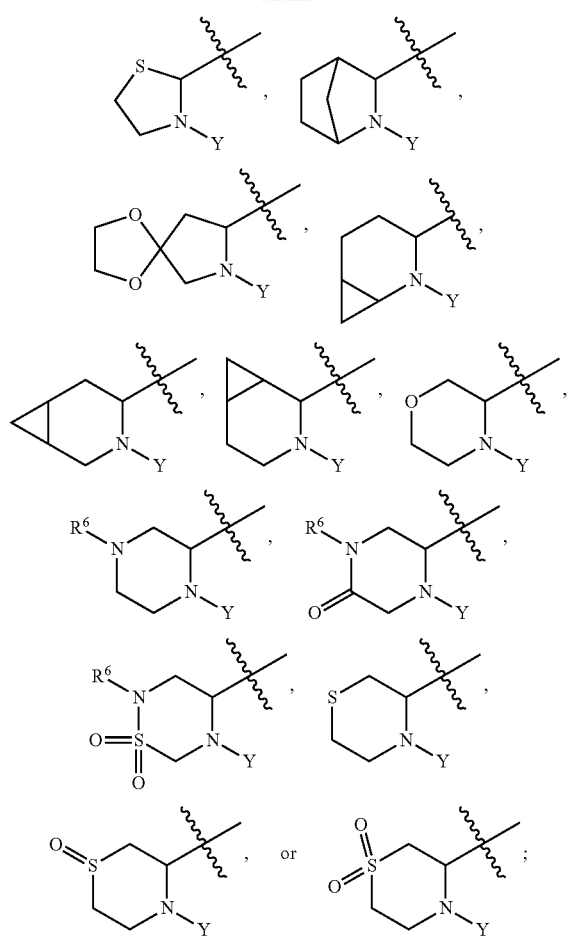

wherein each $R^{15}$ is independently H, deuterium, oxo (=O), F, Cl, Br, I, cyano, hydroxy, $C_{1-3}$ alkyl, $C_{1-3}$ haloalkyl, $C_{1-3}$ alkoxy, $C_{1-3}$ alkylamino, $C_{1-3}$ alkylthio, $C_{6-10}$ arylamino, $C_{6-10}$ aryloxy, $C_{1-9}$ heteroaryl, $C_{1-9}$ heteroaryloxy, $C_{1-9}$ heteroaryl-$C_{1-3}$-alkyl or $C_{2-10}$ heterocyclyl;

each $R^6$ is independently H, deuterium, $C_{1-3}$ alkyl, $C_{1-3}$ haloalkyl, $C_{1-3}$ hydroxyalkyl, $C_{1-3}$ aminoalkyl, $C_{1-3}$ alkoxy-$C_{1-3}$-alkyl, $C_{1-3}$ alkylamino-$C_{1-3}$-alkyl, $C_{1-3}$ alkylthio-$C_{1-3}$-alkyl, $C_{6-10}$ aryl-$C_{1-3}$-alkyl, $C_{1-9}$ heteroaryl, $C_{6-10}$ aryl, $C_{2-10}$ heterocyclyl or $C_{3-8}$ carbocyclyl; and each $n_1$ and $n_2$ is independently 1, 2, 3 or 4.

In other embodiments, $R^3$, $R^4$ and Y'—X'—CH together form one of the following monovalent groups:

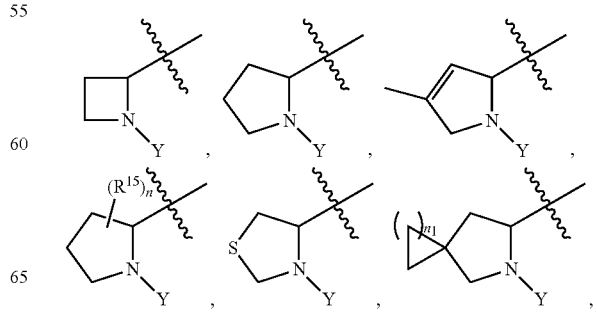

-continued

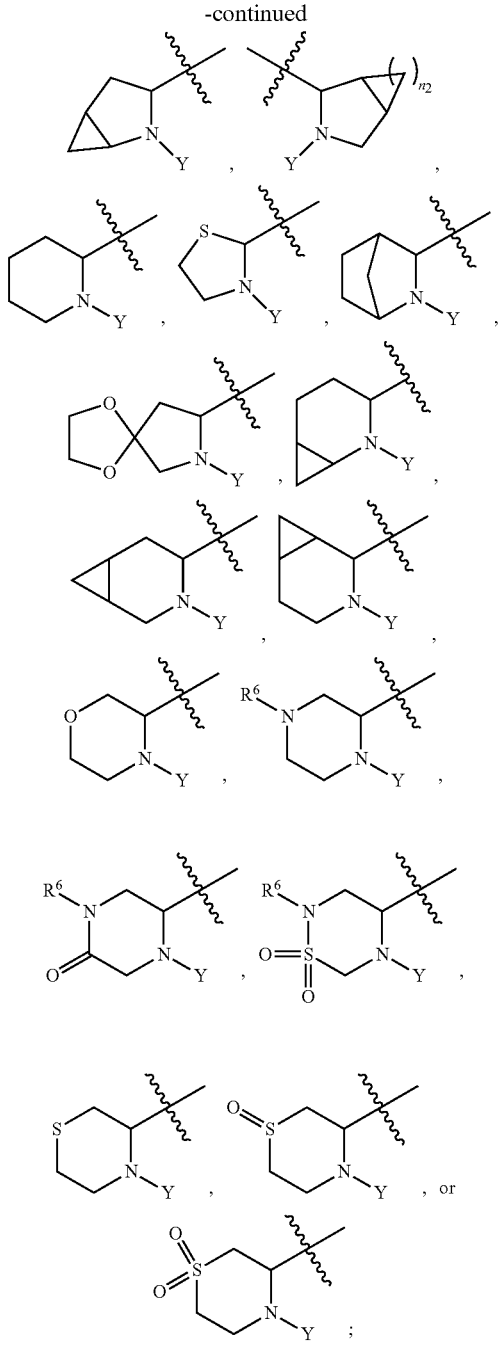

wherein each R[15] is independently H, deuterium, oxo (=O), F, Cl, Br, I, cyano, hydroxy, $C_{1-3}$ alkyl, $C_{1-3}$ haloalkyl, $C_{1-3}$ alkoxy, $C_{1-3}$ alkylamino, $C_{1-3}$ alkylthio, $C_{6-10}$ arylamino, $C_{6-10}$ aryloxy, $C_{1-9}$ heteroaryl, $C_{1-9}$ heteroaryloxy, $C_{1-9}$ heteroaryl-$C_{1-3}$-alkyl or $C_{2-10}$ heterocyclyl;

each R[6] is independently H, deuterium, $C_{1-3}$ alkyl, $C_{1-3}$ haloalkyl, $C_{1-3}$ hydroxyalkyl, $C_{1-3}$ aminoalkyl, $C_{1-3}$ alkoxy-$C_{1-3}$-alkyl, $C_{1-3}$ alkylamino-$C_{1-3}$-alkyl, $C_{1-3}$ alkylthio-$C_{1-3}$-alkyl, $C_{6-10}$ aryl-$C_{1-3}$-alkyl, $C_{1-9}$ heteroaryl, $C_{6-10}$ aryl, $C_{2-10}$ heterocyclyl or $C_{3-8}$ carbocyclyl; and each $n_1$ and $n_2$ is independently 1, 2, 3 or 4.

In some embodiments, the compound may have formula (II):

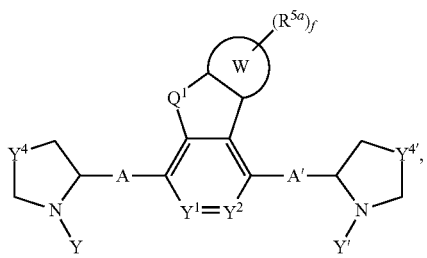

wherein

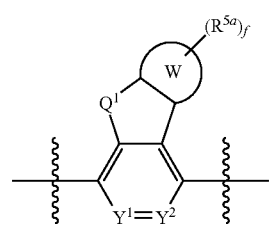

is

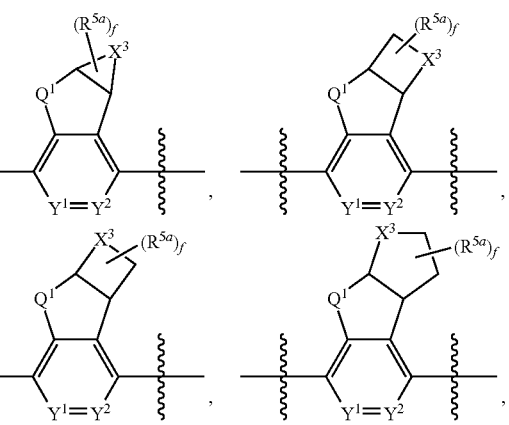

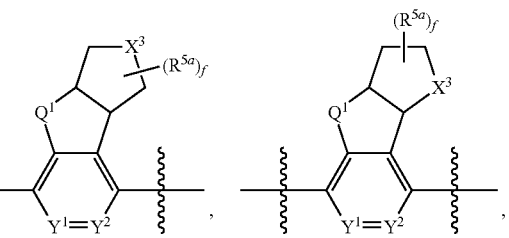

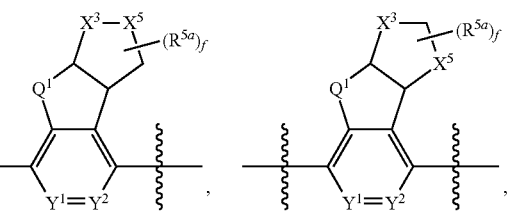

-continued

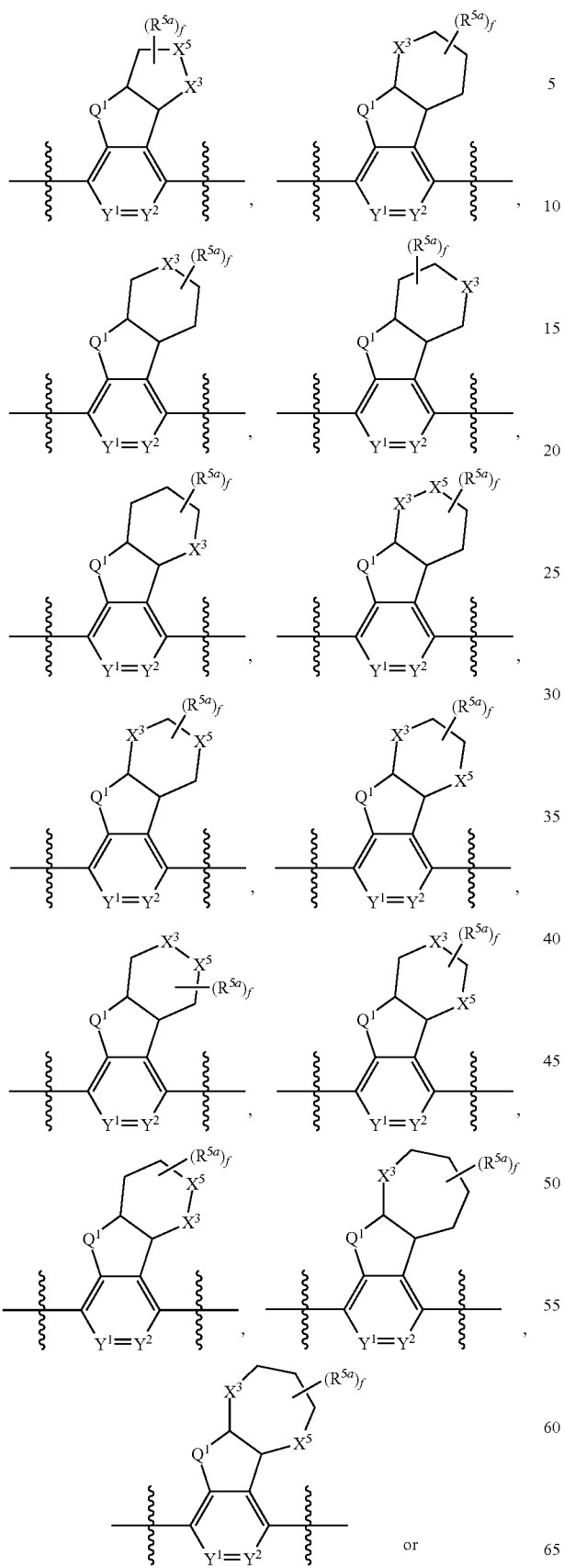

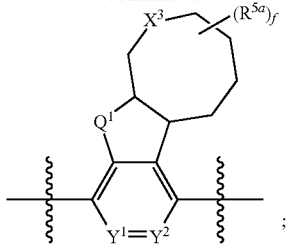

wherein each $X^3$ and $X^5$ is independently $NR^6$, O, S, C(=O) or $(CR^7R^{7a})_e$;

each $Q^1$ is independently a bond, $NR^6$, O, S, C(=O) or $(CR^7R^{7a})_e$;

each e and f is independently 0, 1, 2, 3 or 4;

each $X^1$ is independently O, S, $NR^6$, C(=O) or $CR^7R^{7a}$;

each $Y^1$ and $Y^2$ is independently N or $CR^7$;

each of A and A' is independently a bond, $C_{1-6}$ alkylene, $C_{2-6}$ alkenylene, $C_{3-8}$ cycloalkylene, $C_{2-10}$ heterocycloalkylene, $-(CR^8R^{8a})_n-O-(CR^8R^{8a})_p-$, $-(CR^8R^{8a})_n-N(R^5)-(CR^8R^{8a})_p-$, $-(CR^8R^{8a})_n-S(=O)_r-N(R^5)-(CR^8R^{8a})_p-$, $-(CR^8R^{8a})_n-C(=O)-N(R^5)-(CR^8R^{8a})_p-$, $-(CR^8R^{8a})_n-N(R^5)-C(=)-N(R^5)-(CR^8R^{8a})_p-$, $-(CR^8R^{8a})_n-C(=O)-O-(CR^8R^{8a})_p-$, $-(CR^8R^{8a})_n-N(R^5)-S(=O)_r-N(R^5)-(CR^8R^{8a})_p-$, $-(CR^8R^{8a})_n-S(=O)_r-(CR^8R^{8a})_p-$, $-(CR^8R^{8a})_n-S(=O)_r-O-(CR^8R^{8a})_p-$, $-(CR^8R^{8a})_n-C(=O)-(CR^8R^{8a})_p-$, $-(CR^8R^{8a})_n-C(=S)-(CR^8R^{8a})_p-$, $-(CR^8R^{8a})_n-N(R^5)-C(=O)-O-(CR^8R^{8a})_p-$, or each of A and A' is independently

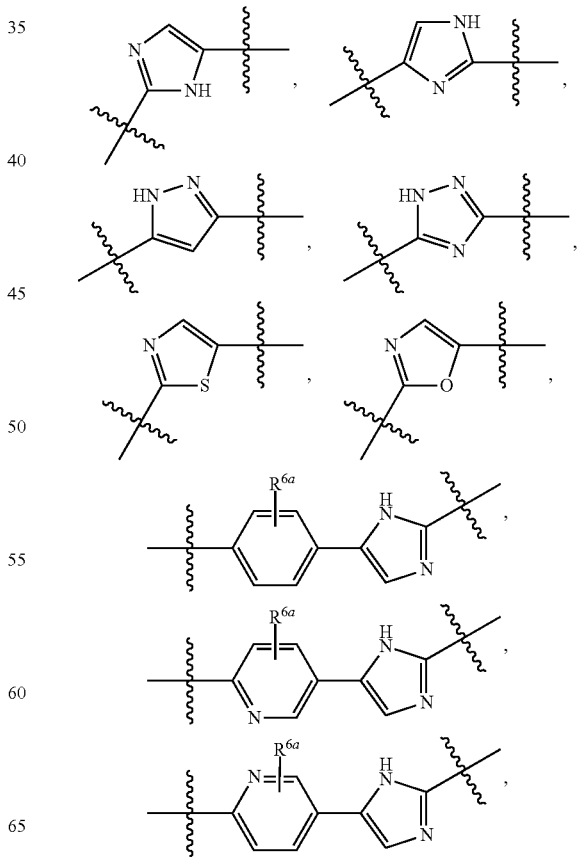

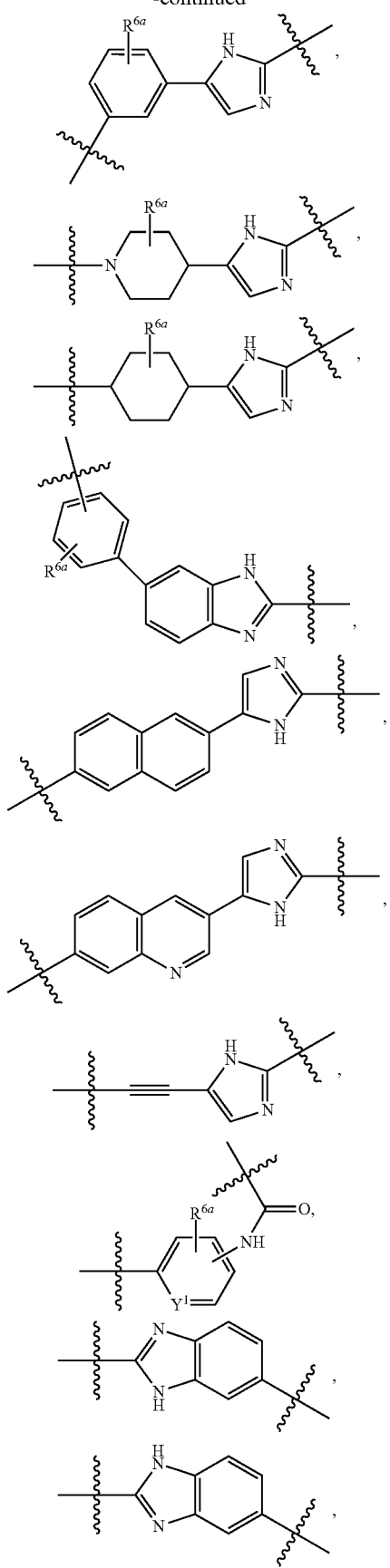
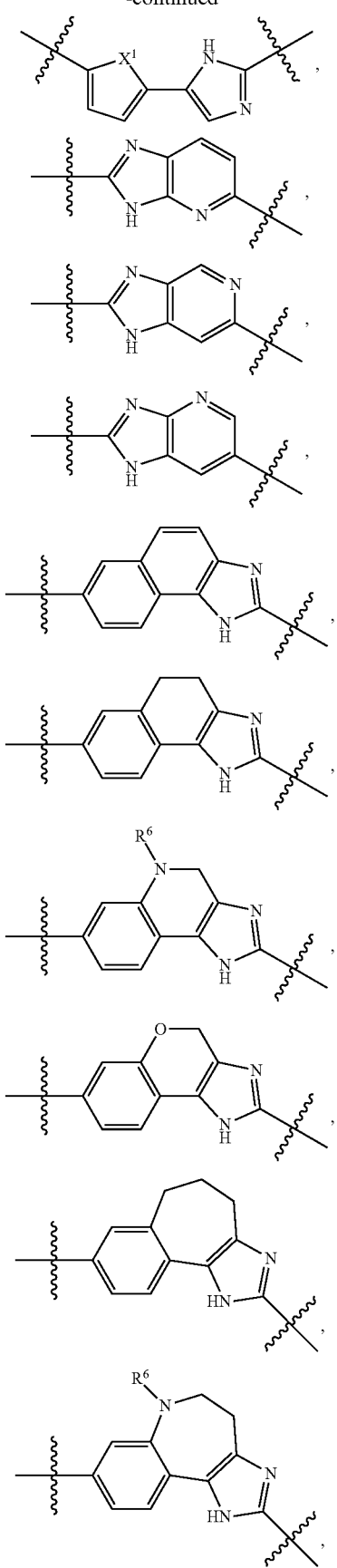

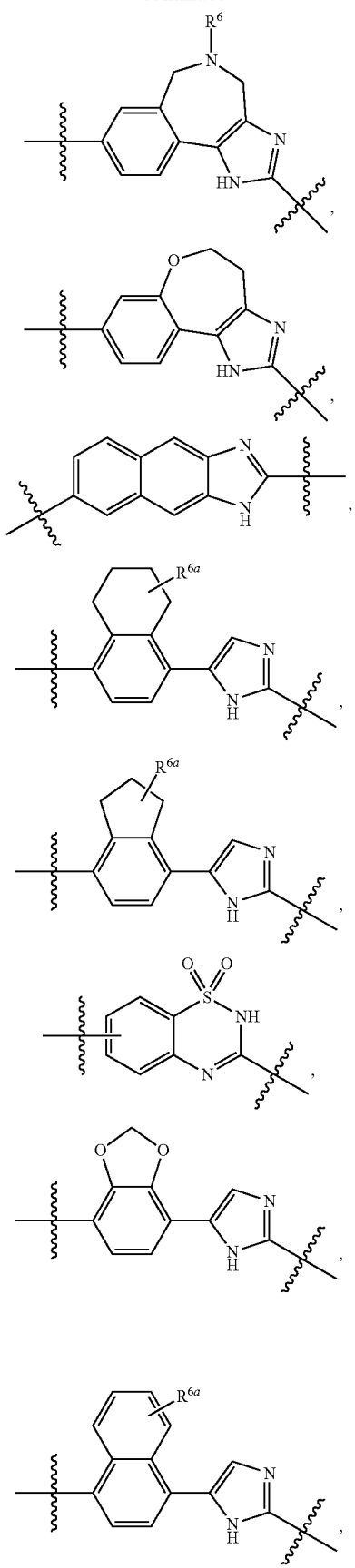

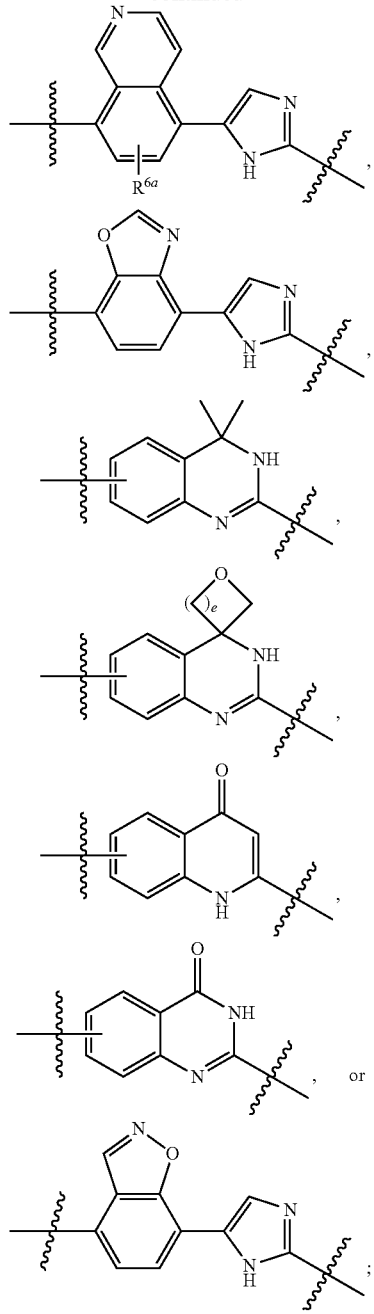

each R⁵ is independently H, deuterium, hydroxy, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;

each $R^{5a}$ and $R^{6a}$ is independently H, deuterium, oxo (=O), hydroxy, amino, F, Cl, Br, I, cyano, $R^{13a}R^{13}N$—, —C(=O)NR¹³R¹³ᵃ, —OC(=O)NR¹³R¹³ᵃ, —OC(=O)OR¹³, —N(R¹³)C(=O)NR¹³R¹³ᵃ, —N(R¹³)C(=O)OR¹³ᵃ, —N(R¹³)C(=O)—R¹³ᵃ, R¹³R¹³ᵃN—S(=O)₂—, R¹³S(=O)₂—, R¹³S(=O)₂N(R¹³ᵃ)—, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$alkylsulfinyloxy, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy;

each $R^6$ is independently H, deuterium, $R^{13}R^{13a}NC(=O)-$, $R^{13}OC(O)-$, $R^{13}C(O)-$, $R^{13}R^{13a}NS(=O)-$, $R^{13}OS(=O)-$, $R^{13}S(=O)-$ $R^{13}R^{13a}NS(=O)_2-$, $R^{13}OS(=O)_2-$, $R^{13}S(=O)_2-$, $C_{1-6}$ aliphatic, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl, or $C_{3-10}$ carbocyclyl; wherein said aliphatic is alkyl; some no-limiting examples of the alkyl group include methyl, ethyl, propyl, i-propyl, butyl and i-butyl;

each $R^7$ and $R^{7a}$ is independently H, deuterium, F, Cl, Br, I, $C_{1-6}$ aliphatic, $C_{2-6}$ heteroalkyl, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; wherein said aliphatic is alkyl; some no-limiting examples of the alkyl group include methyl, ethyl, propyl, i-propyl, butyl and i-butyl;

each $R^8$ and $R^{8a}$ is independently H, deuterium, hydroxy, cyano, nitro, F, Cl, Br, I, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;

each $R^{13}$ and $R^{13a}$ is independently H, deuterium, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; with the proviso that where $R^{13}$ and $R^{13a}$ are bonded to the same nitrogen atom, $R^{13}$ and $R^{13a}$, together with the nitrogen atom they are attached to, optionally form a substituted or unsubstituted 3-8 membered ring, or a substituted or unsubstituted spiro bicyclic ring or fused bicyclic ring;

each n and p is independently 0, 1, 2 or 3;

each r is independently 0, 1 or 2; and each of $Y^4$ and $Y^{4'}$ is independently a bond, O, S, —$(CH_2)_n$—, —CH=CH—, —S(=O)$_r$—, —$CH_2$O—, —$CH_2$S—, —$CH_2$S(=O)$_r$, —$CF_2$—, —$CHR^{5a}$, —$CR^{5a}R^{6a}$ or —$CH_2N(R^6)$—.

In some embodiments, the compound may have formula (II'):

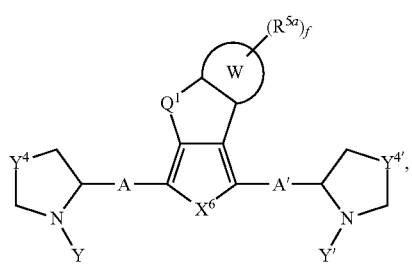

(II')

wherein

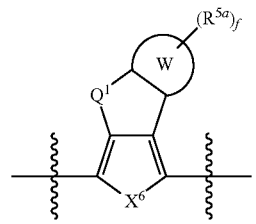

is

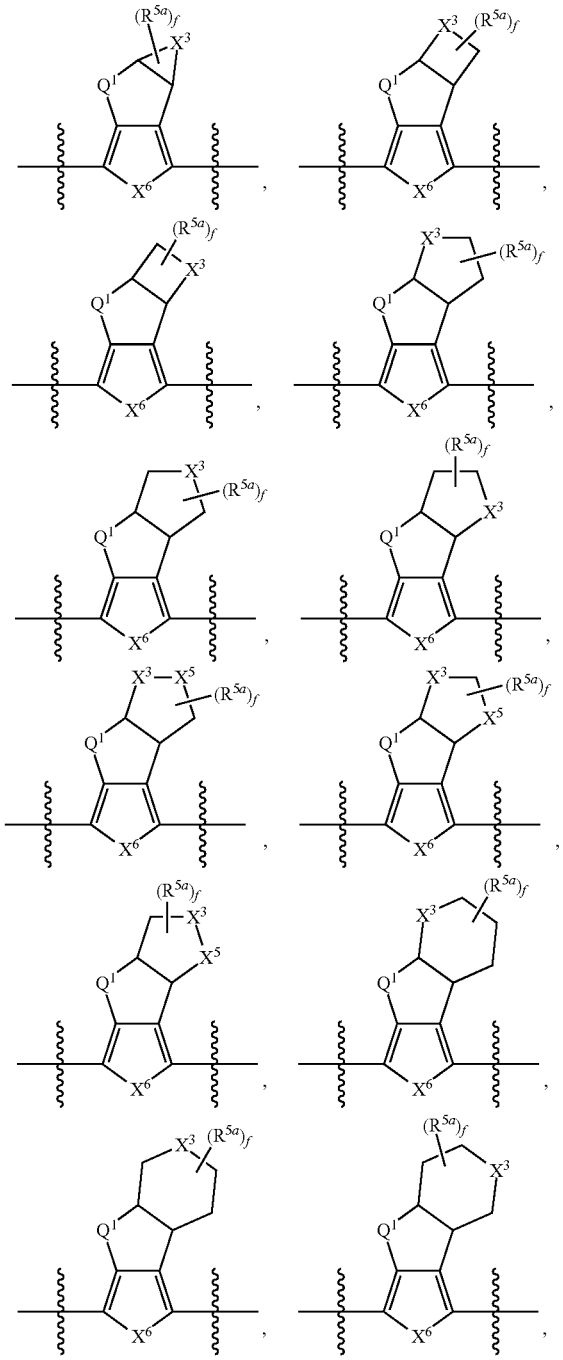

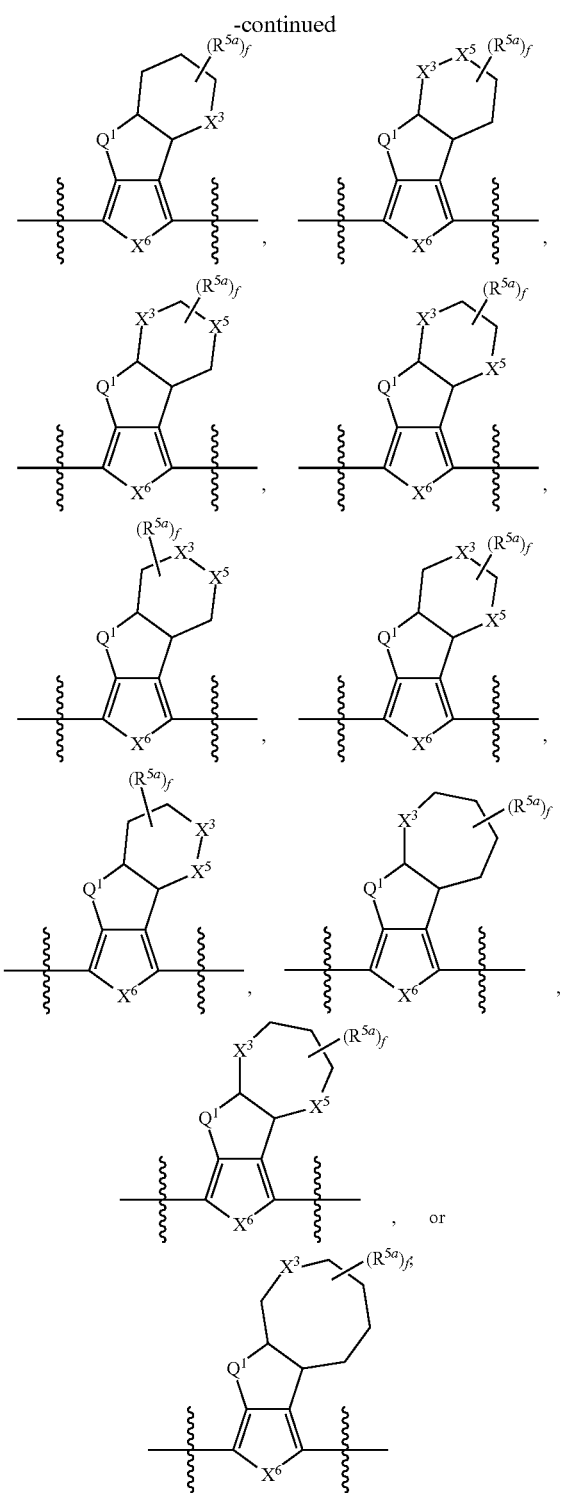

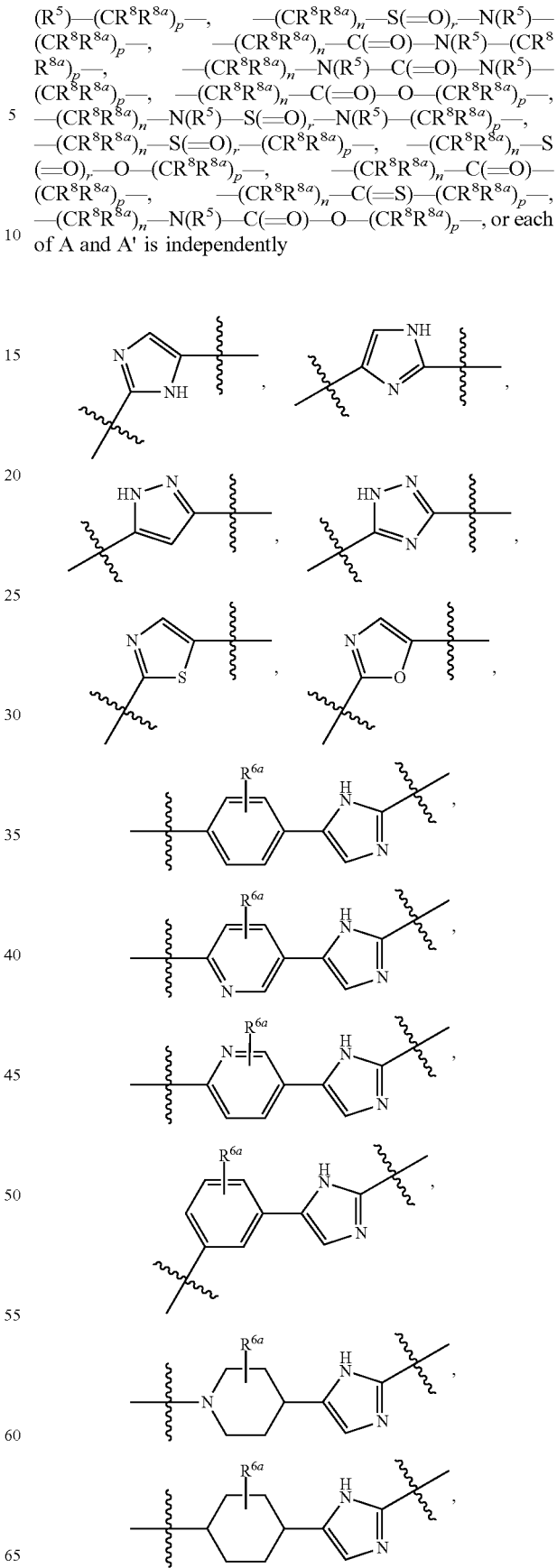

$-(R^5)-(CR^8R^{8a})_p-$, $-(CR^8R^{8a})_n-S(=O)_r-N(R^5)-(CR^8R^{8a})_p-$, $-(CR^8R^{8a})_n-C(=O)-N(R^5)-(CR^8R^{8a})_p-$, $-(CR^8R^{8a})_n-N(R^5)-C(=O)-N(R^5)-(CR^8R^{8a})_p-$, $-(CR^8R^{8a})_n-C(=O)-O-(CR^8R^{8a})_p-$, $-(CR^8R^{8a})_n-N(R^5)-S(=O)_r-N(R^5)-(CR^8R^{8a})_p-$, $-(CR^8R^{8a})_n-S(=O)_r-(CR^8R^{8a})_p-$, $-(CR^8R^{8a})_n-S(=O)_r-O-(CR^8R^{8a})_p-$, $-(CR^8R^{8a})_n-C(=O)-(CR^8R^{8a})_p-$, $-(CR^8R^{8a})_n-C(=S)-(CR^8R^{8a})_p-$, $-(CR^8R^{8a})_n-N(R^5)-C(=O)-O-(CR^8R^{8a})_p-$, or each of A and A' is independently wherein each $X^3$ and $X^5$ is independently $NR^6$, O, S, C(=O) or $(CR^7R^{7a})_e$;

each $Q^1$ is independently a bond, $NR^6$, O, S, C(=O) or $(CR^7R^{7a})_e$;

each e and f is independently 0, 1, 2, 3 or 4;

each $X^6$ is independently $CR^7R^{7a}$, O, S or $NR^6$;

each of A and A' is independently a bond, $C_{1-6}$ alkylene, $C_{2-6}$ alkenylene, $C_{3-8}$ cycloalkylene, $C_{2-10}$ heterocycloalkylene, $-(CR^8R^{8a})_n-O-(CR^8R^{8a})_p-$, $-(CR^8R^{8a})_n-N$

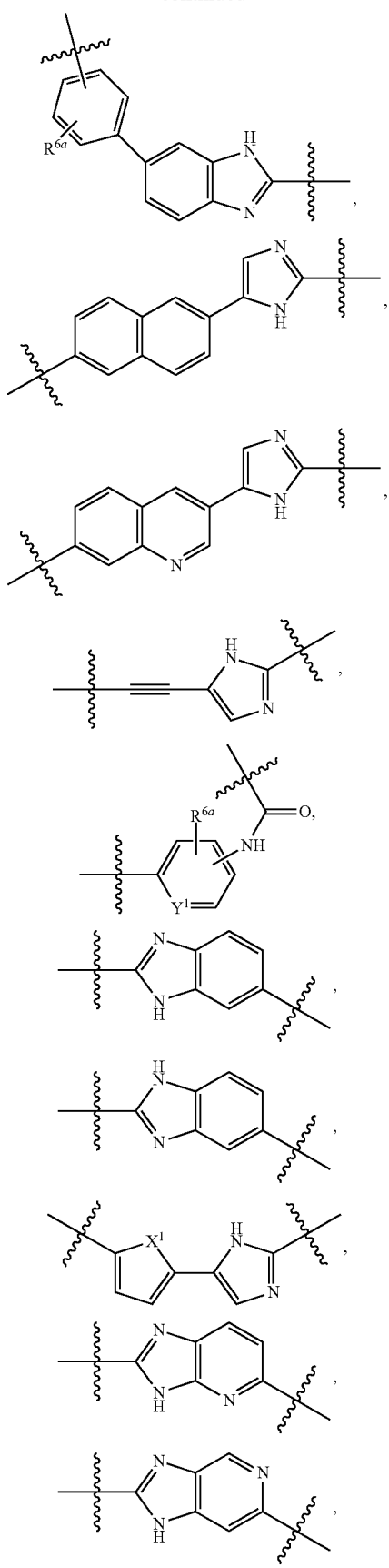
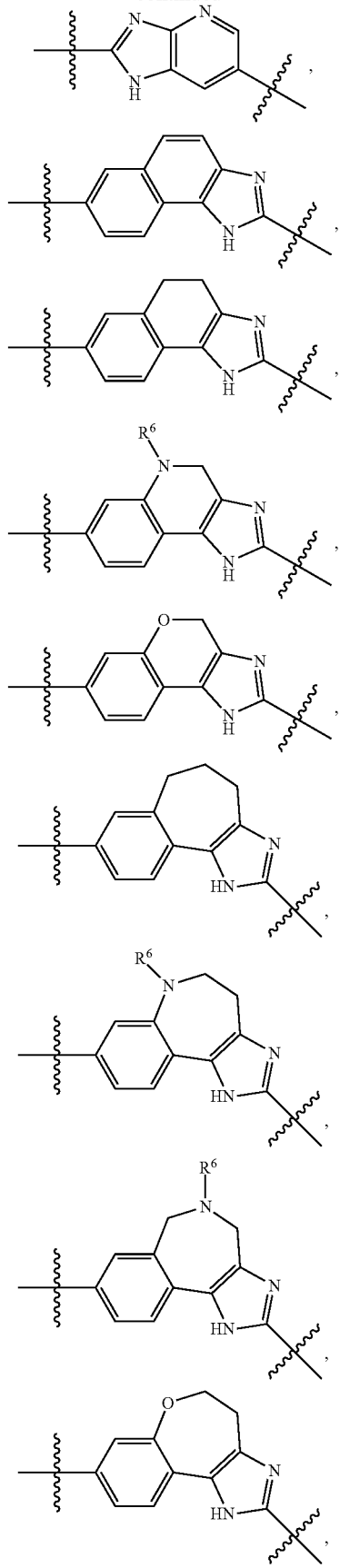

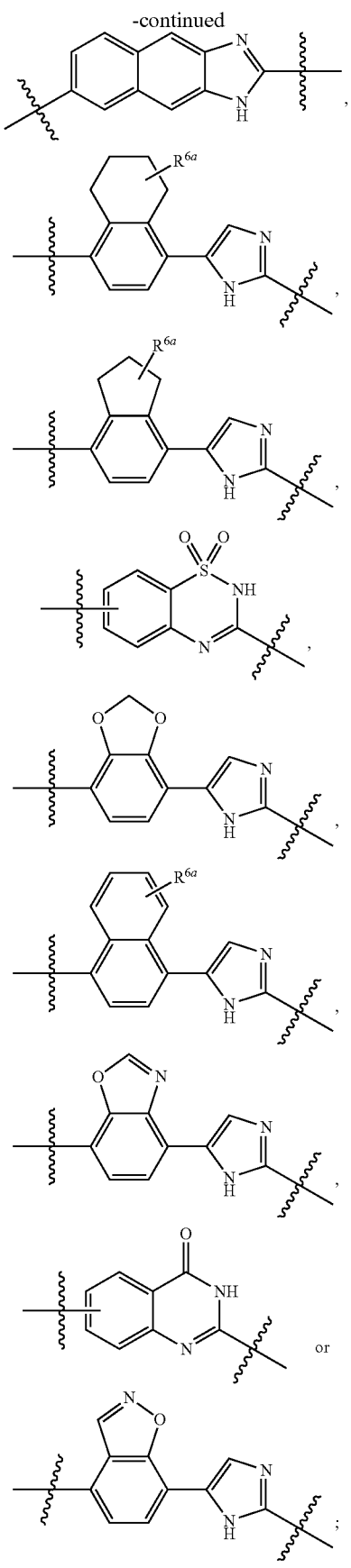

wherein each $X^1$ is independently O, S, $NR^6$, C(=O) or $CR^7CR^{7a}$;

each $Y^1$ is independently N or $CR^7$;

each $R^5$ is independently H, deuterium, hydroxy, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S (=O)$_r$— or aminosulfonyl;

each $R^{5a}$ and $R^{6a}$ is independently H, deuterium, oxo (=O), hydroxy, amino, $R^{13a}R^{13}N$—, —C(=O)$NR^{13}R^{13a}$, —OC(=O)$NR^{13}R^{13a}$, —OC(=O)$OR^{13}$, —N($R^{13}$)C(=O) $NR^{13}R^{13a}$, —N($R^{13}$)C(=O)$OR^{13a}$, —N($R^{13}$C(=O)—$R^{13a}$, $R^{13}R^{13a}N$—S(=O)$_2$—, $R^{13}S$(=O)$_2$—, $R^{13}S$(=O)$_2$N ($R^{13a}$)—, F, Cl, Br, I, cyano, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy;

each $R^6$ is independently H, deuterium, $R^{13}R^{13a}NC$ (=O)—, $R^{13}OC$(=O)—, $R^{13}C$(=O)—, $R^{13}R^{13a}NS$ (=O)—, $R^{13}OS$(=O)—, $R^{13}S$(=O)—, $R^{13}R^{13a}NS$ (=O)$_2$—, $R^{13}OS$(=O)$_2$—, $R^{13}S$(=O)$_2$—, $C_{1-6}$ aliphatic, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; wherein said aliphatic is alkyl; some no-limiting examples of the alkyl group include methyl, ethyl, propyl, i-propyl, butyl and i-butyl;

each $R^7$ and $R^{7a}$ is independently H, deuterium, F, Cl, Br, I, $C_{1-6}$ aliphatic, $C_{2-6}$ heteroalkyl, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; wherein said aliphatic is alkyl; some no-limiting examples of the alkyl group include methyl, ethyl, propyl, i-propyl, butyl and i-butyl;

each $R^8$ and $R^{8a}$ is independently H, deuterium, hydroxy, cyano, nitro, F, Cl, Br, I, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;

each $R^{13}$ and $R^{13a}$ is independently H, deuterium, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; with the proviso that where $R^{13}$ and $R^{13a}$ are bonded to the same nitrogen atom, $R^{13}$ and $R^{3a}$, together with the nitrogen atom they are attached to, optionally form a substituted or unsubstituted 3-8 membered ring, spiro bicyclic ring or fused bicyclic ring;

each n and p is independently 0, 1, 2 or 3;

each r is independently 0, 1 or 2; and each of $Y^4$ and $Y^{4'}$ is independently a bond, O, S, —(CH$_2$)$_n$—, —CH=CH—, —S(=O)$_r$—, —CH$_2$O—, —CH$_2$S—, —CH$_2$S(=O)$_r$, —CF$_2$—, —CHR$^{5a}$, —CR$^{5a}$R$^{6a}$— or —CH$_2$N(R$^6$)—.

In other embodiments, the compound may have formula (III):

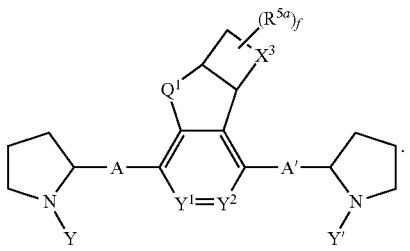

(III)

In other embodiments, the compound may have formula (IV):

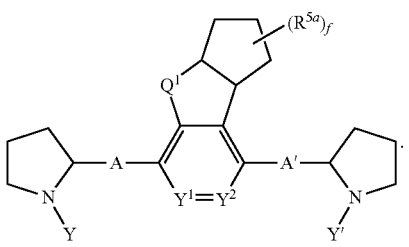

(IV)

In other embodiments, the compound may have formula (III):

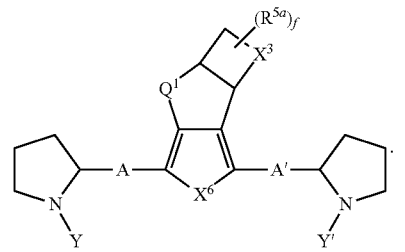

(III')

In other embodiments, the compound may have formula (IV):

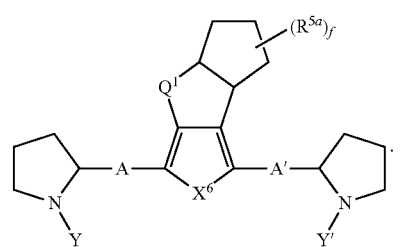

(IV')

In some embodiments, each of Y and Y' is independently a monovalent group derived from an α-amino acid.

In other embodiments, the α-amino acid is isoleucine, leucine, lysine, methionine, phenylalanine, threonine, tryptophane, valine, alanine, asparagine, aspartic acid, glutamic acid, glutamine, proline, serine, p-tyrosine, arginine, histidine, cysteine, glycine, sarcosine, N,N-dimethylglycine, homoserine, norvaline, norleucine, ornithine, homocysteine, homophenylalanine, phenylglycine, o-tyrosine, m-tyrosine or hydroxyproline.

In other embodiments, the α-amino acid is in the D configuration.

In other embodiments, the α-amino acid is in the L configuration.

In some embodiments, each of Y and Y' is independently $-[U-(CR^9R^{9a})_t-NR^{10}-(CR^9R^{9a})_t]_k-U-(CR^9R^{9a})_t-NR^{11}-(CR^9R^{9a})_t-R^{12}$, $-U-(CR^9R^{9a})_t-R^{12}$ or $-[U-(CR^9R^{9a})_t-NR^{10}-(CR^9R^{9a})_t]_k-U-(CR^9R^{9a})_t-O-(CR^9R^{9a})_t-R^{12}$.

In other embodiments, each of Y and Y' is independently $-[U-(CR^9R^{9a})_t-NR^{11}-(CR^9R^{9a})_t]_k-U-(CR^9R^{9a})_t-NR^{11}-(CR^9R^{9a})_t-R^{12}$.

In other embodiments, each of Y and Y' is independently $-U-(CR^9R^{9a})_t-NR^{10}-(CR^9R^{9a})_t-U-(CR^9R^{9a})_t-NR^{11}-(CR^9R^{9a})_t-R^{12}$.

In other embodiments, wherein each of Y and Y' is independently $-U-(CR^9R^{9a})_t-NR^{11}-(CR^9R^{9a})_t-R^{12}$.

In other embodiments, wherein each of Y and Y' is independently $-[C(=O)-(CR^9R^{9a})_t-NR^{10}-(CR^9R^{9a})_t]_k-U-(CR^9R^{9a})_t-NR^{11}-(CR^9R^{9a})_t-R^{12}$.

In other embodiments, each of Y and Y' is independently $-C(=O)-(CR^9R^{9a})_t-NR^{10}-(CR^9R^{9a})_t-U-(CR^9R^{9a})_t-NR^{11}-(CR^9R^{9a})_t-R^{12}$.

In other embodiments, each of Y and Y' is independently $-[C(=O)-(CR^9R^{9a})_t-NR^{10}-(CR^9R^{9a})_t]_k-C(=O)-(CR^9R^{9a})_t-NR^{11}-(CR^9R^{9a})_t-R^{12}$.

In other embodiments, each of Y and Y' is independently $-C(=O)-(CR^9R^{9a})_t-NR^{10}-(CR^9R^{9a})_t-C(=O)-(CR^9R^{9a})_t-NR^{11}-(CR^9R^{9a})_t-R^{12}$.

In other embodiments, each of Y and Y' is independently $-C(=O)-(CR^9R^{9a})_t-NR^{11}-(CR^9R^{9a})_t-R^{12}$.

In other embodiments, each of Y and Y' is independently $-C(=O)-(CR^9R^{9a})_t-NR^{11}-(CR^9R^{9a})_t-C(=O)-R^{13}$.

In other embodiments, each of Y and Y' is independently $-C(=O)-(CR^9R^{9a})_t-NR^{11}-C(=O)-R^{13}$.

In other embodiments, each of Y and Y' is independently $-C(=O)-(CR^9R^{9a})_t-NR^{11}-(CR^9R^{9a})_t-C(=O)-O-R^{13}$.

In other embodiments, each of Y and Y' is independently $-C(=O)-(CR^9R^{9a})_t-NR^{11}-C(=O)-O-R^{13}$.

In other embodiments, each of Y and Y' is independently $-U-(CR^9R^{9a})_t-R^{12}$.

In other embodiments, wherein each of Y and Y' is independently $-C(=O)-(CR^9R^{9a})_t-R^{12}$.

In other embodiments, each of Y and Y' is independently $-[U-(CR^9R^{9a})_t-NR^{10}-(CR^9R^{9a})_t]_k-U-(CR^9R^{9a})_t-O-(CR^9R^{9a})_t-R^{12}$.

In other embodiments, each of Y and Y' is independently $-U-(CR^9R^{9a})_t-NR^{10}-(CR^9R^{9a})_t-U-(CR^9R^{9a})_t-O-(CR^9R^{9a})_t-R^{12}$.

In other embodiments, each of Y and Y' is independently $-C(=O)-(CR^9R^{9a})_t-NR^{10}-(CR^9R^{9a})_t-C(=O)-(CR^9R^{9a})_t-O-(CR^9R^{9a})_t-R^{12}$.

In other embodiments, each of Y and Y' is independently $-U-(CR^9R^{9a})_t-O-(CR^9R^{9a})_t-R^{12}$.

In other embodiments, each of Y and Y' is independently $-C(=O)-(CR^9R^{9a})_t-O-(CR^9R^{9a})_t-R^{12}$.

In other embodiments, each of Y and Y' is independently $-C(=O)-(CR^9R^{9a})_t-NR^{11}-R^{12}$, wherein $R^{11}$ and $R^{12}$, together with the atom they are attached to, form a 4-7 membered ring.

In other embodiments, each $R^9$, $R^{9a}$, $R^{10}$ and $R^{11}$ is independently H, deuterium, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, $C_{1-6}$ haloalkyl, $C_{1-6}$ hydroxyalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, or $C_{3-8}$ cycloalkyl-$C_{1-6}$-alkyl;

each $R^{12}$ is independently $R^{13a}R^{13}N-$, $-C(=O)R^{13}$, $-C(=S)R^{13}$, $-C(=O)-O-R^{13}$, $-C(=O)NR^{13}R^{13a}$, $-OC(=O)NR^{13}R^{13a}$, $-OC(=O)OR^{13}$, $-N(R^{13})C(=O)NR^{13}R^{13a}$, $-N(R^{13})C(=O)OR^{13a}$, $-N(R^{13})C(=O)R^{13a}$, $R^{13}R^{13a}N-S(=O)_2-$, $R^{13}S(=O)_2-$, $R^{13}S(=O)_2N(R^{13a})-$, $R^{13}OS(=O)_2-$, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; or $R^{11}$ and $R^{12}$, together with the atom they are attached to, form a 4-7 membered ring; and each $R^{13}$ and $R^{13a}$ is independently H, deuterium, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; with the proviso that where $R^{13}$ and $R^{13a}$ are bonded to the same nitrogen atom, $R^{13}$ and $R^{13a}$, together with the nitrogen atom they are attached to, optionally form a substituted or unsubstituted 3-8 membered ring, or a substituted or unsubstituted spiro bicyclic ring or fused bicyclic ring.

In other embodiments, each $R^9$, $R^{9a}$, $R^{10}$ and $R^{11}$ is independently H, deuterium, methyl, ethyl, isopropyl, cyclohexyl, isobutyl or phenyl;

each $R^{12}$ is independently $-C(=O)R^{13}$, $-C(=O)-O-R^{13}$, $-C(=O)NR^{13}R^{13a}$, methyl, ethyl, propyl, phenyl, cyclohexyl, morpholinyl or piperidinyl; or $R^{11}$ and $R^{12}$, together with the atom they are attached to, form a 4-7 membered ring; and each $R^{13}$ and $R^{13a}$ is independently H, deuterium, methyl, ethyl, propyl, phenyl, cyclohexyl, morpholinyl or piperidinyl.

In other embodiments, the compound may have formula (V):

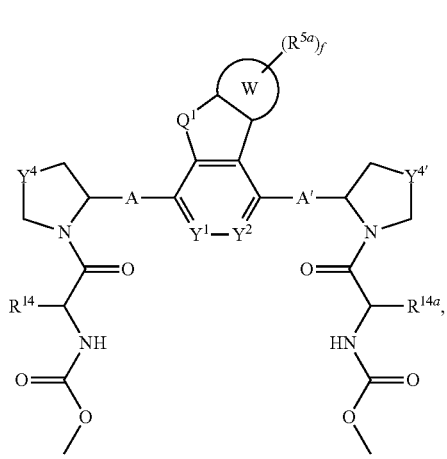

(V)

wherein each of $R^{14}$ and $R^{14a}$ is independently H, deuterium, $C_{1-6}$ alkyl, $C_{1-6}$ haloalkyl, $C_{1-6}$ hydroxyalkyl, $C_{2-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, or $C_{3-8}$ cycloalkyl-$C_{1-6}$-alkyl; wherein each of $C_{1-6}$ alkyl, $C_{1-6}$ haloalkyl, $C_{1-6}$ hydroxyalkyl, $C_{2-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl and $C_{3-8}$ cycloalkyl-$C_{1-6}$-alkyl is optionally substituted with one or more substituents, and wherein the substituent is deuterium, F, Cl, Br, hydroxy or cyano.

In other embodiments, the compound may have formula (VI):

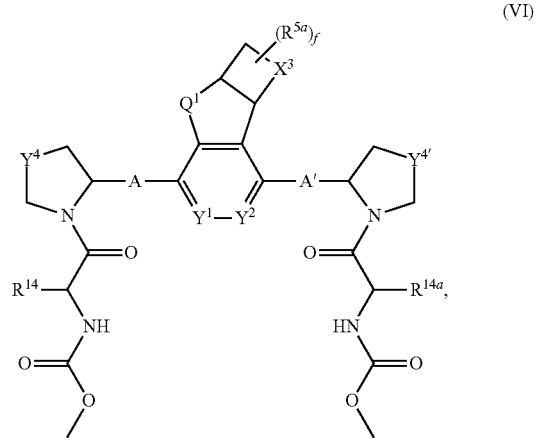

(VI)

wherein each of $R^{14}$ and $R^{14a}$ is independently H, deuterium, $C_{1-3}$ hydroxyalkyl, methyl, ethyl, isopropyl, isobutyl, tert-butyl, allyl, propargyl, trifluoroethyl, phenyl, pyranyl, morpholinyl, benzyl, piperazinyl, cyclopentyl, cyclopropyl, cyclohexyl, or $C_{1-9}$ heteroaryl; wherein each of $C_{1-3}$ hydroxyalkyl, methyl, ethyl, isopropyl, isobutyl, tert-butyl, allyl, propargyl, trifluoroethyl, phenyl, pyranyl, morpholinyl, benzyl, piperazinyl, cyclopentyl, cyclopropyl, cyclohexyl and $C_{1-9}$ heteroaryl is optionally substituted with one or more substituents, and wherein the substituent is deuterium, F, Cl, Br, hydroxy or cyano.

In other embodiments, the compound may have formula (VII):

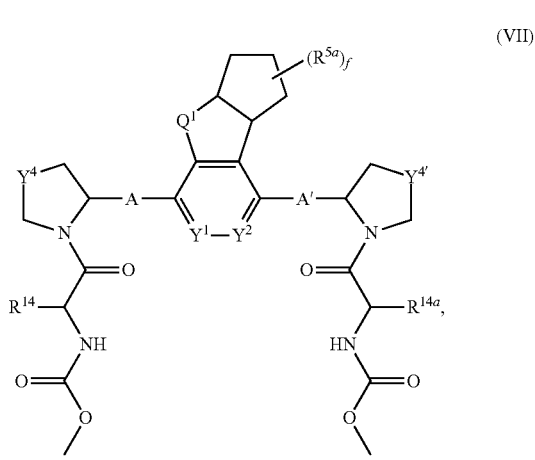

(VII)

wherein each of $R^{14}$ and $R^{14a}$ is independently H, deuterium, $C_{1-3}$ hydroxyalkyl, methyl, ethyl, isopropyl, isobutyl, tert-butyl, allyl, propargyl, trifluoroethyl, phenyl, pyranyl, morpholinyl, benzyl, piperazinyl, cyclopentyl, cyclopropyl, cyclohexyl, or $C_{1-9}$ heteroaryl; wherein each of $C_{1-3}$ hydroxyalkyl, methyl, ethyl, isopropyl, isobutyl, tert-butyl, allyl, propargyl, trifluoroethyl, phenyl, pyranyl, morpholinyl, benzyl, piperazinyl, cyclopentyl, cyclopropyl, cyclohexyl and $C_{1-9}$ heteroaryl is optionally substituted with one or more substituents, and wherein the substituent is deuterium, F, Cl, Br, hydroxy or cyano.

In other embodiments, the compound may have formula (VIII):

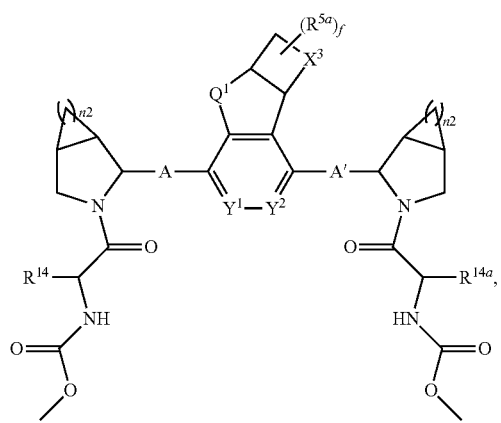

(VIII)

wherein each of $Q^1$ and $X^3$ is independently $NR^6$, O, S, C(=O) or $(CR^7R^{7a})_e$;

e is 0, 1, 2, 3 or 4;

each of $R^{14}$ and $R^{14a}$ is independently H, deuterium, $C_{1-6}$ alkyl, $C_{1-6}$ haloalkyl, $C_{1-6}$ hydroxyalkyl, $C_{2-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; wherein each of $C_{1-6}$ alkyl, $C_{1-6}$ haloalkyl, $C_{1-6}$ hydroxyalkyl, $C_{2-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl and $C_{3-8}$ cycloalkyl-$C_{1-6}$-alkyl is optionally substituted with one or more substituents, wherein the substituent is deuterium, F, Cl, Br, hydroxy or cyano; and each $n_2$ is independently 1, 2, 3 or 4.

In other embodiments, the compound may have formula (IX):

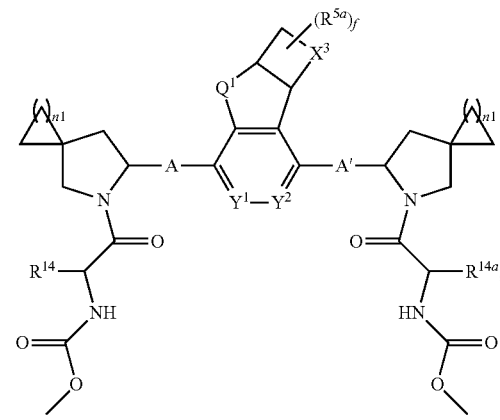

(IX)

wherein each of $Q^1$ and $X^3$ is independently $NR^6$, O, S, C(=O) or $(CR^7R^{7a})_e$;

e is 0, 1, 2, 3 or 4;

each of $R^{14}$ and $R^{14a}$ is independently H, deuterium, $C_{1-6}$ alkyl, $C_{1-6}$ haloalkyl, $C_{1-6}$ hydroxyalkyl, $C_{2-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; wherein each of $C_{1-6}$ alkyl, $C_{1-6}$ haloalkyl, $C_{1-6}$ hydroxyalkyl, $C_{2-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl and $C_{3-8}$ cycloalkyl-$C_{1-6}$-alkyl is optionally substituted with one or more substituents, wherein the substituent is deuterium, F, Cl, Br, hydroxy or cyano; and each $n_1$ is independently 1, 2, 3 or 4.

In other embodiments, the compound may have formula (X):

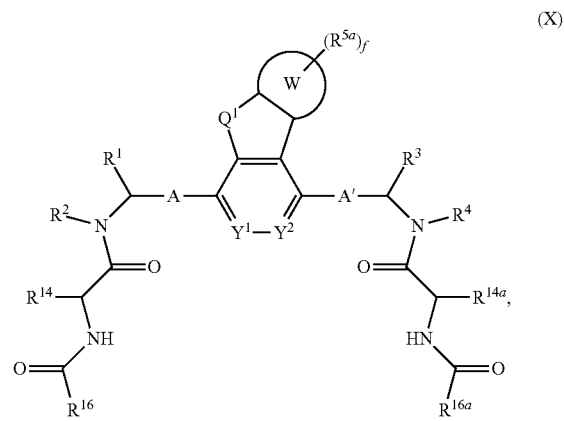

(X)

wherein each $R^{5a}$ is H, deuterium, $C_{1-4}$ alkyl, oxo(=O), benzyl, F, Cl, Br or I;

$Q^1$ is $CH_2$, C(=O), O, S, or $NR^6$;

f is 0, 1, 2 or 3;

each $R^6$ and $R^7$ is independently H, deuterium, $C_{1-4}$ alkyl, $C_{6-10}$ aryl, $C_{2-10}$ heterocyclyl or $C_{3-8}$ cycloalkyl;

each of $R^{14}$ and $R^{14a}$ is independently H, deuterium, $C_{1-4}$ alkyl, $C_{6-10}$ aryl, $C_{2-10}$ heterocyclyl or $C_{3-8}$ cycloalkyl;

each of $R^{16}$ and $R^{16a}$ is independently hydroxy, $C_{1-4}$ alkoxy, $C_{6-10}$ aryloxy, $C_{2-10}$ heterocyclyl or $C_{3-8}$ cycloalkyl;

wherein each of benzyl, $C_{1-4}$ alkyl, $C_{1-4}$ alkoxy, $C_{6-10}$ aryl, $C_{2-10}$ heterocyclyl, $C_{3-8}$ cycloalkyl and $C_{6-10}$ aryloxy is optionally substituted with one or more substituents, wherein the substituent is deuterium, F, Cl, Br, hydroxy or cyano;

wherein

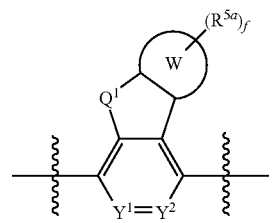

is
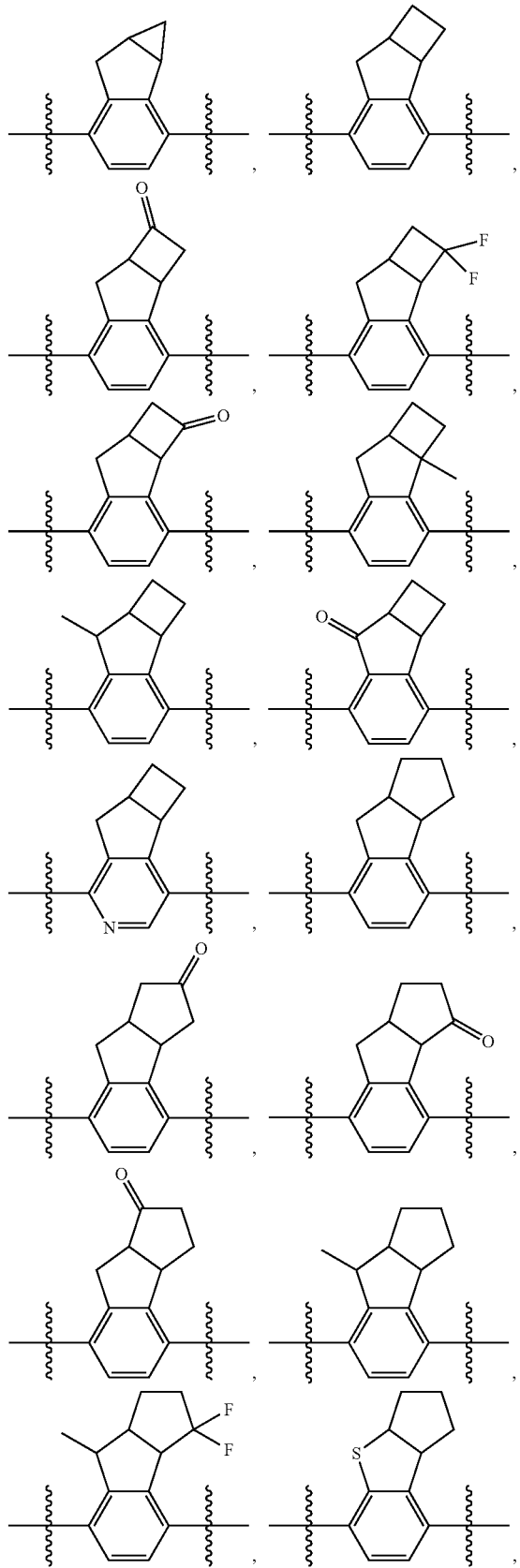
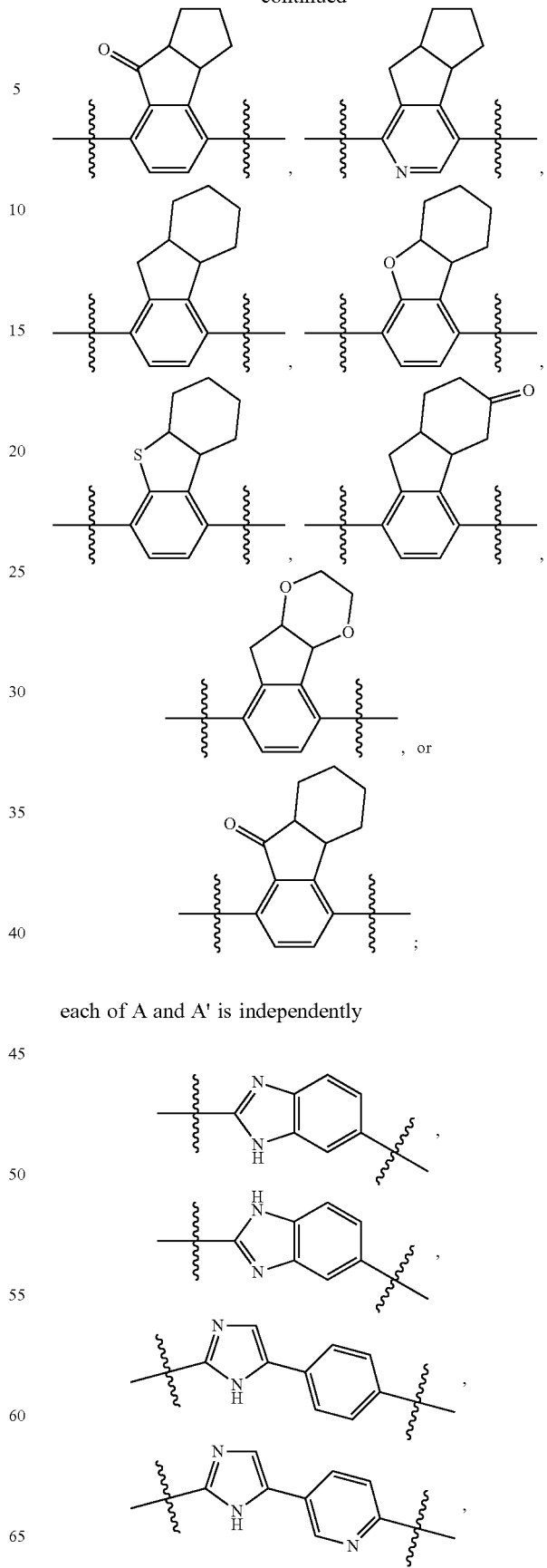
each of A and A' is independently

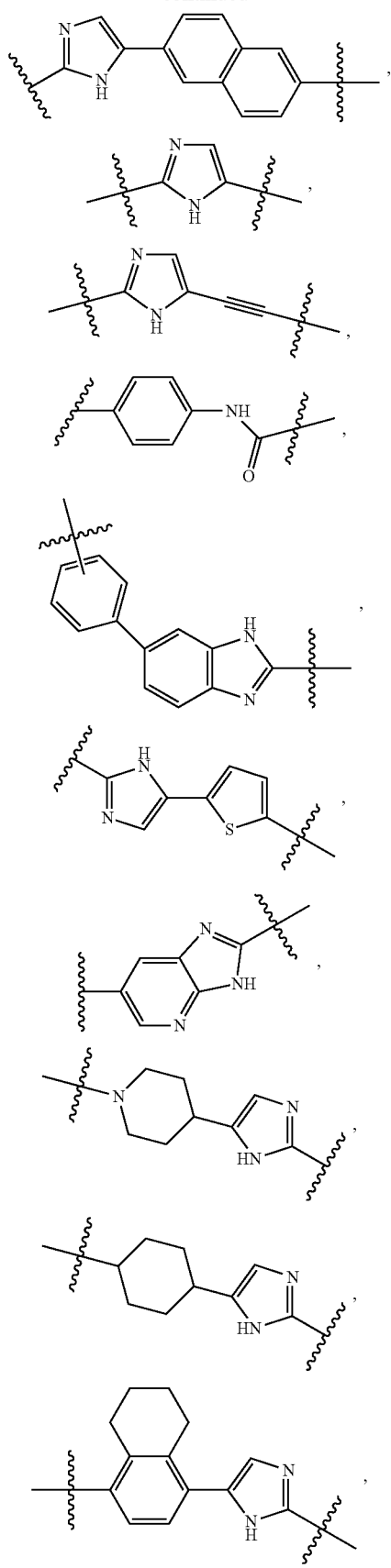
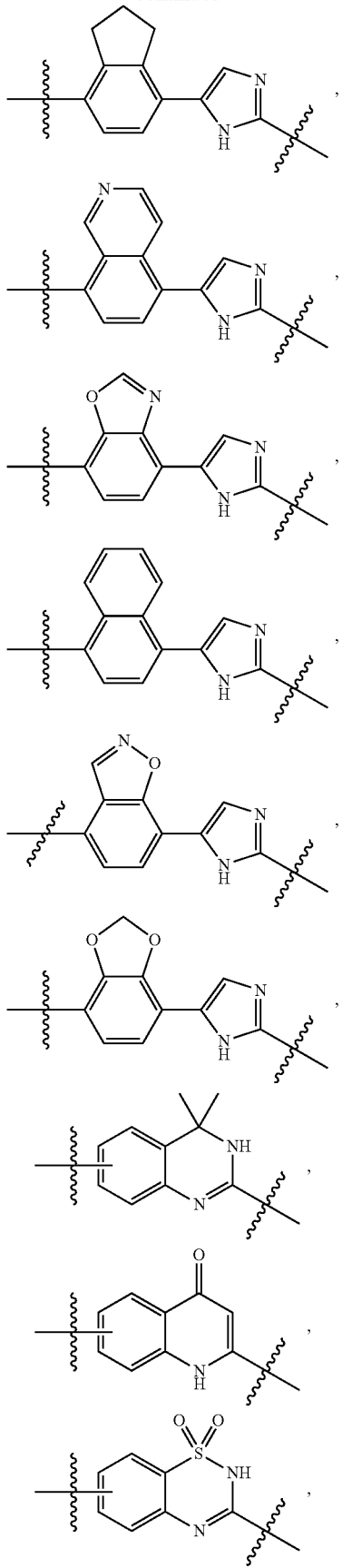

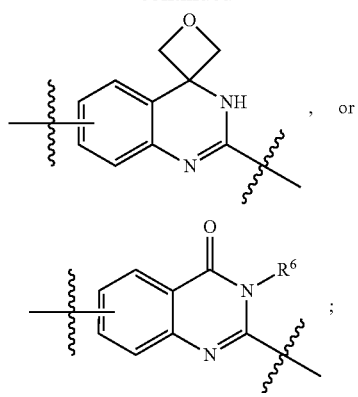

wherein R¹, R² and N—CH together form one of the following divalent groups:

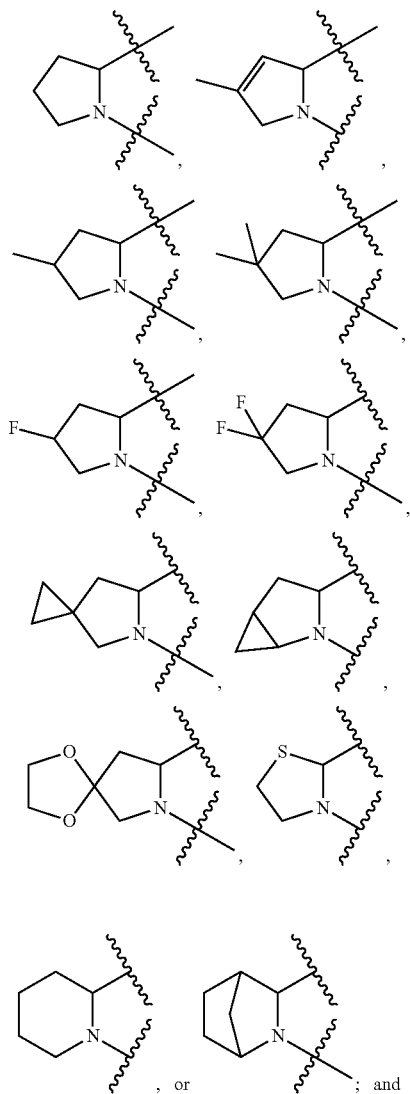

wherein R³, R⁴ and N—CH together form one of the following divalent groups:

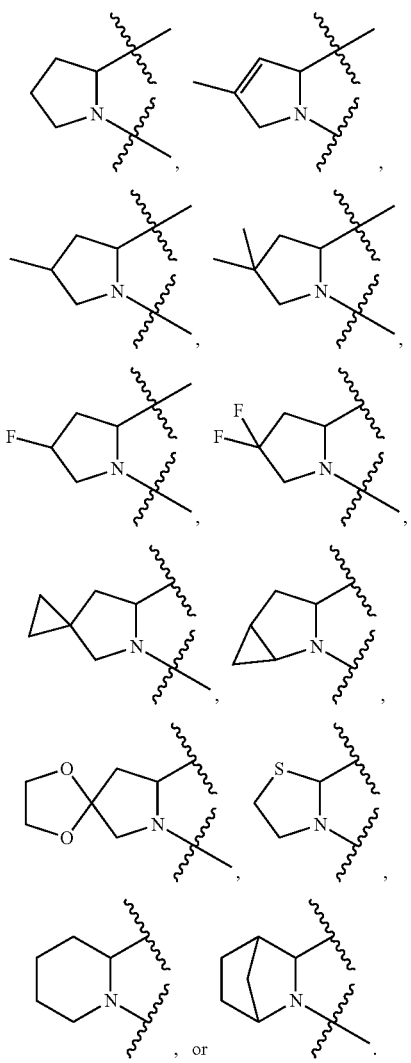

In other embodiments, each $R^{5a}$ is independently H, deuterium, methyl, ethyl, oxo(=O), benzyl, F, $C_1$, Br or I;

each $R^6$ and $R^7$ is independently H, deuterium, methyl, ethyl, isopropyl, phenyl or cyclohexyl;

each of $R^{14}$ and $R^{14a}$ is independently methyl, ethyl, phenyl, cyclohexyl, 1-methyl-propyl, isopropyl, isobutyl or tert-butyl; and each of $R^{16}$ and $R^{16a}$ is independently hydroxy, methoxyl, ethyoxyl, phenoxy,

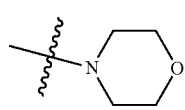 [SMILES: *N1CCOCC1]

or tert-butoxy, wherein each of methyl, ethyl, phenyl, benzyl, cyclohexyl, 1-methyl-propyl, isopropyl, isobutyl, methoxyl, ethyoxyl, tert-butoxy, phenoxy and tert-butyl is optionally substituted with one or more substituents, and wherein the substituent is deuterium, F, Cl, Br, hydroxy or cyano.

In other embodiments, the compound may have formula (XI):

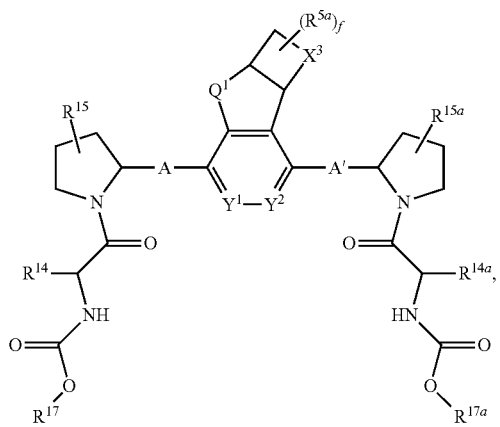

wherein, each $R^{5a}$ is H, deuterium, oxo(=O), benzyl or methyl;
each of $Q^1$ and $X^3$ is independently $(CH_2)_e$, $CF_2$, S, $NR^6$, O or C(=O);
each of f and e is independently 0, 1, 2 or 3;
each of $Y^1$ and $Y^2$ is independently N or $CR^7$;
each of $R^6$ and $R^7$ is independently H, deuterium, methyl, ethyl, isobutyl, cyclohexyl, phenyl or isopropyl;
each of $R^{14}$ and $R^{14a}$ is independently methyl, ethyl, isobutyl, cyclohexyl, phenyl, isobutyl or isopropyl;
each of $R^{15}$ and $R^{15a}$ is independently H, deuterium, F, Cl, Br, methyl, ethyl, isopropyl or tert-butyl; and
each of $R^{17}$ and $R^{17a}$ is independently methyl, phenyl or ethyl,
wherein each of methyl, ethyl, phenyl, benzyl, cyclohexyl, isopropyl, isobutyl or tert-butyl is optionally substituted with one or more substituents, and wherein the substituent is deuterium, F, Cl, Br, hydroxy or cyano.

In other embodiments, the compound may have formula formula (XI'):

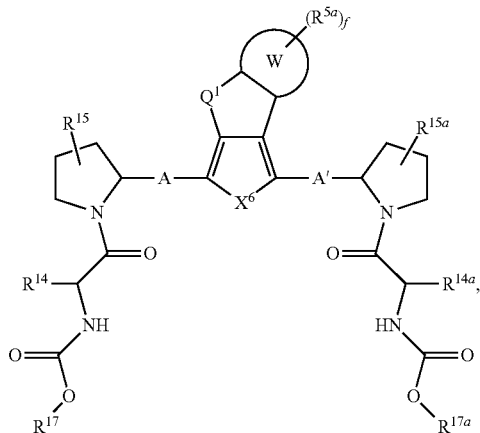

wherein each $R^{5a}$ is H, deuterium, oxo(=O), benzyl, or methyl;
$Q^1$ is $(CH_2)_e$, $CF_2$, S, $NR^6$, O or C(=O);
each of f and e is independently 0, 1, 2 or 3;

each $R^6$ and $R^{6a}$ is independently H, deuterium, methyl, ethyl, isobutyl, cyclohexyl, phenyl or isopropyl;
each of $R^{14}$ and $R^{14a}$ is independently methyl, ethyl, isobutyl, cyclohexyl, phenyl or isopropyl;
each of $R^{15}$ and $R^{15a}$ is independently H, deuterium, F, Cl, Br, methyl, ethyl, isopropyl or tert-butyl; and
each of $R^{17}$ and $R^{17a}$ is independently methyl, phenyl or ethyl,
wherein each of methyl, ethyl, phenyl, benzyl, cyclohexyl, isopropyl, isobutyl or tert-butyl is optionally substituted with one or more substituents, and wherein the substituent is deuterium, F, Cl, Br, hydroxy or cyano;
wherein

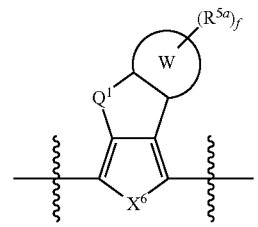

is

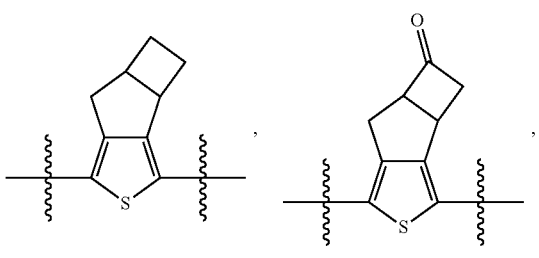

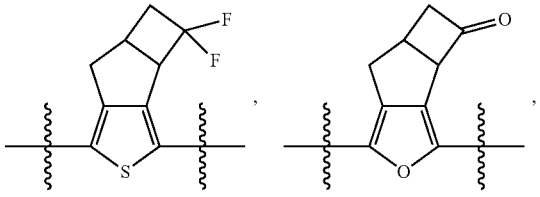

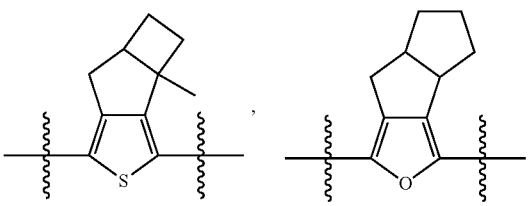

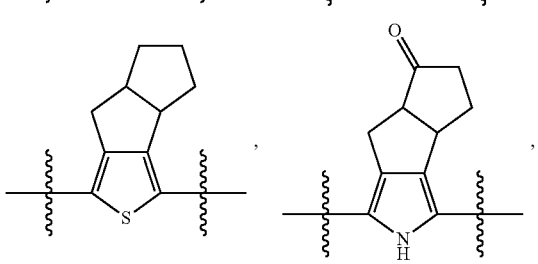

-continued
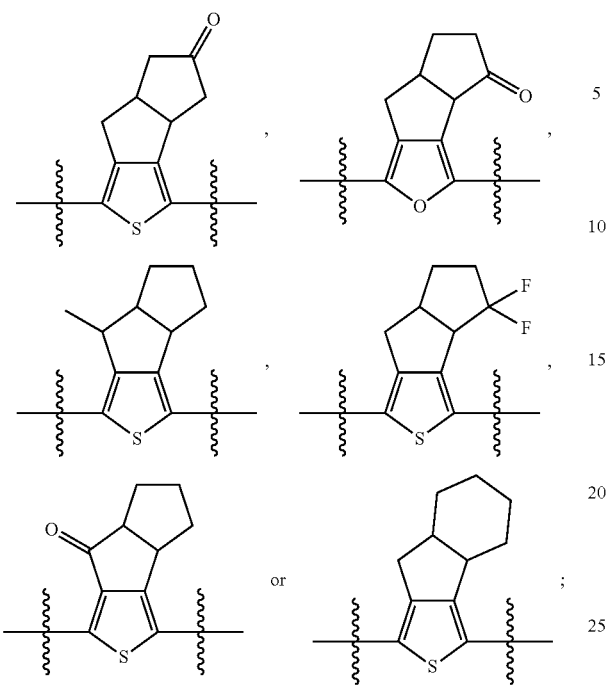
and
each of A and A' is independently
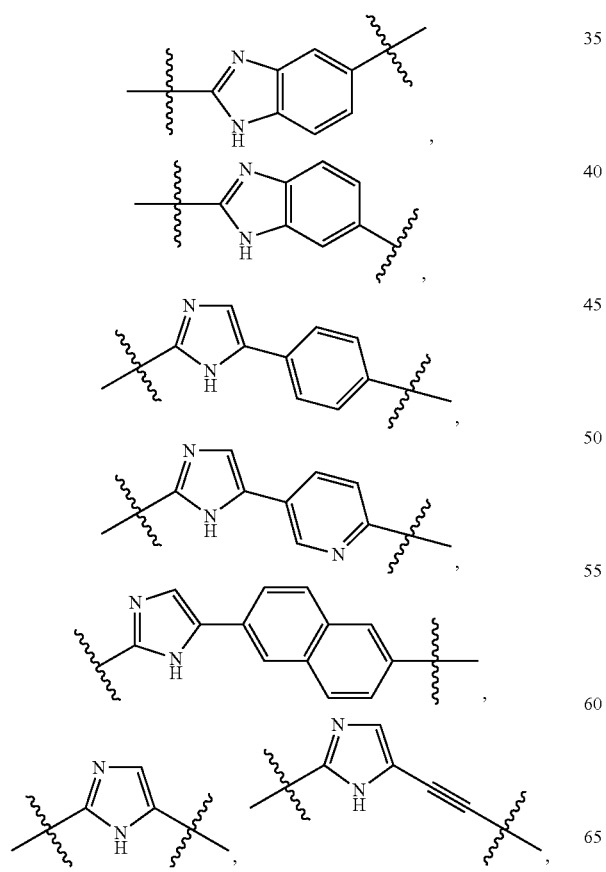
-continued
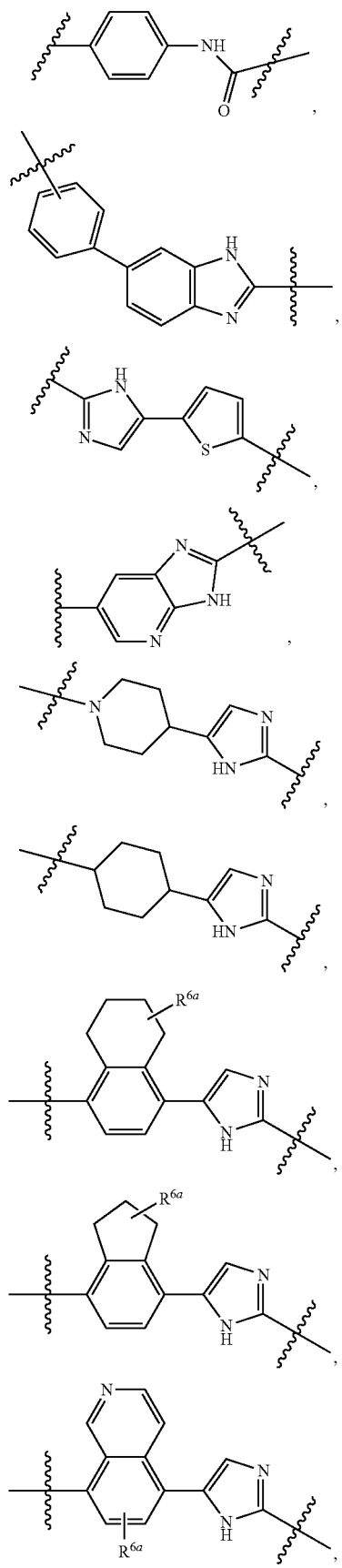

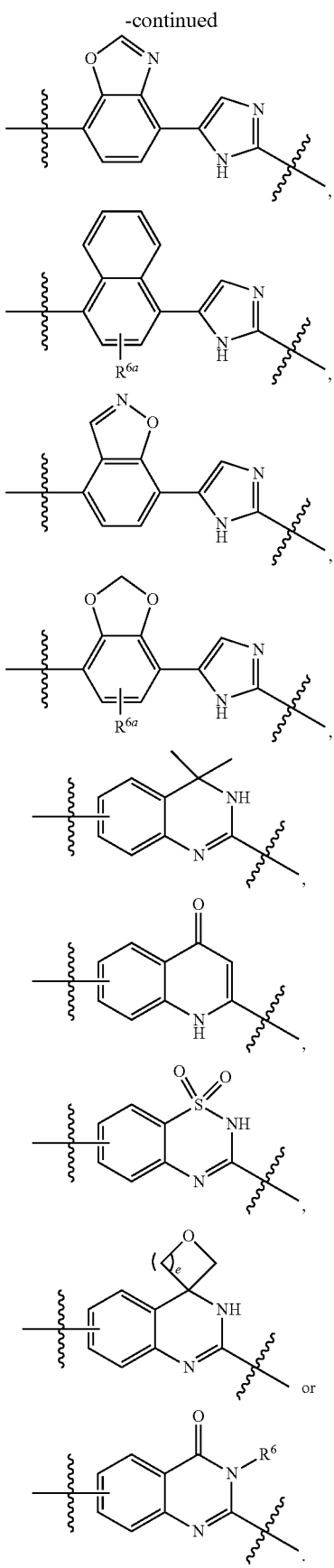

In another aspect, the present disclosure provides a pharmaceutical composition comprising any one of the above compounds.

In some embodiments, the pharmaceutical composition also comprises a pharmaceutically acceptable carrier, excipient, diluent, adjuvant, vehicle or a combination thereof.

In certain embodiments, the pharmaceutical composition disclosed herein further comprises an anti-HCV agent.

In other embodiments, the anti-HCV agent is interferon, ribavirin, IL-2, IL-6, IL-12, a compound that enhances the development of a type 1 helper T cell response, interfering RNA, anti-sense RNA, imiquimod, an inosine-5'-monophosphate dehydrogenase inhibitor, amantadine, rimantadine, ribavirin, bavituximab, human hepatitis C immune globulin (CIVACIR™), boceprevir, telaprevir, erlotinib, daclatasvir, simeprevir, asunaprevir, vaniprevir, faldaprevir, ABT-450, danoprevir, sovaprevir, MK-5172, vedroprevir, BZF-961, GS-9256, narlaprevir, ANA975, ABT-267, EDP239, PPI-668, GS-5816, samatasvir (IDX-719), MK-8742, MK-8325, GSK-2336805, PPI-461, TMC-435, MK-7009, BI-2013335, ciluprevir, BMS-650032, ACH-1625, ACH-1095, VX-985, IDX-375, VX-500, VX-813, PHX-1766, PHX-2054, IDX-136, IDX-316, EP-013420, VBY-376, TMC-649128, R-7128, PSI-7977, INX-189, IDX-184, IDX102, R1479, UNX-08189, PSI-6130, PSI-938, PSI-879, HCV-796, HCV-371, VCH-916, VCH-222, ANA-598, MK-3281, ABT-333, ABT-072, PF-00868554, BI-207127, GS-9190, A-837093, JKT-109, Gl-59728, GL-60667, AZD-2795, TMC647055 or a combination thereof.

In other embodiments, the interferon is interferon α-2b, pegylated interferon α, interferon α-2a, pegylated interferon α-2a, consensus interferon-α, interferon γ or a combination thereof.

In other embodiments, the pharmaceutical composition disclosed herein further comprises at least one HCV inhibitor.

In some embodiments, the HCV inhibitor inhibits at least one of HCV replication process and HCV viral protein function.

In some embodiments, the HCV replication process is a whole viral cycle consisting of HCV entry, uncoating, translation, replication, assembly and egress.

In some embodiments, the HCV viral protein is metalloproteinase, non-structural protein NS2, NS3, NS4A, NS4B, NS5A or NS5B, or an internal ribosome entry site (IRES) or inosine-5'-monophosphate dehydrogenase (IMPDH) required in HCV viral replication.

In another aspect, use of the compound or the pharmaceutical composition in inhibiting at least one of HCV replication process and HCV viral protein function is provided.

In some embodiments, the HCV replication process is a whole viral cycle consisting of HCV entry, uncoating, translation, replication, assembly and egress.

In some embodiments, the HCV viral protein is metalloproteinase, non-structural protein NS2, NS3, NS4A, NS4B, NS5A or NS5B, or an internal ribosome entry site (IRES) or inosine-5'-monophosphate dehydrogenase (IMPDH) required in HCV viral replication.

In another aspect, use of the compound or the pharmaceutical composition disclosed herein for preventing, managing, treating or lessening the severity of HCV infection and a HCV disorder in a patient is provided, which comprises administering a therapeutically effective amount of the (a) compound or pharmaceutical composition disclosed herein to the patient.

In another aspect, the compound or the pharmaceutical composition disclosed herein for use in inhibiting at least one of HCV replication process and HCV viral protein function is provided. In some embodiments, the HCV replication process is a whole viral cycle consisting of HCV entry, uncoating, translation, replication, assembly and egress; In some embodiments, the HCV viral protein is metalloproteinase, non-structural protein NS2, NS3, NS4A, NS4B, NS5A or NS5B, or an internal ribosome entry site (IRES) or inosine-5'-monophosphate dehydrogenase (IMPDH) required in HCV viral replication.

In another aspect, the compound or the pharmaceutical composition disclosed herein for use in preventing, managing, treating or lessening the severity of HCV infection or a HCV disorder in a patient is provided.

In another aspect, a method of inhibiting at least one of HCV replication process and HCV viral protein function is provided. In some embodiments, the HCV replication process is a whole viral cycle consisting of HCV entry, uncoating, translation, replication, assembly and egress; In some embodiments, the HCV viral protein is metalloproteinase, non-structural protein NS2, NS3, NS4A, NS4B, NS5A or NS5B, or an internal ribosome entry site (IRES) or inosine-5'-monophosphate dehydrogenase (IMPDH) required in HCV viral replication.

In another aspect, a method of preventing, managing, treating or lessening the severity of HCV infection or a HCV disorder in a patient is provided, which comprises administering a therapeutically effective amount of the (a) compound or pharmaceutical composition disclosed herein to the patient.

In another aspect, provided herein include methods of preparing, methods of separating, and methods of purifying compounds of Formula (I), (II), (III), (IV), (V), (VI), (VII), (VIII), (IX), (X), (XI), (II), (III), (IV) or (XI).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and the *Handbook of Chemistry and Physics*, 75$^{th}$ Ed. 1994. Additionally, general principles of organic chemistry are described in Sorrell et al., "*Organic Chemistry*", University Science Books, Sausalito: 1999, and Smith et al., "*March's Advanced Organic Chemistry*", John Wiley & Sons, New York: 2007, all of which are incorporated herein by reference in their entireties.

As described herein, compounds may optionally be substituted with one or more substituents, such as those illustrated above, or as exemplified by particular classes, subclasses, and species disclosed herein. It will be appreciated that the phrase "optionally substituted" is used interchangeably with the phrase "substituted or unsubstituted". In general, the term "substituted" whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Wherein the substituents described herein include, but are not limited to, hydroxy, amino, halo, cyano, aryl, heteroaryl, alkoxy, alkylamino, alkylthio, alkyl, alkenyl, alkynyl, heterocyclyl, mercapto, nitro, aryloxy, heteroaryloxy, oxo (=O), carboxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "aliphatic" or "aliphatic group" refers to a straight-chain (i.e., unbranched) or branched, substituted or unsubstituted hydrocarbon chain that is completely saturated or that contains one or more units of unsaturation. Unless otherwise specified, the aliphatic group contains 1-20 carbon atoms. In some embodiments, the aliphatic group contains 1-10 carbon atoms. In other embodiments, the aliphatic group contains 1-8 carbon atoms. In still other embodiments, the aliphatic group contains 1-6 carbon atoms, and in yet other embodiments, the aliphatic group contains 1-4 carbon atoms. In other embodiments, the aliphatic group contains 1-3 carbon atoms. Some non-limiting examples of the aliphatic group include linear or branched, substituted or unsubstituted alkyl, alkenyl, or alkynyl groups, as methyl, ethyl, propyl, isopropyl, butyl, tert-butyl, hexyl, isobutyl, sec-butyl, vinyl, and the like.

The term "haloaliphatic" refers to an aliphatic group substituted with one or more of the same or different halogen atoms (i.e., F, Cl, Br or I), wherein the aliphatic group is as defined herein. Some non-limiting examples of the haloaliphatic group include trifluoromethyl, trifluoroethyl, chloromethyl, 2-chlorovinyl, and the like.

The term "hydroxyaliphatic" refers to an aliphatic group substituted with one or more hydroxy groups, wherein the aliphatic group is as defined herein. Some non-limiting examples of the hydroxyaliphatic group include hydroxyethyl, 2-hydroxypropyl, hydroxymethyl, and the like.

The term "aminoaliphatic" refers to an aliphatic group substituted with one or more amino groups, wherein the aliphatic group is as defined herein. Some non-limiting examples of the aminoaliphatic group include aminomethyl, 2-aminoethyl, 2-amino isopropyl, and the like.

The term "alkyl" refers to a saturated linear or branched chain monovalent hydrocarbon radical of one to twenty carbon atoms, or one to ten carbon atoms, or one to eight carbon atoms, or one to six carbon atoms, or one to four carbon atoms, or one to three carbon atoms, wherein the alkyl radical may be optionally substituted independently with one or more substituents described below. The examples of alkyl group include, but are not limited to, methyl (Me, —CH$_3$), ethyl (Et, —CH$_2$CH$_3$), n-propyl (n-Pr, —CH$_2$CH$_2$CH$_3$), i-propyl (i-Pr, —CH(CH$_3$)$_2$), n-butyl (n-Bu, —CH$_2$CH$_2$CH$_2$CH$_3$), i-butyl (i-Bu, —CH$_2$CH(CH$_3$)$_2$), s-butyl (s-Bu, —CH(CH$_3$)CH$_2$CH$_3$), t-butyl (t-Bu, —C(CH$_3$)$_3$), n-pentyl, (—CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), n-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), n-heptyl, n-octyl, and the like. The prefix "alk-" refers to inclusive of both straight chain and branched saturated carbon chain. The term "alkylene" refers to a saturated divalent hydrocarbon group derived from a straight or branched chain saturated hydrocarbon by the removal of two hydrogen atoms, and is exemplified by methylene, ethylene, isopropylene, and the like.

The term "alkenyl" refers to a linear or branched chain monovalent hydrocarbon radical of two to twelve carbon atoms, or two to eight carbon atoms, or two to six carbon atoms, or two to four carbon atoms, with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Some non-limiting examples of the alkenyl group include ethenyl or vinyl (—CH═CH$_2$), allyl (—CH$_2$CH═CH$_2$), and the like.

The term "alkynyl" refers to a linear or branched chain monovalent hydrocarbon radical of two to twelve carbon atoms, or two to eight carbon atoms, or two to six carbon atoms, or two to four carbon atoms, with at least one site of unsaturation, i.e., a carbon-carbon, sp triple bond, wherein the alkynyl radical may be optionally substituted independently with one or more substituents described herein. Some non-limiting examples of the alkynyl group include ethynyl (—C≡CH), propynyl (propargyl, —CH$_2$C≡CH), and the like.

The term "hydroxy-substituted alkyl" refers to an alkyl group substituted with one or more hydroxy groups, wherein the alkyl group is as defined herein. Some non-limiting examples of the hydroxy-substituted alkyl group include hydroxymethyl, hydroxyethyl, 1,2-dihydroxyethyl, and the like.

The term "haloalkyl" refers to an alkyl group substituted with one or more of the same or different halogen atoms, wherein the alkyl group is as defined herein. Some non-limiting examples of the haloalkyl group include trifluoromethyl, trifluoroethyl, chloromethyl, fluoromethyl, and the like.

The term "hydroxyalkyl" refers to an alkyl group substituted with one or more hydroxy groups, wherein the alkyl group is as defined herein. Some non-limiting examples of the hydroxyalkyl group include hydroxyethyl, 2-hydroxypropyl, hydroxymethyl, and the like.

The term "aminoalkyl" refers to an alkyl group substituted with one or more amino groups, wherein the alkyl group is as defined herein. Some non-limiting examples of the aminoalkyl group include aminomethyl, 2-aminoethyl, 2-amino isopropyl, and the like.

The term "alkylene" refers to a saturated divalent hydrocarbon group derived from a straight or branched-chain saturated hydrocarbon by the removal of two hydrogen atoms. The alkylene group is optionally substituted with one or more substituents. The substituents include, but are not limited to, deuterium, hydroxy, amino, halo, cyano, aryl, heteroaryl, alkoxy, alkyl, alkenyl, alkynyl, heterocyclyl, mercapto, nitro, or aryloxy. Some non-limiting examples of the alkylene group include methylene (—CH$_2$—), ethylene (—CH$_2$—CH$_2$—), isopropylidene (—CH$_2$—CH(CH$_3$)—), ethylidene, 2-methoxy-1,1-propylidene, 2-hydroxy-1,1-propylidene, 2-methyl-2-hydroxy-1,1-propylidene, and the like.

The term "alkenylene" refers to an unsaturated divalent hydrocarbon group derived from a straight or branched-chain unsaturated hydrocarbon alkene by the removal of two hydrogen atoms. The alkenylene group is optionally substituted with one or more substituents. The substituents include, but are not limited to, deuterium, hydroxy, amino, halo, cyano, aryl, heteroaryl, alkoxy, alkyl, alkenyl, alkynyl, heterocyclyl, mercapto, nitro, or aryloxy. Some non-limiting examples of the alkenylene group include ethenylene (—CH═CH—), isopropenylene (—C(CH$_3$)═CH—), 3-methoxy-1,1-propenylidene, 2-methyl-1,1-butenylidene, and the like.

The term "carbocyclylene" or "cycloalkylene" refers to a saturated divalent hydrocarbon ring derived from a monocyclic ring having 3 to 12 carbon atoms or a bicyclic ring having 7 to 12 carbon atoms by the removal of two hydrogen atoms, wherein the carbocyclyl group or the cycloalkyl group is as defined herein. Some non-limiting examples of the cycloalkylene group include cyclopropylene, cyclobutylene, cyclopentylene, cyclohexylene, 1-cyclopent-1-enylene, 1-cyclopent-2-enylene, and the like.

The term "heterocyclylene" refers to a monocyclic, bicyclic, or tricyclic ring system in which one or more ring members are an independently selected heteroatom and that is completely saturated or that contains one or more units of unsaturation, but which is not aromatic, that has two points of attachment to the rest of the molecule, wherein the heterocyclyl group is as defined herein. Some non-limiting examples of the heterocyclylene group include piperidin-1,4-ylene, piperazin-1,4-ylene, tetrahydrofuran-2,4-ylene, tetrahydrofuran-3,4-ylene, azetidin-1,3-ylene, pyrrolidin-1,3-ylene, and the like.

The term "heterocyclylalkylene" refers to a divalent group derived from a heterocyclylalkyl by the removal of two hydrogen atoms, wherein the heterocyclylalkyl group is as defined herein. Some non-limiting examples of the heterocyclylalkylene group include morpholin-4-methylmethylene, piperidin-N-methylmethylene, piperazin-4-ethyl-1-yl, piperidin-4-ethyl-1-yl, pyrrolidon-2-methyl-1-yl, and the like.

The term "haloalkylene" refers to haloalkyl system having two points connected to the rest of the molecule, wherein the haloalkyl group is as defined herein. Some non-limiting examples of the haloalkylene group include difluoromethylene (—CF$_2$—), and the like.

The term "arylene" refers to aryl system having two connection points connected to the rest of the molecule, wherein the aryl radical is as defined herein. Some non-limiting examples of the arylene group include phenylene, p-fluorophenylene, and the like.

The term "aralkylene" refers to aralkyl system having two connection points connected to the rest of the molecule, wherein the aralkyl radical is as defined herein. Some non-limiting examples of the aralkylene group include benzylene, phenylethylene, and the like.

The term "heteroarylene" refers to heteroaryl system having two connection points connected to the rest of the molecule, wherein the heteroaryl radical is as defined herein. Some non-limiting examples of the heteroarylene group include pyridylene, pyrrylene, thiazolylene, imidazolylene, and the like.

The term "heteroarylalkylene" refers to heteroarylalkyl system having two connection points connected to the rest of the molecule, wherein the heteroarylalkyl group is as defined herein. Some non-limiting examples of the heteroarylalkylene group include pyridine-2-ethylene, thiazole-2-methylene, imidazole-2-ethylene, pyrimidine-2-methylene, and the like.

The term "fused bicyclylene" refers to fused bicyclyl system having two connection points connected to the rest of the molecule, wherein the fused bicyclyl group is as defined herein. Some non-limiting examples of the fused bicyclylene group include bicyclo[3.1.0]hexane-3,6-ylene.

The term "fused heterobicyclylene" refers to fused heterobicyclyl system having two connection points connected to the rest of the molecule, wherein the fused heterobicyclyl group is as defined herein. Some non-limiting examples of the fused heterobicyclylene group include 3-azabicyclo[3.1.0]hexane-3,6-ylene.

The term "fused bicyclylalkylene" refers to fused bicyclylalkyl system having two connection points connected to the rest of the molecule, wherein the fused bicyclylalkyl group is as defined herein.

The term "fused heterobicyclylalkylene" refers to fused heterobicyclylalkyl system having two connection points connected to the rest of the molecule, wherein the fused heterobicyclylalkyl group is as defined herein.

The term "spiro bicyclylene" refers to spiro bicyclyl system having two connection points connected to the rest of the molecule, wherein the fused spiro bicyclyl group is as defined herein. Some non-limiting examples of the spiro bicyclylene group include 5-spiro[2,4]heptane-5,7-ylene, spiro[4,4]nonane-2,7-ylene, and the like.

The term "spiro heterobicyclylene" refers to spiro heterobicyclyl system having two connection points connected to the rest of the molecule, wherein the fused spiro heterobicyclyl group is as defined herein. Some non-limiting examples of the spiro heterobicyclylene group include 5-azaspiro[2,4]heptane-5,7-ylene, 2-azaspiro[4,4]nonane-2,7-ylene, and the like.

The term "spiro bicyclylalkylene" refers to spiro bicyclylalkyl system having two connection points connected to the rest of the molecule, wherein the fused spiro bicyclylalkyl group is as defined herein.

The term "spiro heterobicyclylalkylene" refers to spiro heterobicyclylalkyl system having two connection points connected to the rest of the molecule, wherein the fused spiro heterobicyclylalkyl group is as defined herein.

The term "heteroalkyl" refers to hydrocarbon chain, inserted with one or more heteroatoms. Unless otherwise specified, heteroalkyl groups contain 1-10 carbon atoms. In other embodiments, the heteroalkyl group contains 1-8 carbon atoms. In still other embodiments, the heteroalkyl group contains 1-6 carbon atoms, and in yet other embodiments, the heteroalkyl group contains 1-4 carbon atoms. In other embodiments, the heteroalkyl group contains 1-3 carbon atoms. Some non-limiting examples of the heteroalkyl group include $CH_3OCH_2$—, $CH_3CH_2OCH_2$—, $CH_3SCH_2$—, $(CH_3)_2NCH_2$—, $(CH_3)_2CH_2OCH_2$—, $CH_3OCH_2CH_2$—, $CH_3CH_2OCH_2CH_2$—, and the like.

The term "cycloaliphatic", "carbocycle", "carbocyclyl", or "cycloalkyl" refers to a monovalent or multivalent non-aromatic, saturated or partially unsaturated ring exclusive of heteroatoms, having 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system. Some non-limiting examples of the cycloaliphatic group include cycloalkyl, cycloalkenyl, and cycloalkynyl. Further examples of the cycloaliphatic group include cyclopropyl, cyclobutyl, cyclopentyl, 1-cyclopentyl-M-enyl, 1-cyclopentyl-2-enyl, 1-cyclopentyl-3-enyl, cyclohexyl, 1-cyclohexyl-M-enyl, 1-cyclohexyl-2-enyl, 1-cyclohexyl-3-enyl, cyclohexadienyl, cycloheptyl, cyclooctyl, cyclononyl, cyclodecyl, cycloundecyl, cyclododecyl, and the like. The term "cycloaliphatic", "carbocycle", "carbocyclyl", or "cycloalkyl" may be substituted or unsubstituted, wherein the substitutent may be, but is not limited to, hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxy alkoxy, and the like.

The term "cycloalkyloxy" or "carbocyclyloxy" refers to an optionally substituted cycloalkyl or carbocyclyl radical, as defined herein, attached to an oxygen atom, wherein the oxygen atom serves as the attaching point to the rest of the molecule. Some non-limiting examples of the cycloalkyloxy group include cyclopropyloxy, cyclopentyloxy, cyclohexyloxy, hydroxy-substituted cyclopropyloxy, and the like.

The term "cycloalkylamino" refers to an amino group substituted with one or two cycloalkyl radicals, wherein the cycloalkyl group is as defined herein. Some non-limiting examples of the cycloalkylamino group include cyclopropylamino, cyclopentylamino, cyclohexylamino, hydroxy-substituted cyclopropylamino, dicyclohexylamino, dicyclopropylamino, and the like.

The term "carbocyclyloxyalkoxy" refers to an alkoxy group substituted with one or more carbocyclyloxy groups, wherein the alkoxy group and carbocyclyloxy group are as defined herein. Some non-limiting examples of the carbocyclyloxyalkoxy group include cyclopropyloxymethoxy, cyclopropyloxyethoxy, cyclopentyloxyethoxy, cyclohexyloxyethoxy, cyclohexenyl-3-oxyethoxy, and the like.

The term "cycloalkyloxyaliphatic" refers to an aliphatic group substituted with one or more cycloalkyloxy groups, wherein the aliphatic group and cycloalkyloxy group are as defined herein. Some non-limiting examples of the cycloalkyloxyaliphatic group include cyclopropyloxymethyl, cyclopropyloxyethyl, cyclopentyloxymethyl, cyclopentyloxyethyl, cyclohexyloxyethyl, halocyclopropyloxyethyl, and the like.

The term "cycloalkylaminoaliphatic" refers to an aliphatic group substituted with one or more cycloalkylamino groups, wherein the aliphatic group and cycloalkylamino group are as defined herein. Some non-limiting examples of the cycloalkylaminoaliphatic group include cyclopropylaminomethyl, cyclopropylaminoethyl, cyclopentylaminomethyl, cyclopentylaminoethyl, cyclohexylaminoethyl, halocyclopropylaminoethyl, and the like.

The term "cycloalkylaliphatic" refers to an aliphatic group substituted with one or more cycloalkyl groups, wherein the cycloalkyl group and aliphatic group are as defined herein. Some non-limiting examples of the cycloalkylaliphatic group include cyclopropylmethyl, cyclopropylethyl, cyclopropylpropyl, cyclopentylmethyl, cyclohexylethyl, and the like.

The term "cycloalkylalkoxy" or "carbocyclylalkoxy" refers to an alkoxy group substituted with one or more cycloalkyl groups or carbocyclyl groups, wherein the carbocyclyl group, cycloalkyl group and alkoxy group are as defined herein. Some non-limiting examples of the cycloalkylalkoxy group include cyclopropylmethoxy, cyclopropylethoxy, cyclopentylethoxy, cyclohexylethoxy, cyclohexylmethoxy, cyclopropylpropoxy, and the like.

The term "heterocycle", "heterocyclyl", "heterocycloaliphatic", or "heterocyclic" as used interchangeably herein refers to a monocyclic, bicyclic, or tricyclic ring system in which one or more ring members are an independently selected heteroatom and that is completely saturated or that contains one or more units of unsaturation, but not aromatic having a single point of attachment to the rest of the molecule. One or more ring atoms are optionally substituted independently with one or more substituents described herein. In some embodiments, the "heterocycle", "heterocyclyl", "heterocycloaliphatic" or "heterocyclic" group is a monocycle having 3 to 7 ring members (e.g., 1 to 6 carbon atoms and 1 to 3 heteroatoms selected from N, O, P or S, wherein the S or P is optionally substituted with one or more oxo to provide the group SO or $SO_2$, PO or $PO_2$, with the proviso that when the ring is a 3-membered ring, there is only one heteroatom) or a bicycle having 7 to 10 ring members (e.g., 4 to 9 carbon atoms and 1 to 3 heteroatoms selected from N, O, P or S, wherein the S or P is optionally substituted with one or more oxo to provide the group SO or $SO_2$, PO or $PO_2$).

The heterocyclyl may be a carbon radical or heteroatom radical. "Heterocyclyl" also includes radicals where heterocycle radicals are fused with a saturated, partially unsaturated ring, or heterocyclic ring. Some non-limiting examples of heterocyclic rings include pyrrolidinyl, tetrahydrofuranyl, dihydrofuranyl, tetrahydrothienyl, tetrahydropyranyl, dihydropyranyl, tetrahydrothiopyranyl, piperidyl, morpholinyl, thiomorpholinyl, thioxanyl, thiazolidinyl, oxazolidinyl, piperazinyl, homopiperazinyl, azetidinyl, oxetanyl, thietanyl, homopiperidinyl, epoxypropyl (oxiranyl), azepanyl, oxepanyl, thiepanyl, 4-methoxy-piperidin-1-yl, 1,2,3,6-tetrahydropyridine-1-yl, oxazepinyl, diazepinyl, thiazepinyl, pyrrolidin-1-yl, 2-pyrrolinyl, 3-pyrrolinyl, 2H-indolinyl, 2H-pyranyl, 4H-pyranyl, dioxolan-2-yl, 1,3-dioxopenyl, pyrazolinyl, dithianyl, ditholanyl, dihydrothienyl, pyrazolidinylimidazolinyl, imidazolidinyl, 1,2,3,4-tetrahydroisoquinolinyl, 1,2,6-dithiazinyl, 1,1-dioxo-2-yl, 4-hydroxy-1,4-azaphosphine-4-oxide-1-yl, 2-hydroxy-1-(piperazin-1-yl)ethanone-4-yl, 2-hydroxy-1-(5,6-dihydro-1,2,4-triazin-1 (4H)-yl)ethanone-4-yl, 5,6-dihydro-4H-1,2,4-oxadiazine-4-yl, 2-hydroxy-1-(5,6-diludine-1(2H)-yl)ethanone-4-yl, 3-azabicyclo[3,1,0]hexyl, 3-azabicyclo[4,1,0]heptyl, azabicyclo[2,2,2]hexyl, 2-methyl-5,6,7,8-tetrahydro-[1,2,4]triazole[1,5-c]pyrimidine-6-yl, 4,5,6,7-teterhydro-isoxazolo[4,3-c]pyrimidine-5-yl, 3H-indoxyl-2-oxo-5-azabicyclo[2,2,1]heptane-5-yl, 2-oxo-5-azabicyclo[2,2,2]octane-5-yl, quinolizinyl and N-pyridyl urea. Some non-limiting examples of a heterocyclic ring include 1,1-dioxo-thiomorpholinyl and heterocyclic group wherein 2 carbon atoms on the ring are substituted with oxo(=O) moieties are pyrimidindionyl. The heterocyclic groups herein may be substituted or unsubstituted, wherein the substituent may be, but is not limited to, oxo(=O), hydroxy, amino, halo, cyano, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxy alkoxy, and the like.

The term "heterocyclylalkyl" refers to heterocyclic-substituted alkyl radical. The term "heterocyclylalkoxy" refers to heterocyclic-substituted alkoxy radical wherein oxygen atom serves as the attaching point to the rest of the molecule. The term "heterocyclylalkylamino" refers to heterocyclic-substituted alkylamino radical wherein nitrogen atom serves as the attaching point to the rest of the molecule. Wherein the heterocyclyl, alkyl, alkoxy and alkylamino group are as defined herein. Some non-limiting examples of the heterocyclylalkyl group include pyrrol-2-ylmethyl, morpholin-4-ylethyl, morpholin-4-ylethoxy, piperazin-4-ylethoxy, piperidin-4-ylethylamino, and the like.

The term "heterocyclylaliphatic" refers to heterocyclic-substituted aliphatic group, wherein the heterocyclic radical and aliphatic group are as defined herein. Some non-limiting examples of the heterocyclylaliphatic group include pyrrol-2-ylmethyl, piperidin-2-ylethyl, piperazin-2-ylethyl, piperidin-2-ylmethyl, and the like.

The term "heterocyclyloxy" refers to optionally substituted heterocyclyl radical, as defined herein, connected to an oxygen atom, and the oxygen atom serves as the attaching point to the rest of the molecule. Some non-limiting examples of the heterocyclyloxy group include pyrrol-2-yloxy, pyrrol-3-yloxy, piperidin-2-yloxy, piperidin-3-yloxy, piperazin-2-yloxy, piperidin-4-yloxy, and the like.

The term "heterocyclylamino" refers to an amino group substituted with one or two heterocyclyl groups, wherein the heterocyclyl group is as defined herein. Some non-limiting examples of the heterocyclylamino group include pyrrol-2-ylamino, pyrrol-3-ylamino, piperidin-2-ylamino, piperidin-3-ylamino, piperidin-4-ylamino, piperazin-2-ylamino, dipyrrol-2-ylamino, and the like.

The term "heterocyclyloxyalkoxy" refers to an alkoxy radical substituted with one or more heterocyclyloxy groups, wherein the alkoxy radical and heterocyclyloxy group are as defined herein. Some non-limiting examples of the heterocyclyloxyalkoxy group include pyrrol-2-yloxymethoxy, pyrrol-3-yloxyethoxy, piperidin-2-yloxyethoxy, piperidin-3-yloxyethoxy, piperazin-2-yloxymethoxy, piperidin-4-yloxyethoxy, and the like.

The term "heterocyclyloxyaliphatic" refers to an aliphatic group substituted with one or more heterocyclyloxy groups, wherein the aliphatic group and heterocyclyloxy group are as defined herein.

Some non-limiting examples of the heterocyclyloxyaliphatic group include pyrrol-2-yloxymethyl, piperazin-3-yloxyethyl, piperazin-2-yloxyethyl, morpholin-2-yloxymethyl, piperidin-2-yloxyethyl, and the like.

The term "heterocyclylaminoaliphatic" refers to an aliphatic group substituted with one or more heterocyclylamino groups, wherein the aliphatic group and heterocyclylamino group are as defined herein. Some non-limiting examples of the heterocyclylaminoaliphatic group include pyrrol-2-ylaminomethyl, piperazin-3-lyaminoethyl, piperazin-2-lyaminoethyl, piperidin-2-lyaminoethyl, morpholin-2-lyaminomethyl, and the like.

The term "heteroatom" refers to one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" refers to F, Cl, Br or I.

The term "unsaturated" as used herein, refers to a moiety having one or more units of unsaturation.

The term "alkoxy" refers to an alkyl group, as previously defined, attached to the principal carbon chain through an oxygen ("alkoxy") atom. Some non-limiting examples of the alkoxy group include methoxy, ethoxy, propoxy, butoxy, and the like. And the alkoxy defined above may be substituted or unsubstituted, wherein the substituent may be, but is not limited to, hydroxy, amino, halo, cyano, alkoxy, alkyl, alkenyl, alkynyl, mercapto, nitro, and the like.

The term "hydroxy-substituted alkoxy" or "hydroxyalkoxy" refers to an alkoxy group substituted with one or more hydroxy groups, wherein the alkoxy group is as defined above. Some non-limiting examples of the hydroxyalkoxy group include hydroxymethoxy, 2-hydroxyethoxy, 2-hydroxypropoxy, 2-hydroxyisopropoxy, and the like.

The term "aminoalkoxy" refers to an alkoxy group substituted with one or more amino groups, wherein the alkoxy group is as defined above. Some non-limiting examples of the aminoalkoxy group include aminomethoxy, 2-aminoethoxy, 2-aminopropoxy, 2-aminoisopropoxy, and the like.

The term "azidoalkoxy" refers to an alkoxy group substituted with one or more azido groups, wherein the alkoxy group is as defined above. Some non-limiting examples of the azidoalkoxy group include 2-azidoethoxy, 3-azidopropoxy, 2-azidopropoxy, and the like.

The term "alkoxyalkoxy" refers to an alkoxy group substituted with one or more alkoxy groups, wherein the alkoxy group is as defined above. Some non-limiting examples of the alkoxyalkoxy group include methoxymethoxy, methoxyethoxy, ethoxymethoxy, ethoxyethoxy, ethoxypropoxy, and the like.

The term "alkoxyaliphatic" refers to an aliphatic group substituted with one or more alkoxy groups, wherein the aliphatic group and alkoxy group are as defined herein. Some non-limiting examples of the alkoxyaliphatic group include methoxymethyl, ethoxymethyl, ethoxyethyl, ethoxypropenyl, and the like.

The term "alkylaminoaliphatic" refers to an aliphatic group substituted with one or more alkylamino groups, wherein the aliphatic group and alkylamino group are as defined herein. Some non-limiting examples of the alkylaminoaliphatic group include dimethylaminoethyl, methylaminoethyl, diethylaminomethyl, diethylaminoethyl, and the like.

The term "alkylthioaliphatic" refers to an aliphatic group substituted with one or more alkylthio groups, wherein the aliphatic group and alkylthio group are as defined herein. Some non-limiting examples of the alkylthioaliphatic group include methylthioethyl, methylthiopropyl, ethylthioethyl, methylthiopropenyl, and the like.

The term "haloalkyl", "haloalkenyl" or "haloalkoxy" refers to an alkyl group, alkenyl group or alkoxy group substituted with one or more halogen atoms. Some non-limiting examples of the haloalkyl group include trifluoromethyl, 2-chloro-ethenyl, trifluoromethoxy, and the like.

The term "aryl" used alone or as part of a larger moiety as in "aralkyl", "arylalkoxy" or "aryloxyalkyl" refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Some non-limiting examples of aryl rings include phenyl, naphthyl, and anthryl. The aryl may be substituted or unsubstituted, wherein the substituents include, but are not limited to, hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxy alkoxy, and the like.

The term "arylaliphatic" refers to an aliphatic group substituted with one or more aryl groups, wherein the aliphatic group and the aryl group are as defined herein. Some non-limiting examples of the arylaliphatic group include phenylethyl, benzyl, (p-tolyl)ethyl, styryl, and the like.

The term "aryloxy" refers to optionally substituted aryl radicals, as defined herein, attached to an oxygen atom, wherein the oxygen atom serves as the attaching point to the rest of the molecule. Wherein the aryl radical is as defined herein. Some non-limiting examples of the aryloxy group include phenyloxy, methylphenyloxy, ethylphenyloxy, and the like.

The term "arylamino" refers to an amino group substituted with one or two aryl groups, wherein the aryl group is as defined herein. Some non-limiting examples of the arylamino group include phenylamino, (p-fluorophenyl)amino, diphenylamino, ditolylamino, (di-p-tolyl)amino, and the like.

The term "aryloxyalkoxy" refers to an alkoxy group substituted with one or more aryloxy groups, wherein the alkoxy group and the aryloxy group are as defined herein. Some non-limiting examples of the aryloxyalkoxy group include phenyloxymethoxy, phenyloxyethoxy, phenyloxypropoxy, and the like.

The term "aryloxyaliphatic" refers to an aliphatic group substituted with one or more aryloxy groups, wherein the aryloxy group and the aliphatic group are as defined herein. Some non-limiting examples of the aryloxyaliphatic group include phenyloxymethyl, phenyloxyethyl, phenyloxypropyl, and the like.

The term "arylaminoaliphatic" refers to an aliphatic group substituted with one or more arylamino groups, wherein the arylamino group and the aliphatic group are as defined herein. Some non-limiting examples of the arylaminoaliphatic group include phenylaminomethyl, phenylaminoethyl, tolylaminoethyl, phenylaminopropyl, phenylaminoallyl, and the like.

The term "arylalkoxy" refers to an alkoxy group substituted with one or more aryl groups, wherein the aryl group and the alkoxy group are as defined herein. Some non-limiting examples of the arylalkoxy group include phenylmethoxy, phenylethoxy, (p-tolyl)methoxy, phenylpropoxy, and the like.

The term "arylalkylamino" refers to an alkylamino group substituted with one or more aryl groups, wherein the aryl group and the alkylamino group are as defined herein. Some non-limiting examples of the arylalkylamino group include phenylmethylamino, phenylethylamino, phenylpropylamino, (p-tolyl)methylamino, and the like.

The term "heteroaryl" used alone or as part of a larger moiety as in "heteroarylalkyl" or "heteroarylalkoxy" refers to monocyclic, bicyclic, and tricyclic ring systems having a total of five to fourteen ring members, wherein at least one ring in the system is aromatic, and at least one ring in the system is inclusive of one or more heteroatoms, wherein each ring in the system contains 3 to 7 ring members and that has a single point of attachment to the rest of the molecule. The term "heteroaryl" may be used interchangeably with the term "heteroaryl ring" or "heteroaromatic compound". The heteroaryl defined herein may be substituted or unsubstituted, wherein the substituents include, but are not limited to, hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxy alkoxy, and the like.

Some non-limiting examples of the suitable heteroaryl ring include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, 4-methylisoxazolyl-5-yl, N-pyrrolyl, 2-pyrrolyl, 3-pyrrolyl, 2-pyridyl, 3-pyridyl, 4-pyridyl, 2-pyrimidinyl, 4-pyrimidinyl, pyrimidine-5-yl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, 1,3,4-thiadiazol-2-yl, pyrazinyl, pyrazine-2-yl, 1,3,5-triazinyl, benzo[d]thiazol-2-yl, imidazo[1,5-a]pyridin-6-yl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), or isoquinolinyl (e.g., 1-isoquinolinyl, 3-isoquinolinyl, or 4-isoquinolinyl).

The term "heteroaryloxy" refers to an optionally substituted aryl radical, as defined herein, attached to an oxygen atom, wherein the oxygen atom serves as the attaching point to the rest of the molecule. Some non-limiting examples of the heteroaryloxy group include pyrid-2-yloxy, thiazol-2-yloxy, imidazol-2-yloxy, pyrimidin-2-yloxy, and the like.

The term "heteroaryloxyaliphatic" refers to an aliphatic group substituted with one or more heteroaryloxy groups, wherein the aliphatic group and the heteroaryloxy group are as defined herein. Some non-limiting examples of the heteroaryloxy group include pyrid-2-yloxyethyl, thiazol-2-yloxymethyl, imidazol-2-yloxyethyl, pyrimidin-2-yloxypropyl, and the like.

The term "sulfonyl", whether used alone or linked to other terms such as "alkylsulfonyl", refers to respectively divalent radicals —SO$_2$—.

The term "alkylsulfonyl", refers to a sulfonyl radical substituted with an alkyl radical, forming an alkylsulfonyl (—SO$_2$CH$_3$).

The term "sulfamyl", "aminosulfonyl" or "sulfonamidyl" refer to a sulfonyl radical substituted with an amine radical, forming a sulfonamide (—SO$_2$NH$_2$).

The term "carboxy" or "carboxyl", whether used alone or with other terms, such as "carboxyalkyl", refers to —CO$_2$H.

The term "carbonyl", whether used alone or with other terms, such as "aminocarbonyl" or "carbonyloxy", refers to —(C=O)—.

The term "carboxyalkoxy" refers to an alkoxy group substituted with one or more carboxy groups, wherein the alkoxy group and the carboxy group are as defined herein. Some non-limiting examples of the carboxyalkoxy group include carboxymethoxy, carboxyethoxy, and the like.

The term "aralkyl" or "arylalkyl" refers to aryl-substituted alkyl radicals. In some embodiments, the aralkyl radical includes "lower aralkyl" radicals having aryl radicals attached to alkyl radicals having one to six carbon atoms. In other embodiments, the aralkyl radical is "phenylalkylenyl" attached to alkyl portions having one to three carbon atoms. Some non-limiting examples of such radical include benzyl, diphenylmethyl and phenylethyl. The aryl in said aralkyl can be additionally substituted with halo, alkyl, alkoxy, haloalkyl or haloalkoxy.

The term "alkylthio" refers to radicals containing a linear or branched alkyl radical, of one to ten carbon atoms, attached to a divalent sulfur atom. In other embodiments, the alkylthio radical includes lower alkylthio radicals having one to three carbon atoms. Some non-limiting examples of the "alkylthio" include methylthio (CH$_3$S—).

The term "haloalkylthio" refers to radicals containing a haloalkyl radical, of one to ten carbon atoms, attached to a divalent sulfur atom. In other embodiments, the haloalkylthio radical includes lower haloalkylthio radicals having one to three carbon atoms. Some non-limiting examples of the "haloalkylthio" include trifluoromethylthio.

The term "alkylamino" refers to "N-alkylamino" and "N,N-dialkylamino" wherein amino groups are independently substituted with one alkyl radical or with two alkyl radicals, respectively. In other embodiments, the alkylamino radical includes "lower alkylamino" radicals having one or two alkyl radicals of one to six carbon atoms, attached to a nitrogen atom. In still other embodiments, the alkylamino radical includes lower alkylamino radicals having one to three carbon atoms. Some non-limiting examples of the suitable alkylamino radical include mono or dialkylamino such as N-methylamino, N-ethylamino, N,N-dimethylamino, N,N-diethylamino, and the like.

The term "alkylaminohaloalkoxy" refers to a haloalkoxy group substituted with one or more alkylamino groups, wherein the haloalkoxy group and the alkylamino group are as defined herein. Some non-limiting examples of the alkylaminohaloalkoxy group include methylaminodifluoromethoxy, ethylaminotrifluoromethoxy, and the like.

The term "heteroarylamino" refers to amino groups substituted with one or two heteroaryl radicals, wherein the heteroaryl radical is as defined herein. Some non-limiting examples of the heteroarylamino group include N-thienylamino. In other embodiments, the "heteroarylamino" radical include substituted on the heteroaryl ring portion of the radical.

The term "heteroarylaliphatic" refers to aliphatic groups substituted with one or more heteroaryl radicals, wherein the heteroaryl radical and the aliphatic group are as defined herein. Some non-limiting examples of the heteroarylaliphatic group include thiophen-2-ylpropenyl, pyridin-4-ylethyl, imidazol-2-methyl, furan-2-ethyl, indole-3-methyl, and the like.

The term "heteroarylalkyl" refers to alkyl groups substituted with one or more heteroaryl radicals, wherein the heteroaryl radical and the alkyl group are as defined herein. Some non-limiting examples of the heteroarylalkyl group include imidazol-2-methyl, furan-2-ethyl, indol-3-methyl, and the like.

The term "heteroarylalkylamino" refers to nitrogen-containing heteroarylalkyl radicals attached through a nitrogen atom to other radicals, wherein the heteroarylalkyl radicals is as defined herein. Some non-limiting examples of the heteroarylalkylamino radical include pyridin-2-methylamino, thiazol-2-ethylamino, imidazol-2-ethylamino, pyrimidin-2-propylamino, pyrimidin-2-methylamino, and the like.

The term "aminoalkyl" refers to a linear or branched-alkyl radical having one to ten carbon atoms, substituted with one or more amino radicals. In some embodiments, the aminoalkyl radical includes "lower aminoalkyl" radicals having one to six carbon atoms and one or more amino radicals. Some non-limiting examples of such radical include aminomethyl, aminoethyl, aminopropyl, aminobutyl and aminohexyl.

The term "alkylaminoalkyl" refers to alkyl radicals substituted with alkylamino radicals. In some embodiments, the alkylaminoalkyl radical includes "lower alkylaminoalkyl" radicals having alkyl radicals of one to six carbon atoms. In other embodiments, the alkylaminoalkyl radical includes lower alkylaminoalkyl radicals having alkyl radicals of one to three carbon atoms. Some non-limiting examples of the suitable alkylaminoalkyl radical include mono and dialkyl substituted, such as N-methylaminomethyl, N,N-dimethylaminoethyl, N,N-diethylaminomethyl, and the like.

The term "carboxyalkyl" refers to a linear or branched alkyl radical having one to ten carbon atoms substituted with one or more carboxy radicals. Some non-limiting examples of such radical include carboxymethyl, carboxypropyl, and the like.

The term "aryloxy" refers to optionally substituted aryl radicals, as defined above, attached to an oxygen atom, wherein the oxygen atom serves as the attaching point to the rest of the molecule. Some non-limiting examples of such radical include phenoxy.

The term "heteroarylalkoxy" refers to oxy-containing heteroarylalkyl radicals attached through an oxygen atom to other radicals, wherein the heteroarylalkyl radical is as defined herein. Some non-limiting examples of such radical include pyridin-2-ylmethoxy, thiazol-2-ylethoxy, imidazol-2-ylethoxy, pyrimidin-2-ylpropoxy, pyrimidin-2-ylmethoxy, and the like.

The term "cycloalkylalkyl" refers to cycloalkyl-substituted alkyl radicals. Some non-limiting examples of such radical include cyclohexylmethyl. The cycloalkyl in the radicals may be additionally substituted with halo, alkyl, alkoxy or hydroxy.

The term "fused bicyclic", "fused cyclic", "fused bicyclyl" or "fused cyclyl" refer to unsaturated or saturated fused cyclic system and bridged ring system that is not aromatic. For example, as depicted below (Formula (a1)), ring A1 and ring A2 share a bond that is a alkyl or heteroalkyl chain, wherein j is 0, 1, 2, 3 or 4. Such a system may contain isolated or conjugated unsaturation, but not aromatic or heteroaromatic rings in its core structure (but may have aromatic substitution thereon). Each cyclic ring in a fused bicyclyl can be either a carbocyclic or a heteroalicyclic. Some non-limiting examples of the fused bicyclic ring system or bridged ring system include hexahydro-furo[3,2-b]furan, 2,3,3a,4,7,7a-hexahydro-1H-indene, 7-azabicyclo[2.3.0]heptane, fused bicyclo[3.3.0]octane, fused bicyclo[3.1.0]hexane, bicyclo[2.2.1]heptane, 2-azabicyclo[2.2.1]heptane, and 1,2,3,4,4a,5,8,8a-octahydro-naphthalene. The fused bicyclyl defined herein may be substituted or unsubstituted, wherein the substituents include, but are not limited to, deuterium, oxo(=O), hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxy alkoxy, and the like.

(a1)

The term "fused heterobicyclyl" refers to unsaturated or saturated fused cyclic system and bridged ring system that is not aromatic. Such a system may contain isolated or conjugated unsaturation, but not aromatic or heteroaromatic rings in its core structure (but may have aromatic substitution thereon). And at least one ring in the system is inclusive of one or more heteroatoms, wherein each ring in the system contains 3 to 7 ring members, e.g., 1 to 6 carbon atoms and 1 to 3 heteroatoms selected from N, O, P or S, wherein the S or P is optionally substituted with one or more oxo to provide the group SO or SO$_2$, PO or PO$_2$. Some non-limiting examples of fused heterobicyclic ring system include hexahydro-furo[3,2-b]furan, 6-azabicyclo[3.2.0]heptane, 2-azabicyclo[3.1.0]heptane, 3-azabicyclo[3.1.0]heptane, 2-azabicyclo[2.2.1]heptane, and the like. The fused heterobicyclyl defined herein may be substituted or unsubstituted, wherein the substituents include, but are not limited to, deuterium, oxo(=O), hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxy alkoxy, and the like.

The term "spirocyclyl", "spirocyclic", "spiro bicyclyl" or "spiro bicyclic" refers to a ring originating from a particular annular carbon of another ring. For example, as depicted below, ring A and ring B share a carbon atom between the two saturated ring system, which terms as a "spirocyclyl" or "spiro bicyclyl". Each cyclic ring in the spirocyclyl or spiro bicyclyl can be either a carbocyclic or a heteroalicyclic. Some non-limiting examples of such radical include 2,7-diaza-spiro[4.4]non-2-yl, 7-oxo-2-azaspiro[4.5]dec-2-yl, 4-azaspiro[2.4]hept-5-yl, 4-oxaspiro[2.4]hept-5-yl, 5-azaspiro[2.4]hept-5-yl, spiro[2.4]heptyl, spiro[4.4]nonyl, 7-hydroxy-5-azaspiro[2.4]hept-5-yl, and the like. The spirocyclyl or spiro bicyclyl may be substituted or unsubstituted, wherein the substituents include, but are not limited to, oxo(=O), hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxy alkoxy, and the like.

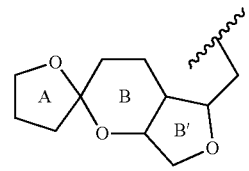

The term "spiro bicyclylene" refers to spiro bicyclyl system having two connection points connected to the rest of the molecule, wherein spiro bicyclyl radical is as defined herein.

The terms "spiro heterobicyclyl" refers to a ring originating from a particular annular carbon of another ring. For example, as depicted above, ring A and ring B share a carbon atom between the two saturated ring system, which terms as a "spirocyclyl". And at least one ring in the system is inclusive of one or more heteroatoms, wherein each ring in the system contains 3 to 7 ring members, e.g., 1 to 6 carbon atoms and 1 to 3 heteroatoms selected from N, O, P or S, wherein the S or P is optionally substituted with one or more oxo to provide the group SO or $SO_2$, PO or $PO_2$. Some non-limiting examples of such radicals include 4-azaspiro[2,4]hept-5-yl, 4-oxaspiro[2,4]hept-5-yl, 5-azaspiro[2,4]hept-5-yl, 7-hydroxy-5-azaspiro[2,4]hept-5-yl, 5-azaspiro[2,4]hept-6-yl, 1,4-dioxo-7-azaspiro[4,4]non-8-yl, and the like. The spiro heterobicyclyl defined herein may be substituted or unsubstituted, wherein the substituents include, but are not limited to, oxo(=O), hydroxy, amino, halo, cyano, aryl, heteroaryl, alkoxy, alkylamino, alkyl, alkenyl, alkynyl, heterocyclyl, mercapto, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxy alkoxy, and the like.

As described herein, the group derived from α-amino acid refers to an α-amino acid radical derived from an α-amino acid by the removal of one hydroxy in carboxy, which attached to X or X, and the group derived from α-amino acid is optionally substituted with one or more substituents, in some embodiments the substituent is deuterium, F, Cl, Br, I, hydroxy, cyano alkoxycarbonyl, aryloxycarbonyl, heteroaryloxycarbonyl, or heterocycylcarbonyl. For example:

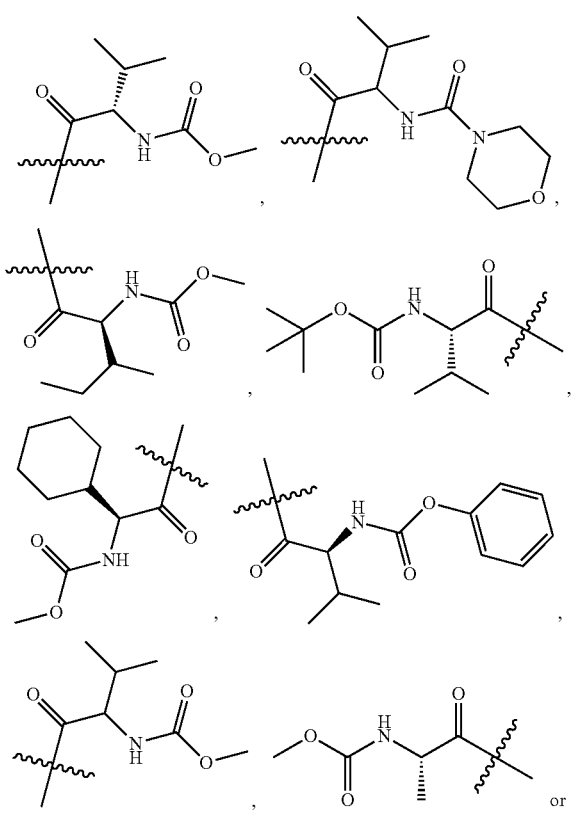

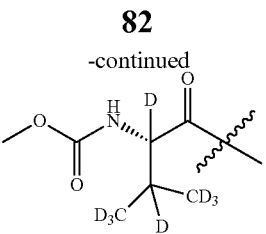

As described herein, a bond drawn from a substituent to the center of one ring within a ring system (as shown below (a)) represents substitution of the substituent $(R^{5a})_f$ at any substitutable position on the rings (W, W1 and W2) to which it is attached. For example, Figure (a) represents possible substitution in any of the positions on the W1, W2, and W ring.

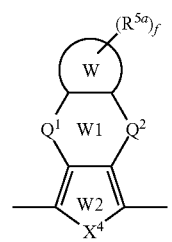

FIG. (a)

As described herein, two attaching points either E or E', within a ring system (as shown in Figure (b)), attach to the rest of the molecule, e.g., E and E' may be used interchangeably with each other.

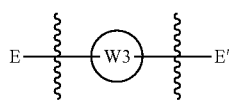

FIG. (b)

As described herein, a dot line drawn together with a bond within a ring system (as shown in Figure (c)) represents either a double bond or a single bond. For example, structure in Figure (c) represents any structures selected from Figure (d).

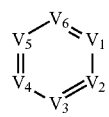

FIG. (c)

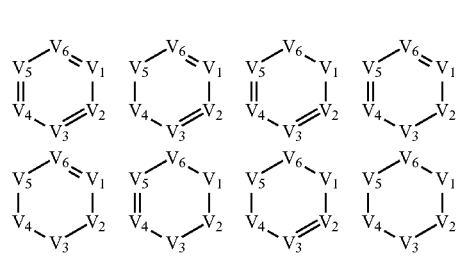

FIG. (d)

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

Furthermore, what need to be explained is that the phrase "each . . . is independently" is used interchangeably with the phrase "each (of) . . . and . . . is independently", unless otherwise stated. It should be broadly understood that the specific options expressed by the same symbol are independently of each other in different radicals; or the specific options expressed by the same symbol are independently of each other in same radicals. For example, $R^9$ of the structure formulas "—U—$(CR^9R^{9a})_t$—$R^{12}$" and "—[U—$(CR^9R^{9a})_t$—N($R^{10}$)—$(CR^9R^{9a})_t]_k$—U—$(CR^9R^{9a})_t$—N($R^{11}$)—$(CR^9R^{9a})_t$—$R^{12}$", whose specific options are independently of each other; meanwhile, multiple $R^9$ of the structure formula "—[U—$(CR^9R^{9a})_t$—N($R^{10}$)—$(CR^9R^{9a})_t]_k$—U—$(CR^9R^{9a})_t$—N($R^{11}$)—$(CR^9R^{9a})_t$—$R^{12}$", whose specific options are independently of each other.

The term "prodrug" refers to a compound that is transformed in vivo into a compound of Formula (I). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in T. Higuchi et al., *Pro-drugs as Novel Delivery Systems*, Vol. 14, A.C.S. Symposium Series; Roche, et al. ed., *Bioreversible Carriers in Drug Design*, American Pharmaceutical Association and Pergamon Press, 1987; Rautio et al., Prodrugs: Design and Clinical Applications, *Nat. Rev. Drug Discovery*, 2008, 7, 255-270, and Hecker et al, Prodrugs of Phosphates and Phosphonates, *J. Med. Chem.*, 2008, 51, 2328-2345, all of which are incorporated herein by reference.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. The metabolites of a compound may be identified using routine techniques known in the art and their activities determined using tests such as those described herein. Such products may result for example from the oxidation, reduction, hydrolysis, amidation, deamidation, esterification, deesterification, enzyme cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

Stereochemical definitions and conventions used herein generally follow Parker et al., McGraw-Hill Dictionary of Chemical Terms (1984) McGraw-Hill Book Company, New York and Eliel et al., "*Stereochemistry of Organic Compounds*", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

A "pharmaceutically acceptable salts" refers to organic or inorganic salts of a compound disclosed herein. The pharmaceutically acceptable salts are well known in the art. For example, Berge et al., describe pharmaceutically acceptable salts in detail in *J. Pharmacol Sci*, 1977, 66: 1-19, which is incorporated herein by reference. Some non-limiting examples of the pharmaceutically salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, sodium malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, $C_{1-8}$ sulfonate or aryl sulfonate.

A "solvate" refers to an association or complex of one or more solvent molecules and a compound disclosed herein. Some non-limiting examples of the solvents that form solvates include water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Some non-limiting examples of suitable hydroxy-protecting groups include acetyl and silyl. A "carboxy-protecting group" refers to a substituent of the carboxy group that blocks or protects the carboxy functionality. Some non-limiting examples of common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfonyl)ethyl, 2-(diphenyl phosphino)-ethyl, nitroethyl, and the like. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

It should be noted that the term of "inhibiting HCV viral protein" should be broadly understood, which comprises inhibiting the expression level of HCV viral protein, inhibiting activity level of HCV viral protein, viral assembly and egress level. The expression level of HCV protein includes but not limited to translation level of the viral protein, posttranslational modification level of the viral protein, replication level of genetic material in offsprings and so on.

DESCRIPTION OF COMPOUNDS OF THE INVENTION

Provided herein are fused ring compounds, and pharmaceutical formulations thereof, that are useful in inhibiting HCV infection, especially inhibiting the activity of the non-structural 5A ("NS5A") protein In one aspect, provided herein are compounds having Formula (I):

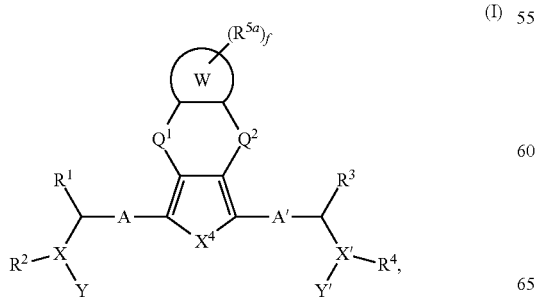

or a stereoisomer, a geometric isomer, a tautomer, an N-oxide, a hydrate, a solvate, a metabolite, a pharmaceutically acceptable salt or a prodrug thereof, wherein each of A and A' is independently a bond, alkylene, alkenylene, cycloalkylene, heterocycloalkylene, —$(CR^8R^{8a})_n$—O—$(CR^8R^{8a})_p$—, —$(CR^8R^{8a})_n$—$N(R^5)$—$(CR^8R^{8a})_p$—, —$(CR^8R^{8a})_n$—$S(=O)_r$—$N(R^5)$—$(CR^8R^{8a})_p$—, —$(CR^8R^{8a})_n$—$C(=O)$—$N(R^5)$—$(CR^8R^{8a})_p$—, —$(CR^8R^{8a})_n$—$N(R^5)$—$C(=O)$—$N(R^5)$—$(CR^8R^{8a})_p$—, —$(CR^8R^{8a})_n$—$C(=O)$—O—$(CR^8R^{8a})_p$—, —$(CR^8R^{8a})_n$—$N(R^5)$—$S(=O)_r$—$N(R^5)$—$(CR^8R^{8a})_p$—, —$(CR^8R^{8a})_n$—$S(=O)_r$—$(CR^8R^{8a})_p$—, —$(CR^8R^{8a})_n$—$S(=O)_r$—O—$(CR^8R^{8a})_p$—, —$(CR^8R^{8a})_n$—$C(=O)$—$C(CR^8R^{8a})_p$—, —$(CR^8R^{8a})_n$—$C(=S)$—$(CR^8R^{8a})_p$—, or —$(CR^8R^{8a})_n$—$N(R^5)$—$C(=O)$—O—$(CR^8R^{8a})_p$—, or each of A and A' is independently

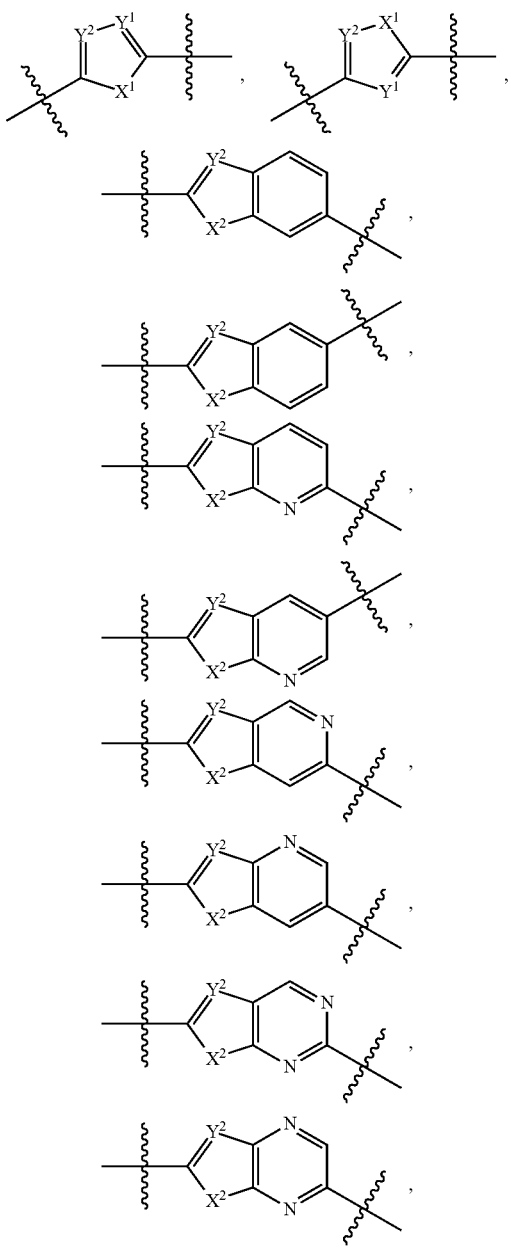

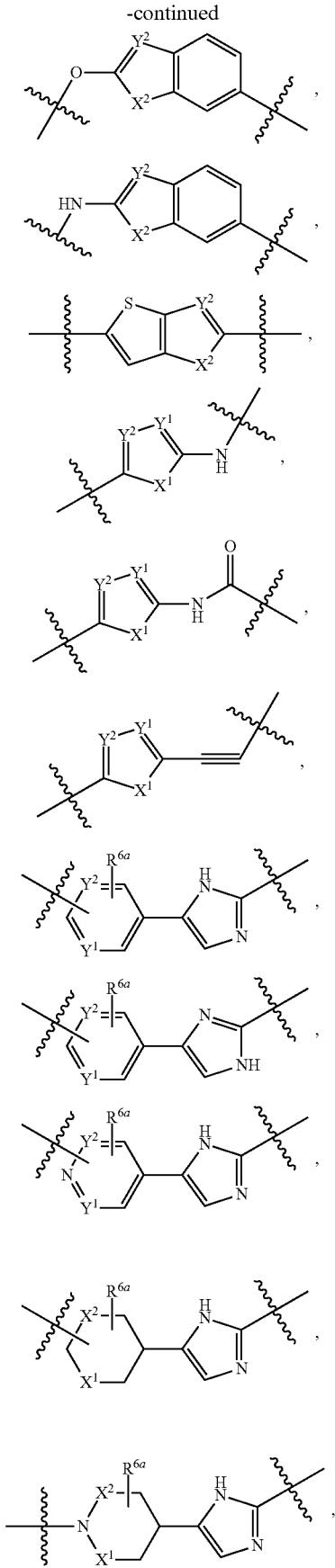
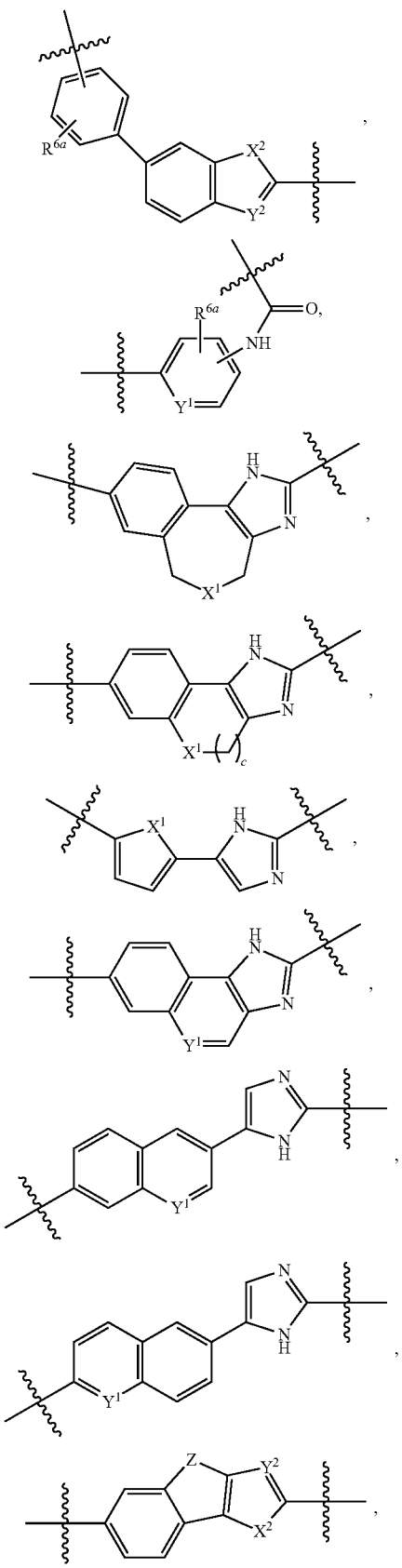

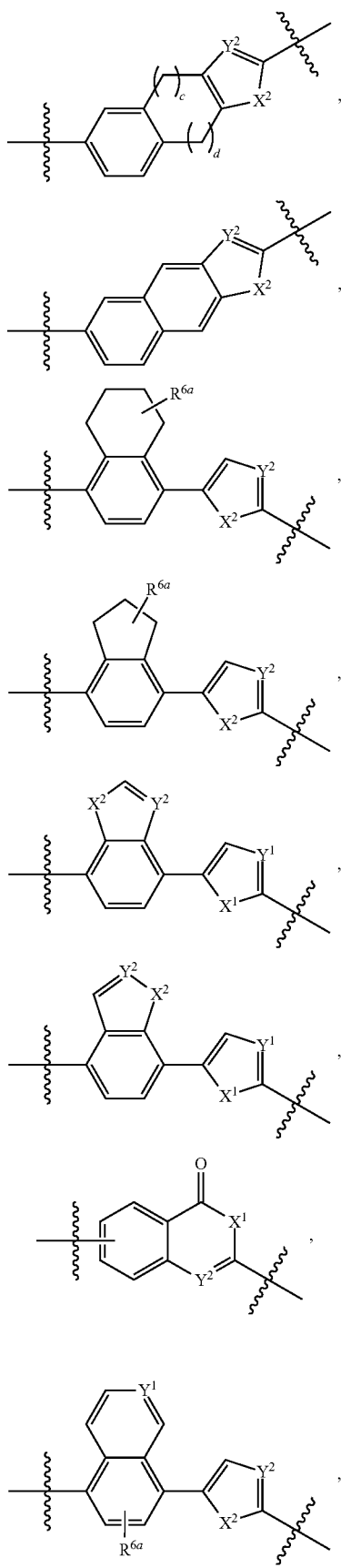

wherein each $X^1$ is independently O, S, $NR^6$, or $CR^7R^{7a}$;
each $X^2$ is independently $NR^6$, O or S;
$X^4$ is $(CR^7R^{7a})_n$, —$Y^1$=$Y^2$—, O, S or $NR^6$;
W is a carbocyclyl or heterocyclyl ring;
each $Y^1$ and $Y^2$ is independently N or $CR^7$;
Z is —$(CH_2)_a$—, —CH=CH—, —N=CH—, —$(CH_2)_a$—N($R^5$)—$(CH_2)_b$—, or —$(CH_2)_a$—O—$(CH_2)_b$—;
each c and d is independently 1 or 2;
each a, b, n and p is independently 0, 1, 2 or 3;
each r is independently 0, 1 or 2;
each of Q and $Q^2$ is independently a bond, $NR^6$, O, S, C(=O) or $(CR^7R^{7a})_e$;
each e and f is independently 0, 1, 2, 3 or 4;
each of X and X' is independently N or $CR^7$;
each of Y and Y' is independently H, deuterium, alkyl, heteroalkyl, cycloalkyl, heterocyclyl, aryl, heteroaryl, aralkyl, a monovalent group derived from an α-amino acid or an optically isomer thereof, or —[U—$(CR^9R^{9a})_t$—N($R^{10}$)—$(CR^9R^{9a})_t]_k$—U—$(CR^9R^{9a})_t$—N($R^{10}$)—$(CR^9R^{9a})_t$—$R^{12}$, —U—$(CR^9R^{9a})_t$—$R^{12}$ or —[U—$(CR^9R^{9a})_t$—N($R^{10}$)—$(CR^9R^{9a})_t]_k$—U—$(CR^9R^{9a})_t$—O—$(CR^9R^{9a})_t$—$R^{12}$;

each U is independently —C(=O)—, —C(=S)—, —S(=O)— or —S(=O)$_2$—;

each t is independently 0, 1, 2, 3 or 4;

each k is independently 0, 1 or 2;

each of $R^1$, $R^2$, $R^3$ and $R^4$ is independently H, deuterium, alkyl, heteroalkyl, aralkyl, cycloalkyl, heterocyclyl, heteroaryl or aryl; or $R^1$ and $R^2$, together with X—CH they are attached to, optionally form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle; or $R^3$ and $R^4$, together with X—CH they are attached to, optionally form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle;

each $R^5$ is independently H, deuterium, hydroxy, alkyl, heteroalkyl, cycloalkyl, heterocyclyl, aryl, heteroaryl, aralkyl, alkoxy, alkyl-OC(=O)—, alkyl-C(=O)—, carbamoyl, alkyl-OS(=O)$_r$—, alkyl-S(=O)$_r$O—, alkyl-S(=O)$_r$— or aminosulfonyl;

each $R^{5a}$ is independently H, deuterium, oxo(=O), hydroxy, amino, F, Cl, Br, I, cyano, $R^{13a}R^{13}N$—, —C(=O)NR$^{13}$R$^{13a}$, —OC(=O)NR$^{13}$R$^{13a}$, —OC(=O)OR$^{13}$, —N(R$^{13}$)C(=O)NR$^{13}$R$^{13a}$, —N(R$^{13}$)C(=O)OR$^{13a}$, —N(R$^{13}$)C(=O)—R$^{13a}$, R$^{13}$R$^{13a}$N—S(=O)$_2$—, R$^{13}$S(=O)$_2$—, R$^{13}$S(=O)$_2$N(R$^{13a}$)—, R$^{13a}$R$^{13}$N-alkyl, R$^{13}$S(=O)-alkyl, R$^{13}$R$^{13a}$N—C(=O)-alkyl, R$^{13a}$R$^{13}$N-alkoxy, R$^{13}$S(=O)-alkoxy, R$^{13}$R$^{13a}$N—C(=O)-alkoxy, aryl, heteroaryl, alkoxy, alkylamino, alkyl, haloalkyl, alkenyl, alkynyl, heterocyclyl, cycloalkyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, alkyacyl, alkylacyloxy, alkoxyacyl, alkylsulfonyl, alkoxysulfonyl, alkylsulfinyl, alkylsulfonyloxy, alkylsulfinyloxy, heterocyclylalkylamino or aryloxy;

each $R^6$ is independently H, deuterium, R$^{13}$R$^{13a}$NC(=O)—, R$^{13}$OC(=O)—, R$^{13}$C(=O)—, R$^{13}$R$^{13a}$NS(=O)—, R$^{13}$OS(=O)—, R$^{13}$S(=O)—, R$^{13}$R$^{13a}$NS(=O)$_2$—, R$^{13}$OS(=O)$_2$—, R$^{13}$S(=O)$_2$—, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl; wherein said aliphatic is alkyl;

each $R^{6a}$ is independently H, deuterium, hydroxy, amino, F, Cl, Br, I, cyano, oxo(=O), R$^{13a}$R$^{13}$N—, —C(=O)NR$^{13}$R$^{13a}$, —OC(=O)NR$^{13}$R$^{13a}$, —OC(=O)OR$^{13}$, —N(R$^{13}$)C(=O)NR$^{13}$R$^{13a}$, —N(R$^{13}$)C(=O)OR$^{13a}$, —N(R$^{13}$)C(=O)—R$^{13a}$, R$^{13}$R$^{13a}$N—S(=O)$_2$—, R$^{13}$S(=O)$_2$—, R$^{13}$S(=O)$_2$N(R$^{13a}$)—, R$^{13a}$R$^{13}$N-alkyl, R$^{13}$S(=O)-alkyl, R$^{13}$R$^{13a}$N—C(=O)-alkyl, R$^{13a}$R$^{13}$N-alkoxy, R$^{13}$S(=O)-alkoxy, R$^{13}$R$^{13a}$N—C(=O)-alkoxy, aryl, heteroaryl, alkoxy, alkylamino, alkyl, haloalkyl, alkenyl, alkynyl, heterocyclyl, cycloalkyl, mercapto, nitro, aralkyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, alkyacyl, alkylacyloxy, alkoxyacyl, alkylsulfonyl, alkoxysulfonyl, alkylsulfinyl, alkylsulfonyloxy, alkylsulfinyloxy, heterocyclylalkylamino or aryloxy;

each $R^7$ and $R^{7a}$ is independently H, deuterium, F, Cl, Br, I, aliphatic, heteroalkyl, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl; wherein said aliphatic is alkyl;

each $R^8$ and $R^{8a}$ is independently H, deuterium, hydroxy, cyano, nitro, F, Cl, Br, I, alkyl, heteroalkyl, cycloalkyl, heterocyclyl, aryl, heteroaryl, aralkyl, alkoxy, alkyl-OC(=O)—, alkyl-C(=O)—, carbamoyl, alkyl-OS(=O)$_r$—, alkyl-S(=O)$_r$O—, alkyl-S(=O)$_r$— or aminosulfonyl;

each $R^9$, $R^{9a}$, $R^{10}$ and $R^{11}$ is independently H, deuterium, alkyl, heteroalkyl, cycloalkyl, heterocyclyl, aryl, heteroaryl, aralkyl, haloalkyl, hydroxyalkyl, heteroarylalkyl, heterocyclylalkyl or cycloalkylalkyl;

each $R^{12}$ is independently R$^{13a}$R$^{13}$N—, —C(=O)R$^{13}$, —C(=S)R$^{13}$, —C(=O)—O—R$^{13}$, —C(=O)NR$^{13}$R$^{13a}$, —OC(=O)NR$^{13}$R$^{13a}$, —OC(=O)OR$^{13}$, —N(R$^{13}$)C(=O)NR$^{13}$R$^{13a}$, —N(R$^{13}$)C(=O)OR$^{13a}$, —N(R$^{13}$)C(=O)—R$^{13a}$, R$^{13}$R$^{13a}$N—S(=O)$_2$—, R$^{13}$S(=O)$_2$—, R$^{13}$S(=O)$_2$N(R$^{13a}$)—, R$^{13}$OS(=O)$_2$—, alkyl, heteroalkyl, cycloalkyl, heterocyclyl, aryl, heteroaryl or aralkyl;

or $R^{11}$ and $R^{12}$ are optionally joined to form a 4-7 membered ring; and each $R^{13}$ and $R^{13a}$ is independently H, deuterium, alkyl, heteroalkyl, cycloalkyl, heterocyclyl, aryl, heteroaryl, or aralkyl; with the proviso that where $R^{13}$ and $R^{13a}$ are bonded to the same nitrogen atom, $R^{13}$ and $R^{13a}$, together with the nitrogen atom they are attached to, optionally form a substituted or unsubstituted 3-8 membered ring, or a substituted or unsubstituted spiro bicyclic ring or fused bicyclic ring, wherein each of alkylene, alkenylene, cycloalkylene, heterocycloalkylene, —(CR$^8$R$^{8a}$)$_n$—O—(CR$^8$R$^{8a}$)$_p$—, —(CR$^8$R$^{8a}$)$_n$—N(R$^5$)—(CR$^8$R$^{8a}$)$_p$—, —(CR$^8$R$^{8a}$)$_n$—S(=O)$_r$—N(R$^5$)—(CR$^8$R$^{8a}$)$_p$—, —(CR$^8$R$^{8a}$)$_n$—C(=)—N(R$^5$)—(CR$^8$R$^{8a}$)$_p$—, —(CR$^8$R$^{8a}$)$_n$—N(R$^5$)—(CR$^8$R$^{8a}$)$_p$—, —(CR$^8$R$^{8a}$)$_n$—C(=O)—O—(CR$^8$R$^{8a}$)$_p$—, —(CR$^8$R$^{8a}$)$_n$—N(R$^5$)—S(=O)$_r$—N(R$^5$)—(CR$^8$R$^{8a}$)$_p$—, —(CR$^8$R$^{8a}$)$_n$—S(=O)$_r$—(CR$^8$R$^{8a}$)$_p$—, —(CR$^8$R$^{8a}$)$_n$—S(=O)$_r$—O—(CR$^8$R$^{8a}$)$_p$—, —(CR$^8$R$^{8a}$)$_n$—C(=O)—(CR$^8$R$^{8a}$)$_p$—, —(CR$^8$R$^{8a}$)$_n$—C(=S)—(CR$^8$R$^{8a}$)$_p$—, —(CR$^8$R$^{8a}$)$_n$—N(R$^5$)—C(=O)—O—(CR$^8$R$^{8a}$)$_p$—, —[U—(CR$^9$R$^{9a}$)$_t$—NR$^{10}$—(CR$^9$R$^{9a}$)$_t$]$_k$—U—(CR$^9$R$^{9a}$)$_t$—NR$^{11}$—(CR$^9$R$^{9a}$)$_t$—R$^{12}$, —U—(CR$^9$R$^{9a}$)$_t$—R$^{12}$, —[U—(CR$^9$R$^{9a}$)$_t$—NR$^{10}$—(CR$^9$R$^{9a}$)$_t$]$_k$—U—(CR$^9$R$^{9a}$)$_t$—O—(CR$^9$R$^{9a}$)$_t$—R$^{12}$, NR$^6$, CR$^7$R$^{7a}$, CR$^7$, —(CH$_2$)$_a$—, —CH=CH—, —N=CH—, —(CH$_2$)$_a$—N(R$^5$)—(CH$_2$)$_b$—, —(CH$_2$)$_a$—O—(CH$_2$)$_b$—, R$^{13a}$R$^{13}$N—, —C(=O)R$^{13}$, —C(=S)R$^{13}$, —C(=O)—O—R$^{13}$, —C(=O)NR$^{13}$R$^{13a}$, —OC(=O)NR$^{13}$R$^{13a}$, —OC(=O)OR$^{13}$, —N(R$^{13}$)C(=O)NR$^{13}$R$^{13a}$, —N(R$^{13}$)C(=O)OR$^{13a}$, —N(R$^{13}$)C(=O)—R$^{13a}$, R$^{13}$R$^{13a}$N—S(=O)$_2$—, R$^{13}$S(=O)$_2$—, R$^{13}$S(=O)$_2$N(R$^{13a}$)—, R$^{13}$OS(=O)$_2$—, R$^{13a}$R$^{13}$N—, alkyl-OC(=O)—, alkyl-C(=O)—, alkyl-OS(=O)$_r$—, alkyl-S(=O)$_r$O—, alkyl-S(=O)$_r$—, R$^{13}$R$^{13a}$NS(=O)—, R$^{13}$OS(=O)—, R$^{13}$S(=O)—, R$^{13a}$R$^{13}$N-alkyl, R$^{13}$S(=O)-alkyl, R$^{13}$R$^{13a}$N—C(=O)-alkyl, R$^{13a}$R$^{13}$N-alkoxy, R$^{13}$S(=O)-alkoxy, R$^{13}$R$^{13a}$N—C(=O)-alkylamino, alkyl, heteroalkyl, carbocyclyl, cycloalkyl, heterocyclyl, aryl, heteroaryl, aralkyl, α-amino acid, $C_{5-12}$ fused bicycle, $C_{5-12}$ fused heterobicycle, $C_{5-12}$ spiro bicycle, $C_{5-12}$ spiro heterobicycle, alkoxy, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, haloalkyl, alkenyl, alkynyl, arylamino, heteroarylamino, arylalkylamino, heteroarylalkylamino, heteroaryloxy, heteroarylalkyl, arylalkoxy, heteroarylalkoxy, heterocyclyloxy, heterocyclylalkoxy, heterocyclylamino, heterocyclylalkylamino and aryloxy is optionally substituted with one or more substituents which independently selected from deuterium, hydroxy, amino, halo, cyano, aryl, heteroaryl, alkoxy, alkylamino, alkylthio, alkyl, alkenyl, alkynyl, heterocyclyl, mercapto, nitro, aryloxy, heteroaryloxy, oxo(=O), carboxy, hydroxy-substituted alkoxy, hydroxy-substituted alkyl-C(=O), alkyl-C(=O), alkyl-S(=O), alkyl-S(=O)$_2$—, hydroxy-substituted alkyl-S(=O), hydroy-substituted alkyl-S(=O)$_2$ or carboxy-substituted alkoxy.

In some embodiments, W is a $C_{3-8}$ carbocyclyl or $C_{2-10}$ heterocyclyl ring.

In some embodiments,

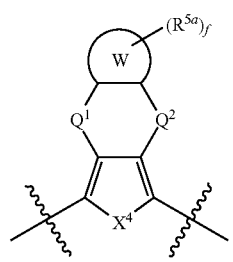

is

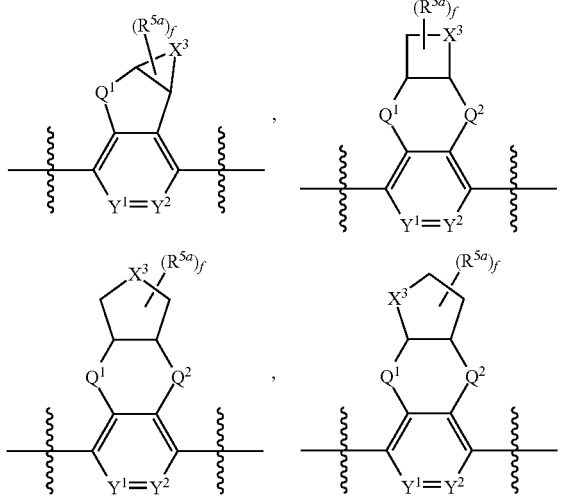

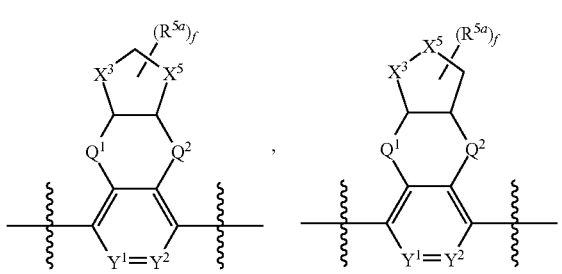

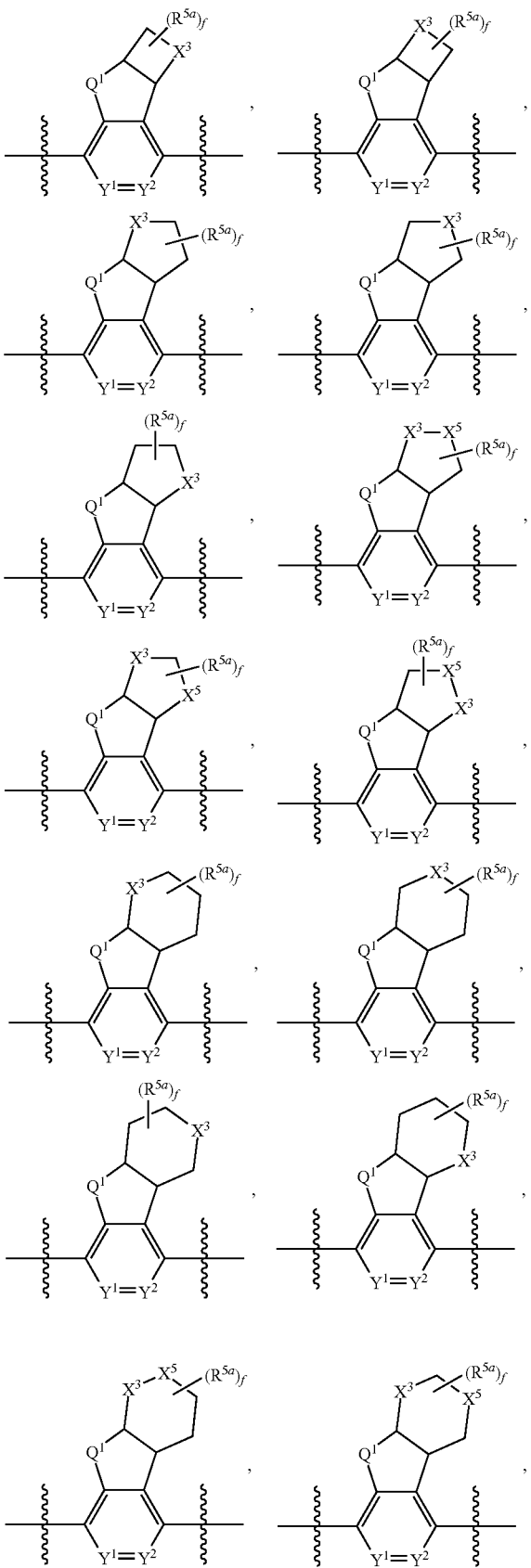

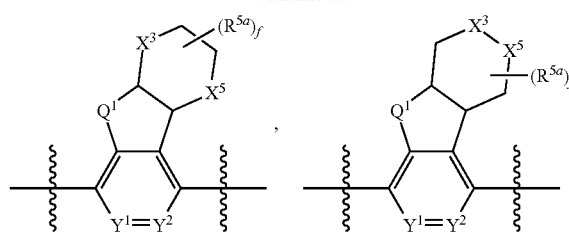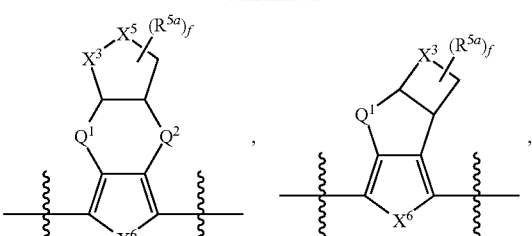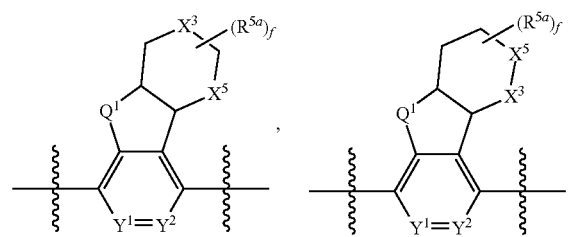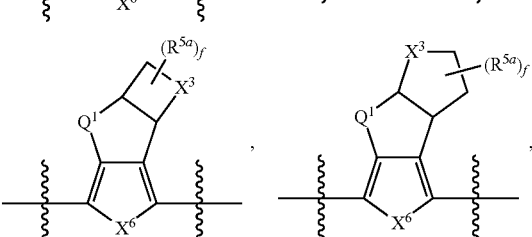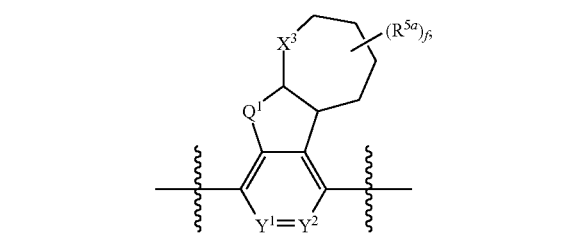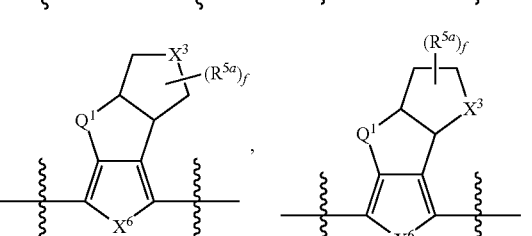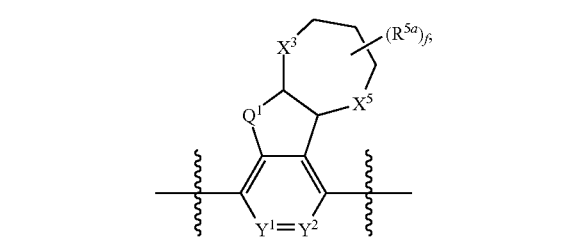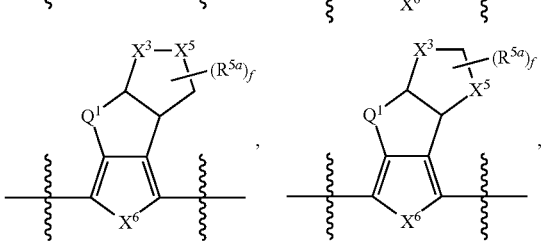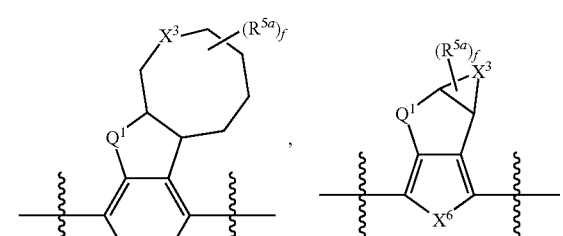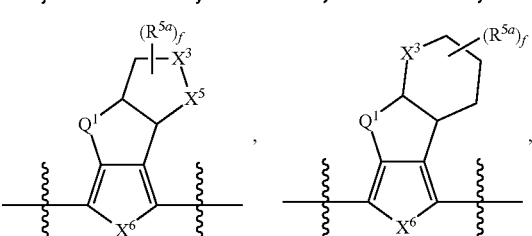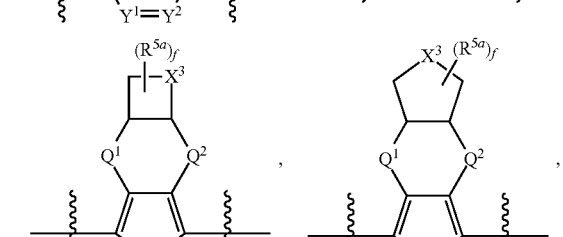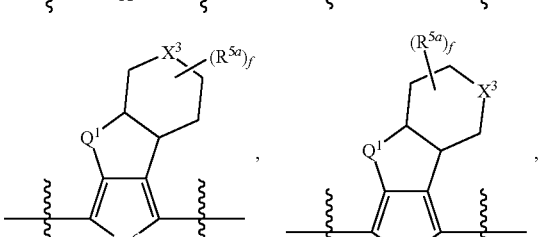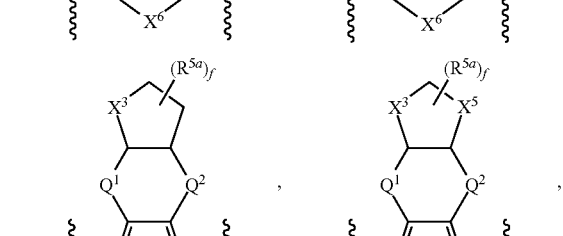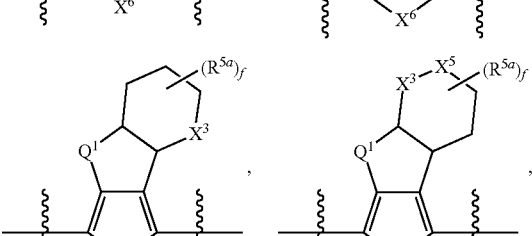

-continued

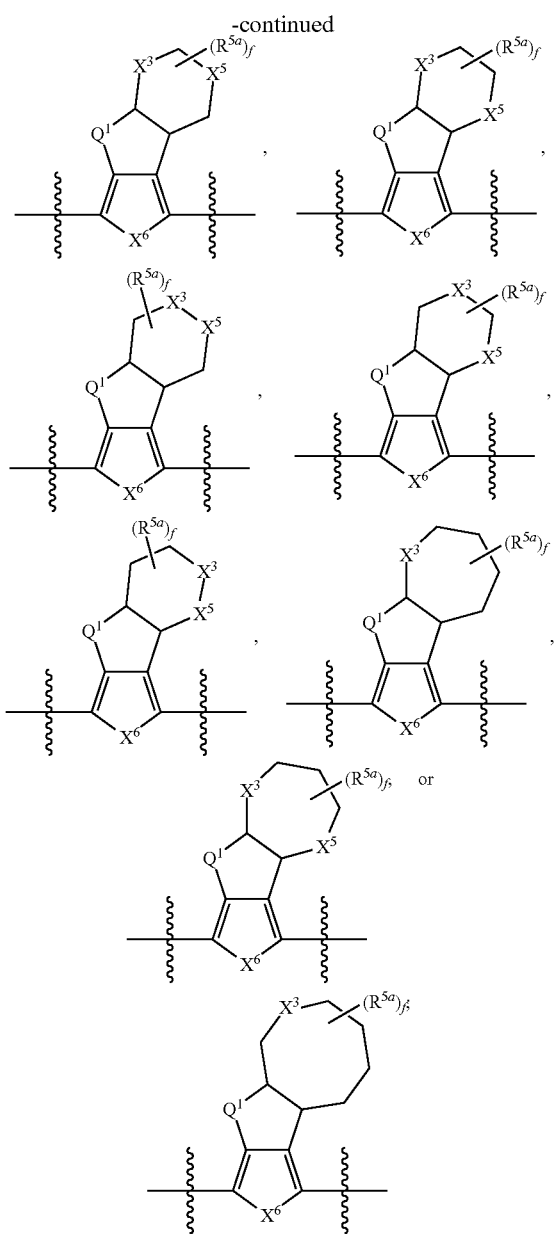

wherein each $X^6$ is independently $CR^7R^{7a}$, O, S or $NR^6$;
each $Y^1$ and $Y^2$ is independently N or $CR^7$;
each f is independently 0, 1, 2, 3 or 4;
each $X^3$ and $X^5$ is independently $NR^6$, O, S, $C(=O)$ or $(CR^7R^{7a})_e$;
each $Q^1$ and $Q^2$ is independently a bond, $NR^6$, O, S, $C(=O)$ or $(CR^7R^{7a})_e$;
each e is independently 0, 1, 2, 3 or 4;
each $R^{5a}$ is independently H, deuterium, oxo($=O$), hydroxy, amino, F, Cl, Br, I, cyano, $R^{13a}R^{13}N-$, $-C(=O)NR^{13}R^{13a}$, $-OC(=O)NR^{13}R^{13a}$, $-OC(=O)OR^{13}$, $-N(R^{13})C(=O)NR^{13}R^{13a}$, $-N(R^{13})C(=O)OR^{13a}$, $-N(R^{13})C(=O)-R^{13a}$, $R^{13}R^{13a}N-S(=O)_2-$, $R^{13}S(=O)_2-$, $R^{13}S(=O)_2N(R^{13a})-$, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, $-CF_3$, $-OCF_3$, mercapto, nitro, $C_{1-6}$ alkylamino, $C_{3-10}$ cycloalkyl or $C_{6-10}$ aryloxy;

each $R^6$ is independently H, deuterium, $R^{13}R^{13a}NC(=O)-$, $R^{13}OC(=O)-$, $R^{13}C(=O)-$, $R^{13}R^{13a}NS(=O)-$, $R^{13}OS(=O)-$, $R^{13}S(=O)-$, $R^{13}R^{13a}NS(=O)_2-$, $R^{13}OS(=O)_2-$, $R^{13}S(=O)_2-$, $C_{1-6}$ alkyl, $C_{1-6}$ haloalkyl, $C_{1-6}$ hydroxyalkyl, $C_{1-6}$ aminoalkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocycyl-$C_{1-6}$-alkyl, $C_{3-10}$ cycloalkyl-$C_{1-6}$-alkyl, $C_{6-10}$ aryloxy-$C_{1-6}$-alkyl, $C_{2-10}$ heterocyclyloxy-$C_{1-6}$-alkyl, $C_{3-10}$ cycloalkyloxy-$C_{1-6}$-alkyl, $C_{6-10}$ arylamino-$C_{1-6}$-alkyl, $C_{2-10}$ heterocyclylamino-$C_{1-6}$-alkyl, $C_{3-10}$ cycloalkylamino-$C_{1-6}$-alkyl, $C_{6-10}$ aryl, $C_{1-9}$ heteroaryl, $C_{2-10}$ heterocyclyl or $C_{3-10}$ carbocyclyl;

each $R^7$ and $R^{7a}$ is independently H, deuterium, F, Cl, Br, I, $C_{1-6}$ alkyl, $C_{2-6}$ heteroalkyl, $C_{1-6}$ haloalkyl, $C_{1-6}$ hydroxyalkyl, $C_{1-6}$ aminoalkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocycyl-$C_{1-6}$-alkyl, $C_{3-10}$ cycloalkyl-$C_{1-6}$-alkyl, $C_{6-10}$ aryloxy-$C_{1-6}$-alkyl, $C_{2-10}$ heterocyclyloxy-$C_{1-6}$-alkyl, $C_{3-10}$ cycloalkyloxy-$C_{1-6}$-alkyl, $C_{6-10}$ arylamino-$C_{1-6}$-alkyl, $C_{2-10}$ heterocyclylamino-$C_{1-6}$-alkyl, $C_{3-10}$ cycloalkylamino-$C_{1-6}$-alkyl, $C_{6-10}$ aryl, $C_{1-9}$ heteroaryl, $C_{2-10}$ heterocyclyl or $C_{3-10}$ carbocyclyl; and each $R^1$ and $R^{13}$ is independently H, deuterium, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; with the proviso that where $R^{13}$ and $R^{13a}$ are bonded to the same nitrogen atom, $R^{13}$ and $R^{13a}$ together with the nitrogen atom they are attached to, optionally form a substituted or unsubstituted 3-8 membered ring, or a substituted or unsubstituted spiro bicyclic ring or fused bicyclic ring.

In some embodiments,

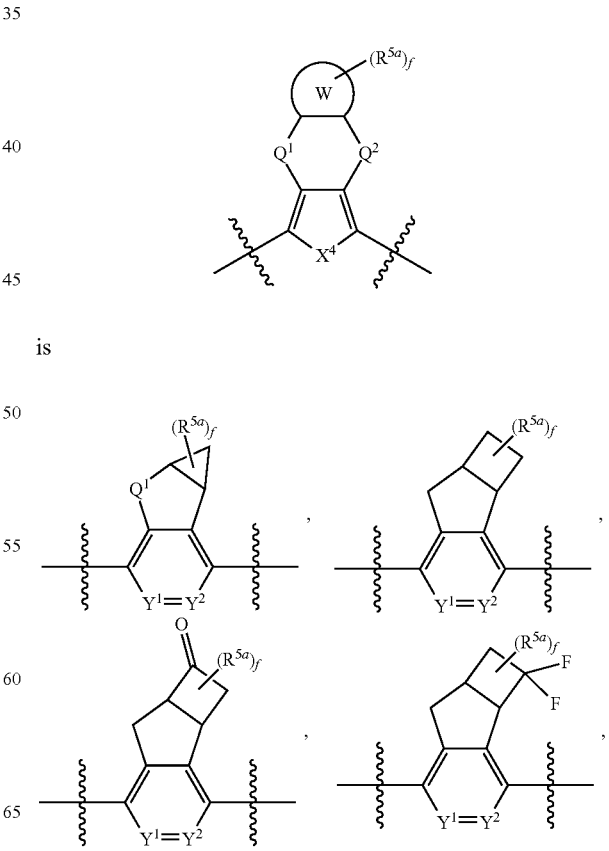

is

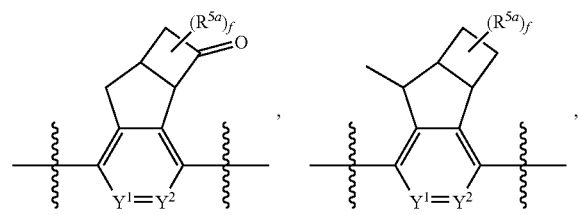,
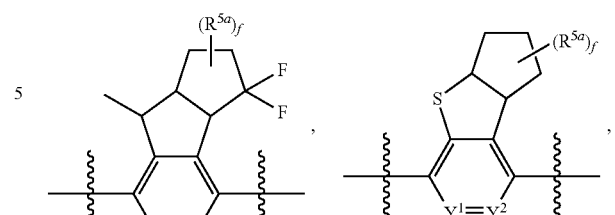,
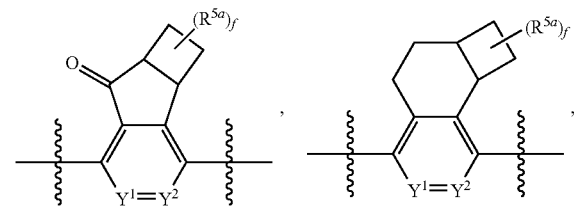,
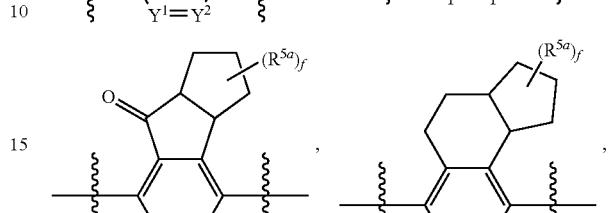,
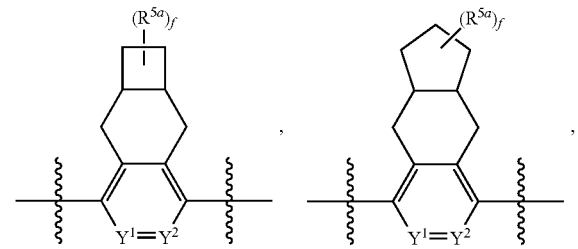,
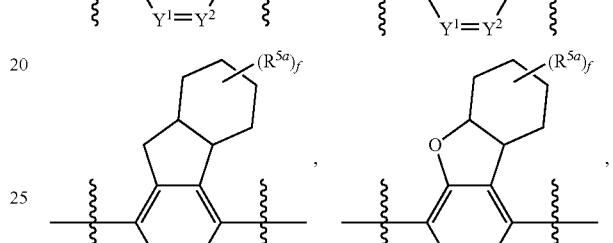,
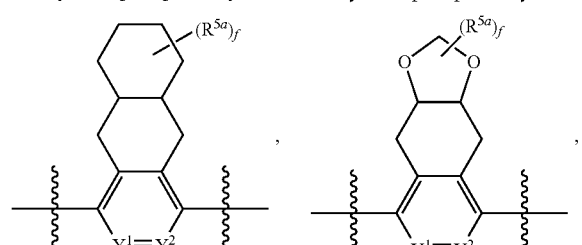,
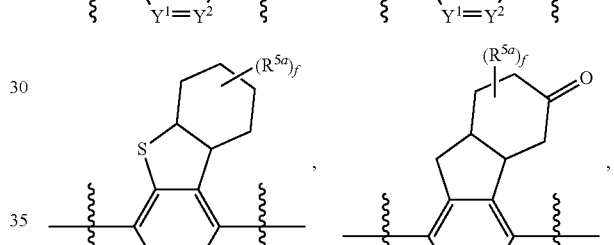,
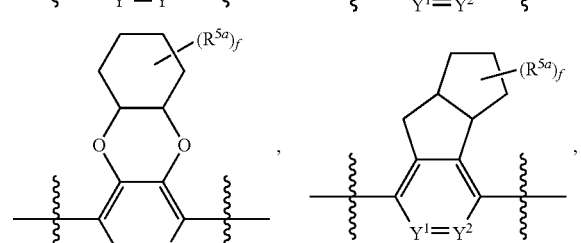,
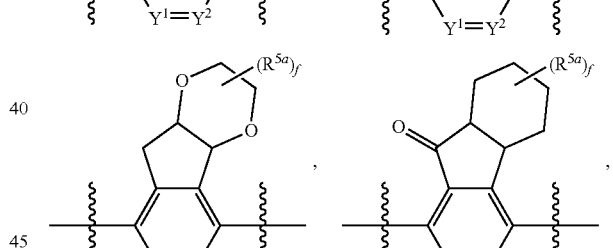,
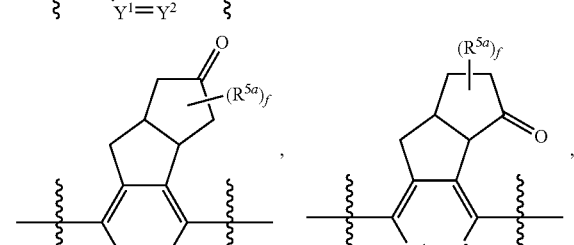,
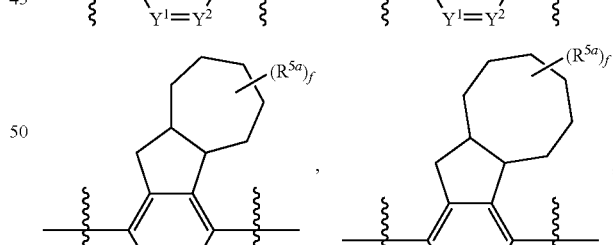,
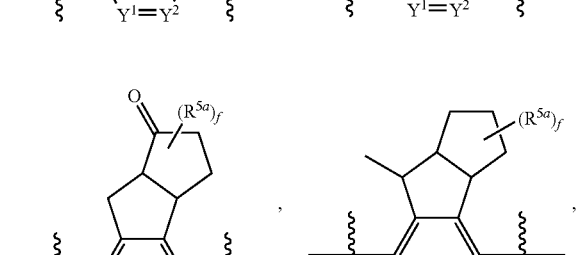,
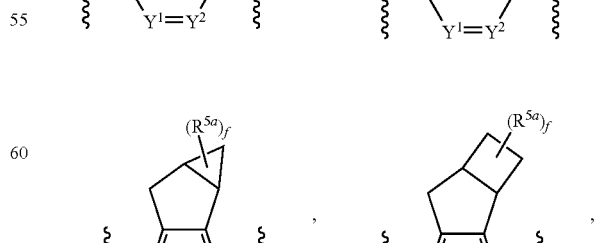, 101
-continued
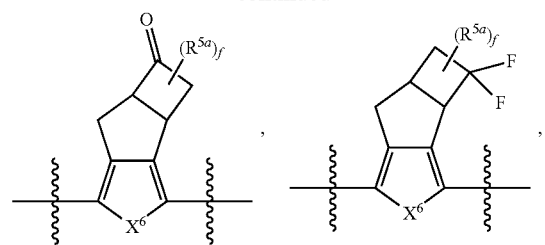
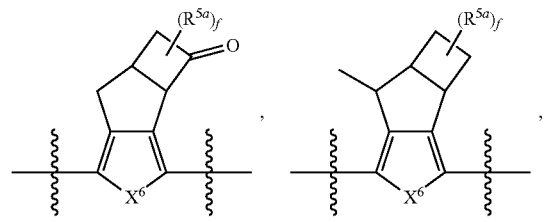
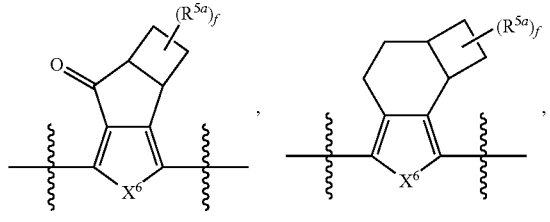
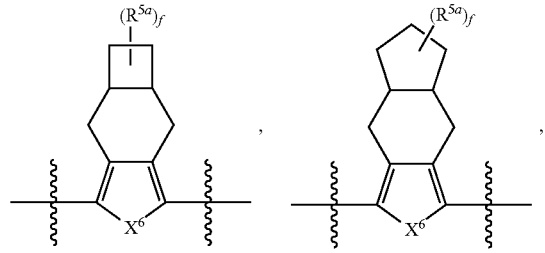
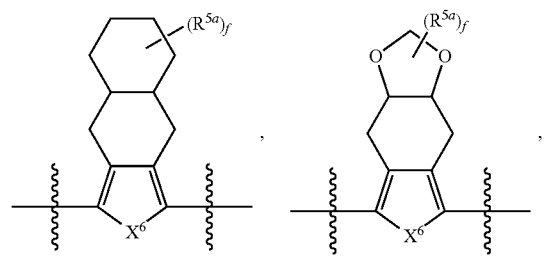
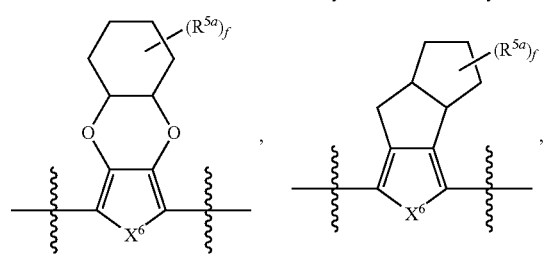
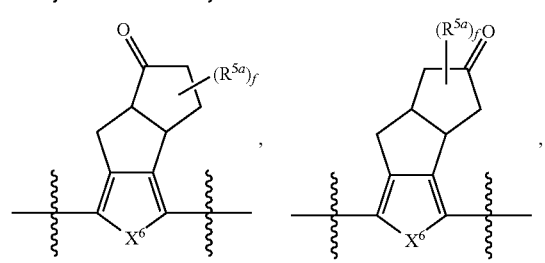
102
-continued
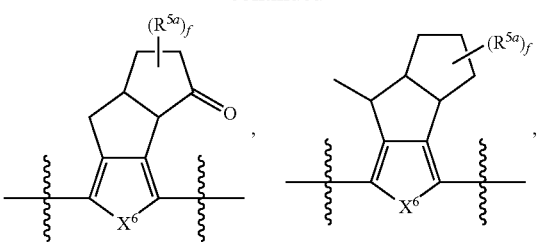
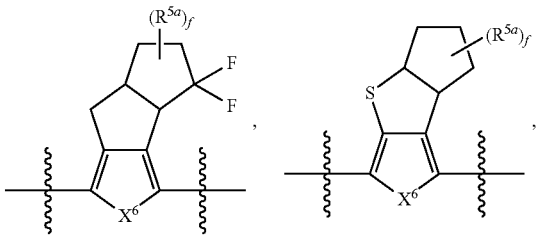
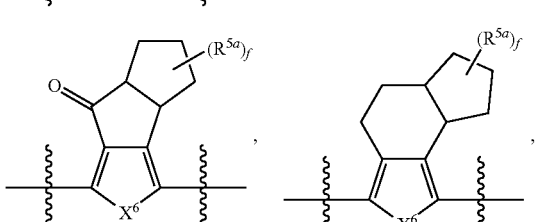
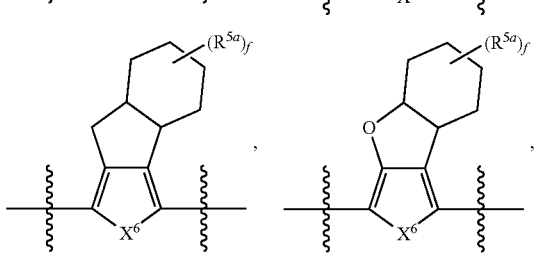
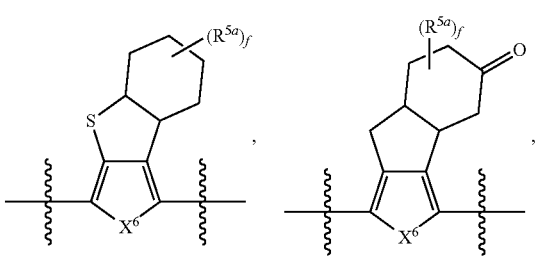
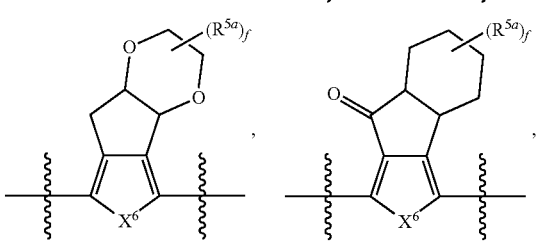
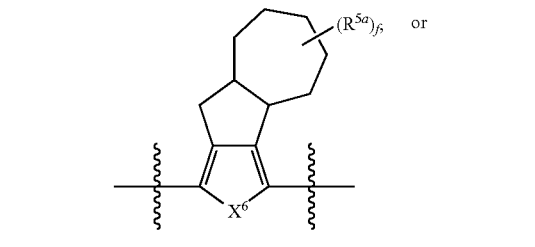

-continued

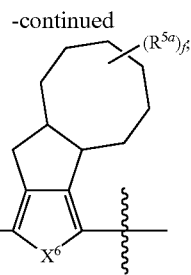

wherein each $Y^1$ and $Y^2$ is independently N or $CR^7$;
each $X^6$ is independently $CR^7R^{7a}$, O, S, or $NR^6$;
each f is independently 0, 1, 2, 3 or 4;
each $R^{5a}$ is independently H, deuterium, oxo(=O), hydroxy, amino, F, Cl, Br, I, cyano, $R^{13a}R^{13}N-$, $-C(=O)NR^{13}R^{13a}$, $-OC(=O)NR^{13}R^{13a}$, $-OC(=O)OR^{13}$, $-N(R^{13})C(=O)NR^{13}R^{13a}$, $-N(R^{13})C(=O)OR^{13a}$, $-N(R^{13})C(=O)-R^{13a}$, $R^{13}R^{13a}N-S(=O)_2-$, $R^{13}S(=O)_2-$, $R^{13}S(=O)_2N(R^{13a})-$, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$ alkylsulfinyloxy, $C_{1-6}$ alkoxy, $C_{1-6}$ alkyl, $C_{6-10}$ aryl, $-CF_3$, $-OCF_3$, mercapto, nitro or $C_{1-6}$ alkylamino;
each $R^6$ is independently H, deuterium, $C_{1-6}$ alkyl, $C_{1-6}$ haloalkyl, $C_{1-6}$ hydroxyalkyl, $C_{1-6}$ aminoalkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, or $C_{3-8}$ cycloalkyl-$C_{1-6}$-alkyl;
each $R^7$ and $R^{7a}$ is independently H, deuterium, F, Cl, Br, I, $C_{1-6}$ alkyl, $C_{2-6}$ heteroalkyl, $C_{1-6}$ haloalkyl, $C_{1-6}$ hydroxyalkyl, $C_{1-6}$ aminoalkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryloxy-$C_{1-6}$-alkyl, $C_{2-10}$ heterocyclyloxy-$C_{1-6}$-alkyl, $C_{3-10}$ cycloalkyloxy-$C_{1-6}$-alkyl, $C_{6-10}$ arylamino-$C_{1-6}$-alkyl, $C_{2-10}$ heterocyclylamino-$C_{1-6}$-alkyl, $C_{3-10}$ cycloalkylamino-$C_{1-6}$-alkyl, $C_{6-10}$ aryl, $C_{1-9}$ heteroaryl, $C_{2-10}$ heterocyclyl or $C_{3-8}$ carbocyclyl; and
each $R^{13}$ and $R^{13a}$ is independently H, deuterium, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; with the proviso that where $R^{13}$ and $R^{13a}$ are bonded to the same nitrogen atom, $R^{13}$ and $R^{13a}$, together with the nitrogen atom they are attached to, optionally form a substituted or unsubstituted 3-8 membered ring, or a substituted or unsubstituted spiro bicyclic ring or fused bicyclic ring.

In some embodiments, each of A and A' is independently a bond, $C_{1-6}$ alkylene, $C_{2-6}$ alkenylene, $C_{3-8}$ cycloalkylene, $C_{2-10}$ heterocycloalkylene, $-(CR^8R^{8a})_n-O-(CR^8R^{8a})_p-$, $-(CR^8R^{8a})_n-N(R^5)-(CR^8R^{8a})_p-$, $-(CR^8R^{8a})_n-S(=O)_r-N(R^5)-(CR^8R^{8a})_p-$, $-(CR^8R^{8a})_n-C(=O)-N(R^5)-(CR^8R^{8a})_p-$, $-(CR^8R^{8a})_n-N(R^5)-C(=O)-N(R^5)-(CR^8R^{8a})_p-$, $-(CR^8R^{8a})_n-C(=O)-O-(CR^8R^{8a})_p-$, $-(CR^8R^{8a})_n-N(R^5)-S(=O)_r-N(R^5)-(CR^8R^{8a})_p-$, $-(CR^8R^{8a})_n-S(=O)_r-(CR^8R^{8a})_p-$, $-(CR^8R^{8a})_n-S(=O)_r-O-(CR^8R^{8a})_p-$, $-(CR^8R^{8a})_n-C(=O)-(CR^8R^{8a})_p-$, $-(CR^8R^{8a})_n-C(=S)-(CR^8R^{8a})_p-$, or $-(CR^8R^{8a})_n-N(R^5)-C(=O)-O-(CR^8R^{8a})_p-$, or each of A and A' is independently

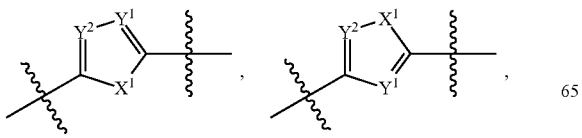

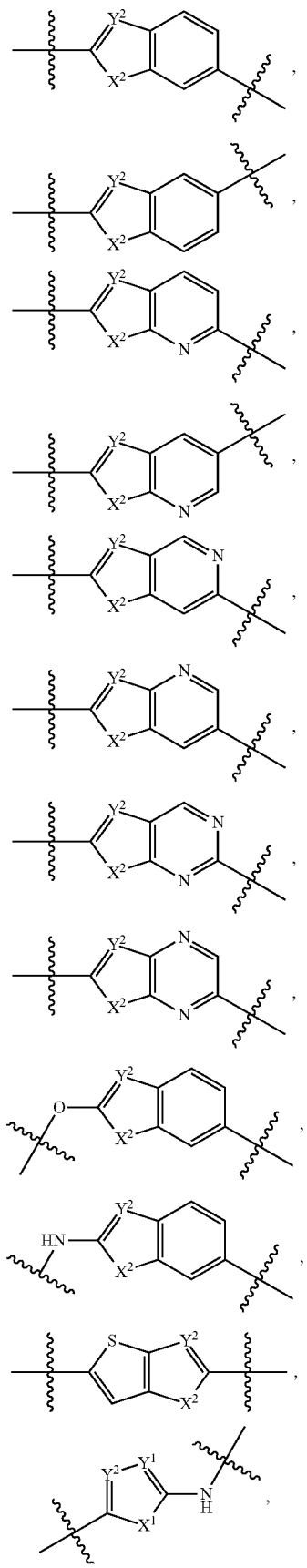

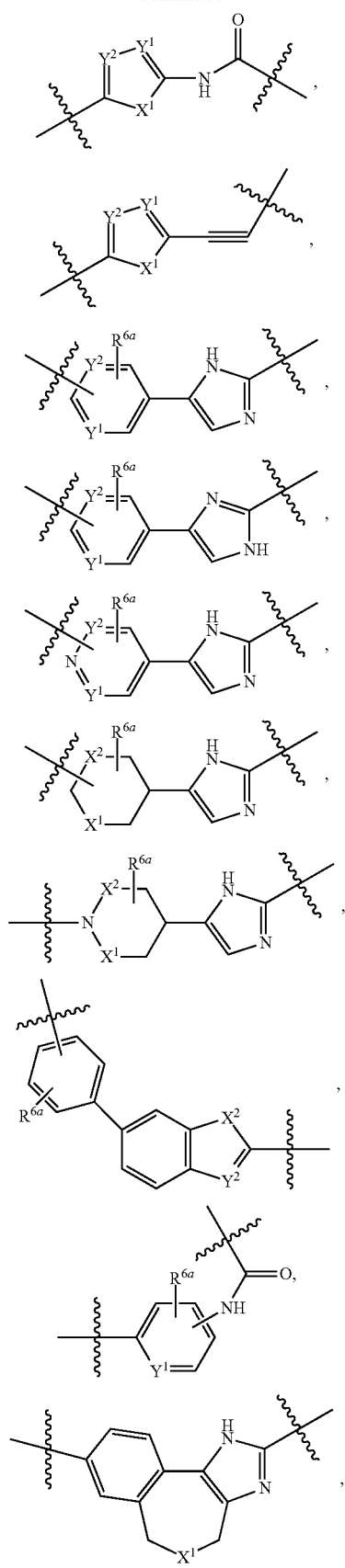
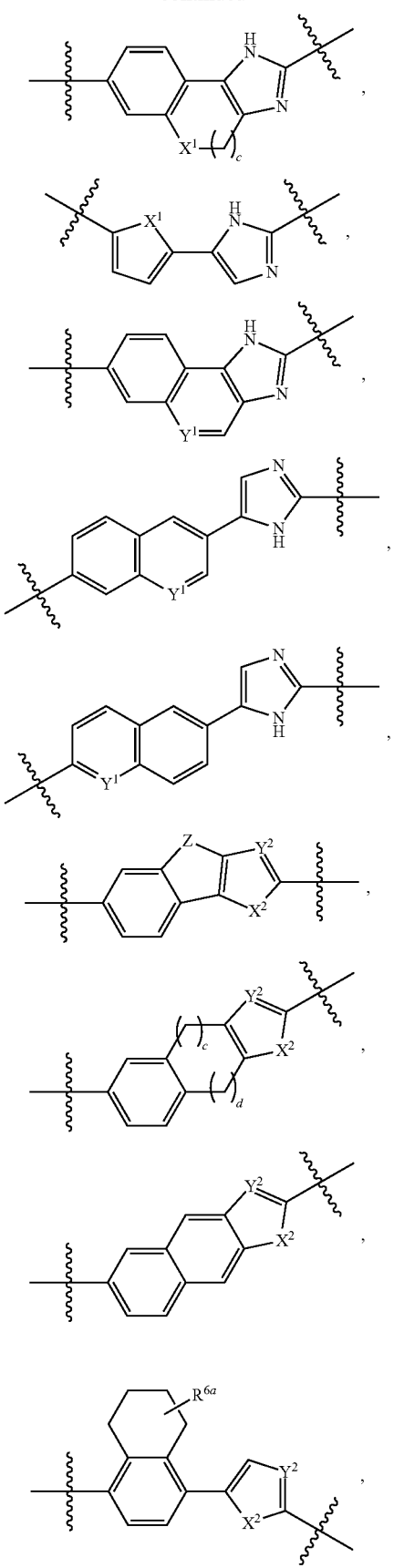

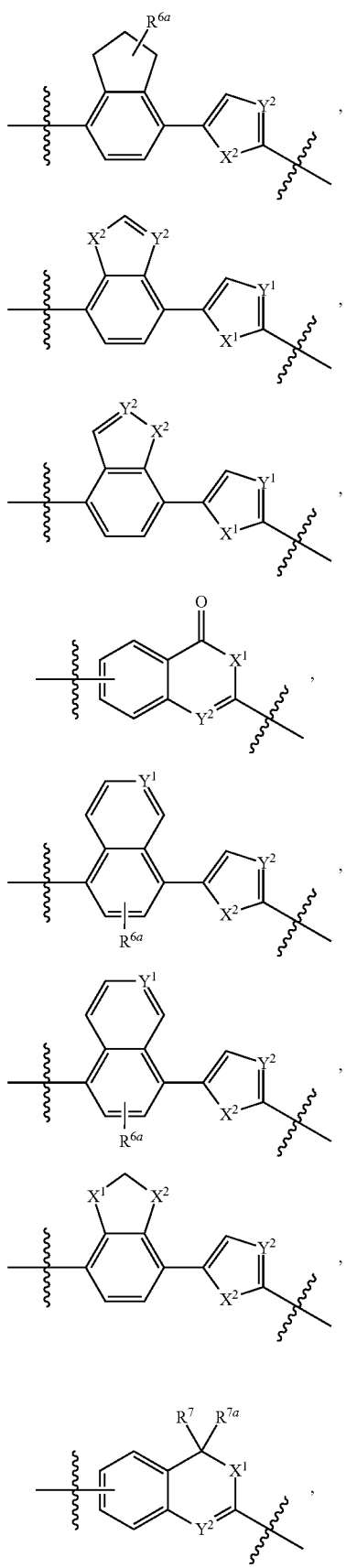

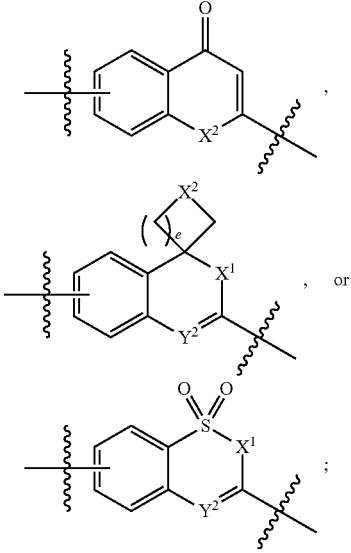

wherein each $X^1$ is independently O, S, $NR^6$, or $CR^7R^{7a}$;
each $X^2$ is independently $NR^6$, O or S;
each $Y^1$ and $Y^2$ is independently N or $CR^7$;
each e is independently 0, 1, 2, 3 or 4;
Z is $—(CH_2)_a—$, $—CH=CH—$, $—N=CH—$, $—(CH_2)_a—N(R^5)—(CH_2)_b—$ or $—(CH_2)_a—O—(CH_2)_b—$;
each c and d is independently 1 or 2;
each a, b, n and p is independently 0, 1, 2 or 3;
each r is independently 0, 1 or 2;
each $R^5$ is independently H, deuterium, hydroxy, $C_{1-6}$ alkyl, $C_{2-6}$ heteroalkyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;
each $R^6$ is independently H, deuterium, $R^{13}R^{13a}NC(=O)—$, $R^{13}OC(=O)—$, $R^{13}C(=O)—$, $R^{13}R^{13a}NS(=O)—$, $R^{13}OS(=O)—$, $R^{13}S(=O)—$, $R^{13}R^{13a}NS(=O)_2—$, $R^{13}OS(=O)_2—$, $R^{13}S(=O)_2—$, $C_{1-6}$ alkyl, $C_{1-6}$ haloalkyl, $C_{1-6}$ hydroxyalkyl, $C_{1-6}$ aminoalkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryloxy-$C_{1-6}$-alkyl, $C_{2-10}$ heterocyclyloxy-$C_{1-6}$-alkyl, $C_{3-10}$ cycloalkyloxy-$C_{1-6}$-alkyl, $C_{6-10}$ arylamino-$C_{1-6}$-alkyl, $C_{2-10}$ heterocyclylamino-$C_{1-6}$-alkyl, $C_{3-10}$ cycloalkylamino-$C_{1-6}$-alkyl, $C_{6-10}$ aryl, $C_{1-9}$ heteroaryl, $C_{2-10}$ heterocyclyl or $C_{3-10}$ carbocyclyl;
each $R^{6a}$ is independently H, deuterium, hydroxy, amino, F, Cl, Br, I, cyano, oxo(=O), $R^{13a}R^{13}N—$, $—C(=O)NR^{13}R^{13a}$, $—OC(=O)NR^{13}R^{13a}$, $—OC(=O)OR^{13}$, $—N(R^{13})C(=O)NR^{13}R^{13a}$, $—N(R^{13})C(=O)OR^{13a}$, $—N(R^{13})C(=O)—R^{13a}$, $R^{13}R^{13a}N—S(=O)_2—$, $R^{13}S(=O)_2—$, $R^{13}S(=O)_2N(R^{13a})—$, $R^{13a}R^{13}N—C_{1-6}$ alkyl, $R^{13}S(=O)—C_{1-6}$ alkyl, $R^{13}R^{13a}N—C(=O)—C_{1-6}$ alkyl, $R^{13a}R^{13}N—C_{1-6}$ alkoxy, $R^{13}S(=O)—C_{1-6}$ alkoxy, $R^{13}R^{13a}N—C(=O)—C_{1-6}$ alkoxy, $C_{6-10}$ aryl, $C_{1-9}$ heteroaryl, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, $C_{2-10}$ heterocyclyl, $C_{3-8}$ cycloalkyl, mercapto, nitro, $C_{6-10}$ aryl-$C_{1-6}$-alkyl, $C_{6-10}$ arylamino, $C_{1-9}$ heteroarylamino or $C_{6-10}$ aryloxy;
each $R^7$ and $R^{7a}$ is independently H, deuterium, F, Cl, Br, I, $C_{1-6}$ alkyl, $C_{2-6}$ heteroalkyl, $C_{1-6}$ haloalkyl, $C_{1-6}$ hydroxyalkyl, $C_{1-6}$ aminoalkyl, $C_{1-6}$ alkoxy-$C_{1-6}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryloxy-$C_{1-6}$-alkyl, $C_{2-10}$ heterocyclyloxy-$C_{1-6}$-alkyl, $C_{3-10}$ cycloalkyloxy-$C_{1-6}$-alkyl, $C_{6-10}$ arylamino-$C_{1-6}$-alkyl, $C_{2-10}$ heterocyclylamino-$C_{1-6}$-alkyl, $C_{3-10}$ cycloalkylamino-$C_{1-6}$-alkyl, $C_{6-10}$ aryl, $C_{1-9}$ heteroaryl, $C_{2-10}$ heterocyclyl or $C_{3-8}$ carbocyclyl;

each $R^{13}$ and $R^{13a}$ is independently H, deuterium, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; with the proviso that where $R^{13}$ and $R^{13a}$ are bonded to the same nitrogen atom, $R^{13}$ and $R^{13a}$, together with the nitrogen atom they are attached to, optionally form a substituted or unsubstituted 3-8 membered ring, or a substituted or unsubstituted spiro bicyclic ring or fused bicyclic ring; and each $R^8$ and $R^{8a}$ is independently H, deuterium, hydroxy, cyano, nitro, F, Cl, Br, I, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl.

In some embodiments, each of A and A' is independently a bond, —CH$_2$—, —(CH$_2$)$_2$—, —CH=CH—, —CH=CH—CH$_2$—, —N(R$^5$)—, —C(=O)—, —C(=S)—, —C(=O)—O—, —C(=O)N(R$^5$)—, —OC(=O)N(R$^5$)—, —OC(=O)O—, —N(R$^5$)C(=O)N(R$^5$)—, —(R$^5$)N—S(=O)$_2$—, —S(=O)$_2$—, —OS(=O)$_2$—, —(R$^5$)N—S(=O)—, —S(=O)—, —OS(=O)—, or each of A and A' is independently selected from

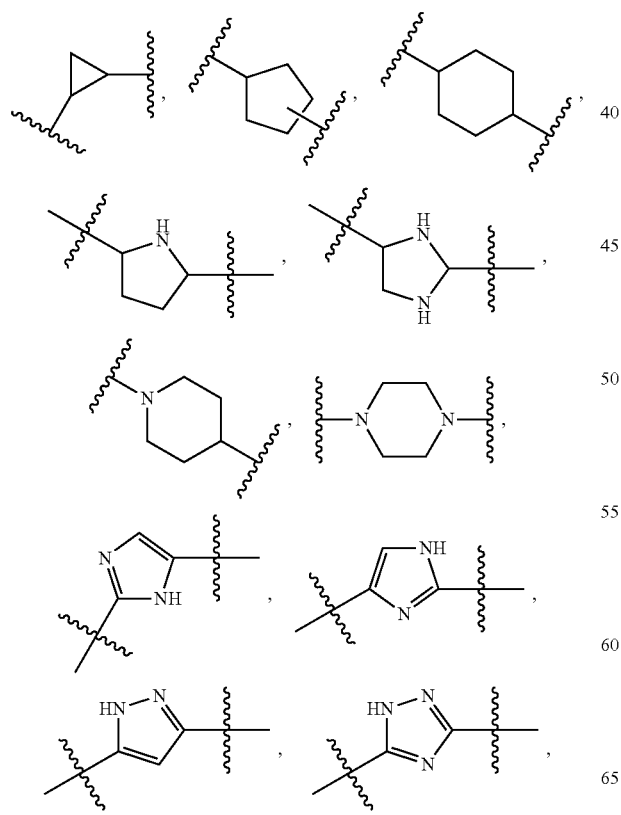

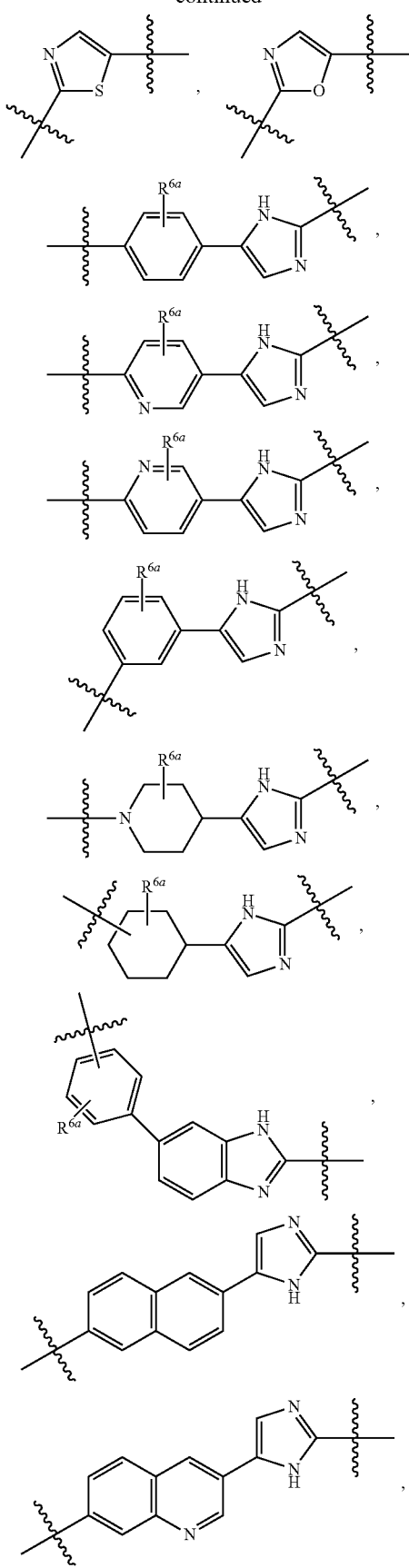

111
-continued
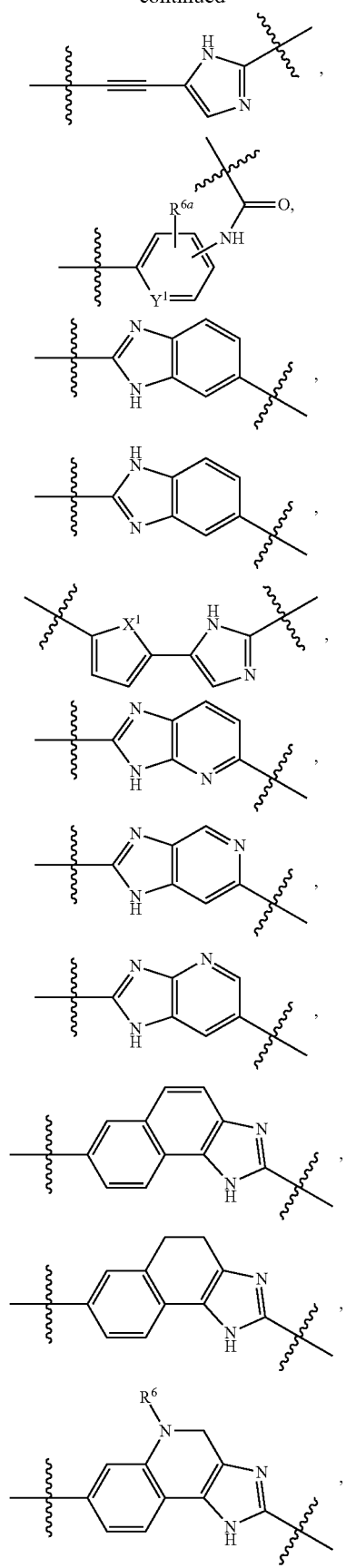
112
-continued
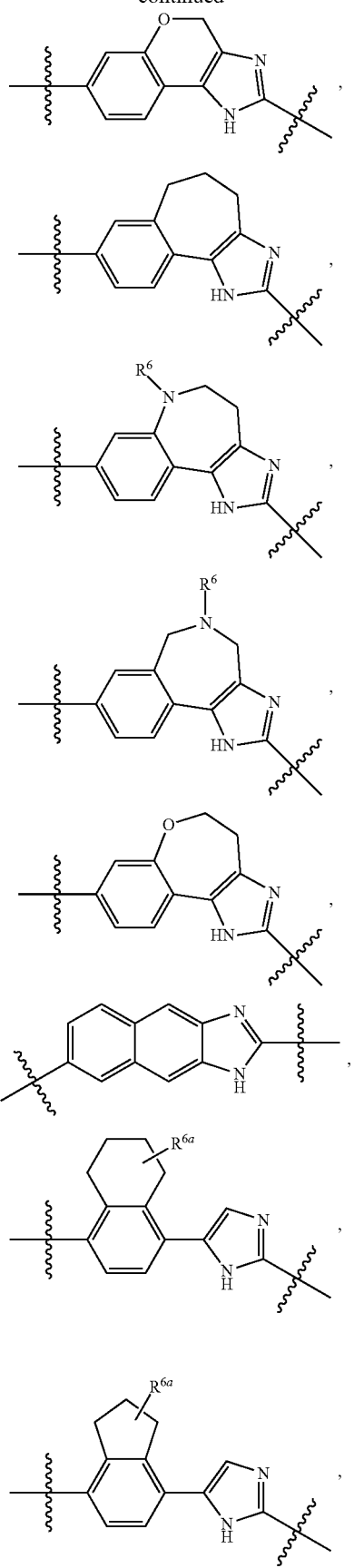

-continued

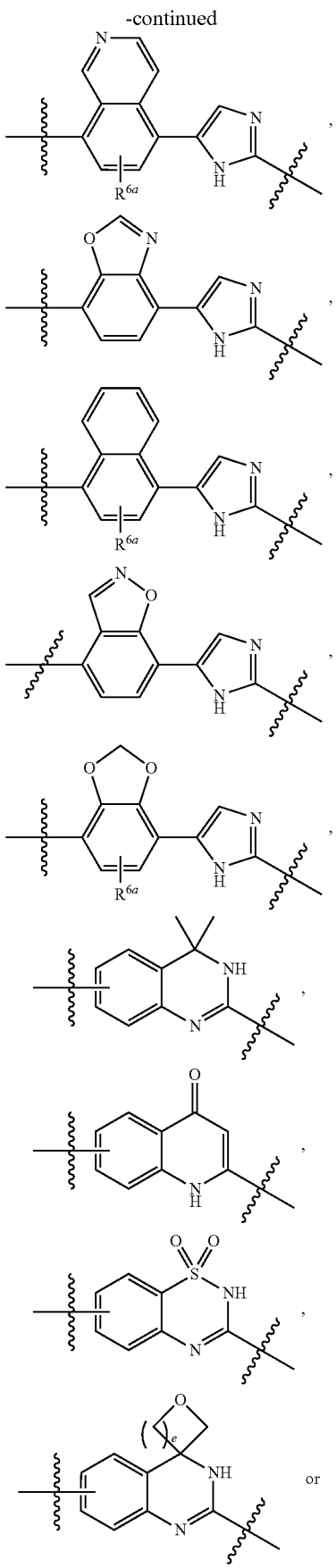

-continued

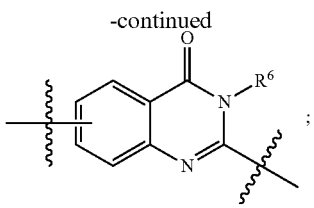

wherein X¹ is O or S;
each Y¹ is independently N or CR⁷;
e is 0, 1, 2, 3 or 4;
each $R^5$ is independently H, deuterium, hydroxy, $C_{1-6}$ alkyl, $C_{2-6}$ heteroalkyl, $C_{3-8}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-C(O)—, $C_{1-6}$ alkyl-C(O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;
each $R^6$ is independently H, deuterium, $C_{1-4}$ alkyl, $C_{1-6}$ haloalkyl, $C_{1-6}$ hydroxyalkyl, $C_{1-6}$ aminoalkyl, $C_{1-6}$ alkoxy-$C_{14}$-alkyl, $C_{1-6}$ alkylamino-$C_{14}$-alkyl, $C_{1-6}$ alkylthio-$C_{1-4}$-alkyl, $C_{6-10}$ aryl-$C_{1-4}$-alkyl, $C_{1-9}$ heteroaryl, $C_{6-10}$ aryl, $C_{2-10}$ heterocyclyl or $C_{3-8}$ carbocyclyl;
each $R^{6a}$ is independently H, deuterium, oxo(=O), hydroxy, amino, F, Cl, Br, I, cyano, $R^{13a}R^{13}N$—, —C(=O)NR¹³R¹³ᵃ, —OC(=O)NR¹³R¹³ᵃ, —OC(=O)OR¹³, —N(R¹³)C(=O)NR¹³R¹³ᵃ, —N(R¹³)C(=O)OR¹³ᵃ, —N(R¹³)C(=O)—R¹³ᵃ, R¹³R¹³ᵃN—S(=O)₂—, R¹³S(=O)₂—, R¹³S(=O)₂N(R¹³ᵃ)—, $C_{1-6}$ alkoxy, $C_{1-6}$ alkylamino, $C_{1-6}$ alkyl, $C_{1-6}$ haloalkyl, $C_{2-6}$ alkenyl, $C_{2-6}$ alkynyl, mercapto or nitro;
each $R^7$ is independently H, deuterium, F, Cl, Br, I, $C_{1-6}$ alkyl, $C_{2-6}$ heteroalkyl, $C_{1-6}$ haloalkyl, $C_{1-6}$ hydroxyalkyl, $C_{1-6}$ aminoalkyl, $C_{1-6}$ alkoxy-$C_{1-16}$-alkyl, $C_{1-6}$ alkylamino-$C_{1-6}$-alkyl, $C_{1-6}$ alkylthio-$C_{1-6}$-alkyl, $C_{6-10}$ aryl-$C_{1-6}$-alkyl, $C_{2-10}$ heterocyclyl-$C_{1-6}$-alkyl, $C_{3-10}$ cycloalkyl-$C_{1-6}$-alkyl, $C_{6-10}$ aryloxy-$C_{1-6}$-alkyl, $C_{2-10}$ heterocyclyloxy-$C_{1-6}$-alkyl, $C_{3-10}$ cycloalkyloxy-$C_{1-6}$-alkyl, $C_{6-10}$ arylamino-$C_{1-6}$-alkyl, $C_{2-10}$ heterocyclylamino-$C_{1-6}$-alkyl, $C_{3-10}$ cycloalkylamino-$C_{1-6}$-alkyl, $C_{6-10}$ aryl, $C_{1-9}$ heteroaryl, $C_{2-10}$ heterocyclyl or $C_{3-8}$ carbocyclyl; and
each of $R^{13}$ and $R^{13a}$ is independently H, deuterium, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; with the proviso that where $R^{13}$ and $R^{13a}$ are bonded to the same nitrogen atom, $R^{13}$ and $R^{13a}$, together with the nitrogen atom they are attached to, optionally form a substituted or unsubstituted 3-8 membered ring, or a substituted or unsubstituted spiro bicyclic ring or fused bicyclic ring.

In some embodiments, each of $R^1$, $R^2$, $R^3$ and $R^4$ is independently H, deuterium, $C_{1-8}$ alkyl, $C_{1-8}$ heteroalkyl, $C_{6-10}$ aryl-$C_{1-6}$-alkyl, $C_{3-10}$ cycloalkyl, $C_{2-10}$ heterocyclyl, $C_{1-9}$ heteroaryl or $C_{6-10}$ aryl; or $R^1$ and $R^2$, together with X—CH they are attached to, optionally form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle; or $R^3$ and $R^4$, together with X—CH they are attached to, optionally form a 3-8 membered heterocycle or carbocycle, $C_{5-12}$ fused bicycle, $C_{5-12}$ fused heterobicycle, $C_{5-12}$ spiro bicycle or $C_{5-12}$ spiro heterobicycle.

In other embodiments, $R^1$ and $R^2$, together with X—CH they are attached to, or $R^3$ and $R^4$, together with X—CH they are attached to, optionally form a 3-8 membered heterocycle, $C_{5-12}$ fused bicycle, $C_{5-12}$ fused heterobicycle, $C_{5-12}$ spiro bicycle or $C_{5-12}$ spiro heterobicycle.

In other embodiments, $R^1$, $R^2$ and Y—X—CH together form one of the following monovalent groups:

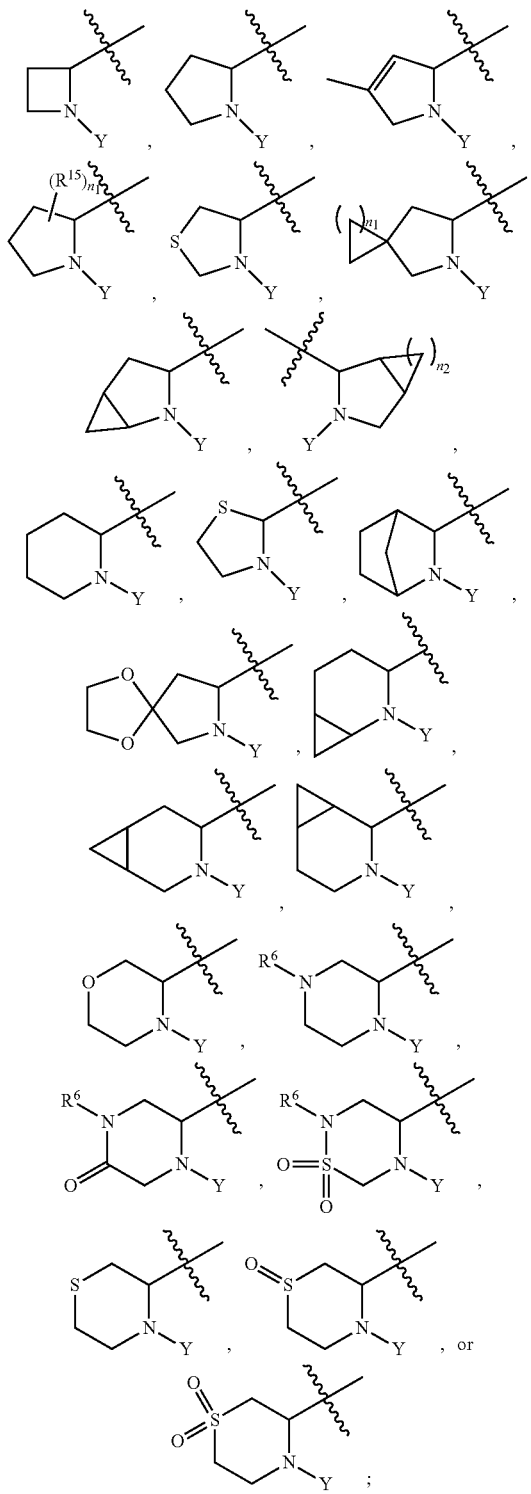

wherein each $R^{15}$ is independently H, deuterium, oxo (=O), F, Cl, Br, I, cyano, hydroxy, $C_{1-3}$ alkyl, $C_{1-3}$ haloalkyl, $C_{1-3}$ alkoxy, $C_{1-3}$ alkylamino, $C_{1-3}$ alkylthio, $C_{6-10}$ arylamino, $C_{6-10}$ aryloxy, $C_{1-9}$ heteroaryl, $C_{1-9}$ heteroaryloxy, $C_{1-9}$ heteroaryl-$C_{1-3}$-alkyl or $C_{2-10}$ heterocyclyl;

each $R^6$ is independently H, deuterium, $C_{1-3}$ alkyl, $C_{1-3}$ haloalkyl, $C_{1-3}$ hydroxyalkyl, $C_{1-3}$ aminoalkyl, $C_{1-3}$ alkoxy-$C_{1-3}$-alkyl, $C_{1-3}$ alkylamino-$C_{1-3}$-alkyl, $C_{1-3}$ alkylthio-$C_{1-3}$-alkyl, $C_{6-10}$ aryl-$C_{1-3}$-alkyl, $C_{1-9}$ heteroaryl, $C_{6-10}$ aryl, $C_{2-10}$ heterocyclyl or $C_{3-8}$ carbocyclyl; and each $n_1$ and $n_2$ is independently 1, 2, 3 or 4.

In other embodiments, $R^3$, $R^4$ and Y'—X'—CH together form one of the following monovalent groups:

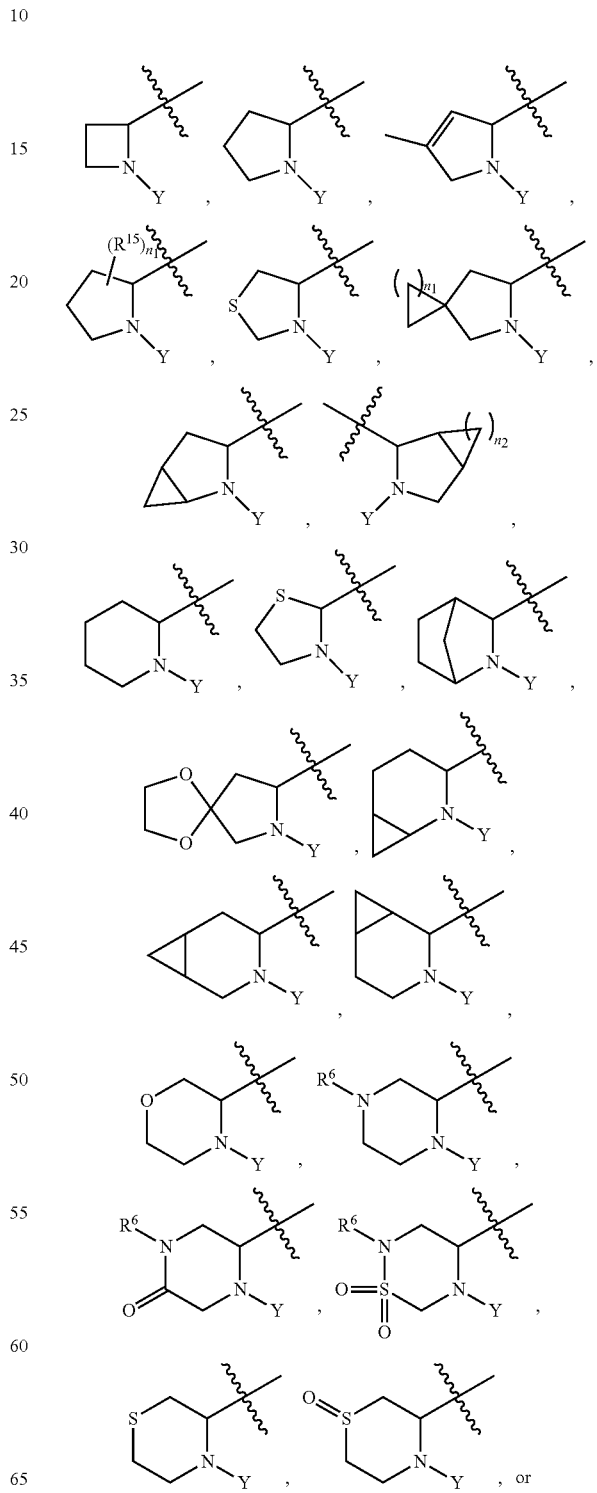

-continued

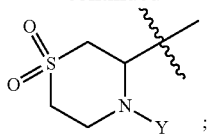

wherein each R[15] is independently H, deuterium, oxo (=O), F, Cl, Br, I, cyano, hydroxy, $C_{1-3}$ alkyl, $C_{1-3}$ haloalkyl, $C_{1-3}$ alkoxy, $C_{1-3}$ alkylamino, $C_{1-3}$ alkylthio, $C_{6-10}$ arylamino, $C_{6-10}$ aryloxy, $C_{1-9}$ heteroaryl, $C_{1-9}$ heteroaryloxy, $C_{1-9}$ heteroaryl-$C_{1-3}$-alkyl or $C_{2-10}$ heterocyclyl;

each R[6] is independently H, deuterium, $C_{1-3}$ alkyl, $C_{1-3}$ haloalkyl, $C_{1-3}$ hydroxyalkyl, $C_{1-3}$ aminoalkyl, $C_{1-3}$ alkoxy-$C_{1-3}$-alkyl, $C_{1-3}$ alkylamino-$C_{1-3}$-alkyl, $C_{1-3}$ alkylthio-$C_{1-3}$-alkyl, $C_{6-10}$ aryl-$C_{1-3}$-alkyl, $C_{1-9}$ heteroaryl, $C_{6-10}$ aryl, $C_{2-10}$ heterocyclyl or $C_{3-8}$ carbocyclyl; and each $n_1$ and $n_2$ is independently 1, 2, 3 or 4.

In some embodiments, the compound may have formula (II):

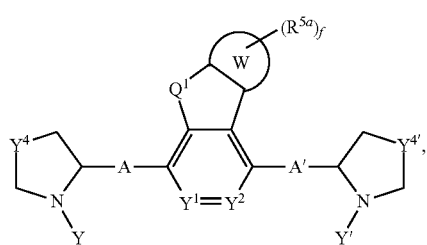

(II)

wherein is

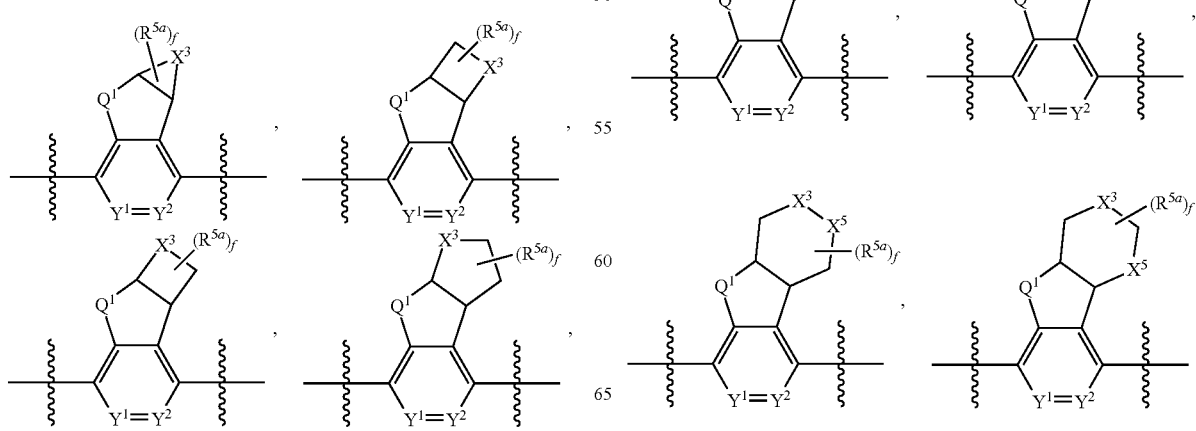

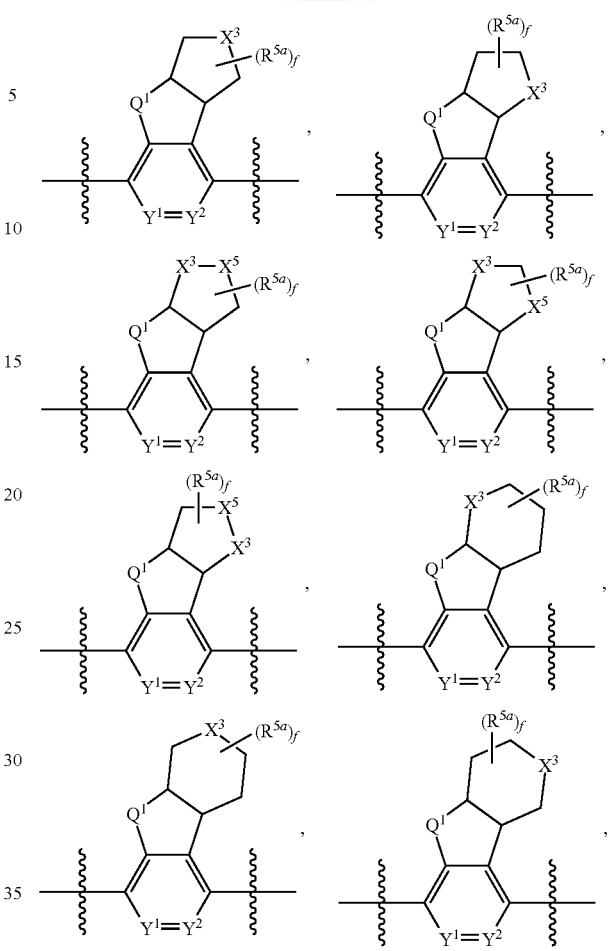

-continued

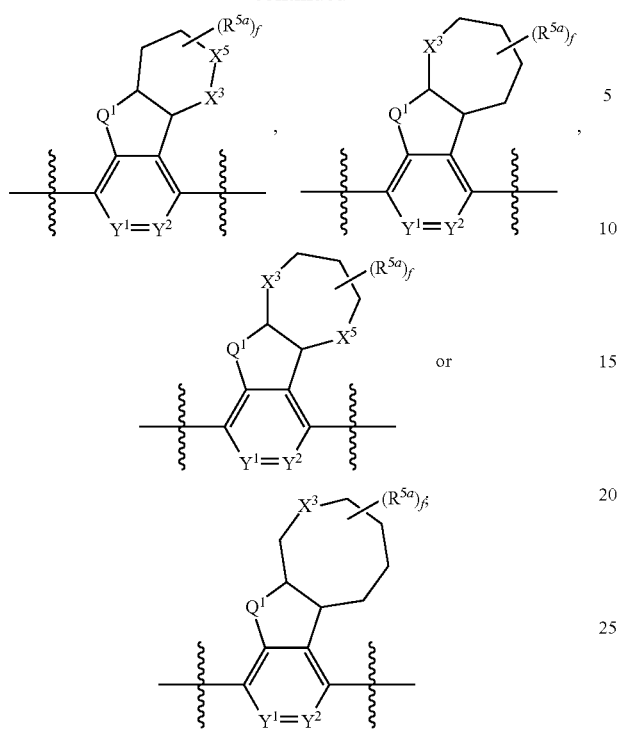

wherein each $X^3$ and $X^5$ is independently $NR^6$, O, S, $C(=O)$ or $(CR^7R^{7a})_e$;

each $Q^1$ is independently a bond, $NR^6$, O, S, $C(=O)$ or $(CR^7R^{7a})_e$;

each e and f is independently 0, 1, 2, 3 or 4;

each $X^1$ is independently O, S, $NR^6$, $C(=O)$ or $CR^7R^{7a}$;

each $Y^1$ and $Y^2$ is independently N or $CR^7$;

each of A and A' is independently a bond, $C_{1-6}$ alkylene, $C_{2-6}$ alkenylene, $C_{3-8}$ cycloalkylene, $C_{2-10}$ heterocycloalkylene, $-(CR^8R^{8a})_n-O-(CR^8R^{8a})_p-$, $-(CR^8R^{8a})_n-N(R^5)-(CR^8R^{8a})_p-$, $-(CR^8R^{8a})_n-S(=O)_r-N(R^5)-(CR^8R^{8a})_p-$, $-(CR^8R^{8a})_n-C(=O)-N(R^5)-(CR^8R^{8a})_p-$, $-(CR^8R^{8a})_n-N(R^5)-C(=O)-N(R^5)-(CR^8R^{8a})_p-$, $-(CR^8R^{8a})_n-C(=O)-O-(CR^8R^{8a})_p-$, $-(CR^8R^{8a})_n-N(R^5)-S(=O)_r-N(R^5)-(CR^8R^{8a})_p-$, $-(CR^8R^{8a})_n-S(=O)_r-(CR^8R^{8a})_p-$, $-(CR^8R^{8a})_n-S(=O)_r-O-(CR^8R^{8a})_p-$, $-(CR^8R^{8a})_n-C(=O)-(CR^8R^{8a})_p-$, $-(CR^8R^{8a})_n-C(=S)-(CR^8R^{8a})_p-$, $-(CR^8R^{8a})_n-N(R^5)-C(=O)-O-(CR^8R^{8a})_p-$, or each of A and A' is independently

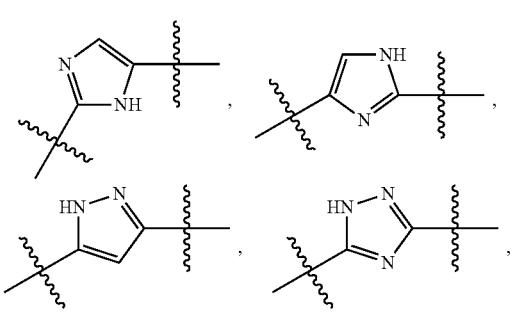

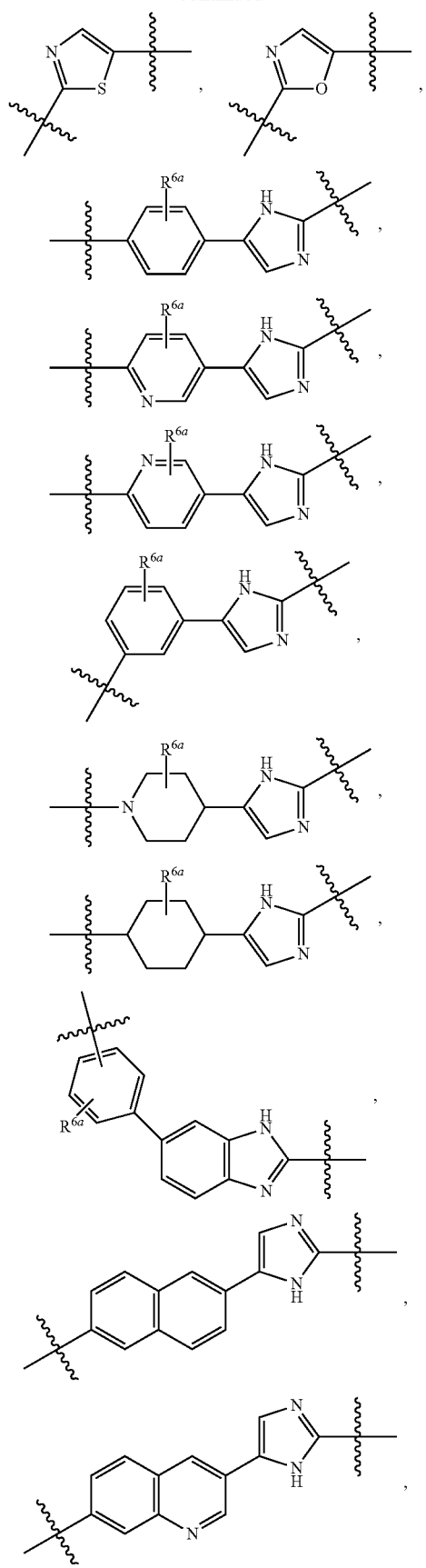

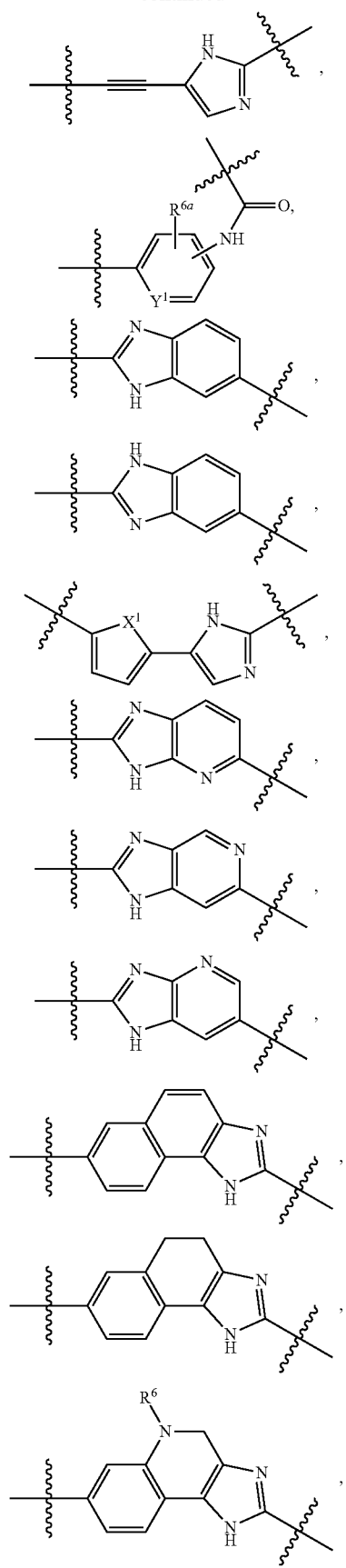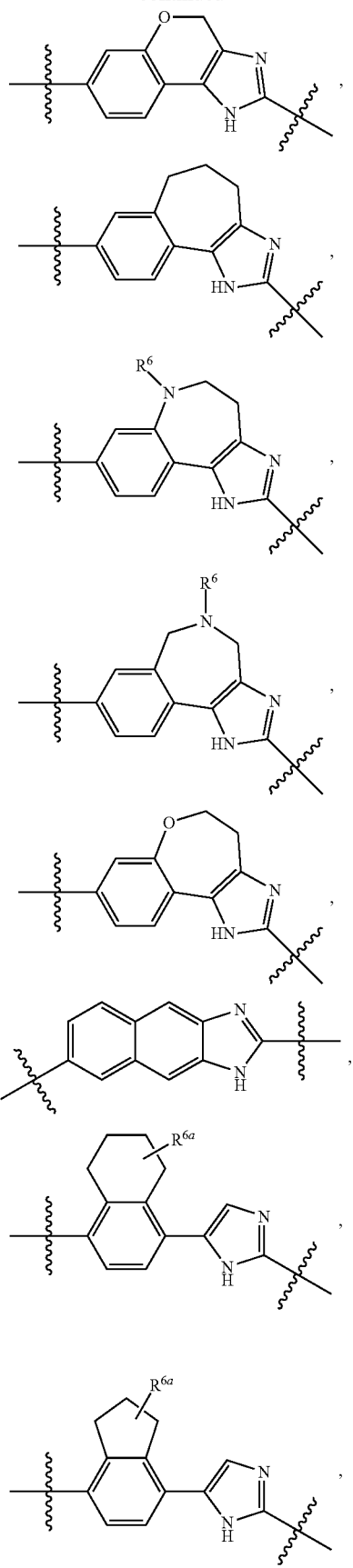

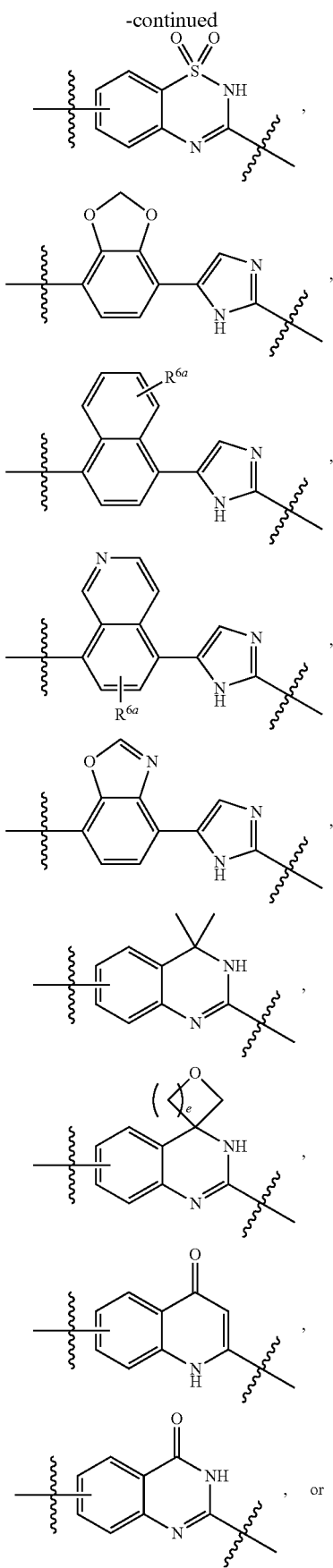

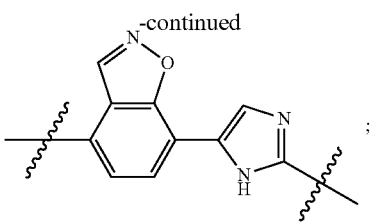

each $R^5$ is independently H, deuterium, hydroxy, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;

each $R^{5a}$ and $R^{6a}$ is independently H, deuterium, oxo (=O), hydroxy, amino, F, Cl, Br, I, cyano, $R^{13a}R^{13}N$—, —C(=O)NR$^{13}$R$^{13a}$, —OC(=O)NR$^{13}$R$^{13a}$, —OC(=O)OR$^{13}$, —N(R$^{13}$)C(=O)NR$^{13}$R$^{13a}$, —N(R$^{13}$)C(=O)OR$^{13a}$, —N(R$^{13}$)C(=O)R$^{13a}$, R$^{13}$R$^{13a}$N—S(=O)$_2$—, R$^{13}$S(=O)$_2$—, R$^{13}$S(=O)$_2$N(R$^{13a}$)—, $C_{1-6}$ alkylacyl, $C_{1-6}$ alkylacyloxy, $C_{1-6}$ alkoxyacyl, $C_{1-6}$ alkylsulfonyl, $C_{1-6}$ alkoxysulfonyl, $C_{1-6}$ alkylsulfinyl, $C_{1-6}$ alkylsulfonyloxy, $C_{1-6}$alkylsulfinyloxy, $C_{1-6}$ alkoxy, $C_{1-6}$ alkyl, $C_{6-10}$ aryl, —CF$_3$, —OCF$_3$, mercapto, nitro, $C_{1-6}$ alkylamino, $C_{3-10}$ cycloalkyl or $C_{6-10}$ aryloxy;

each $R^6$ is independently H, deuterium, $R^{13}R^{13a}NC(=O)$—, $R^{13}OC(O)$—, $R^{13}C(O)$—, $R^{13}R^{13a}NS(=O)$—, $R^{13}OS(=O)$—, $R^{13}S(=O)$—, $R^{13}R^{13a}NS(=O)_2$—, $R^{13}OS(=O)_2$—, $R^{13}S(=O)_2$—, $C_{1-6}$ aliphatic, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; wherein said aliphatic is alkyl; some no-limiting examples of the alkyl group include methyl, ethyl, propyl, i-propyl, butyl and i-butyl;

each $R^7$ and $R^{7a}$ is independently H, deuterium, F, Cl, Br, I, $C_{1-6}$ aliphatic, $C_{2-6}$ heteroalkyl, $C_{1-6}$ alkoxy-$C_{1-6}$-aliphatic, $C_{1-6}$ alkylamino-$C_{1-6}$-aliphatic, $C_{6-10}$ aryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; wherein said aliphatic is alkyl; some no-limiting examples of the alkyl group include methyl, ethyl, propyl, i-propyl, butyl and i-butyl;

each $R^8$ and $R^{8a}$ is independently H, deuterium, hydroxy, cyano, nitro, F, Cl, Br, I, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;

each $R^{13}$ and $R^{13a}$ is independently H, deuterium, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; with the proviso that where $R^{13}$ and $R^{13a}$ are bonded to the same nitrogen atom, $R^{13}$ and $R^{13a}$, together with the nitrogen atom they are attached to, optionally form a substituted or unsubstituted 3-8 membered ring, or a substituted or unsubstituted spiro bicyclic ring or fused bicyclic ring;

each n and p is independently 0, 1, 2 or 3;
each r is independently 0, 1 or 2; and
each of $Y^4$ and $Y^{4'}$ is independently a bond, O, S, —(CH$_2$)$_n$—, —CH=CH—, —S(=O)$_r$—, —CH$_2$O—, —CH$_2$S—, —CH$_2$S(=O)$_r$, —CF$_2$—, —CHR$^{5a}$, —CR$^{5a}$R$^{6a}$ or —CH$_2$N(R$^6$)—.

In some embodiments, the compound may have formula (II):
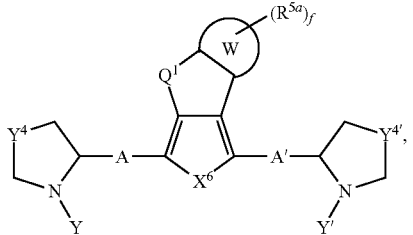
(II')
wherein
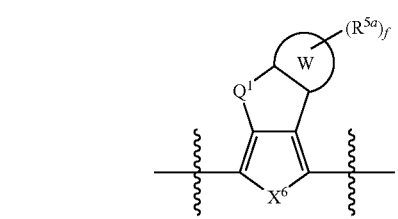
is
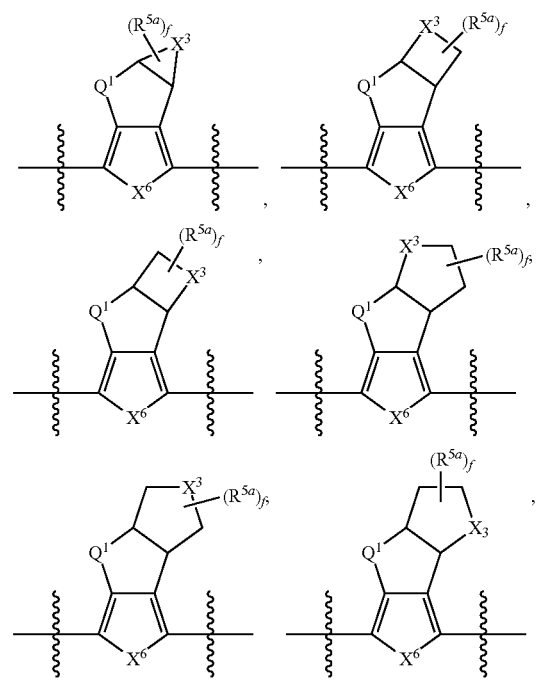
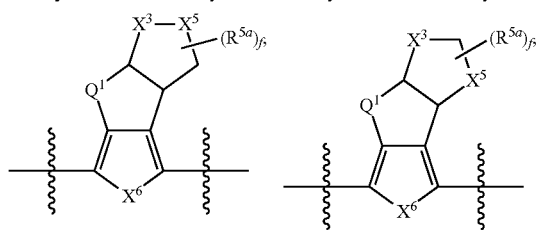
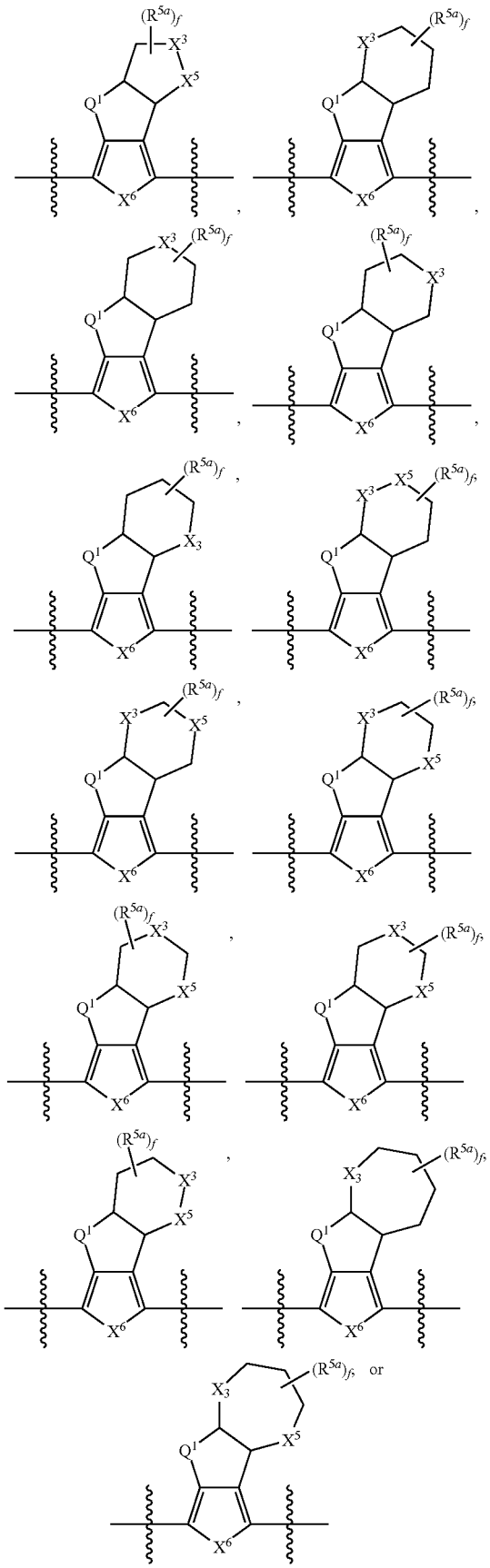

-continued

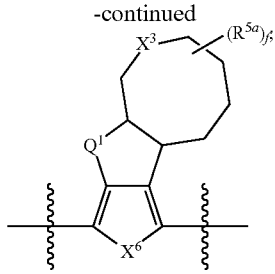

wherein each $X^3$ and $X^5$ is independently $NR^6$, O, S, C(=O) or $(CR^7R^{7a})_e$;

each $Q^1$ is independently a bond, $NR^6$, O, S, C(=O) or $(CR^7R^{7a})_e$;

each e and f is independently 0, 1, 2, 3 or 4;

each $X^6$ is independently $CR^7R^{7a}$, O, S or $NR^6$;

each of A and A' is independently a bond, $C_{1-6}$ alkylene, $C_{2-6}$ alkenylene, $C_{3-8}$ cycloalkylene, $C_{2-10}$ heterocycloalkylene, $-(CR^8R^{8a})_n-O-(CR^8R^{8a})_p-$, $-(CR^8R^{8a})_n-N(R^5)-(CR^8R^{8a})_p-$, $-(CR^8R^{8a})_n-S(=O)_r-N(R^5)-(CR^8R^{8a})_p-$, $-(CR^8R^{8a})_n-C(=O)-N(R^5)-(CR^8R^{8a})_p-$, $-(CR^8R^{8a})_n-N(R^5)-C(=)-N(R^5)-(CR^8R^{8a})_p-$, $-(CR^8R^{8a})_n-C(=)-O-(CR^8R^{8a})_p-$, $-(CR^8R^{8a})_n-N(R^5)-S(=O)_r-N(R^5)-(CR^8R^{8a})_p-$, $-(CR^8R^{8a})_n-S(=O)_r-(CR^8R^{8a})_p-$, $-(CR^8R^{8a})_n-S(=O)_r-O-(CR^8R^{8a})_p-$, $-(CR^8R^{8a})_n-C(=O)-(CR^8R^{8a})_p-$, $-(CR^8R^{8a})_n-C(=S)-(CR^8R^{8a})_p-$, $-(CR^8R^{8a})_n-N(R^5)-C(=O)-O-(CR^8R^{8a})_p-$, or each of A and A' is independently

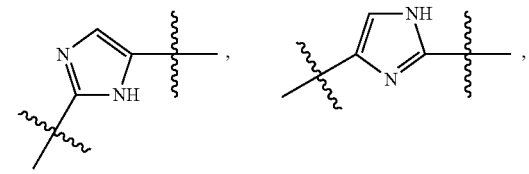

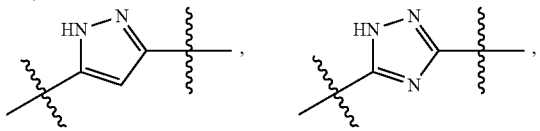

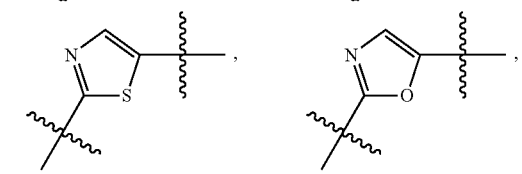

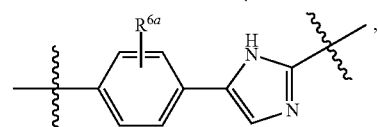

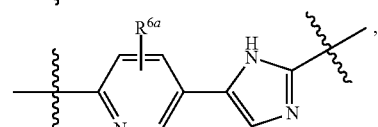

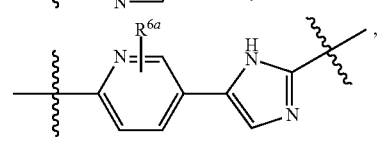

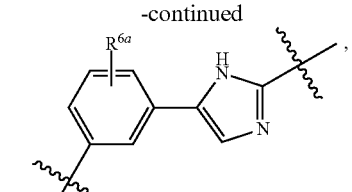

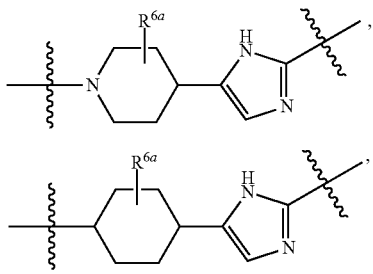

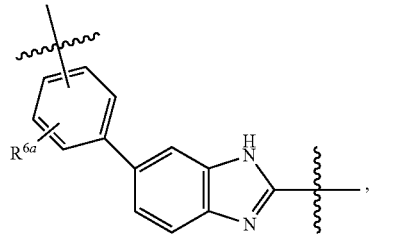

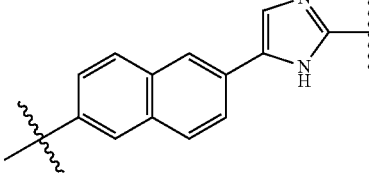

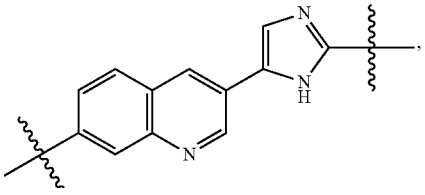

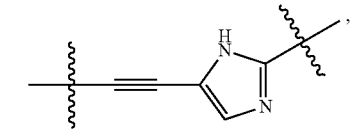

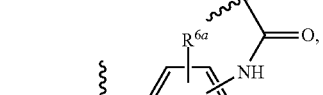

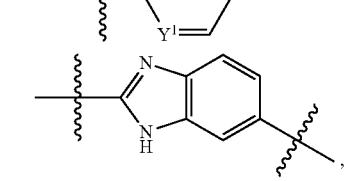

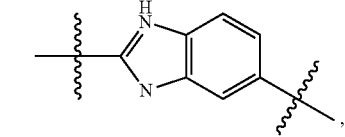

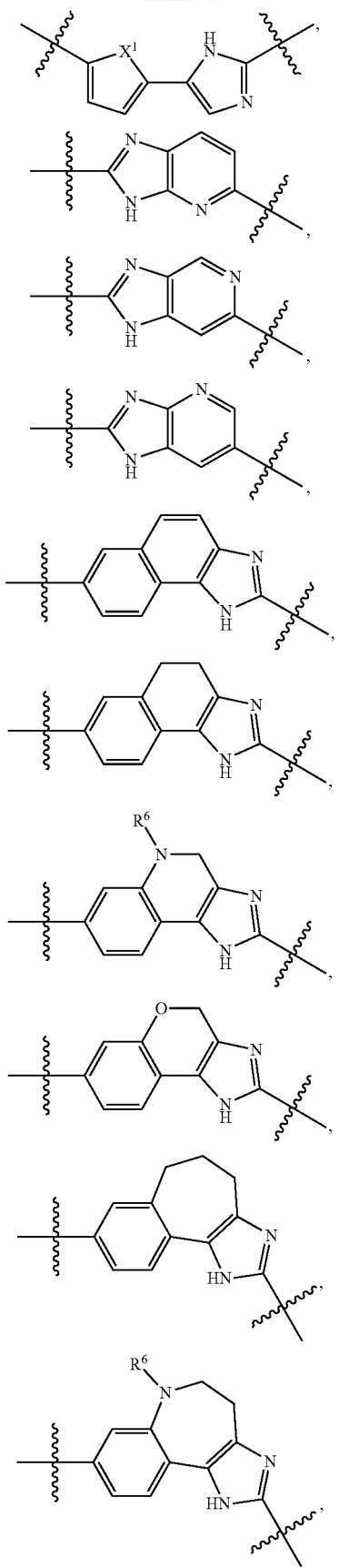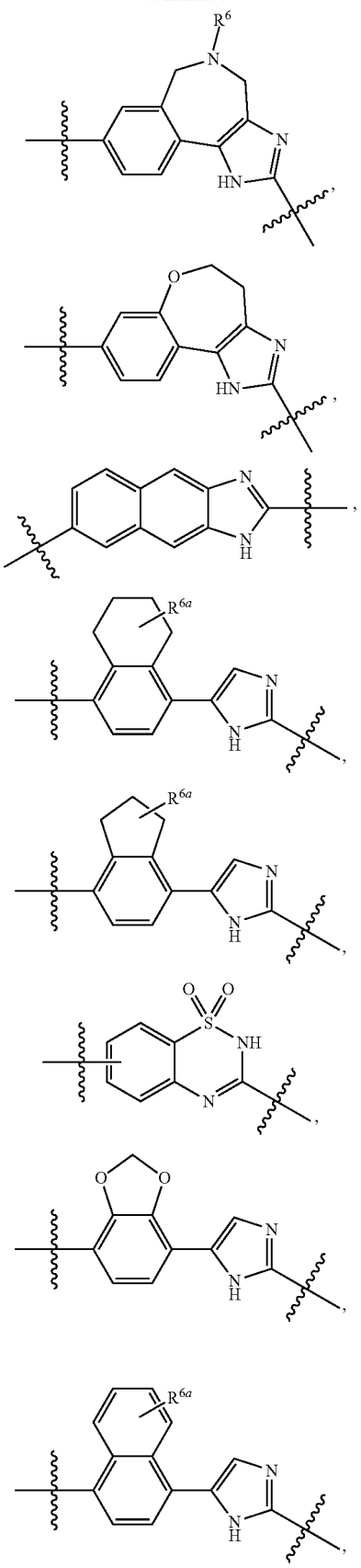

-continued

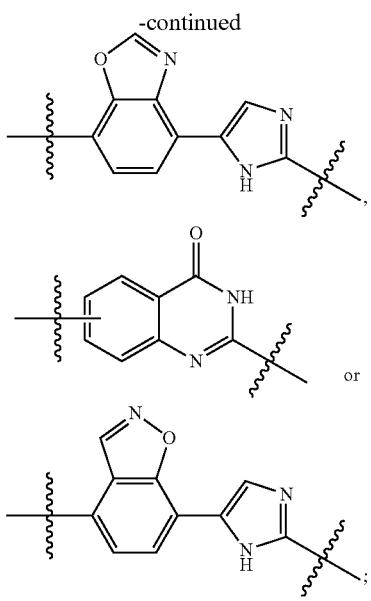

wherein each $X^1$ is independently O, S, $NR^6$, C(=O) or $CR^7R^{7a}$;

each $Y^1$ is independently N or $CR^7$;

each $R^5$ is independently H, deuterium, hydroxy, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;

each $R^{5a}$ and $R^{6a}$ is independently H, deuterium, oxo (=O), hydroxy, amino, $R^{13a}R^{13}N$—, —C(=O)$NR^{13}R^{13a}$, —OC(=O)$NR^{13}R^{13a}$, —OC(=O)$OR^{13}$, —$N(R^{13})C(=O)NR^{13}R^{13a}$, —$N(R^{13})C(=O)OR^{13a}$, —$N(R^{13})C(=O)$—$R^{13a}$, $R^{13}R^{13a}N$—S(=O)$_2$—, $R^{13}S(=O)_2$—, $R^{13}S(=O)_2N(R^{13a})$—, F, Cl, Br, I, cyano, $C_{1-6}$ alkoxy, $C_{1-6}$ alkyl, $C_{6-10}$ aryl, —$CF_3$, —$OCF_3$, mercapto, nitro, $C_{1-6}$ alkylamino, $C_{3-10}$ cycloalkyl or $C_{6-10}$ aryloxy;

each $R^6$ is independently H, deuterium, $R^{13}R^{13a}NC(=O)$—, $R^{13}OC(=O)$—, $R^{13}C(=O)$—, $R^{13}R^{13a}NS(=O)$—, $R^{13}OS(=O)$—, $R^{13}S(=O)$—, $R^{13}R^{13a}NS(=O)_2$—, $R^{13}OS(=O)_2$—, $R^{13}S(=O)_2$—, $C_{1-6}$ aliphatic, $C_{1-6}$ alkoxy-$C_{1-6}$-aliphatic, $C_{1-6}$ alkylamino-$C_{1-6}$-aliphatic, $C_{6-10}$ aryl-C-6-aliphatic, $C_{1-9}$ heteroaryl-$C_{1-6}$-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; wherein said aliphatic is alkyl; some no-limiting examples of the alkyl group include methyl, ethyl, propyl, i-propyl, butyl and i-butyl;

each $R^7$ and $R^{7a}$ is independently H, deuterium, F, Cl, Br, I, $C_{1-6}$ aliphatic, $C_{2-6}$ heteroalkyl, $C_{1-6}$ alkoxy-$C_{1-6}$-aliphatic, $C_{1-6}$ alkylamino-$C_{1-6}$-aliphatic, $C_{6-10}$ aryl-C-6-aliphatic, $C_{2-10}$ heterocyclyl-$C_{1-6}$-aliphatic, $C_{3-10}$ cycloalkyl-$C_{1-6}$-aliphatic, $C_{6-10}$ aryl, $C_{1-9}$ heteroaryl, $C_{2-10}$ heterocyclyl or $C_{3-10}$ carbocyclyl; wherein said aliphatic is alkyl; some no-limiting examples of the alkyl group include methyl, ethyl, propyl, i-propyl, butyl and i-butyl;

each $R^8$ and $R^{8a}$ is independently H, deuterium, hydroxy, cyano, nitro, F, Cl, Br, I, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, $C_{6-10}$ aryl-$C_{1-6}$-alkyl, $C_{1-6}$ alkoxy, $C_{1-6}$ alkyl-OC(=O)—, $C_{1-6}$ alkyl-C(=O)—, carbamoyl, $C_{1-6}$ alkyl-OS(=O)$_r$—, $C_{1-6}$ alkyl-S(=O)$_r$O—, $C_{1-6}$ alkyl-S(=O)$_r$— or aminosulfonyl;

each $R^{13}$ and $R^{13a}$ is independently H, deuterium, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; with the proviso that where $R^{13}$ and $R^{13a}$ are bonded to the same nitrogen atom, $R^{13}$ and $R^{13a}$, together with the nitrogen atom they are attached to, optionally form a substituted or unsubstituted 3-8 membered ring, spiro bicyclic ring or fused bicyclic ring;

each n and p is independently 0, 1, 2 or 3;

each r is independently 0, 1 or 2; and each of $Y^4$ and $Y^{4'}$ is independently a bond, O, S, —(CH$_2$)$_n$—, —CH=CH—, —S(=O)$_r$—, —CH$_2$O—, —CH$_2$S—, —CH$_2$S(=O)$_r$—, —CF$_2$—, —CHR$^{5a}$—, —CR$^{5a}$R$^{6a}$— or —CH$_2$N(R$^6$)—.

In other embodiments, the compound may have formula (III):

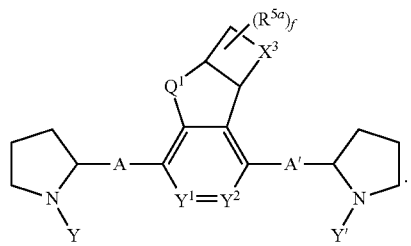

(III)

In other embodiments, the compound may have formula (IV):

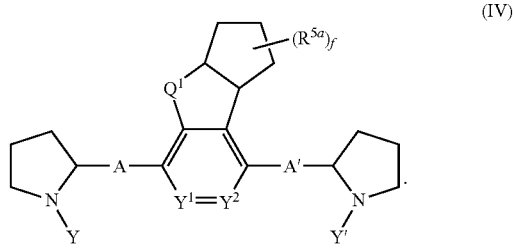

(IV)

In other embodiments, the compound may have formula (III'):

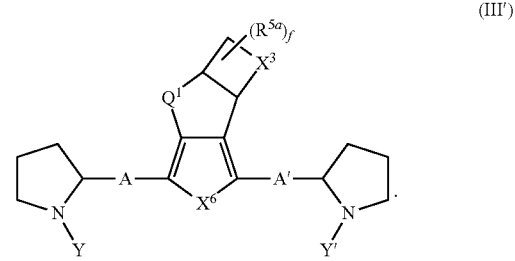

(III')

In other embodiments, the compound may have formula (IV'):

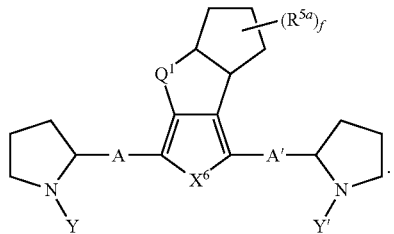

In some embodiments, each of Y and Y' is independently a monovalent group derived from an α-amino acid.

In other embodiments, the α-amino acid is isoleucine, leucine, lysine, methionine, phenylalanine, threonine, tryptophane, valine, alanine, asparagine, aspartic acid, glutamic acid, glutamine, proline, serine, p-tyrosine, arginine, histidine, cysteine, glycine, sarcosine, N,N-dimethylglycine, homoserine, norvaline, norleucine, ornithine, homocysteine, homophenylalanine, phenylglycine, o-tyrosine, m-tyrosine or hydroxyproline.

In other embodiments, the α-amino acid is in the D configuration.

In other embodiments, the α-amino acid is in the L configuration.

In some embodiments, each of Y and Y' is independently —[U—$(CR^9R^{9a})_t$—$NR^{10}$—$(CR^9R^{9a})_t]_k$—U—$(CR^9R^{9a})_t$—$NR^{11}$—$(CR^9R^{9a})_t$—$R^{12}$, —U—$(CR^9R^{9a})_t$—$R^{12}$ or —[U—$(CR^9R^{9a})_t$—$NR^{10}$—$(CR^9R^{9a})_t]_k$—U—$(CR^9R^{9a})_t$—O—$(CR^9R^{9a})_t$—$R^{12}$.

In other embodiments, each of Y and Y' is independently —[U—$(CR^9R^{9a})_t$—$NR^{10}$—$(CR^9R^{9a})_t]_k$—U—$(CR^9R^{9a})_t$—$NR^{11}$—$(CR^9R^{9a})_t$—$R^{12}$.

In other embodiments, each of Y and Y' is independently —U—$(CR^9R^{9a})_t$—$NR^{10}$—$(CR^9R^{9a})_t$—U—$(CR^9R^{9a})_t$—$NR^{11}$—$(CR^9R^{9a})_t$—$R^{12}$.

In other embodiments, wherein each of Y and Y' is independently —U—$(CR^9R^{9a})_t$—$NR^{11}$—$(CR^9R^{9a})_t$—$R^{12}$.

In other embodiments, wherein each of Y and Y' is independently —[C(=O)—$(CR^9R^{9a})_t$—$NR^{11}$—$(CR^9R^{9a})_t]_k$—U—$(CR^9R^{9a})_t$—$NR^{11}$—$(CR^9R^{9a})_t$—$R^{12}$.

In other embodiments, each of Y and Y' is independently —C(=O)—$(CR^9R^{9a})_t$—$NR^{10}$—$(CR^9R^{9a})_t$—U—$(CR^9R^{9a})_t$—$NR^{11}$—$(CR^9R^{9a})_t$—$R^{12}$.

In other embodiments, each of Y and Y' is independently —[C(=O)—$(CR^9R^{9a})_t$—$NR^{10}$—$(CR^9R^{9a})_t]_k$—C(=O)—$(CR^9R^{9a})_t$—$NR^{11}$—$(CR^9R^{9a})_t$—$R^{12}$.

In other embodiments, each of Y and Y' is independently —C(=O)—$(CR^9R^{9a})_t$—$NR^{10}$—$(CR^9R^{9a})_t$—C(=O)—$(CR^9R^{9a})_t$—$NR^{11}$—$(CR^9R^{9a})_t$—$R^{12}$.

In other embodiments, each of Y and Y' is independently —C(=O)—$(CR^9R^{9a})_t$—$NR^{11}$—$(CR^9R^{9a})_t$—$R^{12}$.

In other embodiments, each of Y and Y' is independently —C(=O)—$(CR^9R^{9a})_t$—$NR^{11}$—$(CR^9R^{9a})_t$—C(=O)—$R^{13}$.

In other embodiments, each of Y and Y' is independently —C(=O)—$(CR^9R^{9a})_t$—$NR^{11}$—C(=O)—$R^{13}$.

In other embodiments, each of Y and Y' is independently —C(=O)—$(CR^9R^{9a})_t$—$NR^{11}$—$(CR^9R^{9a})_t$—C(=O)—O—$R^{13}$.

In other embodiments, each of Y and Y' is independently —C(=O)—$(CR^9R^{9a})_t$—$NR^{11}$—C(=O)—O—$R^{13}$.

In other embodiments, each of Y and Y' is independently —U—$(CR^9R^{9a})_t$—$R^{12}$.

In other embodiments, wherein each of Y and Y' is independently —C(=)—$(CR^9R^{9a})_t$—$R^{12}$.

In other embodiments, each of Y and Y' is independently —[U—$(CR^9R^{9a})_t$—$NR^{10}$—$(CR^9R^{9a})_t]_k$—U—$(CR^9R^{9a})_t$—O—$(CR^9R^{9a})_t$—$R^{12}$.

In other embodiments, each of Y and Y' is independently —U—$(CR^9R^{9a})_t$—$NR^{10}$—$(CR^9R^{9a})_t$—U—$(CR^9R^{9a})_t$—O—$(CR^9R^{9a})_t$—$R^{12}$.

In other embodiments, each of Y and Y' is independently —C(=O)—$(CR^9R^{9a})_t$—$NR^{10}$—$(CR^9R^{9a})_t$—C(=O)—$(CR^9R^{9a})_t$—O—$(CR^9R^{9a})_t$—$R^{12}$.

In other embodiments, each of Y and Y' is independently —U—$(CR^9R^{9a})_t$—O—$(CR^9R^{9a})_t$—$R^{12}$.

In other embodiments, each of Y and Y' is independently —C(=O)—$(CR^9R^{9a})_t$—O—$(CR^9R^{9a})_t$—$R^{12}$.

In other embodiments, each of Y and Y' is independently —C(=O)—$(CR^9R^{9a})_t$—$NR^{11}$—$R^{12}$, wherein $R^{11}$ and $R^{12}$, together with the atom they are attached to, form a 4-7 membered ring.

In other embodiments, each $R^9$, $R^{9a}$, $R^{10}$ and $R^{11}$ is independently H, deuterium, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, $C_{1-6}$ haloalkyl, $C_{1-6}$ hydroxyalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, or $C_{3-8}$ cycloalkyl-$C_{1-6}$-alkyl;

each $R^{12}$ is independently $R^{13a}R^{13}N$—, —C(=O)$R^{13}$, —C(=S)$R^{13}$, —C(=O)—O—$R^{13}$, —C(=O)$NR^{13}R^{13a}$, —OC(=O)$NR^{13}R^{13a}$, —OC(=O)O$R^{13}$, —N($R^{13}$)C(=O)$NR^{13}R^{13a}$, —N($R^{13}$)C(=O)O$R^{13a}$, —N($R^{13}$)C(=O)—$R^{13a}$, $R^{13}R^{13a}N$—S(=O)$_2$—, $R^{13}S$(=O)$_2$—, $R^{13}S$(=O)$_2$N($R^{13a}$)—, $R^{13}OS$(=O)$_2$—, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; or $R^{11}$ and $R^{12}$, together with the atom they are attached to, form a 4-7 membered ring; and each $R^{13}$ and $R^{13a}$ is independently H, deuterium, $C_{1-6}$ alkyl, $C_{2-6}$ heteroalkyl, $C_{3-10}$ cycloalkyl, $C_{2-10}$ heterocyclyl, $C_{6-10}$ aryl, $C_{1-9}$ heteroaryl, or $C_{6-10}$ aryl-$C_{1-6}$-alkyl; with the proviso that where $R^{13}$ and $R^{13a}$ are bonded to the same nitrogen atom, $R^{13}$ and $R^{13a}$, together with the nitrogen atom they are attached to, optionally form a substituted or unsubstituted 3-8 membered ring, or a substituted or unsubstituted spiro bicyclic ring or fused bicyclic ring.

In other embodiments, each $R^9$, $R^{9a}$, $R^{10}$ and $R^{11}$ is independently H, deuterium, methyl, ethyl, isopropyl, cyclohexyl, isobutyl or phenyl;

each $R^{12}$ is independently —C(=O)$R^{13}$, —C(=O)—O—$R^{13}$, —C(=O)$NR^{13}R^{13a}$, methyl, ethyl, propyl, phenyl, cyclohexyl, morpholinyl or piperidinyl; or $R^{11}$ and $R^{12}$, together with the atom they are attached to, form a 4-7 membered ring; and each $R^{13}$ and $R^{13a}$ is independently H, deuterium, methyl, ethyl, propyl, phenyl, cyclohexyl, morpholinyl or piperidinyl.

135

In other embodiments, the compound may have formula (V):

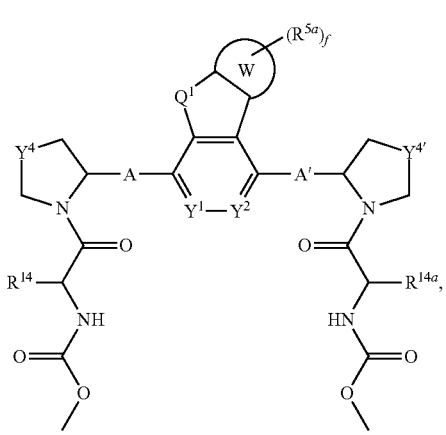
(V)

wherein each of $R^{14}$ and $R^{14a}$ is independently H, deuterium, $C_{1-6}$ alkyl, $C_{1-6}$ haloalkyl, $C_{1-6}$ hydroxyalkyl, $C_{2-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl, or $C_{3-8}$ cycloalkyl-$C_{1-6}$-alkyl; wherein each of $C_{1-6}$ alkyl, $C_{1-6}$ haloalkyl, $C_{1-6}$ hydroxyalkyl, $C_{2-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl and $C_{3-8}$ cycloalkyl-$C_{1-6}$-alkyl is optionally substituted with one or more substituents, and wherein the substituent is deuterium, F, Cl, Br, hydroxy or cyano.

In other embodiments, the compound may have formula (VI):

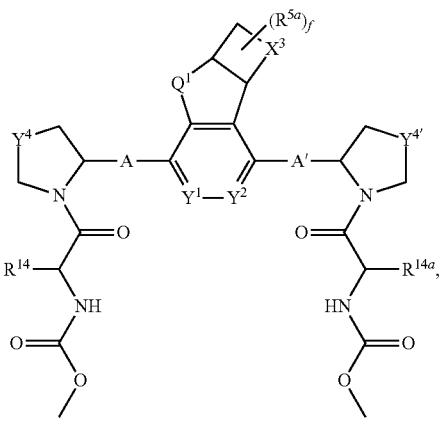
(VI)

wherein each of $R^{14}$ and $R^{14a}$ is independently H, deuterium, $C_{1-3}$ hydroxyalkyl, methyl, ethyl, isopropyl, isobutyl, tert-butyl, allyl, propargyl, trifluoroethyl, phenyl, pyranyl, morpholinyl, benzyl, piperazinyl, cyclopentyl, cyclopropyl, cyclohexyl, or $C_{1-9}$ heteroaryl; wherein each of $C_{1-3}$ hydroxyalkyl, methyl, ethyl, isopropyl, isobutyl, tert-butyl, allyl, propargyl, trifluoroethyl, phenyl, pyranyl, morpholinyl, benzyl, piperazinyl, cyclopentyl, cyclopropyl, cyclohexyl and $C_{1-9}$ heteroaryl is optionally substituted with one or more substituents, and wherein the substituent is deuterium, F, Cl, Br, hydroxy or cyano.

136

In other embodiments, the compound may have formula (VII):

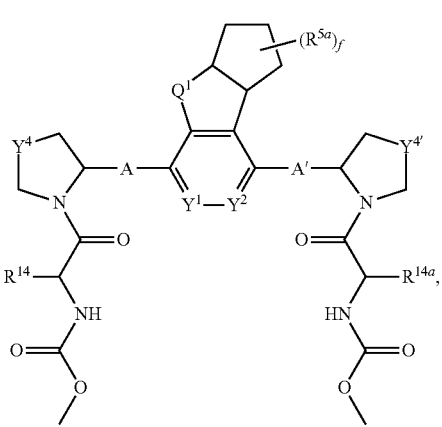
(VII)

wherein each of $R^{14}$ and $R^{14a}$ is independently H, deuterium, $C_{1-3}$ hydroxyalkyl, methyl, ethyl, isopropyl, isobutyl, tert-butyl, allyl, propargyl, trifluoroethyl, phenyl, pyranyl, morpholinyl, benzyl, piperazinyl, cyclopentyl, cyclopropyl, cyclohexyl, or $C_{1-9}$ heteroaryl; wherein each of $C_{1-3}$ hydroxyalkyl, methyl, ethyl, isopropyl, isobutyl, tert-butyl, allyl, propargyl, trifluoroethyl, phenyl, pyranyl, morpholinyl, benzyl, piperazinyl, cyclopentyl, cyclopropyl, cyclohexyl and $C_{1-9}$ heteroaryl is optionally substituted with one or more substituents, and wherein the substituent is deuterium, F, Cl, Br, hydroxy or cyano.

In other embodiments, the compound may have formula (VIII):

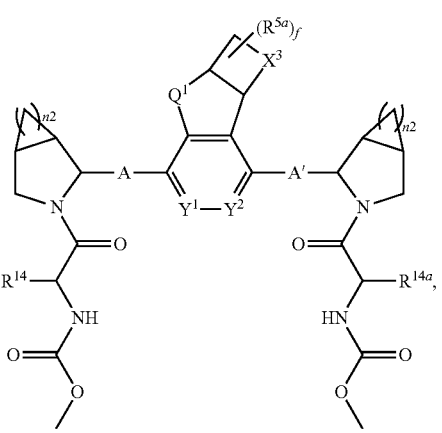
(VIII)

wherein each of $Q^1$ and $X^3$ is independently $NR^6$, O, S, C(=O) or $(CR^7R^{7a})_e$;

e is 0, 1, 2, 3 or 4;

each of $R^{14}$ and $R^{14a}$ is independently H, deuterium, $C_{1-6}$ alkyl, $C_{1-6}$ haloalkyl, $C_{1-6}$ hydroxyalkyl, $C_{2-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; wherein each of $C_{1-6}$ alkyl, $C_{1-6}$ haloalkyl, $C_{1-6}$ hydroxyalkyl, $C_{2-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl and $C_{3-8}$ cycloalkyl-$C_{1-6}$-alkyl is optionally substituted with one or more substituents, wherein the substituent is deuterium, F, Cl, Br, hydroxy or cyano; and each $n_2$ is independently 1, 2, 3 or 4.

In other embodiments, the compound may have formula (IX):

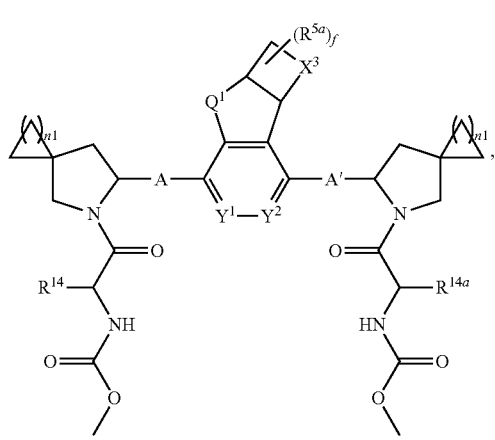

wherein each of $Q^1$ and $X^3$ is independently $NR^6$, O, S, $C(=O)$ or $(CR^7R^{7a})_e$;

e is 0, 1, 2, 3 or 4;

each of $R^{14}$ and $R^{14a}$ is independently H, deuterium, $C_{1-6}$ alkyl, $C_{1-6}$ haloalkyl, $C_{1-6}$ hydroxyalkyl, $C_{2-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl or $C_{3-8}$ cycloalkyl-$C_{1-6}$-alkyl; wherein each of $C_{1-6}$ alkyl, $C_{1-6}$ haloalkyl, $C_{1-6}$ hydroxyalkyl, $C_{2-6}$ heteroalkyl, $C_{6-10}$ aryl, $C_{1-9}$ heteroaryl, $C_{2-10}$ heterocyclyl, $C_{3-8}$ cycloalkyl, $C_{6-10}$ aryl-$C_{1-6}$-alkyl, $C_{1-9}$ heteroaryl-$C_{1-6}$-alkyl, $C_{2-10}$ heterocyclyl-$C_{1-6}$-alkyl and $C_{3-8}$ cycloalkyl-$C_{1-6}$-alkyl is optionally substituted with one or more substituents, wherein the substituent is deuterium, F, Cl, Br, hydroxy or cyano; and each $n_1$ is independently 1, 2, 3 or 4.

In other embodiments, the compound may have formula (X):

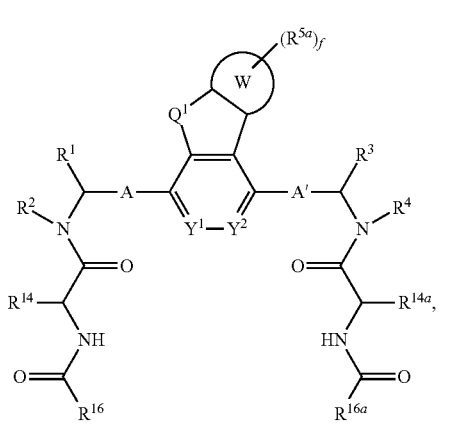

wherein each $R^{5a}$ is H, deuterium, $C_{1-4}$ alkyl, oxo(=O), benzyl, F, Cl, Br or I;

$Q^1$ is $CH_2$, $C(=O)$, O, S, or $NR^6$;

f is 0, 1, 2 or 3;

each $R^6$ and $R^7$ is independently H, deuterium, $C_{1-4}$ alkyl, $C_{6-10}$ aryl, $C_{2-10}$ heterocyclyl or $C_{3-8}$ cycloalkyl;

each of $R^{14}$ and $R^{14a}$ is independently H, deuterium, $C_{1-4}$ alkyl, $C_{6-10}$ aryl, $C_{2-10}$ heterocyclyl or $C_{3-8}$ cycloalkyl;

each of $R^{16}$ and $R^{16a}$ is independently hydroxy, $C_{1-4}$ alkoxy, $C_{6-10}$ aryloxy, $C_{2-10}$ heterocyclyl or $C_{3-8}$ cycloalkyl;

wherein each of benzyl, $C_{1-4}$ alkyl, $C_{1-4}$ alkoxy, $C_{6-10}$ aryl, $C_{2-10}$ heterocyclyl, $C_{3-8}$ cycloalkyl and $C_{6-10}$ aryloxy is optionally substituted with one or more substituents, wherein the substituent is deuterium, F, Cl, Br, hydroxy or cyano;

wherein

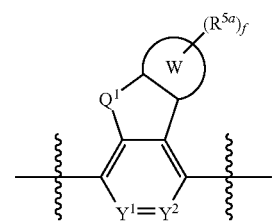

is

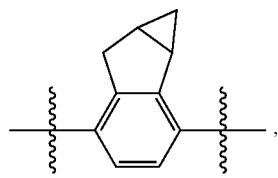

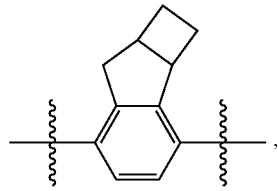

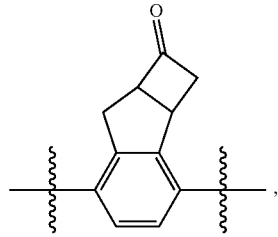

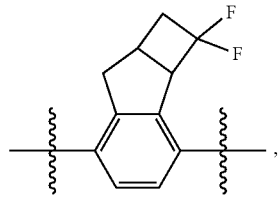

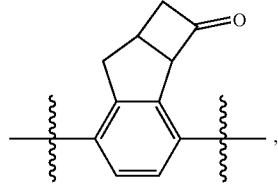

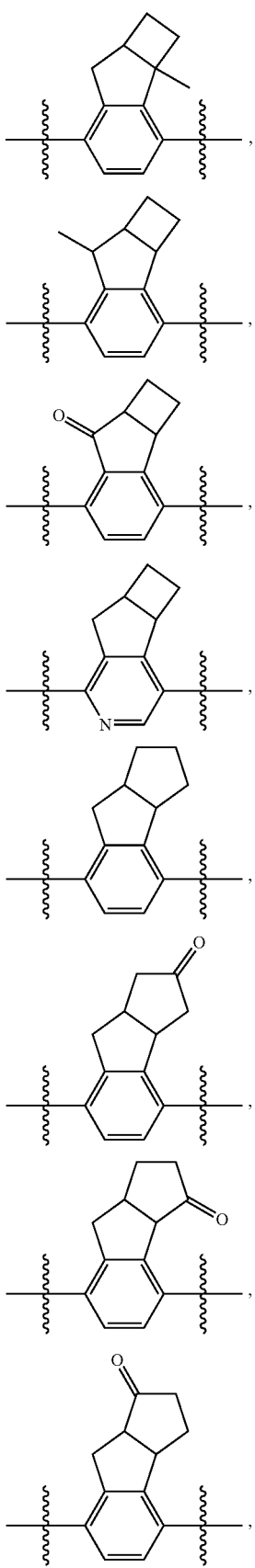
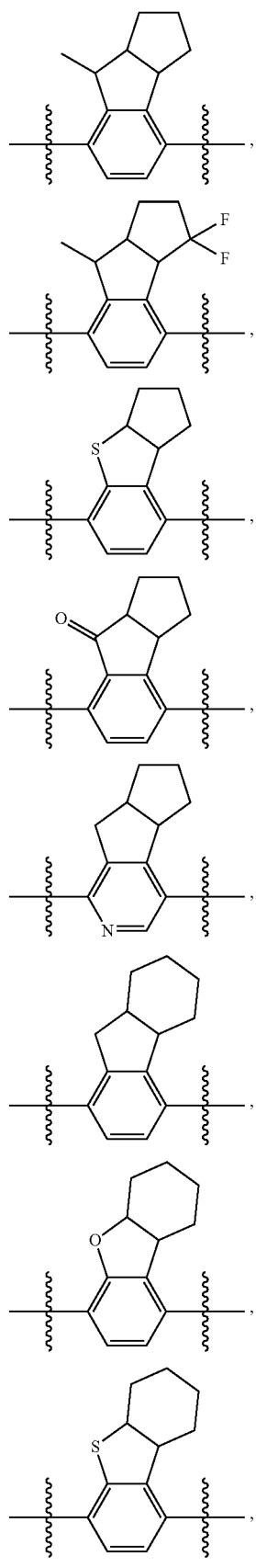

141
-continued
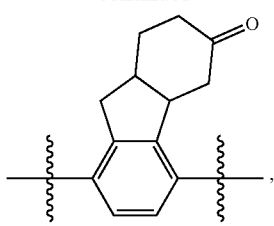,
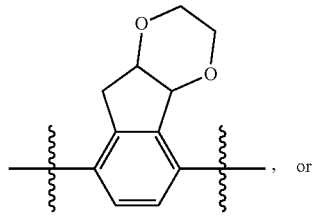, or
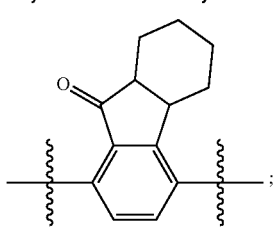;
each of A and A' is independently
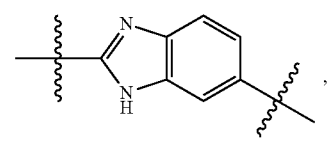,
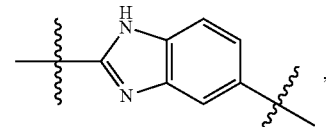,
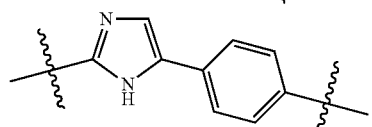,
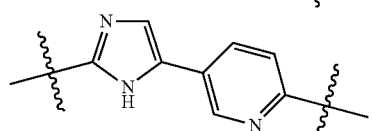,
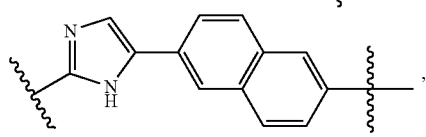,
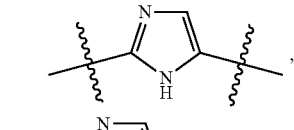,
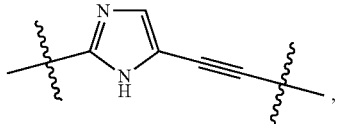,
142
-continued
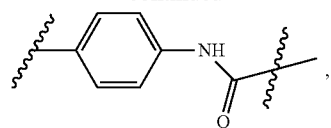,
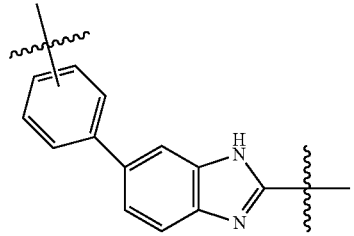,
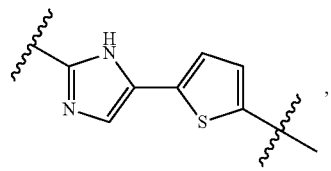,
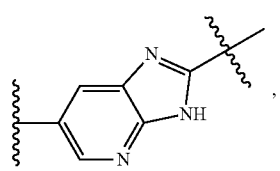,
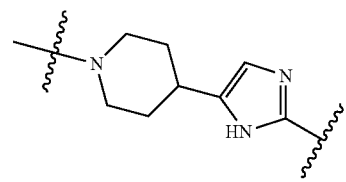,
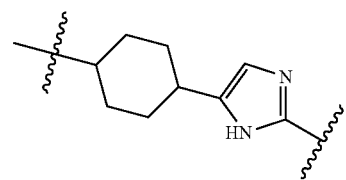,
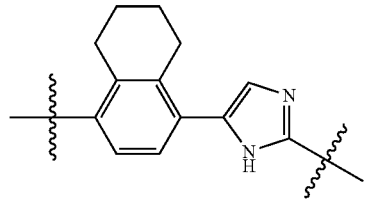,
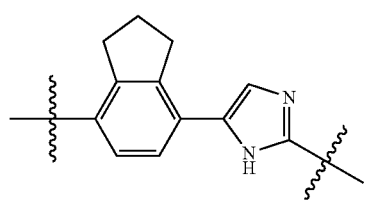,
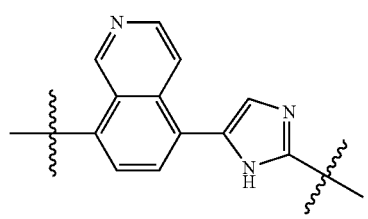,

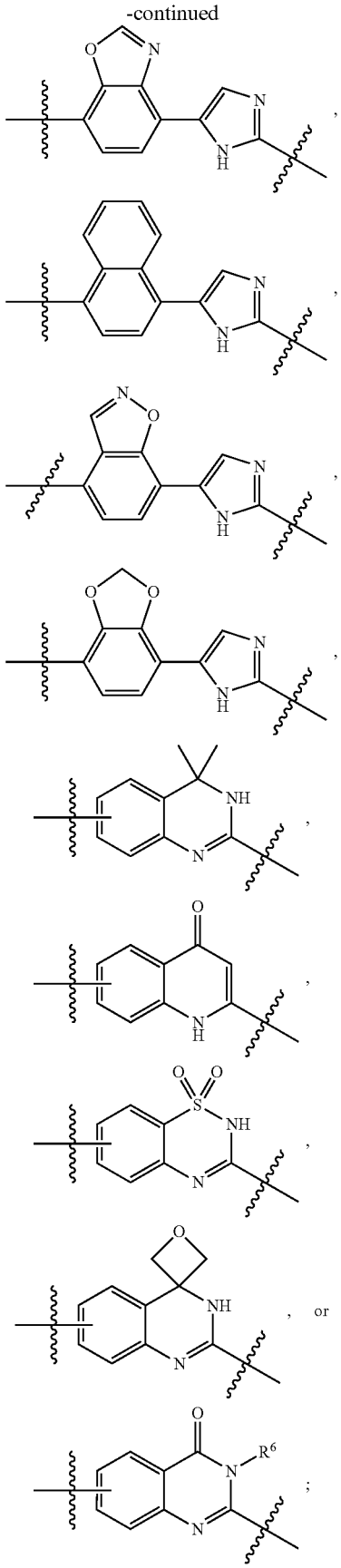
wherein R¹, R² and N—CH together form one of the following divalent groups:
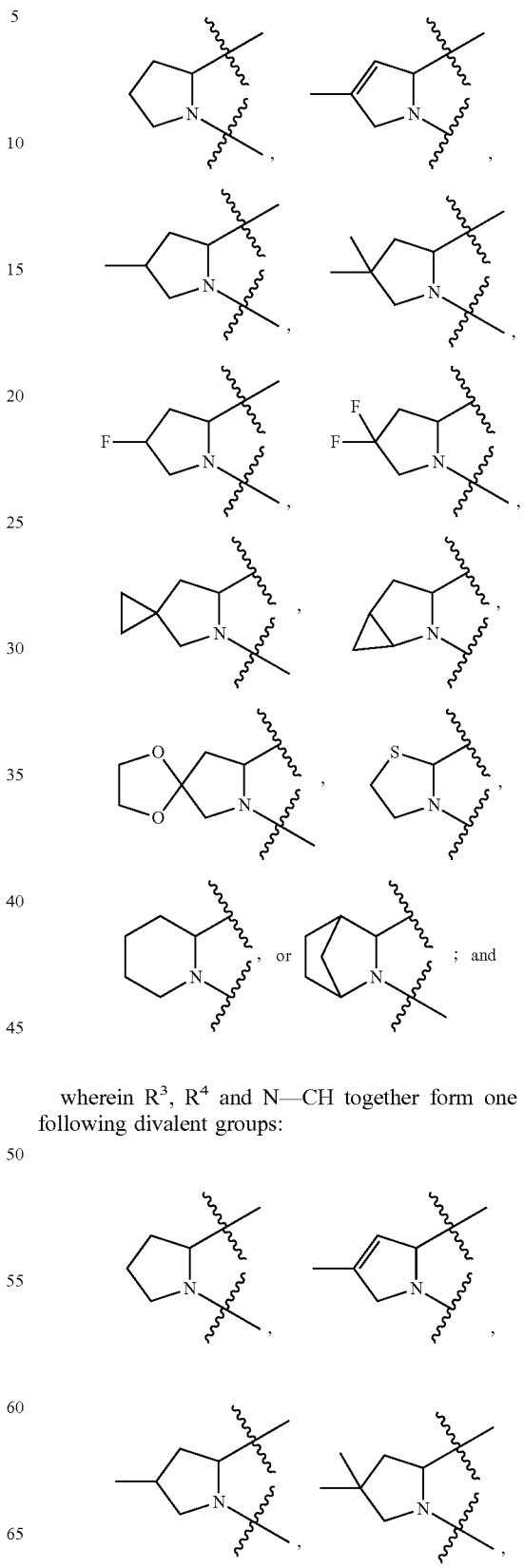
wherein R³, R⁴ and N—CH together form one of the following divalent groups:

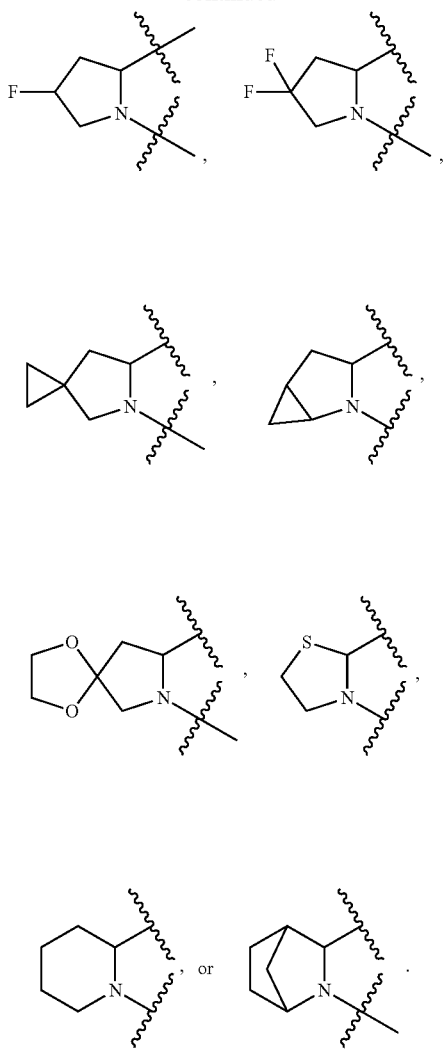

In other embodiments, each $R^{5a}$ is independently H, deuterium, methyl, ethyl, oxo(=O), benzyl, F, CL, Br or I;

each $R^6$ and $R^7$ is independently H, deuterium, methyl, ethyl, isopropyl, phenyl or cyclohexyl;

each of $R^{14}$ and $R^{14a}$ is independently methyl, ethyl, phenyl, cyclohexyl, 1-methyl-propyl, isopropyl, isobutyl or tert-butyl; and each of $R^{16}$ and $R^{16a}$ is independently hydroxy, methoxyl, ethyoxyl, phenoxy,

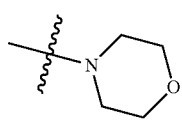

or tert-butoxy, wherein each of methyl, ethyl, phenyl, benzyl, cyclohexyl, 1-methyl-propyl, isopropyl, isobutyl, methoxyl, ethyoxyl, tert-butoxy, phenoxy and tert-butyl is optionally substituted with one or more substituents, and wherein the substituent is deuterium, F, Cl, Br, hydroxy or cyano.

In other embodiments, the compound may have formula (XI):

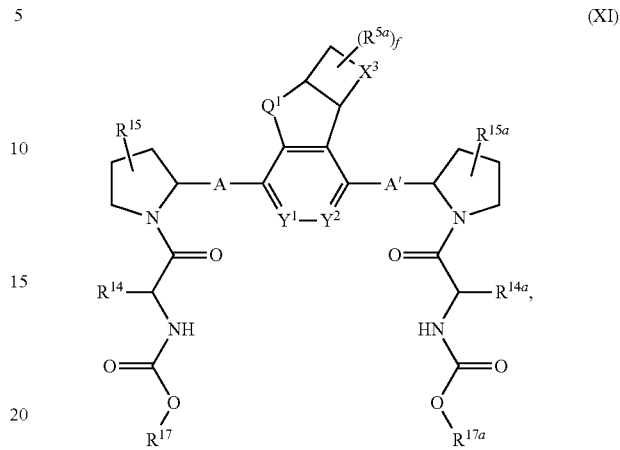

wherein, each $R^{5a}$ is H, deuterium, oxo(=O), benzyl or methyl;

each of $Q^1$ and $X^3$ is independently $(CH_2)_e$, $CF_2$, S, $NR^6$, O or C(=O);

each of f and e is independently 0, 1, 2 or 3;

each of $Y^1$ and $Y^2$ is independently N or $CR^7$;

each of $R^6$ and $R^7$ is independently H, deuterium, methyl, ethyl, isobutyl, cyclohexyl, phenyl or isopropyl;

each of $R^{14}$ and $R^{14a}$ is independently methyl, ethyl, isobutyl, cyclohexyl, phenyl, isobutyl or isopropyl;

each of $R^{15}$ and $R^{15a}$ is independently H, deuterium, F, Cl, Br, methyl, ethyl, isopropyl or tert-butyl; and each of $R^{17}$ and $R^{17a}$ is independently methyl, phenyl or ethyl, wherein each of methyl, ethyl, phenyl, benzyl, cyclohexyl, isopropyl, isobutyl or tert-butyl is optionally substituted with one or more substituents, and wherein the substituent is deuterium, F, Cl, Br, hydroxy or cyano.

In other embodiments, the compound may have formula formula (XI'):

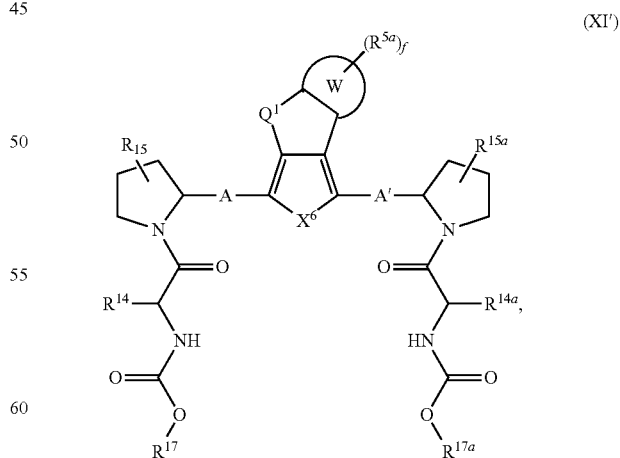

wherein each $R^{5a}$ is H, deuterium, oxo(=O), benzyl, or methyl;

$Q^1$ is $(CH_2)_e$, $CF_2$, S, $NR^6$, O or C(=O);

each of f and e is independently 0, 1, 2 or 3;

each $R^6$ and $R^{6a}$ is independently H, deuterium, methyl, ethyl, isobutyl, cyclohexyl, phenyl or isopropyl;

each of $R^{14}$ and $R^{14a}$ is independently methyl, ethyl, isobutyl, cyclohexyl, phenyl or isopropyl;

each of $R^{15}$ and $R^{15a}$ is independently H, deuterium, F, Cl, Br, methyl, ethyl, isopropyl or tert-butyl; and each of $R^{17}$ and $R^{17a}$ is independently methyl, phenyl or ethyl, wherein each of methyl, ethyl, phenyl, benzyl, cyclohexyl, isopropyl, isobutyl or tert-butyl is optionally substituted with one or more substituents, and wherein the substituent is deuterium, F, Cl, Br, hydroxy or cyano;

wherein

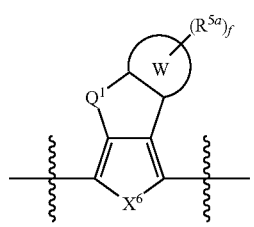

is

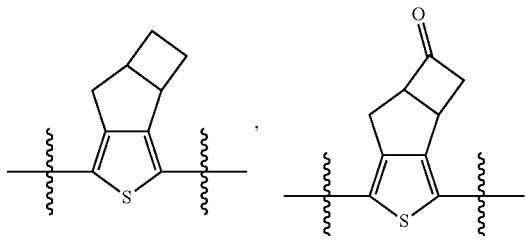,

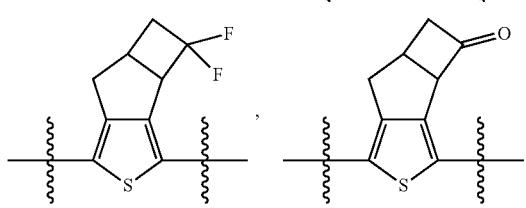,

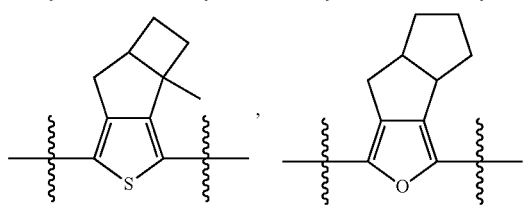,

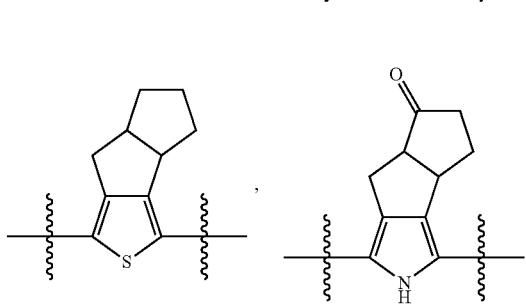,

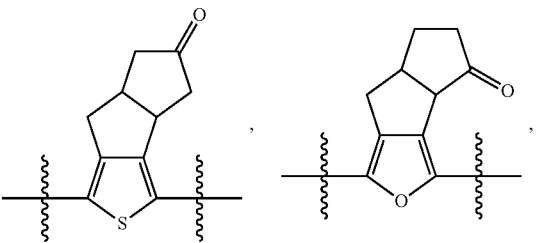,

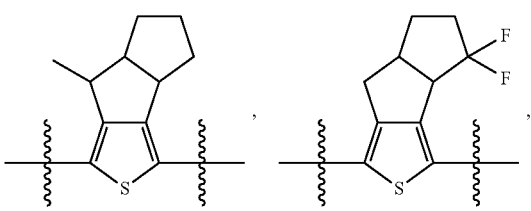,

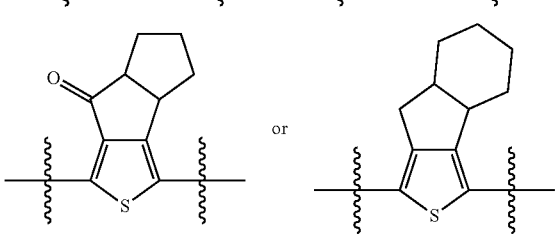

or ;

and each of A and A' is independently

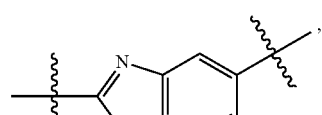,

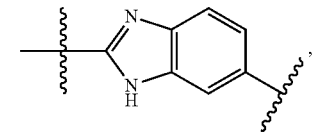,

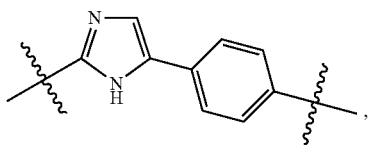,

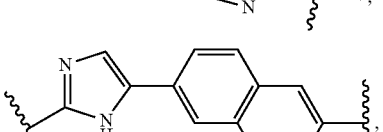,

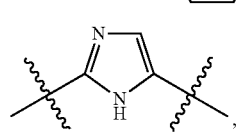,

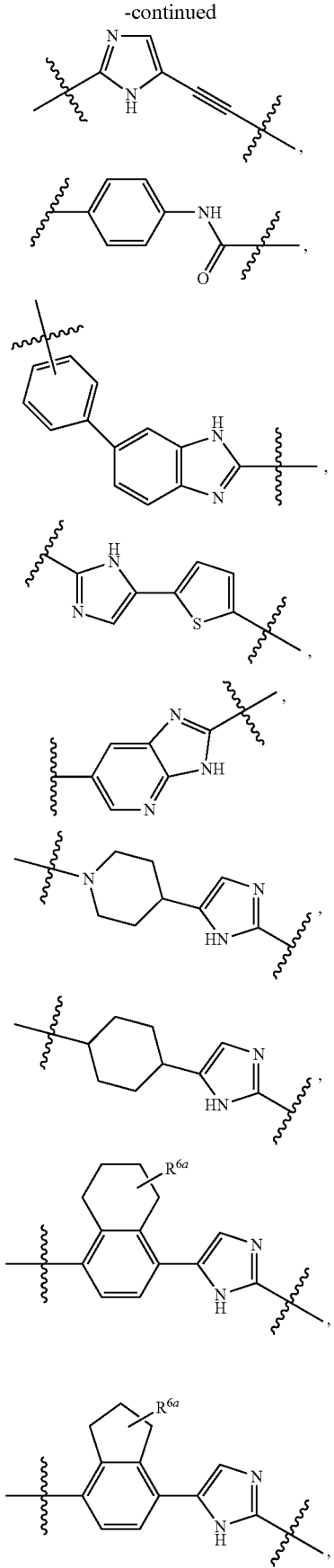
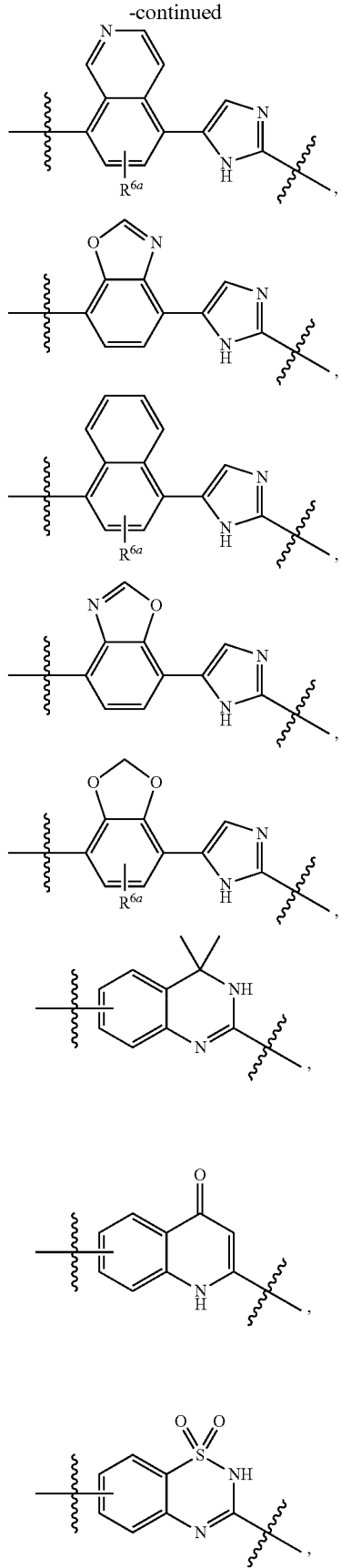

151
-continued
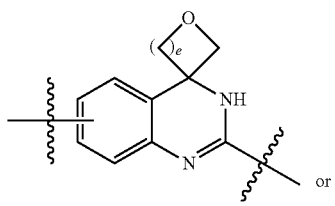
or
152
-continued
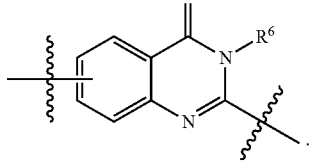
In some embodiments, non-limiting examples of compounds disclosed herein, or a stereoisomer, a geometric isomer, a tautomer, an N-oxide, a hydrate, a solvate, or a pharmaceutically acceptable salt thereof, are shown in the following:
(1)
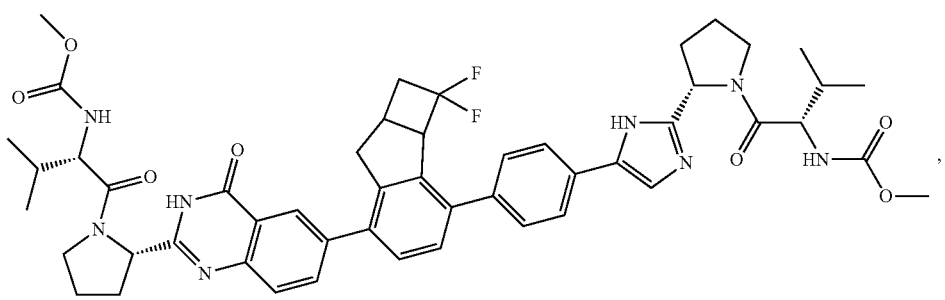
(2)
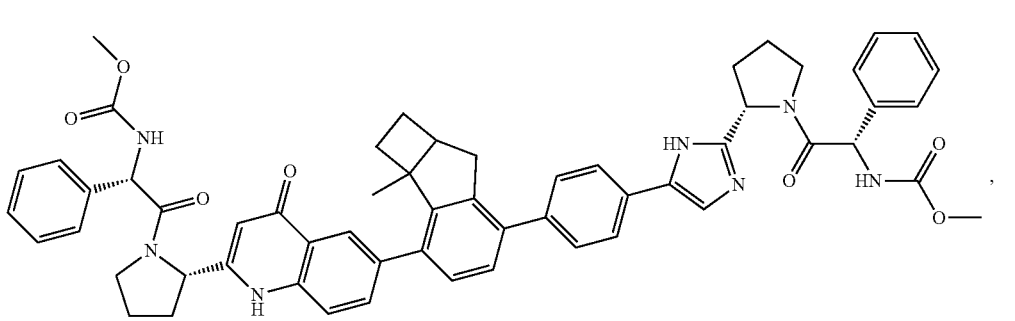
(3)
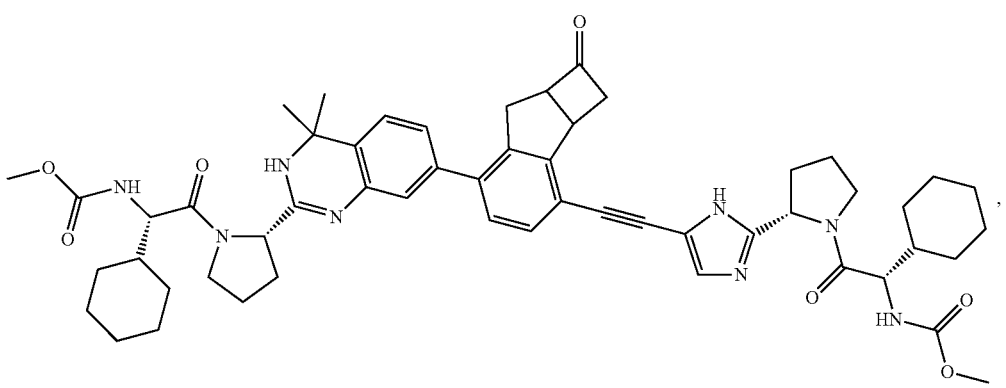

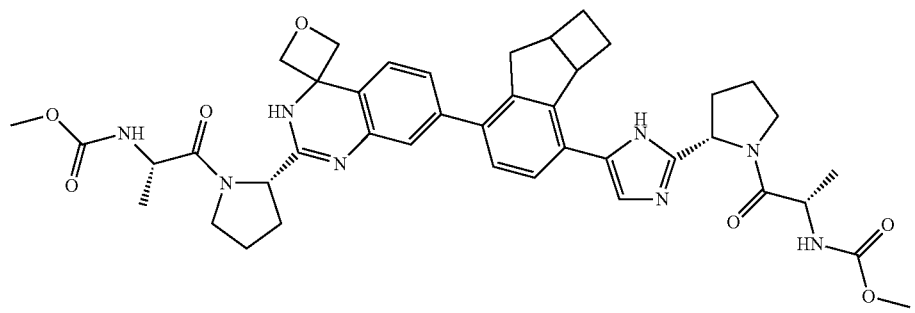
(4)
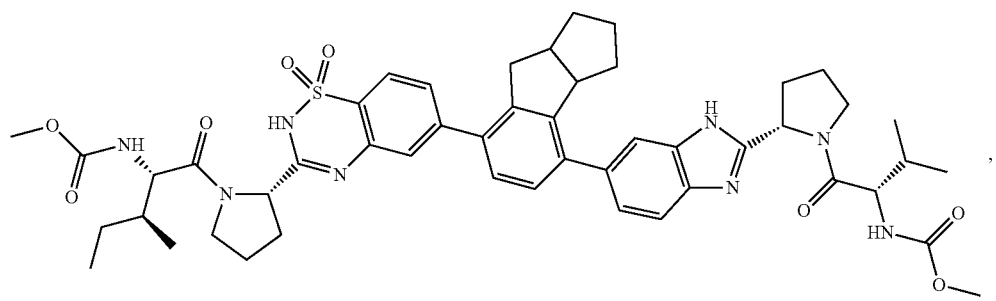
(5)
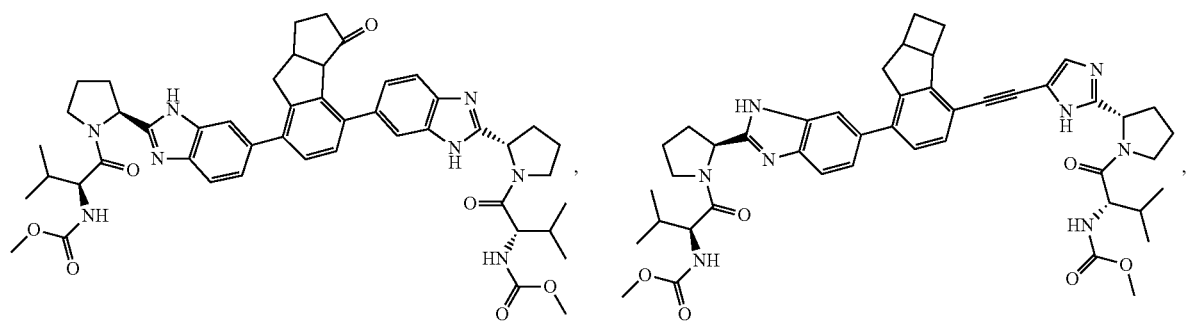
(6) (7)
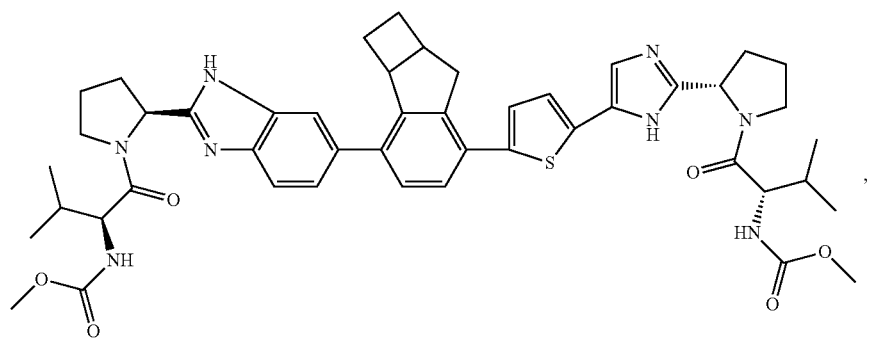
(8)
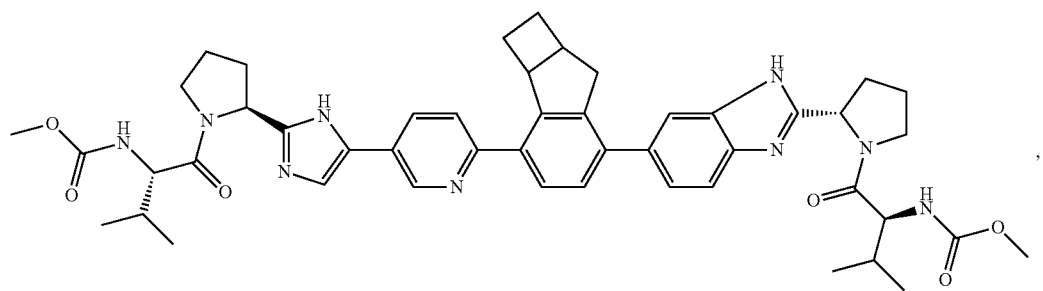
(9)

-continued
(10)
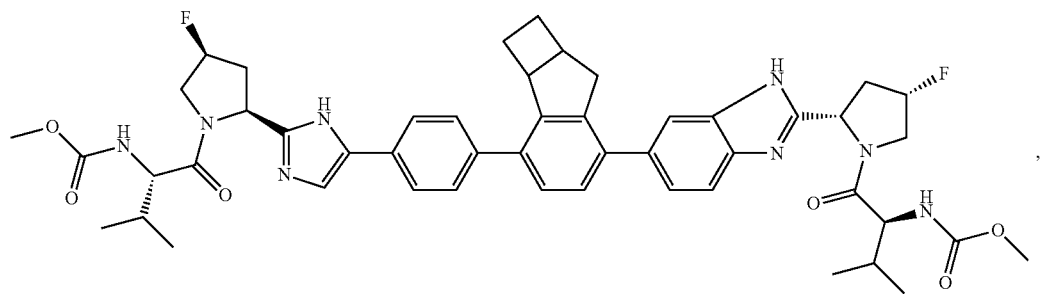
(11)
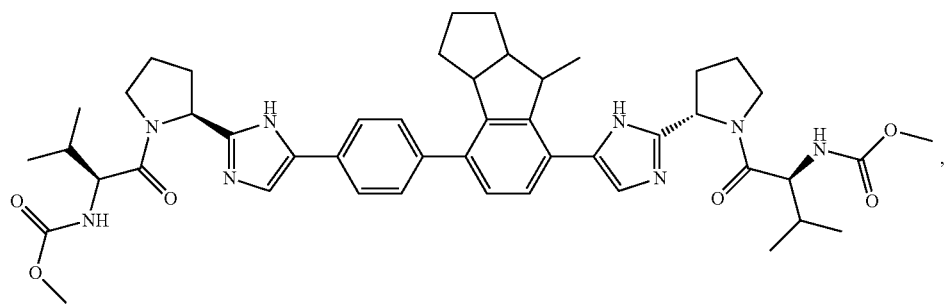
(12)
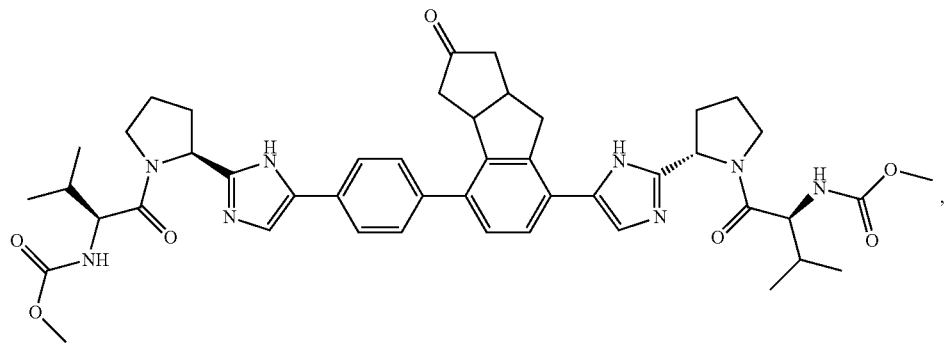
(13)
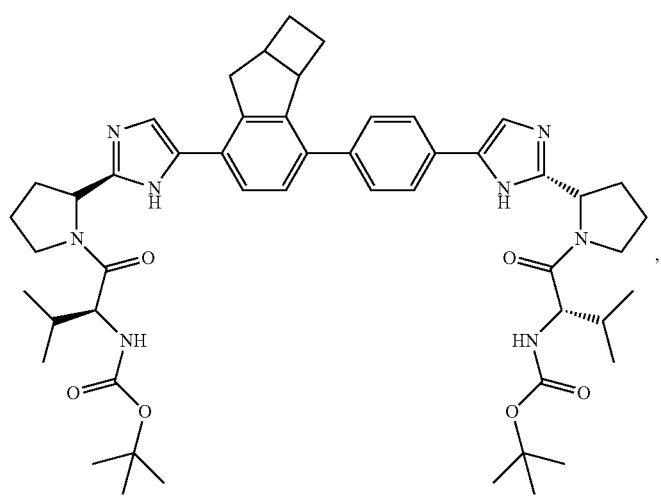

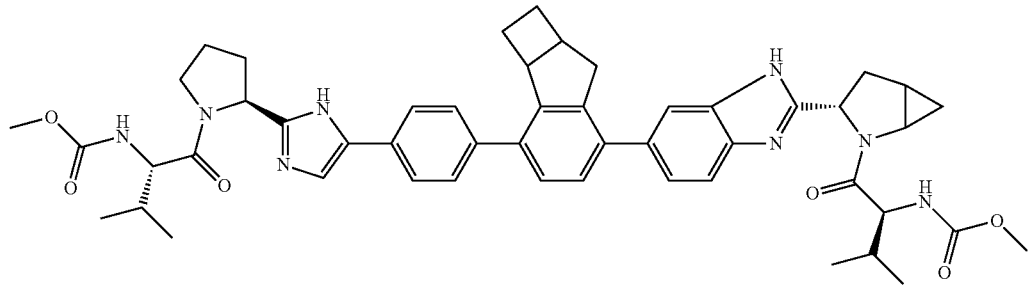
(14)
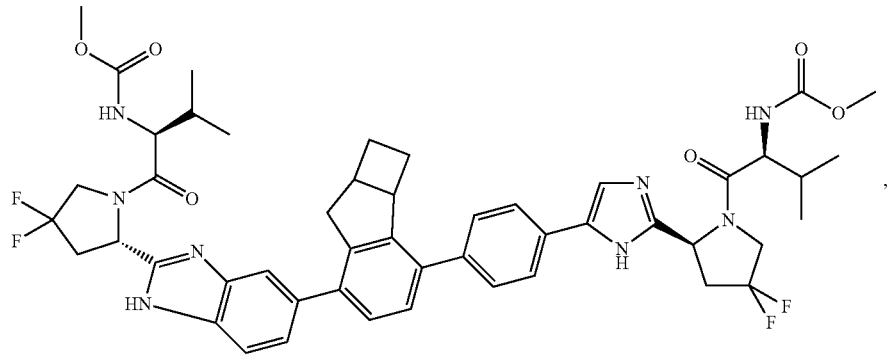
(15)
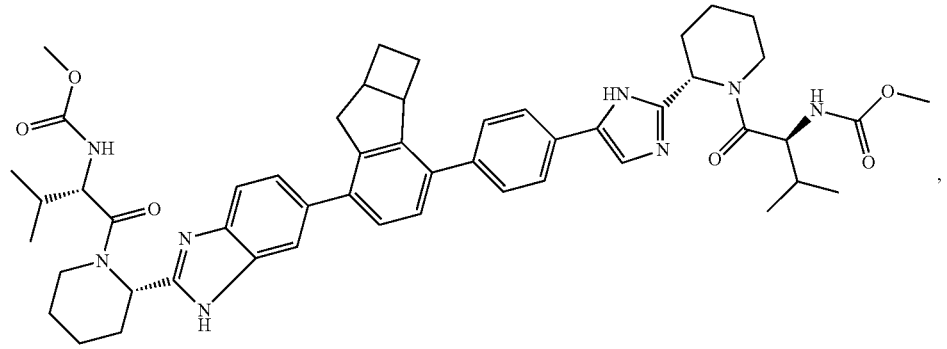
(16)
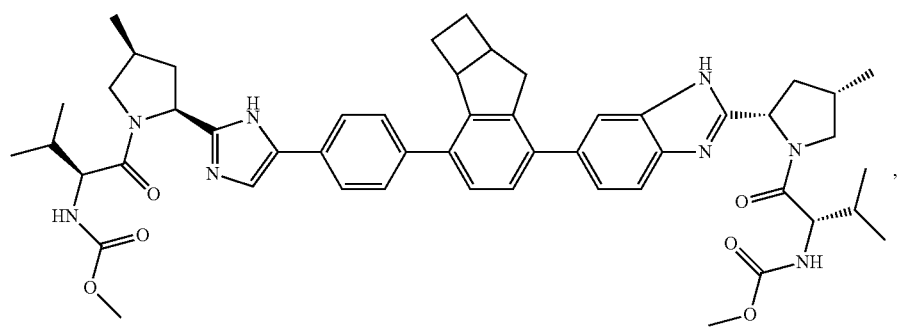
(17)

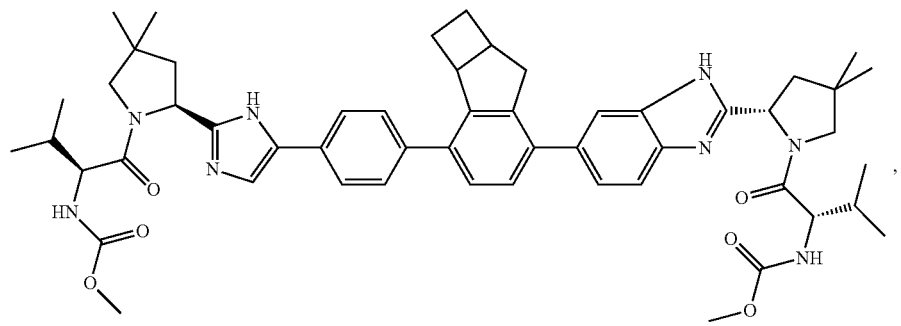
(18)
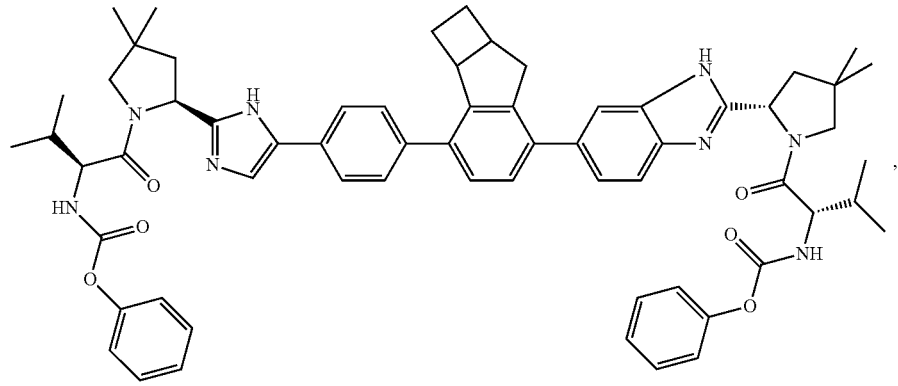
(19)
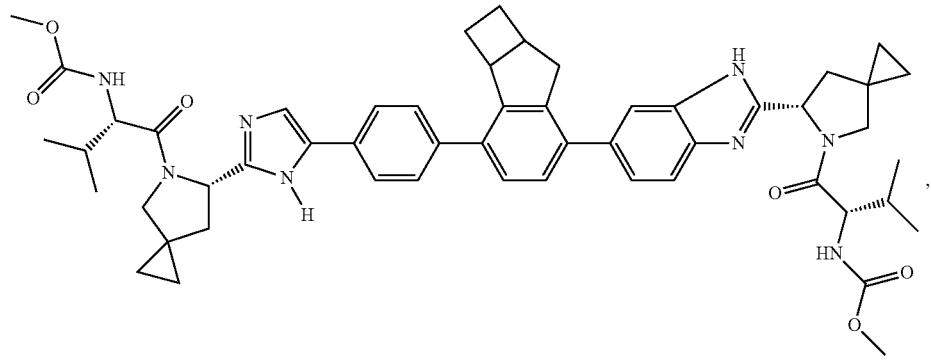
(20)
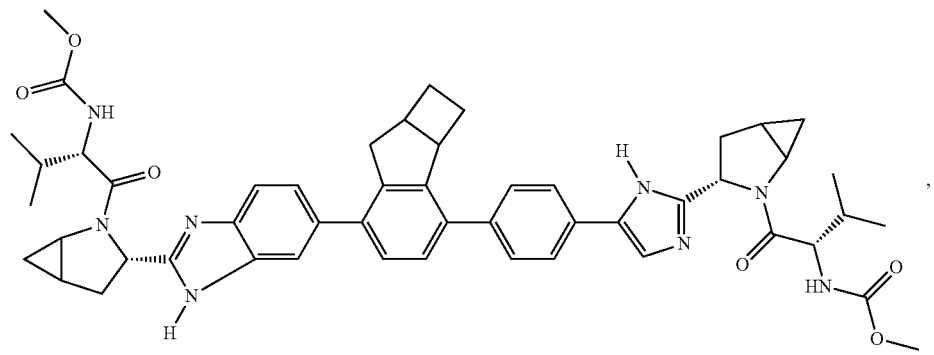
(21)

-continued
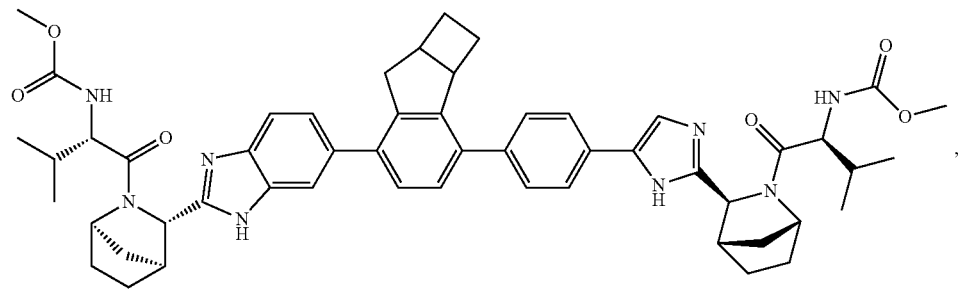
(22)
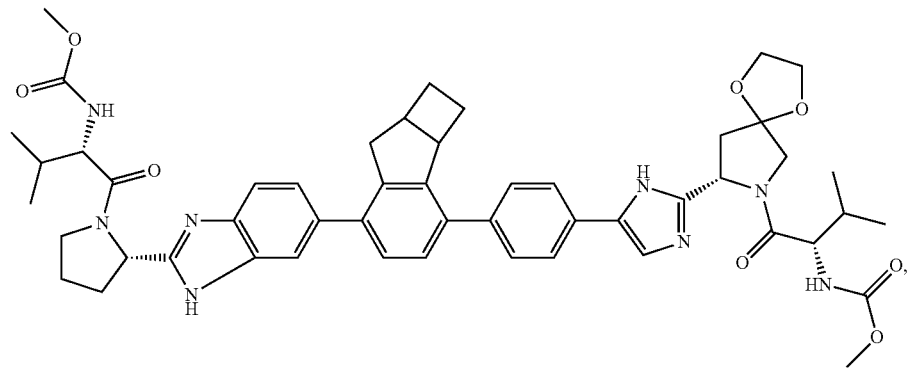
(23)
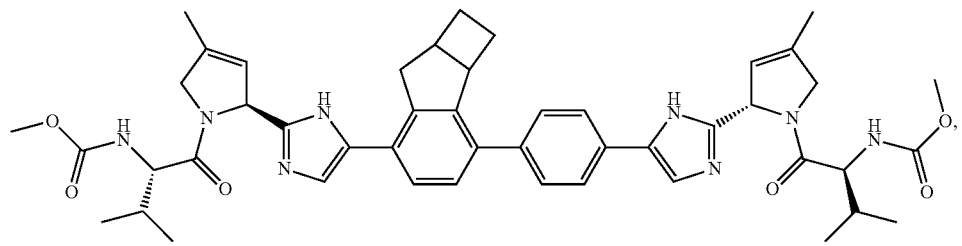
(24)
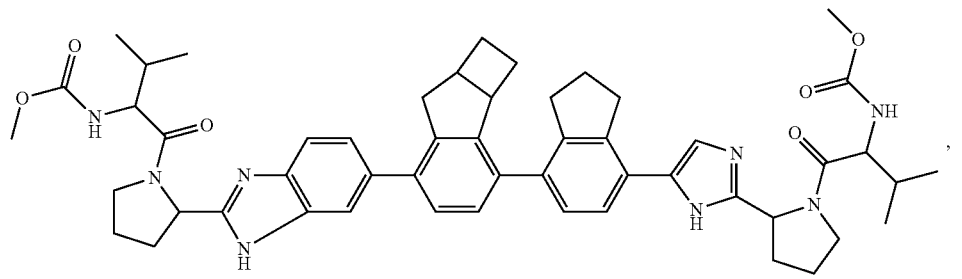
(25)
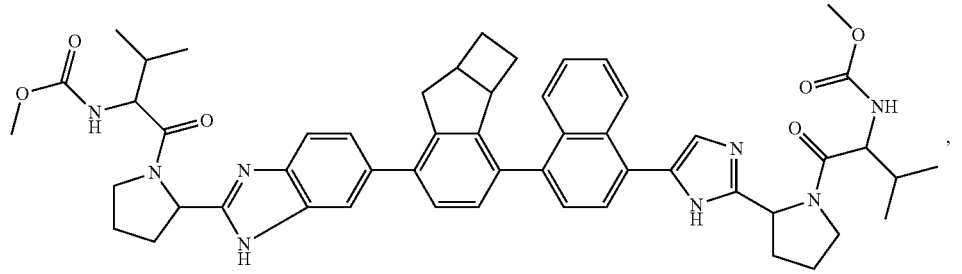
(26)

(27)
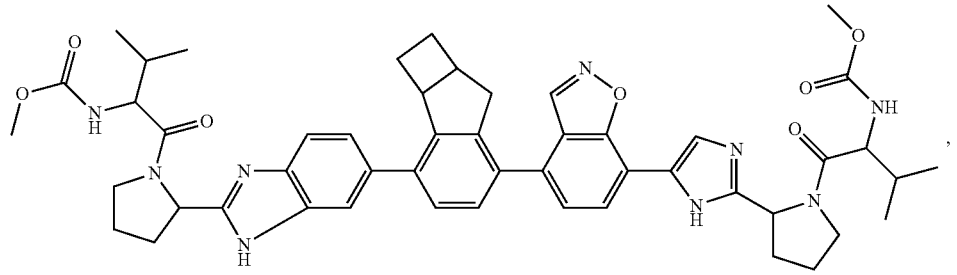
(28)
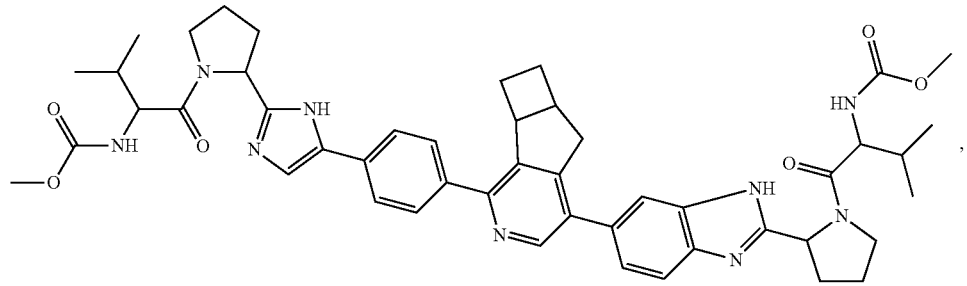
(29)
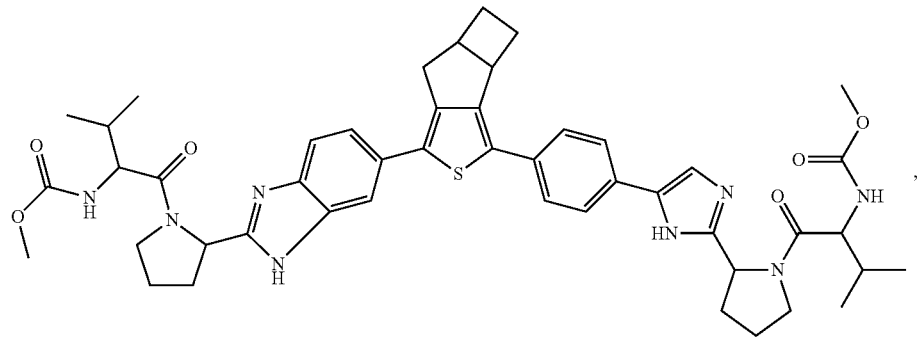
(30)
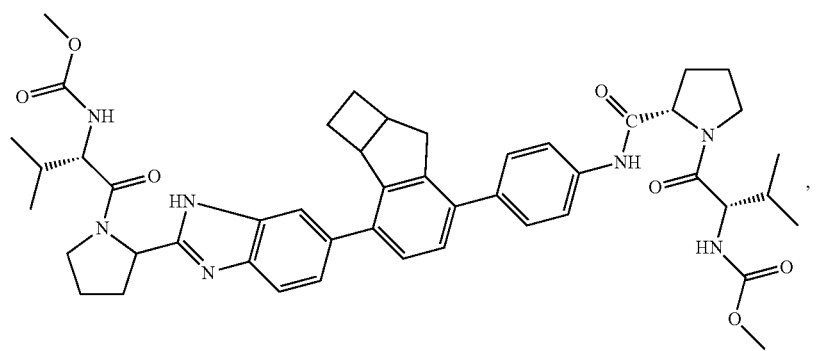
(31)
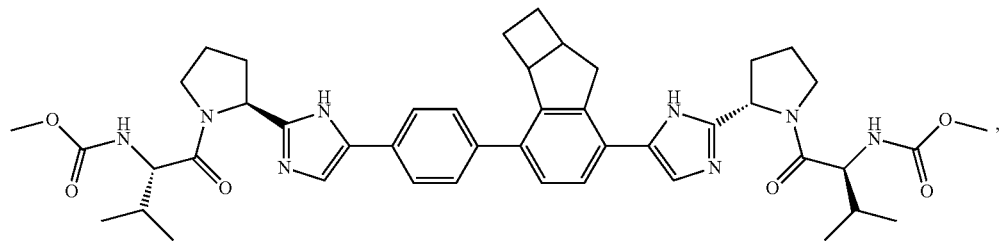

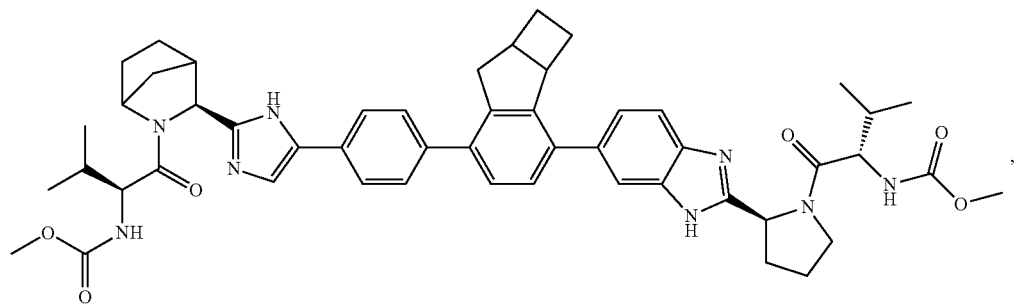
(32)
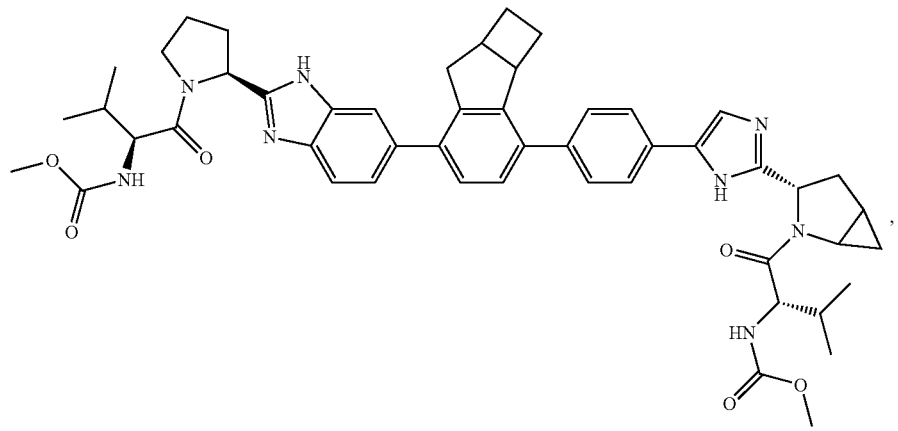
(33)
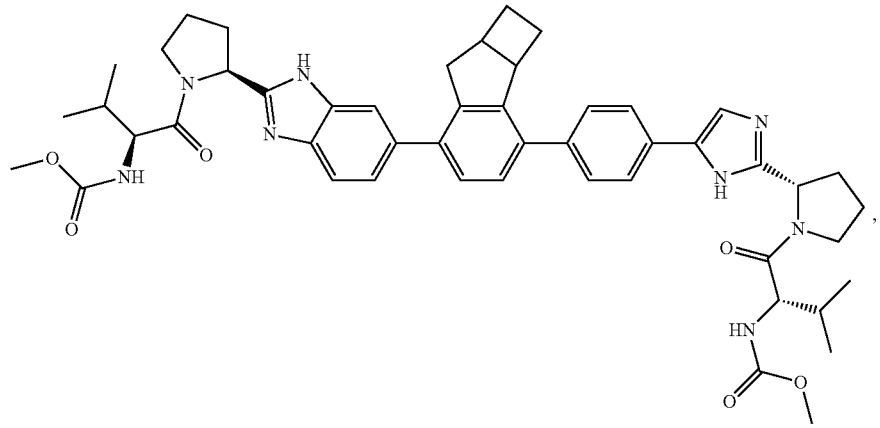
(34)
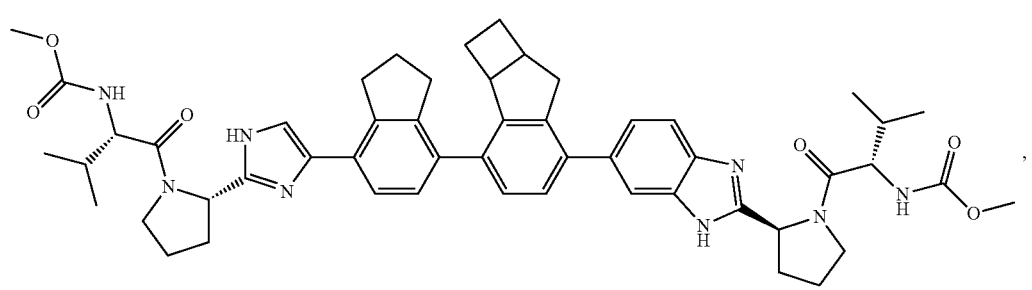
(35)

(36)
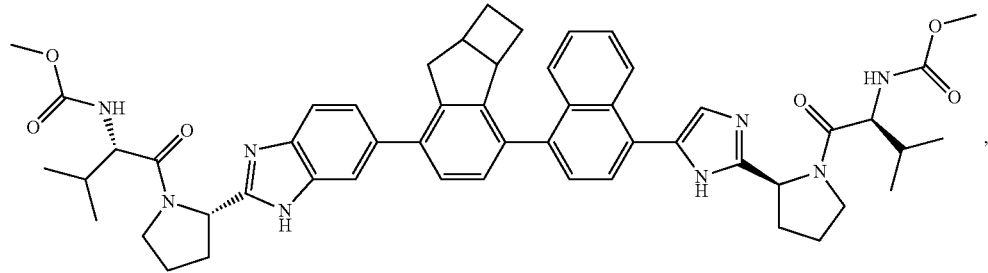
(37)
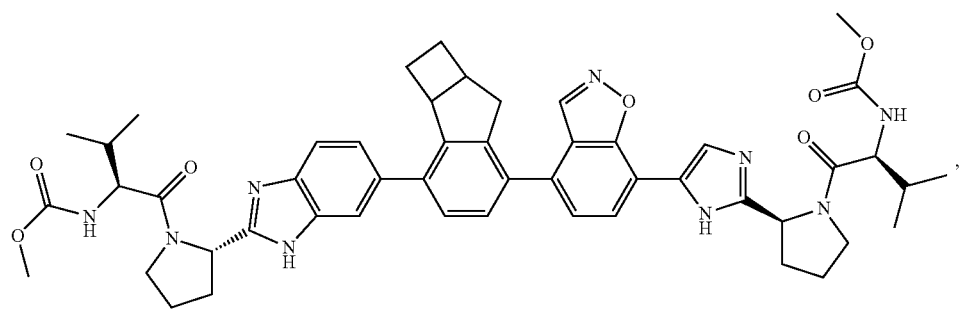
(38)
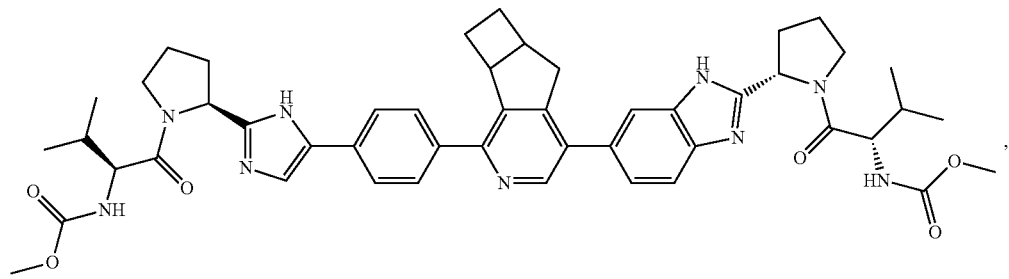
(39)
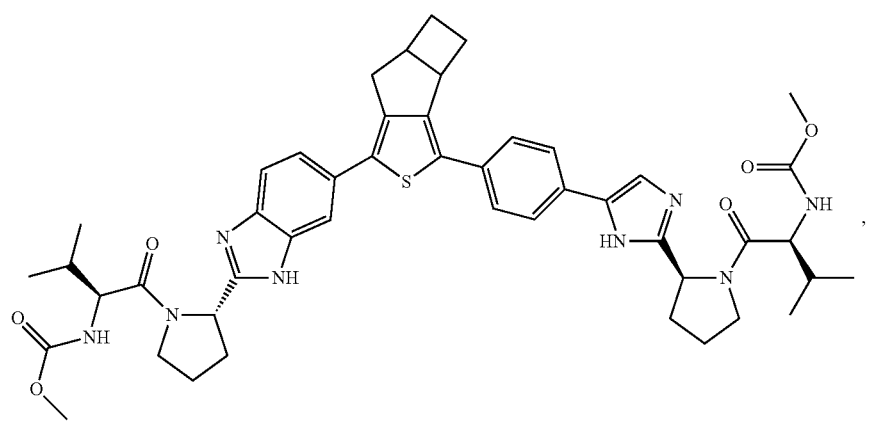

-continued
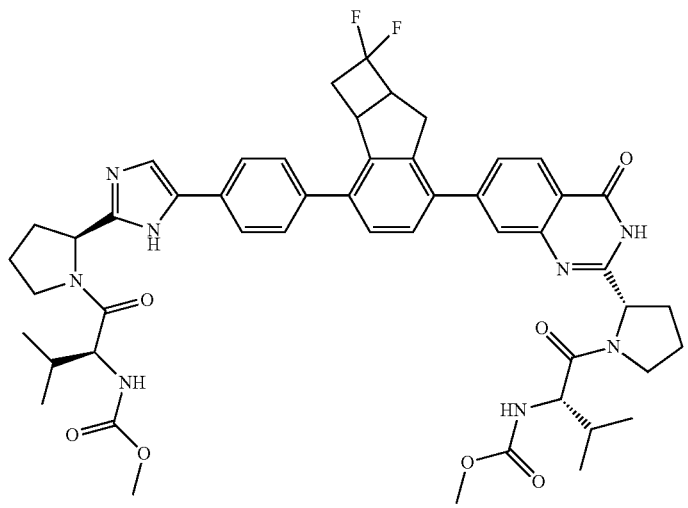
(40)
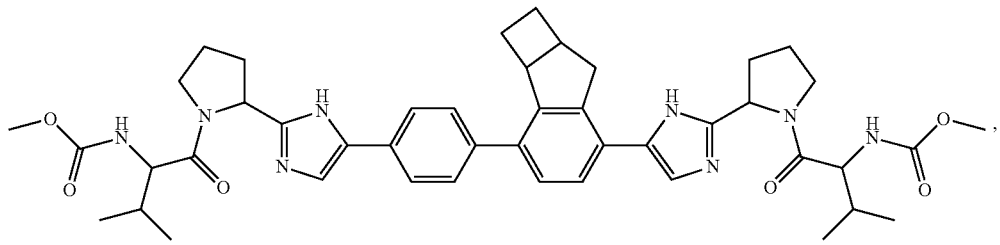
(41)
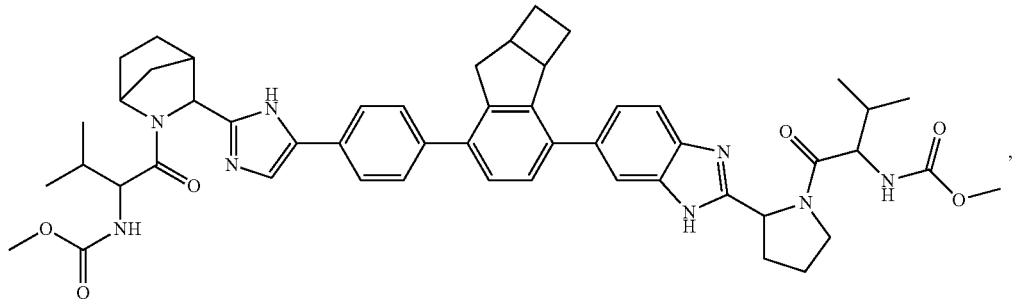
(42)
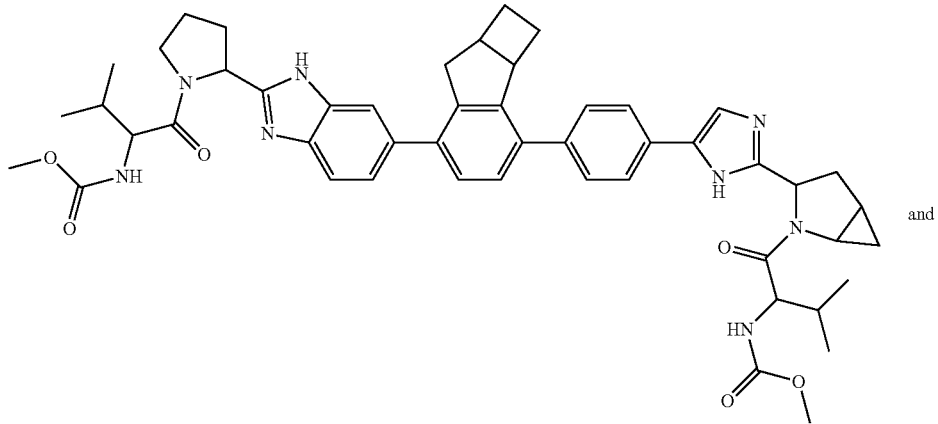
(43)
and (44)

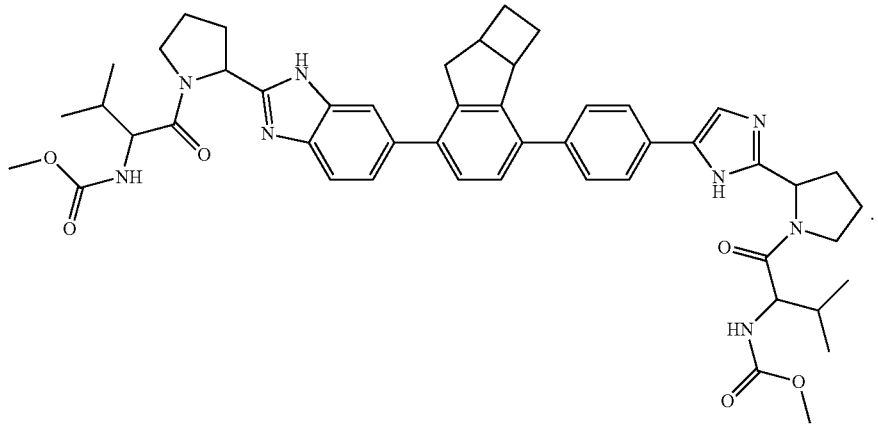

Provided herein includes the use of a compound disclosed herein (In present disclosure, "a compound disclosed herein" comprises a compound of formula (I), a stereoisomer, a geometric isomer, a tautomer, an N-oxide, a hydrate, a solvate and a pharmaceutically acceptable salt thereof), in the manufacture of a medicament for the treatment either acutely or chronically of HCV infection in a patient, including those described herein. Provided herein is use of the compound in the manufacture of an anti-HCV medicament. Provided herein is the use of the compound disclosed herein, in the manufacture of a medicament to attenuate, prevent, manage or treat disorders through inhibition of HCV, especially HCV's NS5A protein. Also provided herein is a pharmaceutical composition comprising a therapeutically effective amount of a compound of Formula (I) in association with at least one pharmaceutically acceptable carrier, adjuvant or diluent.

In certain embodiments, the salt is a pharmaceutically acceptable salt. The phrase "pharmaceutically acceptable" refers to that the substance or composition must be compatible chemically and/or toxicologically, with the other ingredients comprising a Formulation, and/or the mammal being treated therewith. The skills in the art could choose "pharmaceutically acceptable" substance or composition base on the other ingredients and the objects for treatment such as human.

The compounds disclosed herein also include salts of such compounds which are not necessarily pharmaceutically acceptable salts, and which may be useful as intermediates for preparing and/or purifying compounds of Formula (I) and/or for separating enantiomers of compounds of Formula (I).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like. Or with an organic acid, such as acetic acid, maleic acid, succinic acid, mandelic acid, fumaric acid, malonic acid, pyruvic acid, oxalic acid, glycolic acid, salicylic acid; a pyranosidyl acid, such as glucuronic acid or galacturonic acid; an alpha hydroxy acid, such as citric acid or tartaric acid; an amino acid, such as aspartic acid or glutamic acid; an aromatic acid, such as benzoic acid or cinnamic acid, a sulfonic acid, such as p-toluenesulfonic acid or ethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide or alkaline earth metal hydroxide, and the like. Some non-limiting examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum, lithium, and the like.

Composition, Formulations and Administration of Compounds of the Invention

The pharmaceutical composition disclosed herein comprises any one of the compounds. The pharmaceutical composition further comprises a pharmaceutically acceptable carrier, excipient, diluent, adjuvant, vehicle or a combination thereof. The pharmaceutical composition can be used for treating HCV infection or a HCV disorder, especially, it is great for inhibiting HCV NS5A protein.

The pharmaceutical composition disclosed herein further comprises anti-HCV agents. The anti-HCV agent may be any other known anti-HCV agent except the compound described herein, such as interferon, ribavirin, IL-2, IL-6, IL-12, a compound that enhances the development of a type 1 helper T cell response, interfering RNA, anti-sense RNA, imiquimod, an inosine-5'-monophosphate dehydrogenase inhibitor, amantadine, rimantadine, virazole, bavituximab, Civacir™, boceprevir, telaprevir, erlotinib, daclatasvir, simeprevir, asunaprevir, vaniprevir, faldaprevir, ABT-450, danoprevir, sovaprevir, MK-5172, vedroprevir, BZF-961, GS-9256, narlaprevir, ANA975, ABT-267, EDP239, PPI-668, GS-5816, samatasvir (IDX-719), MK-8742, MK-8325, GSK-2336805, PPI-461, TMC-435, MK-7009, BI-2013335, ciluprevir, BMS-650032, ACH-1625, ACH-1095, VX-985, IDX-375, VX-500, VX-813, PHX-1766, PHX-2054, IDX-136, IDX-316, EP-013420, VBY-376, TMC-649128, R-7128, PSI-7977, INX-189, IDX-184, IDX102, R1479, UNX-08189, PSI-6130, PSI-938, PSI-879, HCV-796, HCV-371, VCH-916, VCH-222, ANA-598, MK-3281, ABT-333, ABT-072, PF-00868554, BI-207127, GS-9190, A-837093, JKT-109, Gl-59728, GL-60667, AZD-2795, TMC647055 or a combination thereof. The interferon is interferon α-2b, pegylated interferon α, interferon α-2a, pegylated interferon α-2a, consensus interferon-α, interferon γ or a combination thereof. The pharmaceutical composition disclosed herein further comprises at least one HCV inhibitor. In some embodiments, the HCV inhibitor inhibits at least one of HCV replication process and HCV viral protein function. In some embodiments, the HCV replication process is a whole viral cycle consisting of HCV entry, uncoating, translation, replication, assembly and egress. In some embodiments, the HCV viral protein is non-structural protein or an internal ribosome entry site (IRES) or inosine-5'-monophosphate dehydrogenase (IMPDH) required in HCV viral replication.

When it is possible that, for use in therapy, therapeutically effective amounts of a compound of formula (I), as well as pharmaceutically acceptable salts thereof, may be administered as the raw chemical, it is possible to present the active ingredient as a pharmaceutical compositions, which include therapeutically effective amounts of compounds of formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit (e.g., a reduction in viral load). When applied to individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluents(s), or excipient(s) must be acceptable in the sense of being compatible with the other ingredients of the formulation and not deleterious to recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, composition, and/or dosage forms which are, within the scope of sound medical judgment, suitable for use in contact with the tissues of patients without excessive toxicity, irritation, allergic response, or other problem complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen. Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intraarticular, intrasynovial, intrastemal, intrathecal, intralesional, intravenous, or intradermal injections or infusions) route. Such formulations may be prepared by any method known in the art of pharmacy, for example by bringing into association the active ingredient with the carrier(s) or excipient(s). oral administration of administration by injection are preferred.

Pharmaceutical formulations adapted for oral administration may be presented as discrete units such as capsules of tablets; powders or granules; solution or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are maded by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluents or base as described above, and optionally, with a binder such as carboxymethylcellulose, an alginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solution of cellulosic or polymeric materials and forcing through a screen. As an alternative to granulation, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating of embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carrier to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, poly(s-caprolactone), polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmacol. Res.*, 1986, 3(6), 318.

Pharmaceutical formulations adapted for topical administration may be formulated as ointments, creams, suspensions, lotions, powders, solutions, pastes, gels, sprays, aerosols, oils or transdermal patch.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain antioxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to ingredients particularly mentioned above, the formulations may include other agents conventional in the art having regard to the type of formulation in question, for example those suitable for oral administration may include flavoring agents.

Uses of the Compounds and Compositions of the Invention

Provided herein is use of the compound or the pharmaceutical composition in the manufacture of a medicament for inhibiting at least one of HCV replication process and HCV viral protein function. In some embodiments, the HCV replication process is a whole viral cycle consisting of HCV entry, uncoating, translation, replication, assembly and egress. In some embodiments, the HCV viral protein is non-structural protein or an internal ribosome entry site (IRES) or inosine-5'-monophosphate dehydrogenase (IMPDH) required in HCV viral replication. And any one of the compounds or the pharmaceutical compositions disclosed herein can be used for treating HCV infection or a HCV disorder, especially it is effective as inhibitor of the non-structural 5A (NS5A) protein of HCV.

Also provided herein is a method, which comprises administering the compound or the pharmaceutical composition disclosed herein, further comprising administering to the patient additional anti-HCV agents (combination therapy), wherein the anti-HCV agent is an interferon, ribavirin, IL-2, IL-6, IL-12, a compound that enhances the development of a type 1 helper T cell response, interfering RNA, anti-sense RNA, imiquimod, an inosine-5'-monophosphate dehydrogenase inhibitor, amantadine, rimantadine, ribavirin, bavituximab, human hepatitis C immune globulin (CIVACIR™), boceprevir, telaprevir, erlotinib, daclatasvir, simeprevir, asunaprevir, vaniprevir, faldaprevir, ABT-450, danoprevir, sovaprevir, MK-5172, vedroprevir, BZF-961, GS-9256, narlaprevir, ANA975, ABT-267, EDP239, PPI-668, GS-5816, samatasvir (IDX-719), MK-8742, MK-8325, GSK-2336805, PPI-461, TMC-435, MK-7009, BI-2013335, ciluprevir, BMS-650032, ACH-1625, ACH-1095, VX-985, IDX-375, VX-500, VX-813, PHX-1766, PHX-2054, IDX-136, IDX-316, EP-013420, VBY-376, TMC-649128, R-7128, PSI-7977, INX-189, IDX-184, IDX102, R1479, UNX-08189, PSI-6130, PSI-938, PSI-879, HCV-796, HCV-371, VCH-916, VCH-222, ANA-598, MK-3281, ABT-333, ABT-072, PF-00868554, BI-207127, GS-9190, A-837093, JKT-109, Gl-59728, GL-60667, AZd-2795, TMC647055 or a combination thereof. Wherein the interferon is interferon α-2b, pegylated interferon α, interferon α-2a, pegylated interferon α-2a, consensus interferon-α, interferon γ or a combination thereof.

The treatment method that includes administering a compound or composition disclosed herein can further include administering to the patient an additional anti-HCV agent, wherein the additional anti-HCV drug is administered together with a compound or composition disclosed herein as a single dosage form or separately from the compound or composition as part of a multiple dosage form. The additional anti-HCV agent may be administered at the same time as a compound disclosed herein or at a different time. In the latter case, administration may be staggered by, for example, 6 hours, 12 hours, 1 day, 2 days, 3 days, 1 week, 2 weeks, 3 weeks, 1 month, or 2 months.

In certain embodiments disclosed herein, an "effective amount" or "effective dose" of the compound or pharmaceutically acceptable composition is that amount effective for treating or lessening the severity of one or more of the aforementioned disorders. The compounds and compositions, according to the method disclosed herein, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents, as discussed above.

General Synthetic Procedures

Generally, the compounds disclosed herein may be prepared by methods described herein, wherein the substituents are as defined for Formula (I), above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous tetrahydrofuran, dioxane, toluene, and ether were obtained by refluxing the solvent with sodium. Anhydrous dichloromethane and chloroform were obtained by refluxing the solvent with calcium hydride. ethyl acetate, petroleum ether, hexane, N,N-dimethylacetamide and N,N-dimethylformamide were treated with anhydrous sodium sulfate prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1$H NMR spectra were recorded with a Bruker 400 MHz spectrometer at ambient temperature. $^1$H NMR spectra were obtained as $CDCl_3$, $d_6$-DMSO, $CD_3OD$ or $d_6$-acetone solutions (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Low-resolution mass spectral (MS) data were also determined on an Agilent 6320 series LC-MS spectrometer equipped with G1312A binary pumps, a G1316A TCC (Temperature Control of Column, maintained at 30° C.), a G1329A autosampler and a G1315B DAD detector were used in the analysis. An ESI source was used on the LC-MS spectrometer.

Low-resolution mass spectral (MS) data were also determined on an Agilent 6120 series LC-MS spectrometer equipped with G1311A Quaternary pump, a G1316A TCC (Temperature Control of Column, maintained at 30° C.), a G1329A autosampler and a G1315D DAD detector were used in the analysis. An ESI source was used on the LC-MS spectrometer.

Both LC-MS spectrometers were equipped with an Agilent Zorbax SB-C18, 2.1×30 mm, 5 m column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient condition is shown in Table 1:

TABLE 1

| Time (min) | A ($CH_3CN$, 0.1% HCOOH) | B ($H_2O$, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micom, 10 min, 0.6 mL/min flow rate, 5 to 95% (0.1% formic acid in $CH_3CN$) in (0.1% formic acid in $H_2O$). Column was operated at 40° C.

The following abbreviations are used throughout the specification:
HOAc acetic acid
MeCN, $CH_3CN$ acetonitrile
$NH_3$ ammonia NH₄Cl ammonium chloride
BBr₃ boron tribromide
BSA bovine serum albumin
Br₂ bromine
BOC, Boc tert-butyloxycarbonyl
Cs₂CO₃ cesium carbonate
CHCl₃ chloroform
CDCl₃ chloroform deuterated
Cu copper
CuI copper (I) iodide
Et₂O diethyl ether
DMF dimethylformamide
DMAP 4-dimethylaminopyridine
DMSO dimethylsulfoxide
EDC, EDCI 1-(3-dimethylaminopropyl)-3-ethylcarbodiimide hydrochloride
Dppa diphenylphosphoryl azide
EtOAc ethyl acetate
EA ethyl acetate
HBr hydrobromic acid
HCl hydrochloric acid
HOAt, HOAT 1-hydroxy-7-azabenzotriazole
HOBT 1-hydroxybenzotriazole hydrate
H₂ hydrogen
H₂O₂ hydrogen peroxide
Fe iron
LDA lithium diisopropylamide
MCPBA meta-chloroperbenzoic acid
MgSO₄ magnesium sulfate
MeOH, CH₃OH methanol
MeI methyl iodide
CH₂Cl₂, DCM methylene chloride
NMP N-methylpyrrolidinone
mL, m milliliter
N₂ nitrogen
Pd/C palladium on activated carbon
PE petroleum ether (60-90° C.)
PBS phosphate buffered saline
POCl₃ phosphorous oxychloride
Pd(PPh₃)₄ palladium tetrakis triphenylphosphine
Pd(dppf)Cl₂ 1,1-bis(diphenylphosphino)ferrocene palladium chloride
K₂CO₃ potassium carbonate
KOH potassium hydroxide
RT, rt room temperature
Rt retention time
NaHCO₃ sodium bicarbonate
NaBH₄ sodium borohydride
NaBH₃CN sodium cyanoborohydride
NaOtBu sodium tert-butoxide
NaOH sodium hydroxide
NaClO₂ sodium chlorite
NaCl sodium chloride
NaH₂PO₄ sodium dihydric phosphate
NaH sodium hydride
NaI sodium iodide
Na₂SO₄ sodium sulfate
TBTU O-benzotriazol-1-yl-N,N,N',N-tetramethyluronium tetrafluoroborate
THF tetrahydrofuran
Et₃N, TEA triethylamine
TFA trifluoroacetic acid
P(t-bu)₃ tri(tert-butyl)phosphine
NBS N-bromosuccinimide
TBAI tetrabutylammonium iodide
H₂O water
TEAF formic acid triethylamine complex 5:2
PPA polyphosphoric acid
Tf₂O trifluoromethanesulfonic anhydride
HCl.EA a solution of HCl in ethyl acetate
DIPEA N,N-diisopropylethylamine
DME 1,2-dimethoxyethane
HATU 2-(7-aza-1H-benzotriazole-1-yl)-1,1,3,3-tetramethyluronium hexafluorophosphate
NIS N-iodosuccinimide
TFAA trifluoroaceticanhydride
SEMCI 2-(Trimethylsilyl)ethoxymethyl chloride
Dess-Martin (Dess-Martin periodinane) (1,1,1-Triacetoxy)-1,1-dihydro-1,2-benziodoxol-3(1H)-one
TsOH p-toluenesulfonic acid
TMSA trimethyl silyl acetylene
Meldrum's acid 2,2-dimethyl-1,3-dioxane-4,6-dione
BAST bis(2-methoxyethyl)aminosulphurtrifluoride Deoxofluor
SbCl₃ antimony trichloride
SmCl3 samarium chloride
LiHMDS lithium hexamethyldisilazide
TMSC₁ trimethyl chlorosilane
PhNTf₂ N,N-bis(trifluoromethylsulfonyl)aniline
TBDMSOTf trifluoromethanesulfonic acid tert-butyldimethylsilyl ester
Et₂NSF₃ diethylaminosulfur trifluoride
MTBE methyl tert-butyl ether
LiN(SiMe₃)₂ lithium bis(trimethylsilyl)amide
PPh₃MeBr methyltriphenylphosphonium bromide
Lawesson's Reagent 2,4-bis(4-methoxyphenyl)-1,3-dithia-2,4-diphosphetane 2,4-disulfide
TEBAC benzyltriethylammonium chloride
I₂ iodine
DAST diethylaminosulfur trifluoride
IPA isopropanol
TCCA trichloroisocyanuric acid
TEMPO 2,2,6,6-tetramethylpiperidinooxy
IMPDH inosine monophosphate dehydrogenase
IRES internal ribosome entry site Scheme 1

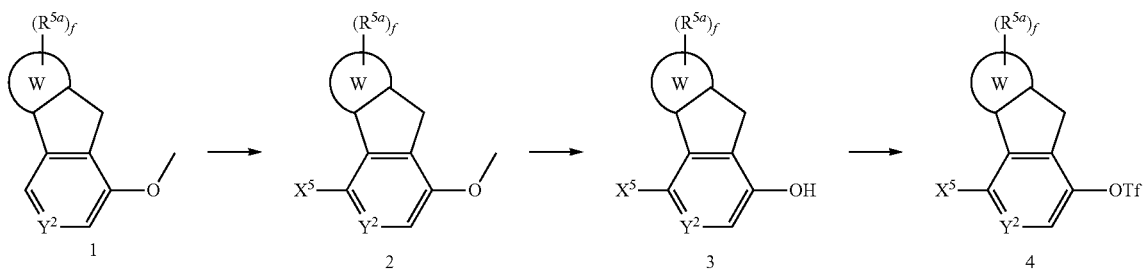

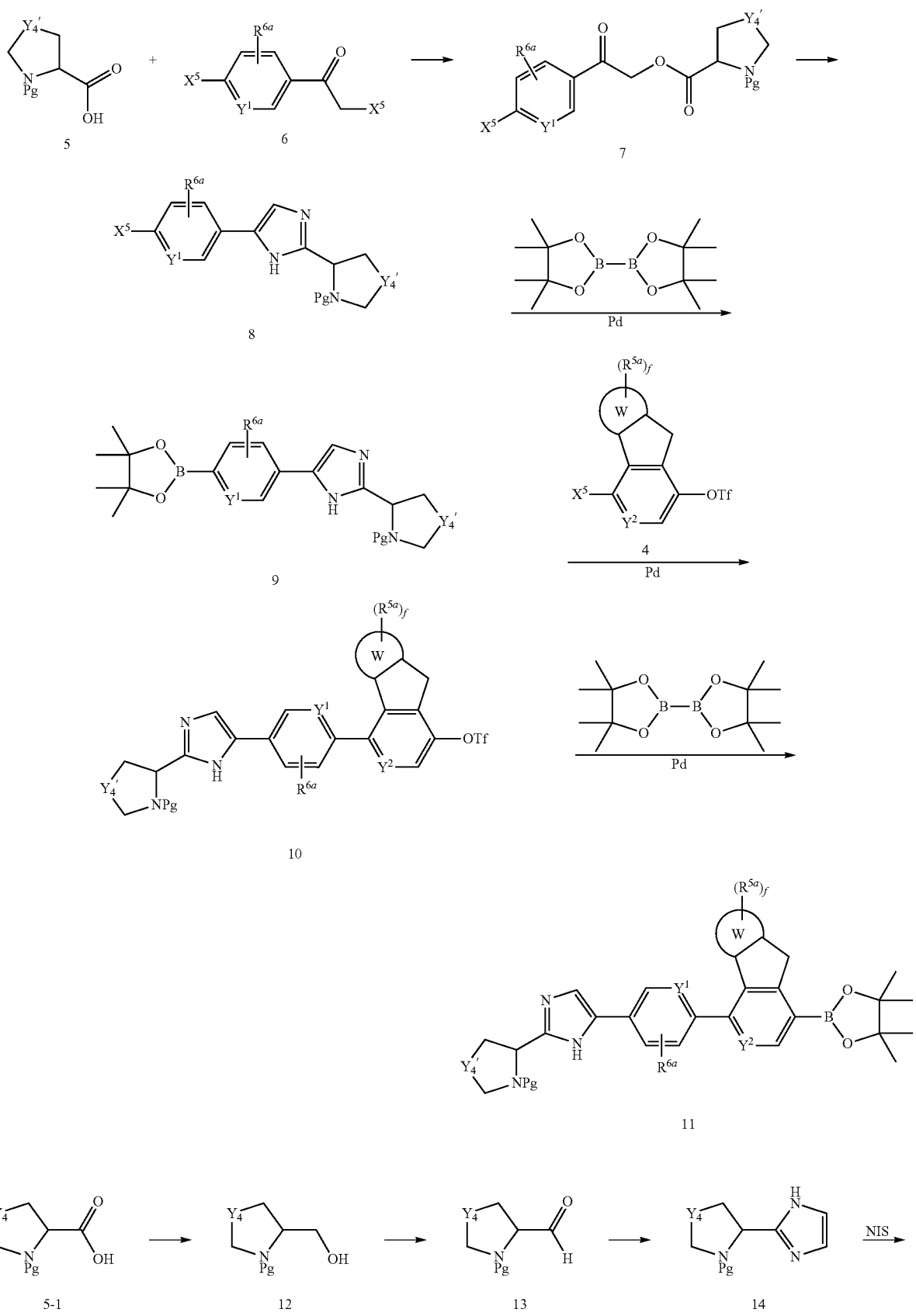

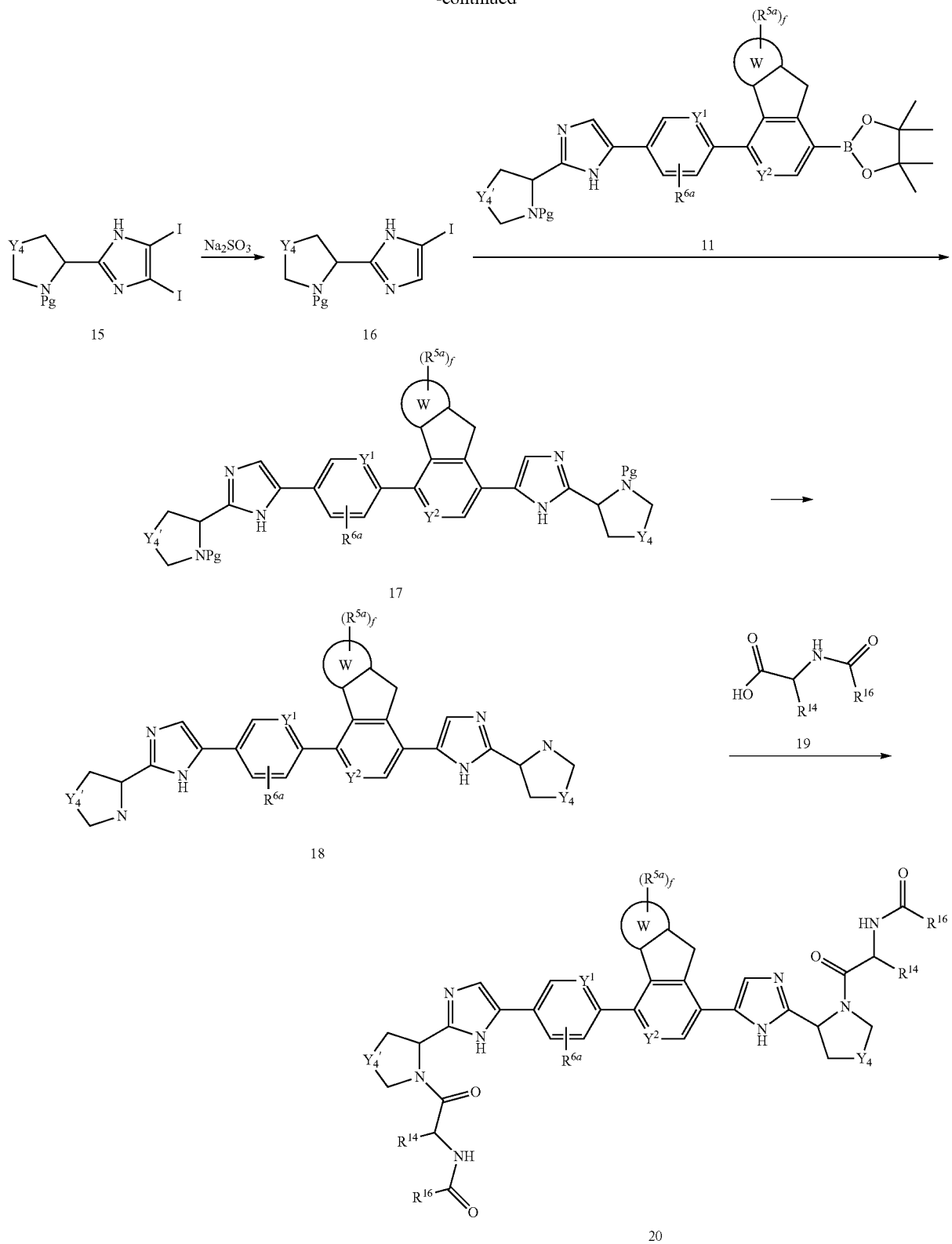

Compound 20 can be prepared by a general synthetic procedure illustrated in Scheme 1, wherein $X^5$ is F, Cl, Br or I; each of W, $Y_4$, $Y_4'$, $R^{5a}$, $R^{6a}$, $Y^1$, $Y^2$, f, $R^{14}$ and $R^{16}$ is as defined herein; and Pg is an amino-protecting group such as Boc, Fmoc or Cbz, etc. Halogenation of compound 1 with a halogenating agent such as NIS can give compound 2. The methyl group of compound 2 can then be removed in the presence of boron tribromide to provide compound 3. Compound 3 can react with trifluoromethanesulfonic anhydride to afford compound 4 by base catalysis. Condensation of compound 5 with compound 6 can give compound 7. Compound 7 can be cyclized in the presence of ammonium acetate to afford compound 8. Compound 8 can further react with bis(pinacolato)diboron to afford compound 9 by Pd catalysis. Coupling reaction of compound 9 with compound 4 in the presence of a Pd catalyst can give compound 10. Compound 10 can further react with bis(pinacolato)diboron in the presence of a Pd catalyst to afford compound 11. Reduction of compound 5-1 with borane-tetrahydrofuran can give compound 12. Compound 12 can be oxidized to give compound 13 with an oxidant such as Dess-Martin Periodinane. Compound 13 can be cyclized in the presence of ammonium hydroxide and glyoxal to give compound 14. Compound 14 can react with NIS to afford di-iodo compound 15. One iodine atom of di-iodo compound 15 can then be removed in the presence of sodium sulfite to provide compound 16. Coupling reaction of compound 16 with compound 11 in the presence of a Pd catalyst can give compound 17. The protecting group Pg of compound 17 can be removed to afford compound 18. Compound 18 can be condensed with compound 19 to provide compound 20.

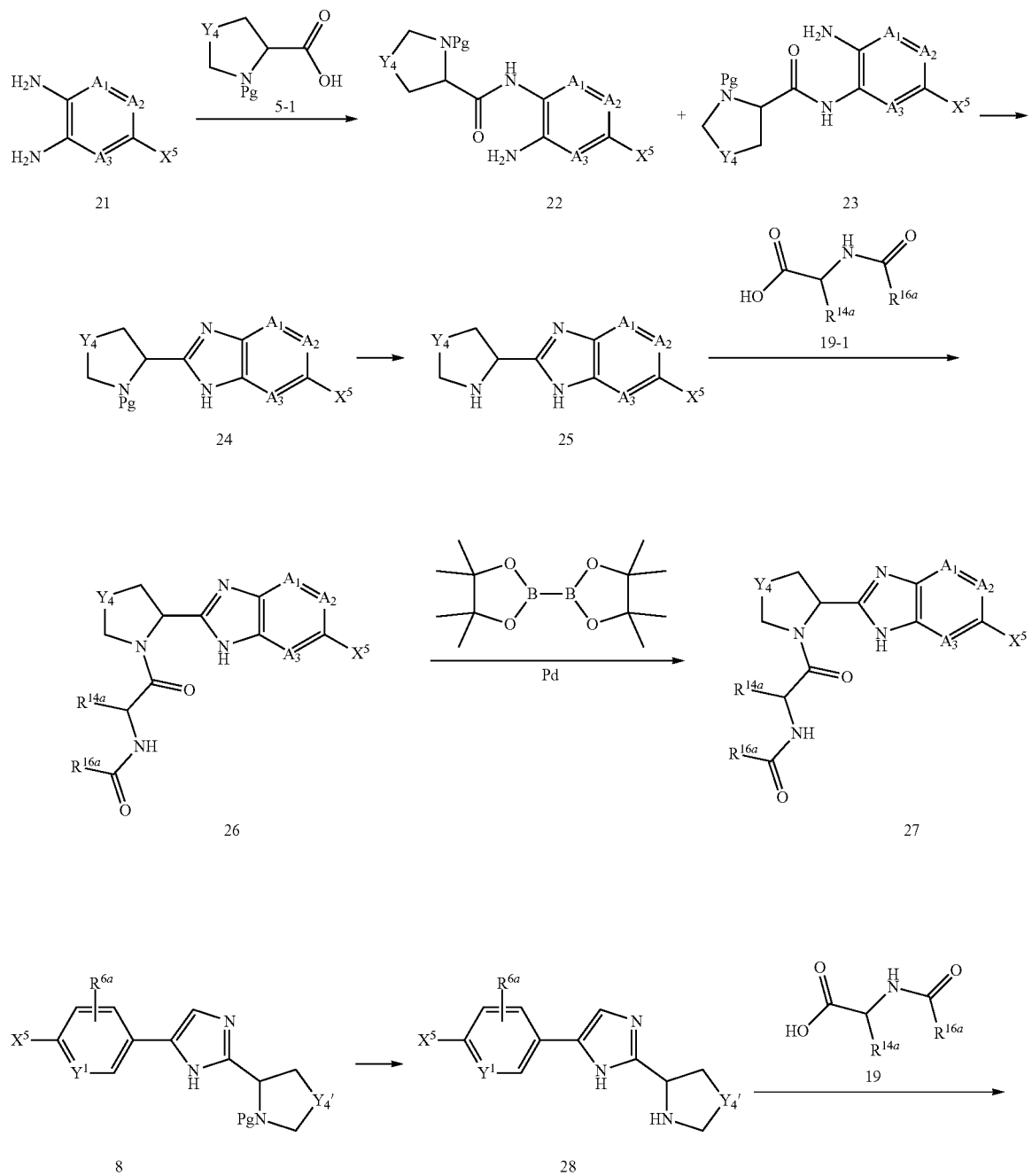

Scheme 2

-continued

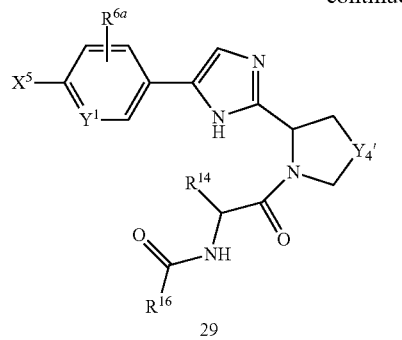
29

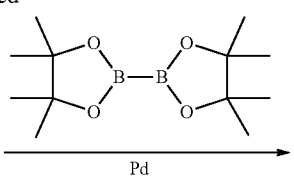

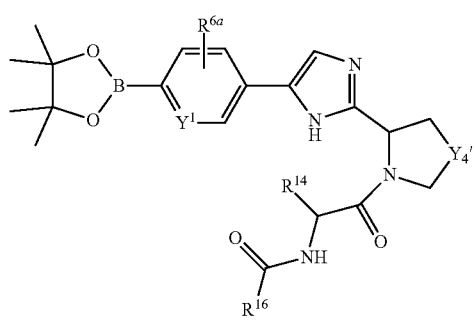
30

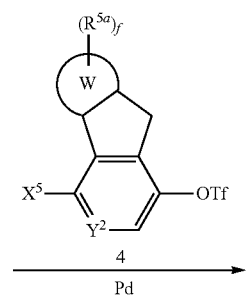
4
Pd

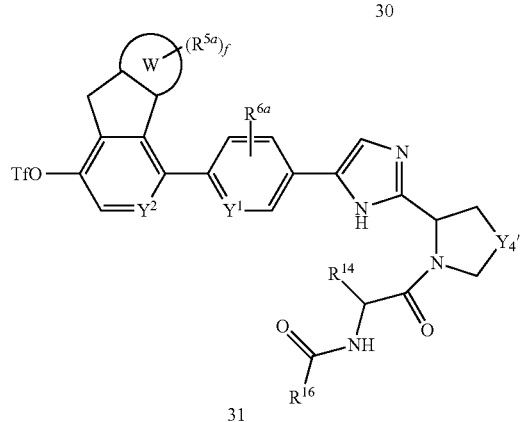
31

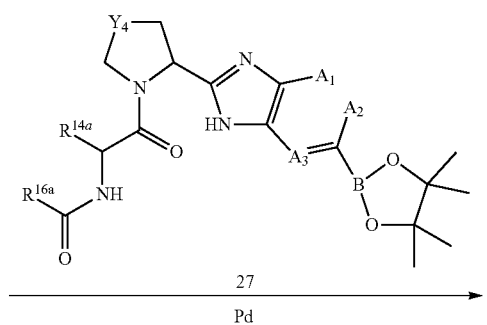
27
Pd

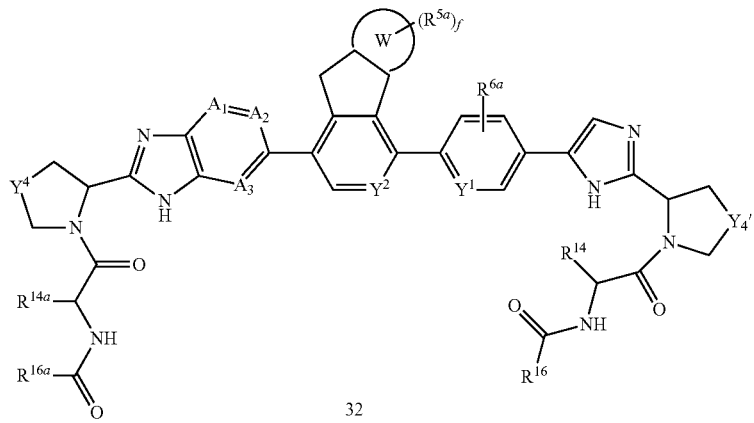
32

Compound 32 can be prepared by a general synthetic procedure illustrated in Scheme 2, wherein each of $A^1$, $A^2$ and $A^3$ is independently N or $CR^7$; $X^5$ is F, Cl, Br or I; each of W, $Y_4'$, $Y_4$, $R^{5a}$, $R^{6a}$, $Y^1$, $Y^2$, f, $R^{14}$, $R^{14a}$, $R^{16}$ and $R^{16a}$ is as defined herein; and Pg is an amino-protecting group such as Boc, Fmoc or Cbz, etc. Condensation of compound 21 with compound 5-1 can give a mixture of compound 22 and compound 23. Then the mixture of compound 22 and compound 23 can be cyclized at an elevated temperature in acetic acid to give compound 24. The protecting group Pg of compound 24 can be removed to provide compound 25. Compound 25 can be condensed with compound 19-1 to afford compound 26. Compound 26 can further react with bis(pinacolato)diboron in the presence of a Pd catalyst to afford compound 27. The protecting group Pg of compound 8 can be removed to provide compound 28. Compound 28 can be condensed with compound 19 to afford compound 29.

Compound 29 can further react with bis(pinacolato)diboron in the presence of a Pd catalyst to afford compound 30. Coupling reaction of compound 4 with compound 30 in the presence of a Pd catalyst can give compound 31. Compound 31 can further react with compound 27 in the presence of a Pd catalyst to afford compound 32.

Scheme 3

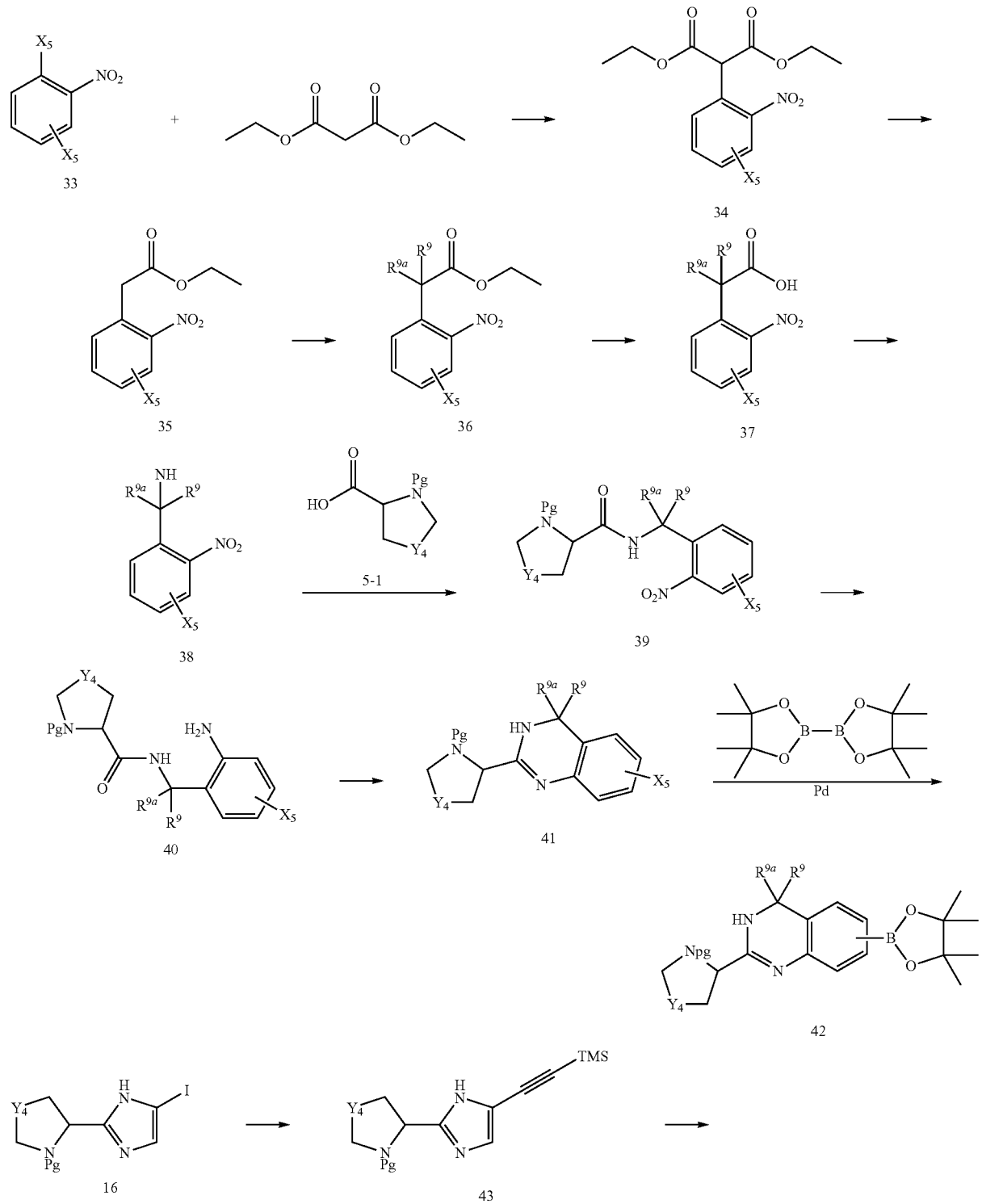

-continued
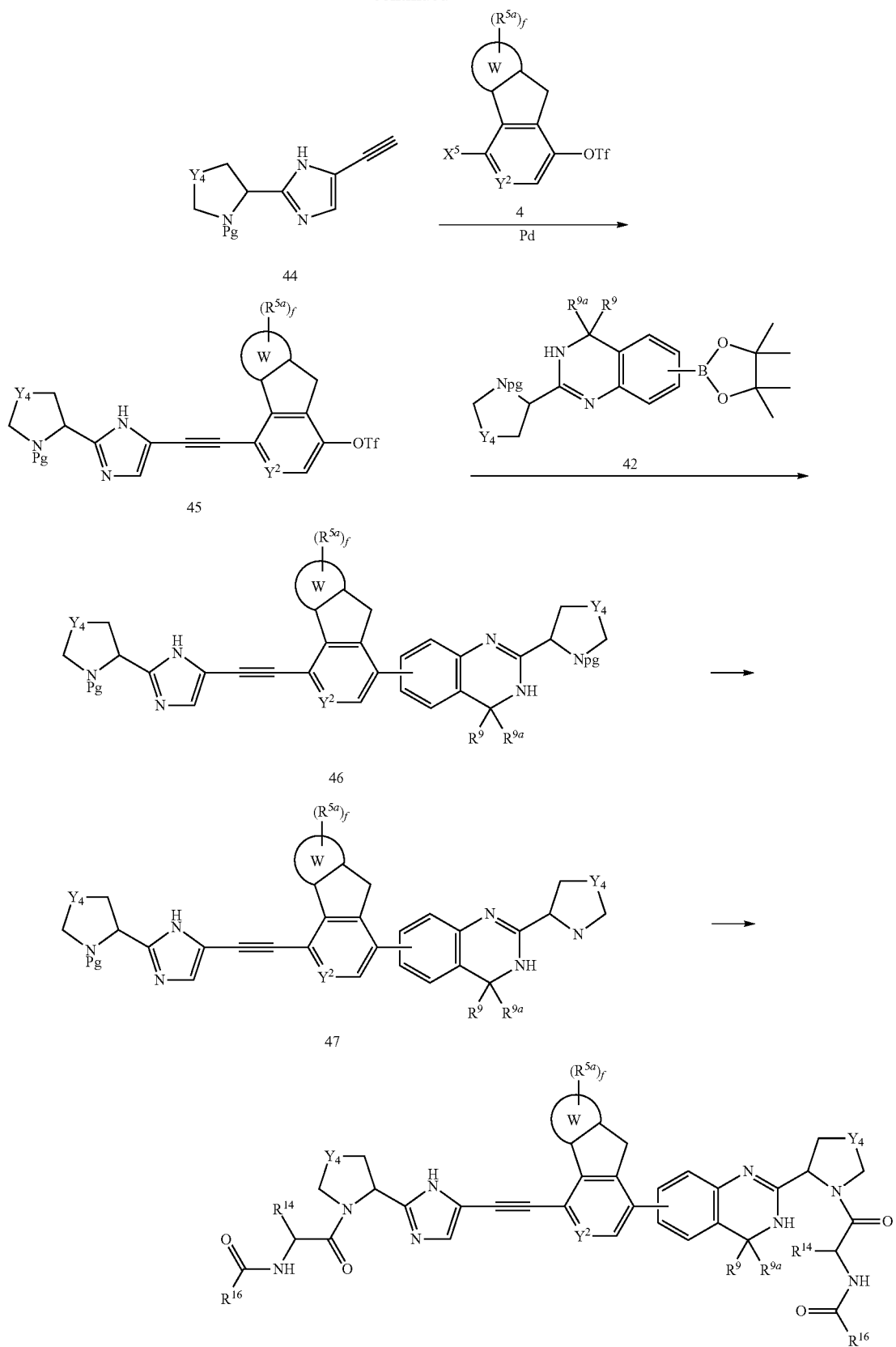

Compound 48 can be prepared by the process illustrated in Scheme 3. Wherein each $X^5$ is F, Cl, Br or I; each of $Y^2$, W, $R^{5a}$, f, $Y_4$, R, $R^{9a}$, $R^{14}$ and $R^{16}$ is as defined above; and Pg is an amino-protecting group such as Boc, Fmoc or Cbz, etc. Compound 33 can be converted to compound 34 by reacting with diethyl malonate by base catalysis. Compound 34 can be converted to compound 35 in the presence of LiCl and water. Compound 35 can give compound 36 at an elevated temperature in the presence of a base by alkylation. Compound 36 can afford compound 37 by base catalysis. Compound 37 can be converted to compound 38 in the presence of a base and DPPA. Condensation of compound 38 with compound 5-1 can give compound 39 by base catalysis. Compound 39 can react with a reductant to give compound 40. Then compound 40 can give compound 41 at an elevated temperature in the presence of acetic acid by cyclization. Compound 41 is further reacted with bis(pinacolato)diboron in the presence of a Pd catalyst to afford compound 42. Reaction of compound 16 with TMSA can afford compound 43 by Pd catalysis. Removing TMS from compound 43 can give compound 44 in the presence of a base. Coupling reaction of compound 44 with compound 4 in the presence of a Pd catalyst can give compound 45. Compound 45 can further react with compound 42 in the presence of a Pd catalyst to afford compound 46, then the protecting group Pg of compound 46 can be removed to afford compound 47. Compound 47 can be condensed with compound 19 to provide compound 48.

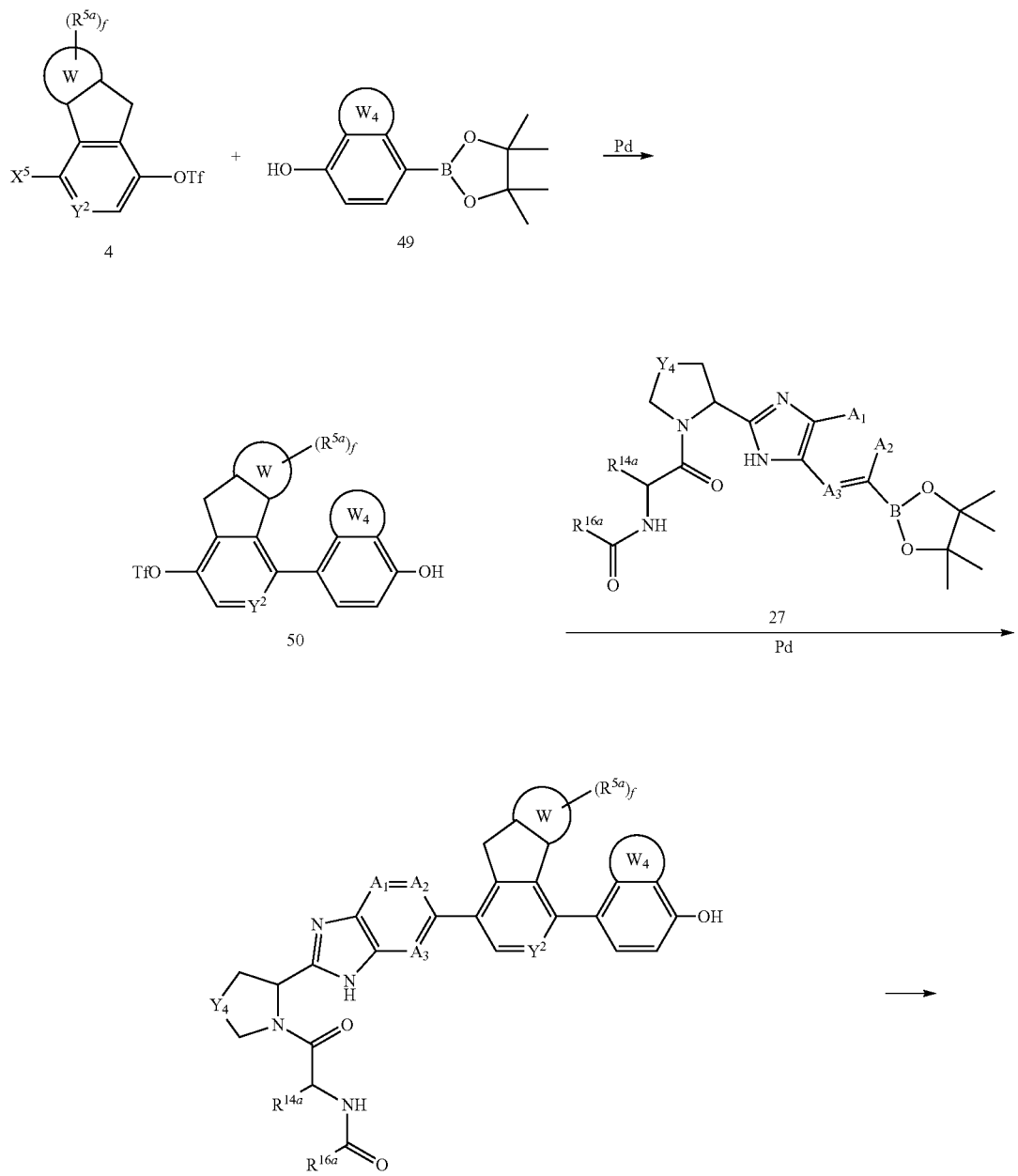

-continued

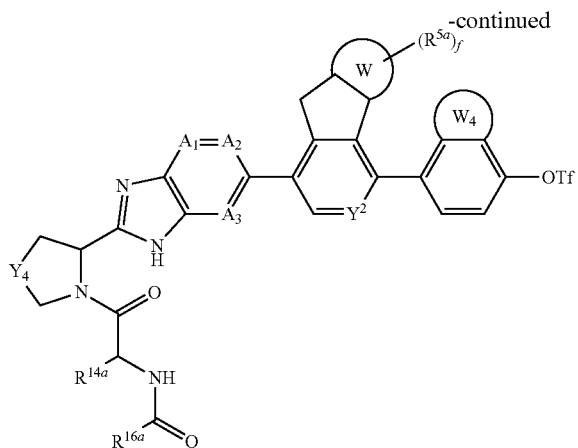

51

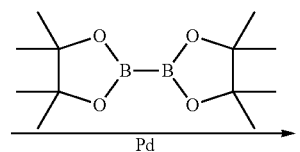

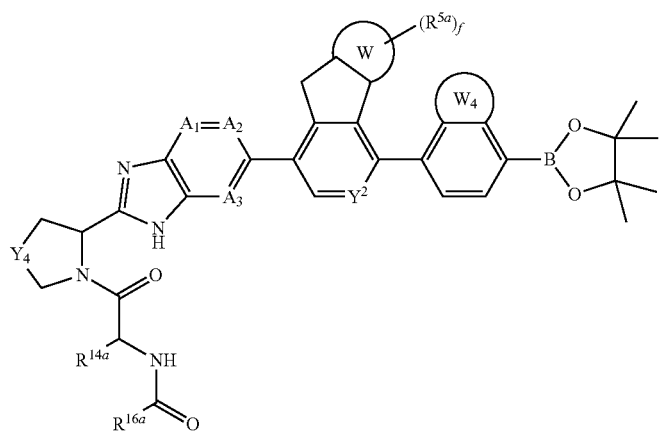

53

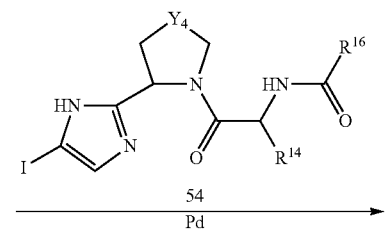

54

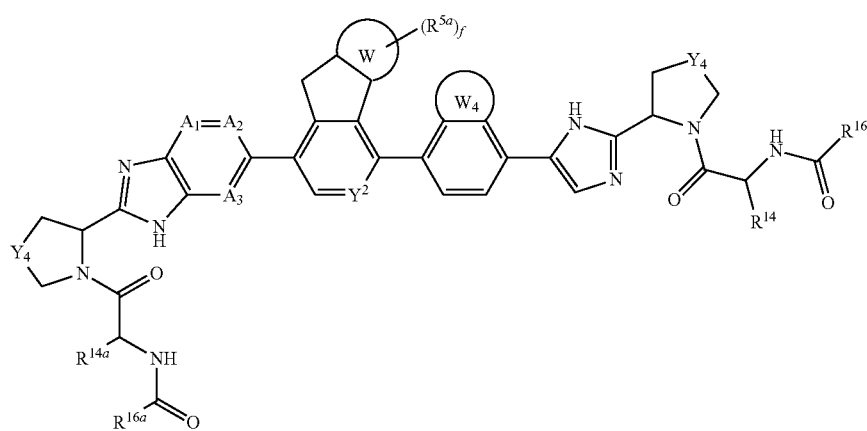

55

Compound 55 can be prepared by a general synthetic procedure illustrated in Scheme 4, wherein $W_4$ is a carbocyclyl or aromatic ring; each of $A^1$, $A^2$ and $A^3$ is independently N or $CR^7$; $X^5$ is F, C, Br or I; each of W, $Y_4'$, $Y_4$, $R^{5a}$ f, $R^{14}$, $R^{14a}$, $R^{16}$ and $R^{16a}$ is as defined herein; and Pg is an amino-protecting group such as Boc, Fmoc or Cbz, etc. Coupling reaction of compound 4 with compound 49 in the presence of a Pd catalyst can give compound 50. Compound 50 can further react with compound 27 in the presence of a Pd catalyst to afford compound 51. Compound 51 can react with trifluoromethanesulfonic anhydride to afford compound 52 by base catalysis. Reaction of compound 52 with bis(pinacolato)diboron can afford compound 53 by a Pd catalysis. Coupling reaction of compound 53 with compound 54 in the presence of a Pd catalyst can give compound 55.

Scheme 5

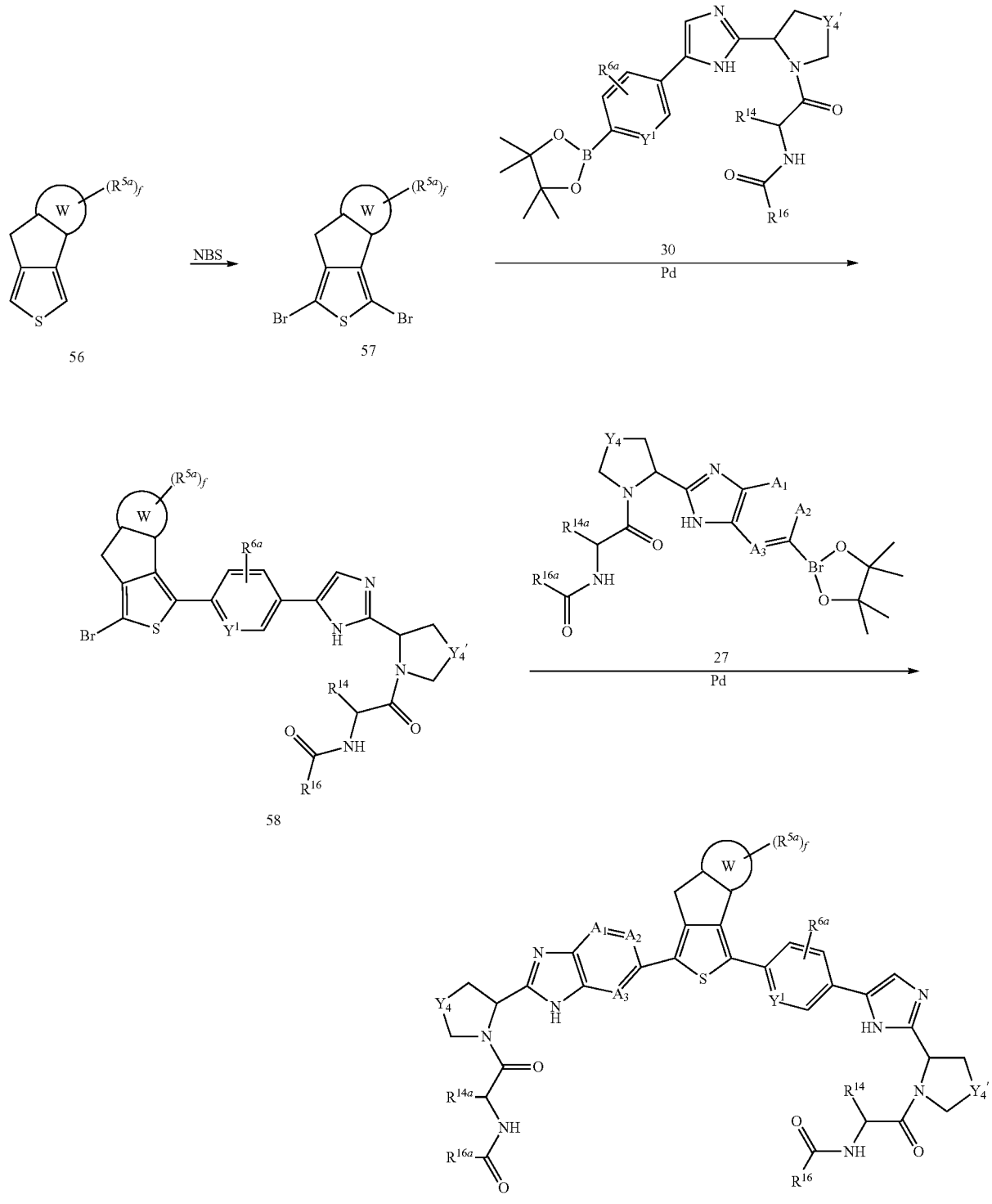

Compound 59 can be prepared by a general synthetic procedure illustrated in Scheme 5, wherein each of $A^1$, $A^2$ and $A^3$ is independently N or $CR^7$; each of W, $Y_4'$, $Y_4$, $R^{5a}$, $R^{6a}$, f, $Y^1$, $R^{14}$, $R^{14a}$, $R^{16}$ and $R^{16a}$ is as defined herein. Compound 56 can be converted to compound 57 in the presence of a brominating agent such as NBS. Coupling reaction of compound 57 with compound 30 in the presence of a Pd catalyst can give compound 58. Compound 58 can further react with compound 27 in the presence of a Pd catalyst to afford compound 59.

Scheme 6
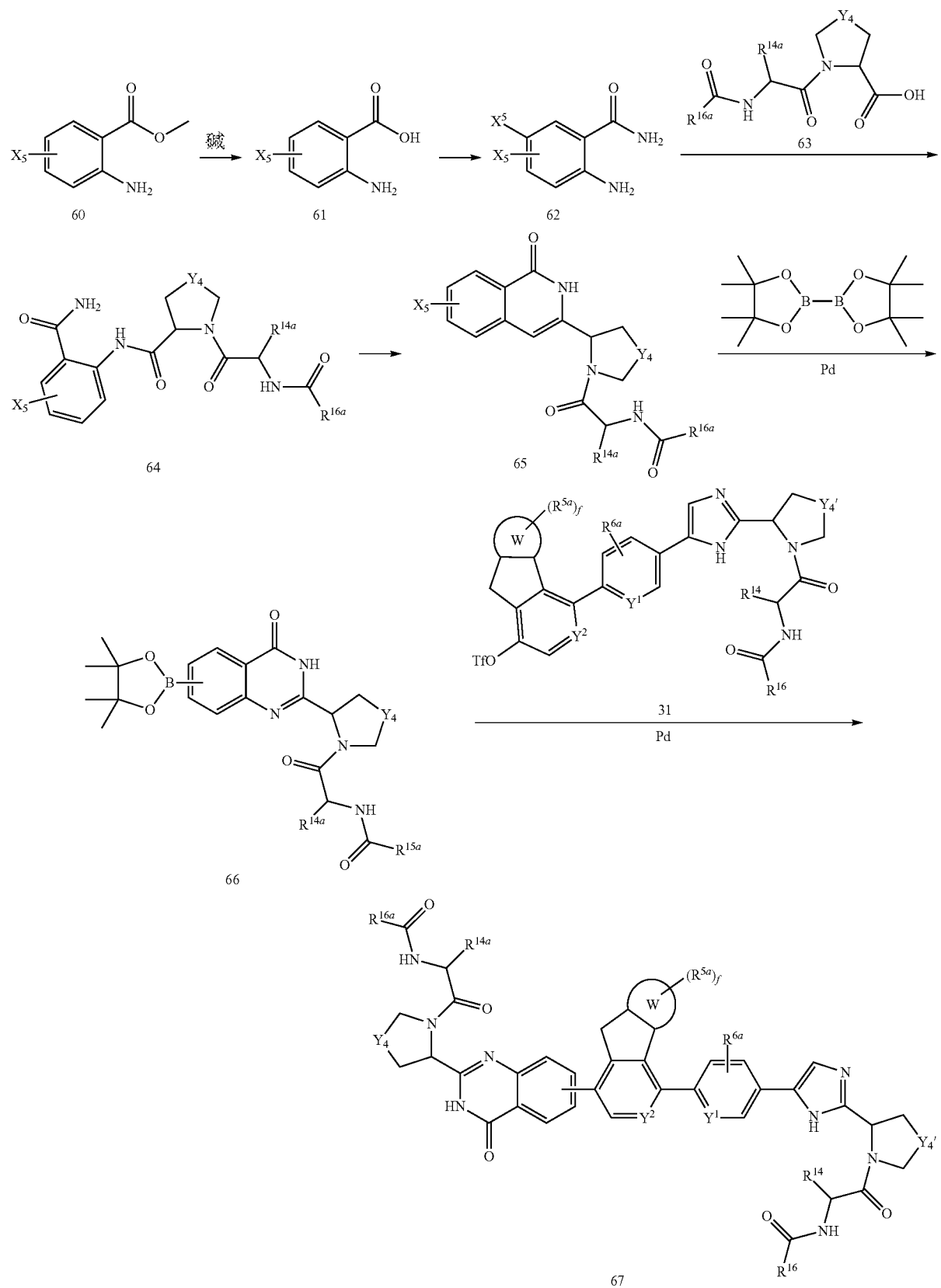

201

Compound 67 can be prepared by the process illustrated in Scheme 6, wherein each $X^5$ is F, Cl, Br or I; each of $Y^2$, W, $R^{5a}$, f, $Y_4{}'$, $Y^1$, $Y_4$, $R^{6a}$, $R^{14}$, $R^{14a}$, $R^{16}$ and $R^{16a}$ is as defined above. Compound 60 can be converted to compound 61 by base catalysis. Compound 61 can be converted to compound 62 in the presence of CDI and ammonium hydroxide. Condensation of compound 62 with compound

202

63 can give compound 64 by base catalysis. Compound 64 can be cyclized in the presence of a base to form compound 65. Reaction of compound 65 with bis(pinacolato)diboron can afford compound 66 by Pd catalysis. Coupling reaction of compound 66 with compound 31 in the presence of a Pd catalyst can give compound 67.

Scheme 7

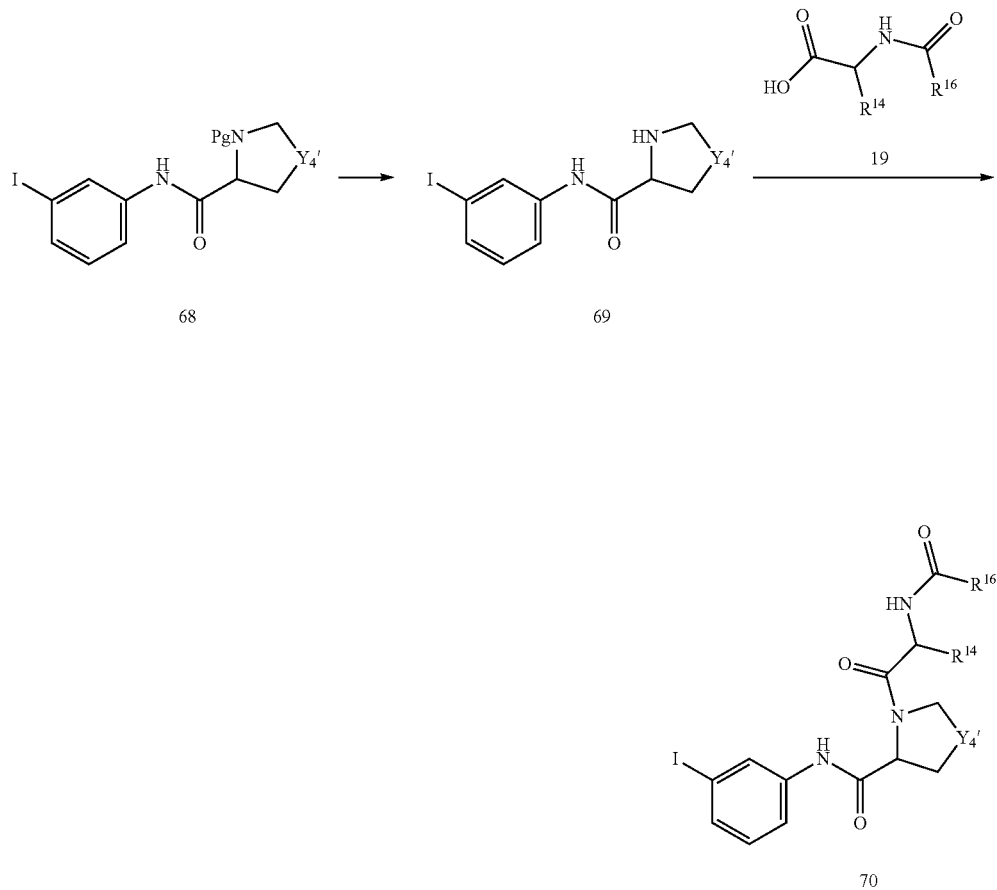

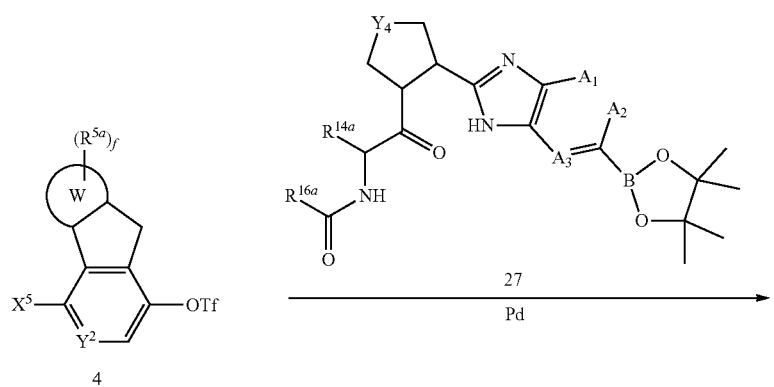

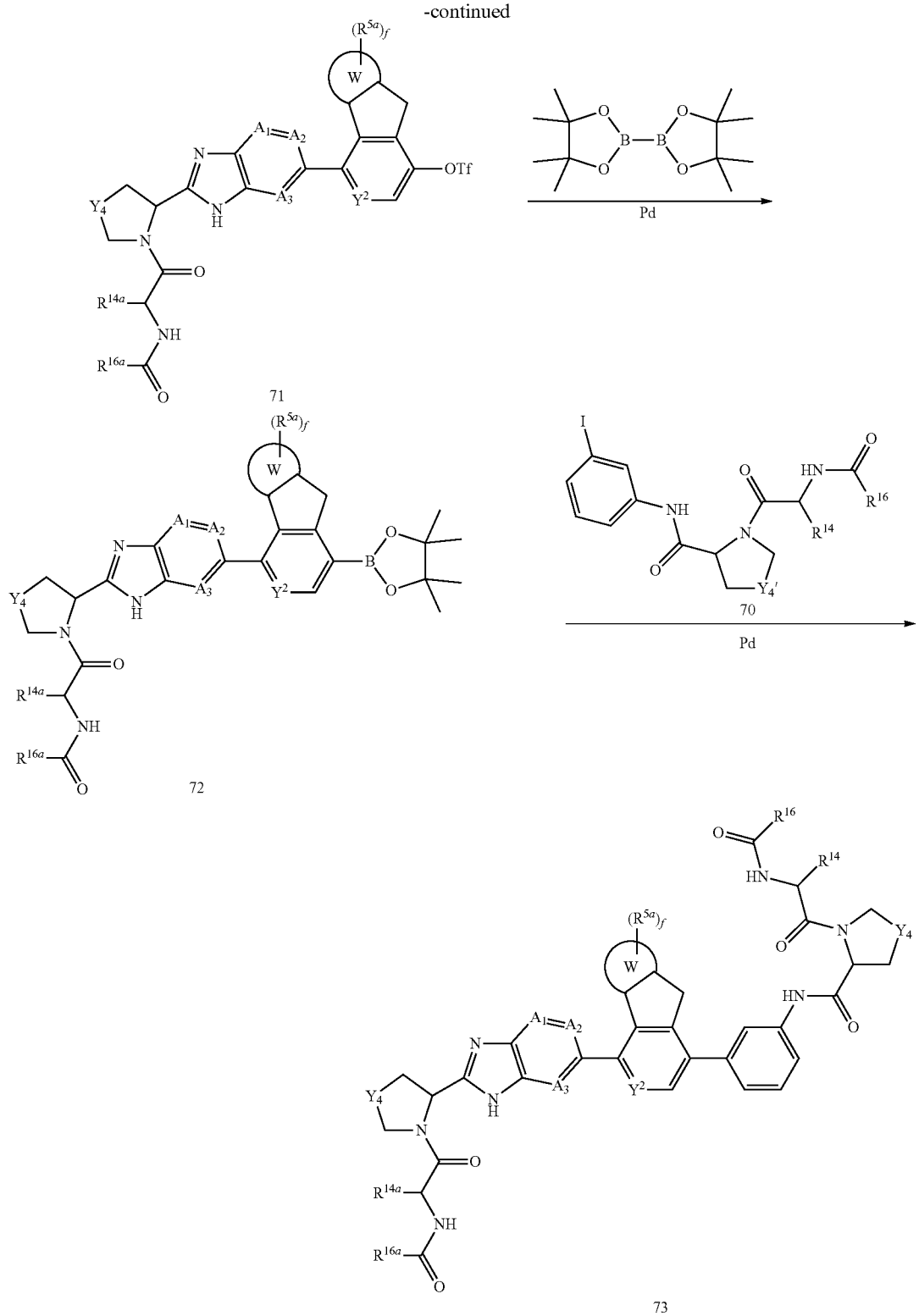

Compound 73 can be prepared by a general synthetic procedure illustrated in Scheme 7, wherein each of $A^1$, $A^2$ and $A^3$ is independently N or $CR^7$; each of W, $Y_4'$, $Y_4$, $R^{5a}$, $Y^2$, $R^{14}$, $R^{14a}$, $R^{16}$ and $R^{16a}$ is as defined herein; and Pg is an amino-protecting group such as Boc, Fmoc or Cbz, etc. The protecting group Pg of compound 68 can be removed to provide compound 69. Compound 69 can be condensed with compound 19 to afford compound 70. Coupling reaction of compound 4 with compound 27 in the presence of a Pd catalyst can give compound 71. Compound 71 can further react with bis(pinacolato)diboron in the presence of a Pd catalyst to afford compound 72. Compound 72 can further react with compound 70 in the presence of a Pd catalyst to afford compound 73.

W, $R^{5a}$, f, $Y_4$, Y, $Y_4$, $R^{6a}$, $R^{14}$, $R^{14a}$, $R^{16}$ and $R^{16a}$ is as defined above; and Pg is an amino-protecting group such as Boc, Fmoc or Cbz, etc. Compound 5-1 can be converted to

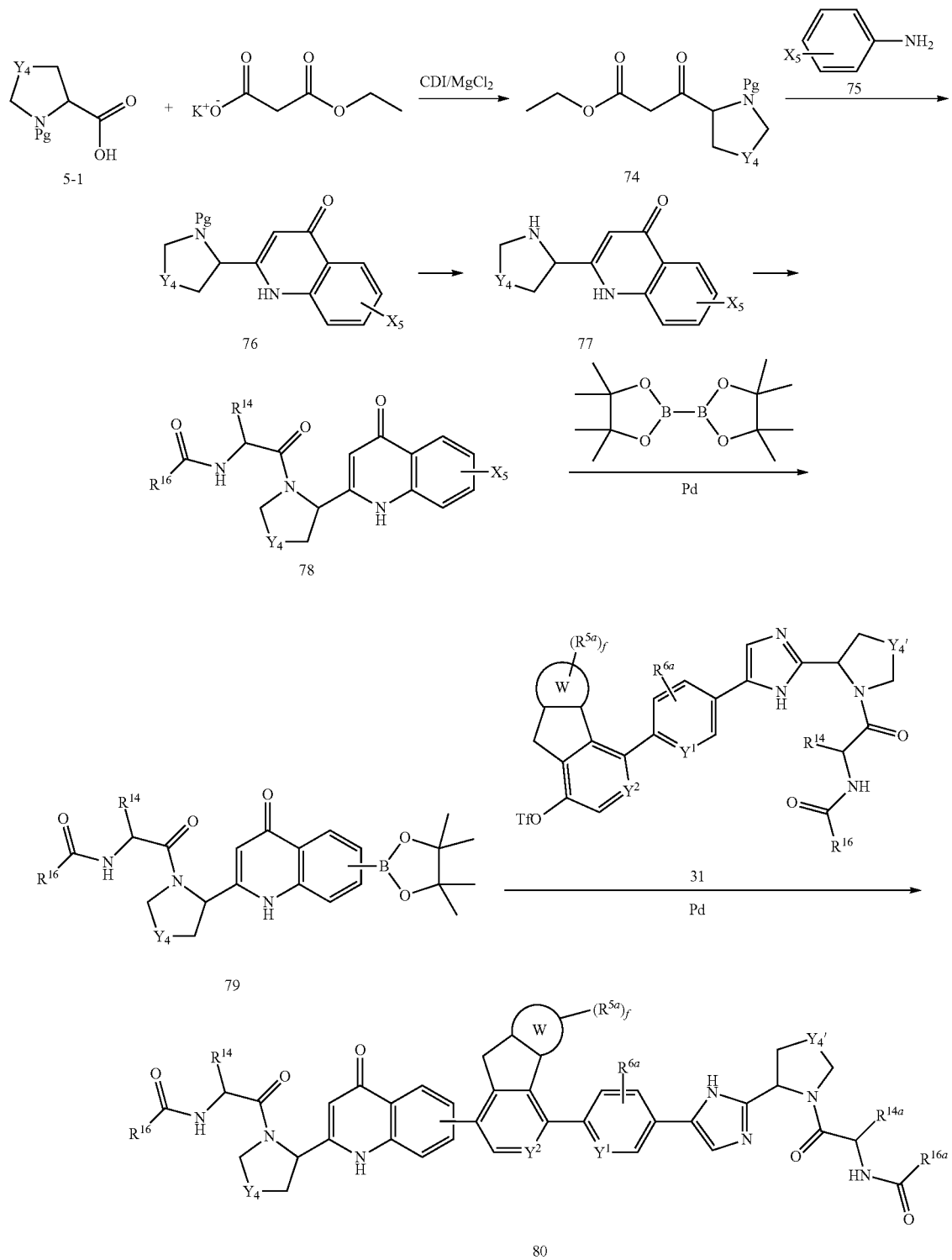

Scheme 8

Compound 80 can be prepared by the process illustrated in Scheme 8. Wherein each $X^5$ is F, $C_1$, Br or I; each of $Y^2$, compound 74 by reacting with ethyl potassium malonate in the presence of $CDI/MgCl_2$. Reaction of compound 74 with compound 75 can afford compound 76 by acid catalysis. The protecting group Pg of compound 76 is removed to provide compound 77. Compound 77 condensed with an amino acid to afford compound 78. Compound 78 is further reacted with bis(pinacolato)diboron in the presence of a Pd catalyst to afford compound 79. Coupling reaction of compound 79 with compound 31 in the presence of a Pd catalyst can give compound 80.

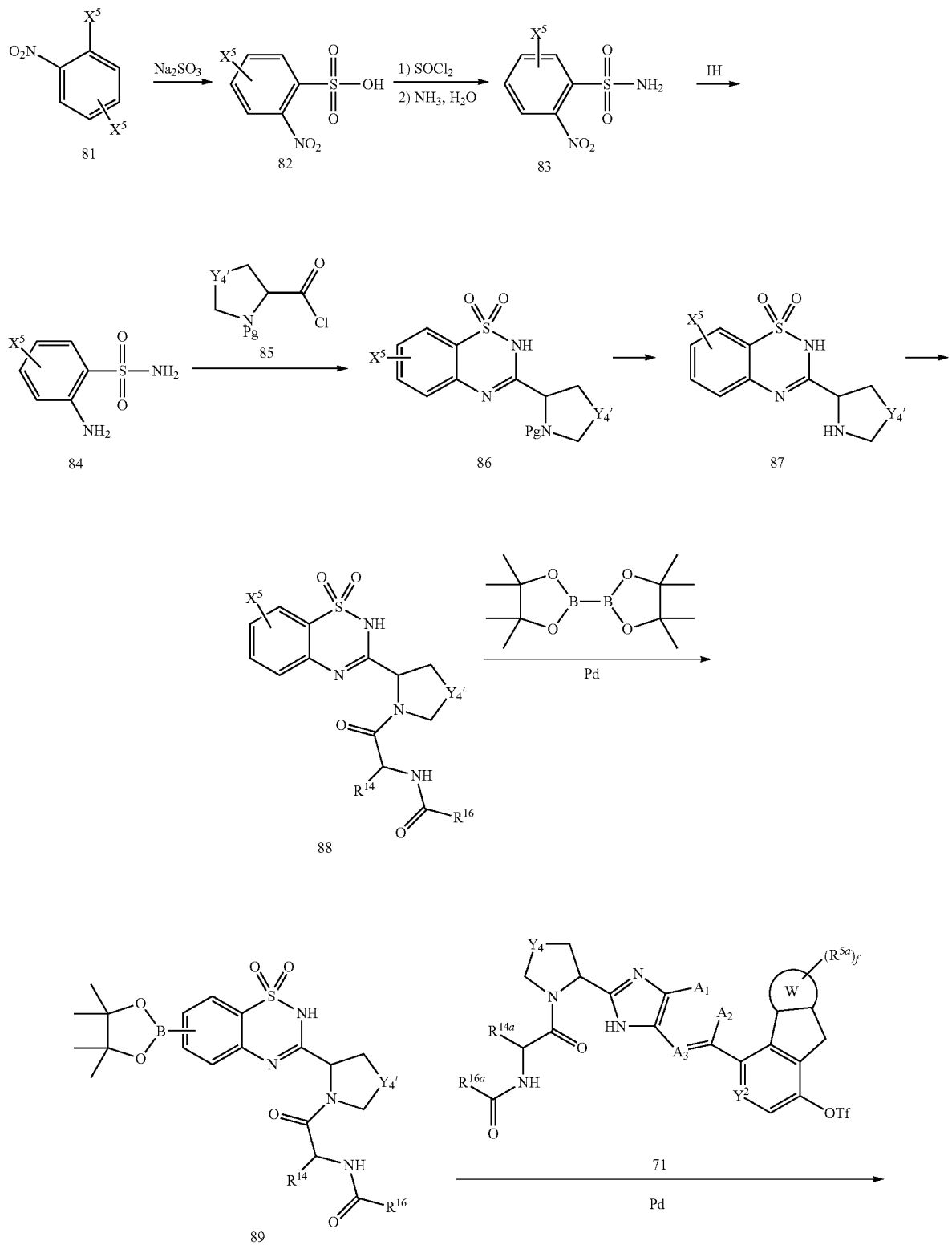

Scheme 9

-continued

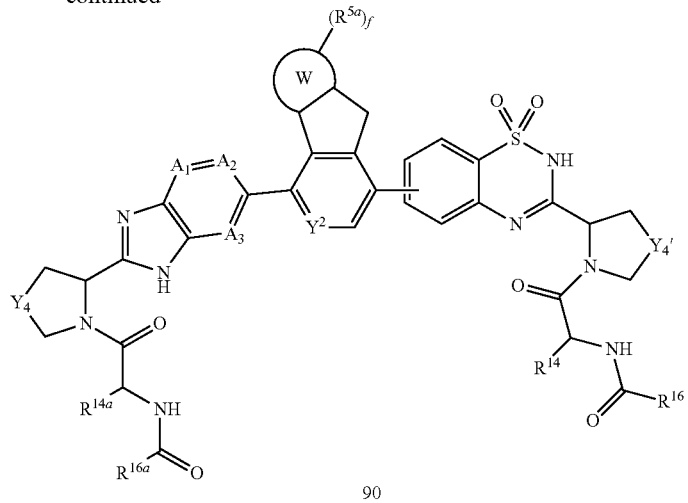
90

Compound 90 can be synthesized through a general synthetic procedure depicted in Scheme 9, wherein $X^5$ is F, Cl, Br or I; each of $A^1$, $A^2$ and $A^3$ is independently N or $CR^7$; each of W, $Y_4'$, $Y_4$, $Y^2$, $R^{5a}$, f, $R^{14}$, $R^{14a}$, $R^{16}$ and $R^{16a}$ is as defined herein; and Pg is an amino-protecting group such as Boc, Fmoc or Cbz, etc. Compound 81 can be transformed to compound 82 by reacting with sodium sulfite. Compound 82 can be converted to compound 83 in the presence of thionyl chloride and ammonium hydroxide. Reduction of compound 83 with a reducing agent such as HI can afford compound 84. Condensation of compound 84 with compound 85 can afford compound 86 in the presence of a base. The protecting group a Pg in compound 86 can be removed to afford compound 87, which can be condensed with compound 19 to provide compound 88. Reaction of compound 88 with bis(pinacolato)diboron can afford compound 89 by Pd catalysis. Coupling reaction of compound 89 with compound 71 in the presence of a Pd catalyst can give compound 90.

Scheme 10

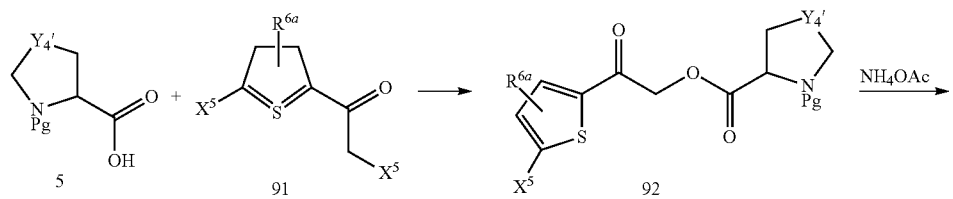

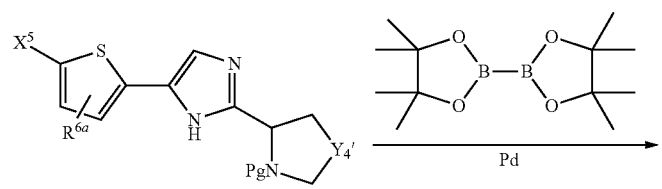

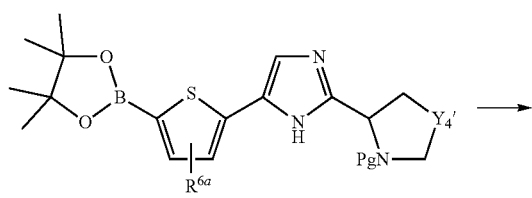

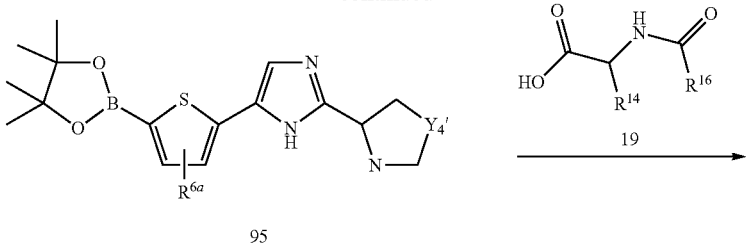

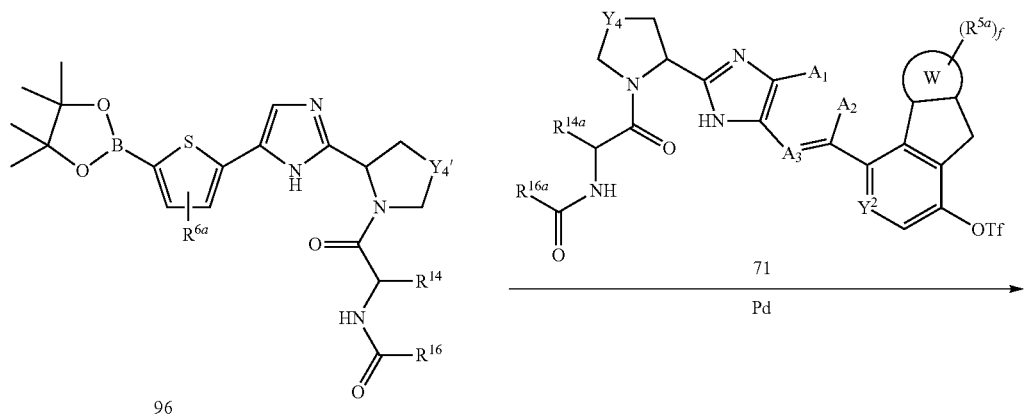

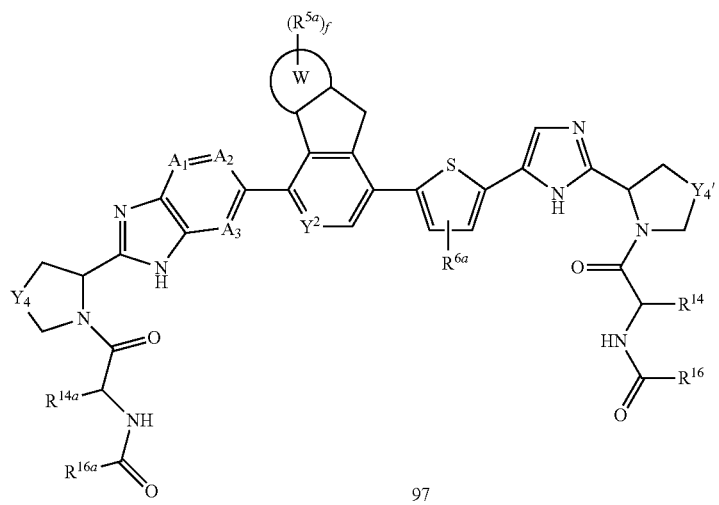

Compound 97 can be synthesized through a general synthetic procedure depicted in Scheme 10, wherein each of $A^1$, $A^2$ and $A^3$ is independently N or $CR^7$; $X^5$ is F, Cl, Br or I; each of W, $Y_4'$, $Y_4$, $Y^2$, $R^{5a}$, $R^{6a}$, f, $R^4$, $R^{16}$, $R^{14a}$ and $R^{16a}$ is as defined herein; and Pg is an amino-protecting group such as Boc, Fmoc or Cbz, etc. Condensation of compound 5 with compound 91 can give compound 92 by base catalysis. Compound 92 can be cyclized at an elevated temperature in the presence of ammonium acetate to afford compound 93. Reaction of compound 93 with bis(pinacolato)diboron can afford compound 94 by Pd catalysis. The protecting group Pg of compound 94 can be removed to afford compound 95, which can be condensed with compound 19 to provide compound 96. Coupling reaction of compound 96 with compound 71 in the presence of a Pd catalyst can give compound 97.

213  214
EXAMPLES
Example 1
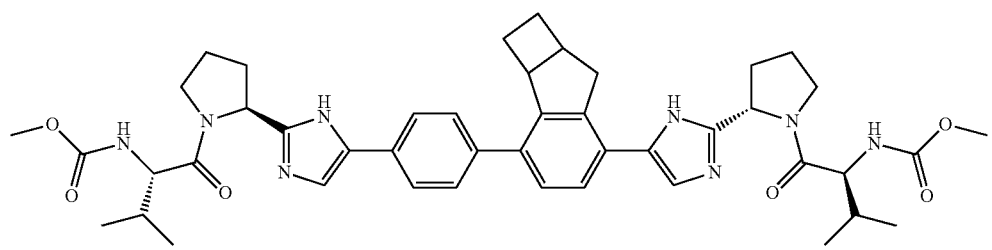
Synthetic Route:
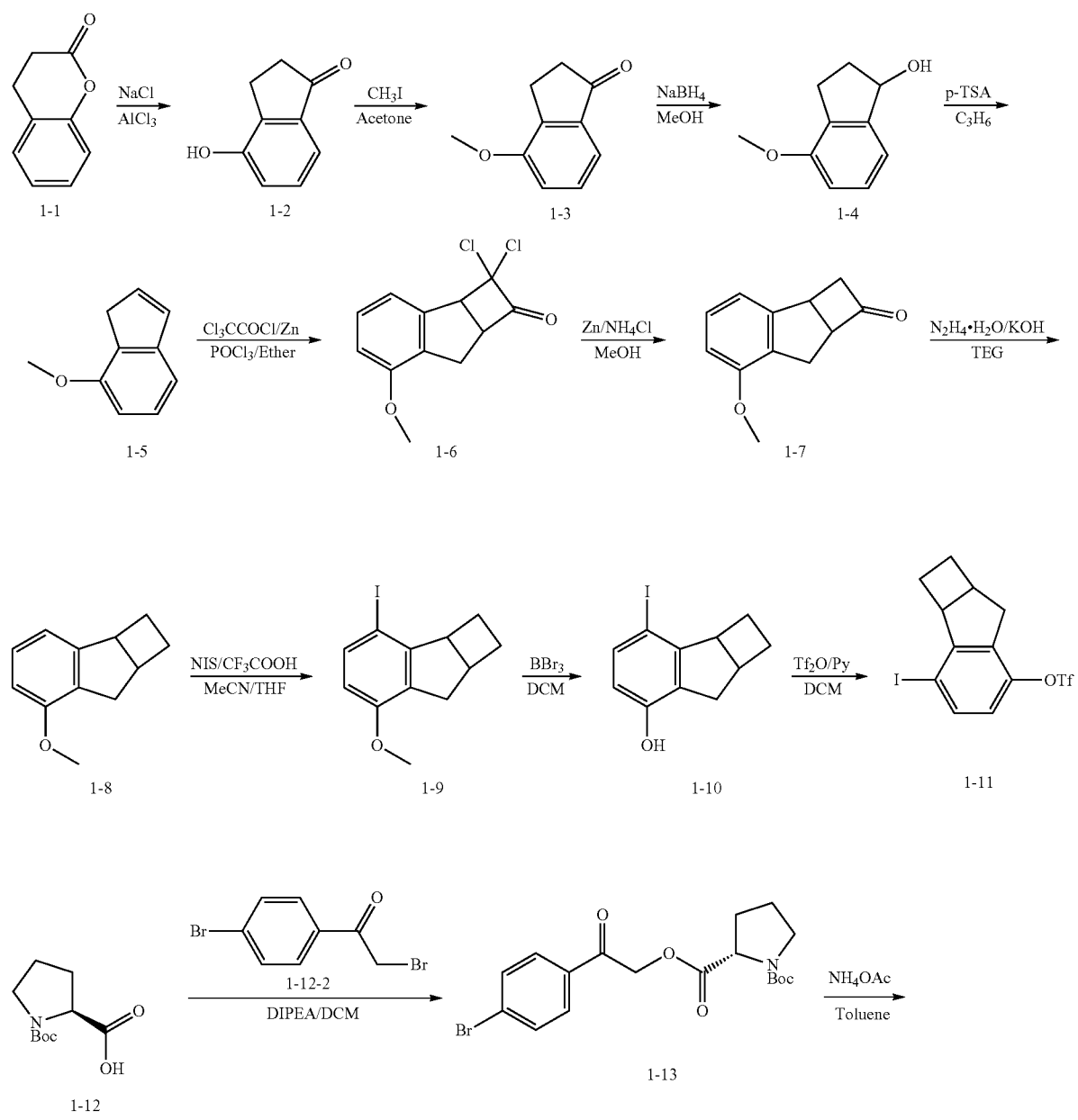

-continued
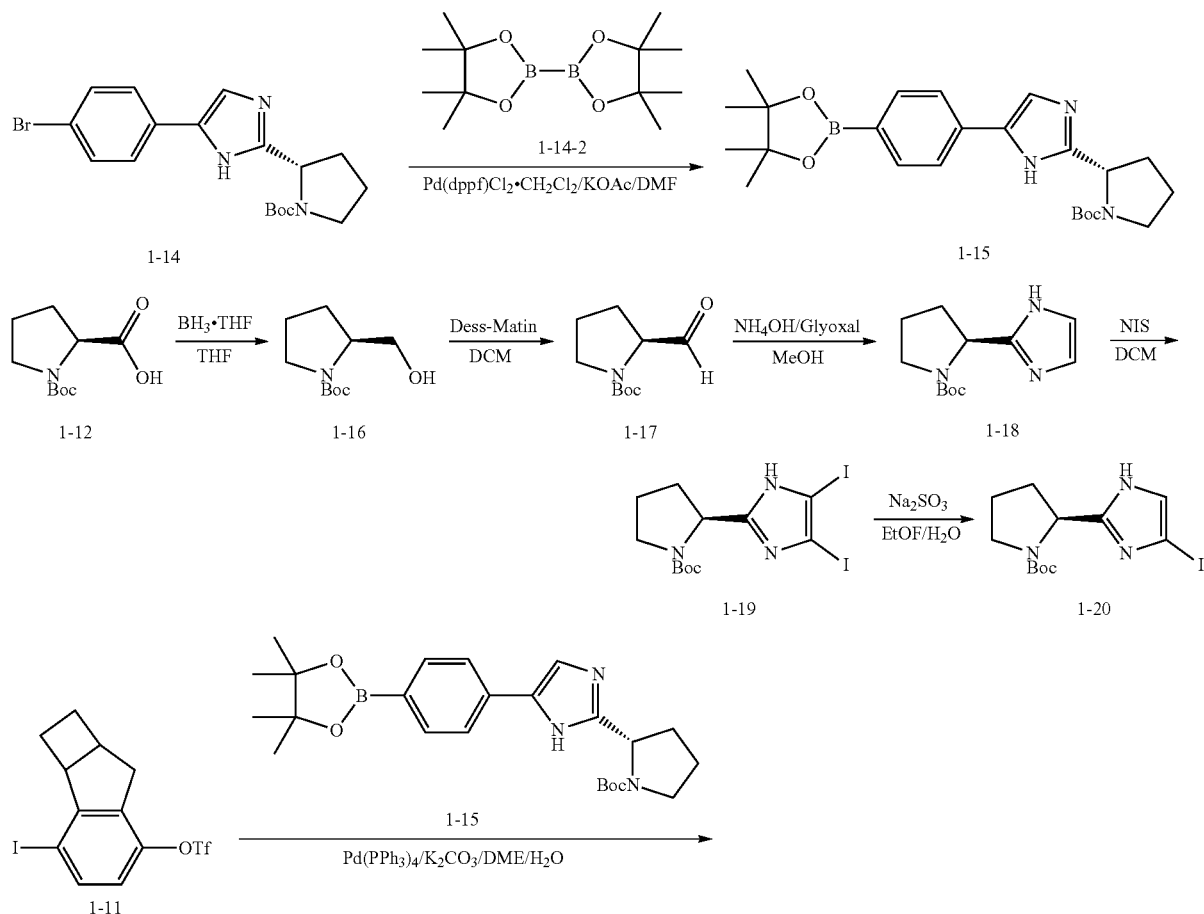
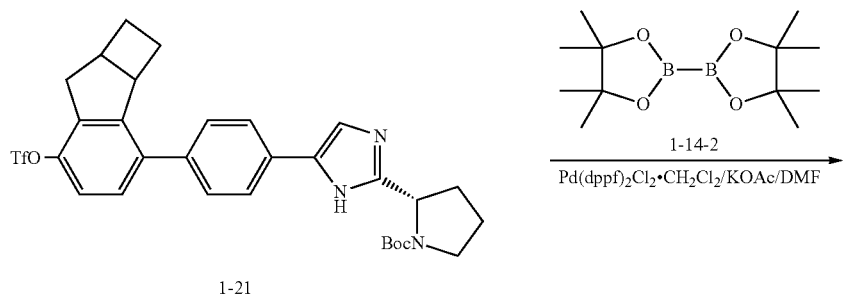
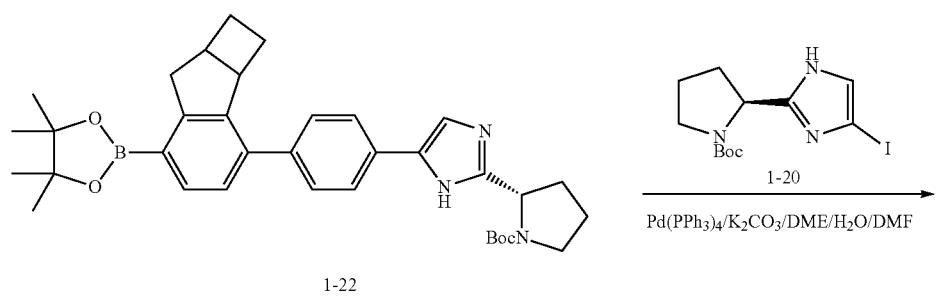

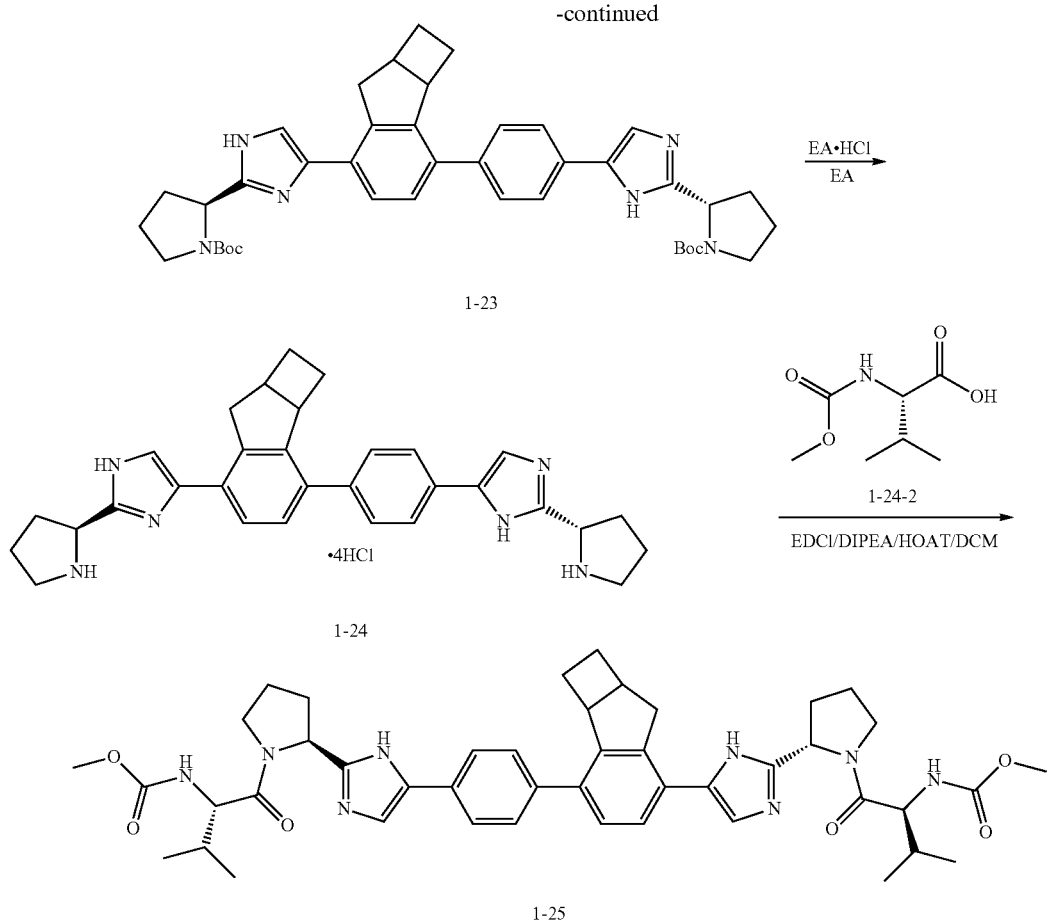

Step 1) The Preparation of Compound 1-2

A mixture of aluminium chloride (90.0 g, 676 mmol) and sodium chloride (25 g, 432 mmol) was stirred at 150° C. until the mixture was in molten state, and then compound 1-1 (20.0 g, 135 mmol) was added dropwise. At the end of the addition, the mixture was stirred at 200° C. for 1.0 hr. After the reaction was completed, the mixture was cooled to rt, poured slowly into ice water (500 mL) and filtered to get the crude product. The crude product was triturated with MeOH and filtered to give the title compound as a gray solid (19 g, 95%). The compound was characterized by the following spectroscopic data:

MS (ESI, pos.ion) m/z: 149.5 [M+H]$^+$; and $^1$H NMR (400 MHz, CDCl$_3$) δ (ppm): 7.41-7.38 (m, 1H), 7.24-7.19 (m, 1H), 6.80-6.79, 6.78-6.77 (d, d, 1H, J=4.0 Hz), 5.46 (br, 1H), 3.06-3.03 (m, 2H), 2.69-2.66 (m, 2H).

Step 2) The Preparation of Compound 1-3

To a mixture of compound 1-2 (5.0 g, 33.7 mmol) and K$_2$CO$_3$ (23.4 g, 168.5 mmol) in acetone (50.0 mL) was added iodomethane (3.15 mL, 50.55 mmol) dropwise. At the end of the addition, the mixture was stirred at 60° C. for 5.0 hrs. After the reaction was completed, the mixture was concentrated in vacuo. To the residue were added EtOAc (150 mL) and water (150 mL), and the mixture was filtered through a celite pad. The aqueous layer was extracted with EtOAc (150 mL×2). The combine organic layers were washed with brine, dried over anhydrous Na$_2$SO$_4$ and concentrated in vacuo. The residue was purified by silica gel column chromatography (PE/EtOAc (v/v)=10/1) to give the title compound as a yellow solid (2.5 g, 45%). The compound was characterized by the following spectroscopic data:

MS (ESI, pos.ion) m/z: 163.5 [M+H]$^+$; and $^1$H NMR (400 MHz, CDCl$_3$) δ (ppm): 7.51-7.48 (m, 1H), 7.30-7.26 (m, 1H), 6.91-6.87 (m, 1H), 3.90 (s, 3H), 3.08-3.05 (m, 2H), 2.70-2.67 (m, 2H).

Step 3) The Preparation of Compound 1-4

To a solution of compound 1-3 (20 g, 123.3 mmol) in MeOH (250 mL) was added NaBH$_4$ (2.8 g, 74.0 mmol) portionwise. At the end of the addition, the mixture was stirred at rt for 1.0 hr. After the reaction was completed, the MeOH solvent was removed and the residue was dissolved in EtOAc (400 mL). The resulting mixture was washed with water (50 mL×2) and brine (50 mL), dried over anhydrous Na$_2$SO$_4$ and concentrated in vacuo. The residue was purified by silica gel column chromatography (PE/EtOAc (v/v)=5/1) to give the title compound as a pale yellow solid (17.6 g, 87%). The compound was characterized by the following spectroscopic data:

MS (ESI, pos.ion) m/z: 165.5 [M+H]$^+$; and $^1$H NMR (400 MHz, CDCl$_3$) δ (ppm): 7.13-7.09 (m, 1H), 7.08-7.05 (m, 1H), 6.75-6.72 (m, 1H), 5.29-5.25 (m, 1H), 3.84 (d, 3H), 3.70 (brs, 1H), 2.84-2.80 (m, 2H), 2.49-2.40 (m, 1H), 1.96-1.88 (m, 1H).

Step 4) The Preparation of Compound 1-5

To a solution of compound 1-4 (2.0 g, 12.2 mmol) in THF (20 mL) was added p-TSA (1.0 g, 6.1 mmol) at 0° C. At the end of the addition, the mixture was refluxed for 3.0 hrs.

After the reaction was completed, the THF solvent was removed. To the residue was added EtOAc (100 mL). The resulting mixture was washed with water (50 mL×3) and brine, dried over anhydrous $Na_2SO_4$ and concentrated in vacuo. The residue was purified by silica gel column chromatography (PE) to give the title compound as colorless oil (1.23 g, 69%). The compound was characterized by the following spectroscopic data:

MS (ESI, pos.ion) m/z: 147.1 $[M+H]^+$; and
$^1$H NMR (400 MHz, $CDCl_3$) δ (ppm): 7.29 (t, 1H, J=7.8 Hz), 7.09 (d, 1H, J=7.4 Hz), 6.90-6.86 (m, 1H), 6.77 (d, 1H, J=8.0 Hz), 6.61-6.57 (m, 1H), 3.92 (s, 3H), 3.39 (s, 2H).

Step 5) The Preparation of Compound 1-6

To a solution of compound 1-5 (5.0 g, 34.2 mmol) in anhydrous diethyl ether (35 mL) was added activated zinc powder (2.5 g, 37.6 mmol). After the mixture was stirred for 10 mins, a solution of trichloroacetyl chloride (4.0 mL, 35.9 mmol) and phosphorus oxychloride (3.3 mL, 35.9 mmol) in diethyl ether (35 mL) was added dropwise under $N_2$ to the reaction mixture. At the end of the addition, the mixture was refluxed overnight. After the reaction was completed, the mixture was filtered, and then to the filtrate was added water (50 mL). The resulting mixture was extracted with EtOAc (60 mL×3). The combined organic layers were washed with brine, dried over anhydrous $Na_2SO_4$ and concentrated in vacuo. The residue was purified by silica gel column chromatography (PE) to give the title compound as a pale yellow solid (6.5 g, 74%). The compound was characterized by the following spectroscopic data:

MS (ESI, pos.ion) m/z: 257.1 $[M+H]^+$; and
$^1$H NMR (400 MHz, $CDCl_3$) δ (ppm): 7.28 (t, 1H, J=7.8 Hz), 7.02 (d, 1H, J=7.6 Hz), 6.79 (d, 1H, J=8.0 Hz), 4.53-4.45 (m, 2H), 3.82 (s, 3H), 3.36 (d, 1H, J=17.2 Hz), 3.09-3.00 (m, 1H).

Step 6) The Preparation of Compound 1-7

To a solution of compound 1-6 (6.45 g, 25.2 mmol) in MeOH (80 mL) were added zinc powder (8.2 g, 126 mmol) and $NH_4Cl$ (6.7 g, 126 mmol) in turn at rt. At the end of the addition, the mixture was stirred at 45° C. overnight. After the reaction was completed, the mixture was filtered through a celite pad. The filtrate was concentrated in vacuo, and then to the residue was added water (50 mL). The resulting mixture was extracted with EtOAc (60 mL×3). The combined organic layers were washed with brine, dried over anhydrous $Na_2SO_4$ and concentrated in vacuo. The residue was purified by silica gel column chromatography (PE/EtOAc (v/v)=60/1) to give the title compound as colorless liquid (3.69 g, 78%). The compound was characterized by the following spectroscopic data:

MS (ESI, pos.ion) m/z: 189.1 $[M+H]^+$; and
$^1$H NMR (400 MHz, $CDCl_3$) δ (ppm): 7.22 (t, 1H, J=7.8 Hz), 6.89 (d, 1H, J=7.6 Hz), 6.71 (d, 1H, J=8.0 Hz), 4.11-3.99 (m, 2H), 3.82 (s, 3H), 3.63-3.52 (m, 1H), 3.27 (d, 1H, J=17.2 Hz), 3.03-2.93 (m, 1H), 2.92-2.84 (m, 1H).

Step 7) The Preparation of Compound 1-8

To a solution of compound 1-7 (2.3 g, 12.2 mmol) in TEG (15 mL) were added KOH(2.1 g, 36.7 mmol) and hydrazine hydrate (4.8 mL, 97.8 mmol) in turn. After the mixture was stirred at 130° C. for 20 mins, a Dean-Stark trap was added, and then the mixture was stirred at 200° C. for 50 mins. After the reaction was completed, the mixture was cooled to rt and 100 mL of water was added. The aqueous layer was extracted with PE (150 mL×3). The combined organic layers were washed with brine, dried over anhydrous $Na_2SO_4$ and concentrated in vacuo. The residue was purified by silica gel column chromatography (PE) to give the title compound as colorless oil (1.42 g, 67%). The compound was characterized by the following spectroscopic data:

MS (ESI, pos.ion) m/z: 175.1 $[M+H]^+$; and
$^1$H NMR (400 MHz, $CDCl_3$) δ (ppm): 7.19 (t, 1H, J=7.7 Hz), 6.84 (d, 1H, J=7.5 Hz), 6.71 (d, 1H, J=8.0 Hz), 3.84 (s, 3H), 3.78-3.70 (m, 1H), 3.20-3.08 (m, 1H), 3.04-2.94 (m, 1H), 2.80-2.70 (m, 1H), 2.60-2.46 (m, 1H), 2.30-2.17 (m, 1H), 1.86-1.70 (m, 2H).

Step 8) The Preparation of Compound 1-9

To a solution of compound 1-8 (9.92 g, 57.0 mmol) in THF (40 mL) and MeCN (80 mL) was added NIS (14.2 g, 63.0 mmol). After the mixture was stirred for 10 mins, a catalytic amount of trifluoroacetic acid was added dropwise. At the end of the addition, the mixture was stirred at rt for 5.0 hrs. After the reaction was completed, the mixture was concentrated in vacuo. To the residue was added EtOAc (200 mL). The resulting mixture was washed with saturated sodium sulfite aqueous solution (50 mL×3), dried over anhydrous $Na_2SO_4$ and concentrated in vacuo. The residue was purified by silica gel column chromatography (PE) to give the title compound as colorless liquid (12.8 g, 75%). The compound was characterized by the following spectroscopic data:

MS (ESI, pos.ion) m/z: 301.1 $[M+H]^+$; and
$^1$H NMR (400 MHz, $CDCl_3$) δ (ppm): 7.52 (d, 1H, J=8.4 Hz), 6.49 (d, 1H, J=8.4 Hz), 3.81 (s, 3H), 3.70-3.62 (m, 1H), 3.17-3.08 (m, 1H), 3.08-3.00 (m, 1H), 2.94-2.85 (m, 1H), 2.60-2.48 (m, 1H), 2.32-2.20 (m, 1H), 1.94-1.84 (m, 1H), 1.82-1.68 (m, 1H).

Step 9) The Preparation of Compound 1-10

To a solution of compound 1-9 (2.16 g, 7.2 mmo) in DCM (20 mL) was added boron tribromide (2.7 mL, 28.8 mmol) dropwise at −78° C. At the end of the addition, the mixture was stirred at −78° C. for 10 mins and at rt for another 4.0 hr. After the reaction was completed, the mixture was poured slowly into ice water (100 mL) and the organic phase was separated. The aqueous layer was extracted with DCM (50 mL×3). The combined organic layers were washed with brine, dried over anhydrous $Na_2SO_4$ and concentrated in vacuo. The residue was purified by silica gel column chromatography (PE/EtOAc (v/v)=20/1) to give the title compound as colorless liquid (1.85 g, 90%). The compound was characterized by the following spectroscopic data:

MS (ESI, pos.ion) m/z: 287.1 $[M+H]^+$; and
$^1$H NMR (400 MHz, $CDCl_3$) δ (ppm): 7.43 (d, 1H, J=8.3 Hz), 6.46 (d, 1H, J=8.3 Hz), 5.05 (s, 1H), 3.70-3.62 (m, 1H), 3.17-3.08 (m, 1H), 3.08-3.00 (m, 1H), 2.94-2.85 (m, 1H), 2.60-2.48 (m, 1H), 2.32-2.20 (m, 1H), 1.94-1.84 (m, 1H), 1.82-1.68 (m, 1H).

Step 10) The Preparation of Compound 1-11

To a solution of compound 1-10 (1.55 g, 5.4 mmol) in DCM (20 mL) was added pyridine (1.1 mL, 13.5 mmol) dropwise at 0° C. After the mixture was stirred for 10 mins, trifluoromethanesulfonic anhydride (1.4 mL, 8.1 mmol) was added dropwise. At the end of the addition, the mixture was stirred at rt for 1.0 hr. After the reaction was completed, the mixture was quenched with ice water (50 mL). The aqueous layer was extracted with DCM (50 mL×3). The combined organic layers were washed with brine, dried over anhydrous $Na_2SO_4$ and concentrated in vacuo. The residue was purified by silica gel column chromatography (PE) to give the title compound as colorless liquid (2.21 g, 98%). The compound was characterized by the following spectroscopic data:

MS (ESI, pos.ion) m/z: 419.0 $[M+H]^+$; and
$^1$H NMR (400 MHz, $CDCl_3$) δ (ppm): 7.64 (d, 1H, J=8.5 Hz), 6.86 (d, 1H, J=8.5 Hz), 3.76-3.67 (m, 1H), 3.30-3.14

(m, 2H), 3.12-3.00 (m, 1H), 2.65-2.50 (m, 1H), 2.35-2.23 (m, 1H), 1.94-1.84 (m, 1H), 1.83-1.72 (m, 1H).

Step 11) The Preparation of Compound 1-13

To a solution of compound 1-12-2 (30 g, 107.9 mmol) and compound 1-12 (25.6 g, 118.7 mmol) in DCM (250 mL) was added DIPEA (21.4 mL, 129.5 mmol) dropwise at 0° C. At the end of the addition, the mixture was stirred at rt for 3.0 hrs. After the reaction was completed, the mixture was quenched with ice water (100 mL). The aqueous layer was extracted with EtOAc (100 mL×3). The combined organic layers were washed with brine, dried over anhydrous $Na_2SO_4$ and concentrated in vacuo. The residue was purified by silica gel column chromatography (PE/EtOAc (v/v)=10/1) to give the title compound as a white solid (40 g, 91%). The compound was characterized by the following spectroscopic data:

MS (ESI, pos.ion) m/z: 412.7 $[M+H]^+$; and
$^1$H NMR (400 MHz, $CDCl_3$) δ (ppm): 7.78-7.75 (m, 2H), 7.65-7.63 (m, 2H), 5.53-5.15 (m, 2H), 4.49-4.39 (m, 1H), 3.59-3.54 (m, 1H), 3.48-3.38 (m, 1H), 2.31-2.21 (m, 2H), 2.12-2.01 (m, 1H), 1.98-1.85 (m, 1H), 1.45 (d, 9H).

Step 12) The Preparation of Compound 1-14

A suspension of compound 1-13 (15 g, 36.4 mmol) and ammonium acetate (42 g, 54.6 mmol) in toluene (150 mL) was stirred at 110° C. for 5.0 hrs. After cooling to rt, the reaction was quenched with water (100 mL). The resulting mixture was extracted with EtOAc (100 mL×3). The combined organic layers were washed with brine, dried over anhydrous $Na_2SO_4$ and concentrated in vacuo. The residue was purified by silica gel column chromatography (PE/EtOAc (v/v)=5/1) to give the title compound (12.1 g, 85%). The compound was characterized by the following spectroscopic data:

MS (ESI, pos.ion) m/z: 392.2 $[M+H]^+$; and
$^1$H NMR (400 MHz, $CDCl_3$) δ (ppm): 7.78-7.75 (m, 2H), 7.65-7.63 (m, 2H), 7.21-7.20 (m, 1H), 5.53-5.15 (m, 2H), 4.49-4.39 (m, 1H), 3.59-3.54 (m, 1H), 3.48-3.38 (m, 1H), 2.31-2.21 (m, 2H), 2.12-2.01 (m, 1H), 1.98-1.85 (m, 1H), 1.45 (d, 9H).

Step 13) The Preparation of Compound 1-15

A mixture of compound 1-14 (4.0 g, 10.23 mmol), compound 1-14-2 (2.86 g, 11.25 mmol), $Pd(dppf)Cl_2 \cdot CH_2Cl_2$ (0.42 g, 0.51 mmol) and KOAc (2.51 g, 25.57 mmol) in DMF (40 mL) was stirred at 90° C. under $N_2$ for 3.0 hrs. After the reaction was completed, the mixture was cooled to rt, diluted with EtOAc (250 mL) and filtered through a celite pad. The filtrate was washed with water (80 mL×3) and brine, dried over anhydrous $Na_2SO_4$ and concentrated in vacuo. The residue was purified by silica gel column chromatography (PE/EtOAc (v/v)=2/1) to give the title compound (3.6 g, 80%). The compound was characterized by the following spectroscopic data:

$^1$H NMR (400 MHz, $CDCl_3$) δ (ppm): 7.35 (m, 4H), 7.10 (s, 1H), 4.93 (t, 1H, J=8.2 Hz), 3.88-3.66 (m, 2H), 2.90 (t, 1H, J=8.0 Hz), 2.50-2.47 (m, 2H), 2.27-2.25 (m, 1H), 1.48 (s, 9H), 1.26 (s, 12H).

Step 14) The Preparation of Compound 1-16

To a solution of compound 1-12 (10.0 g, 46.6 mmol) in THF (100 mL) was added diborane (100 mL, 1M in THF) dropwise at 0° C. At the end of the addition, the mixture was stirred at 0° C. for 3.0 hrs. After the reaction was completed, the mixture was quenched with MeOH (80 mL) and concentrated in vacuo. The residue was purified by silica gel column chromatography (PE/EtOAc (v/v)=3/2) to give the title compound as colorless oil (7.0 g, 75.2%). The compound was characterized by the following spectroscopic data:

$^1$H NMR (400 MHz, $CDCl_3$) δ (ppm): 3.99-3.87 (br, 1H), 3.68-3.51 (m, 2H), 3.48-3.39 (m, 1H), 3.34-3.25 (m, 1H), 2.05-1.92 (m, 2H), 1.88-1.71 (m, 2H), 1.45 (s, 9H).

Step 15) The Preparation of Compound 1-17

To a solution of compound 1-16 (7.0 g, 34.8 mmol) in DCM (250 mL) was added Dess-Martin periodinane (20.7 g, 48.8 mmol) in a portionwise manner at 0° C. At the end of the addition, the mixture was stirred at rt for 2.0 hrs. After the reaction was completed, the mixture was diluted with water (250 mL), and the resulting mixture was filtered. After the layers were partitioned, the organic layer was washed with brine, dried over anhydrous $Na_2SO_4$ and concentrated in vacuo. The residue was purified by silica gel column chromatography (PE/EtOAc (v/v)=3/2) to give the title compound as colorless oil (3.5 g, 50.7%). The compound was characterized by the following spectroscopic data:

$^1$H NMR (400 MHz, $CDCl_3$) δ (ppm): 9.46 (d, 1H, J=2.8 Hz), 4.08-4.03 (m, 1H), 3.51-3.42 (m, 2H), 2.01-1.93 (m, 2H), 1.91-1.84 (m, 2H), 1.43 (s, 9H).

Step 16) The Preparation of Compound 1-18

To a solution of compound 1-17 (3.5 g, 17.6 mmol) and ammonia (13 mL) in MeOH (30 mL) was added glyoxal (8 mL, 40% in $H_2O$) dropwise at 0° C. At the end of the addition, the mixture was stirred at rt overnight.

After the reaction was completed, the mixture was concentrated in vacuo. The residue was purified by silica gel column chromatography (PE/EtOAc (v/v)=3/2) to give the title compound as a white solid (2.0 g, 47.6%). The compound was characterized by the following spectroscopic data:

MS (ESI, pos.ion) m/z: 238.2 $[M+H]^+$; and
$^1$H NMR (400 MHz, $CDCl_3$) δ (ppm): 6.96 (s, 1H), 4.94 (dd, 1H, J=7.68 Hz, 2.40 Hz), 3.38 (t, 2H, J=6.24 Hz), 2.17-2.03 (m, 2H), 1.99-1.91 (m, 2H), 1.48 (s, 9H).

Step 17) The Preparation of Compound 1-19

To a solution of compound 1-18 (2.0 g, 8.4 mmol) in DCM (60 mL) was added N-iodosuccinimide (3.8 g, 16.8 mmol) at 0° C. in a portionwise manner. At the end of the addition, the mixture was stirred at 0° C. for 1.5 hrs.

After the reaction was completed, the mixture was washed with brine, dried over anhydrous $Na_2SO_4$ and concentrated in vacuo. The residue was purified by silica gel column chromatography (PE/EtOAc (v/v)=3/2) to give the title compound as a white solid (2.6 g, 63.1%). The compound was characterized by the following spectroscopic data:

MS (ESI, pos.ion) m/z: 490.0 $[M+H]^+$; and
$^1$H NMR (400 MHz, $CDCl_3$) δ (ppm): 4.89 (dd, 1H, J=7.64 Hz, 2.52 Hz), 3.36 (t, 2H), 2.14-2.02 (m, 2H), 1.97-1.85 (m, 2H), 1.49 (s, 9H).

Step 18) The Preparation of Compound 1-20

To a suspension of compound 1-19 (1.6 g, 3.27 mmol) in mixed solvents of ethanol and water (50 mL, v/v=3/7) was added $Na_2SO_3$ (3.7 g, 29 mmol), and the mixture was refluxed for 17 hrs. After the reaction was completed, the ethanol solvent was removed in vacuo, and to the residue was added water (50 mL). The resulting mixture was extracted with EtOAc (50 mL×3). The combined organic layers were washed with brine, dried over anhydrous $Na_2SO_4$ and concentrated in vacuo. The residue was purified by silica gel column chromatography (PE/EtOAc (v/v)=3/2) to give the title compound as a white solid (1.0 g, 84%). The compound was characterized by the following spectroscopic data:

MS (ESI, pos.ion) m/z: 364.1 $[M+H]^+$; and
$^1$H NMR (400 MHz, $CDCl_3$) δ (ppm): 7.04 (d, 1H, J=1.84 Hz), 4.89 (dd, 1H, J=7.72 Hz, 2.56 Hz), 3.36 (t, 2H), 2.18-2.03 (m, 2H), 1.97-1.82 (m, 2H), 1.47 (s, 9H).

Step 19) The Preparation of Compound 1-21

A mixture of compound 1-11 (2.23 g, 5.33 mmol), compound 1-15 (2.34 g, 5.33 mmol), Pd(PPh$_3$)$_4$ (0.62 g, 0.53 mmol) and K$_2$CO$_3$ (1.84 g, 13.33 mmol) in mixed solvents of DME and H$_2$O (18.0 mL, v/v=5/1) was stirred at 90° C. under N$_2$ for 35.0 hrs. After the reaction was completed, the mixture was cooled to rt and diluted with EtOAc (100 mL). The resulting mixture was washed with brine, dried over anhydrous Na$_2$SO$_4$ and concentrated in vacuo. The residue was purified by silica gel column chromatography (PE/EtOAc (v/v)=3/1) to give the title compound as a pale yellow solid (2.64 g, 82%). The compound was characterized by the following spectroscopic data:

MS (ESI, pos.ion) m/z: 604.3 [M+H]$^+$; and $^1$H NMR (400 MHz, CDCl$_3$) δ (ppm): 7.90-7.70 (m, 1H), 7.60-7.30 (m, 2H), 7.30-7.20 (m, 2H), 7.18 (d, 1H, J=8.4 Hz), 5.03-4.94 (m, 1H), 4.05-3.97 (m, 1H), 3.48-3.35 (m, 2H), 3.31-3.22 (m, 1H), 3.21-3.12 (m, 1H), 3.05-2.93 (m, 1H), 2.41-2.29 (m, 1H), 2.28-2.10 (m, 3H), 2.09-1.90 (m, 2H), 1.80-1.60 (m, 2H), 1.50 (s, 9H).

Step 20) The Preparation of Compound 1-22

A mixture of compound 1-21-1 (1.00 g, 1.66 mmol), compound 1-14-2 (0.46 g, 1.82 mmol), Pd(dppf)Cl$_2$.CH$_2$Cl$_2$ (68 mg, 0.083 mmol) and KOAc (0.41 g, 4.14 mmol) in DMF (5.0 mL) was stirred at 90° C. under N$_2$ for 3.0 hrs. After the reaction was completed, the mixture was cooled to rt, diluted with EtOAc (100 mL) and filtered through a celite pad. The filtrate was washed with water (30 mL×3) and brine, dried over anhydrous Na$_2$SO$_4$ and concentrated in vacuo. The residue was purified by silica gel column chromatography (PE/EtOAc (v/v)=3/1) to give the title compound as a pale yellow solid (0.87 g, 90%). The compound was characterized by the following spectroscopic data:

MS (ESI, pos.ion) m/z: 582.5 [M+H]$^+$; and $^1$H NMR (400 MHz, CDCl$_3$) δ (ppm): 7.78 (d, 1H, J=7.5 Hz), 7.72-7.58 (m, 2H), 7.45-7.38 (m, 2H), 7.30-7.22 (m, 2H), 5.07-4.98 (m, 1H), 4.02-3.93 (m, 1H), 3.55-3.37 (m, 3H), 3.25-3.16 (m, 1H), 3.15-3.04 (m, 1H), 2.96-2.83 (m, 1H), 2.45-2.33 (m, 1H), 2.28-2.13 (m, 3H), 2.03-1.91 (m, 1H), 1.80-1.70 (m, 2H), 1.52 (s, 9H), 1.37 (d, 12H, J=3.0 Hz).

Step 21) The Preparation of Compound 1-23

To a mixture of compound 1-22 (0.62 g, 1.07 mmol), compound 1-20 (0.4 g, 1.09 mmol), Pd(PPh$_3$)$_4$ (0.13 g, 0.11 mmol) and K$_2$CO$_3$ (0.37 g, 2.67 mmol) were added EtOH (6.0 mL), DMF (2.0 mL) and H$_2$O (2.0 mL) via syringe, and the mixture was stirred at 90° C. under N$_2$ for 3.0 hrs. After the reaction was completed, the mixture was cooled to rt, and diluted with water (50 mL). The aqueous layer was extracted with EtOAc (60 mL×3). The combined organic layers were washed with brine, dried over anhydrous Na$_2$SO$_4$ and concentrated in vacuo. The residue was purified by silica gel column chromatography (DCM/MeOH (v/v) =100/1) to give the title compound as pale yellow foam (0.67 g, 91%). The compound was characterized by the following spectroscopic data:

MS (ESI, pos.ion) m/z: 691.5 [M+H]$^+$; and $^1$H NMR (400 MHz, CDCl$_3$) δ (ppm): 7.75-7.56 (m, 3H), 7.42-7.35 (m, 2H), 7.30-7.25 (m, 1H), 7.23 (s, 1H), 7.20-7.17 (m, 1H), 5.06-4.97 (m, 2H), 4.05-3.98 (m, 1H), 3.50-3.40 (m, 4H), 3.18-3.09 (m, 1H), 2.98-2.82 (m, 4H), 2.44-2.27 (m, 2H), 2.26-2.10 (m, 4H), 2.03-1.90 (m, 2H), 1.79-1.67 (m, 2H), 1.55-1.31 (m, 20H).

Step 22) The Preparation of Compound 1-24

To a solution of compound 1-23 (0.67 g, 0.97 mmol) in EtOAc (5.0 mL) was added a solution of HCl in EtOAc (5.0 mL, 4 M) dropwise. At the end of the addition, the mixture was stirred at rt for 8.0 hrs. After the reaction was completed, the mixture was concentrated in vacuo. The residue was purified by beating in EtOAc (10 mL) and filtered to give the title compound as pale yellow powder (0.48 g, 77%). The compound was characterized by the following spectroscopic data:

MS (ESI, pos.ion) m/z: 491.5 [M+H]$^+$.

Step 23) The Preparation of Compound 1-25

To a mixture of compound 1-24 (0.48 g, 0.75 mmol), compound 1-24-2 (0.28 g, 1.58 mmol), EDCI (0.3 g, 1.58 mmol) and HOAT (0.2 g, 1.50 mmol) in DCM (4 mL) was added DIPEA (0.352 mL, 2.02 mmol) dropwise at 0° C. At the end of the addition, the mixture was stirred at rt for 3.0 hrs. After the reaction was completed, the mixture was diluted with DCM (50 mL). The organic layer was washed with saturated NH$_4$Cl aqueous solution and brine, dried over anhydrous Na$_2$SO$_4$ and concentrated in vacuo. The residue was purified by silica gel column chromatography (DCM/MeOH (v/v)=60/1) to give the title compound as pale yellow powder (0.47 g, 78%). The compound was characterized by the following spectroscopic data:

MS (ESI, pos.ion) m/z: 805.3 [M+H]$^+$; and $^1$H NMR (400 MHz, CDCl$_3$) δ (ppm): 11.00 (brs, 1H), 10.63 (brs, 1H), 7.98-7.64 (m, 2H), 7.46-7.27 (m, 3H), 7.25-7.10 (m, 3H), 6.14-5.88 (m, 2H), 5.38-5.19 (m, 2H), 4.33 (t, 2H, J=8.0 Hz), 3.98-3.78 (m, 2H), 3.79-3.58 (m, 8H), 3.31-3.20 (m, 1H), 3.16-3.00 (m, 1H), 3.00-2.80 (m, 3H), 2.44-2.26 (m, 3H), 2.23-2.13 (m, 3H), 2.13-2.03 (m, 3H), 2.01-1.89 (m, 2H), 1.75-1.55 (m, 2H), 0.94-0.76 (m, 12H).

Example 2

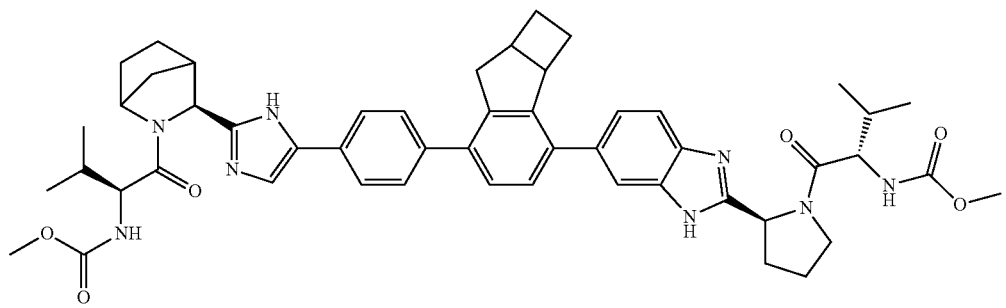

Synthetic Route:
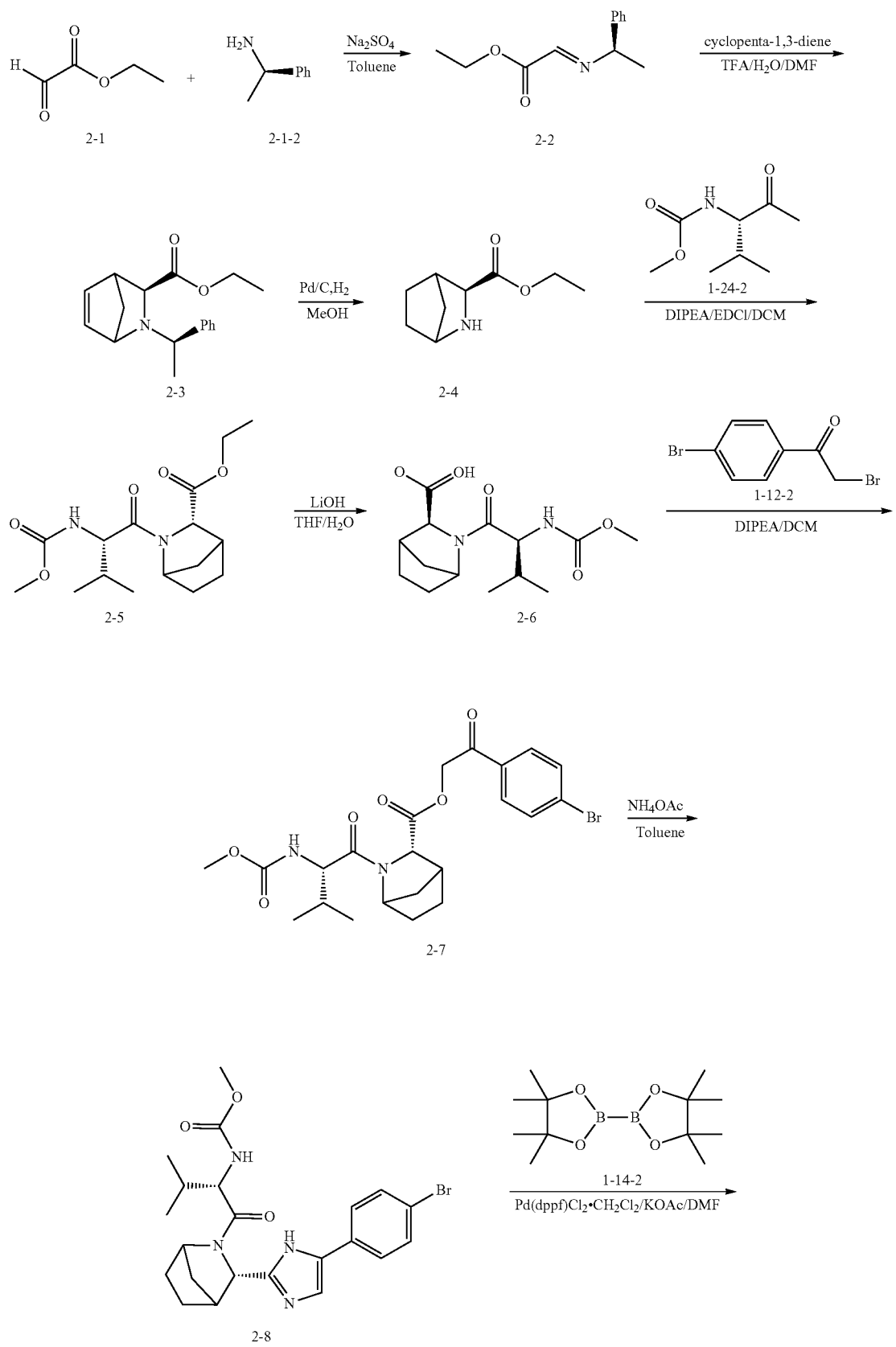

-continued
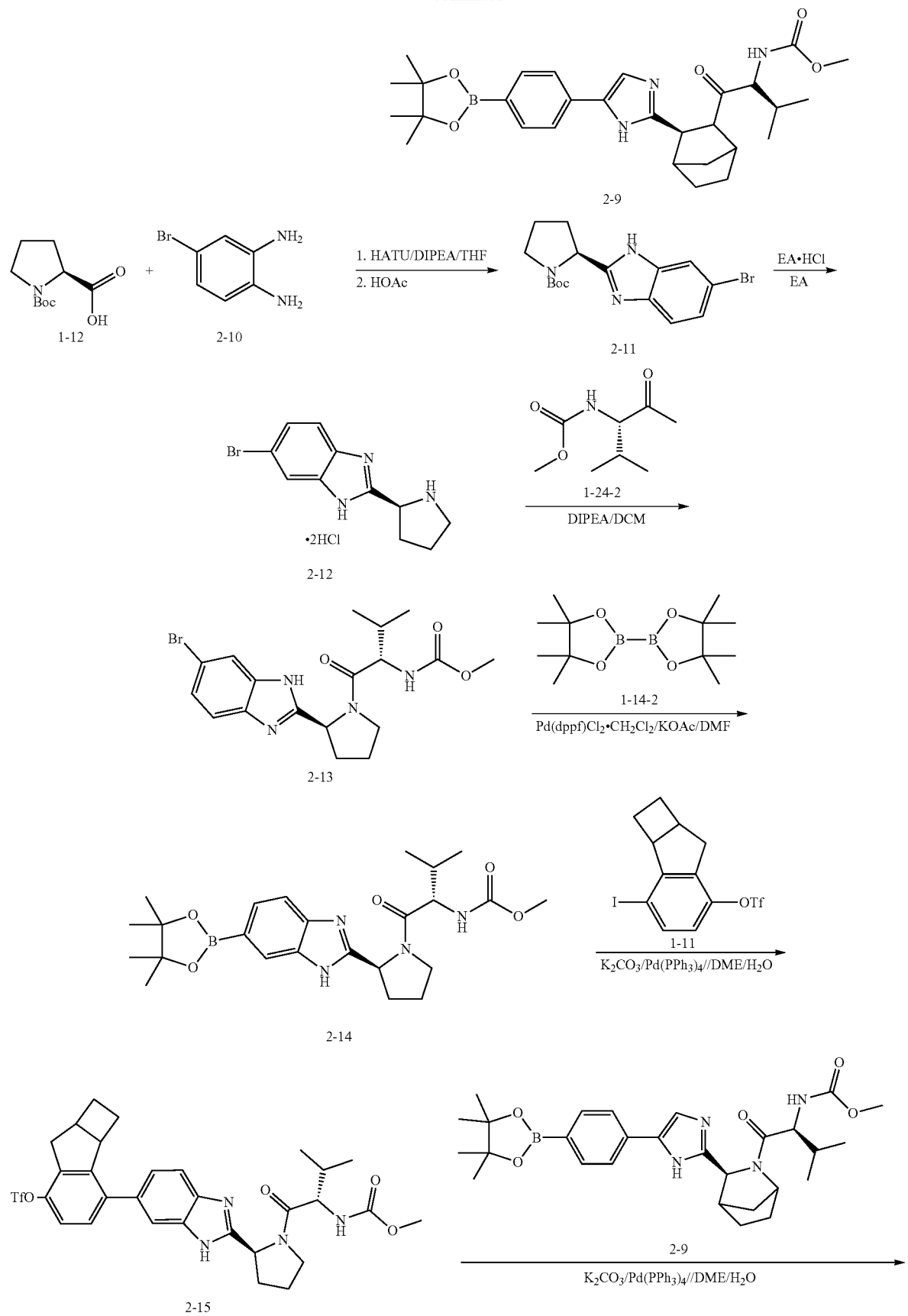

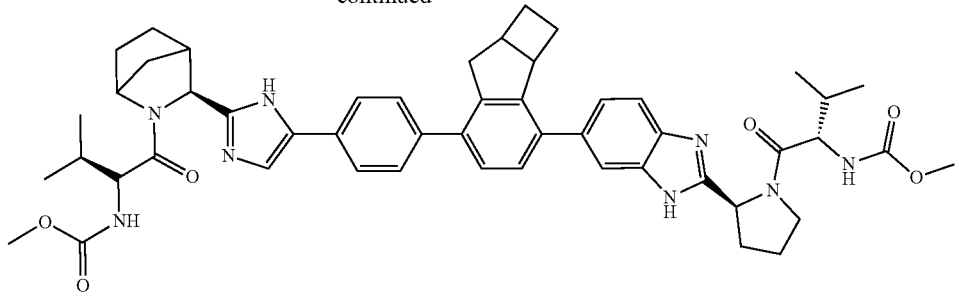

2-16

Step 1) The Preparation of Compound 2-2

To a solution of (R)-1-phenylethylamine 2-1-2 (1.3 mL, 10.1 mmol) in toluene (15 mL) was added anhydrous Na$_2$SO$_4$ (3.48 g, 24.5 mmol) dropwise at rt, followed by ethyl glyoxalate 2-1 (1.0 mL, 10.1 mmol). At the end of the addition, the mixture was stirred at rt for 1.0 hr. After the reaction was completed, the mixture was filtered. The filtrate was concentrated in vacuo to give the title compound as yellow liquid (1.9 g, 91.8%), which was used for the next step without further purification.

Step 2) The Preparation of Compound 2-3

To a solution of compound 2-2 (2.0 g, 9.7 mmol) in DMF (15 mL) was added TFA (0.75 mL, 10.1 mmol). After stirring for 10 mins, to the mixture were added freshly prepared 1,3-cyclopentadiene (1.29 g, 19.5 mmol) and two drops of water in turn. The reaction mixture was stirred at rt for 12 hrs. After the reaction was completed, the DMF solvent was removed and to the residue was added NaHCO$_3$ aqueous solution (20 mL, 10%). The mixture was adjusted to pH 8 with Na$_2$CO$_3$ and extracted with PE (25 mL×3). The combined organic layers were washed with brine, dried over anhydrous Na$_2$SO$_4$ and concentrated in vacuo. The residue was purified by silica gel column chromatography (PE/EtOAc (v/v)=10/1) to give the title compound as pale yellow liquid (2.38 g, 90.0%). The compound was characterized by the following spectroscopic data:

$^1$H NMR (400 MHz, CDCl$_3$) δ (ppm): 7.35-7.17 (m, 5H), 6.42 (br, 1H), 6.28-6.26 (br, 1H), 4.34-4.30 (m, 2H), 3.82-3.78 (m, 2H), 3.04-3.02 (m, 1H), 2.90 (br, 1H), 2.20 (br, 1H), 2.13 (m, 1H), 1.41 (d, 3H, J=6.6 Hz), 0.95 (t, 3H, J=7.2 Hz).

Step 3) The Preparation of Compound 2-4

To a solution of compound 2-3 (2.0 g, 7.37 mmol) in MeOH (60 mL) was added Pd/C (0.2 g). The mixture was stirred at rt under 20 atm of H$_2$ gas for 24 hrs. After the reaction was completed, the mixture was filtered. The filtrate was concentrated in vacuo to give the title compound as yellow liquid (1.2 g, 96.2%). The compound was characterized by the following spectroscopic data:

MS (ESI, pos.ion) m/z: 170.2 [M+H]$^+$; and $^1$H NMR (400 MHz, CDCl$_3$) δ (ppm): 4.21-4.15 (m, 2H), 3.55 (br, 1H), 3.33 (br, 1H), 2.63 (br, 1H), 2.32 (br, 1H), 1.64-1.60 (m, 2H), 1.53-1.47 (m, 2H), 1.42-1.36 (m, 2H), 1.28 (t, 3H, J=7.1 Hz).

Step 4) The Preparation of Compound 2-5

To a suspension of compound 2-4 (0.68 g, 4.02 mmol), compound 1-24-2 (1.06 g, 6.03 mmol) and EDCI (1.54 g, 8.05 mmol) in DCM (25 mL) was added DIPEA (2.1 mL, 12.7 mmol) dropwise at 0° C. At the end of the addition, the mixture was stirred at rt overnight. After the reaction was completed, the mixture was quenched with water (30 mL). The aqueous layer was extracted with DCM (35 mL×3). The combined organic layers were washed with brine, dried over anhydrous Na$_2$SO$_4$ and concentrated in vacuo. The residue was purified by silica gel column chromatography (PE/EtOAc (v/v)=2/1) to give the title compound as a white solid (0.74 g, 56.4%). The compound was characterized by the following spectroscopic data:

MS (ESI, pos.ion) m/z: 327.3 [M+H]$^+$; and $^1$H NMR (400 MHz, CDCl$_3$) δ (ppm): 5.44 (br, 1H), 4.40 (br, 1H), 4.33-4.30 (m, 1H), 4.19-4.14 (m, 2H), 4.02 (br, 1H), 3.66 (s, 3H), 2.74 (br, 1H), 2.04 (br, 1H), 1.91-1.88 (m, 2H), 1.80-1.74 (m, 2H), 1.56-1.54 (m, 1H), 1.43-1.38 (m, 1H), 1.26 (t, 3H, J=7.1 Hz), 1.07 (d, 3H, J=6.8 Hz), 0.97 (d, 3H, J=6.8 Hz).

Step 5) The Preparation of Compound 2-6

To a solution of compound 2-5 (0.74 g, 2.27 mmol) in THF (25 mL) was added lithium hydroxide monohydrate aqueous solution (0.48 g, 11.35 mmol, 10 mL) at 0° C. At the end of the addition, the mixture was stirred at 40° C. for 12 hrs. After the reaction was completed, the THF solvent was removed and to the residue was added water (20 mL). The aqueous layer was washed with EtOAc (15 mL×3) and separated. The aqueous phase was adjusted to pH 1 with hydrochloric acid (10%) and extracted with EtOAc (25 mL×3). The combined organic layers were washed with brine, dried over anhydrous Na$_2$SO$_4$ and concentrated in vacuo to give the title compound as a white solid (0.55 g, 81.3%). The compound was characterized by the following spectroscopic data:

MS (ESI, pos.ion) m/z: 299.2 [M+H]$^+$; and $^1$H NMR (400 MHz, CD$_3$OD) δ (ppm): 4.52 (br, 1H), 4.20 (d, 1H, J=7.8 Hz), 3.93 (br, 1H), 3.63 (s, 3H), 2.73 (br, 1H), 2.01-1.98 (m, 4H), 1.85-1.75 (m, 2H), 1.54-1.46 (m, 2H), 1.05 (d, 3H, J=6.8 Hz), 0.98 (d, 3H, J=6.8 Hz).

Step 6) The Preparation of Compound 2-7

To a mixture of compound 1-12-2 (0.31 g, 1.1074 mmol) and compound 2-6 (0.3 g, 1.0067 mmol) in DCM (30.0 mL) was added DIPEA (0.20 mL, 1.2081 mmol) dropwise at 0° C. At the end of the addition, the mixture was stirred at rt for 3.0 hrs. After the reaction was completed, the mixture was quenched with water (20 mL). The aqueous layer was extracted with EtOAc (30 mL×3). The combined organic layers were washed with brine, dried over anhydrous Na$_2$SO$_4$ and concentrated in vacuo. The residue was purified by silica gel column chromatography (PE/EtOAc (v/v)=1/2) to give the title compound as a pale yellow solid (0.33 g, 66.7%). The compound was characterized by the following spectroscopic data:

MS (ESI, pos.ion) m/z: 495.3 [M+H]$^+$; and $^1$H NMR (400 MHz, CDCl$_3$) δ (ppm): 7.75 (d, 2H, J=8.52 Hz), 7.68 (d, 2H, J=8.56 Hz), 5.45 (d, 1H, J=9.4 Hz), 5.24 (d, 1H, J=16.56 Hz), 4.55-4.59 (m, 1H), 3.67 (s, 3H), 3.57 (m, 1H), 2.73-2.65 (m, 2H), 2.27-2.19 (m, 1H), 2.04 (s, 1H), 1.84-1.77 (m, 2H), 1.49-1.46 (m, 1H), 1.27-1.24 (m, 1H), 1.08-1.07 (br, 1H), 1.05-1.03 (m, 1H), 0.91-0.89 (m, 6H).

Step 7) The Preparation of Compound 2-8

A suspension of compound 2-7 (0.33 g, 0.6714 mmol) and NH$_4$OAc (1.04 g, 13.43 mmol) in toluene (8.0 mL) was stirred at 110° C. for 5.0 hrs. After the reaction was completed, the mixture was cooled to rt and quenched with water (20 mL). The aqueous layer was extracted with EtOAc (20 mL×3). The combined organic layers were washed with brine, dried over anhydrous Na$_2$SO$_4$ and concentrated in vacuo. The residue was purified by silica gel column chromatography (PE/EtOAc (v/v)=1/2) to give the title compound as a yellow solid (0.19 g, 58.94%). The compound was characterized by the following spectroscopic data:

MS (ESI, pos.ion) m/z: 476.3 [M+H]$^+$; and $^1$H NMR (400 MHz, CDCl$_3$) δ (ppm): 10.35 (s, 1H), 7.64-7.62 (d, 2H, J=8.52 Hz), 7.55-7.45 (d, 2H, J=1.84 Hz), 7.16 (s, 1H), 5.54-5.46 (br, 2H), 4.57-4.53 (m, 1H), 3.70 (s, 3H), 3.58 (m, 1H), 2.69 (m, 1H), 2.54-2.48 (m, 1H), 1.87-1.76 (m, 4H), 1.47-1.45 (m, 2H), 0.85-0.81 (m, 6H).

Step 8) The Preparation of Compound 2-9

To a mixture of compound 2-8 (0.19 g, 0.3957 mmol), compound 1-14-2 (0.15 g, 0.5935 mmol), Pd(dppf)Cl$_2$.CH$_2$Cl$_2$ (33 mg, 0.03956 mmol) and KOAc (0.12 g, 1.187 mmol) was added DMF (5.0 mL) via syringe under N$_2$, and the mixture was stirred at 90° C. for 3.0 hrs. After the reaction was completed, the mixture was cooled to rt, diluted with EtOAc (50 mL) and filtered through a celite pad. The filtrate was washed with water (20 mL×3) and brine, dried over anhydrous Na$_2$SO$_4$ and concentrated in vacuo. The residue was purified by silica gel column chromatography (PE/EtOAc (v/v)=1/2) to give the title compound as a beige solid (0.2 g, 80%). The compound was characterized by the following spectroscopic data:

MS (ESI, pos.ion) m/z: 523.3 [M+H]$^+$; and $^1$H NMR (400 MHz, CDCl$_3$) δ (ppm): 10.48 (s, 1H), 7.81-7.75 (m, 4H), 7.43-7.41 (d, 1H, J=8.0 Hz), 5.49-5.39 (m, 2H), 4.58-4.53 (m, 2H), 3.67 (s, 3H), 3.57 (m, 1H), 2.65 (m, 1H), 2.54-2.47 (m, 1H), 2.10-2.04 (m, 2H), 1.83-1.79 (m, 1H), 1.49-1.46 (m, 2H), 1.38 (s, 12H), 0.85-0.81 (m, 6H).

Step 9) The Preparation of Compound 2-11

To a suspension of compound 1-12 (20 g, 107 mmol) and HATU (48.82 g, 128.4 mmol) in THF (250 mL) was added DIPEA (19.5 mL, 118 mmol) dropwise at 0° C. After stirring at 0° C. for 0.5 hr, compound 2-10 (25.6 g, 119 mmol) was added to the mixture in a portionwise manner. At the end of the addition, the mixture was stirred at rt for 4.0 hrs. After the reaction was completed, the THF solvent was removed and 150 mL of water was added. The resulting mixture was extracted with EtOAc (200 mL×3). The combined organic layers were washed with brine, dried over anhydrous Na$_2$SO$_4$ and concentrated in vacuo. The residue was dissolved in glacial acetic acid (100 mL), and the solution was stirred at 40° C. overnight. After the reaction was completed, HOAc was removed. The residue was dissolved in EtOAc (400 mL). The resulting mixture was washed with Na$_2$CO$_3$ aqueous solution (150 mL×3), dried over anhydrous Na$_2$SO$_4$ and concentrated in vacuo. The residue was purified by silica gel column chromatography (PE/EtOAc (v/v)=1/2) to give the title compound as a brown solid (35 g, 81%). The compound was characterized by the following spectroscopic data:

MS (ESI, pos.ion) m/z: 367.3 [M+H]$^+$; and $^1$H NMR (400 MHz, CDCl$_3$) δ (ppm): 7.68 (s, 1H), 7.42-7.40 (m, 1H), 7.30-7.28 (m, 1H), 5.11-5.09 (m, 1H), 3.45-3.43 (m, 2H), 2.94-2.93 (m, 1H), 2.21-2.18 (m, 2H), 2.01-1.91 (m, 1H), 1.49 (s, 9H).

Step 10) The Preparation of Compound 2-12

To a solution of compound 2-11 (10.0 g, 27.39 mmol) in EtOAc (50 mL) was added a solution of HCl in EtOAc (60 mL, 4 M) dropwise at 0° C. At the end of the addition, the mixture was stirred at rt for 8.0 hrs. After the reaction was completed, the mixture was concentrated in vacuo. The residue was purified by beating in EtOAc (30 mL) and filtered to give the title compound as pale yellow powder (8.0 g, 86.49%). The compound was characterized by the following spectroscopic data:

MS (ESI, pos.ion) m/z: 313.2 [M+H]$^+$; and $^1$H NMR (400 MHz, CDCl$_3$) δ (ppm): 8.01 (s, 1H), 7.70-7.76 (m, 2H), 5.27-5.25 (m, 1H), 3.31-3.30 (m, 2H), 2.77-2.74 (m, 1H), 2.54-2.52 (m, 1H), 2.40-2.37 (m, 1H), 2.30-2.10 (m, 1H).

Step 11) The Preparation of Compound 2-13

To a solution of compound 2-12 (6.0 g, 18.8 mmol), compound 1-24-2 (4.9 g, 28.2 mmol) and EDCI (5.4 g, 28.2 mmol) in DCM (100 mL) was added DIPEA (18.64 mL, 112.8 mmol) dropwise at 0° C. At the end of the addition, the mixture was stirred at rt for 3.0 hrs. After the reaction was completed, the mixture was quenched with water (100 mL) and extracted with DCM (150 mL×3). The combined organic layers were washed with brine, dried over anhydrous Na$_2$SO$_4$ and concentrated in vacuo. The residue was purified by silica gel column chromatography (PE/EtOAc (v/v)=1/2) to give the title compound as a solid (5.77 g, 85%). The compound was characterized by the following spectroscopic data:

MS (ESI, pos.ion) m/z: 423.3 [M+H]$^+$; and $^1$H NMR (400 MHz, CDCl$_3$) δ (ppm): 7.59-7.51 (m, 1H), 7.34-7.21 (m, 2H), 5.42-5.38 (m, 2H), 4.34-4.30 (m, 1H), 3.87-3.76 (m, 1H), 3.70 (s, 3H), 3.66-3.62 (m, 1H), 3.04-2.98 (m, 1H), 2.25-2.21 (m, 1H), 2.20-2.13 (m, 2H), 1.96-1.94 (m, 1H), 0.88-0.84 (m, 6H).

Step 12) The Preparation of Compound 2-14

To a mixture of compound 2-13 (3.0 g, 7.1 mmol), compound 1-14-2 (2.72 g, 10.7 mmol), Pd(dppf)Cl$_2$.CH$_2$Cl$_2$ (0.65 g, 0.8 mmol) and KOAc (2.09 g, 21.3 mmol) was added DMF (30 mL) via syringe under N$_2$, and the mixture was stirred at 90° C. for 3.0 hrs. After the reaction was completed, the mixture was cooled to rt and diluted with EtOAc (200 mL). The resulting mixture was filtered through a celite pad. The filtrate was washed with water (50 mL×3) and brine, dried over anhydrous Na$_2$SO$_4$ and concentrated in vacuo. The residue was purified by silica gel column chromatography (PE/EtOAc (v/v)=1/2) to give the title compound as a beige solid (2.1 g, 62.87%). The compound was characterized by the following spectroscopic data:

MS (ESI, pos.ion) m/z: 471.3 [M+H]$^+$; and $^1$H NMR (400 MHz, CDCl$_3$) δ (ppm): 7.87-7.80 (m, 1H), 7.71-7.66 (m, 2H), 5.47-5.42 (m, 2H), 4.34-4.30 (m, 1H), 3.86-3.84 (m, 1H), 3.70 (s, 3H), 3.64-3.62 (m, 1H), 3.04-2.98 (m, 1H), 2.25-2.21 (m, 1H), 2.20-2.13 (m, 2H), 1.96-1.94 (m, 1H), 1.35 (s, 12H), 0.88-0.84 (m, 6H).

Step 13) The Preparation of Compound 2-15

To a suspension of compound 1-11 (0.4 g, 0.957 mmol), compound 2-14 (0.45 g, 0.957 mmol), Pd(PPh$_3$)$_4$ (0.11 g, 0.0957 mmol) and K$_2$CO$_3$ (0.40 g, 2.87 mmol) were added DME (10 mL) and pure water (2.5 mL) via syringe, and the mixture was stirred at 90° C. under $N_2$ for 5.0 hrs. After the reaction was completed, the mixture was cooled to rt and diluted with EtOAc (50 mL). The resulting mixture was washed with water (20 mL×3) and brine, dried over anhydrous $Na_2SO_4$ and concentrated in vacuo. The residue was purified by silica gel column chromatography (DCM/MeOH (v/v)=100/1) to give the title compound as a beige solid (0.33 g, 54.7%). The compound was characterized by the following spectroscopic data:

MS (ESI, pos.ion) m/z: 635.3 [M+H]$^+$; and $^1$H NMR (400 MHz, CDCl$_3$) δ (ppm): 7.85-7.79 (m, 2H), 7.42-7.41 (m, 2H), 7.27 (s, 1H), 5.12-4.95 (m, 1H), 4.83-4.68 (m, 1H), 3.72 (s, 3H), 3.63-3.59 (m, 2H), 3.35-3.32 (m, 2H), 3.12-3.02 (m, 2H), 2.94-2.89 (m, 1H), 2.02-1.98 (m, 2H), 1.87-1.75 (m, 6H), 1.02-0.91 (m, 6H).

Step 14) The Preparation of Compound 2-16

To a suspension of compound 2-15 (0.33 g, 0.522 mmol), compound 2-9 (0.3 g, 0.574 mmol), Pd(PPh$_3$)$_4$ (60.29 mg, 0.0522 mmol) and K$_2$CO$_3$ (0.22 g, 1.566 mmol) were added DME (6.0 mL) and pure water (1.5 mL) via syringe, and the mixture was stirred at 90° C. under $N_2$ for 5.0 hrs. After the reaction was completed, the mixture was cooled to rt and diluted with EtOAc (50 mL). The resulting mixture was washed with water (20 mL×3) and brine, dried over anhydrous $Na_2SO_4$ and concentrated in vacuo. The residue was purified by silica gel column chromatography (DCM/MeOH (v/v)=80/1) to give the title compound as a pale yellow solid (0.23 g, 50%). The compound was characterized by the following spectroscopic data:

MS (ESI, pos.ion) m/z: 441.3 [M+2H]$^{2+}$; and $^1$H NMR (400 MHz, CDCl$_3$) δ (ppm): 7.91-7.89 (m, 2H), 7.74-7.71 (m, 2H), 7.59-7.52 (m, 4H), 7.33-7.31 (m, 2H), 5.44-5.40 (m, 2H), 4.71-4.69 (m, 1H), 4.30-4.21 (br, 1H), 3.73 (s, 6H), 3.54-3.49 (m, 2H), 3.02-3.00 (d, 4H, J=8.0 Hz), 2.60-2.51 (br, 1H), 2.41-2.32 (br, 1H), 2.20-2.17 (br, 2H), 2.10 (s, 1H), 2.04 (s, 1H), 1.96-1.91 (br, 2H), 1.66-1.58 (m, 2H), 1.27-1.24 (m, 2H), 1.14 (s, 6H), 0.85-0.81 (m, 12H).

Example 3

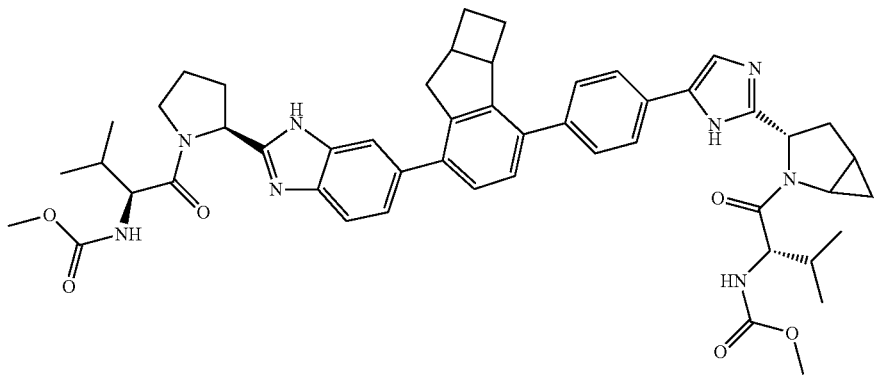 [SMILES: COC(=O)N[C@H](C(=O)N1CCC[C@H]1c1nc2ccc(-c3ccc(-c4ccc(-c5cnc([C@@H]6CC7CC7N6C(=O)[C@@H](NC(=O)OC)C(C)C)[nH]5)cc4)c4c3CC3CCC43)cc2[nH]1)C(C)C]

Synthetic Route:

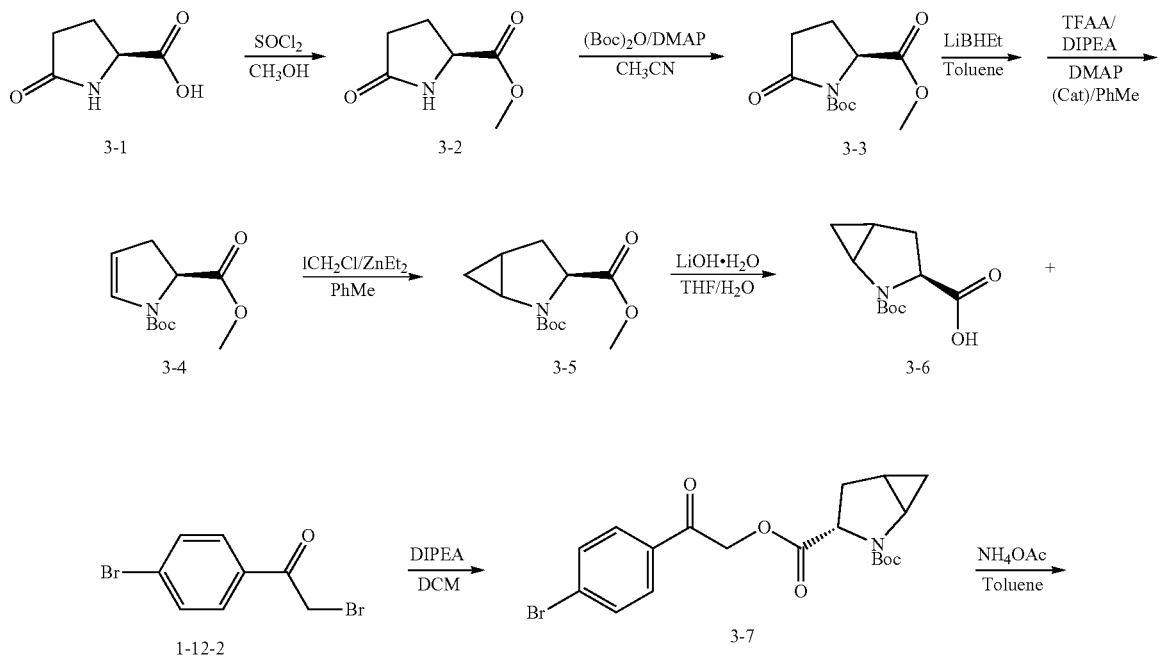

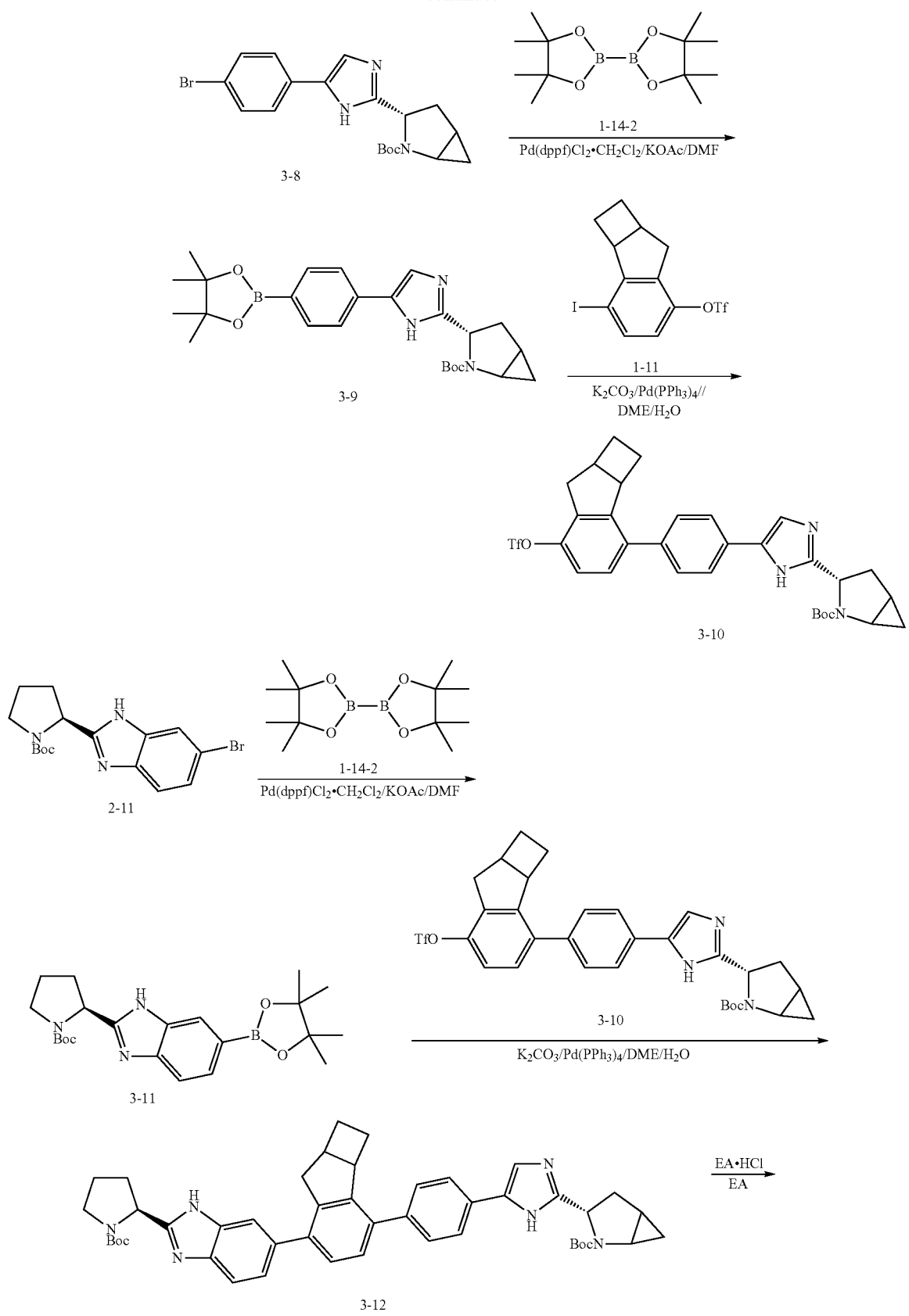

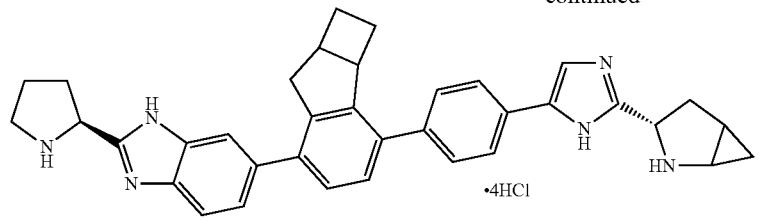
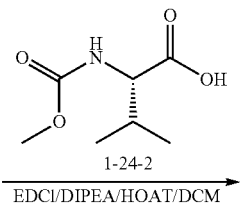

3-13

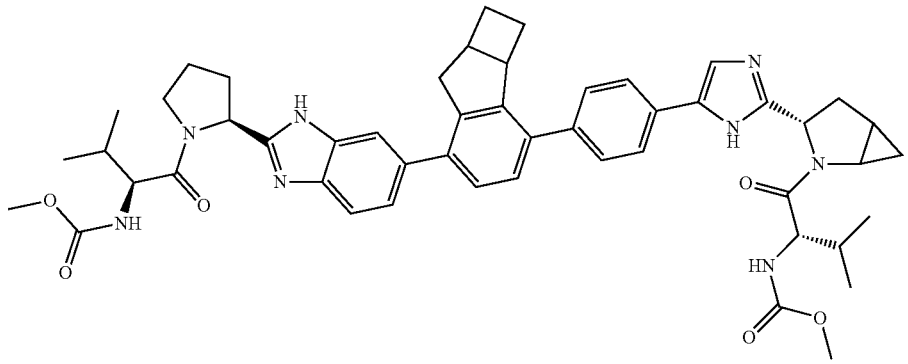

3-14

Step 1) The Preparation of Compound 3-2

To a solution of compound 3-1 (10 g, 77.5 mmol) in MeOH (50 mL) was added thionyl chloride (5.5 mL, 75.8 mmol) dropwise at 0° C. At the end of the addition, the mixture was stirred at 0° C. for 1.0 hr and at rt for another 2.0 hrs. After the reaction was completed, the mixture was quenched with NaHCO$_3$ aqueous solution (50 mL), and the MeOH solvent was removed. The resulting mixture was extracted with DCM (35 mL×3). The combined organic layers were washed with brine, dried over anhydrous Na$_2$SO$_4$ and concentrated in vacuo. The residue was purified by silica gel column chromatography (EtOAc) to give the title compound as colorless liquid (7.5 g, 67.6%). The compound was characterized by the following spectroscopic data:

MS (ESI, pos.ion) m/z: 144.2 [M+H]$^+$; and $^1$H NMR (400 MHz, CDCl$_3$) δ (ppm): 7.38 (br, 1H), 4.20-4.16 (m, 1H), 3.67 (s, 3H), 2.39-2.23 (m, 3H), 2.14-2.07 (m, 1H).

Step 2) The Preparation of Compound 3-3

To a solution of compound 3-2 (6.45 g, 45.06 mmol) in MeCN (30 mL) was added DMAP (0.55 g, 4.5 mmol) at 0° C. After the mixture was stirred for 10 mins, di-tert-butyl dicarbonate (10.82 g, 49.56 mmol) was added dropwise. At the end of the addition, the mixture was stirred at 0° C. for 30 mins and at rt for another 2.0 hrs. After the reaction was completed, the mixture was concentrated in vacuo. The residue was purified by silica gel column chromatography (PE/EtOAc (v/v)=1/1) to give the title compound as colorless liquid (5.0 g, 45.6%). The compound was characterized by the following spectroscopic data:

MS (ESI, pos.ion) m/z: 144.2 [M-Boc]$^+$; and $^1$H NMR (400 MHz, CDCl$_3$) δ (ppm): 4.60-4.57 (m, 1H), 3.75 (s, 3H), 2.65-2.55 (m, 1H), 2.50-2.42 (m, 1H), 2.36-2.24 (m, 1H), 2.04-1.96 (m, 1H), 1.45 (s, 9H).

Step 3) The Preparation of Compound 3-4

To a solution of compound 3-3 (3.74 g, 15.4 mmol) in toluene (50 mL) was added lithium triethylborohydride (1.79 g, 16.9 mmol) dropwise at −78° C. After the mixture was stirred at −78° C. for 70 mins, DIPEA (3.2 mL, 19.4 mmol), DMAP (0.19 g, 1.54 mmol) and TFAA (3.0 mL, 40.4 mmol) were added separately, and the mixture was stirred at rt for 2.0 hrs. After the reaction was completed, the mixture was concentrated in vacuo. The residue was purified by silica gel column chromatography (PE/EtOAc (v/v)=10/1) to give the title compound as yellow liquid (2.26 g, 64.8%). The compound was characterized by the following spectroscopic data:

MS (ESI, pos.ion) m/z: 128.2 [M-Boc]$^+$; and $^1$H NMR (400 MHz, CDCl$_3$) δ (ppm): 6.65-6.52 (br, 1H), 4.96-4.91 (br, 1H), 4.68-4.57 (m, 1H), 3.76 (s, 3H), 3.12-3.00 (m, 1H), 2.71-2.61 (m, 1H), 1.49-1.44 (br, 9H).

Step 4) The Preparation of Compound 3-5

To a solution of diethylzinc (0.49 g, 3.94 mmol) in toluene (6.0 mL) was added chloroiodomethane (1.4 g, 7.9 mmol) dropwise at 0° C. After the mixture was stirred at 0° C. for 45 mins, a solution of compound 3-4 (0.3 g, 1.32 mmol) in toluene (4.0 mL) was added dropwise. At the end of the addition, the mixture was stirred at 0° C. for 18 hrs. After the reaction was completed, the mixture was quenched with saturated NH$_4$Cl aqueous solution (15 mL). The aqueous layer was extracted with EtOAc (25 mL×3). The combined organic layers were dried over anhydrous Na$_2$SO$_4$ and concentrated in vacuo. The residue was purified by silica gel column chromatography (PE/EtOAc (v/v)=10/1) to give the title compound as yellow liquid (0.19 g, 59.7%). The compound was characterized by the following spectroscopic data:

MS (ESI, pos.ion) m/z: 142.2 [M-Boc]$^+$; and $^1$H NMR (400 MHz, CDCl$_3$) δ (ppm): 4.64-4.51 (m, 1H), 3.70 (s, 3H), 3.56-3.45 (m, 1H), 2.64-2.54 (m, 1H), 2.05-2.01 (m, 1H), 1.50, 1.41 (s, s, 9H), 0.75-0.65 (m, 3H).

Step 5) The Preparation of Compound 3-6

To a solution of compound 3-5 (1.02 g, 4.23 mmol) in THF (20 mL) was added lithium hydroxide monohydrate aqueous solution (0.89 g, 21.2 mmol, 10 mL) dropwise at 0°

C. At the end of the addition, the mixture was stirred at 40° C. for 12 hrs. After the reaction was completed, the THF solvent was removed and 20 mL of water was added to the mixture. The resulting mixture was washed with EtOAc (15 mL×3) and separated. The aqueous phase was adjusted to pH 1 with hydrochloric acid (10%) and extracted with EtOAc (25 mL×3). The combined organic layers were washed with brine, dried over anhydrous $Na_2SO_4$ and concentrated in vacuo to give the title compound as a white solid (0.84 g, 87%). The compound was characterized by the following spectroscopic data:

MS (ESI, neg.ion) m/z: 226.2 [M−H]$^-$; and $^1$H NMR (400 MHz, $CD_3OD$) δ (ppm): 4.53-4.46 (m, 1H), 3.48-3.42 (m, 1H), 2.70-2.57 (m, 1H), 2.05-2.01 (m, 1H), 1.60-1.54 (m, 1H), 1.48, 1.41 (s, s, 9H), 0.89-0.80 (m, 1H), 0.73-0.66 (m, 1H).

Step 6) The Preparation of Compound 3-7

To a solution of compound 3-6 (3.91 g, 17.22 mmol) and compound 1-12-2 (5.47 g, 19.81 mmol) in DCM (60 mL) was added DIPEA (3.4 mL, 20.67 mmol) dropwise at 0° C. At the end of the addition, the mixture was stirred at rt for 3.0 hrs. After the reaction was completed, the mixture was quenched with water (50 mL). The aqueous layer was extracted with DCM (100 mL×3). The combined organic layers were washed with brine, dried over anhydrous $Na_2SO_4$ and concentrated in vacuo. The residue was purified by silica gel column chromatography (PE/EtOAc (v/v)=5/1) to give the title compound as a white solid (4.5 g, 61.73%). The compound was characterized by the following spectroscopic data:

MS (ESI, pos.ion) m/z: 424.3 [M+H]$^+$; and $^1$H NMR (400 MHz, $CDCl_3$) δ (ppm): 7.77-7.73 (m, 2H), 7.64-7.62 (m, 2H), 5.53-5.09 (m, 2H), 4.78-4.67 (m, 1H), 3.59-3.46 (m, 1H), 2.69-2.62 (m, 1H), 2.43-2.40 (m, 1H), 1.42 (s, 9H), 1.00-0.96 (m, 1H), 0.76-0.69 (m, 2H).

Step 7) The Preparation of Compound 3-8

A suspension of compound 3-7 (4.5 g, 10.64 mmol) and ammonium acetate (16.4 g, 212.73 mmol) in toluene (50 mL) was stirred at 110° C. for 5.0 hrs. After the reaction was completed, the mixture was cooled to rt, and quenched with water (50 mL). The aqueous layer was extracted with EtOAc (100 mL×3). The combined organic layers were washed with brine, dried over anhydrous $Na_2SO_4$ and concentrated in vacuo. The residue was purified by silica gel column chromatography (PE/EtOAc (v/v)=8/1) to give the title compound (2.14 g, 50%). The compound was characterized by the following spectroscopic data:

MS (ESI, pos.ion) m/z: 404.3 [M+H]$^+$; and $^1$H NMR (400 MHz, $CDCl_3$) δ (ppm): 7.62-7.52 (br, 2H), 7.49-7.46 (d, 2H, J=12 Hz), 7.21 (s, 1H), 5.27-5.24 (d, 1H, J=10.0 Hz), 3.31-3.27 (m, 1H), 1.71-1.67 (m, 2H), 1.52 (s, 9H), 0.89-0.86 (m, 1H), 0.64-0.69 (m, 2H).

Step 8) The Preparation of Compound 3-9

A mixture of compound 3-8 (2.1 g, 5.2 mmol), compound 1-14-2 (1.59 g, 6.25 mmol), Pd(dppf)$Cl_2$.$CH_2Cl_2$ (0.43 g, 0.52 mmol) and KOAc (1.54 g, 15.63 mmol) in DMF (30 mL) was stirred at 90° C. under $N_2$ for 3.0 hrs. After the reaction was completed, the mixture was cooled to rt, diluted with EtOAc (100 mL) and filtered through a celite pad. The filtrate was washed with water (60 mL×3) and brine, dried over anhydrous $Na_2SO_4$ and concentrated in vacuo. The residue was purified by silica gel column chromatography (PE/EtOAc (v/v)=2/1) to give the title compound (2.27 g, 97%). The compound was characterized by the following spectroscopic data:

MS (ESI, pos.ion) m/z: 452.3 [M+H]$^+$; and $^1$H NMR (400 MHz, $CDCl_3$) δ (ppm): 7.81-7.79 (d, 2H, J=8.04 Hz), 7.60 (br, 2H), 7.26 (s, 1H), 5.28-5.26 (d, 1H, J=8.0 Hz), 3.53 (br, 1H), 3.30-3.27 (br, 1H), 1.67-1.66 (m, 2H), 1.52 (s, 9H), 1.34 (s, 12H), 0.89-0.86 (m, 1H), 0.69-0.64 (m, 2H).

Step 9) The Preparation of Compound 3-10

A suspension of compound 1-11 (0.25 g, 0.598 mmol), compound 3-9 (0.27 g, 0.598 mmol), Pd(PPh$_3$)$_4$ (69 mg, 0.0598 mmol) and $K_2CO_3$ (0.21 g, 1.495 mmol) in mixed solvents of DME and $H_2O$ (5.0 mL, v/v=4/1) was stirred at 90° C. under $N_2$ for 5.0 hrs. After the reaction was completed, the mixture was cooled to rt and diluted with EtOAc (50 mL). The resulting mixture was washed with water (20 mL×3) and brine, dried over anhydrous $Na_2SO_4$ and concentrated in vacuo. The residue was purified by silica gel column chromatography (DCM/MeOH (v/v)=100/1) to give the title compound as a pale yellow solid (0.24 g, 65%). The compound was characterized by the following spectroscopic data:

MS (ESI, pos.ion) m/z: 616.3 [M+H]$^+$; and $^1$H NMR (400 MHz, $CDCl_3$) δ (ppm): 7.72 (br, 2H), 7.52-7.42 (m, 1H), 7.41-7.38 (s, 2H), 7.31-7.28 (m, 1H), 7.13-7.11 (m, 1H), 5.31-5.28 (m, 1H), 3.25-3.17 (m, 3H), 2.54-2.50 (br, 2H), 2.40-2.33 (m, 2H), 2.23-2.03 (m, 2H), 1.80-1.71 (m, 2H), 1.56 (s, 9H), 0.92-0.84 (m, 1H), 0.67-0.65 (m, 2H).

Step 10) The Preparation of Compound 3-11

To a mixture of compound 2-11 (4.11 g, 11.27 mmol), compound 1-14-2 (4.29 g, 16.9 mmol), Pd(dppf)$Cl_2$.$CH_2Cl_2$ (0.65 g, 0.8 mmol) and KOAc (2.09 g, 21.3 mmol) was added DMF (30 mL) via syringe, and the mixture was stirred at 90° C. under $N_2$ for 3.0 hrs. After cooling to rt, the mixture was diluted with EtOAc (200 mL) and filtered through a celite pad. The filtrate was washed with water (60 mL×3) and brine, dried over anhydrous $Na_2SO_4$ and concentrated in vacuo. The residue was purified by silica gel column chromatography (PE/EtOAc (v/v)=1/2) to give the title compound as a beige solid (3.03 g, 65%). The compound was characterized by the following spectroscopic data:

MS (ESI, pos.ion) m/z: 414.3 [M+H]$^+$; and $^1$H NMR (400 MHz, $CDCl_3$) δ (ppm): 7.69 (s, 1H), 7.45-7.43 (m, 1H), 7.32-7.30 (m, 1H), 5.12-5.10 (m, 1H), 3.45-3.43 (m, 2H), 2.95-2.94 (m, 1H), 2.25-2.22 (m, 2H), 2.01-1.91 (m, 1H), 1.49 (s, 9H), 1.35 (s, 12H).

Step 11) The Preparation of Compound 3-12

To a mixture of compound 3-10 (0.15 g, 0.24 mmol), compound 3-11 (0.1 g, 0.24 mmol), Pd(PPh$_3$)$_4$ (28 mg, 0.0243 mmol) and $K_2CO_3$ (84.12 mg, 0.61 mmol) were added DME (4 mL) and pure water (1 mL) via syringe, and the mixture was stirred at 90° C. under $N_2$ for 5.0 hrs. After the reaction was completed, the mixture was cooled to rt and diluted with EtOAc (50 mL). The resulting mixture was washed with water (20 mL×3) and brine, dried over anhydrous $Na_2SO_4$ and concentrated in vacuo. The residue was purified by silica gel column chromatography (DCM/EtOH (v/v)=80/1) to give the title compound as a pale yellow solid (0.11 g, 60%). The compound was characterized by the following spectroscopic data:

MS (ESI, pos.ion) m/z: 753.3 [M+H]$^+$; and $^1$H NMR (400 MHz, $CDCl_3$) δ (ppm): 7.68-7.65 (m, 2H), 7.55-7.50 (m, 2H), 7.47-7.43 (m, 4H), 7.32 (s, 1H), 7.23 (s, 1H), 5.30-5.27 (m, 1H), 5.18-5.17 (m, 1H), 3.56 (br, 1H), 3.47-3.46 (br, 1H), 3.23-3.21 (br, 1H), 3.08-3.06 (br, 1H), 2.93-2.89 (br, 2H), 2.23-2.19 (m, 2H), 2.21-1.93 (m, 4H), 1.83-1.62 (m, 5H), 1.51 (s, 18H), 0.80-0.85 (m, 1H), 0.63-0.61 (m, 2H).

Step 12) The Preparation of Compound 3-13 To a solution of compound 3-12 (0.19 g, 0.245 mmol) in EtOAc (4.0 mL) was added a solution of HCl in
EtOAc (3.0 mL, 4 M) dropwise. At the end of the addition, the mixture was stirred at rt for 8.0 hrs. After the reaction was completed, the mixture was concentrated in vacuo. The residue was purified by beating in EtOAc (5.0 mL) and filtered to give the title compound as a pale yellow solid (0.11 g, 64.34%). The compound was characterized by the following spectroscopic data:

MS (ESI, pos.ion) m/z: 553.3 [M+H]$^+$.

Step 13) The Preparation of Compound 3-14

To a mixture of compound 3-13 (0.11 g, 0.157 mmol), compound 1-24-2 (57.95 mg, 0.33 mmol), EDCI (63.42 mg, 0.33 mmol) and HOAT (32.16 mg, 0.236 mmol) in DCM (5 mL) was added DIPEA (0.22 mL, 1.26 mmol) dropwise at 0° C. At the end of the addition, the mixture was stirred at rt for 3.0 hrs. After the reaction was completed, the mixture was diluted with DCM (50 mL). The organic layer was washed with saturated NH$_4$Cl aqueous solution and brine, dried over anhydrous Na$_2$SO$_4$ and concentrated in vacuo. The residue was purified by silica gel column chromatography (DCM/MeOH (v/v)=50/1) to give the title compound as pale yellow powder (0.11 g, 78%). The compound was characterized by the following spectroscopic data:

MS (ESI, pos.ion) m/z: 434.3 [M+2H]$^{2+}$; and $^1$H NMR (400 MHz, CDCl$_3$) δ (ppm): 7.73-7.69 (m, 3H), 7.52-7.49 (m, 1H), 7.44-7.42 (d, 1H, J=8.0 Hz), 7.31 (s, 2H), 7.20 (s, 1H), 5.60-5.56 (m, 2H), 5.53-5.50 (m, 1H), 5.44-5.43 (m, 1H), 3.71 (s, 6H), 3.09-3.07 (m, 1H), 2.93-2.89 (m, 1H), 2.54-2.53 (m, 1H), 2.37-2.28 (m, 2H), 2.25-2.16 (m, 2H), 2.14-2.04 (m, 4H), 1.92-1.88 (m, 2H), 1.72-1.65 (m, 6H), 1.23 (s, 12H), 0.85-0.80 (m, 1H), 0.63-0.61 (m, 2H).

Example 4

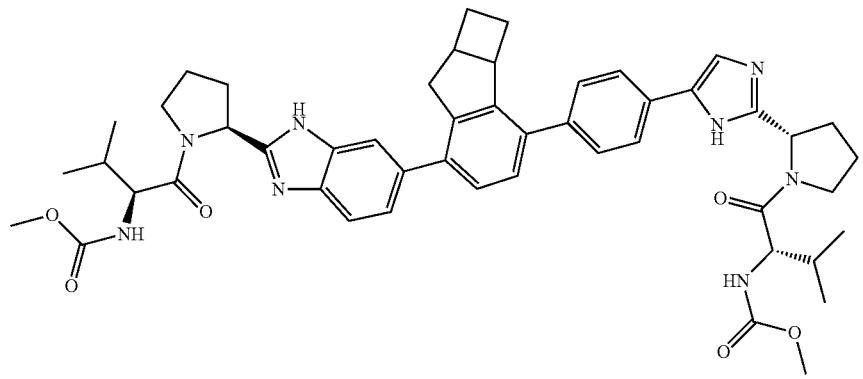 [SMILES: COC(=O)N[C@H](C(=O)N1CCC[C@H]1c1ncc(-c2ccc(-c3ccc(-c4ccc5nc([C@@H]6CCCN6C(=O)[C@@H](NC(=O)OC)C(C)C)[nH]c5c4)c4c3C3CCC3C4)cc2)[nH]1)C(C)C]

Synthetic Route:

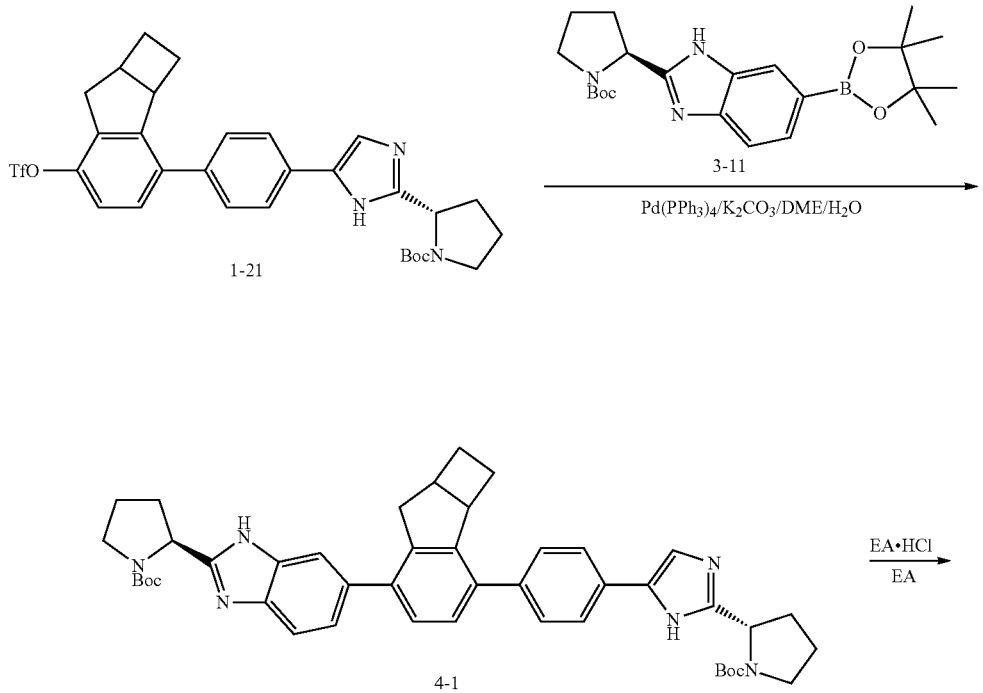

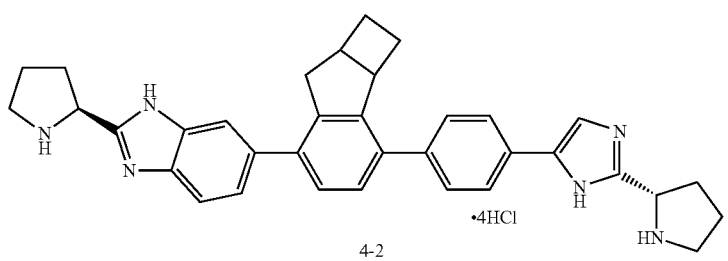

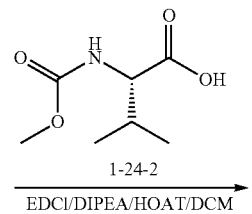

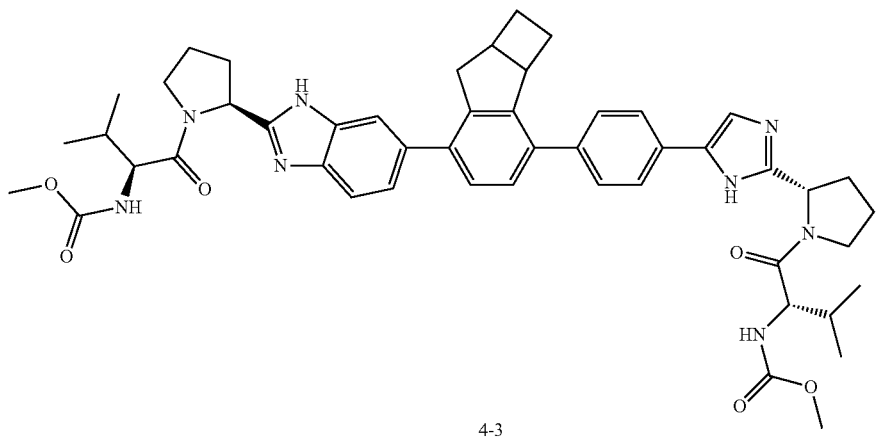

Step 1) The Preparation of Compound 4-1

To a mixture of compound 1-21 (0.42 g, 0.69 mmol), compound 3-11 (0.39 g, 0.69 mmol), Pd(PPh$_3$)$_4$ (80 mg, 0.069 mmol) and K$_2$CO$_3$ (0.24 g, 1.72 mmol) were added DME (3 mL) and pure water (0.6 mL) via syringe, and the mixture was stirred at 90° C. under N$_2$ for 4.0 hrs. After the reaction was completed, the mixture was cooled to rt and diluted with EtOAc (50 mL). The resulting mixture was washed with water (20 mL×3) and brine, dried over anhydrous Na$_2$SO$_4$ and concentrated in vacuo. The residue was purified by silica gel column chromatography (PE/EtOAc (v/v)=1/4) to give the title compound as a pale yellow solid (0.48 g, 94%). The compound was characterized by the following spectroscopic data:

MS (ESI, pos.ion) m/z: 741.3 [M+H]$^+$; and $^1$H NMR (400 MHz, CDCl$_3$) δ (ppm): 7.85, 7.83 (d, d, 1H), 7.62, 7.60 (s, s, 1H), 7.59 (s, 1H), 7.58-7.51 (m, 6H), 7.44, 7.42 (t, t, 1H), 5.04-4.99 (m, 1H), 4.97-4.93 (m, 1H), 3.82-3.76 (m, 1H), 3.75-3.67 (m, 1H), 3.64-3.57 (m, 2H), 3.31-3.23 (m, 1H), 3.13-3.03 (m, 1H), 2.68-2.54 (m, 3H), 2.47-2.36 (m, 2H), 2.29-1.94 (m, 8H), 1.62-1.56 (m, 1H), 1.53 (s, 9H), 1.41 (s, 9H).

Step 2) The Preparation of Compound 4-2

To a solution of compound 4-1 (0.47 g, 0.64 mmol) in EtOAc (5.0 mL) was added a solution of HCl in EtOAc (5.0 mL, 4 M) dropwise. At the end of the addition, the mixture was stirred at rt for 8.0 hrs. After the reaction was completed, the mixture was concentrated in vacuo. The residue was purified by beating in EtOAc (15 mL) and filtered to give the title compound as a pale yellow solid (0.35 g, 80%). The compound was characterized by the following spectroscopic data:

MS (ESI, pos.ion) m/z: 541.3 [M+H]$^+$.

Step 3) The Preparation of Compound 4-3 To a mixture of compound 4-2 (0.35 g, 0.51 mmol), compound 1-24-2 (0.19 g, 1.07 mmol), EDCI (0.2 g, 1.07 mmol) and HOAT (0.14 g, 1.01 mmol) in DCM (5 mL) was added DIPEA (0.71 mL, 4.06 mmol) dropwise at 0° C. At the end of the addition, the mixture was stirred at rt for 3.0 hrs. After the reaction was completed, the mixture was diluted with DCM (50 mL). The organic layer was washed with saturated NH$_4$Cl aqueous solution and brine, dried over anhydrous Na$_2$SO$_4$ and concentrated in vacuo. The residue was purified by silica gel column chromatography (DCM/MeOH (v/v)=100/1) to give the title compound as pale yellow powder (0.27 g, 62%). The compound was characterized by the following spectroscopic data:

MS (ESI, pos.ion) m/z: 855.5 [M+H]$^+$; and $^1$H NMR (400 MHz, CDCl$_3$) δ (ppm): 7.85, 7.83 (d, d, 1H), 7.62, 7.60 (s, s, 1H), 7.59 (s, 1H), 7.58-7.51 (m, 6H), 7.44, 7.42 (t, t, 1H), 5.56, 5.55 (d, d, 1H), 5.46-5.44 (d, d, 1H), 5.25-5.19 (m, 2H), 4.40-4.30 (m, 2H), 3.85-3.78 (m, 2H), 3.75-3.68 (m, 2H), 3.66 (s, 6H), 3.65-3.60 (m, 1H), 3.13-3.03 (m, 1H), 2.68-2.54 (m, 2H), 2.37-1.88 (m, 13H), 1.62-1.52 (m, 1H), 1.02-0.89 (m, 12H).

Example 5
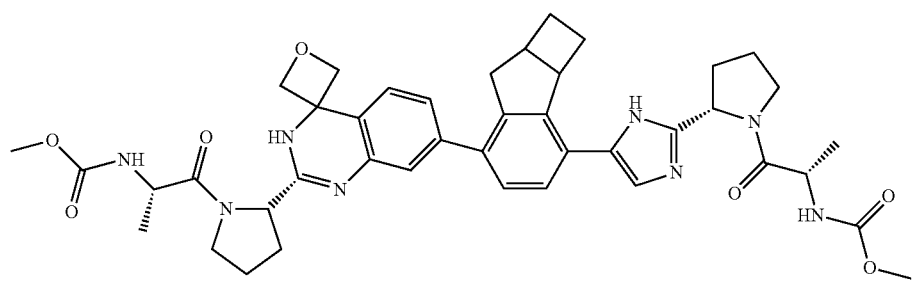
Synthetic Route:
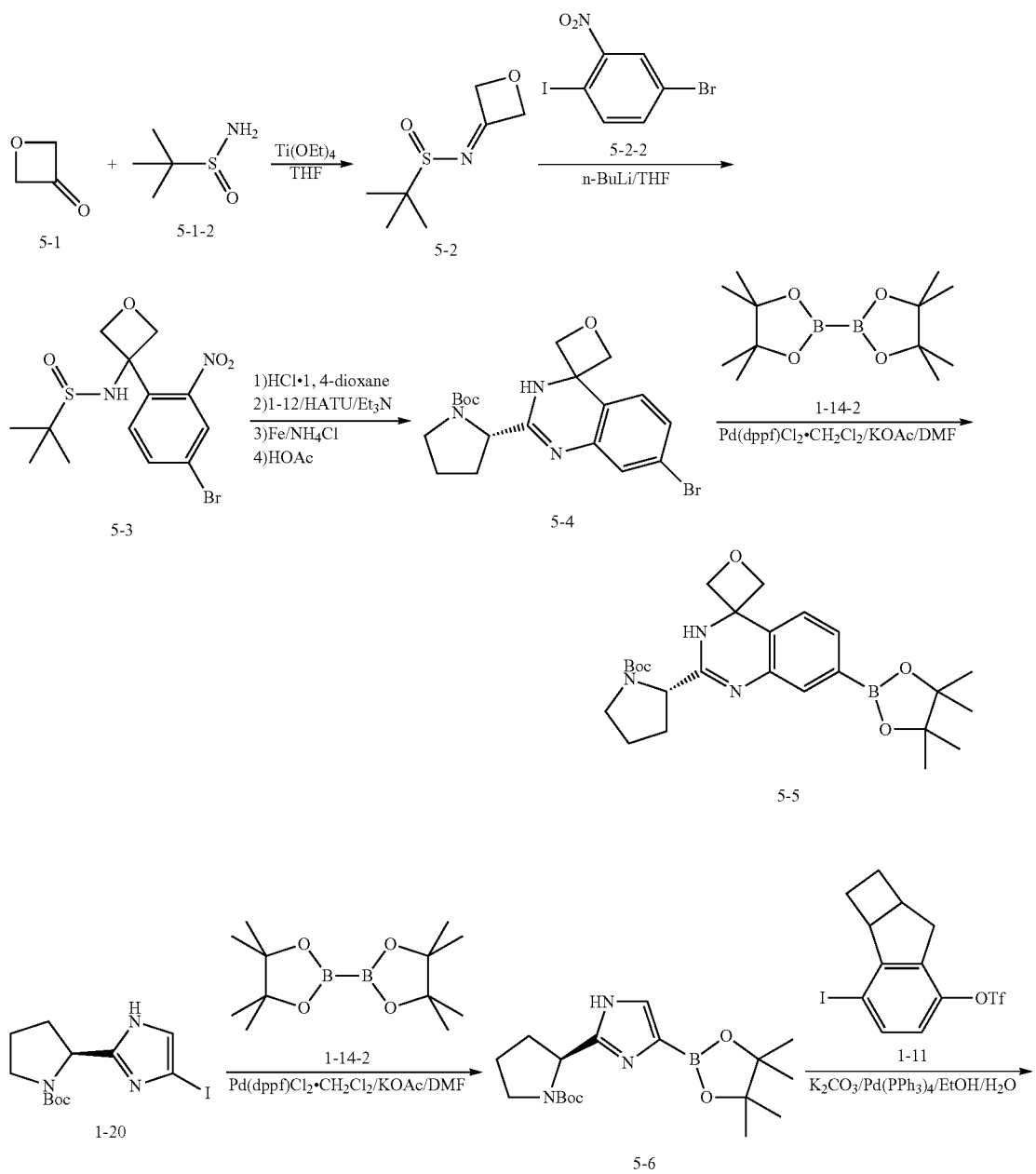

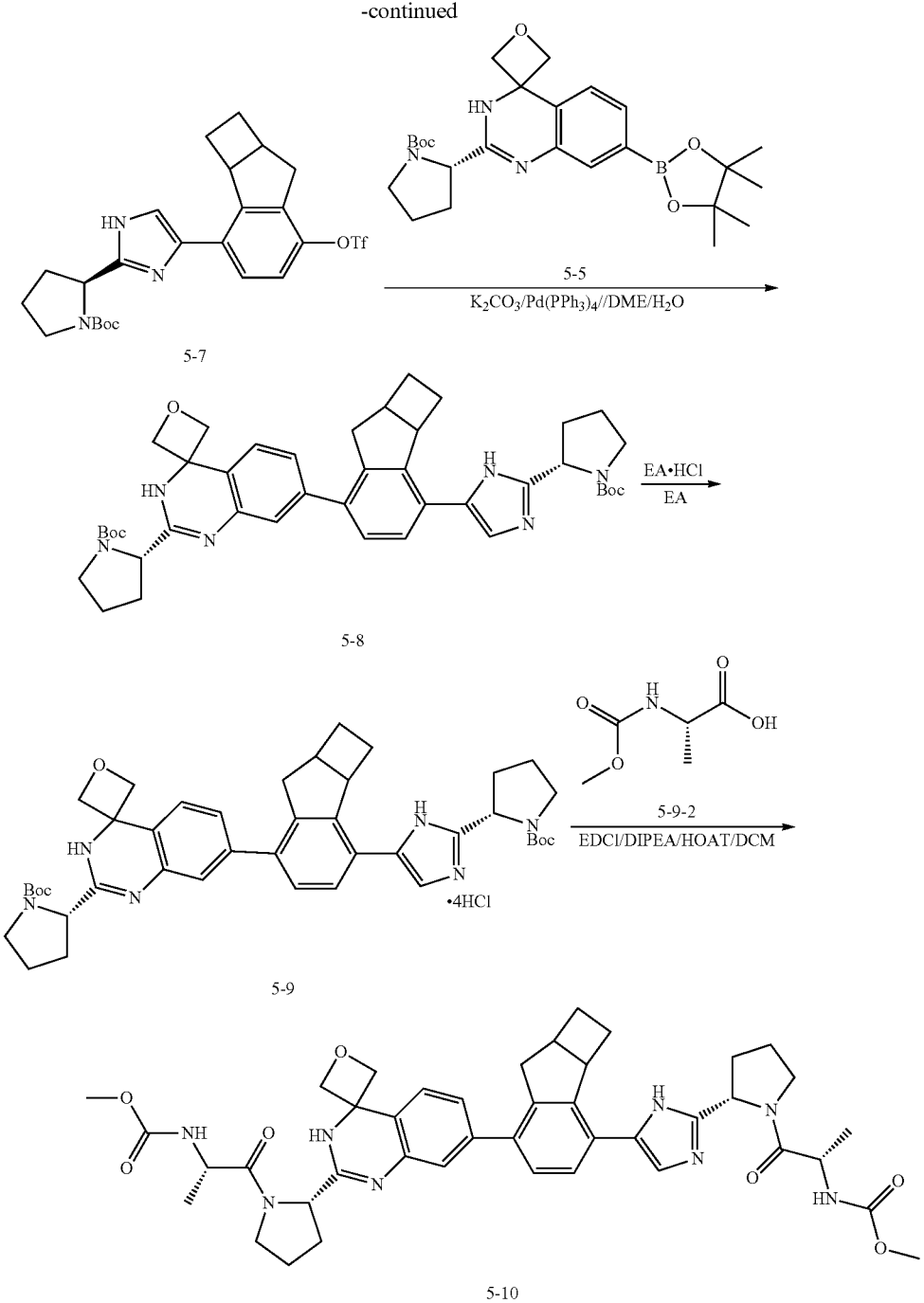

Step 1) The Preparation of Compound 5-2

To a solution of compound 5-1 (4.97 g, 69 mmol) in THF (50 mL) was added compound 5-1-2 (8.35 g, 69 mmol) and Ti(OEt)$_4$ (20 mL) dropwise. At the end of the addition, the mixture was stirred at 50° C. for 5.0 hrs.

After the reaction was completed, the mixture was cooled to rt and quenched with water (200 mL). The resulting mixture was filtered and the filtrate was extracted with DCM (50 mL×3). The combined organic layers were washed with brine, dried over anhydrous Na$_2$SO$_4$ and concentrated in vacuo. The residue was purified by a silica gel column chromatography (DCM) to give the title compound as a solid (5.5 g, 46%). The compound was characterized by the following spectroscopic data:

$^1$H NMR (400 MHz, CDCl$_3$) δ (ppm): 5.39 (s, 4H), 1.31 (s, 9H).

Step 2) The Preparation of Compound 5-3

To a solution of compound 5-2-2 (3.0 g, 9.18 mmol) in THF (20 mL) was added n-BuLi (4.4 mL, 2.5 M) dropwise at −78° C. After stirring at −78° C. for 15 mins, compound 5-2 (1.92 g, 11 mmol) was added to the mixture. At the end of the addition, the reaction was stirred at −78° C. for 30 mins and stirred at rt for another 5.0 hrs. After the reaction was completed, the mixture was poured slowly into icewater (50 mL) and the organic phase separated. The aqueous layer was extracted with DCM (20 mL×3). The combined organic layers were washed with brine, dried over anhydrous $Na_2SO_4$ and concentrated in vacuo. The residue was purified by a silica gel column chromatography (PE/EtOAc (v/v)=3/1) to give the title compound (1.3 g, 38%). The compound was characterized by the following spectroscopic data:

MS (ESI, pos.ion) m/z: 378.7 [M+H]$^+$; and $^1$H NMR (400 MHz, CDCl$_3$) δ (ppm): 8.14-8.13 (m, 1H), 7.69, 7.67 (d, d, 1H), 7.43, 7.41 (d, d, 1H), 4.45 (brs, 1H), 4.36, 4.35 (brs, brs, 2H), 4.15, 4.13 (brs, brs, 2H), 1.21 (s, 9H).

Step 3) The Preparation of Compound 5-4

To a solution of compound 5-3 (1.3 g, 3.45 mmol) in MeOH (10 mL) was added a solution of HCl in 1,4-dioxane (10 mL, 4 M) dropwise. After stirring at rt for 30 mins, the mixture was concentrated in vacuo. The residue was dissolved in DCM (10 mL), and compound 1-24-2 (0.84 g, 3.94 mmol), HATU (1.49 g, 3.94 mmol), triethylamine (0.66 g, 6.56 mmol) were added to the solution in turn. At the end of addition, the mixture was stirred at rt for 1.0 hr. After the reaction was completed, the mixture was quenched with water (20 mL) and the organic phase separated. The aqueous layer was extracted with DCM (20 mL×2). The combined organic layers were washed with brine, dried over anhydrous $Na_2SO_4$ and concentrated in vacuo. The residue was purified by silica gel column chromatography (PE/EtOAc (v/v)=2/1) to give the intermediate compound (a) (1.27 g). To a solution of compound (a) (1.0 g, 2.1 mmol) in mixed solvent MeOH and water (20 mL, v/v=1/1) were added Fe (0.35 g, 6.3 mmol) and NH$_4$Cl (0.55 g, 10.5 mmol) in turn. At the end of the addition, the mixture was refluxed for 3.0 hrs. After the reaction was cooled to rt, the mixture was concentrated in vacuo and 10 mL of water was added. The aqueous layer was extracted with DCM (10 mL×2). The combined organic layers were washed with brine, dried over anhydrous $Na_2SO_4$ and concentrated in vacuo. The residue was dissolved in acetic acid glacial (20 mL) and stirred at 80° C. for 30 mins. After the reaction was completed, the mixture was concentrated in vacuo. The residue was purified by silica gel column chromatography (PE/EtOAc (v/v)=1/1) to give the title compound (0.95 g, 66%). The compound was characterized by the following spectroscopic data:

MS (ESI, pos.ion) m/z: 422 [M+H]$^+$; and $^1$H NMR (400 MHz, CDCl$_3$) δ (ppm): 7.40, 7.37 (d, d, 1H), 7.19 (q, 1H), 6.91, 6.88 (d, d, 1H), 5.14 (brs, 1H), 4.82-4.78 (m, 1H), 4.45-4.39 (m, 2H), 4.23-4.18 (m, 2H), 3.62-3.55 (m, 1H), 3.44-3.36 (m, 1H), 2.24-2.16 (m, 1H), 2.11-2.01 (m, 1H), 2.00-1.91 (m, 1H), 1.89-1.79 (m, 1H), 1.43 (s, 9H).

Step 4) The Preparation of Compound 5-5

To a mixture of compound 5-4 (2.11 g, 5.0 mmol), compound 1-14-2 (1.52 g, 6.0 mmol), Pd(dppf)Cl$_2$.CH$_2$Cl$_2$ (0.41 g, 0.5 mmol) and KOAc (1.23 g, 12.5 mmol) was added DMF (10.0 mL) via syringe under N$_2$, and the mixture was stirred at 90° C. for 3.0 hrs. After the reaction was completed, the mixture was diluted with EtOAc (150 mL). The resulting mixture was filtered through a celite pad. The filtrate was washed with water (60 mL×3) and brine, dried over anhydrous $Na_2SO_4$ and concentrated in vacuo. The residue was purified by silica gel column chromatography (PE/EtOAc (v/v)=1/2) to give the title compound (1.88 g, 80%). The compound was characterized by the following spectroscopic data:

MS (ESI, pos.ion) m/z: 470.5 [M+H]$^+$; and $^1$H NMR (400 MHz, CDCl$_3$) δ (ppm): 7.97 (q, 1H), 7.73, 7.71 (d, d, 1H), 7.36-7.34 (d, d, 1H), 5.14 (brs, 1H), 4.83-4.79 (m, 1H), 4.44-4.39 (m, 2H), 4.23-4.17 (m, 2H), 3.55-3.48 (m, 1H), 3.43-3.36 (m, 1H), 2.46-2.39 (m, 1H), 2.09-2.00 (m, 1H), 1.96-1.88 (m, 1H), 1.86-1.76 (m, 1H), 1.42 (s, 9H), 1.25-1.24 (m, 6H), 1.22-1.21 (m, 6H).

Step 5) The Preparation of Compound 5-6

A mixture of compound 1-20 (0.36 g, 1.0 mmol), compound 1-14-2 (0.30 g, 1.2 mmol), Pd(dppf)Cl$_2$.CH$_2$Cl$_2$ (40.8 mg, 0.05 mmol) and KOAc (0.25 g, 2.5 mmol) in DMF (5.0 mL) was stirred at 90° C. under N$_2$ for 6.0 hrs. After the reaction was completed, the mixture was cooled to rt, diluted with EtOAc (50 mL) and filtered through a celite pad. The filtrate was washed with water (30 mL×3) and brine, dried over anhydrous $Na_2SO_4$ and concentrated in vacuo. The residue was purified by silica gel column chromatography (PE/EtOAc (v/v)=1/2) to give the title compound (0.31 g, 85%). The compound was characterized by the following spectroscopic data:

MS (ESI, pos.ion) m/z: 364.5 [M+H]$^+$; and $^1$H NMR (400 MHz, CDCl$_3$) δ (ppm): 7.50 (s, 1H), 4.93-4.88 (m, 1H), 3.59-3.53 (m, 1H), 3.28-3.21 (m, 1H), 2.38-2.30 (m, 1H), 2.27-2.12 (m, 2H), 2.08-1.98 (m, 1H), 1.41 (s, 9H), 1.40-1.39 (m, 6H), 1.37-1.36 (m, 6H).

Step 6) The Preparation of Compound 5-7

To a mixture of compound 5-6 (1.82 g, 5.0 mmol), compound 1-11 (2.09 g, 5.0 mmol), Pd(PPh$_3$)$_4$ (0.29 g, 0.25 mmol) and K$_2$CO$_3$ (1.72 g, 12.5 mmol) were added EtOH (20 mL) and H$_2$O (4.0 mL) via syringe, and the mixture was stirred at 90° C. under N$_2$ for 6.0 hrs. After the reaction was completed, the EtOH solvent was removed, and the residue was dissolved in EtOAc (100 mL). The resulting mixture was washed with water (50 mL×3) and brine, dried over anhydrous $Na_2SO_4$ and concentrated in vacuo. The residue was purified by silica gel column chromatography (DCM/MeOH (v/v)=100/1) to give the title compound as a pale yellow solid (1.58 g, 60%). The compound was characterized by the following spectroscopic data:

$^1$H NMR (400 MHz, CDCl$_3$) δ (ppm): 7.60 (s, 1H), 7.52-7.51, 7.50-7.49 (m, m, 1H), 7.23, 7.21 (s, s, 1H), 4.91-4.85 (m, 1H), 4.18-4.11 (m, 1H), 3.64-3.58 (m, 1H), 3.45-3.35 (m, 1H), 3.31-3.23 (m, 1H), 3.09-2.97 (m, 2H), 2.47-2.38 (m, 1H), 2.30-1.97 (m, 5H), 1.63-1.53 (m, 8H), 1.41 (s, 9H).

Step 7) The Preparation of Compound 5-8

To a mixture of compound 5-7 (0.53 g, 1.0 mmol), compound 5-5 (0.49 g, 1.0 mmol), Pd(PPh$_3$)$_4$ (57.8 mg, 0.05 mmol) and K$_2$CO$_3$ (0.35 g, 2.5 mmol) were added DME (12 mL) and H$_2$O (3 mL) via syringe, and the mixture was stirred at 90° C. under N$_2$ for 3.0 hrs. After the reaction was completed, the mixture was cooled to rt and diluted with EtOAc (50 mL). The resulting mixture was washed with water (20 mL×3) and brine, dried over anhydrous $Na_2SO_4$ and concentrated in vacuo. The residue was purified by silica gel column chromatography (DCM/MeOH (v/v)=80/1) to give the title compound as a white solid (0.40 g, 55%). The compound was characterized by the following spectroscopic data:

MS (ESI, pos.ion) m/z: 721.5 [M+H]$^+$; and $^1$H NMR (400 MHz, CDCl$_3$) δ (ppm): 8.23 (s, 1H), 7.69 (brs, 2H), 7.59, 7.57 (d, d, 1H), 7.47, 7.44 (s, s, 1H), 7.26, 7.24 (d, d, 1H), 7.19, 7.17 (t, t, 1H), 7.15 (q, 1H), 5.06-5.01 (m, 1H), 4.83-4.79 (m, 1H), 4.36-4.25 (m, 3H), 4.15-4.09 (m, 2H), 3.64-3.58 (m, 1H), 3.55-3.48 (m, 1H), 3.43-3.36

(m, 1H), 3.31-3.24 (m, 1H), 3.22-3.13 (m, 1H), 2.81-2.73 (m, 1H), 2.58-1.76 (m, 12H), 1.66-1.56 (m, 1H), 1.53 (s, 9H), 1.42 (s, 9H).

Step 8) The Preparation of Compound 5-9

To a solution of compound 5-8 (0.46 g, 0.64 mmol) in EtOAc (5.0 mL) was added a solution of HCl in EtOAc (5.0 mL, 4 M) dropwise. At the end of the addition, the mixture was stirred at rt for 8.0 hrs. After the reaction was completed, the mixture was concentrated in vacuo. The residue was purified by beating in EtOAc (10 mL) and filtered to give the title compound as a white solid (0.36 g, 85%). The compound was characterized by the following spectroscopic data:

MS (ESI, pos.ion) m/z: 521.5 [M+H]$^+$.

Step 9) The Preparation of Compound 5-10

To a mixture of compound 5-9 (0.36 g, 0.54 mmol), compound 5-9-2 (0.17 g, 1.134 mmol), EDCI (0.22 g, 1.134 mmol) and HOAT (0.15 g, 1.08 mmol) in DCM (5 mL) was added DIPEA (0.72 mL, 4.32 mmol) dropwise at 0° C. At the end of the addition, the mixture was stirred at rt for 3.0 hrs. After the reaction was completed, the mixture was diluted with DCM (40 mL). The organic layer was washed with saturated NH$_4$Cl aqueous solution and brine, dried over anhydrous Na$_2$SO$_4$ and concentrated in vacuo. The residue was purified by silica gel column chromatography (DCM/MeOH (v/v)=50/1) to give the title compound as a white solid (0.29 g, 68%). The compound was characterized by the following spectroscopic data:

MS (ESI, pos.ion) m/z: 779.5 [M+H]$^+$; and $^1$H NMR (400 MHz, CDCl$_3$) δ (ppm): 8.14 (s, 1H), 7.69 (brs, 2H), 7.50, 7.48 (d, d, 1H), 7.47, 7.44 (s, s, 1H), 7.26, 7.24 (d, d, 1H), 7.19, 7.17 (t, t, 1H), 7.15 (q, 1H), 5.44, 5.42 (m, m, 2H), 5.15-5.11 (m, 1H), 4.81-4.76 (m, 1H), 4.64-4.48 (m, 2H), 4.36-4.25 (m, 3H), 4.15-4.09 (m, 2H), 3.88-3.81 (m, 1H), 3.72-3.66 (m, 1H), 3.64 (s, 6H), 3.63-3.61 (m, 1H), 3.31-3.23 (m, 1H), 3.21-3.13 (m, 1H), 2.81-2.73 (m, 1H), 2.58-2.48 (m, 1H), 2.40-1.73 (m, 11H), 1.66-1.56 (m, 1H), 1.36, 1.34 (d, d, 3H), 1.31, 1.30 (d, d, 3H).

Example 6

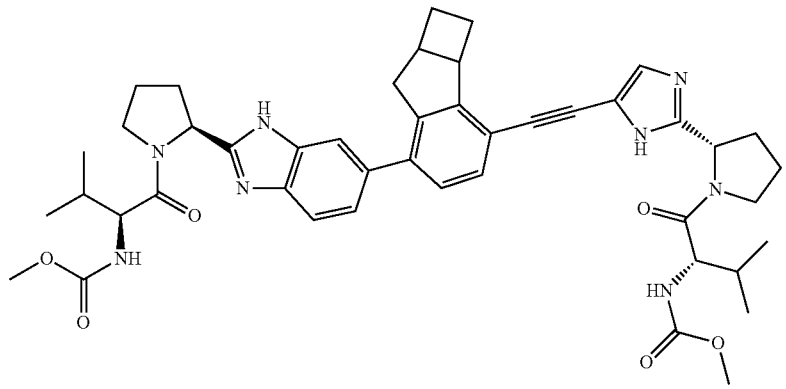 [SMILES: COC(=O)N[C@H](C(=O)N1CCC[C@H]1c1ncc(C#Cc2ccc(-c3ccc4nc([C@@H]5CCCN5C(=O)[C@@H](NC(=O)OC)C(C)C)[nH]c4c3)c3c2C2CCC2C3)[nH]1)C(C)C]

Synthetic Route:

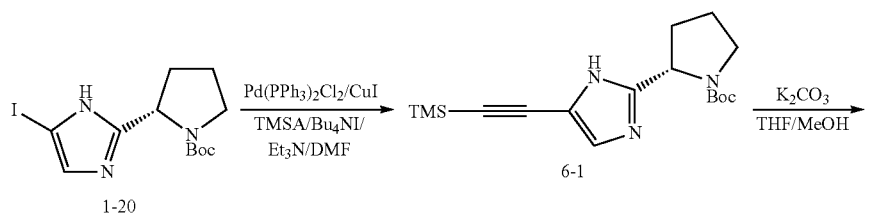

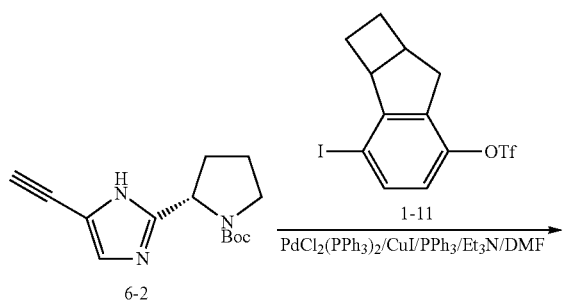

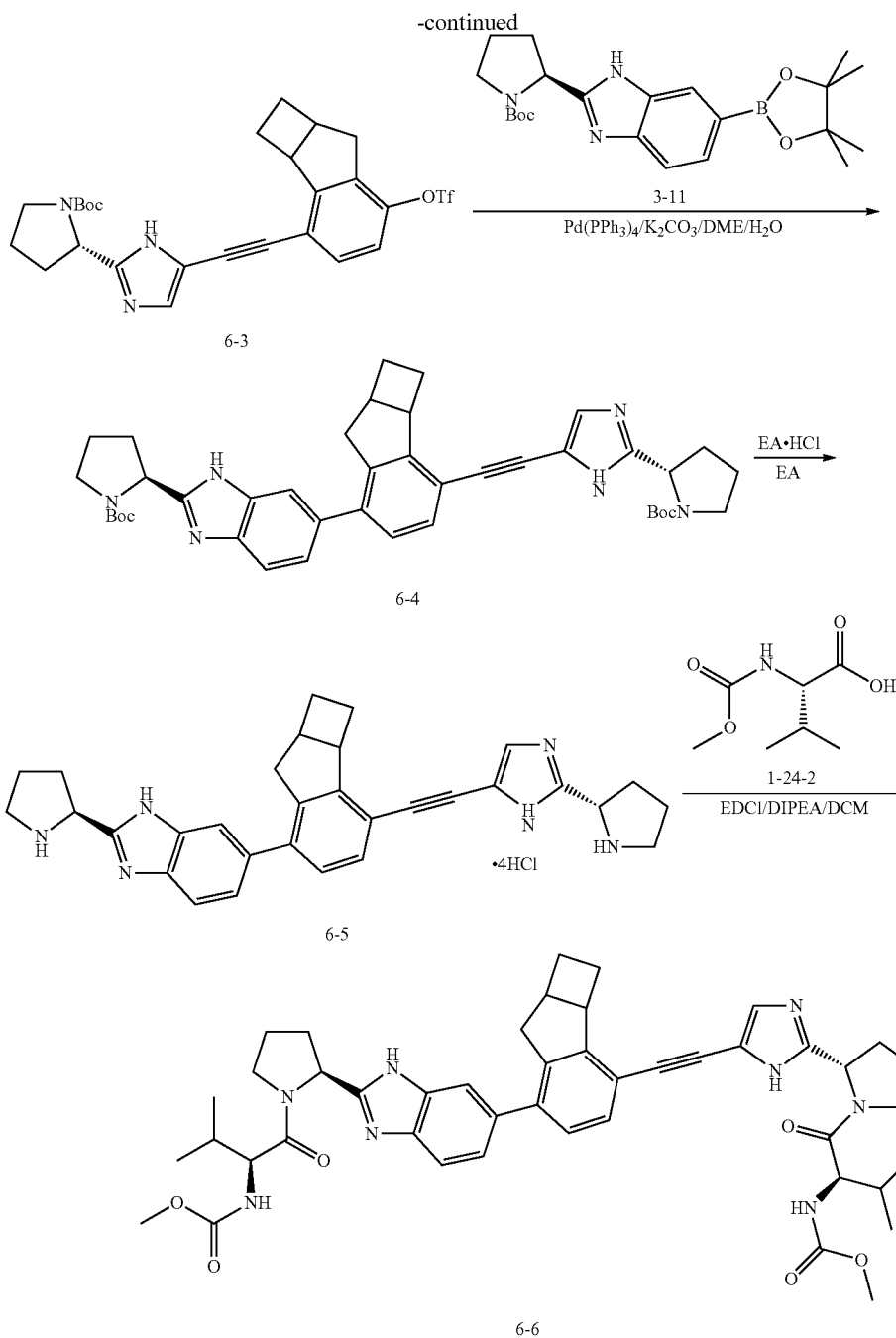

Step 1) The Preparation of Compound 6-1

To a mixture of compound 1-20 (0.5 g, 1.38 mmol), Pd(PPh$_3$)$_2$Cl$_2$ (98 mg, 0.14 mmol), tetrabutylammonium iodide (1.53 g, 4.14 mmol) and CuI (78 mg, 0.41 mmol) in DMF (8.0 mL) was added Et$_3$N (2.0 mL) dropwise under N$_2$. After the mixture was stirred at rt for 10 mins, TMSA (0.98 mL, 6.89 mmol) was added. At the end of the addition, the reaction mixture was stirred at rt for 10 mins and at 70° C. overnight. After the reaction was completed, the mixture was filtered through a celite pad. To the filtrate was added water (30 mL) and the mixture was extracted with EtOAc (20 mL×3). The combined organic layers were washed with brine, dried over anhydrous Na$_2$SO$_4$ and concentrated in vacuo. The residue was purified by silica gel column chromatography (PE/EtOAc (v/v)=5/1) to give the title compound (0.29 g, 63%). The compound was characterized by the following spectroscopic data:

MS (ESI, pos.ion) m/z: 334.2 [M+H]$^+$; and $^1$H NMR (400 MHz, CDCl$_3$) δ (ppm): 7.24 (s, 1H), 4.95-4.90 (m, 1H), 3.72-3.66 (m, 1H), 3.38-3.30 (m, 1H), 2.56-2.48 (m, 1H), 2.40-2.30 (m, 1H), 2.38-2.19 (m, 1H), 2.07-1.97 (m, 1H), 1.41 (s, 9H), 0.32 (s, 9H).

Step 2) The Preparation of Compound 6-2

A mixture of compound 6-1 (0.29 g, 0.87 mmol) and K$_2$CO$_3$ (0.6 g, 4.35 mmol) in mixed solvents of MeOH (2.0 mL) and THF (2.0 mL) was stirred at rt for 6.0 hrs. After the reaction was completed, the mixture was diluted with EtOAc (20 mL) and filtered. The filtrate was concentrated in vacuo, and the residue was purified by silica gel column chromatography (PE/EtOAc (v/v)=2/1) to give the title compound (0.21 g, 91%). The compound was characterized by the following spectroscopic data:

MS (ESI, pos.ion) m/z: 262.2 [M+H]$^+$; and $^1$H NMR (400 MHz, CDCl$_3$) δ (ppm): 7.25 (s, 1H), 4.99-4.94 (m, 1H), 3.72-3.66 (m, 1H), 3.36 (s, 1H), 3.35-3.30 (m, 1H), 2.56-2.48 (m, 1H), 2.40-2.30 (m, 1H), 2.28-2.19 (m, 1H), 2.07-1.97 (m, 1H), 1.41 (s, 9H).

Step 3) The Preparation of Compound 6-3

To a mixture of compound 1-11 (0.16 g, 0.39 mmol), compound 6-2 (0.11 g, 0.43 mmol), CuI (33 mg, 0.172 mmol), Pd (PPh$_3$)$_2$Cl$_2$ (66 mg, 0.057 mmol) and PPh$_3$ (0.23 g, 0.86 mmol) were added anhydrous DMF (10.0 mL) and Et$_3$N (5.0 mL) separately under N$_2$. At the end of the addition, the mixture was stirred at rt for 10 mins and at 90° C. for another 6.0 hrs. After the reaction was completed, the mixture was diluted with EtOAc (50 mL) and filtered through a celite pad. The filtrate was washed with water (20 mL×3) and brine, dried over anhydrous Na$_2$SO$_4$ and concentrated in vacuo. The residue was purified by silica gel column chromatography (PE/EtOAc (v/v)=1/2) to give the title compound (0.12 g, 55%). The compound was characterized by the following spectroscopic data:

$^1$H NMR (400 MHz, CDCl$_3$) δ (ppm): 7.50, 7.48 (t, t, 1H), 7.47 (s, 1H), 7.15, 7.13 (s, s, 1H), 4.96-4.91 (m, 1H), 4.06-3.96 (m, 1H), 3.72-3.66 (m, 1H), 3.38-3.31 (m, 1H), 3.06-2.92 (m, 2H), 2.72-2.47 (m, 3H), 2.41-2.30 (m, 1H), 2.28-1.96 (m, 4H), 1.59-1.49 (m, 1H), 1.41 (s, 9H).

Step 4) The Preparation of Compound 6-4

To a mixture of compound 6-3 (0.28 g, 0.5 mmol), compound 3-11 (0.2 g, 0.5 mmol), Pd(PPh$_3$)$_4$ (57.8 mg, 0.05 mmol) and K$_2$CO$_3$ (0.35 g, 2.5 mmol) were added DME (6 mL) and H$_2$O (1.5 mL) via syringe, and the mixture was stirred at 90° C. under N$_2$ for 3.0 hrs. After the reaction was completed, the mixture was cooled to rt and diluted with EtOAc (50 mL). The resulting mixture was washed with water (20 mL×3) and brine, dried over anhydrous Na$_2$SO$_4$ and concentrated in vacuo. The residue was purified by silica gel column chromatography (DCM/MeOH (v/v)=80/1) to give the title compound as a white solid (0.22 g, 65%). The compound was characterized by the following spectroscopic data:

MS (ESI, pos.ion) m/z: 689.5 [M+H]$^+$; and $^1$H NMR (400 MHz, CDCl$_3$) δ (ppm): 7.86, 7.83 (d, d, 1H), 7.65-7.64 (q, 1H), 7.53, 7.51 (d, d, 1H), 7.48 (s, 1H), 7.28, 7.26 (t, t, 1H), 7.19, 7.17 (s, s, 1H), 5.18-5.14 (m, 1H), 5.04-4.99 (m, 1H), 4.22-4.15 (m, 1H), 3.82-3.76 (m, 1H), 3.72-3.66 (m, 1H), 3.64-3.57 (m, 1H), 3.38-3.31 (m, 1H), 3.06-2.96 (m, 1H), 2.83-2.75 (m, 1H), 2.71-1.93 (m, 12H), 1.60-1.50 (m, 1H), 1.41 (s, 18H).

Step 5) The Preparation of Compound 6-5

To a solution of compound 6-3 (0.34 g, 0.5 mmol) in EtOAc (5.0 mL) was added a solution of HCl in EtOAc (5.0 mL, 4 M) dropwise. At the end of the addition, the mixture was stirred at rt for 8.0 hrs. After the reaction was completed, the mixture was concentrated in vacuo. The residue was purified by beating in EtOAc (10 mL) and filtered to give the title compound as a white solid (0.28 g, 90%). The compound was characterized by the following spectroscopic data:

MS (ESI, pos.ion) m/z: 489.5 [M+H]$^+$.

Step 6) The Preparation of Compound 6-6

To a suspension of compound 6-5 (0.29 g, 0.45 mmol), compound 1-24-2 (0.17 g, 0.945 mmol) and EDCI (0.18 g, 0.945 mmol) in DCM (5.0 mL) was added DIPEA (0.6 mL, 2.54 mmol) dropwise at 0° C. At the end of the addition, the mixture was stirred at rt for 3.0 hrs. After the reaction was completed, the mixture was diluted with DCM (20 mL). The resulting mixture was washed with saturated NH$_4$Cl aqueous solution, dried over anhydrous Na$_2$SO$_4$ and concentrated in vacuo. The residue was purified by silica gel column chromatography (DCM/MeOH (v/v)=60/1) to give the title compound as a white solid (0.24 g, 65%). The compound was characterized by the following spectroscopic data:

MS (ESI, pos.ion) m/z: 803.5 [M+H]$^+$; and $^1$H NMR (400 MHz, CDCl$_3$) δ (ppm): 7.86, 7.83 (d, d, 1H), 7.65-7.64 (q, 1H), 7.53, 7.51 (d, d, 1H), 7.46 (s, 1H), 7.28, 7.26 (t, t, 1H), 7.19, 7.17 (s, s, 1H), 5.56-5.55 (d, d, 1H), 5.51-5.47 (m, 1H), 5.46-5.44 (d, d, 1H), 5.24-5.20 (m, 1H), 4.40-4.30 (m, 2H), 4.22-4.15 (m, 1H), 3.89-3.78 (m, 2H), 3.73-3.68 (m, 1H), 3.66 (s, 6H), 3.65-3.60 (m, 1H), 3.06-2.96 (m, 1H), 2.82-2.75 (m, 1H), 2.71-2.60 (m, 1H), 2.38-1.87 (m, 13H), 1.60-1.50 (m, 1H), 1.02-0.89 (m, 12H).

Example 7

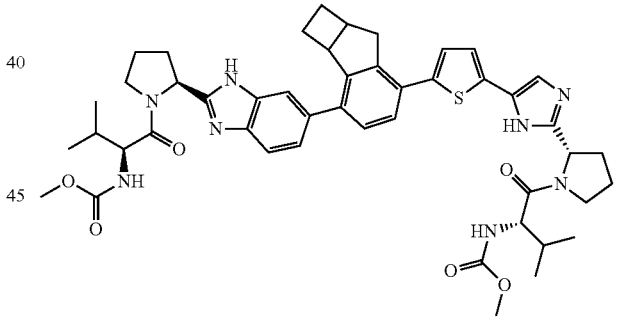

Synthetic Route:

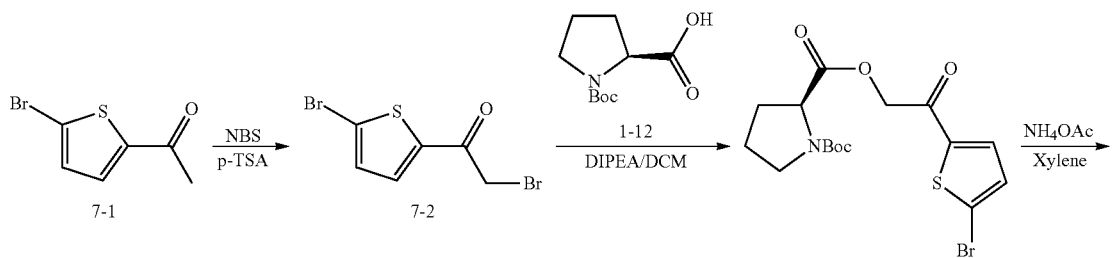

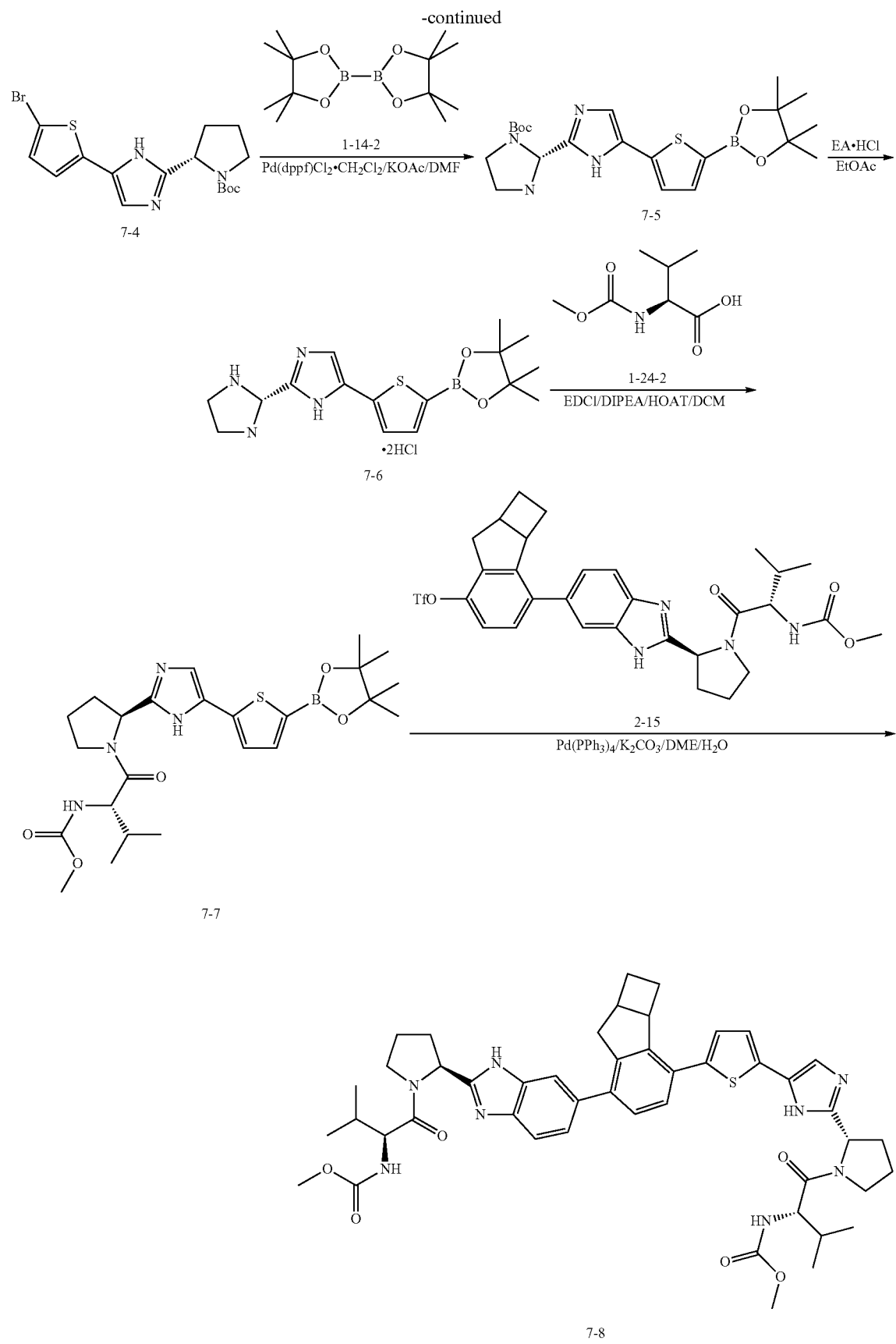

Step 1) The Preparation of Compound 7-2

A mixture of compound 7-1 (5.94 g, 29 mmol), NBS (5.76 g, 32 mmol) and p-TSA (1.0 g, 5.2 mmol) was stirred at 100° C. for 0.5 hr. After the reaction was completed, the mixture was cooled to rt, and DCM (100 mL) and water (50 mL) were added. After the layers were partitioned, the aqueous layer was extracted with DCM (50 mL×3). The combined organic layers were washed with brine, dried over anhydrous $Na_2SO_4$ and concentrated in vacuo. The residue was purified by silica gel column chromatography (PE/DCM/ (v/v)=5/1) to give the title compound as yellow slurry (5.76 g, 70%). The compound was characterized by the following spectroscopic data:

MS (ESI, pos.ion) m/z: 285.1 [M+H]$^+$; and $^1$H NMR (400 MHz, CDCl$_3$) δ (ppm): 7.55 (d, 1H, J=4.0 Hz), 7.14 (d, 1H, J=4.0 Hz), 4.29 (s, 2H).

Step 2) The Preparation of Compound 7-3

To a mixture of compound 7-2 (5.63 g, 19.8 mmol) and compound 1-12 (4.7 g, 21.8 mmol) in DCM (100 mL) was added DIPEA (3.62 mL, 21.9 mmol) dropwise at 0° C. At the end of the addition, the mixture was stirred at rt for 3.0 hrs. After the reaction was completed, the mixture was quenched with water (50 mL). The aqueous layer was extracted with EtOAc (50 mL×3). The combined organic layers were washed with brine, dried over anhydrous $Na_2SO_4$ and concentrated in vacuo. The residue was purified by silica gel column chromatography (PE/EtOAc (v/v)=2/1) to give the title compound as a yellow solid (5.8 g, 70%). The compound was characterized by the following spectroscopic data:

MS (ESI, pos.ion) m/z: 418.3 [M+H]$^+$; and $^1$H NMR (400 MHz, CDCl$_3$) δ (ppm): 7.49 (d, 1H, J=4.0 Hz), 7.13 (t, 1H, J=4.0 Hz), 5.23-5.02 (m, 2H), 4.48-4.37 (m, 1H), 3.60-3.38 (m, 2H), 2.29-2.26 (m, 2H), 2.11-1.92 (m, 2H), 1.44 (s, 9H).

Step 3) The Preparation of Compound 7-4

A mixture of compound 7-3 (7.94 g, 19 mmol) and NH$_4$OAc (22.2 g, 288 mmol) in xylene (100 mL) was stirred at 140° C. for 5.0 hrs. After the reaction was completed, the mixture was cooled to rt and quenched with water (100 mL). The aqueous layer was extracted with EtOAc (100 mL×3). The combined organic layers were washed with brine, dried over anhydrous $Na_2SO_4$ and concentrated in vacuo. The residue was purified by silica gel column chromatography (PE/EtOAc (v/v)=4/1) to give the title compound as a yellow solid (6.96 g, 92%). The compound was characterized by the following spectroscopic data:

MS (ESI, pos.ion) m/z: 399.4 [M+H]$^+$; and $^1$H NMR (400 MHz, CDCl$_3$) δ (ppm): 10.51 (br, 1H), 7.07 (s, 1H), 6.94 (s, 2H), 4.91-4.90 (m, 1H), 3.39 (s, 2H), 2.98 (s, 1H), 2.12 (s, 2H), 1.95 (s, 1H), 1.48 (s, 9H).

Step 4) The Preparation of Compound 7-5

A mixture of compound 7-4 (1.0 g, 2.5 mmol), bis(pinacolato)diboron (0.96 g, 3.8 mmol), Pd(dppf)Cl$_2$.CH$_2$Cl$_2$ (0.11 g, 0.13 mmo) and KOAc (0.74 g, 7.5 mmol) in DMF (12 mL) was stirred at 90° C. under N$_2$ for 4.0 hrs. After the reaction was completed, the mixture was cooled to rt, diluted with EtOAc (60 mL) and filtered through a celite pad. The filtrate was washed with water (30 mL×3) and brine, dried over anhydrous $Na_2SO_4$ and concentrated in vacuo. The residue was purified by silica gel column chromatography (PE/EtOAc (v/v)=3/1) to give the title compound as a white solid (0.89 g, 80%). The compound was characterized by the following spectroscopic data:

$^1$H NMR (400 MHz, CDCl$_3$) δ (ppm): 10.51 (br, 1H), 7.53 (s, 1H), 7.27 (s, 1H), 7.15 (s, 1H), 4.94-4.93 (m, 1H), 3.39 (s, 2H), 2.99 (s, 1H), 2.12-1.94 (m, 4H), 1.49 (s, 9H), 1.34 (s, 12H), 1.24 (m, 8H).

Step 5) The Preparation of Compound 7-6

To a solution of compound 7-5 (0.23 g, 0.51 mmol) in EtOAc (4.0 mL) was added a solution of HCl in EtOAc (3.0 mL, 4 M) dropwise, and the mixture was stirred at rt for 8.0 hrs. After the reaction was completed, the mixture was concentrated in vacuo. The residue was purified by beating in EtOAc (5.0 mL) and filtered to give the title compound as a pale yellow solid (0.17 g, 80%). The compound was characterized by the following spectroscopic data:

MS (ESI, pos.ion) m/z: 346.5 [M+H]$^+$.

Step 6) The Preparation of Compound 7-7

To a mixture of compound 7-6 (0.12 g, 0.29 mmol), compound 1-24-2-2 (0.11 g, 0.65 mmol), EDCI (0.12 g, 0.65 mmol) and HOAT (0.08 g, 0.59 mmol) in DCM (5.0 mL) was added DIPEA (0.6 mL, 3.63 mmol) dropwise at 0° C. At the end of the addition, the mixture was stirred at rt for 3.0 hrs. After the reaction was completed, the mixture was diluted with DCM (20 mL). The resulting mixture was washed with NH$_4$Cl aqueous solution and brine, dried over anhydrous $Na_2SO_4$ and concentrated in vacuo. The residue was purified by silica gel column chromatography (PE/EtOAc (v/v)=2/1) to give the title compound as a white solid (0.12 g, 80%). The compound was characterized by the following spectroscopic data:

MS (ESI, pos.ion) m/z: 503.5 [M+H]$^+$; and $^1$H NMR (400 MHz, CDCl$_3$) δ (ppm): 7.68, 7.67 (s, s, 1H), 7.27 (d, 1H), 7.11 (dd, 1H), 5.56, 5.55 (d, d, 1H), 5.42-5.37 (m, 1H), 4.34-4.30 (m, 1H), 3.85-3.78 (m, 1H), 3.66 (s, 3H), 3.65-3.61 (m, 1H), 2.32-1.92 (m, 5H), 1.33, 1.30 (m, m, 12H), 1.02, 1.00 (m, m, 3H), 0.93, 0.91 (m, m, 3H).

Step 7) The Preparation of Compound 7-8

To a mixture of compound 7-7 (1.71 g, 3.4 mmol), compound 2-15 (2.16 g, 3.4 mmol), Pd(PPh$_3$)$_4$ (0.20 g, 0.17 mmol) and K$_2$CO$_3$ (1.41 g, 10.22 mmol) were added DME (24.0 mL) and H$_2$O (6.0 mL) via syringe, and the mixture was stirred at 90° C. under N$_2$ for 4.0 hrs. After the reaction was completed, the mixture was cooled to rt and diluted with EtOAc (100 mL). The resulting mixture was washed with water (50 mL×3) and brine, dried over anhydrous $Na_2SO_4$ and concentrated in vacuo. The residue was purified by silica gel column chromatography (DCM/MeOH (v/v)=50/1) to give the title compound as a pale yellow solid (1.46 g, 50%). The compound was characterized by the following spectroscopic data:

MS (ESI, pos.ion) m/z: 862.5 [M+H]$^+$; and $^1$H NMR (400 MHz, CDCl$_3$) δ (ppm): 7.64-7.60 (m, 3H), 7.41 (d, 1H), 7.38, 7.36 (t, t, 1H), 7.24, 7.22 (m, 1H), 7.15, 7.13 (d, d, 1H), 6.99, 6.98 (s, s, 1H), 5.56, 5.55 (d, d, 1H), 5.46, 5.44 (d, d, 1H), 5.42-5.37 (m, 1H), 5.24-5.20 (m, 1H), 4.40-4.30 (m, 2H), 3.85-3.78 (m, 2H), 3.74-3.67 (m, 2H), 3.66 (s, 6H), 3.64-3.60 (m, 1H), 3.13-3.02 (m, 1H), 2.77-2.69 (m, 1H), 2.67-2.55 (m, 1H), 2.38-2.04 (m, 11H), 2.03-1.88 (m, 2H), 1.63-1.53 (m, 1H), 1.02-0.89 (m, 12H).

Example 8
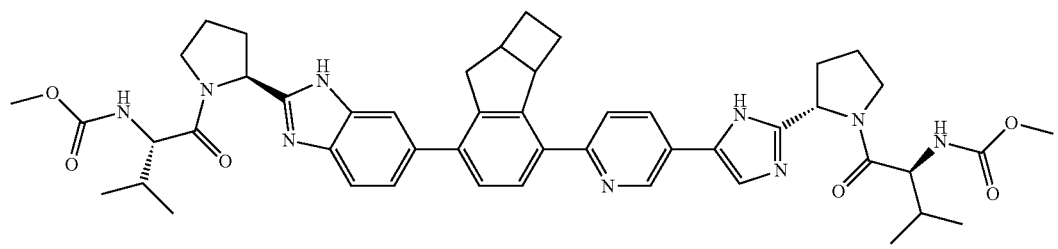
Synthetic Route:
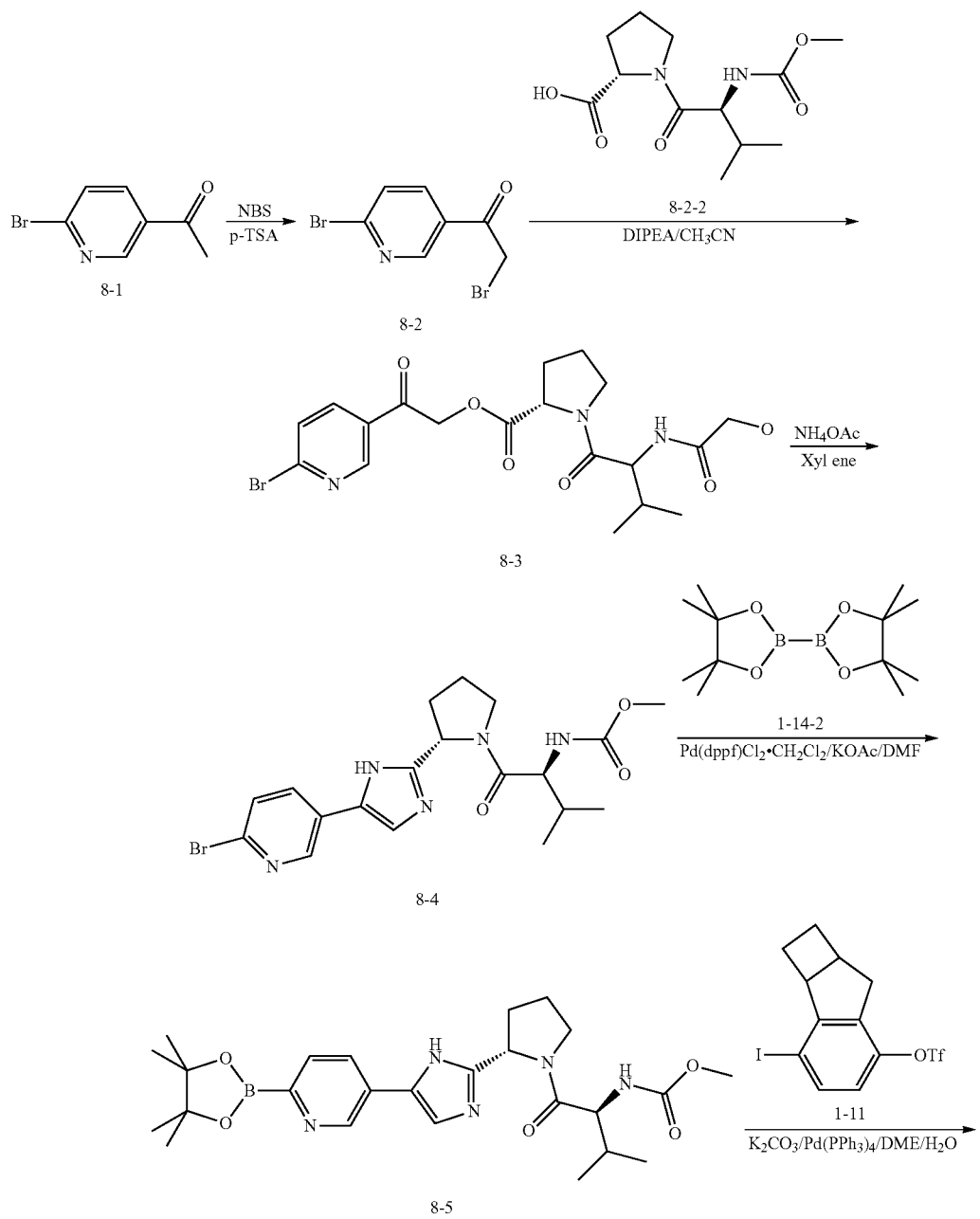

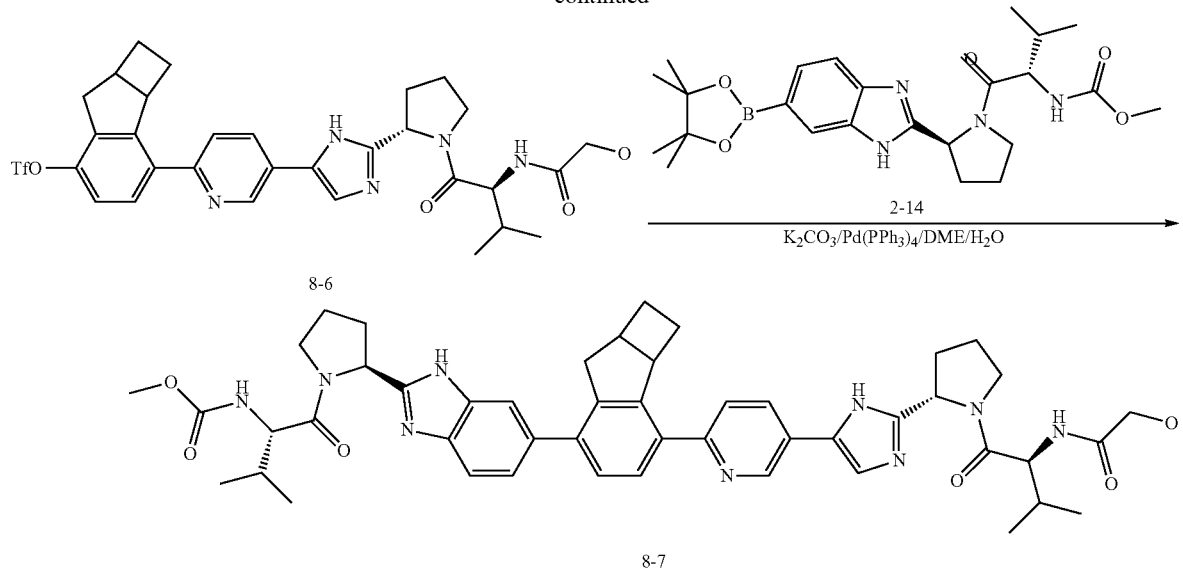

Step 1) The Preparation of Compound 8-2

A mixture of compound 8-1 (25 g, 125.6 mmol), NBS (24.5 g, 138.2 mmol) and p-TSA (3.4 g, 20.9 mmol) was stirred at 100° C. under $N_2$ for 2.0 hrs. After the reaction was completed, the mixture was cooled to rt, and diluted with DCM (200 mL). The resulting mixture was washed with water (50 mL×3) and brine, dried over anhydrous $Na_2SO_4$ and concentrated in vacuo. The residue was purified by silica gel column chromatography (PE/EtOAc (v/v)=5/1) to give the title compound (24.7 g, 71%). The compound was characterized by the following spectroscopic data:

MS (ESI, pos.ion) m/z: 279.9 [M+H]$^+$; and $^1$H NMR (400 MHz, CDCl$_3$) δ (ppm): 8.95 (d, 1H, J=1.12 Hz), 8.14-8.11 (m, 1H), 7.68-7.66 (m, 1H), 4.41 (s, 2H).

Step 2) The Preparation of Compound 8-3

To a solution of compound 8-2 (4.96 g, 17.9 mmol) and compound 8-2-2 (5.36 g, 19.7 mmol) in MeCN (100 mL) was added DIPEA (3.3 mL, 19.7 mmol) dropwise at 0° C. At the end of the addition, the mixture was stirred at rt for 3.0 hrs. After the reaction was completed, the mixture was concentrated in vacuo and to the residue was added water (100 mL). The resulting mixture was extracted with EtOAc (100 mL×3). The combined organic layers were dried over anhydrous $Na_2SO_4$ and concentrated in vacuo. The residue was purified by silica gel column chromatography (PE/EtOAc (v/v)=3/1) to give the title compound (8.06 g, 96%). The compound was characterized by the following spectroscopic data:

MS (ESI, pos.ion) m/z: 470.1 [M+H]$^+$; and $^1$H NMR (400 MHz, CDCl$_3$) δ (ppm): 8.88 (s, 1H), 8.04 (d, 1H, J=3.88 Hz), 7.65 (d, 1H, J=4.16 Hz), 5.61-5.59 (m, 1H), 5.48 (d, 1H, J=8.32 Hz), 5.23 (d, 1H, J=8.3 Hz), 4.67 (t, 1H, J=5.72 Hz), 4.31 (t, 1H, J=7.52 Hz), 3.86-3.84 (m, 1H), 3.73-3.71 (m, 1H), 3.66 (s, 3H), 2.34-2.15 (m, 4H), 1.01 (t, 3H), 0.94-0.93 (m, 3H), 0.88-0.85 (m, 1H).

Step 3) The Preparation of Compound 8-4

A mixture of compound 8-3 (2.0 g, 4.25 mmol) and ammonium acetate (4.9 g, 83 mmol) in xylene (50 mL) was stirred at 130° C. for 5.0 hrs. After the reaction was completed, the mixture was cooled to rt and quenched with water (50 mL). The aqueous layer was extracted with EtOAc (50 mL×3). The combined organic layers were dried over anhydrous $Na_2SO_4$ and concentrated in vacuo. The residue was purified by silica gel column chromatography (PE/EtOAc (v/v)=2/1) to give the title compound (1.39 g, 73%). The compound was characterized by the following spectroscopic data:

MS (ESI, pos.ion) m/z: 450.1 [M+H]$^+$; and $^1$H NMR (400 MHz, CDCl$_3$) δ (ppm): 8.70 (s, 1H), 7.93 (d, 1H, J=6.92 Hz), 7.45 (d, 1H, J=8.28 Hz), 5.41 (d, 1H, J=4.6 Hz), 5.24-5.22 (m, 1H), 4.32 (m, 1H), 3.85-3.83 (m, 1H), 3.67 (s, 3H), 3.63-3.62 (m, 3H), 3.05-3.03 (m, 1H), 2.31-1.93 (m, 4H), 1.04-1.03 (m, 1H), 0.88 (s, 3H), 0.86 (s, 3H).

Step 4) The Preparation of Compound 8-5

A mixture of compound 8-4 (1.13 g, 2.5 mmol), bis(pinacolato)diboron (0.96 g, 3.8 mmol), Pd(dppf)Cl$_2$.CH$_2$Cl$_2$ (0.11 g, 0.13 mmo) and KOAc (0.74 g, 7.5 mmol) in DMF (12 mL) was stirred at 90° C. under $N_2$ for 4.0 hrs. After the reaction was completed, the mixture was cooled to rt, diluted with EtOAc (60 mL) and filtered through a celite pad. The filtrate was washed with water (30 mL×3) and brine, dried over anhydrous $Na_2SO_4$ and concentrated in vacuo. The residue was purified by silica gel column chromatography (PE/EtOAc (v/v)=2/1) to give the title compound as a pale yellow solid (1.06 g, 85%). The compound was characterized by the following spectroscopic data:

$^1$H NMR (400 MHz, CDCl$_3$) δ (ppm): 8.76-8.75 (q, 1H), 8.00-7.98 (d, d, 1H), 7.73-7.71 (d, d, 1H), 7.37 (s, 1H), 5.38-5.33 (m, 1H), 5.32, 5.29 (d, d, 1H), 4.41-4.36 (m, 1H), 3.85-3.78 (m, 1H), 3.69-3.64 (m, 1H), 3.63 (s, 3H), 2.30-1.92 (m, 5H), 1.40-1.39 (m, 6H), 1.37-1.36 (m, 6H), 0.97, 0.95 (m, m, 3H), 0.90, 0.89 (m, m, 3H).

Step 5) The Preparation of Compound 8-6

To a mixture of compound 8-5 (0.36 g, 0.72 mmol), compound 1-11 (0.30 g, 0.72 mmol), Pd(PPh$_3$)$_4$ (83 mg, 0.07 mmol) and K$_2$CO$_3$ (0.30 g, 2.12 mmol) were added DME (4.0 mL) and H$_2$O (1.0 mL) via syringe, and the mixture was stirred at 90° C. under $N_2$ for 4.0 hrs. After the reaction was completed, the mixture was diluted with water (10 mL). The resulting mixture was extracted with EtOAc (20 mL×3) and brine, dried over anhydrous $Na_2SO_4$ and concentrated in vacuo. The residue was purified by silica gel column chromatography (PE/EtOAc (v/v)=1/2) to give the title compound (0.31 g, 65%). The compound was characterized by the following spectroscopic data:

MS (ESI, pos.ion) m/z: 662.5 [M+H]+; and $^1$H NMR (400 MHz, CDCl$_3$) δ (ppm): 8.68 (q, 1H), 7.71, 7.69 (d, d, 1H), 7.67 (s, 1H), 7.64-7.61 (d, d, 1H), 7.40, 7.38 (t, t, 1H), 7.28, 7.26 (s, s, 1H), 5.38-5.33 (m, 1H), 5.32, 5.29 (d, d, 1H), 4.41-4.36 (m, 1H), 3.85-3.78 (m, 1H), 3.69-3.64 (m, 2H), 3.63 (s, 3H), 3.42-3.34 (m, 1H), 3.11-2.99 (m, 2H), 2.81-2.61 (m, 2H), 2.37-1.92 (m, 7H), 1.63-1.53 (m, 1H), 0.97-0.89 (m, 6H).

Step 6) The Preparation of Compound 8-7

To a mixture of compound 8-6 (0.40 g, 0.61 mmol), compound 2-14 (0.29 g, 0.61 mmol), Pd(PPh$_3$)$_4$ (70 mg, 0.05 mmol) and K$_2$CO$_3$ (0.25 g, 1.83 mmol) were added DME (5.0 mL) and H$_2$O (1.0 mL) via syringe, and the mixture was stirred at 90° C. under N$_2$ for 4.0 hrs. After the reaction was completed, the mixture was concentrated in vacuo. The residue was dissolved in EtOAc (50 mL). The resulting mixture was washed with brine, dried over anhydrous Na$_2$SO$_4$ and concentrated in vacuo. The residue was purified by silica gel column chromatography (DCM/MeOH (v/v)=80/1) to give the title compound (0.44 g, 85%). The compound was characterized by the following spectroscopic data:

MS (ESI, pos.ion) m/z: 857.5 [M+H]+; and $^1$H NMR (400 MHz, CDCl$_3$) δ (ppm): 8.68 (q, 1H), 8.06, 8.04 (t, t, 1H), 7.85, 7.83 (d, d, 1H), 7.72, 7.69 (d, d, 1H), 7.68-7.65 (m, 2H), 7.56-7.55 (m, 1H), 7.53-7.49 (m, 2H), 5.38-5.33 (m, 1H), 5.32, 5.29 (d, d, 2H), 5.24-5.20 (m, 1H), 4.41-4.35 (m, 2H), 3.85-3.78 (m, 2H), 3.69-3.66 (m, 3H), 3.63 (s, 6H), 3.31-3.24 (m, 1H), 3.15-3.05 (m, 1H), 2.86-2.70 (m, 2H), 2.38-1.89 (m, 12H), 1.64-1.53 (m, 1H), 0.97, 0.95 (m, m, 6H), 0.91, 0.89 (m, m, 6H).

Example 9

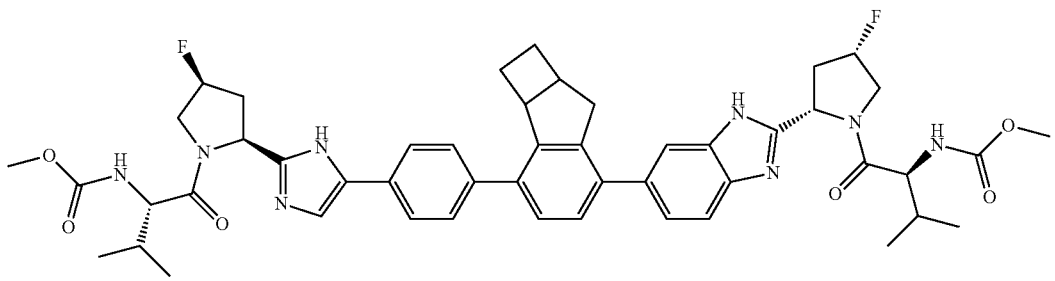

Synthetic Route:

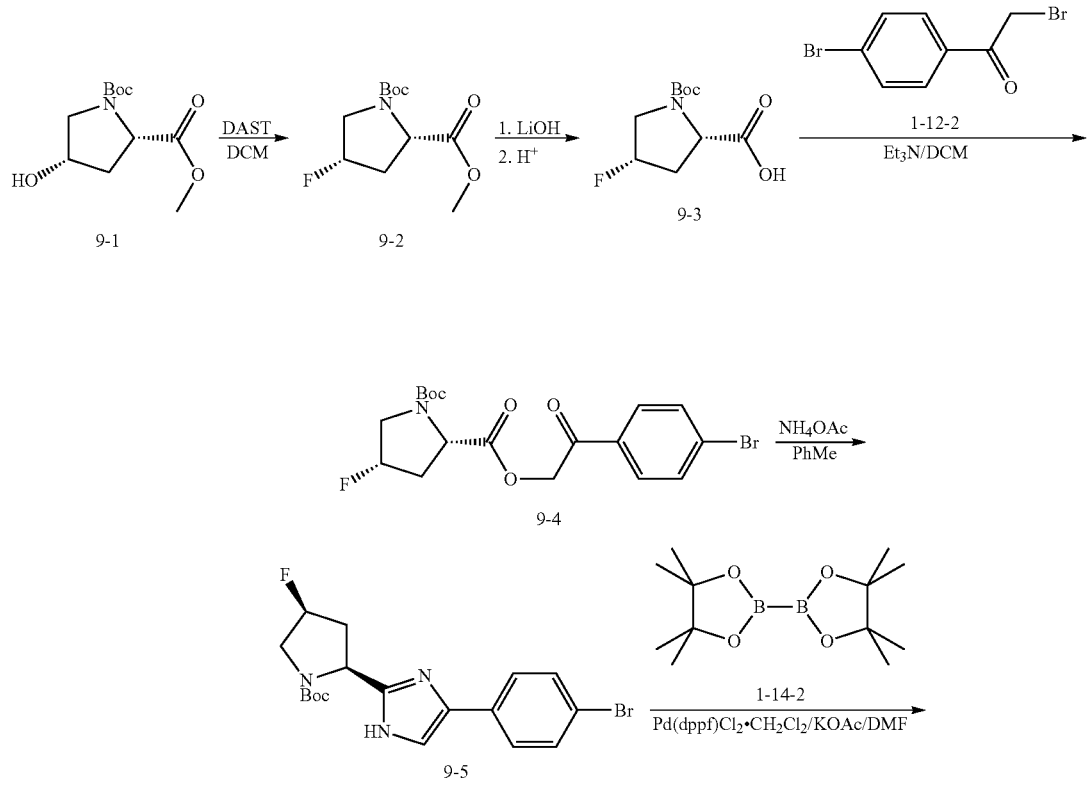

-continued
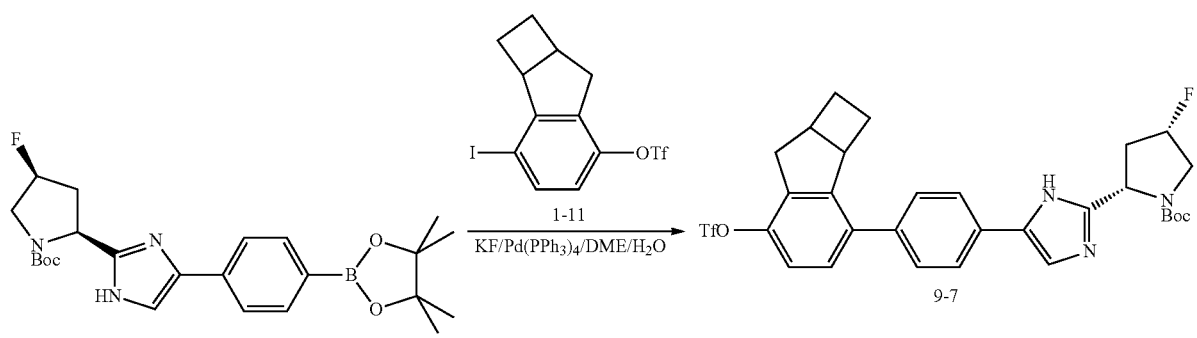
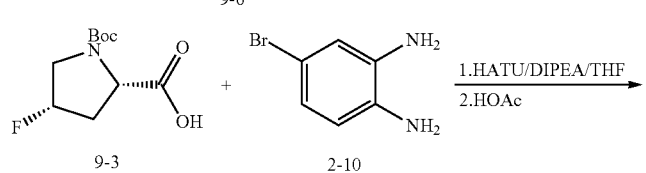
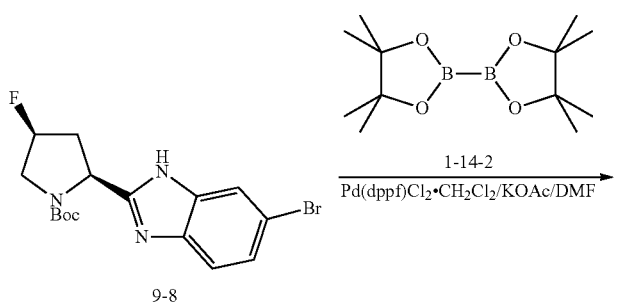
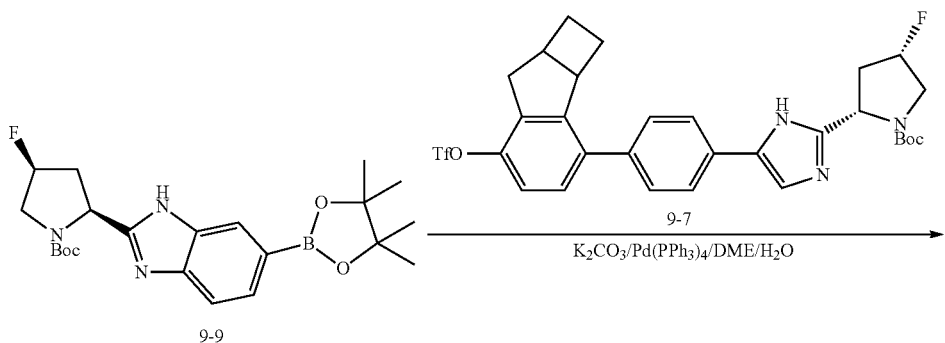
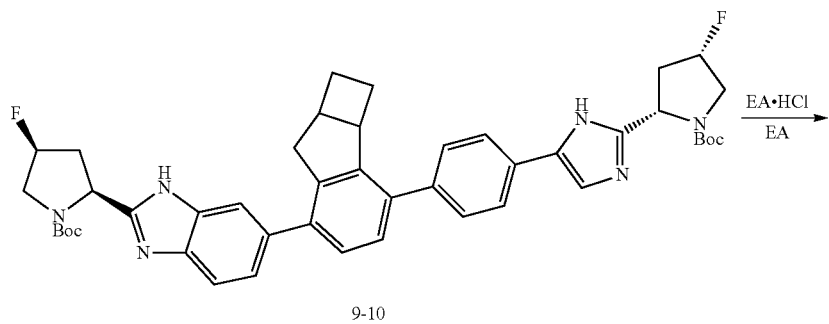

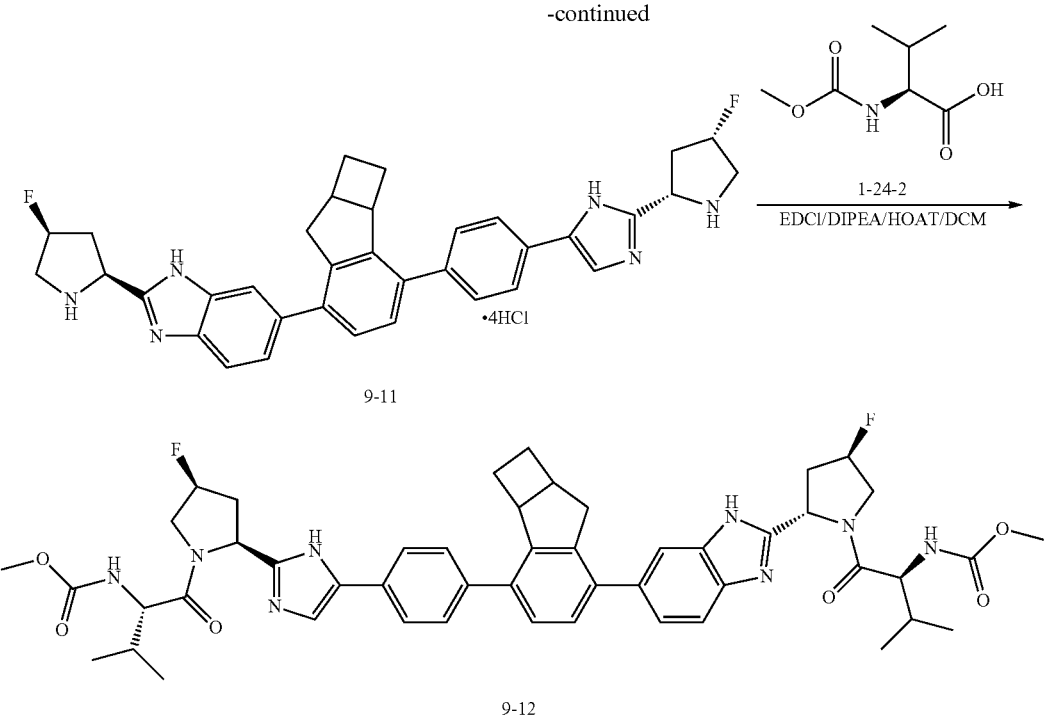

Step 1) The Preparation of Compound 9-2

To a solution of compound 9-1 (11.0 g, 44.84 mmol) in DCM (200 mL) was added Et$_2$NSF$_3$ (8.85 mL, 67.3 mmol) dropwise at −78° C. At the end of the addition, the mixture was stirred at −78° C. for 2.0 hrs and at rt for another 19 hrs. After the reaction was completed, the mixture was quenched with NH$_4$Cl aqueous solution (100 mL). The resulting mixture was extracted with DCM (100 mL×3). The combined organic layers were washed with brine, dried over anhydrous Na$_2$SO$_4$ and concentrated in vacuo. The residue was purified by silica gel column chromatography (PE/EtOAc (v/v)=20/1) to give the title compound as pale yellow liquid (7.75 g, 70%).

The compound was characterized by the following spectroscopic data:

MS (ESI, pos.ion) m/z: 248.2 [M+H]$^+$; and $^1$H NMR (400 MHz, CDCl$_3$) δ (ppm): 5.26, 5.13 (ds, ds, 1H), 4.55-4.41 (m, 1H), 3.88-3.74 (m, 1H), 3.73 (s, 3H), 3.64-3.58 (m, 1H), 2.52-2.44 (m, 1H), 2.40-2.32 (m, 1H), 1.42-1.47 (d, 9H, J=20 Hz).

Step 2) The Preparation of Compound 9-3

To a solution of compound 9-2 (5.83 g, 23.58 mmol) in THF (30 mL) was added LiOH aqueous solution (1.98 g, 30 mL) at 0° C. At the end of the addition, the mixture was stirred at rt for 2.0 hrs. After the reaction was completed, the mixture was adjusted to pH 5 with diluted hydrochloric acid (1 M) and the THF solvent was removed in vacuo. The aqueous layer was adjusted to pH 2 with diluted hydrochloric acid (1 M) and extracted with EtOAc (80 mL×3). The combined organic layers were washed with brine, dried over Na$_2$SO$_4$ and concentrated in vacuo to give the title compound as a white solid (5.28 g, 96%). The compound was characterized by the following spectroscopic data:

MS (ESI, pos.ion) m/z: 234.2 [M+H]$^+$; and $^1$H NMR (400 MHz, CDCl$_3$) δ (ppm): 8.76 (brs, 1H), 5.28-5.12 (m, 1H), 4.56-4.44 (m, 1H), 3.86-3.58 (m, 2H), 2.77-2.01 (m, 2H), 1.48-1.44 (d, 9H, J=16 Hz).

Step 3) The Preparation of Compound 9-4

To a solution of compound 9-3 (5.0 g, 21.45 mmol) and compound 1-12-2 (4.93 g, 17.87 mmol) in DCM (100 mL) was added Et$_3$N (4.34 g, 42.9 mmol) dropwise at 0° C. At the end of the addition, the mixture was stirred at rt for 3.0 hrs. After the reaction was completed, the mixture was quenched with water (50 mL). The resulting mixture was extracted with DCM (50 mL×3). The combined organic layers were washed with brine, dried over anhydrous Na$_2$SO$_4$ and concentrated in vacuo. The residue was purified by silica gel column chromatography (PE/EtOAc (v/v)=8/1) to give the title compound (4.49 g, 52.2%). The compound was characterized by the following spectroscopic data:

MS (ESI, pos.ion) m/z: 403.2 [M+H]$^+$.

Step 4) The Preparation of Compound 9-5

A mixture of compound 9-4 (4.48 g, 11.19 mmol) and ammonium acetate (12.5 g, 162 mmol) in toluene (50 mL) was stirred at 110° C. for 5.0 hrs. After the reaction was completed, the mixture was cooled to rt and quenched with water (50 mL). The aqueous layer was extracted with EtOAc (80 mL×3). The combined organic layers were washed with brine, dried over anhydrous Na$_2$SO$_4$ and concentrated in vacuo. The residue was purified by silica gel column chromatography (PE/EtOAc (v/v)=3/1) to give the title compound (4.2 g, 92%).

The compound was characterized by the following spectroscopic data:

MS (ESI, pos.ion) m/z: 411.2 [M+H]$^+$; and $^1$H NMR (400 MHz, CDCl$_3$) δ (ppm): 7.56-7.51 (m, 2H), 7.47-7.45 (m, 2H), 7.22 (s, 1H), 5.38-5.29 (m, 1H), 5.25-5.17 (m, 1H), 4.13-4.07, 3.62-3.39 (m, m, 1H), 3.68-3.58 (m, 1H), 2.68-2.38 (m, 2H), 1.38 (s, 9H).

Step 5) The Preparation of Compound 9-6

A mixture of compound 9-5 (2.0 g, 4.87 mmol), compound 1-14-2 (1.26 g, 4.97 mmol), Pd(dppf)Cl$_2$.CH$_2$Cl$_2$ (70 mg, 0.097 mmol) and KOAc (1.19 g, 12.2 mmol) in DME (20 mL) was stirred at 90° C. under N$_2$ for 2.0 hrs. After the reaction was completed, the mixture was cooled to rt, diluted with EtOAc (100 mL) and filtered through a celite pad. The filtrate was washed with water (30 mL×3) and brine, dried over anhydrous $Na_2SO_4$ and concentrated in vacuo. The residue was purified by silica gel column chromatography (PE/EtOAc (v/v)=1/2) to give the title compound (1.42 g, 64%). The compound was characterized by the following spectroscopic data:

MS (ESI, pos.ion) m/z: 458.3 $[M+H]^+$; and
$^1$H NMR (400 MHz, $CDCl_3$) δ (ppm): 7.81-7.79 (m, 2H), 7.65-7.60 (m, 2H), 7.28 (s, 1H), 5.39-5.26 (m, 1H), 5.20-5.12 (m, 1H), 4.07-3.99, 3.59-3.41 (m, 1H), 3.69-3.62 (m, 1H), 2.62-2.51 (m, 2H), 1.34 (s, 12H), 1.28 (s, 9H).

Step 6) The Preparation of Compound 9-7

To a mixture of compound 9-6 (1.2 g, 2.62 mmol), compound 1-11 (1.10 g, 2.62 mmol), $Pd(PPh_3)_4$ (0.12 g, 0.1 mmol) and KF (0.30 g, 5.24 mmol) were added DME (12 mL) and pure water (3.0 mL) via syringe. The mixture was stirred at 90° C. for 2.0 hrs. After the reaction was completed, the mixture was cooled to rt and diluted with EtOAc (50 mL). The resulting mixture was washed with water (20 mL×3) and brine, dried over anhydrous $Na_2SO_4$ and concentrated in vacuo. The residue was purified by silica gel column chromatography (DCM/MeOH (v/v)=100/1) to give the title compound as a white solid (1.06 g, 65%). The compound was characterized by the following spectroscopic data:

MS (ESI, pos.ion) m/z: 622.5 $[M+H]^+$; and
$^1$H NMR (400 MHz, $CDCl_3$) δ (ppm): 7.59-7.56 (m, 2H), 7.52-7.49 (m, 2H), 7.41 (s, 1H), 7.26, 7.23 (s, s, 1H), 6.98, 6.96 (t, t, 1H), 5.35-5.28 (m, 0.5H), 5.23-5.15 (m, 0.5H), 4.85-4.80 (m, 1H), 4.11-3.99 (m, 1H), 3.80-3.73 (m, 1H), 3.44-3.35 (m, 1H), 3.09-2.97 (m, 2H), 2.92-2.75 (m, 1H), 2.70-2.52 (m, 2H), 2.27-2.07 (m, 3H), 1.61-1.51 (m, 1H), 1.41 (s, 9H).

Step 7) The Preparation of Compound 9-8

To a suspension of compound 9-3 (2.49 g, 10.7 mmol) and HATU (4.88 g, 12.84 mmol) in THF (25 mL) was added DIPEA (1.95 mL, 11.8 mmol) dropwise at 0° C. After stirring at 0° C. for 0.5 hr, compound 2-10 (2.56 g, 11.9 mmol) was added to the mixture in a portionwise manner. At the end of the addition, the mixture was stirred at rt for 4.0 hrs. After the reaction was completed, the THF solvent was removed and 50 mL of water was added. The resulting mixture was extracted with EtOAc (60 mL×3). The combined organic layers were washed with brine, dried over anhydrous $Na_2SO_4$ and concentrated in vacuo. The residue was dissolved in glacial acetic acid (20 mL), and the solution was stirred at 40° C. overnight. After the reaction was completed, HOAc was removed. The residue was dissolved in EtOAc (100 mL). The resulting mixture was washed with $Na_2CO_3$ aqueous solution (50 mL×3), dried over anhydrous $Na_2SO_4$ and concentrated in vacuo. The residue was purified by silica gel column chromatography (PE/EtOAc (v/v)=1/2) to give the title compound (3.32 g, 81%). The compound was characterized by the following spectroscopic data:

MS (ESI, pos.ion) m/z: 385.3 $[M+H]^+$; and
$^1$H NMR (400 MHz, $CDCl_3$) δ (ppm): 7.69 (m, 1H), 7.27, 7.25 (d, d, 1H), 7.19, 7.17 (d, d, 1H), 5.34-5.27, 5.21-5.14 (m, m, 1H), 4.99-4.94 (m, 1H), 4.10-3.98 (m, 1H), 3.72-3.59 (m, 1H), 3.09-2.92 (m, 1H), 2.42-2.28 (m, 1H), 1.42 (s, 9H).

Step 8) The Preparation of Compound 9-9

To a mixture of compound 9-8 (4.32 g, 11.27 mmol), compound 1-14-2 (4.29 g, 16.9 mmol), $Pd(dppf)Cl_2 \cdot CH_2Cl_2$ (0.65 g, 0.8 mmol) and KOAc (2.09 g, 21.3 mmol) was added DMF (30 mL) via syringe, and the mixture was stirred at 90° C. under $N_2$ for 3.0 hrs. After cooling to rt, the mixture was diluted with EtOAc (200 mL) and filtered through a celite pad. The filtrate was washed with water (60 mL×3) and brine, dried over anhydrous $Na_2SO_4$ and concentrated in vacuo. The residue was purified by silica gel column chromatography (PE/EtOAc (v/v)=1/2) to give the title compound as a beige solid (3.16 g, 65%). The compound was characterized by the following spectroscopic data:

MS (ESI, pos.ion) m/z: 432.3 $[M+H]^+$; and
$^1$H NMR (400 MHz, $CDCl_3$) δ (ppm): 7.82-7.81 (m, 1H), 7.65, 7.63 (d, d, 1H), 7.27, 7.25 (d, d, 1H), 5.34-5.27, 5.21-5.14 (m, m, 1H), 4.97-4.92 (m, 1H), 4.10-3.98 (m, 1H), 3.72-3.59 (m, 1H), 3.09-2.92 (m, 1H), 2.42-2.28 (m, 1H), 1.42 (s, 9H), 1.32, 1.29 (m, m, 12H).

Step 9) The Preparation of Compound 9-10

To a mixture of compound 9-9 (0.10 g, 0.24 mmol), compound 9-7 (0.15 g, 0.24 mmol), $Pd(PPh_3)_4$ (28 mg, 0.0243 mmol) and $K_2CO_3$ (84.12 mg, 0.61 mmol) were added DME (4 mL) and pure water (1 mL) via syringe, and the mixture was stirred at 90° C. under $N_2$ for 5.0 hrs. After the reaction was completed, the mixture was cooled to rt and diluted with EtOAc (50 mL). The resulting mixture was washed with water (20 mL×3) and brine, dried over anhydrous $Na_2SO_4$ and concentrated in vacuo. The residue was purified by silica gel column chromatography (DCM/EtOH (v/v)=80/1) to give the title compound as a pale yellow solid (0.11 g, 60%). The compound was characterized by the following spectroscopic data:

MS (ESI, pos.ion) m/z: 778.3 $[M+H]^+$; and
$^1$H NMR (400 MHz, $CDCl_3$) δ (ppm): 7.85-7.83 (m, 1H), 7.62, 7.60 (s, s, 1H), 7.59-7.51 (m, 6H), 7.44, 7.42 (t, t, 1H), 7.41 (s, 1H), 5.35-5.27, 5.23-5.14 (m, m, 2H), 5.05-5.01 (m, 1H), 4.85-4.80 (m, 1H), 4.11-3.98 (m, 2H), 3.75-3.59 (m, 3H), 3.13-2.75 (m, 3H), 2.68-2.54 (m, 2H), 2.42-2.08 (m, 5H), 1.62-1.52 (m, 1H), 1.42 (s, 9H), 1.41 (s, 9H).

Step 10) The Preparation of Compound 9-11

To a solution of compound 9-10 (0.23 g, 0.3 mmol) in EtOAc (4.0 mL) was added a solution of HCl in EtOAc (3.0 mL, 4 M) dropwise. At the end of the addition, the mixture was stirred at rt for 8.0 hrs. After the reaction was completed, the mixture was concentrated in vacuo. The residue was purified by beating in EtOAc (5.0 mL) and filtered to give the title compound as a pale yellow solid (0.18 g, 85%). The compound was characterized by the following spectroscopic data:

MS (ESI, pos.ion) m/z: 577.3 $[M+H]^+$.

Step 11) The Preparation of Compound 9-12

A suspension of compound 9-11 (0.11 g, 0.157 mmol), compound 1-24-2 (57.95 mg, 0.33 mmol), EDCI (63.42 mg, 0.33 mmol) and HOAT (32.16 mg, 0.236 mmol) in DCM (5.0 mL) was added DIPEA (0.22 mL, 1.26 mmol) dropwise at 0° C. At the end of the addition, the mixture was stirred at rt for 3.0 hrs. After the reaction was completed, the mixture was diluted with DCM (50 mL). The resulting mixture was washed with saturated $NH_4Cl$ aqueous solution, dried over anhydrous $Na_2SO_4$ and concentrated in vacuo. The residue was purified by silica gel column chromatography (DCM/MeOH (v/v)=50/1) to give the title compound as pale yellow powder (90.92 mg, 65%). The compound was characterized by the following spectroscopic data:

MS (ESI, pos.ion) m/z: 446.5 $[M+2H]^{2+}$; and
$^1$H NMR (400 MHz, $CDCl_3$) δ (ppm): 7.85-7.83 (m, 1H), 7.62, 7.60 (s, s, 1H), 7.59-7.51 (m, 6H), 7.44, 7.42 (t, t, 1H), 7.38 (s, 1H), 5.32, 5.29 (d, d, 2H), 5.28-5.23 (m, 1H), 5.19-5.09 (m, 2H), 4.99-4.94 (m, 1H), 4.45-4.39 (m, 2H), 4.13-4.00 (m, 2H), 3.76-3.66 (m, 2H), 3.63 (s, 6H), 3.14-2.97 (m, 2H), 2.93-2.77 (m, 2H), 2.68-2.54 (m, 2H), 2.45-2.31 (m, 1H), 2.28-2.09 (m, 6H), 1.62-1.52 (m, 1H), 0.97, 0.95 (m, m, 6H), 0.91, 0.89 (m, m, 6H).

Example 10

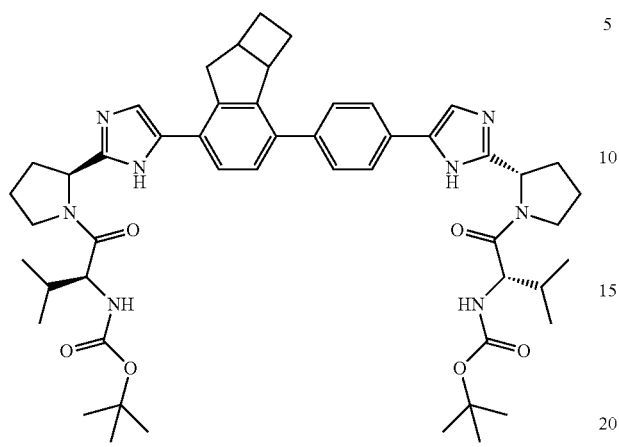

Synthetic Route:

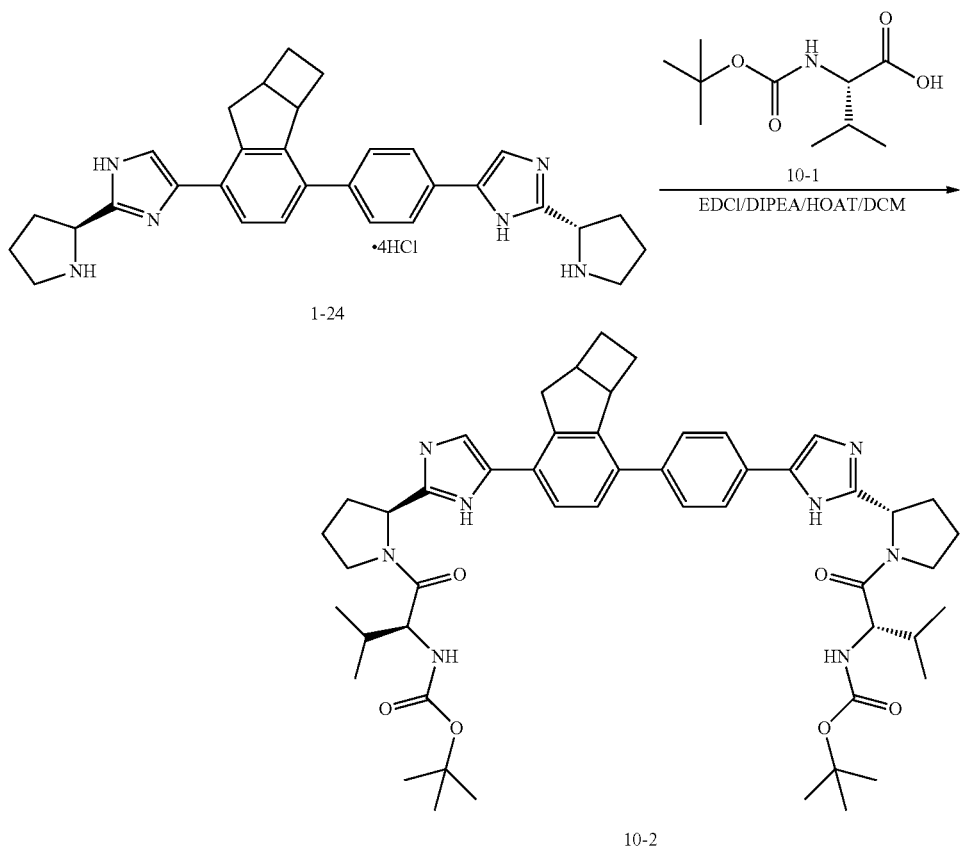

Step 1) The Preparation of Compound 10-2

To a suspension of compound 1-24 (0.48 g, 0.75 mmol), compound 10-1 (0.34 g, 1.58 mmol), EDCI (0.30 g, 1.58 mmol) and HOAT (0.20 g, 1.50 mmol) in DCM (4.0 mL) was added DIPEA (1.05 mL, 6.01 mmol) dropwise at 0° C. At the end of the addition, the mixture was stirred at rt for 3.0 hrs. After the reaction was completed, the mixture was diluted with DCM (50 mL). The resulting mixture was washed with saturated NH$_4$Cl aqueous solution and brine, dried over anhydrous Na$_2$SO$_4$ and concentrated in vacuo. The residue was purified by silica gel column chromatography (PE/EtOAc (v/v)=10/1) to give the title compound as pale yellow powder (0.37 g, 55%). The compound was characterized by the following spectroscopic data:

MS (ESI, pos.ion) m/z: 445.5 [M+2H]$^{2+}$; and $^1$H NMR (400 MHz, CDCl$_3$) δ (ppm): 7.59-7.53 (m, 6H), 7.47, 7.44 (t, t, 1H), 7.27, 7.24 (s, s, 1H), 5.32-5.28 (m, 1H), 5.23-5.21 (m, 1H), 5.20, 5.18 (d, d, 2H), 4.46-4.35 (m, 3H), 3.85-3.78 (m, 2H), 3.69-3.61 (m, 2H), 3.24-3.14 (m, 1H), 2.82-2.64 (m, 2H), 2.37-1.92 (m, 13H), 1.66-1.56 (m, 1H), 1.43 (s, 18H), 0.97, 0.95 (m, m, 6H), 0.91, 0.89 (m, m, 6H).
Example 11
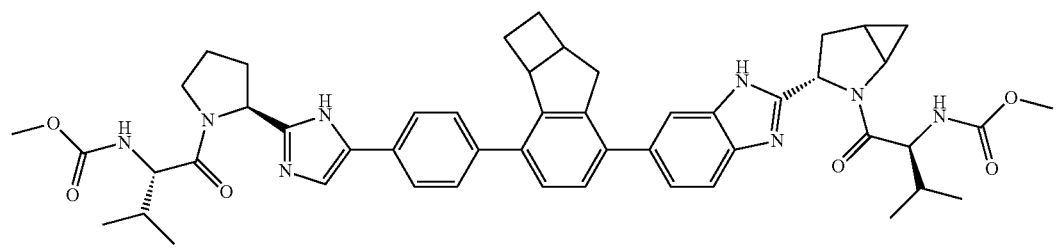
Synthetic Route:
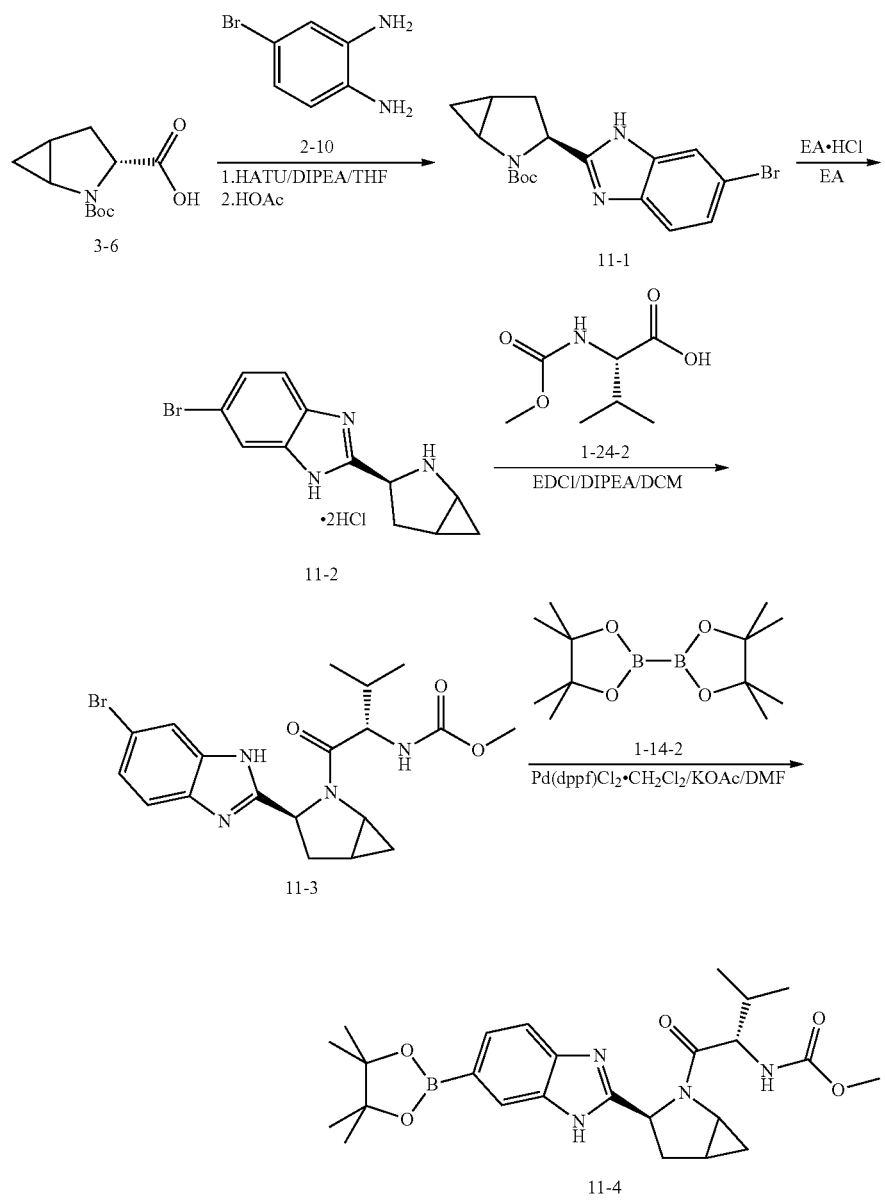

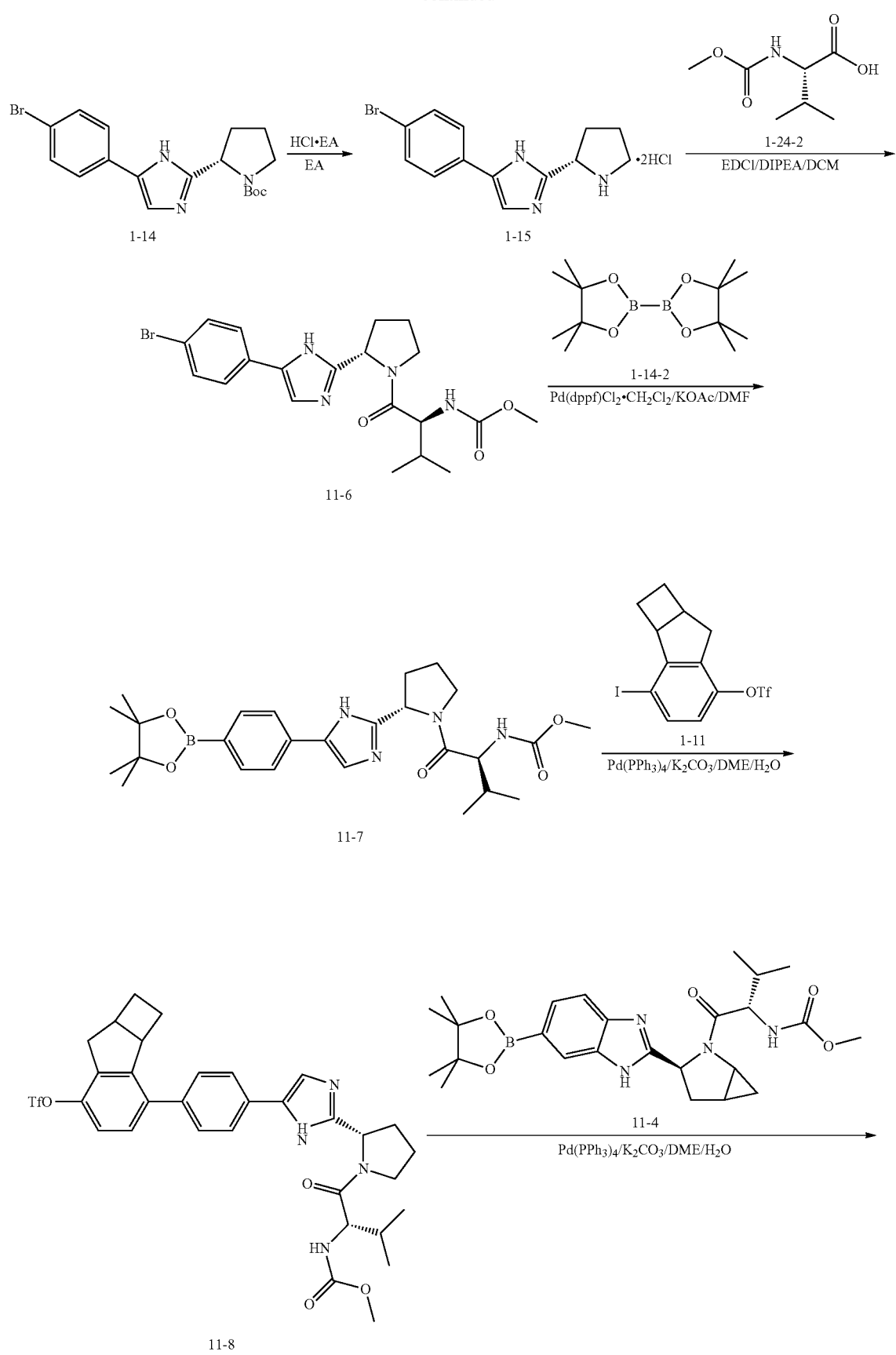

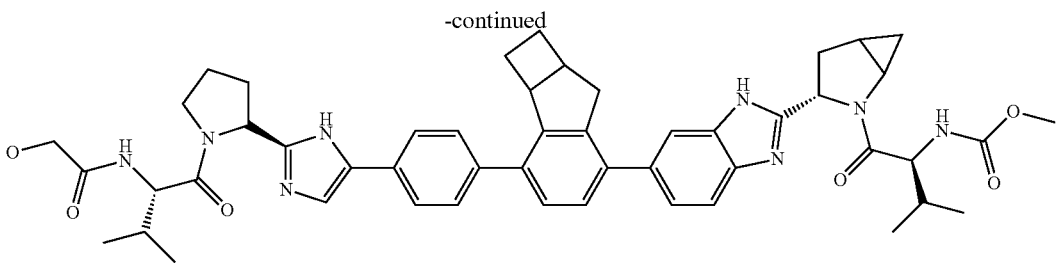

11-9

Step 1) The Preparation of Compound 11-1

To a solution of compound 3-6 (2.43 g, 10.7 mmol) and HATU (4.88 g, 12.84 mmol) in THF (25 mL) was added DIPEA (1.95 mL, 11.8 mmol) at 0° C. After stirring at 0° C. for 0.5 hr, compound 2-10 (2.22 g, 11.9 mmol) was added in a portionwise manner. At the end of the addition, the reaction mixture was stirred at rt for 4.0 hrs. After the reaction was completed, the mixture was quenched with water (50 mL), and the THF solvent was removed. The resulting mixture was extracted with EtOAc (50 mL×3). The combined organic layers were washed with brine, dried over anhydrous $Na_2SO_4$ and concentrated in vacuo. The residue was dissolved in glacial acetic acid (20 mL), and the solution was stirred at 40° C. overnight. After the reaction was completed, the solvent was removed under reduced pressure. The resulting mixture was dissolved in EtOAc (100 mL), washed with $Na_2CO_3$ aqueous solution (50 mL×3), dried over anhydrous $Na_2SO_4$ and concentrated in vacuo. The residue was purified by silica gel column chromatography (PE/EtOAc (v/v)=1/2) to give the title compound (2.02 g, 50%). The compound was characterized by the following spectroscopic data:

MS (ESI, pos.ion) m/z: 378.3 [M+H]$^+$; and $^1$H NMR (400 MHz, CDCl$_3$) δ (ppm): 7.67 (dd, 1H), 7.22, 7.20 (d, d, 1H), 7.19, 7.17 (d, d, 1H), 5.03-5.00 (m, 1H), 3.31-3.24 (m, 1H), 2.56-2.49 (m, 1H), 2.12-2.07 (m, 1H), 1.53-1.48 (m, 1H), 1.46 (s, 9H), 1.42-1.38 (m, 1H), 1.00-0.97 (m, 1H).

Step 2) The Preparation of Compound 11-2

To a solution of compound 11-1 (1.03 g, 2.74 mmol) in EtOAc (5.0 mL) was added a solution of HCl in EtOAc (6.0 mL, 4 M) dropwise at 0° C. At the end the of addition, the mixture was stirred at rt for 8.0 hrs. After the reaction was completed, the mixture was concentrated in vacuo. The residue was purified by beating in EtOAc (10 mL) and filtered to give the title compound as a pale yellow solid (0.82 g, 85%). The compound was characterized by the following spectroscopic data:

MS (ESI, pos.ion) m/z: 278.2 [M+H]$^+$.

Step 8) The Preparation of Compound 11-3

To a suspension of compound 11-2 (0.66 g, 1.88 mmol), compound 1-24-2 (0.49 mg, 2.82 mmol) and EDCI (0.54 g, 2.82 mmol) in DCM (10 mL) was added DIPEA (1.86 mL, 11.28 mmol) dropwise at 0° C. At the end of the addition, the mixture was stirred at rt for 3.0 hrs. After the reaction was completed, the mixture was diluted with DCM (50 mL). The resulting mixture was washed with water (50 mL×3) and brine, dried over anhydrous $Na_2SO_4$ and concentrated in vacuo. The residue was purified by silica gel column chromatography (PE/EtOAc (v/v)=1/2) to give the title compound as a solid (0.69 g, 85%). The compound was characterized by the following spectroscopic data:

MS (ESI, pos.ion) m/z: 435.5 [M+H]$^+$; and $^1$H NMR (400 MHz, CDCl$_3$) δ (ppm): 7.67 (dd, 1H), 7.22, 7.20 (d, d, 1H), 7.19, 7.17 (d, d, 1H), 5.32, 5.30 (d, d, 1H), 5.16-5.12 (m, 1H), 4.13-4.08 (m, 1H), 3.63 (s, 3H), 3.42-3.36 (m, 1H), 2.62-2.55 (m, 1H), 2.21-2.09 (m, 2H), 1.53-1.45 (m, 1H), 0.97-0.89 (m, 7H), 0.50-0.46 (m, 1H).

Step 4) The Preparation of Compound 11-4

To a mixture of compound 11-3 (3.08 g, 7.1 mmol), compound 1-14-2 (2.72 g, 10.7 mmol), Pd(dppf)Cl$_2$.CH$_2$Cl$_2$ (0.65 g, 0.8 mmol) and KOAc (2.09 g, 21.3 mmol) was added DMF (30 mL) via syringe under N$_2$, and the mixture was stirred at 90° C. for 3.0 hrs. After the reaction was completed, the mixture was cooled to rt and diluted with EtOAc (200 mL). The resulting mixture was filtered through a celite pad. The filtrate was washed with water (50 mL×3) and brine, dried over anhydrous Na$_2$SO$_4$ and concentrated in vacuo. The residue was purified by silica gel column chromatography (PE/EtOAc (v/v)=1/2) to give the title compound as a beige solid (2.22 g, 65%). The compound was characterized by the following spectroscopic data:

MS (ESI, pos.ion) m/z: 483.5 [M+H]$^+$; and $^1$H NMR (400 MHz, CDCl$_3$) δ (ppm): 7.82 (dd, 1H), 7.65, 7.63 (d, d, 1H), 7.45, 7.42 (d, d, 1H), 5.32, 5.30 (d, d, 1H), 5.16-5.12 (m, 1H), 4.13-4.08 (m, 1H), 3.63 (s, 3H), 3.42-3.36 (m, 1H), 2.62-2.55 (m, 1H), 2.22-2.09 (m, 2H), 1.53-1.45 (m, 1H), 1.32, 1.29 (m, 12H), 0.97-0.89 (m, 7H), 0.50-0.46 (m, 1H).

Step 5) The Preparation of Compound 11-5

To a solution of compound 1-14 (10.0 g, 25.5 mmol) in EtOAc (50.0 mL) was added a solution of HCl in EtOAc (60.0 mL, 4 M) dropwise. At the end of the addition, the mixture was stirred at rt for 8.0 hrs. After the reaction was completed, the mixture was concentrated in vacuo. The residue was purified by beating in EtOAc (30 mL) and filtered to give the title compound as a pale yellow solid (8.0 g, 86.2%). The compound was characterized by the following spectroscopic data:

MS (ESI, pos.ion) m/z: 292.6 [M+H]$^+$; and $^1$H NMR (400 MHz, CDCl$_3$) δ (ppm): 7.76-7.73 (m, 2H), 7.66-7.63 (m, 2H), 7.21-7.20 (m, 1H), 5.50-5.22 (m, 2H), 4.49-4.39 (m, 1H), 3.61-3.56 (m, 1H), 3.49-3.39 (m, 1H), 2.31-2.21 (m, 2H), 2.12-2.01 (m, 1H), 1.98-1.85 (m, 1H).

Step 6) The Preparation of Compound 11-6

To a solution of compound 11-5 (7.03 g, 19.26 mmol), compound 1-24-2 (5.06 g, 28.88 mmol) and EDCI (5.56 g, 28.88 mmol) in DCM (100 mL) was added DIPEA (21 mL, 127 mmol) dropwise at 0° C. At the end of the addition, the mixture was stirred at rt for 3.0 hrs. After the reaction was completed, the mixture was diluted with water (100 mL) and extracted with DCM (100 mL×3). The combined organic layers were washed with brine, dried over anhydrous Na$_2$SO$_4$ and concentrated in vacuo. The residue was purified by silica gel column chromatography (PE/EtOAc (v/v)=1/2)

to give the title compound as a solid (7.6 g, 88%). The compound was characterized by the following spectroscopic data:

MS (ESI, pos.ion) m/z: 450.3 [M+H]$^+$; and $^1$H NMR (400 MHz, CDCl$_3$) δ (ppm): 7.65-7.60 (m, 2H), 7.47-7.43 (m, 2H), 7.22-7.20 (m, 1H), 5.67-5.65 (m, 1H), 5.24-5.22 (m, 1H), 4.34-4.30 (m, 1H), 3.85-3.81 (m, 1H), 3.72 (s, 3H), 3.71-3.64 (m, 1H), 3.00 (s, 1H), 2.34-2.31 (m, 1H), 2.21-1.95 (m, 5H), 1.04-1.02 (m, 1H), 0.88-0.86 (d, 6H).

Step 7) The Preparation of Compound 11-7

To a mixture of compound 11-6 (5.0 g, 11.13 mmol), compound 1-14-2 (4.3 g, 16.7 mmol), Pd(dppf)Cl$_2$.CH$_2$Cl$_2$ (0.91 g, 1.11 mmol) and KOAc (3.3 g, 33.4 mmol) was added DMF (50 mL) via syringe under N$_2$, and the mixture was stirred at 90° C. for 3.0 hrs. After the reaction was completed, the mixture was cooled to rt, diluted with EtOAc (200 mL) and filtered through a celite pad. The filtrater was washed with water (100 mL×3) and brine, dried over anhydrous Na$_2$SO$_4$ and concentrated in vacuo. The residue was purified by silica gel column chromatography (PE/EtOAc (v/v)=1/2) to give the title compound as a beige solid (3.94 g, 71.4%). The compound was characterized by the following spectroscopic data:

$^1$H NMR (400 MHz, CDCl$_3$) δ (ppm): 7.65-7.60 (m, 2H), 7.47-7.43 (m, 2H), 7.22-7.20 (m, 1H), 5.67-5.65 (m, 1H), 5.24-5.22 (m, 1H), 4.34-4.30 (m, 1H), 3.85-3.81 (m, 1H), 3.72 (s, 3H), 3.71-3.64 (m, 1H), 3.00 (s, 1H), 2.34-2.31 (m, 1H), 2.21-1.95 (m, 5H), 1.45-1.32 (m, 12H), 1.04-1.02 (m, 1H), 0.88-0.86 (d, 6H).

Step 8) The Preparation of Compound 11-8

A mixture of compound 1-11 (0.22 g, 0.522 mmol), compound 11-7 (0.26 g, 0.522 mmol), Pd(PPh$_3$)$_4$ (60.29 mg, 0.0522 mmol) and K$_2$CO$_3$ (0.22 g, 1.566 mmol) in mixed solvents of DME and H$_2$O (8 mL, v/v=3/1) was stirred at 90° C. under N$_2$ for 3.0 hrs. After the reaction was completed, the mixture was cooled to rt and diluted with EtOAc (40 mL). The resulting mixture was washed with water (20 mL×3) and brine, dried over anhydrous Na$_2$SO$_4$ and concentrated in vacuo. The residue was purified by silica gel column chromatography (DCM/EtOH (v/v)=150/1) to give the title compound as a pale yellow solid (0.17 g, 50%). The compound was characterized by the following spectroscopic data:

MS (ESI, pos.ion) m/z: 661.5 [M+H]$^+$; and $^1$H NMR (400 MHz, CDCl$_3$) δ (ppm): 7.59-7.56 (m, 3H), 7.52-7.49 (m, 2H), 7.26, 7.23 (s, s, 1H), 6.98-6.96 (t, t, 1H), 5.56, 5.55 (d, d, 1H), 5.23-5.19 (m, 1H), 4.34-4.30 (m, 1H), 3.85-3.78 (m, 1H), 3.66 (s, 3H), 3.65-3.61 (m, 1H), 3.44-3.36 (m, 1H), 3.09-2.97 (m, 2H), 2.70-2.52 (m, 2H), 2.30-1.92 (m, 7H), 1.61-1.50 (m, 1H), 1.02, 1.00 (m, m, 3H), 0.93, 0.91 (m, m, 3H).

Step 9) The Preparation of Compound 11-9

A suspension of compound 11-8 (0.35 g, 0.522 mmol), compound 11-4 (0.25 g, 0.522 mmol), Pd(PPh$_3$)$_4$ (60.29 mg, 0.0522 mmol) and K$_2$CO$_3$ (0.22 g, 1.566 mmol) in mixed solvents of DME and H$_2$O (8 mL, v/v=3/1) was stirred at 90° C. under N$_2$ for 3.0 hrs. After the reaction cooling to rt, the mixture was diluted with EtOAc (40 mL). The resulting mixture was washed with water (20 mL×3) and brine, dried over anhydrous Na$_2$SO$_4$ and concentrated in vacuo. The residue was purified by silica gel column chromatography (DCM/EtOH (v/v)=50/1) to give the title compound as a pale yellow solid (0.25 g, 55%). The compound was characterized by the following spectroscopic data:

MS (ESI, pos.ion) m/z: 434.5 [M+2H]$^{2+}$; and $^1$H NMR (400 MHz, CDCl$_3$) δ (ppm): 7.85-7.83 (d, d, 1H), 7.62, 7.60 (s, s, 1H), 7.59 (s, 1H), 7.58-7.50 (m, 6H), 7.44, 7.42 (t, t, 1H), 5.32, 5.29 (m, m, 2H), 5.23-5.19 (m, 1H), 5.14-5.10 (m, 1H), 4.41-4.37 (m, 1H), 4.13-4.08 (m, 1H), 3.85-3.78 (m, 1H), 3.75-3.66 (m, 2H), 3.63 (s, 6H), 3.42-3.36 (m, 1H), 3.13-3.02 (m, 1H), 2.68-2.54 (m, 3H), 2.30-1.92 (m, 10H), 1.62-1.45 (m, 2H), 0.97, 0.95 (m, m, 6H), 0.90, 0.88 (m, m, 6H), 0.50-0.46 (m, 2H).

Example 12

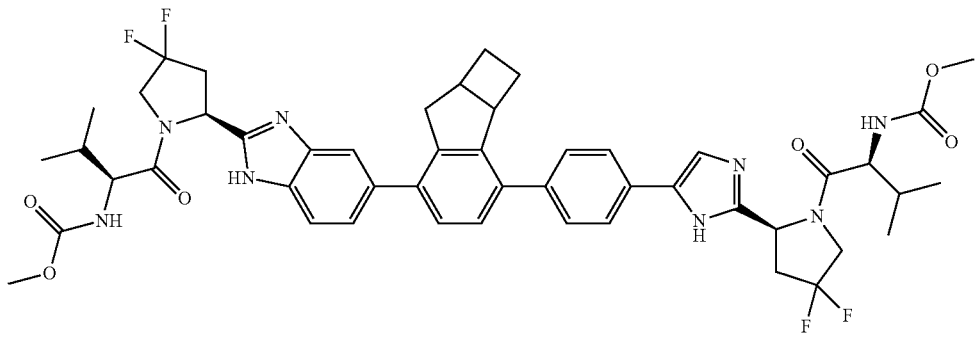

Synthetic Route:

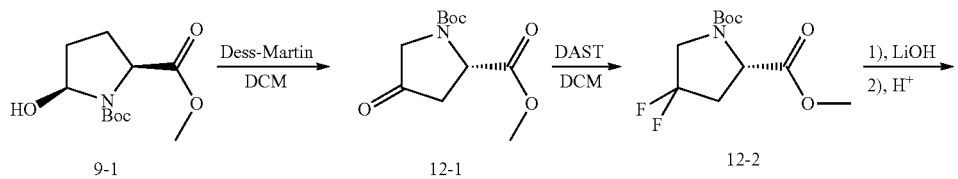

-continued
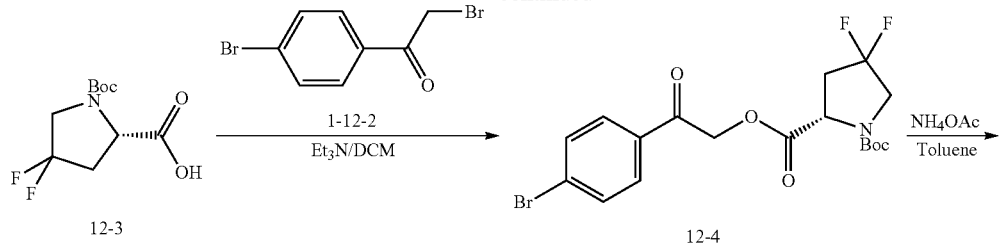
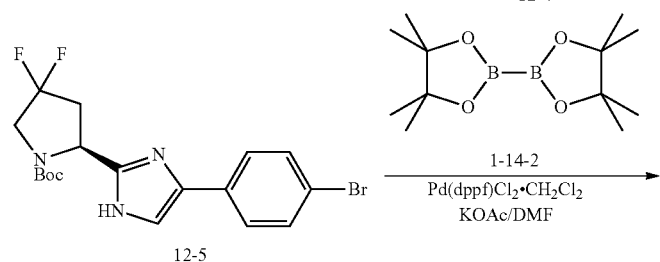
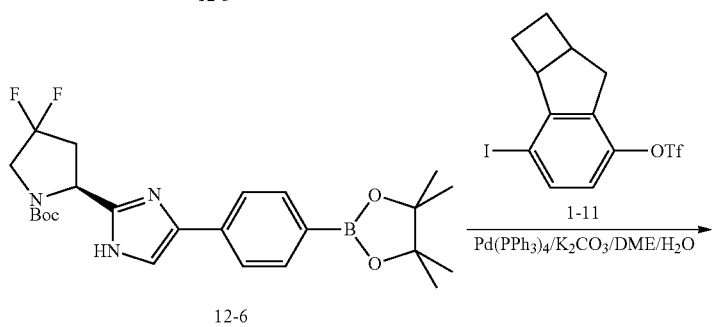
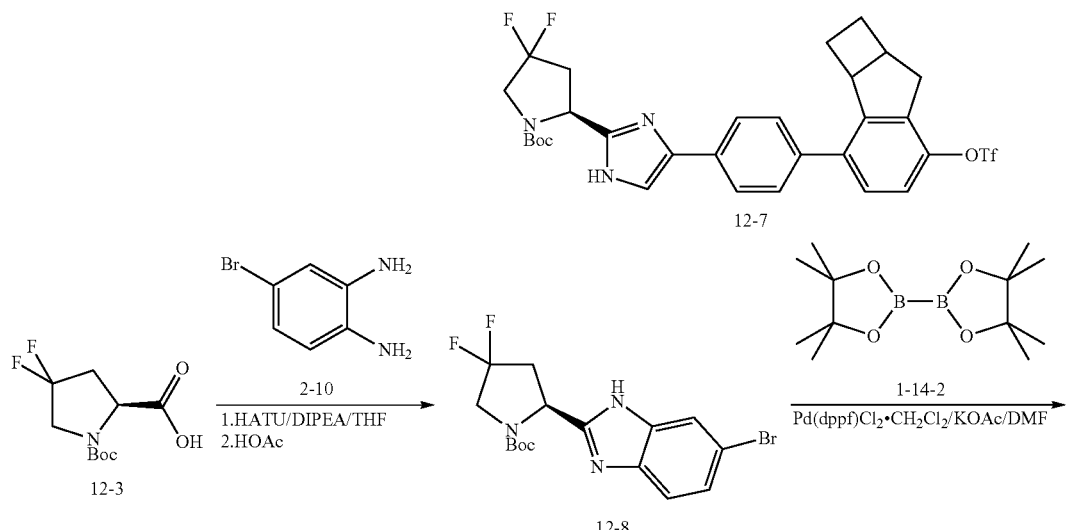
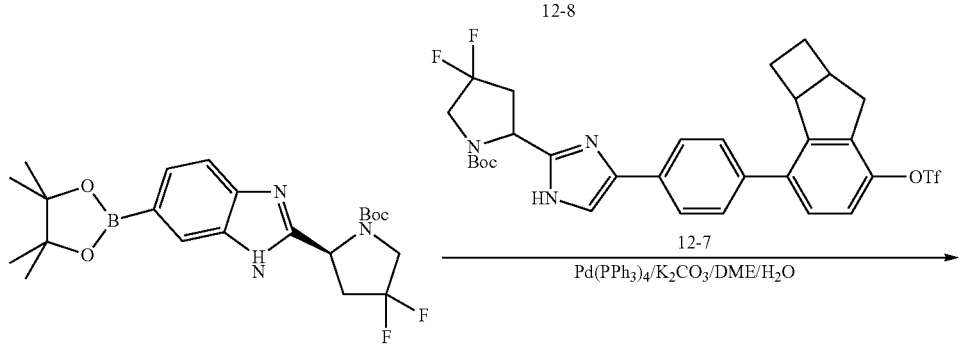

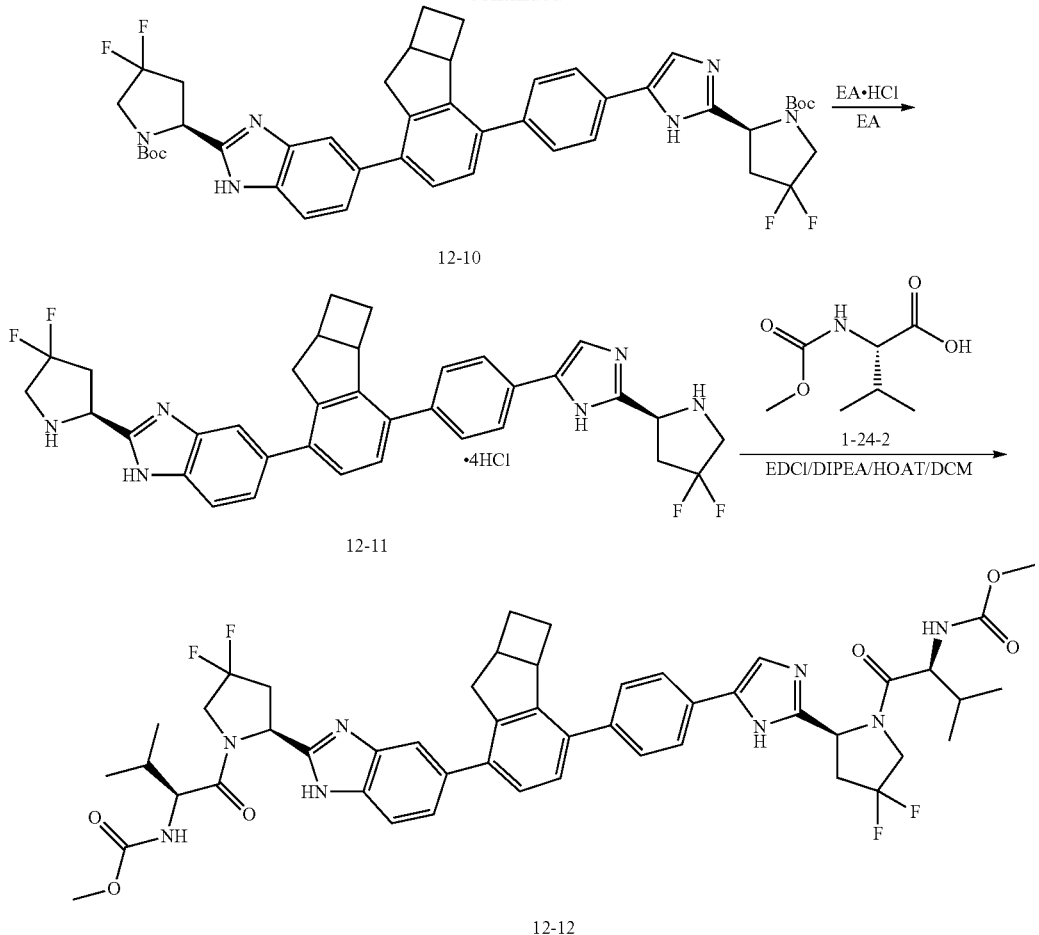

Step 1) The Preparation of Compound 12-1

To a solution of compound 9-1 (6.85 g, 27.97 mmol) in DCM (70 mL) was added Dess-Martin periodinane (23.7 g, 56 mmol) in a portionwise manner at 0° C. At the end of the addition, the mixture was stirred at rt for 7.0 hrs. After the mixture was completed, the mixture was quenched with Na$_2$S$_2$O$_3$ aqueous solution (100 mL) and filtered through a celite pad. The filtrate was extracted with DCM (100 mL×3). The combined organic layers were dried over anhydrous Na$_2$SO$_4$ and concentrated in vacuo. The residue was purified by silica gel column chromatography (PE/EtOAc (v/v)=6/1) to give the title compound as pale yellow liquid (5.78 g, 85%).

Step 2) The Preparation of Compound 12-2

To a solution of compound 12-1 (5.81 g, 23.9 mmol) in DCM (70 mL) was added Et$_2$NSF$_3$ (4.85 mL, 35.9 mmol) dropwise at −78° C. At the end of the addition, the mixture was stirred at −78° C. for 2.0 hrs and at rt for another 19 hrs. After the reaction was completed, the mixture was quenched with NH$_4$Cl aqueous solution (50 mL). The aqueous layer was extracted with DCM (100 mL×3). The combined organic layers were dried over anhydrous Na$_2$SO$_4$ and concentrated in vacuo. The residue was purified by silica gel column chromatography (PE/EtOAc (v/v)=20/1) to give the title compound as pale yellow liquid (5.0 g, 79%). The compound was characterized by the following spectroscopic data:

MS (ESI, pos.ion) m/z: 266.2 [M+H]$^+$; and $^1$H NMR (400 MHz, CDCl$_3$) δ (ppm): 9.60 (brs, 1H), 4.60-4.57, 4.94-4.72 (m, m, 1H), 3.93-3.84 (m, 2H), 3.77 (s, 3H), 2.78-2.48 (m, 2H), 1.44 (d, 9H, J=16 Hz).

Step 3) The Preparation of Compound 12-3

To a solution of compound 12-2 (5.0 g, 18.86 mmol) in THF (40 mL) was added LiOH aqueous solution (1.5 g, 20 mL) at 0° C., and the mixture was stirred at rt for 2.0 hrs. After the reaction was completed, the mixture was adjusted to pH 5 with diluted hydrochloric acid (1 M), and then the THF solvent was removed in vacuo. The aqueous layer was adjusted to pH 2 with diluted hydrochloric acid (1 M) and extracted with EtOAc (80 mL×3). The combined organic layers were washed with brine, dried over anhydrous Na$_2$SO$_4$ and concentrated in vacuo to give the title compound as a white solid (4.44 g, 94%). The compound was characterized by the following spectroscopic data:

MS (ESI, pos.ion) m/z: 252.2 [M+H]$^+$; and $^1$H NMR (400 MHz, CDCl$_3$) δ (ppm): 9.60 (brs, 1H), 4.94-4.72, 4.60-4.57 (m, m, 1H), 3.89-3.74 (m, 2H), 2.78-2.48 (m, 2H), 1.44 (d, 9H, J=16 Hz).

Step 4) The Preparation of Compound 12-4

To a solution of compound 1-12-2 (2.39 g, 8.66 mmol) and compound 12-3 (2.17 g, 8.66 mmol) in DCM (30 mL) was added Et$_3$N (2.5 mL, 17.32 mmol) dropwise at 0° C. At the end of the addition, the mixture was stirred at rt for 3.0 hrs. After the reaction was completed, the mixture was quenched with water (50 mL). The resulting mixture was extracted with DCM (30 mL×3). The combined organic layers were dried over anhydrous $Na_2SO_4$ and concentrated in vacuo to give the crude product (3.6 g), which was used for the next step without further purification. The compound was characterized by the following spectroscopic data:

MS (ESI, pos.ion) m/z: 448.5 [M+H]$^+$.

Step 5) The Preparation of Compound 12-5

A suspension of compound 12-4 (3.84 g, 8.6 mmol) and ammonium acetate (7.0 g, 86 mmol) in toluene (30 mL) was stirred at 110° C. for 5.0 hrs. After the reaction was completed, the mixture was cooled to rt and quenched with water (60 mL). The resulting mixture was extracted with EtOAc (80 mL×3). The combined organic layers were dried over anhydrous $Na_2SO_4$ and concentrated in vacuo. The residue was purified by silica gel column chromatography (PE/EtOAc (v/v)=6/1) to give the title compound (1.47 g, 40%). The compound was characterized by the following spectroscopic data:

MS (ESI, pos.ion) m/z: 429.2 [M+H]$^+$; and $^1$H NMR (400 MHz, CDCl$_3$) δ (ppm): 7.54-7.52 (m, 2H), 7.48-7.46 (m, 2H), 7.26-7.25 (m, 1H), 5.19-5.18 (m, 1H), 3.70-3.52 (m, 2H), 2.78-2.65 (m, 2H), 1.48 (s, 9H).

Step 6) The Preparation of Compound 12-6

A mixture of compound 12-5 (1.4 g, 3.27 mmol), compound 1-14-2 (0.92 g, 3.6 mmol), Pd(dppf)Cl$_2$.CH$_2$Cl$_2$ (0.13 g, 1.16 mmol) and KOAc (0.81 g, 8.17 mmol) in DME (25 mL) was stirred at 90° C. under $N_2$ for 2.0 hrs. After the reaction was completed, the mixture was diluted with EtOAc (80 mL) and filtered through a celite pad. The filtrate was washed with water (30 mL×3) and brine, dried over anhydrous $Na_2SO_4$ and concentrated in vacuo. The residue was purified by silica gel column chromatography (PE/EtOAc (v/v)=1/2) to give the title compound as a solid (1.5 g, 96%). The compound was characterized by the following spectroscopic data:

MS (ESI, pos.ion) m/z: 476.2 [M+H]$^+$; and $^1$H NMR (400 MHz, CDCl$_3$) δ (ppm): 7.54-7.52 (m, 2H), 7.48-7.46 (m, 2H), 7.26-7.25 (m, 1H), 5.19-5.18 (m, 1H), 3.70-3.52 (m, 2H), 2.78-2.65 (m, 2H), 1.48 (s, 9H), 1.35 (s, 12H).

Step 7) The Preparation of Compound 12-7

To a mixture of compound 12-6 (2.14 g, 4.5 mmol), compound 1-11 (1.88 g, 4.5 mmol), Pd(PPh$_3$)$_4$ (01.26 g, 0.225 mmol) and K$_2$CO$_3$ (1.24 g, 9.0 mmol) were added DME (20 mL) and pure water (4.0 mL) via syringe under $N_2$. The mixture was stirred at 90° C. for 2.0 hrs. After the reaction was completed, the mixture was diluted with EtOAc (100 mL). The resulting mixture was washed with water (30 mL×3) and brine, dried over anhydrous $Na_2SO_4$ and concentrated in vacuo. The residue was purified by silica gel column chromatography (PE/EtOAc (v/v)=6/1) to give the title compound as a white solid (1.87 g, 65%). The compound was characterized by the following spectroscopic data:

MS (ESI, pos.ion) m/z: 640.5 [M+H]$^+$; and $^1$H NMR (400 MHz, CDCl$_3$) δ (ppm): 7.74-7.66 (m, 4H), 7.46 (s, 1H), 7.26, 7.23 (s, s, 1H), 6.98, 6.96 (t, t, 1H), 4.93-4.88 (m, 1H), 4.18-4.05 (m, 1H), 3.92-3.79 (m, 1H), 3.44-3.36 (m, 1H), 3.10-2.97 (m, 2H), 2.86-2.52 (m, 3H), 2.47-2.26 (m, 1H), 2.20-2.08 (m, 2H), 1.61-1.51 (m, 1H), 1.41 (s, 9H).

Step 8) The Preparation of Compound 12-8

To a solution of compound 12-3 (2.7 g, 10.7 mmol) and HATU (4.88 g, 12.84 mmol) in THF (25 mL) was added DIPEA (1.95 mL, 11.8 mmol) at 0° C. After stirring at 0° C. for 0.5 hr, compound 2-10 (2.22 g, 11.9 mmol) was added in a portionwise manner. At the end of the addition, the mixture was stirred at rt for 4.0 hrs. After the reaction was completed, the mixture was quenched with water (50 mL), the THF solvent was removed, and the resulting mixture was extracted with EtOAc (50 mL×3). The combined organic layers were washed with brine, dried over anhydrous $Na_2SO_4$ and concentrated in vacuo. The residue was dissolved in glacial acetic acid (20 mL), and the solution was stirred at 40° C. overnight. After the reaction was completed, the mixture was concentrated in vacuo. The residue was dissolved in EtOAc (100 mL). The mixture was washed with $Na_2CO_3$ aqueous solution (50 mL×3), dried over anhydrous $Na_2SO_4$ and concentrated in vacuo. The residue was purified by silica gel column chromatography (PE/EtOAc (v/v)=1/2) to give the title compound (2.14 g, 50%). The compound was characterized by the following spectroscopic data:

MS (ESI, pos.ion) m/z: 403.5 [M+H]$^+$; and $^1$H NMR (400 MHz, CDCl$_3$) δ (ppm): 7.71-7.70 (m, 1H), 7.33, 7.30 (d, d, 1H), 7.19, 7.17 (d, d, 1H), 5.13-5.08 (m, 1H), 4.18-4.04 (m, 1H), 3.91-3.78 (m, 1H), 3.00-2.82 (m, 1H), 2.61-2.41 (m, 1H), 1.41 (s, 9H).

Step 9) The Preparation of Compound 12-9

To a mixture of compound 12-8 (2.85 g, 7.1 mmol), compound 1-14-2 (2.72 g, 10.7 mmol), Pd(dppf)Cl$_2$.CH$_2$Cl$_2$ (0.65 g, 0.8 mmol) and KOAc (2.09 g, 21.3 mmol) was added DMF (30 mL) via syringe, and the mixture was stirred at 90° C. under $N_2$ for 3.0 hrs. After cooling to rt, the mixture was diluted with EtOAc (200 mL) and filtered through a celite pad. The filtrate was washed with water (50 mL×3) and brine, dried over anhydrous $Na_2SO_4$ and concentrated in vacuo. The residue was purified by silica gel column chromatography (PE/EtOAc (v/v)=1/2) to give the title compound as a beige solid (2.07 g, 65%). The compound was characterized by the following spectroscopic data:

MS (ESI, pos.ion) m/z: 450.5 [M+H]$^+$; and $^1$H NMR (400 MHz, CDCl$_3$) δ (ppm): 7.84-7.83 (m, 1H), 7.65, 7.63 (d, d, 1H), 7.36, 7.34 (d, d, 1H), 5.13-5.08 (m, 1H), 4.18-4.04 (m, 1H), 3.91-3.78 (m, 1H), 3.00-2.82 (m, 1H), 2.61-2.41 (m, 1H), 1.41 (s, 9H), 1.32, 1.29 (m, m, 12H).

Step 10) The Preparation of Compound 12-10

To a mixture of compound 12-9 (0.23 g, 0.522 mmol), compound 12-7 (0.33 g, 0.522 mmol), Pd(PPh$_3$)$_4$ (60.29 mg, 0.0522 mmol) and K$_2$CO$_3$ (0.22 g, 1.566 mmol) were added DME (6.0 mL) and pure water (2.0 mL) via syringe, and the mixture was stirred at 90° C. under $N_2$ for 3.0 hrs. After the reaction was completed, the mixture was cooled to rt and diluted with EtOAc (40 mL). The resulting mixture was washed with brine, dried over anhydrous $Na_2SO_4$ and concentrated in vacuo. The residue was purified by silica gel column chromatography (DCM/EtOH (v/v)=100/1) to give the title compound as a pale yellow solid (0.23 g, 55%). The compound was characterized by the following spectroscopic data:

MS (ESI, pos.ion) m/z: 813.5 [M+H]$^+$; and $^1$H NMR (400 MHz, CDCl$_3$) δ (ppm): 7.78, 7.76 (s, s, 1H), 7.61-7.53 (m, 6H), 7.52, 7.50 (t, t, 1H), 7.44-7.42 (m, 2H), 5.16-5.11 (m, 1H), 5.00-4.95 (m, 1H), 4.18-4.04 (m, 2H), 3.92-3.78 (m, 2H), 3.75-3.67 (m, 1H), 3.13-3.03 (m, 1H), 3.00-2.26 (m, 7H), 2.22-2.08 (m, 2H), 1.62-1.52 (m, 1H), 1.41 (s, 18H).

Step 11) The Preparation of Compound 12-11

To a solution of compound 12-10 (0.40 g, 0.5 mmol) in EtOAc (4.0 mL) was added a solution of HCl in EtOAc (3.0 mL, 4 M) dropwise. At the end of the addition, the mixture was stirred at rt overnight. After the reaction was completed, the mixture was concentrated in vacuo. The residue was purified by beating in EtOAc (5.0 mL) and filtered to give the title compound as a pale yellow solid (0.32 g, 85%). The compound was characterized by the following spectroscopic data:

MS (ESI, pos.ion) m/z: 613.5 [M+H]$^+$.

Step 12) The Preparation of Compound 12-12

To a mixture of compound 12-11 (0.15 g, 0.2 mmol), compound 1-24-2 (73.57 mg, 0.42 mmol), EDCI (80.52 mg, 0.42 mmol) and HOAT (54.44 mg, 0.4 mmol) in DCM (5.0 mL) was added DIPEA (0.26 mL, 1.6 mmol) dropwise at 0° C. At the end of the addition, the mixture was stirred at rt for 3.0 hrs. After the reaction was completed, the mixture was diluted with DCM (50 mL) and washed with NH$_4$Cl aqueous solution and brine, dried over anhydrous Na$_2$SO$_4$ and concentrated in vacuo. The residue was purified by silica gel column chromatography (DCM/MeOH (v/v)=50/1) to give the title compound as pale yellow powder (0.10 g, 55%). The compound was characterized by the following spectroscopic data:

MS (ESI, pos.ion) m/z: 464.5 [M+2H]$^{2+}$; and $^1$H NMR (400 MHz, CDCl$_3$) δ (ppm): 7.78, 7.76 (s, s, 1H), 7.61-7.53 (m, 6H), 7.52, 7.50 (t, t, 1H), 7.44, 7.42 (d, d, 1H), 7.41 (s, 1H), 5.32, 5.29 (d, d, 2H), 5.28-5.26 (m, 1H), 5.16-5.11 (m, 1H), 4.47-4.42 (m, 2H), 4.21-4.07 (m, 2H), 3.94-3.80 (m, 2H), 3.75-3.67 (m, 1H), 3.63 (s, 6H), 3.13-3.72 (m, 4H), 2.67-2.28 (m, 4H), 2.23-2.08 (m, 4H), 1.62-1.52 (m, 1H), 0.97, 0.95 (m, m, 6H), 0.91, 0.89 (m, m, 6H).

Example 13

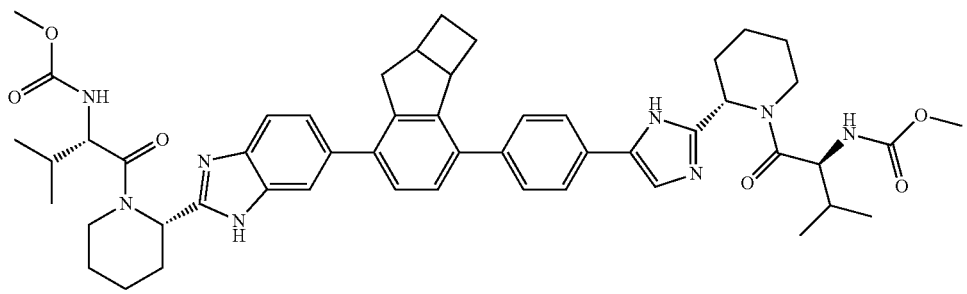

Synthetic Route:

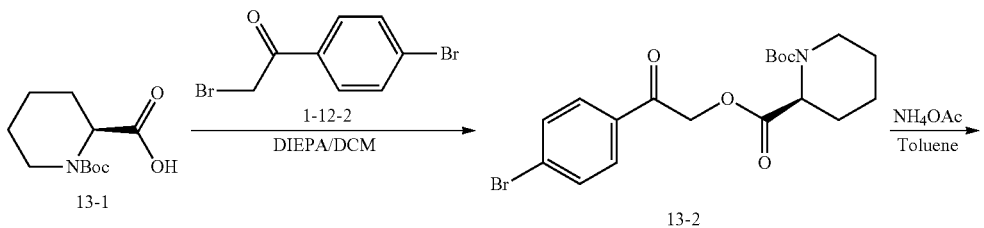

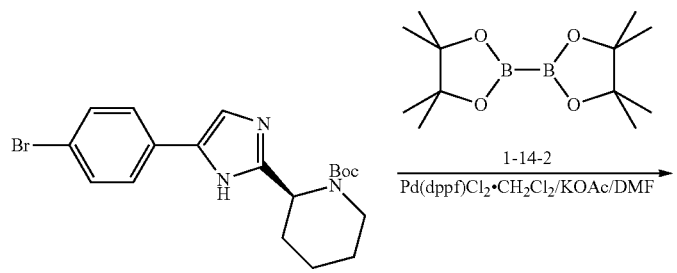

-continued
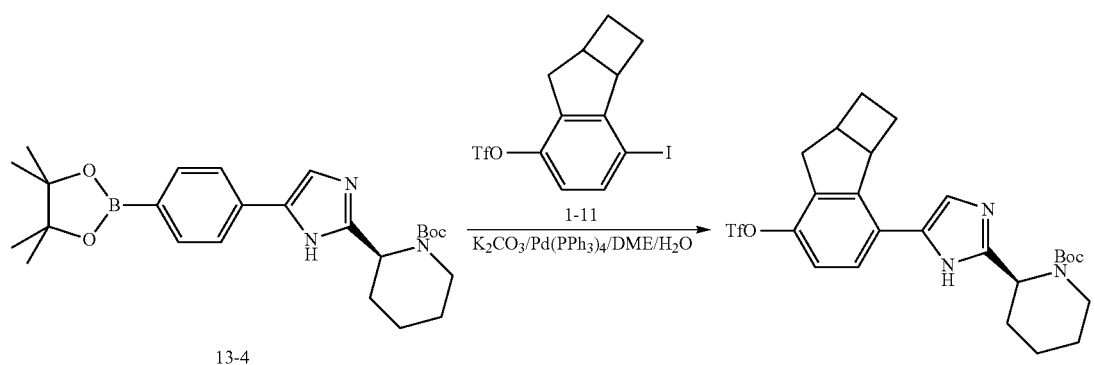
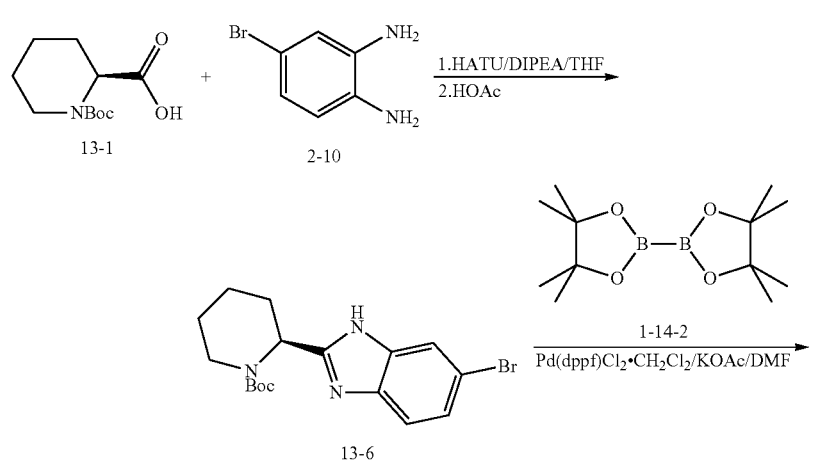
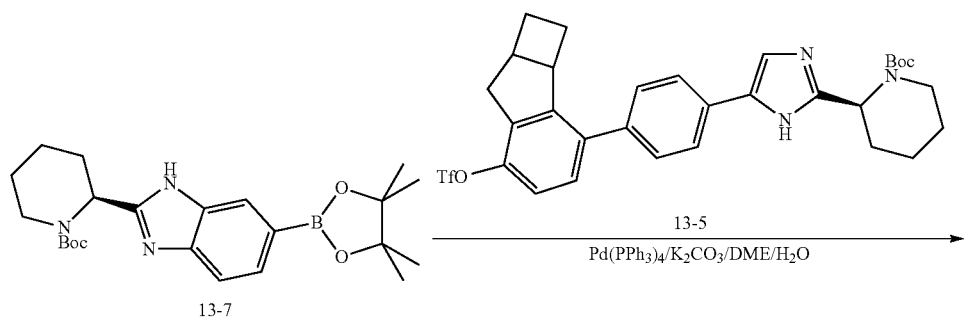
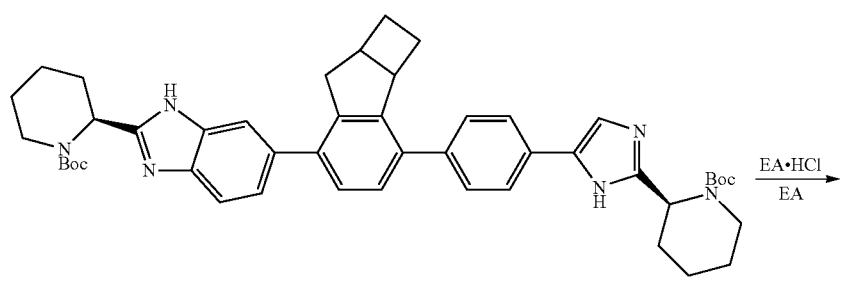

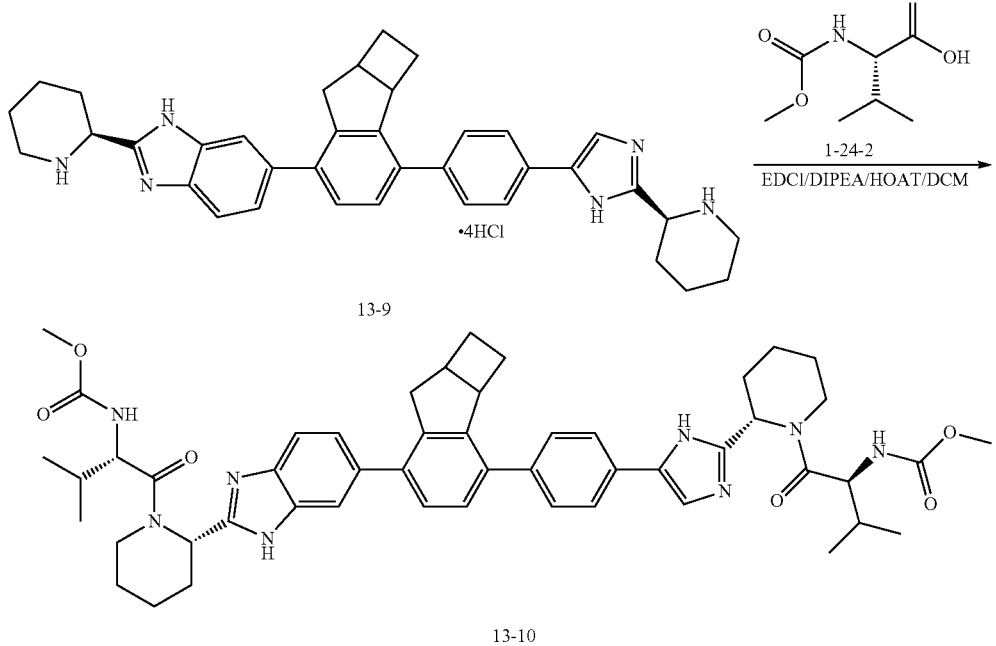

Step 1) The Preparation of Compound 13-2

To a solution of compound 13-1 (3.96 g, 17.28 mmol) and compound 1-12-2 (5.46 g, 19.81 mmol) in DCM (60 mL) was added DIPEA (3.4 mL, 20.67 mmol) dropwise at 0° C. At the end of the addition, the mixture was stirred at rt for 3.0 hrs. After the reaction was completed, the mixture was quenched with ice water (50 mL). The aqueous layer was extracted with DCM (50 mL×3). The combined organic layers were washed with brine, dried over anhydrous $Na_2SO_4$ and concentrated in vacuo. The residue was purified by silica gel column chromatography (PE/EtOAc (v/v)=5/1) to give the title compound as a white solid (4.48 g, 61%). The compound was characterized by the following spectroscopic data:

MS (ESI, pos.ion) m/z: 426.3 [M+H]$^+$; and $^1$H NMR (400 MHz, CDCl$_3$) δ (ppm): 7.82-7.78 (m, 2H), 7.67-7.64 (m, 2H), 5.27 (m, 2H), 4.79-4.74 (m, 1H), 3.96-3.89 (m, 1H), 3.09-3.00 (m, 1H), 2.15-2.06 (m, 2H), 1.42 (s, 9H), 1.27-1.02 (m, 4H).

Step 2) The Preparation of Compound 13-3

A suspension of compound 13-2 (4.52 g, 10.64 mmol) and ammonium acetate (16.4 g, 212.73 mmol) in toluene (50 mL) was stirred at 110° C. for 5.0 hrs. After the reaction was completed, the mixture was cooled to rt and quenched with water (50 mL). The aqueous layer was extracted with EtOAc (100 mL×3). The combined organic layers were washed with brine, dried over anhydrous $Na_2SO_4$ and concentrated in vacuo. The residue was purified by silica gel column chromatography (PE/EtOAc (v/v)=8/1) to give the title compound (2.15 g, 50%). The compound was characterized by the following spectroscopic data:

MS (ESI, pos.ion) m/z: 406.3 [M+H]$^+$; and $^1$H NMR (400 MHz, CDCl$_3$) δ (ppm): 7.58 (s, 1H), 7.45-7.41 (m, 2H), 7.29-7.26 (m, 2H), 4.78-4.73 (m, 1H), 3.80-3.73 (m, 1H), 3.15-3.05 (m, 1H), 2.11-2.03 (m, 1H), 1.86-1.74 (m, 1H), 1.72-1.51 (m, 2H), 1.39 (s, 9H), 1.25-1.02 (m, 2H).

Step 3) The Preparation of Compound 13-4

A mixture of compound 13-3 (2.11 g, 5.2 mmol), compound 1-14-2 (1.59 g, 6.25 mmol), Pd(dppf)Cl$_2$.CH$_2$Cl$_2$ (0.43 g, 0.52 mmol) and KOAc (1.54 g, 15.63 mmol) in DMF (30 mL) was stirred at 90° C. under N$_2$ for 3.0 hrs. After the reaction was completed, the mixture was cooled to rt, diluted with EtOAc (250 mL) and filtered through a celite pad. The filtrate was washed with water (80 mL×3) and brine, dried over anhydrous Na$_2$SO$_4$ and concentrated in vacuo. The residue was purified by silica gel column chromatography (PE/EtOAc (v/v)=2/1) to give the title compound (2.0 g, 85%). The compound was characterized by the following spectroscopic data:

MS (ESI, pos.ion) m/z: 454.3 [M+H]$^+$; and $^1$H NMR (400 MHz, CDCl$_3$) δ (ppm): 7.64-7.61 (m, 2H), 7.60-7.57 (m, 2H), 7.21 (s, 1H), 4.78-4.73 (m, 1H), 3.80-3.73 (m, 1H), 3.15-3.05 (m, 1H), 2.11-2.03 (m, 1H), 1.86-1.74 (m, 1H), 1.72-1.51 (m, 2H), 1.39 (s, 9H), 1.35 (q, 6H), 1.32 (q, 6H), 1.25-1.02 (m, 2H).

Step 4) The Preparation of Compound 13-5

To a mixture of compound 13-4 (1.19 g, 2.62 mmol), compound 1-11 (1.1 g, 2.62 mmol), Pd(PPh$_3$)$_4$ (0.12 g, 0.1 mmol) and KF (0.30 g, 5.24 mmol) were added DME (12 mL) and H$_2$O (3 mL) via syringe under N$_2$, and the mixture was stirred at 90° C. for 2.0 hrs. After the reaction was completed, the mixture was cooled to rt, and diluted with EtOAc (100 mL). The resulting mixture was washed with water (50 mL×3) and brine, dried over anhydrous Na$_2$SO$_4$ and concentrated in vacuo. The residue was purified by silica gel column chromatography (DCM/MeOH (v/v)=150/1) to give the title compound as a white solid (0.97 g, 60%). The compound was characterized by the following spectroscopic data:

MS (ESI, pos.ion) m/z: 618.5 [M+H]$^+$; and $^1$H NMR (400 MHz, CDCl$_3$) δ (ppm): 7.59-7.56 (m, 3H), 7.52-7.47 (m, 2H), 7.26, 7.23 (s, s, 1H), 6.98, 6.96 (t, t, 1H), 4.78-4.72 (m, 1H), 4.28-4.20 (m, 1H), 3.44-3.35 (m, 1H), 3.09-2.87 (m, 3H), 2.70-2.52 (m, 2H), 2.20-2.03 (m, 3H), 1.87-1.74 (m, 1H), 1.72-1.64 (m, 1H), 1.63-1.51 (m, 2H), 1.50 (s, 9H), 1.25-1.02 (m, 2H).

Step 5) The Preparation of Compound 13-6

To a solution of compound 13-1 (2.45 g, 10.7 mmol) and HATU (4.88 g, 12.84 mmol) in THF (25 mL) was added DIPEA (1.95 mL, 11.8 mmol) at 0° C. After stirring at 0° C. for 0.5 hr, compound 2-10 (2.22 g, 11.9 mmol) was added in a portionwise manner. At the end of the addition, the mixture was stirred at rt for 4.0 hrs. After the reaction was completed, the mixture was quenched with water (50 mL), the THF solvent was removed, and the resulting mixture was extracted with EtOAc (50 mL×3). The combined organic layers were washed with brine, dried over anhydrous $Na_2SO_4$ and concentrated in vacuo. The residue was dissolved in glacial acetic acid (20 mL), and the solution was stirred at 40° C. overnight. After the reaction was completed, the mixture was concentrated in vacuo. The residue was dissolved in EtOAc (100 mL). The mixture was washed with $Na_2CO_3$ aqueous solution (50 mL×3), dried over anhydrous $Na_2SO_4$ and concentrated in vacuo. The residue was purified by silica gel column chromatography (PE/EtOAc (v/v)=1/2) to give the title compound (2.02 g, 50%). The compound was characterized by the following spectroscopic data:

MS (ESI, pos.ion) m/z: 381.5 [M+H]$^+$; and $^1$H NMR (400 MHz, CDCl$_3$) δ (ppm): 7.75-7.74 (m, 1H), 7.36, 7.33 (d, d, 1H), 7.20, 7.19, 7.17 (s, s, s, 1H), 5.12-5.06 (m, 1H), 4.30-4.22 (m, 1H), 2.96-2.87 (m, 1H), 2.21-2.13 (m, 1H), 1.93-1.80 (m, 1H), 1.70-1.63 (m, 1H), 1.54-1.51 (m, 1H), 1.50 (s, 9H), 1.24-1.06 (m, 2H).

Step 6) The Preparation of Compound 13-7

To a mixture of compound 13-6 (2.69 g, 7.1 mmol), compound 1-14-2 (2.72 g, 10.7 mmol), Pd(dppf)Cl$_2$.CH$_2$Cl$_2$ (0.65 g, 0.8 mmol) and KOAc (2.09 g, 21.3 mmol) was added DMF (30 mL) via syringe, and the mixture was stirred at 90° C. under N$_2$ for 3.0 hrs. After cooling to rt, the mixture was diluted with EtOAc (200 mL) and filtered through a celite pad. The filtrate was washed with water (50 mL×3) and brine, dried over anhydrous Na$_2$SO$_4$ and concentrated in vacuo. The residue was purified by silica gel column chromatography (PE/EtOAc (v/v)=1/2) to give the title compound as a beige solid (1.97 g, 65%). The compound was characterized by the following spectroscopic data:

MS (ESI, pos.ion) m/z: 428.5 [M+H]$^+$; and $^1$H NMR (400 MHz, CDCl$_3$) δ (ppm): 7.88 (q, 1H), 7.65, 7.63 (d, d, 1H), 7.38, 7.35 (d, d, 1H), 5.13-5.07 (m, 1H), 4.30-4.22 (m, 1H), 2.96-2.87 (m, 1H), 2.21-2.12 (m, 1H), 1.92-1.80 (m, 1H), 1.70-1.62 (m, 1H), 1.58-1.53 (m, 1H), 1.50 (s, 9H), 1.32, 1.29 (m, m, 12H), 1.25-1.06 (m, 2H).

Step 7) The Preparation of Compound 13-8

To a mixture of compound 13-7 (0.22 g, 0.522 mmol), compound 13-5 (0.32 g, 0.522 mmol), Pd(PPh$_3$)$_4$ (60.29 mg, 0.0522 mmol) and K$_2$CO$_3$ (0.22 g, 1.566 mmol) were added DME (6.0 mL) and pure water (2.0 mL) via syringe, and the mixture was stirred at 90° C. under N$_2$ for 3.0 hrs. After the reaction was completed, the mixture was cooled to rt and diluted with EtOAc (40 mL). The resulting mixture was washed with water (20 mL×3) and brine, dried over anhydrous Na$_2$SO$_4$ and concentrated in vacuo. The residue was purified by silica gel column chromatography (DCM/EtOH (v/v)=100/1) to give the title compound as a pale yellow solid (0.22 g, 55%). The compound was characterized by the following spectroscopic data:

MS (ESI, pos.ion) m/z: 769.5 [M+H]$^+$; and $^1$H NMR (400 MHz, CDCl$_3$) δ (ppm): 7.85, 7.83 (d, d, 1H), 7.62-7.53 (m, 7H), 7.52, 7.50 (d, d, 1H), 7.44, 7.42 (t, t, 1H), 5.06-4.99 (m, 1H), 4.78-4.72 (m, 1H), 4.29-4.20 (m, 2H), 3.75-3.67 (m, 1H), 3.13-3.03 (m, 1H), 2.97-2.87 (m, 2H), 2.68-2.54 (m, 2H), 2.22-2.03 (m, 5H), 1.92-1.74 (m, 2H), 1.72-1.53 (m, 5H), 1.50 (s, 18H), 1.25-1.02 (m, 4H).

Step 8) The Preparation of Compound 13-9

To a solution of compound 13-8 (0.46 g, 0.6 mmol) in EtOAc (4.0 mL) was added a solution of HCl in EtOAc (3.0 mL, 4 M) dropwise. At the end of the addition, the mixture was stirred at rt for 8.0 hrs. After the reaction was completed, the mixture was concentrated in vacuo. The residue was purified by beating in EtOAc (5.0 mL) and filtered to give the title compound as a pale yellow solid (0.39 g, 90%). The compound was characterized by the following spectroscopic data:

MS (ESI, pos.ion) m/z: 569.5 [M+H]$^+$.

Step 9) The Preparation of Compound 13-10

To a mixture of compound 13-9 (0.14 g, 0.2 mmol), compound 1-24-2 (73.57 mg, 0.42 mmol), EDCI (80.52 mg, 0.42 mmol) and HOAT (54.44 mg, 0.4 mmol) in DCM (5.0 mL) was added DIPEA (0.26 mL, 1.6 mmol) dropwise at 0° C. At the end of the addition, the mixture was stirred at rt for 3.0 hrs. After the reaction was completed, the mixture was diluted with DCM (50 mL) and washed with NH$_4$Cl aqueous solution and brine, dried over anhydrous Na$_2$SO$_4$ and concentrated in vacuo. The residue was purified by silica gel column chromatography (DCM/MeOH (v/v)=50/1) to give the title compound as pale yellow powder (97.14 mg, 55%). The compound was characterized by the following spectroscopic data:

MS (ESI, pos.ion) m/z: 442.5 [M+2H]$^{2+}$; and $^1$H NMR (400 MHz, CDCl$_3$) δ (ppm): 7.85, 7.83 (d, d, 1H), 7.62, 7.60 (s, s, 1H), 7.59-7.53 (m, 1H), 7.52, 7.50 (d, d, 1H), 7.44, 7.42 (t, t, 1H), 5.44-5.37 (m, 1H), 5.32, 5.29 (d, d, 2H), 4.78-4.72 (m, 1H), 4.40-4.34 (m, 2H), 3.79-3.67 (m, 3H), 3.63 (s, 6H), 3.13-3.03 (m, 1H), 2.86-2.76 (m, 2H), 2.68-2.54 (m, 2H), 2.25-2.08 (m, 5H), 2.06-1.93 (m, 2H), 1.88-1.69 (m, 2H), 1.67-1.42 (m, 5H), 1.22-1.00 (m, 4H), 0.97, 0.95 (m, m, 6H), 0.90, 0.89 (m, m, 6H).

Example 14

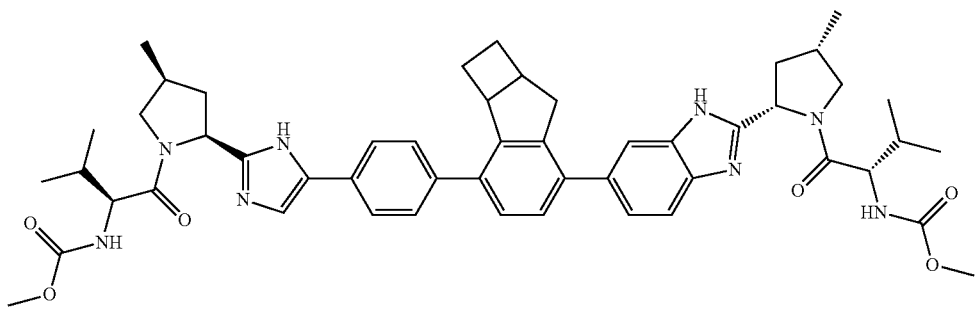

Synthetic Route:
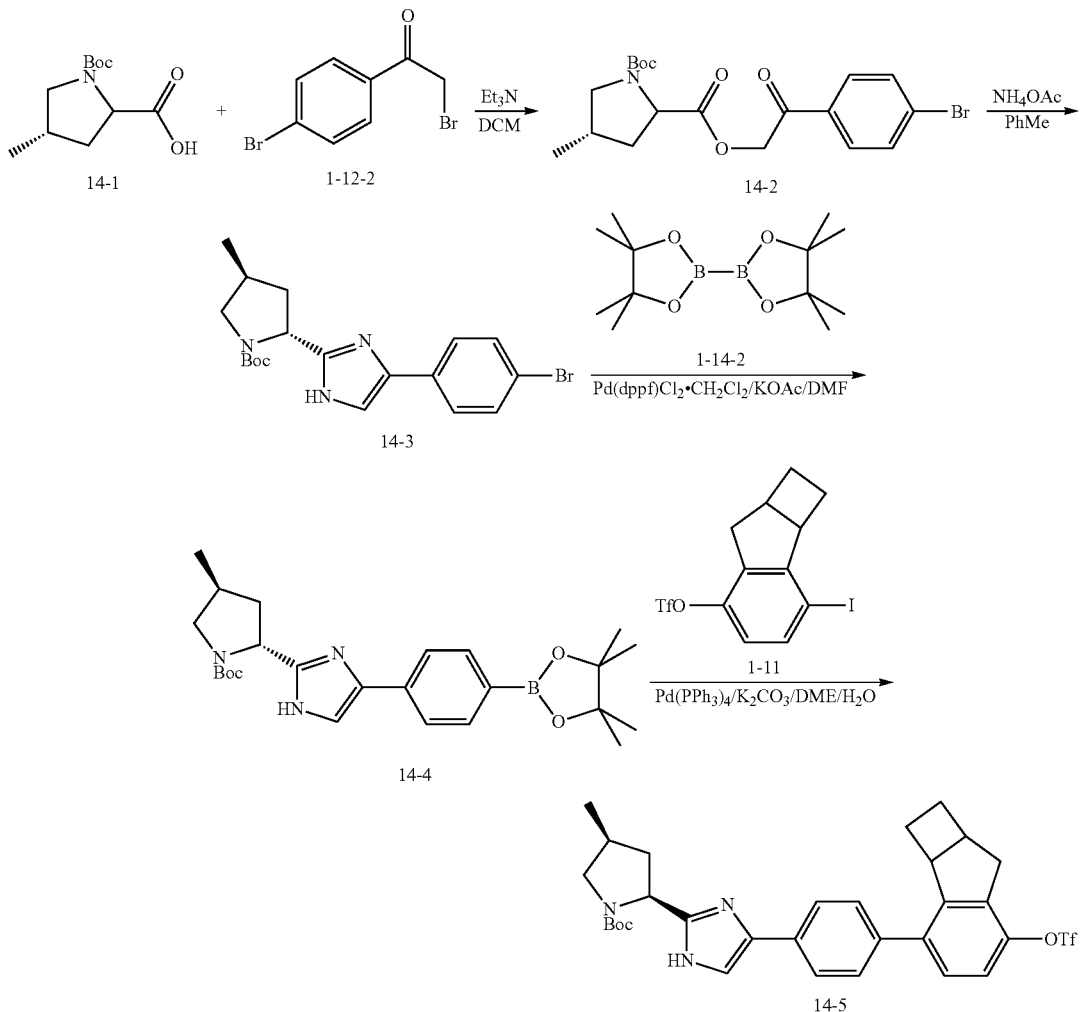
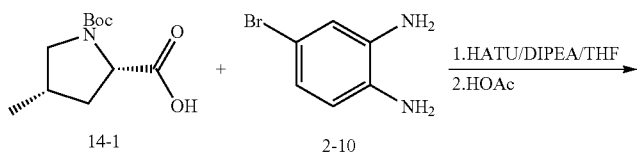
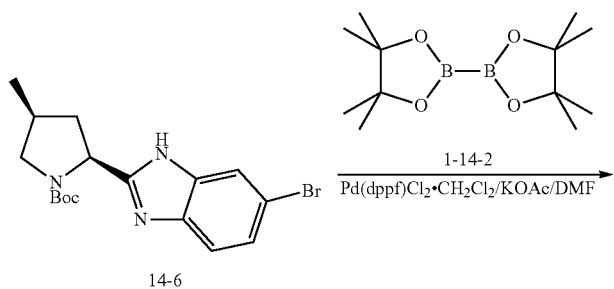

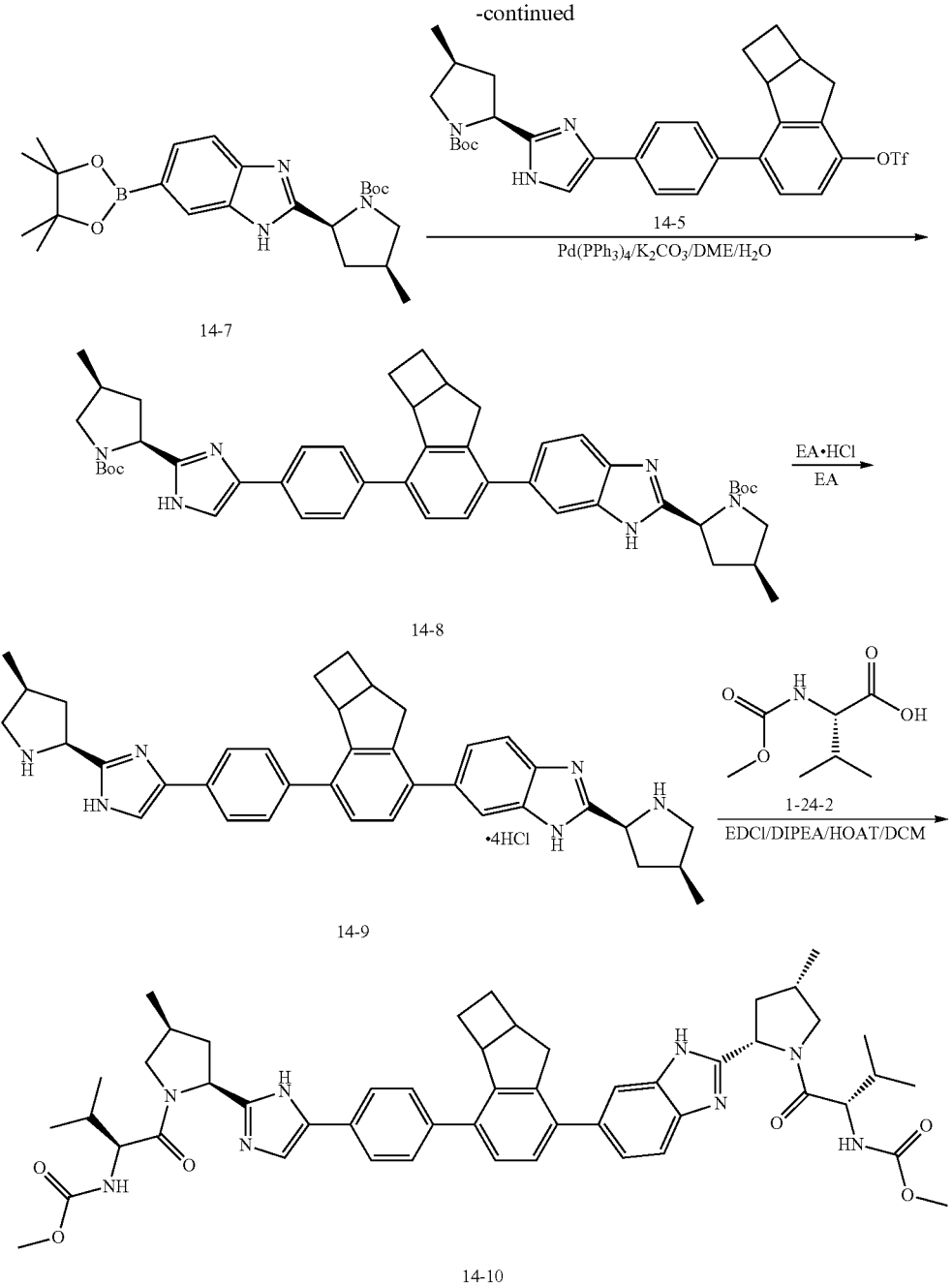

Step 1) The Preparation of Compound 14-2

To a solution of compound 14-1 (3.0 g, 13.1 mmol) and compound 1-12-2 (3.63 g, 13.1 mmol) in DCM (40 mL) was added Et$_3$N (3.9 mL, 26.3 mmol) dropwise at 0° C. At the end of the addition, the mixture was stirred at rt for 2.0 hrs. After the reaction was completed, the mixture was quenched with water (50 mL). The aqueous layer was extracted with DCM (50 mL×3). The combined organic layers were washed with brine, dried over anhydrous Na$_2$SO$_4$ and concentrated in vacuo to give the crude product (3.27 g), which was used for the next step without further purification. The compound was characterized by the following spectroscopic data:

MS (ESI, pos.ion) m/z: 499.5 [M+H]$^+$.

Step 2) The Preparation of Compound 14-3

A mixture of compound 14-2 (4.08 g, 8.2 mmol) and ammonium acetate (5.1 g, 66 mmol) in toluene (30 mL) was stirred at 110° C. for 5.0 hrs. After the reaction was cooled to rt, the mixture was quenched with water (50 mL). The aqueous layer was extracted with EtOAc (80 mL×3). The combined organic layers were washed with brine, dried over anhydrous Na$_2$SO$_4$ and concentrated in vacuo. The residue was purified by silica gel column chromatography (PE/EtOAc (v/v)=4/1) to give the title compound (2.85 g, 86%). The compound was characterized by the following spectroscopic data:

MS (ESI, pos.ion) m/z: 407.3 [M+H]$^+$; and $^1$H NMR (400 MHz, CDCl$_3$) δ (ppm): 7.45 (m, 4H), 7.20 (s, 1H), 4.93 (t, 1H, J=8.2 Hz), 3.88-3.66 (m, 1H), 2.90 (t, 1H, J=8.0 Hz), 2.50-2.47 (m, 2H), 2.27-2.25 (m, 1H), 1.48 (s, 7H), 1.26 (s, 2H), 1.12 (d, 3H, J=6.2 Hz).

Step 3) The Preparation of Compound 14-4

A mixture of compound 14-3 (2.8 g, 6.9 mmol), compound 1-14-2 (1.93 g, 7.6 mmol), Pd(dppf)Cl$_2$.CH$_2$Cl$_2$ (0.28 g, 0.34 mmol) and KOAc (1.7 g, 17.25 mmol) in DME (30 mL) was stirred at 90° C. under N$_2$ for 2.0 hrs. After the reaction was completed, the mixture was cooled to rt, diluted with EtOAc (200 mL) and filtered through a celite pad. The filtrate was washed with water (20 mL×3) and brine, dried over anhydrous Na$_2$SO$_4$ and concentrated in vacuo. The residue was purified by silica gel column chromatography (PE/EtOAc (v/v)=1/2) to give the title compound as a pale yellow solid (2.76 g, 88.2%). The compound was characterized by the following spectroscopic data:

MS (ESI, pos.ion) m/z: 454.3 [M+H]$^+$; and $^1$H NMR (400 MHz, CDCl$_3$) δ (ppm): 7.35 (m, 4H), 7.10 (s, 1H), 4.93 (t, 1H, J=8.2 Hz), 3.88-3.66 (m, 1H), 2.90 (t, 1H, J=8.0 Hz), 2.50-2.47 (m, 2H), 2.27-2.25 (m, 1H), 1.48 (s, 9H), 1.26 (s, 12H), 1.02 (d, 3H, J=6.2 Hz).

Step 4) The Preparation of Compound 14-5

To a mixture of compound 14-4 (3.49 g, 7.7 mmol), compound 1-11 (3.22 g, 7.7 mmol), Pd(PPh$_3$)$_4$ (0.45 g, 0.38 mmol) and K$_2$CO$_3$ (2.1 g, 15.4 mmol) were added DME (32 mL) and pure water (8.0 mL) via syringe. The mixture was stirred at 90° C. for 3.0 hrs. After the reaction was completed, the mixture was cooled to rt and diluted with EtOAc (250 mL). The resulting mixture was washed with water (50 mL×3) and brine, dried over anhydrous Na$_2$SO$_4$ and concentrated in vacuo. The residue was purified by silica gel column chromatography (PE/EtOAc (v/v)=2/1) to give the title compound as a pale yellow solid (2.85 g, 60%). The compound was characterized by the following spectroscopic data:

MS (ESI, pos.ion) m/z: 618.5 [M+H]$^+$; and $^1$H NMR (400 MHz, CDCl$_3$) δ (ppm): 7.74-7.66 (m, 4H), 7.36 (s, 1H), 7.26, 7.23 (s, s, 1H), 6.98, 6.96 (t, t, 1H), 4.81-4.76 (m, 1H), 3.80-3.73 (m, 1H), 3.44-3.36 (m, 1H), 3.10-2.97 (m, 3H), 2.70-2.52 (m, 2H), 2.33-2.08 (m, 4H), 1.74-1.66 (m, 1H), 1.61-1.51 (m, 1H), 1.42 (s, 9H), 0.96-0.93 (m, 3H).

Step 5) The Preparation of Compound 14-6

To a solution of compound 14-1 (2.45 g, 10.7 mmol) and HATU (4.88 g, 12.84 mmol) in THF (30 mL) was added DIPEA (1.95 mL, 11.8 mmol) at 0° C. After stirring at 0° C. for 0.5 hr, compound 2-10 (2.22 g, 11.9 mmol) was added in a portionwise manner. At the end of the addition, the mixture was stirred at rt for 4.0 hrs. After the reaction was completed, the mixture was quenched with water (50 mL), the THF solvent was removed, and the resulting mixture was extracted with EtOAc (50 mL×3). The combined organic layers were washed with brine, dried over anhydrous Na$_2$SO$_4$ and concentrated in vacuo. The residue was dissolved in glacial acetic acid (20 mL), and the solution was stirred at 40° C. overnight. After the reaction was completed, the mixture was concentrated in vacuo. The residue was dissolved in EtOAc (100 mL). The mixture was washed with Na$_2$CO$_3$ aqueous solution (50 mL×3), dried over anhydrous Na$_2$SO$_4$ and concentrated in vacuo. The residue was purified by silica gel column chromatography (PE/EtOAc (v/v)=1/2) to give the title compound (3.24 g, 80%). The compound was characterized by the following spectroscopic data:

MS (ESI, pos.ion) m/z: 380.5 [M+H]$^+$; and $^1$H NMR (400 MHz, CDCl$_3$) δ (ppm): 7.84 (d, 1H, J=2.9 Hz), 7.44 (d, 1H, J=15.0 Hz), 7.33 (dd, 1H, J=15.0 Hz, 2.9 Hz), 4.88 (t, 1H, J=16.9 Hz), 4.27 (dd, 1H, J=24.8 Hz, 17.3 Hz), 3.14 (dd, 1H, J=24.7 Hz, 17.3 Hz), 2.53 (dt, 1H, J=24.4 Hz, 17.2 Hz), 2.21-2.03 (m, 1H), 1.81 (dt, 1H, J=24.4 Hz, 17.2 Hz), 1.41 (s, 9H), 0.95 (d, 3H, J=12.7 Hz).

Step 6) The Preparation of Compound 14-7

To a mixture of compound 14-6 (4.27 g, 11.27 mmol), compound 1-14-2 (4.29 g, 16.9 mmol), Pd(dppf)Cl$_2$.CH$_2$Cl$_2$ (0.65 g, 0.8 mmol) and KOAc (2.09 g, 21.3 mmol) was added DME (30 mL) via syringe, and the mixture was stirred at 90° C. under N$_2$ for 3.0 hrs. After the reaction was completed, the DME solvent was removed, and 50 mL of water was added. The resulting mixture was extracted with EtOAc (50 mL×3). The combined organic layers were washed with brine, dried over anhydrous Na$_2$SO$_4$ and concentrated in vacuo. The residue was purified by silica gel column chromatography (PE/EtOAc (v/v)=3/1) to give the title compound as a beige solid (2.9 g, 60%). The compound was characterized by the following spectroscopic data:

MS (ESI, pos.ion) m/z: 428.5 [M+H]$^+$; and $^1$H NMR (400 MHz, CDCl$_3$) δ (ppm): 7.82 (dd, 1H), 7.65, 7.63 (d, d, 1H), 7.27, 7.25 (d, d, 1H), 5.07-5.02 (m, 1H), 3.85-3.78 (m, 1H), 3.14-3.07 (m, 1H), 2.51-2.42 (m, 1H), 2.30-2.16 (m, 1H), 1.86-1.78 (m, 1H), 1.41 (s, 9H), 1.32, 1.29 (m, m, 12H), 0.96-0.93 (m, 3H).

Step 7) The Preparation of Compound 14-8

To a mixture of compound 14-5 (0.36 g, 0.58 mmol), compound 14-7 (0.27 g, 0.63 mmol), Pd(PPh$_3$)$_4$ (35 mg, 0.03 mmol) and K$_2$CO$_3$ (0.08 g, 1.4 mmol) were added DME (8.0 mL) and pure water (2.0 mL) via syringe, and the mixture was stirred at 90° C. under N$_2$ for 4.0 hrs. After the reaction was completed, the mixture was cooled to rt and diluted with EtOAc (50 mL). The resulting mixture was washed with water (30 mL×3) and brine, dried over anhydrous Na$_2$SO$_4$ and concentrated in vacuo. The residue was purified by silica gel column chromatography (DCM/MeOH (v/v)=100/1) to give the title compound as a pale yellow solid (0.29 g, 65%). The compound was characterized by the following spectroscopic data:

MS (ESI, pos.ion) m/z: 769.5 [M+H]$^+$; and $^1$H NMR (400 MHz, CDCl$_3$) δ (ppm): 7.85, 7.83 (m, m, 1H), 7.78-7.74 (m, 2H), 7.70-7.66 (m, 2H), 7.62, 7.60 (s, s, 1H), 7.53, 7.51 (m, m, 1H), 7.44, 7.42 (m, m, 1H), 7.36 (s, 1H), 5.14-5.09 (m, 1H), 4.81-4.76 (m, 1H), 3.85-3.68 (m, 3H), 3.14-3.02 (m, 3H), 2.66-2.54 (m, 2H), 2.51-2.42 (m, 1H), 2.33-2.08 (m, 7H), 1.86-1.78 (m, 1H), 1.74-1.66 (m, 1H), 1.62-1.52 (m, 1H), 1.42 (s, 18H), 0.96-0.93 (m, 6H).

Step 8) The Preparation of Compound 14-9

To a solution of compound 14-8 (0.30 g, 0.4 mmol) in EtOAc (4.0 mL) was added a solution of HCl in EtOAc (3.0 mL, 4 M) dropwise. At the end of the addition, the mixture was stirred at rt for 8.0 hrs. After the reaction was completed, the mixture was concentrated in vacuo. The residue was purified by beating in EtOAc (5.0 mL) and filtered to give the title compound as a pale yellow solid (0.26 g, 90%), which was used for the next step without further purification. The compound was characterized by the following spectroscopic data: MS (ESI, pos.ion) m/z: 569.3 [M+H]$^+$.

Step 9) The Preparation of Compound 14-10

To a mixture of compound 14-9 (0.22 g, 0.31 mmol), compound 1-24-2 (0.12 g, 0.68 mmol), EDCI (0.13 g, 0.68 mmol) and HOAT (85 mg, 0.62 mmol) in DCM (20 mL) was added DIPEA (0.51 mL, 3.1 mmol) dropwise at 0° C. At the end of the addition, the mixture was stirred at rt for 3.0 hrs. After the reaction was completed, the mixture was diluted with DCM (20 mL) and washed with NH$_4$Cl aqueous solution and brine, dried over anhydrous Na$_2$SO$_4$ and concentrated in vacuo. The residue was purified by silica gel column chromatography (DCM/MeOH (v/v)=50/1) to give the title compound as a white solid (0.15 g, 56%). The compound was characterized by the following spectroscopic data:
MS (ESI, pos.ion) m/z: 442.3 [M+2H]$^{2+}$; and
$^1$H NMR (400 MHz, CDCl$_3$) δ (ppm): 7.85-7.83 (m, 1H), 7.62, 7.60 (s, s, 1H), 7.59 (s, 1H), 7.58-7.51 (m, 6H), 7.44, 7.42 (t, t, 1H), 5.32, 5.29 (d, d, 2H), 5.28-5.26 (m, 1H), 5.07-5.02 (m, 1H), 4.42-4.36 (m, 1H), 3.92-3.84 (m, 2H), 3.75-3.68 (m, 1H), 3.63 (s, 6H), 3.61-3.54 (m, 2H), 3.13-3.02 (m, 2H), 2.68-2.47 (m, 3H), 2.37-2.08 (m, 8H), 1.83-1.75 (m, 1H), 1.71-1.63 (m, 1H), 1.62-1.52 (m, 1H), 0.97-0.89 (m, 18H).
Example 15
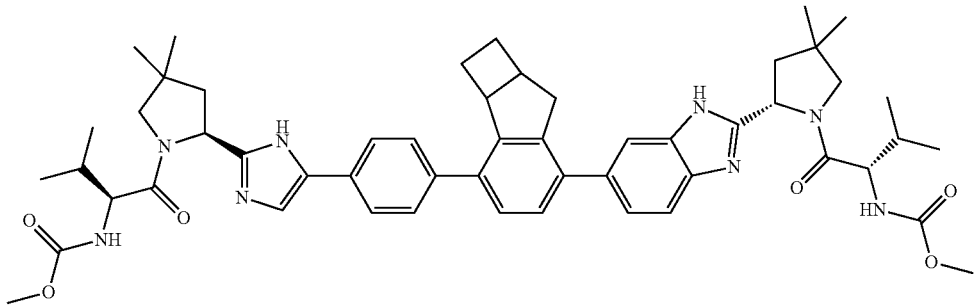
Synthetic Route:
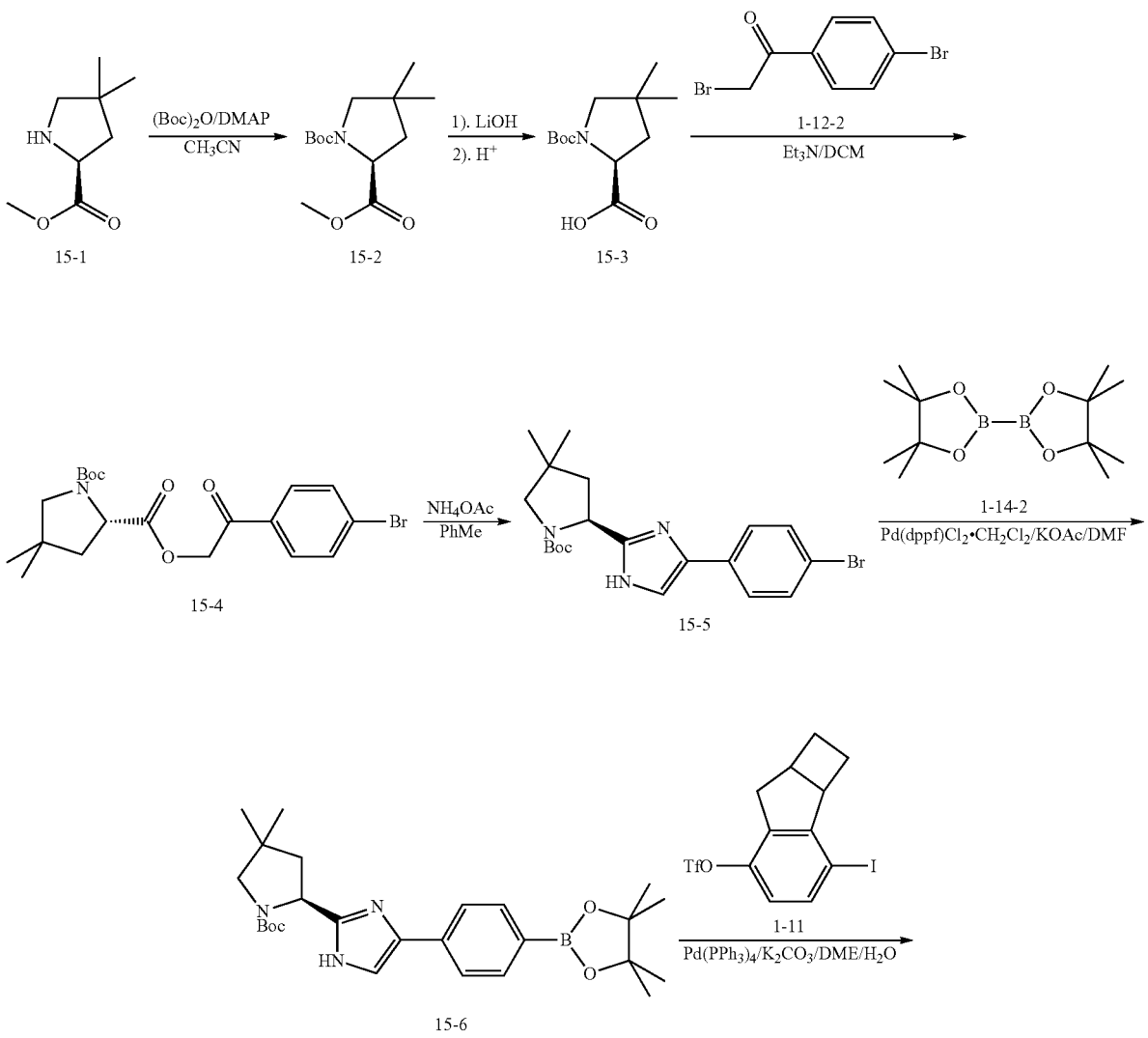

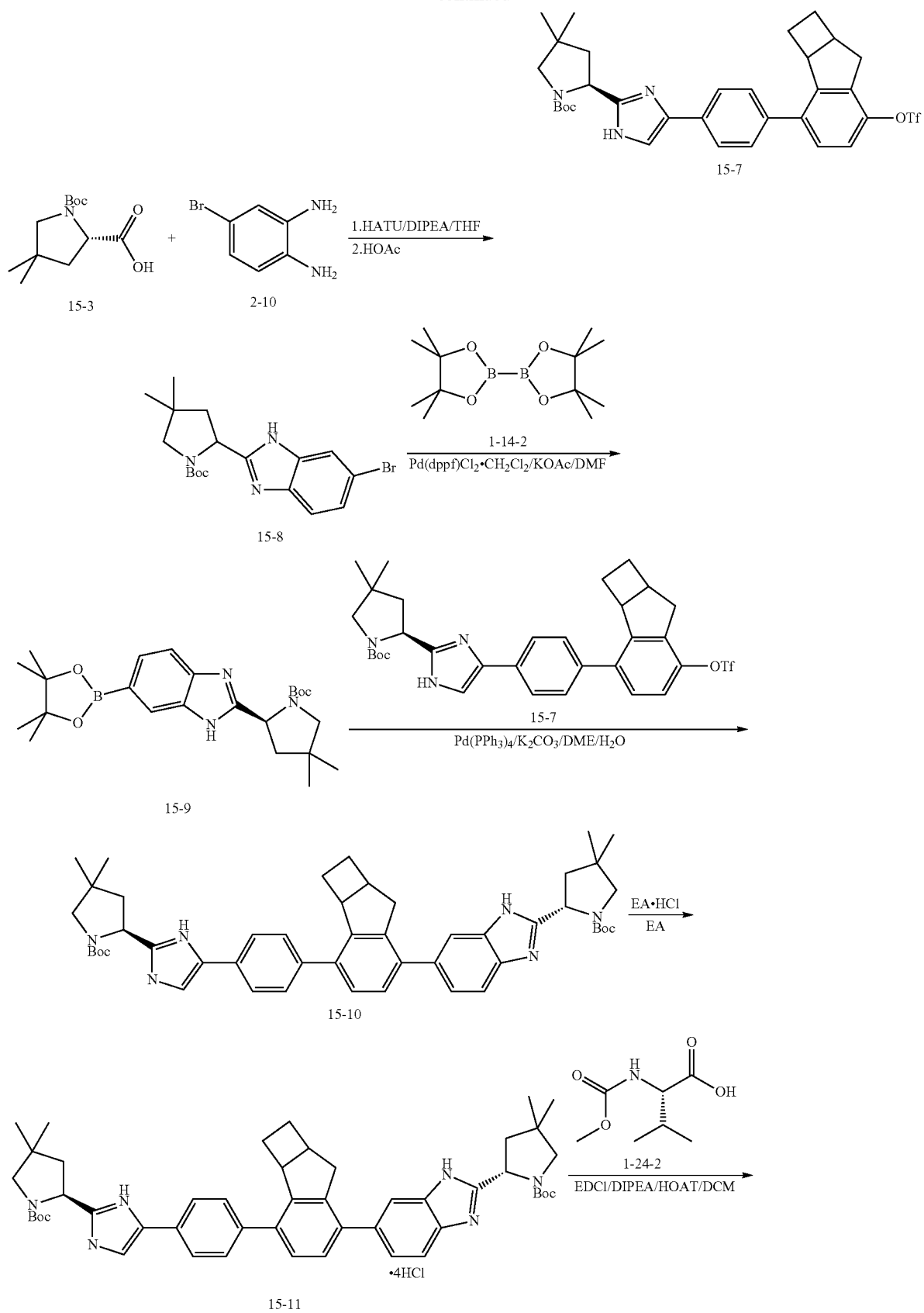

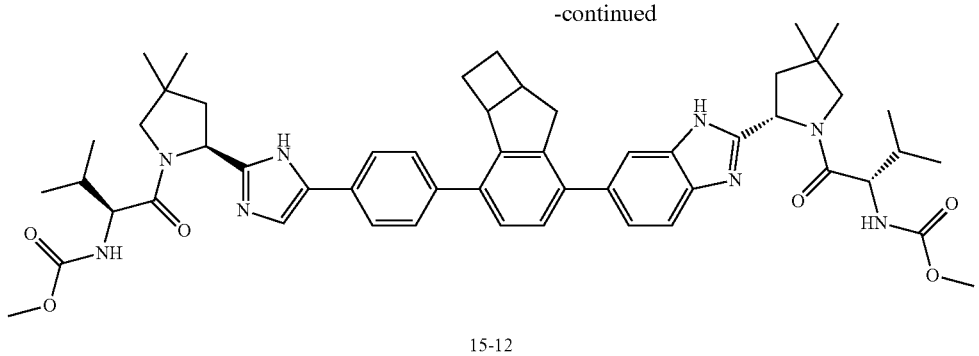

15-12

Step 1) The Preparation of Compound 15-2

To a solution of compound 15-1 (7.08 g, 45.06 mmol) in MeCN (50 mL) was added DMAP (0.55 g, 4.5 mmol) at 0° C. After the mixture was stirred for 10 mins, di-tert-butyl dicarbonate (10.82 g, 49.56 mmol) was added dropwise. At the end of the addition, the mixture was stirred at 0° C. for 30 mins and at rt for another 2.0 hrs. After the reaction was completed, the mixture was concentrated in vacuo. The residue was purified by silica gel column chromatography (PE/EtOAc (v/v)=1/1) to give the title compound as colorless liquid (7.54 g, 65%).

The compound was characterized by the following spectroscopic data:

MS (ESI, pos.ion) m/z: 157.2 [M-Boc]$^+$;

$^1$H NMR (400 MHz, CDCl$_3$) δ (ppm): 4.29-4.26 (m, 1H), 3.71 (s, 3H), 3.25-3.18 (m, 1H), 3.16-3.10 (m, 1H), 2.25-2.20 (m, 1H), 1.84-1.79 (m, 1H), 1.46 (s, 9H), 1.01-0.99 (m, 3H), 0.86-0.84 (m, 3H).

Step 2) The Preparation of Compound 15-3

To a solution of compound 15-2 (4.85 g, 18.86 mmol) in THF (40 mL) was added lithium hydroxide monohydrate aqueous solution (1.5 g, 20 mL) dropwise at 0° C. At the end of the addition, the mixture was stirred at rt for 2.0 hrs. After the reaction was completed, the THF solvent was removed and 50 mL of water was added to the mixture. The resulting mixture was washed with EtOAc (30 mL×3). The aqueous phase was adjusted to pH 1 with hydrochloric acid (1 M) and extracted with EtOAc (50 mL×3). The combined organic layers were washed with brine, dried over anhydrous Na$_2$SO$_4$ and concentrated in vacuo to give the title compound as a white solid (4.35 g, 95%). The compound was characterized by the following spectroscopic data:

MS (ESI, pos.ion) m/z: 244.5 [M+H]$^+$;

$^1$H NMR (400 MHz, CD$_3$OD) δ (ppm): 4.34-4.31 (m, 1H), 3.28-3.22 (m, 1H), 3.20-3.13 (m, 1H), 2.23-2.18 (m, 1H), 1.85-1.80 (m, 1H), 1.46 (s, 9H), 1.01-0.99 (m, 3H), 0.86-0.84 (m, 3H).

Step 3) The Preparation of Compound 15-4

To a solution of compound 15-3 (3.18 g, 13.1 mmol) and compound 1-12-2 (3.63 g, 13.1 mmol) in DCM (40 mL) was added Et$_3$N (3.9 mL, 26.3 mmol) dropwise at 0° C. At the end of the addition, the mixture was stirred at rt for 2.0 hrs. After the reaction was completed, the mixture was quenched with water (50 mL). The aqueous layer was extracted with DCM (50 mL×3). The combined organic layers were washed with brine, dried over anhydrous Na$_2$SO$_4$ and concentrated in vacuo to give the crude product (3.27 g), which was used for the next step without further purification. The compound was characterized by the following spectroscopic data:

MS (ESI, pos.ion) m/z: 413.5 [M+H]$^+$.

Step 4) The Preparation of Compound 15-5

A mixture of compound 15-4 (3.37 g, 8.2 mmol) and ammonium acetate (5.1 g, 66 mmol) in toluene (30 mL) was stirred at 110° C. for 5.0 hrs. After the reaction was cooled to rt, the mixture was quenched with water (50 mL). The aqueous layer was extracted with EtOAc (80 mL×3). The combined organic layers were washed with brine, dried over anhydrous Na$_2$SO$_4$ and concentrated in vacuo. The residue was purified by silica gel column chromatography (PE/EtOAc (v/v)=2/1) to give the title compound (2.75 g, 80%). The compound was characterized by the following spectroscopic data:

MS (ESI, pos.ion) m/z: 421.5 [M+H]$^+$; and $^1$H NMR (400 MHz, CDCl$_3$) δ (ppm): 7.63-7.60 (m, 2H), 7.49-7.45 (m, 2H), 7.31 (s, 1H), 5.04-4.99 (m, 1H), 3.41-3.34 (m, 1H), 3.30-3.24 (m, 1H), 2.25-2.19 (m, 1H), 1.87-1.81 (m, 1H), 1.53 (s, 9H), 1.01-0.99 (m, 3H), 0.86-0.84 (m, 3H).

Step 5) The Preparation of Compound 15-6

A mixture of compound 15-5 (2.89 g, 6.9 mmol), compound 1-14-2 (1.93 g, 7.6 mmol), Pd(dppf)Cl$_2$.CH$_2$Cl$_2$ (0.28 g, 0.34 mmol) and KOAc (1.7 g, 17.25 mmol) in DME (30 mL) was stirred at 90° C. under N$_2$ for 2.0 hrs. After the reaction was completed, the mixture was cooled to rt, diluted with EtOAc (200 mL) and filtered through a celite pad. The filtrate was washed with water (20 mL×3) and brine, dried over anhydrous Na$_2$SO$_4$ and concentrated in vacuo. The residue was purified by silica gel column chromatography (PE/EtOAc (v/v)=1/1) to give the title compound as a pale yellow solid (2.74 g, 85%). The compound was characterized by the following spectroscopic data:

MS (ESI, pos.ion) m/z: 468.5 [M+H]$^+$; and $^1$H NMR (400 MHz, CDCl$_3$) δ (ppm): 8.23-8.20 (m, 2H), 7.79-7.76 (m, 2H), 7.23 (s, 1H), 5.04-4.99 (m, 1H), 3.41-3.34 (m, 1H), 3.30-3.24 (m, 1H), 2.25-2.19 (m, 1H), 1.87-1.81 (m, 1H), 1.53 (s, 9H), 1.35, 1.32 (m, m, 12H), 1.01-0.99 (m, 3H), 0.86-0.84 (m, 3H).

Step 6) The Preparation of Compound 15-7

To a mixture of compound 15-6 (3.60 g, 7.7 mmol), compound 1-11 (3.22 g, 7.7 mmol), Pd(PPh$_3$)$_4$ (0.45 g, 0.38 mmol) and K$_2$CO$_3$ (2.1 g, 15.4 mmol) were added DME (32 mL) and pure water (8.0 mL) via syringe. The mixture was stirred at 90° C. for 3.0 hrs. After the reaction was completed, the mixture was cooled to rt and diluted with EtOAc (250 mL). The resulting mixture was washed with water (50 mL×3) and brine, dried over anhydrous Na$_2$SO$_4$ and concentrated in vacuo. The residue was purified by silica gel column chromatography (PE/EtOAc (v/v)=1/2) to give the title compound as a pale yellow solid (2.92 g, 60%). The compound was characterized by the following spectroscopic data:

MS (ESI, pos.ion) m/z: 632.5 [M+H]$^+$; and $^1$H NMR (400 MHz, CDCl$_3$) δ (ppm): 7.74-7.66 (m, 4H), 7.39 (s, 1H), 7.26, 7.23 (s, s, 1H), 6.98, 6.96 (t, t, 1H), 5.04-4.99 (m, 1H), 3.44-3.34 (m, 2H), 3.30-3.24 (m, 1H), 3.10-2.97 (m, 2H), 2.70-2.52 (m, 2H), 2.25-2.08 (m, 3H), 1.87-1.81 (m, 1H), 1.61-1.51 (m, 1H), 1.41 (s, 9H), 1.01-0.99 (m, 3H), 0.86-0.84 (m, 3H).

Step 7) The Preparation of Compound 15-8

To a solution of compound 15-3 (2.6 g, 10.7 mmol) and HATU (4.88 g, 12.84 mmol) in THF (30 mL) was added DIPEA (1.95 mL, 11.8 mmol) at 0° C. After stirring at 0° C. for 0.5 hr, compound 2-10 (2.22 g, 11.9 mmol) was added in a portionwise manner. At the end of the addition, the mixture was stirred at rt for 4.0 hrs. After the reaction was completed, the mixture was quenched with water (50 mL), the THF solvent was removed, and the resulting mixture was extracted with EtOAc (50 mL×3). The combined organic layers were washed with brine, dried over anhydrous Na$_2$SO$_4$ and concentrated in vacuo. The residue was dissolved in glacial acetic acid (20 mL), and the solution was stirred at 40° C. overnight. After the reaction was completed, the mixture was concentrated in vacuo. The residue was dissolved in EtOAc (100 mL). The mixture was washed with Na$_2$CO$_3$ aqueous solution (50 mL×3), dried over anhydrous Na$_2$SO$_4$ and concentrated in vacuo. The residue was purified by silica gel column chromatography (PE/EtOAc (v/v)=1/2) to give the title compound (2.70 g, 65%). The compound was characterized by the following spectroscopic data:

MS (ESI, pos.ion) m/z: 395.5 [M+H]$^+$; and $^1$H NMR (400 MHz, CDCl$_3$) δ (ppm): 7.71-7.70 (q, 1H), 7.33, 7.30 (d, d, 1H), 7.20, 7.18 (d, d, 1H), 5.32-5.27 (m, 1H), 3.41-3.34 (m, 1H), 3.30-3.23 (m, 1H), 2.38-2.32 (m, 1H), 2.00-1.94 (m, 1H), 1.41 (s, 9H), 1.01-0.99 (m, 3H), 0.86-0.84 (m, 3H).

Step 8) The Preparation of Compound 15-9

To a mixture of compound 15-8 (4.43 g, 11.27 mmol), compound 1-14-2 (4.29 g, 16.9 mmol), Pd(dppf)Cl$_2$.CH$_2$Cl$_2$ (0.65 g, 0.8 mmol) and KOAc (2.09 g, 21.3 mmol) was added DME (30 mL) via syringe, and the mixture was stirred at 90° C. under N$_2$ for 3.0 hrs. After the reaction was completed, the DME solvent was removed, and 50 mL of water was added. The resulting mixture was extracted with EtOAc (50 mL×3). The combined organic layers were washed with brine, dried over anhydrous Na$_2$SO$_4$ and concentrated in vacuo. The residue was purified by silica gel column chromatography (PE/EtOAc (v/v)=3/1) to give the title compound as a beige solid (2.74 g, 55%). The compound was characterized by the following spectroscopic data:

MS (ESI, pos.ion) m/z: 442.5 [M+H]$^+$; and $^1$H NMR (400 MHz, CDCl$_3$) δ (ppm): 7.84-7.83 (q, 1H), 7.65, 7.63 (d, d, 1H), 7.36, 7.34 (d, d, 1H), 5.26-5.21 (m, 1H), 3.40-3.34 (m, 1H), 3.30-3.23 (m, 1H), 2.38-2.32 (m, 1H), 2.00-1.94 (m, 1H), 1.41 (s, 9H), 1.32, 1.29 (m, m, 12H), 1.01-0.99 (m, 3H), 0.86-0.84 (m, 3H).

Step 9) The Preparation of Compound 15-10

To a mixture of compound 15-7 (0.37 g, 0.58 mmol), compound 15-9 (0.28 g, 0.63 mmol), Pd(PPh$_3$)$_4$ (35 mg, 0.03 mmol) and K$_2$CO$_3$ (80 mg, 1.4 mmol) were added DME (8.0 mL) and pure water (2.0 mL) via syringe, and the mixture was stirred at 90° C. under N$_2$ for 4.0 hrs. After the reaction was completed, the mixture was cooled to rt and diluted with EtOAc (50 mL). The resulting mixture was washed with water (30 mL×3) and brine, dried over anhydrous Na$_2$SO$_4$ and concentrated in vacuo. The residue was purified by silica gel column chromatography (DCM/MeOH (v/v)=100/1) to give the title compound as a pale yellow solid (0.3 g, 65%). The compound was characterized by the following spectroscopic data:

MS (ESI, pos.ion) m/z: 798.5 [M+H]$^+$; and $^1$H NMR (400 MHz, CDCl$_3$) δ (ppm): 7.85, 7.83 (d, d, 1H), 7.62, 7.60 (s, s, 1H), 7.59-7.52 (m, 7H), 7.44, 7.42 (t, t, 1H), 5.27-5.22 (m, 1H), 5.08-5.03 (m, 1H), 3.76-3.68 (m, 1H), 3.41-3.34 (m, 2H), 3.30-3.23 (m, 2H), 3.13-3.02 (m, 1H), 2.68-2.54 (m, 2H), 2.38-2.32 (m, 1H), 2.25-2.08 (m, 4H), 2.00-1.94 (m, 1H), 1.87-1.81 (m, 1H), 1.62-1.54 (m, 1H), 1.53 (s, 9H), 1.41 (s, 9H), 1.01-0.99 (m, 6H), 0.86-0.84 (m, 6H).

Step 10) The Preparation of Compound 15-11

To a solution of compound 15-10 (0.32 g, 0.4 mmol) in EtOAc (4.0 mL) was added a solution of HCl in EtOAc (3.0 mL, 4 M) dropwise. At the end of the addition, the mixture was stirred at rt for 8.0 hrs. After the reaction was completed, the mixture was concentrated in vacuo. The residue was purified by beating in EtOAc (5.0 mL) and filtered to give the title compound as a pale yellow solid (0.27 g, 90%), which was used for the next step without further purification. The compound was characterized by the following spectroscopic data:

MS (ESI, pos.ion) m/z: 597.3 [M+H]$^+$.

Step 11) The Preparation of Compound 15-12

To a mixture of compound 15-11 (0.23 g, 0.31 mmol), compound 1-24-2 (0.12 g, 0.68 mmol), EDCI (0.13 g, 0.68 mmol) and HOAT (85 mg, 0.62 mmol) in DCM (20 mL) was added DIPEA (0.51 mL, 3.1 mmol) dropwise at 0° C. At the end of the addition, the mixture was stirred at rt for 3.0 hrs. After the reaction was completed, the mixture was diluted with DCM (20 mL) and washed with NH$_4$Cl aqueous solution and brine, dried over anhydrous Na$_2$SO$_4$ and concentrated in vacuo. The residue was purified by silica gel column chromatography (DCM/MeOH (v/v)=50/1) to give the title compound as a white solid (0.16 g, 56%). The compound was characterized by the following spectroscopic data:

MS (ESI, pos.ion) m/z: 456.5 [M+2H]$^{2+}$; and $^1$H NMR (400 MHz, CDCl$_3$) δ (ppm): 7.85, 7.83 (d, d, 1H), 7.62, 7.60 (s, s, 1H), 7.59-7.52 (m, 7H), 7.44, 7.42 (t, t, 1H), 5.40-5.34 (m, 1H), 5.32, 5.30 (d, d, 1H), 5.21-5.16 (m, 1H), 4.40-4.34 (m, 2H), 3.76-3.68 (m, 1H), 3.63 (s, 6H), 3.57-3.50 (m, 1H), 3.48-3.39 (m, 2H), 3.27-3.20 (m, 1H), 3.13-3.02 (m, 2H), 2.68-2.54 (m, 2H), 2.38-2.33 (m, 1H), 2.28-2.08 (m, 6H), 1.99-1.93 (m, 1H), 1.88-1.81 (m, 1H), 1.62-1.52 (m, 1H), 1.01-0.99 (m, 6H), 0.97, 0.95 (m, m, 6H), 0.91, 0.89 (m, m, 6H), 0.86-0.84 (m, 6H).

Example 16

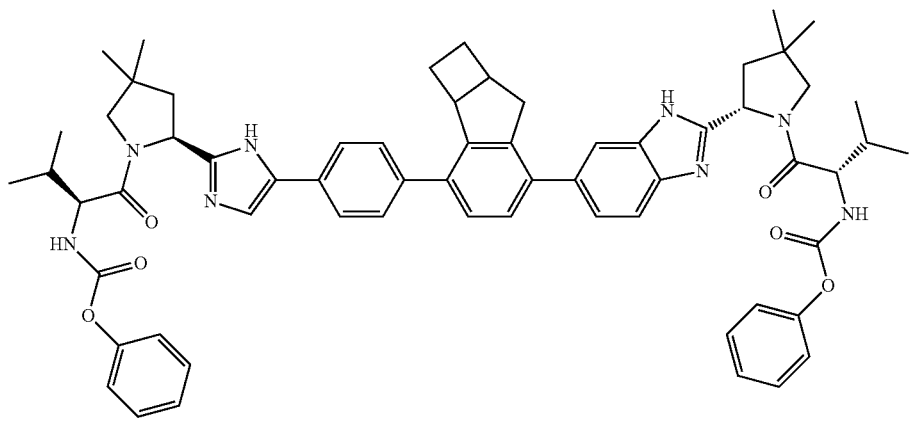 [SMILES: CC(C)[C@H](NC(=O)Oc1ccccc1)C(=O)N1CC(C)(C)C[C@H]1c1ncc(-c2ccc(-c3ccc(-c4ccc5nc([C@@H]6CC(C)(C)CN6C(=O)[C@@H](NC(=O)Oc6ccccc6)C(C)C)[nH]c5c4)c4c3C3CCC3C4)cc2)[nH]1]

Synthetic Route:

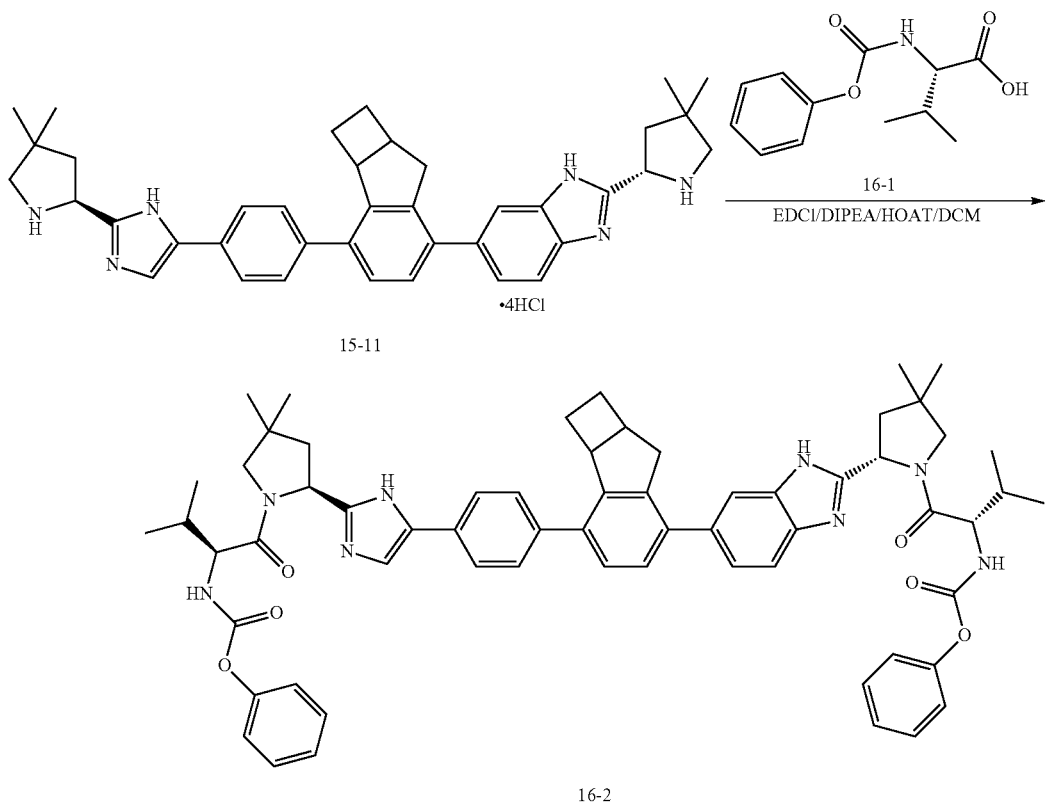

Step 1) The Preparation of Compound 16-2

To a mixture of compound 15-11 (0.23 g, 0.31 mmol), compound 16-1 (0.16 g, 0.68 mmol), EDCI (0.13 g, 0.68 mmol) and HOAT (85 mg, 0.62 mmol) in DCM (20 mL) was added DIPEA (0.51 mL, 3.1 mmol) dropwise at 0° C. At the end of the addition, the mixture was stirred at rt for 3.0 hrs. After the reaction was completed, the mixture was diluted with DCM (20 mL) and washed with NH$_4$Cl aqueous solution and brine, dried over anhydrous Na$_2$SO$_4$ and concentrated in vacuo. The residue was purified by silica gel column chromatography (DCM/MeOH (v/v)=50/1) to give the title compound as a white solid (0.21 g, 65%). The compound was characterized by the following spectroscopic data:

MS (ESI, pos.ion) m/z: 518.6 [M+2H]$^{2+}$; and $^1$H NMR (400 MHz, CDCl$_3$) δ (ppm): 10.28 (brs, 2H), 7.85, 7.83 (d, d, 1H), 7.62, 7.60 (s, s, 1H), 7.59-7.52 (m, 7H), 7.44, 7.42 (t, t, 1H), 7.36-7.30 (m, 4H), 7.24-7.19 (m, 2H), 7.13-7.10 (m, 4H), 5.48, 5.46 (d, d, 2H), 5.40-5.35 (m, 1H), 5.21-5.16 (m, 1H), 4.47-4.41 (m, 2H), 3.75-3.68 (m, 1H), 3.57-3.50 (m, 1H), 3.48-3.39 (m, 2H), 3.27-3.20 (m, 1H), 3.13-3.02 (m, 1H), 2.68-2.54 (m, 2H), 2.38-2.33 (m, 1H), 2.28-2.08 (m, 6H), 1.99-1.93 (m, 1H), 1.88-1.81 (m, 1H), 1.62-1.52 (m, 1H), 1.01-0.99 (m, 6H), 0.97, 0.95 (m, m, 6H), 0.90, 0.88 (m, m, 6H), 0.86-0.84 (m, 6H).

Example 17
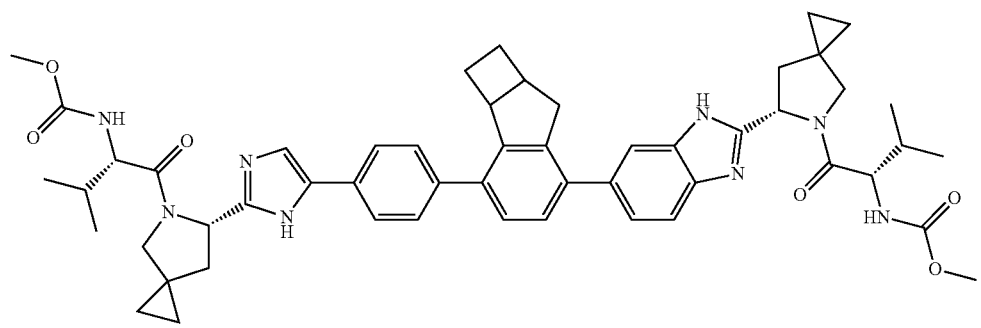
Synthetic Route:
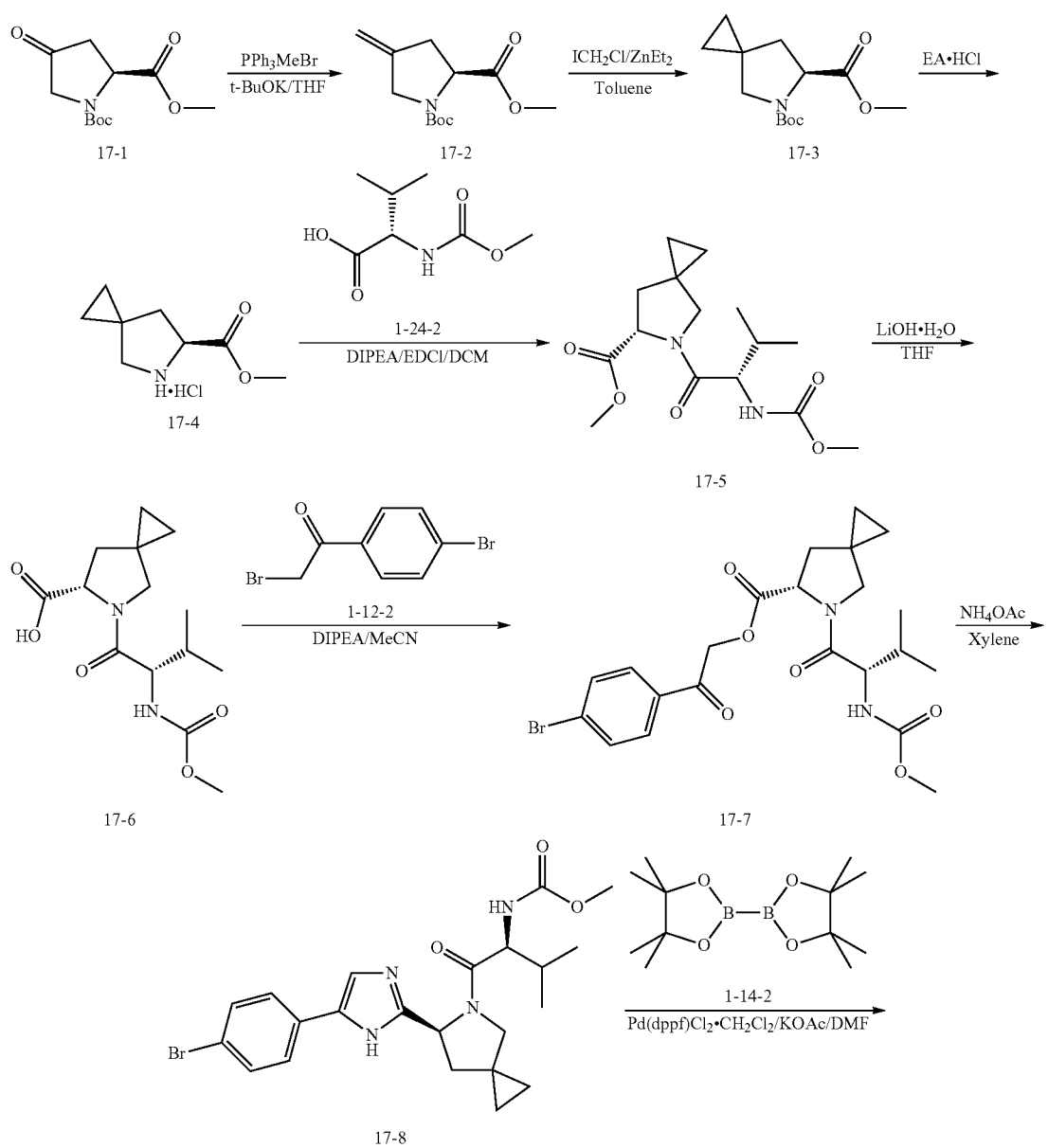

-continued
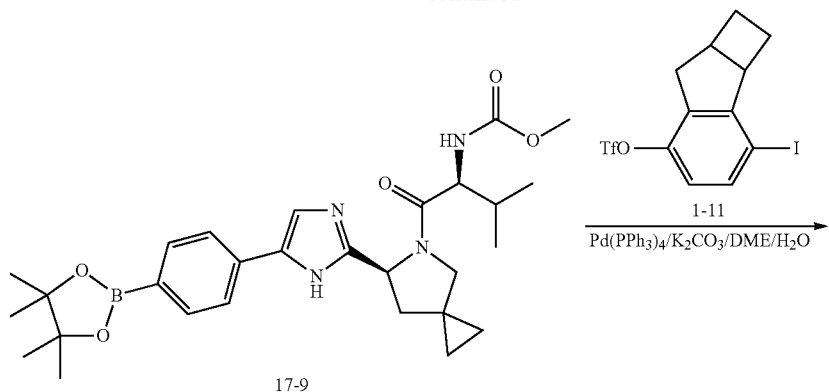
17-9
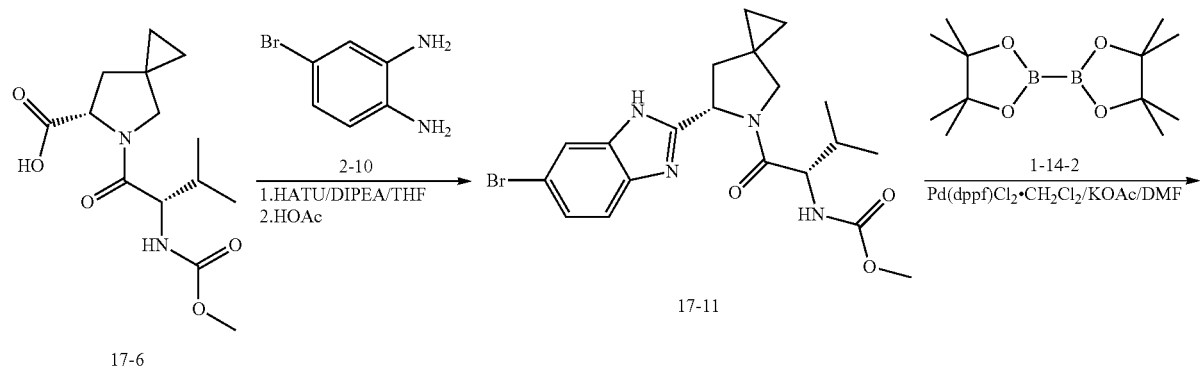
17-10
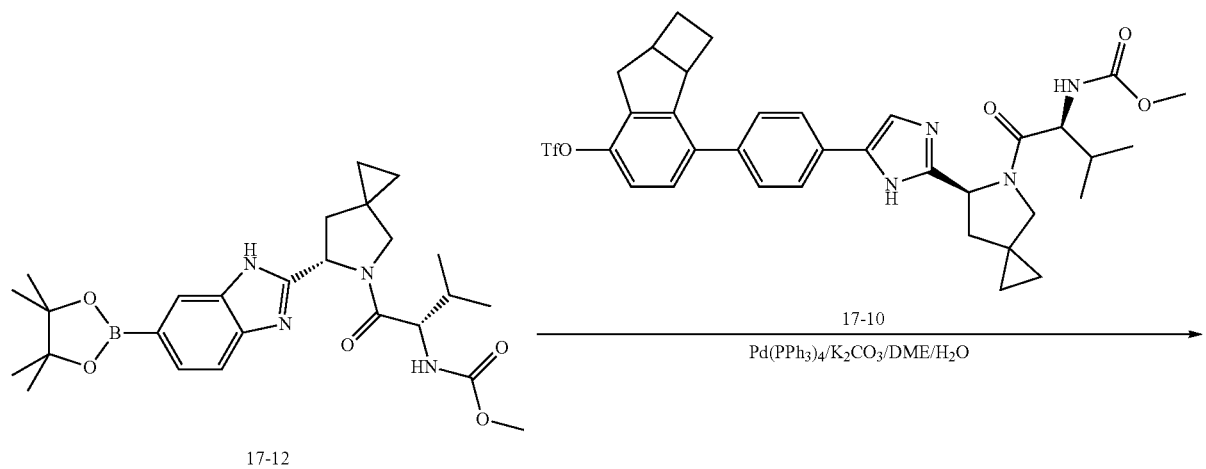
17-11
17-12

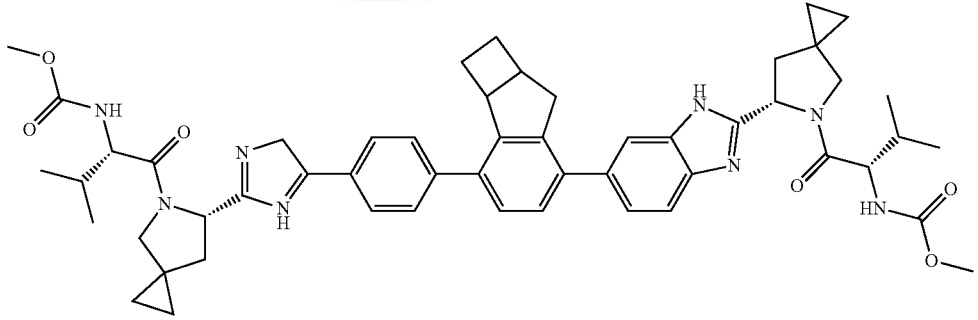

17-13

Step 1) The Preparation of Compound 17-2

To a suspension of PPh₃MeBr (5.05 g, 14.2 mmol) in THF (50.0 m) was added potassium tert-butanolate (14.9 mL, 14.9 mmol, 1.0 M in THF) dropwise at −20° C. At the end of the addition, the mixture was heated to −5 OC and stirred for 30 mins, and then compound 17-1 (1.72 g, 7.07 mmol) was added. The mixture was stirred at rt for 1.0 hrs. After the reaction was completed, the mixture was quenched with ice water (50 mL), and the THF solvent was removed. The aqueous layer was extracted with EtOAc (50 mL×3). The combined organic layers were washed with brine, dried over anhydrous Na₂SO₄ and concentrated in vacuo. The residue was purified by silica gel column chromatography (PE/EtOAc (v/v)=5/1) to give the title compound as pale yellow oil (1.07 g, 62.9%). The compound was characterized by the following spectroscopic data:

MS (ESI, pos.ion) m/z: 242.1 [M+H]⁺; and

¹H NMR (400 MHz, DMSO-d₆) δ (ppm): 5.01 (d, 2H, J=10.8 Hz), 4.36 (t, 1H, J=11.2 Hz), 3.95 (s, 2H), 3.24 (s, 3H), 3.01 (q, 1H, J=14.6 Hz), 2.57-2.50 (m, 1H), 1.38 (s, 9H).

Step 2) The Preparation of Compound 17-3

To a solution of diethylzinc (2.30 g, 18.60 mmol) in toluene (30 mL) was added chloroiodomethane (6.57 g, 37.24 mmol) dropwise at 0° C. At the end of the addition, the mixture was stirred at 0° C. for 45 mins, and then a solution of compound 17-2 (1.5 g, 6.22 mmol) in toluene (15 mL) was added. The mixture was stirred at 0° C. for 18 hrs. After the reaction was completed, the mixture was quenched with saturated NH₄Cl aqueous solution (20 mL). The aqueous layer was extracted with EtOAc (25 mL×3). The combined organic layers were dried over anhydrous Na₂SO₄ and concentrated in vacuo. The residue was purified by silica gel column chromatography (PE/EtOAc (v/v)=10/1) to give the title compound as white liquid (0.58 g, 36.5%). The compound was characterized by the following spectroscopic data:

MS (ESI, pos.ion) m/z: 156.2 [M-Boc]⁺; and

¹H NMR (400 MHz, CDCl₃) δ (ppm): 4.47-4.33 (m, 1H), 3.71 (s, 3H), 3.37-3.29 (m, 2H), 2.25-2.17 (m, 1H), 1.86-1.75 (m, 1H), 1.44, 1.40 (s, s, 9H), 0.62-0.50 (m, 4H).

Step 3) The Preparation of Compound 17-4

To a solution of compound 17-3 (0.69 g, 2.7 mmol) in EtOAc (6.0 mL) was added a solution of HCl in EtOAc (5.0 mL, 4 M) dropwise. At the end of the addition, the mixture was stirred at rt for 8.0 hrs. After the reaction was completed, the mixture was concentrated in vacuo to give the title compound as colorless oil (0.5 g, 96.5%). The compound was characterized by the following spectroscopic data:

MS (ESI, pos.ion) m/z: 156.2 [M+H]⁺; and

¹H NMR (400 MHz, CD₃OD) δ (ppm): 4.66-4.62 (m, 1H), 4.45-4.44 (m, 1H), 3.86 (s, 3H), 3.61-3.60 (m, 1H), 2.39-2.34 (m, 1H), 2.19-2.14 (m, 1H), 1.49-1.46 (m, 1H), 1.19-1.16 (m, 1H), 0.88-0.87 (m, 1H), 0.81-0.79 (m, 1H).

Step 4) The Preparation of Compound 17-5

To a suspension of compound 17-4 (0.53 g, 2.77 mmol), compound 1-24-2 (0.73 g, 4.16 mmol) and EDCI (1.06 g, 5.55 mmol) in DCM (10 mL) was added DIPEA (2.4 mL, 14.52 mmol) dropwise at 0° C. At the end of the addition, the mixture was stirred at rt for 3.0 hrs. After the reaction was completed, the mixture was diluted with DCM (20 mL), washed with NH₄Cl aqueous solution and brine, dried over anhydrous Na₂SO₄ and concentrated in vacuo. The residue was purified by silica gel column chromatography (PE/EtOAc (v/v)=1/1) to give the title compound as white liquid (0.61 g, 70.2%). The compound was characterized by the following spectroscopic data:

MS (ESI, pos.ion) m/z: 313.2 [M+H]⁺; and

¹H NMR (400 MHz, CDCl₃) δ (ppm): 5.44-5.42 (br, 1H), 4.71-4.68 (m, 1H), 4.29-4.20 (m, 1H), 3.73 (s, 3H), 3.72-3.69 (m, 1H), 3.67 (s, 3H), 3.59-3.54 (m, 1H), 2.20-2.15 (m, 1H), 2.06-2.01 (m, 1H), 1.95-1.90 (m, 1H), 1.05-0.93 (m, 6H), 0.66-0.61 (m, 4H).

Step 5) The Preparation of Compound 17-6

To a solution of compound 17-5 (0.2 g, 0.64 mmol) in THF (5.0 mL) was added lithium hydroxide aqueous solution (0.14 g, 3.2 mmol, 5.0 mL) dropwise at 0° C. At the end of the addition, the mixture was stirred at 40° C. for 12 hrs. After the reaction was completed, the THF solvent was removed and 30 mL of water was added. The resulting mixture was extracted with EtOAc (10 mL×3). The aqueous layer was adjusted to pH 1 with hydrochloric acid (10%), and extracted with EtOAc (25 mL×3). The combined organic layers were dried over anhydrous Na₂SO₄ and concentrated in vacuo to give the title compound as a white solid (0.16 g, 82.8%). The compound was characterized by the following spectroscopic data:

MS (ESI, pos.ion) m/z: 299.2 [M+H]⁺; and

¹H NMR (400 MHz, CDCl₃) δ (ppm): 7.06 (br, 1H), 5.76 (br, 1H), 4.73-4.69 (m, 1H), 4.23-4.18 (m, 1H), 3.79 (d, 1H, J=9.7 Hz), 3.66 (s, 3H), 3.49 (d, 1H, J=9.7 Hz), 2.26-2.18 (m, 1H), 2.07-1.93 (m, 2H), 1.00-0.94 (m, 6H), 0.68-0.64 (m, 4H).

Step 6) The Preparation of Compound 17-7

To a solution of compound 1-12-2 (0.31 g, 1.1074 mmol), compound 17-6 (0.3 g, 1.0067 mmol) in MeCN (30 mL) was added DIPEA (0.21 mL, 1.27 mmol) dropwise at 0° C. At the end of the addition, the mixture was stirred at rt for 2.0 hrs. After the reaction was completed, 20 mL of water was added and the MeCN solvent was removed. The residue was dissolved in EtOAc (30 mL), washed with NH$_4$Cl aqueous solution and brine, dried over anhydrous Na$_2$SO$_4$ and concentrated in vacuo. The residue was purified by silica gel column chromatography (PE/EtOAc (v/v)=1/1) to give the title compound as a pale yellow solid (0.33 g, 66.7%). The compound was characterized by the following spectroscopic data:

MS (ESI, pos.ion) m/z: 495.3 [M+H]$^+$; and
$^1$H NMR (400 MHz, CDCl$_3$) δ (ppm): 7.82-7.78 (m, 2H), 7.67-7.64 (m, 2H), 5.32, 5.29 (br, br, 1H), 5.31 (s, 2H), 4.72-4.70 (m, 1H), 4.35-4.30 (m, 1H), 3.67 (s, 3H), 3.61-3.59 (m, 1H), 3.55-3.49 (m, 1H), 2.20-2.07 (m, 2H), 1.83-1.76 (m, 1H), 0.97, 0.96 (m, m, 3H), 0.91, 0.89 (m, m, 3H), 0.52-0.39 (m, 4H).

Step 7) The Preparation of Compound 17-8

A mixture of compound 17-7 (0.33 g, 0.6714 mmol) and NH$_4$OAc (1.04 g, 13.43 mmol) in xylene (10 mL) was stirred at 120° C. for 5.0 hrs. After the reaction was completed, the mixture was cooled to rt and quenched with water (20 mL). The aqueous layer was extracted with EtOAc (20 mL×3). The combined organic layers were washed with brine, dried over anhydrous Na$_2$SO$_4$ and concentrated in vacuo. The residue was purified by silica gel column chromatography (PE/EtOAc (v/v)=1/2) to give the title compound as a yellow solid (0.19 g, 58.94%). The compound was characterized by the following spectroscopic data:

MS (ESI, pos.ion) m/z: 475.3 [M+H]$^+$; and
$^1$H NMR (400 MHz, CDCl$_3$) δ (ppm): 7.58 (s, 1H), 7.45-7.41 (m, 2H), 7.29-7.26 (m, 2H), 5.46, 5.44 (br, br, 1H), 4.93-4.89 (m, 1H), 4.41-4.37 (m, 1H), 3.71-3.67 (m, 1H), 3.67 (s, 3H), 3.50-3.44 (m, 1H), 2.39-2.32 (m, 1H), 2.23-2.11 (m, 1H), 2.05-1.97 (m, 1H), 0.97, 0.95 (m, m, 3H), 0.91, 0.89 (m, m, 3H), 0.52-0.39 (m, 4H).

Step 8) The Preparation of Compound 17-9

To a mixture of compound 17-8 (0.19 g, 0.3957 mmol), compound 1-14-2 (0.15 g, 0.5935 mmol), Pd(dppf)Cl$_2$.CH$_2$Cl$_2$ (33 mg, 0.03956 mmol) and KOAc (0.12 g, 1.187 mmol) was added DMF (5.0 mL) via syringe under N$_2$, and the mixture was stirred at 90° C. for 3.0 hrs. After the reaction was completed, the mixture was cooled to rt, diluted with EtOAc (50 mL) and filtered through a celite pad. The filtrate was washed with water (20 mL×3) and brine, dried over anhydrous Na$_2$SO$_4$ and concentrated in vacuo. The residue was purified by silica gel column chromatography (PE/EtOAc (v/v)=1/2) to give the title compound as a beige solid (0.16 g, 80%). The compound was characterized by the following spectroscopic data:

MS (ESI, pos.ion) m/z: 523.3 [M+H]$^+$; and
$^1$H NMR (400 MHz, CDCl$_3$) δ (ppm): 7.64-7.57 (m, 4H), 7.21 (s, 1H), 5.46, 5.44 (br, br, 1H), 4.93-4.89 (m, 1H), 4.42-4.37 (m, 1H), 3.71-3.67 (m, 1H), 3.66 (s, 3H), 3.50-3.44 (m, 1H), 2.39-2.32 (m, 1H), 2.23-2.11 (m, 1H), 2.05-1.97 (m, 1H), 1.35 (m, 6H), 1.32 (m, 6H), 0.97, 0.95 (m, m, 3H), 0.91, 0.89 (m, m, 3H), 0.55-0.42 (m, 4H).

Step 9) The Preparation of Compound 22-10

To a mixture of compound 1-11 (0.22 g, 0.522 mmol), compound 17-9 (0.27 g, 0.522 mmol), Pd(PPh$_3$)$_4$ (60.29 mg, 0.0522 mmol) and K$_2$CO$_3$ (0.22 g, 1.566 mmol) were added DME (6.0 mL) and water (1.5 mL) under N$_2$ via syringe, and the mixture was stirred at 90° C. for 3.0 hrs. After the reaction was completed, the mixture was cooled to rt and diluted with EtOAc (30 mL). The resulting mixture was washed with water (10 mL×3) and brine, dried over anhydrous Na$_2$SO$_4$ and concentrated in vacuo. The residue was purified by silica gel column chromatography (DCM/EtOH (v/v)=100/1) to give the title compound as a pale yellow solid (0.18 g, 50%). The compound was characterized by the following spectroscopic data:

MS (ESI, pos.ion) m/z: 687.5 [M+H]$^+$; and
$^1$H NMR (400 MHz, CDCl$_3$) δ (ppm): 7.59-7.56 (m, 3H), 7.52-7.49 (m, 2H), 7.26, 7.23 (s, s, 1H), 6.98, 6.96 (t, t, 1H), 5.46, 5.44 (dd, dd, 1H), 4.93-4.89 (m, 1H), 4.42-4.37 (m, 1H), 3.71-3.67 (m, 1H), 3.66 (s, 3H), 3.50-3.35 (m, 2H), 3.09-2.97 (m, 2H), 2.70-2.52 (m, 2H), 2.39-2.32 (m, 1H), 2.23-2.07 (m, 3H), 2.05-1.97 (m, 1H), 1.61-1.51 (m, 1H), 0.97, 0.95 (m, m, 3H), 0.91, 0.89 (m, m, 3H), 0.55-0.42 (m, 4H).

Step 10) The Preparation of Compound 17-11

To a solution of compound 17-6 (0.32 g, 1.07 mmol) and HATU (0.49 g, 1.284 mmol) in THF (10 mL) was added DIPEA (0.195 mL, 1.18 mmol) at 0° C. After stirring at 0° C. for 0.5 hr, compound 2-10 (0.22 g, 1.19 mmol) was added in a portionwise manner. At the end of the addition, the mixture was stirred at rt for 4.0 hrs. After the reaction was completed, the mixture was quenched with water (10 mL), the THF solvent was removed, and the resulting mixture was extracted with EtOAc (20 mL×3). The combined organic layers were washed with brine, dried over anhydrous Na$_2$SO$_4$ and concentrated in vacuo. The residue was dissolved in glacial acetic acid (5 mL), and the solution was stirred at 40° C. overnight. After the reaction was completed, the mixture was concentrated in vacuo. The residue was dissolved in EtOAc (20 mL). The mixture was washed with Na$_2$CO$_3$ aqueous solution (10 mL×3), dried over anhydrous Na$_2$SO$_4$ and concentrated in vacuo. The residue was purified by silica gel column chromatography (PE/EtOAc (v/v)=1/2) to give the title compound (0.32 g, 65%). The compound was characterized by the following spectroscopic data:

MS (ESI, pos.ion) m/z: 450.5 [M+H]$^+$; and
$^1$H NMR (400 MHz, CDCl$_3$) δ (ppm): 7.71 (d, 1H), 7.33, 7.30 (d, d, 1H), 7.20, 7.17 (d, d, 1H), 5.32, 5.29 (d, d, 1H), 5.18-5.14 (m, 1H), 4.41-4.35 (m, 1H), 3.63 (s, 3H), 3.54-3.48 (m, 1H), 3.16-3.10 (m, 1H), 2.46-2.38 (m, 1H), 2.23-2.11 (m, 1H), 1.95-1.87 (m, 1H), 0.97, 0.95 (m, m, 3H), 0.91, 0.89 (m, m, 3H), 0.55-0.42 (m, 4H).

Step 11) The Preparation of Compound 17-12

To a mixture of compound 17-11 (0.22 g, 0.5 mmol), compound 1-14-2 (0.15 g, 0.6 mmol), Pd(dppf)Cl$_2$.CH$_2$Cl$_2$ (20.42 mg, 0.025 mmol) and KOAc (0.12 g, 1.25 mmol) was added DMF (3 mL) via syringe, and the mixture was stirred at 90° C. under N$_2$ for 3.0 hrs. After the reaction was completed, 15 mL of water was added. The resulting mixture was extracted with EtOAc (20 mL×3). The combined organic layers were washed with brine, dried over anhydrous Na$_2$SO$_4$ and concentrated in vacuo. The residue was purified by silica gel column chromatography (PE/EtOAc (v/v)=3/1) to give the title compound as a beige solid (0.16 g, 65%). The compound was characterized by the following spectroscopic data:

MS (ESI, pos.ion) m/z: 497.5 [M+H]$^+$; and
$^1$H NMR (400 MHz, CDCl$_3$) δ (ppm): 7.84-7.83 (q, 1H), 7.65, 7.63 (d, d, 1H), 7.36, 7.34 (d, d, 1H), 5.32, 5.29 (d, d, 1H), 5.20-5.16 (m, 1H), 4.40-4.36 (m, 1H), 3.63 (s, 3H), 3.54-3.48 (m, 1H), 3.16-3.10 (m, 1H), 2.46-2.38 (m, 1H), 2.23-2.11 (m, 1H), 1.95-1.87 (m, 1H), 1.32, 1.29 (q, q, 12H), 0.97, 0.95 (m, m, 3H), 0.91, 0.89 (m, m, 3H), 0.55-0.42 (m, 4H).

Step 12) The Preparation of Compound 17-13

To a mixture of compound 17-10 (0.399 g, 0.58 mmol), compound 17-12 (0.29 g, 0.58 mmol), Pd(PPh$_3$)$_4$ (35 mg, 0.03 mmol) and K$_2$CO$_3$ (80 mg, 1.4 mmol) were added DME (8.0 mL) and pure water (2.0 mL) via syringe, and the mixture was stirred at 90° C. under N$_2$ for 4.0 hrs. After the reaction was completed, the mixture was cooled to rt and diluted with EtOAc (50 mL). The resulting mixture was washed with water (30 mL×3) and brine, dried over anhydrous Na$_2$SO$_4$ and concentrated in vacuo. The residue was purified by silica gel column chromatography (DCM/MeOH (v/v)=50/1) to give the title compound as a pale yellow solid (0.29 g, 55%). The compound was characterized by the following spectroscopic data:
MS (ESI, pos.ion) m/z: 454.5 [M+2H]$^{2+}$; and
$^1$H NMR (400 MHz, CDCl$_3$) δ (ppm): 7.85, 7.83 (d, d, 1H), 7.62, 7.60 (s, s, 1H), 7.59-7.52 (m, 7H), 7.44, 7.42 (t, t, 1H), 5.32, 5.29 (d, d, 2H), 5.19-5.15 (m, 1H), 4.93-4.89 (m, 1H), 4.41-4.36 (m, 2H), 3.76-3.66 (m, 2H), 3.63 (s, 6H), 3.54-3.44 (m, 2H), 3.16-3.02 (m, 2H), 2.68-2.54 (m, 2H), 2.46-2.32 (m, 2H), 2.23-2.08 (m, 5H), 2.05-1.97 (m, 1H), 1.95-1.87 (m, 1H), 1.62-1.52 (m, 1H), 0.97, 0.95 (m, m, 6H), 0.90, 0.89 (m, m, 6H), 0.56-0.42 (m, 8H).
Example 18
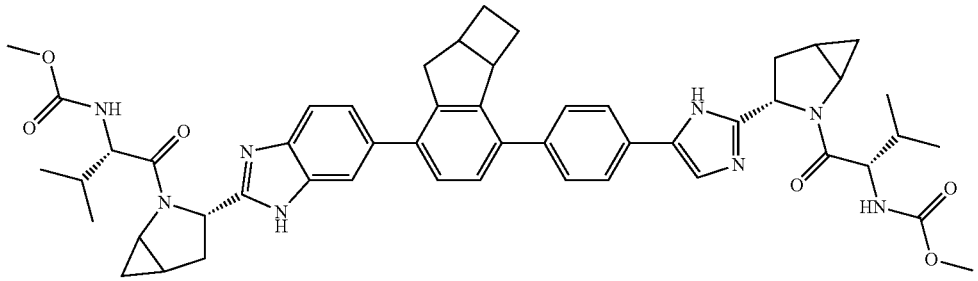
Synthetic Route:
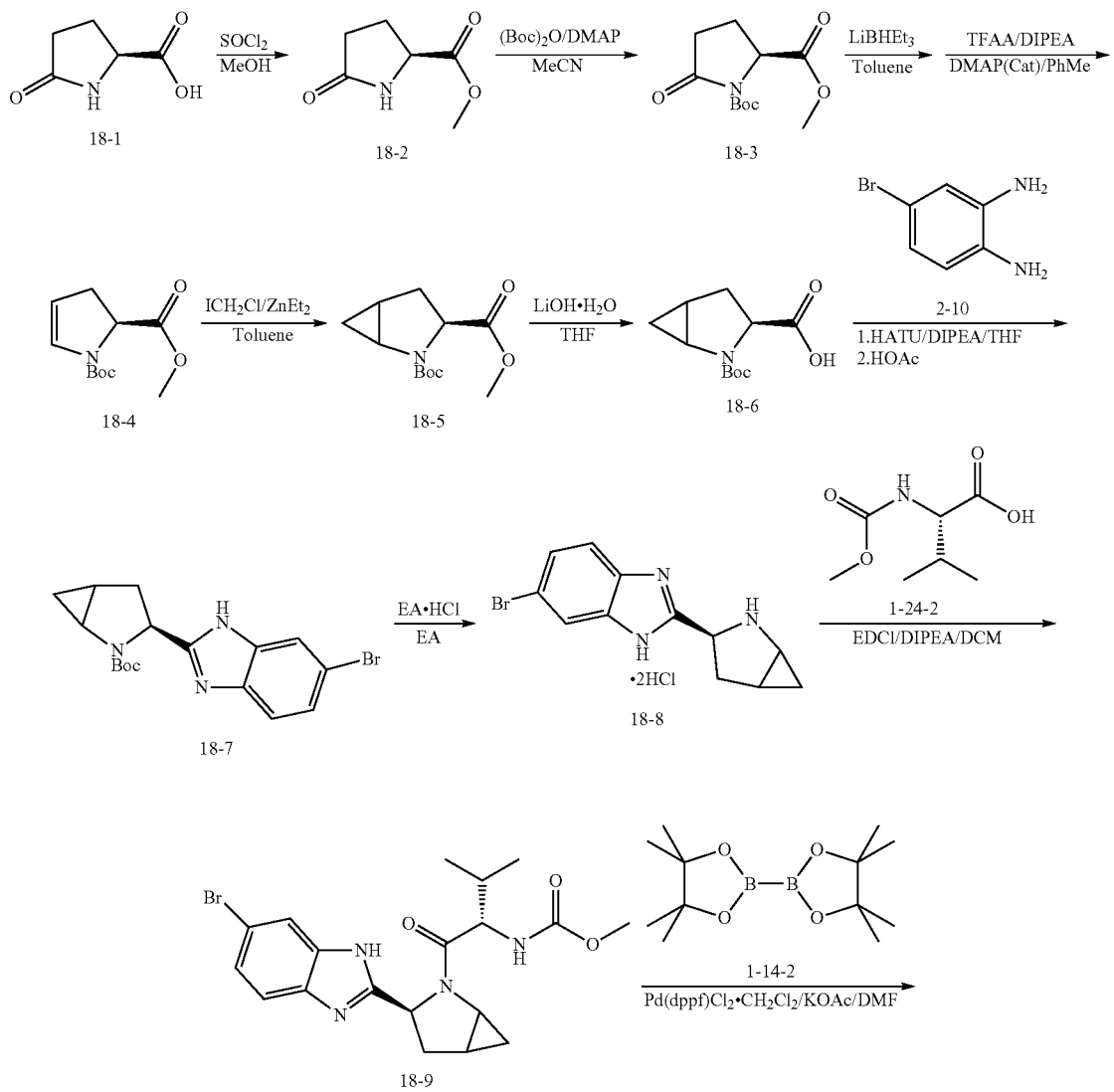

-continued
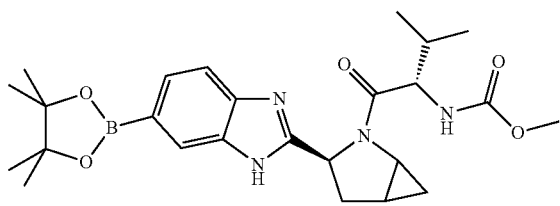
18-10
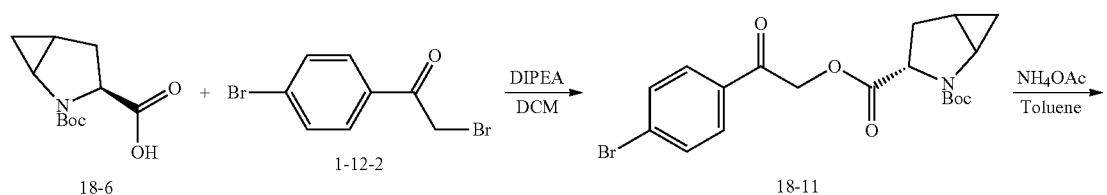
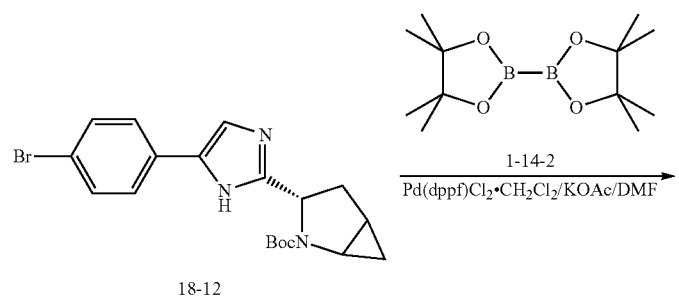
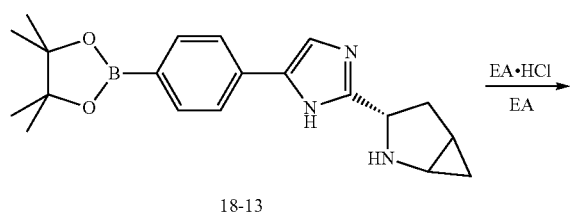
18-13
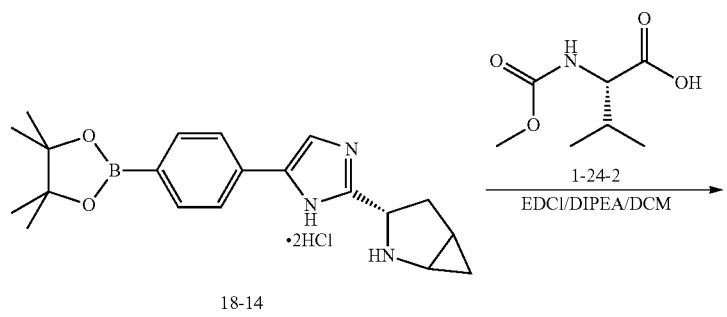

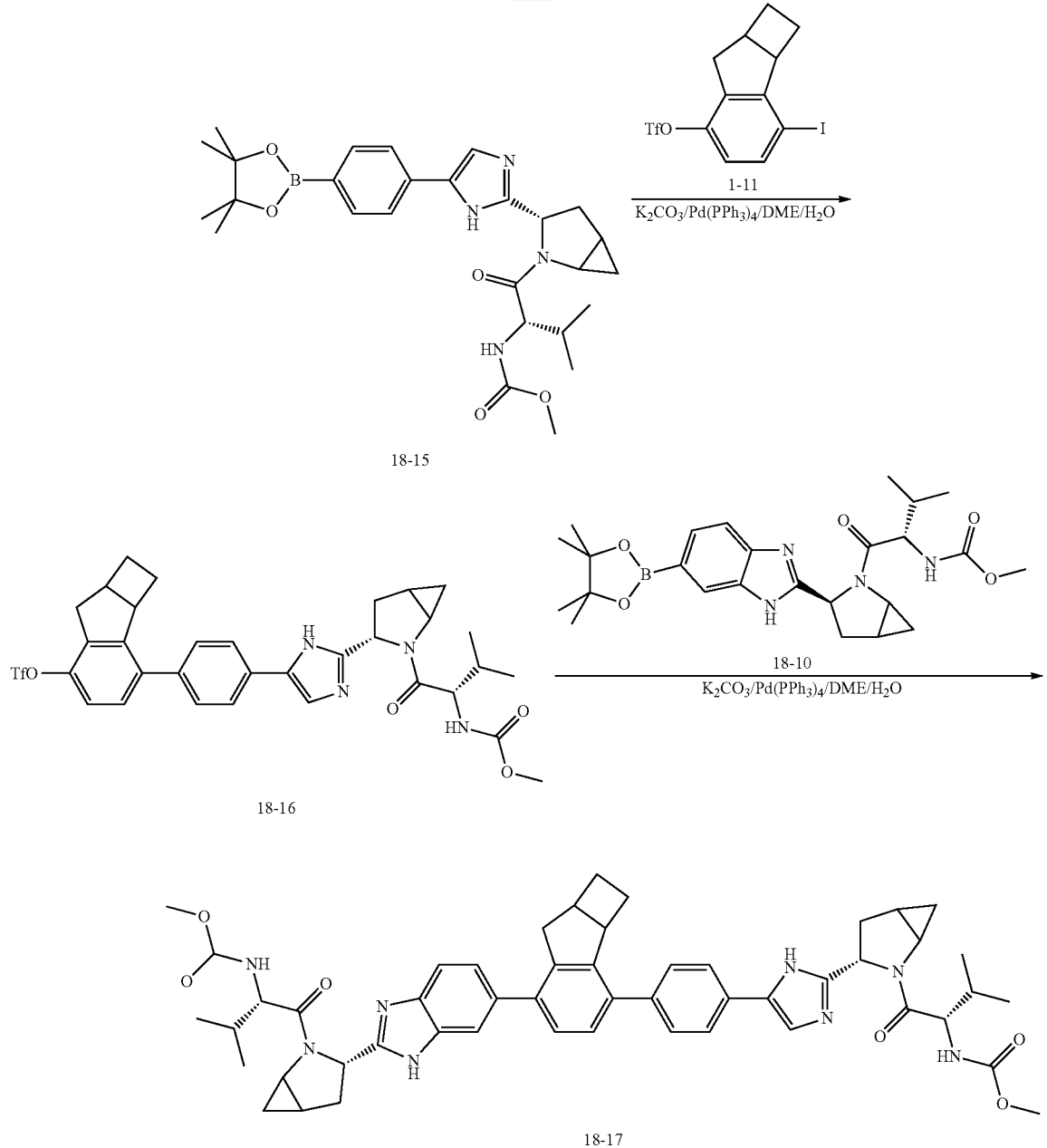

Step 1) The Preparation of Compound 18-2

To a solution of compound 18-1 (10 g, 77.5 mmol) in MeOH (50 mL) was added thionyl chloride (5.5 mL, 75.8 mmol) dropwise at 0° C. At the end of the addition, the mixture was stirred at 0° C. for 1.0 hr and at rt for another 2.0 hrs. After the reaction was completed, the mixture was quenched with NaHCO$_3$ aqueous solution (50 mL), and the MeOH solvent was removed. The resulting mixture was extracted with DCM (35 mL×3). The combined organic layers were washed with brine, dried over anhydrous Na$_2$SO$_4$ and concentrated in vacuo. The residue was purified by silica gel column chromatography (EtOAc) to give the title compound as colorless liquid (7.5 g, 67.6%). The compound was characterized by the following spectroscopic data:

MS (ESI, pos.ion) m/z: 144.2 [M+H]$^+$; and $^1$H NMR (400 MHz, CDCl$_3$) δ (ppm): 7.38 (br, 1H), 4.20-4.16 (m, 1H), 3.67 (s, 3H), 2.39-2.23 (m, 3H), 2.14-2.07 (m, 1H).

Step 2) The Preparation of Compound 18-3

To a solution of compound 18-2 (6.45 g, 45.06 mmol) in MeCN (30 mL) was added DMAP (0.55 g, 4.5 mmol) at 0° C. After the mixture was stirred for 10 mins, di-tert-butyl dicarbonate (10.82 g, 49.56 mmol) was added dropwise. At the end of the addition, the mixture was stirred at 0° C. for 30 mins and at rt for another 2.0 hrs. After the reaction was completed, the mixture was concentrated in vacuo. The residue was purified by silica gel column chromatography (PE/EtOAc (v/v)=1/1) to give the title compound as colorless liquid (5.0 g, 45.6%). The compound was characterized by the following spectroscopic data:

MS (ESI, pos.ion) m/z: 144.2 [M-Boc]$^+$; and $^1$H NMR (400 MHz, CDCl$_3$) δ (ppm): 4.60-4.57 (m, 1H), 3.75 (s, 3H), 2.65-2.55 (m, 1H), 2.50-2.42 (m, 1H), 2.36-2.24 (m, 1H), 2.04-1.96 (m, 1H), 1.45 (s, 9H).

Step 3) The Preparation of Compound 18-4

To a solution of compound 18-3 (3.74 g, 15.4 mmol) in toluene (50 mL) was added lithium triethylborohydride (1.8 g, 16.9 mmol) dropwise at −78° C. After the mixture was stirred at −78° C. for 70 mins, DIPEA (3.2 mL, 19.4 mmol), DMAP (0.19 g, 1.54 mmol) and TFAA (3.0 mL, 40.4 mmol) were added separately, and the mixture was stirred at rt for 2.0 hrs. After the reaction was completed, the mixture was concentrated in vacuo. The residue was purified by silica gel column chromatography (PE/EtOAc (v/v)=10/1) to give the title compound as yellow liquid (2.26 g, 64.8%). The compound was characterized by the following spectroscopic data:

MS (ESI, pos.ion) m/z: 128.2 [M-Boc]$^+$; and $^1$H NMR (400 MHz, CDCl$_3$) δ (ppm): 6.65-6.52 (br, 1H), 4.96-4.91 (br, 1H), 4.68-4.57 (m, 1H), 3.76 (s, 3H), 3.12-3.00 (m, 1H), 2.71-2.61 (m, 1H), 1.49-1.44 (br, 9H).

Step 4) The Preparation of Compound 18-5

To a solution of diethylzinc (0.49 g, 3.94 mmol) in toluene (6.0 mL) was added chloroiodomethane (1.40 g, 7.9 mmol) dropwise at 0° C. After the mixture was stirred at 0° C. for 45 mins, a solution of compound 18-4 (0.3 g, 1.32 mmol) in toluene (4.0 mL) was added dropwise. At the end of the addition, the mixture was stirred at 0° C. for 18 hrs. After the reaction was completed, the mixture was quenched with saturated NH$_4$Cl aqueous solution (15 mL). The aqueous layer was extracted with EtOAc (25 mL×3). The combined organic layers were dried over anhydrous Na$_2$SO$_4$ and concentrated in vacuo. The residue was purified by silica gel column chromatography (PE/EtOAc (v/v)=10/1) to give the title compound as yellow liquid (0.19 g, 59.7%). The compound was characterized by the following spectroscopic data:

MS (ESI, pos.ion) m/z: 142.2 [M-Boc]$^+$; and $^1$H NMR (400 MHz, CDCl$_3$) δ (ppm): 4.64-4.51 (m, 1H), 3.70 (s, 3H), 3.56-3.45 (m, 1H), 2.64-2.54 (m, 1H), 2.05-2.01 (m, 1H), 1.50, 1.41 (s, s, 9H), 0.75-0.65 (m, 3H).

Step 5) The Preparation of Compound 18-6

To a solution of compound 18-5 (1.02 g, 4.23 mmol) in THF (20 mL) was added lithium hydroxide monohydrate aqueous solution (0.89 g, 21.2 mmol, 10 mL) dropwise at 0° C. At the end of the addition, the mixture was stirred at 40° C. for 12 hrs. After the reaction was completed, the THF solvent was removed and 20 mL of water was added to the mixture. The resulting mixture was washed with EtOAc (15 mL×3). The aqueous phase was adjusted to pH 1 with hydrochloric acid (10%) and extracted with EtOAc (25 mL×3). The combined organic layers were washed with brine, dried over anhydrous Na$_2$SO$_4$ and concentrated in vacuo to give the title compound as a white solid (0.84 g, 87%). The compound was characterized by the following spectroscopic data:

MS (ESI, neg.ion) m/z: 226.2 [M−H]$^-$; and $^1$H NMR (400 MHz, CD$_3$OD) δ (ppm): 4.53-4.46 (m, 1H), 3.48-3.42 (m, 1H), 2.70-2.57 (m, 1H), 2.05-2.01 (m, 1H), 1.60-1.54 (m, 1H), 1.48, 1.41 (s, s, 9H), 0.89-0.80 (m, 1H), 0.73-0.66 (m, 1H).

Step 6) The Preparation of Compound 18-7

To a solution of compound 18-6 (2.43 g, 10.7 mmol) and HATU (4.88 g, 12.84 mmol) in THF (25 mL) was added DIPEA (1.95 mL, 11.8 mmol) at 0° C. After stirring at 0° C. for 0.5 hr, compound 2-10 (2.22 g, 11.9 mmol) was added in a portionwise manner. At the end of the addition, the reaction mixture was stirred at rt for 4.0 hrs. After the reaction was completed, the mixture was quenched with water (50 mL), and the THF solvent was removed. The resulting mixture was extracted with EtOAc (50 mL×3). The combined organic layers were washed with brine, dried over anhydrous Na$_2$SO$_4$ and concentrated in vacuo. The residue was dissolved in glacial acetic acid (20 mL), and the solution was stirred at 40° C. overnight. After the reaction was completed, the solvent was removed under reduced pressure. The resulting mixture was dissolved in EtOAc (100 mL), washed with Na$_2$CO$_3$ aqueous solution (50 mL×3), dried over anhydrous Na$_2$SO$_4$ and concentrated in vacuo. The residue was purified by silica gel column chromatography (PE/EtOAc (v/v)=1/2) to give the title compound (2.02 g, 50%). The compound was characterized by the following spectroscopic data:

MS (ESI, pos.ion) m/z: 378.3 [M+H]$^+$; and $^1$H NMR (400 MHz, CDCl$_3$) δ (ppm): 7.67 (dd, 1H), 7.22, 7.20 (d, d, 1H), 7.19, 7.17 (d, d, 1H), 5.03-5.00 (m, 1H), 3.31-3.24 (m, 1H), 2.56-2.49 (m, 1H), 2.12-2.07 (m, 1H), 1.53-1.48 (m, 1H), 1.46 (s, 9H), 1.42-1.38 (m, 1H), 1.00-0.97 (m, 1H).

Step 7) The Preparation of Compound 18-8 To a solution of compound 18-7 (1.03 g, 2.74 mmol) in EtOAc (5.0 mL) was added a solution of HCl in EtOAc (6.0 mL, 4 M) dropwise at 0° C. At the end of the addition, the mixture was stirred at rt for 8.0 hrs. After the reaction was completed, the mixture was concentrated in vacuo. The residue was purified by beating in EtOAc (10 mL) and filtered to give the title compound as a pale yellow solid (0.82 g, 85%). The compound was characterized by the following spectroscopic data:

MS (ESI, pos.ion) m/z: 278.2 [M+H]$^+$.

Step 8) The Preparation of Compound 18-9

To a suspension of compound 18-8 (0.66 g, 1.88 mmol), compound 1-24-2 (0.49 mg, 2.82 mmol) and EDCI (0.54 g, 2.82 mmol) in DCM (10 mL) was added DIPEA (1.86 mL, 11.28 mmol) dropwise at 0° C. At the end of the addition, the mixture was stirred at rt for 3.0 hrs. After the reaction was completed, the mixture was diluted with DCM (50 mL). The resulting mixture was washed with water (20 mL×3) and brine, dried over anhydrous Na$_2$SO$_4$ and concentrated in vacuo. The residue was purified by silica gel column chromatography (PE/EtOAc (v/v)=1/2) to give the title compound as a solid (0.69 g, 85%). The compound was characterized by the following spectroscopic data:

MS (ESI, pos.ion) m/z: 435.5 [M+H]$^+$; and $^1$H NMR (400 MHz, CDCl$_3$) δ (ppm): 7.67 (dd, 1H), 7.22, 7.20 (d, d, 1H), 7.19, 7.17 (d, d, 1H), 5.32, 5.30 (d, d, 1H), 5.16-5.12 (m, 1H), 4.13-4.08 (m, 1H), 3.63 (s, 3H), 3.42-3.36 (m, 1H), 2.62-2.55 (m, 1H), 2.21-2.09 (m, 2H), 1.53-1.45 (m, 1H), 0.97-0.89 (m, 7H), 0.50-0.46 (m, 1H).

Step 9) The Preparation of Compound 18-10

To a mixture of compound 18-9 (3.08 g, 7.1 mmol), compound 1-14-2 (2.72 g, 10.7 mmol), Pd(dppf)Cl$_2$.CH$_2$Cl$_2$ (0.65 g, 0.8 mmol) and KOAc (2.09 g, 21.3 mmol) was added DMF (30 mL) via syringe under N$_2$, and the mixture was stirred at 90° C. for 3.0 hrs. After the reaction was completed, the mixture was cooled to rt and diluted with EtOAc (200 mL). The resulting mixture was filtered through a celite pad. The filtrate was washed with water (50 mL×3) and brine, dried over anhydrous Na$_2$SO$_4$ and concentrated in vacuo. The residue was purified by silica gel column chromatography (PE/EtOAc (v/v)=1/2) to give the title compound as a beige solid (2.22 g, 65%). The compound was characterized by the following spectroscopic data:

MS (ESI, pos.ion) m/z: 483.5 [M+H]⁺; and
¹H NMR (400 MHz, CDCl₃) δ (ppm): 7.82 (dd, 1H), 7.65, 7.63 (d, d, 1H), 7.45, 7.42 (d, d, 1H), 5.32, 5.30 (d, d, 1H), 5.16-5.12 (m, 1H), 4.13-4.08 (m, 1H), 3.63 (s, 3H), 3.42-3.36 (m, 1H), 2.62-2.55 (m, 1H), 2.22-2.09 (m, 2H), 1.53-1.45 (m, 1H), 1.32, 1.29 (m, 12H), 0.97-0.89 (m, 7H), 0.50-0.46 (m, 1H).

Step 10) The Preparation of Compound 18-11

To a solution of compound 18-6 (3.91 g, 17.22 mmol) and compound 1-12-2 (5.46 g, 19.81 mmol) in DCM (60 mL) was added DIPEA (3.4 mL, 20.67 mmol) dropwise at 0° C. At the end of the addition, the mixture was stirred at rt for 3.0 hrs. After the reaction was completed, the mixture was quenched with water (50 mL). The aqueous layer was extracted with DCM (100 mL×3). The combined organic layers were washed with brine, dried over anhydrous Na₂SO₄ and concentrated in vacuo. The residue was purified by silica gel column chromatography (PE/EtOAc (v/v)=5/1) to give the title compound as a white solid (4.5 g, 61.73%). The compound was characterized by the following spectroscopic data:

MS (ESI, pos.ion) m/z: 424.3 [M+H]⁺; and
¹H NMR (400 MHz, CDCl₃) δ (ppm): 7.77-7.73 (m, 2H), 7.64-7.62 (m, 2H), 5.53-5.09 (m, 2H), 4.78-4.67 (m, 1H), 3.59-3.46 (m, 1H), 2.69-2.62 (m, 1H), 2.43-2.40 (m, 1H), 1.42 (s, 9H), 1.00-0.96 (m, 1H), 0.76-0.69 (m, 2H).

Step 11) The Preparation of Compound 18-12

A suspension of compound 18-11 (4.5 g, 10.64 mmol) and ammonium acetate (16.4 g, 212.73 mmol) in toluene (50 mL) was stirred at 110° C. for 5.0 hrs. After the reaction was completed, the mixture was cooled to rt, and quenched with water (50 mL). The aqueous layer was extracted with EtOAc (100 mL×3). The combined organic layers were washed with brine, dried over anhydrous Na₂SO₄ and concentrated in vacuo. The residue was purified by silica gel column chromatography (PE/EtOAc (v/v)=8/1) to give the title compound (2.14 g, 50%). The compound was characterized by the following spectroscopic data:

MS (ESI, pos.ion) m/z: 404.3 [M+H]⁺; and
¹H NMR (400 MHz, CDCl₃) δ (ppm): 7.62-7.52 (br, 2H), 7.49-7.46 (d, 2H, J=12 Hz), 7.21 (s, 1H), 5.27-5.24 (d, 1H, J=10.0 Hz), 3.31-3.27 (m, 1H), 1.71-1.67 (m, 2H), 1.52 (s, 9H), 0.89-0.86 (m, 1H), 0.64-0.69 (m, 2H).

Step 12) The Preparation of Compound 18-13

A mixture of compound 18-12 (2.1 g, 5.2 mmol), compound 1-14-2 (1.59 g, 6.25 mmol), Pd(dppf)Cl₂·CH₂Cl₂ (0.43 g, 0.52 mmol) and KOAc (1.54 g, 15.63 mmol) in DMF (30 mL) was stirred at 90° C. under N₂ for 3.0 hrs. After the reaction was completed, the mixture was cooled to rt, diluted with EtOAc (100 mL) and filtered through a celite pad. The filtrate was washed with water (60 mL×3) and brine, dried over anhydrous Na₂SO₄ and concentrated in vacuo. The residue was purified by silica gel column chromatography (PE/EtOAc (v/v)=2/1) to give the title compound (2.27 g, 97%). The compound was characterized by the following spectroscopic data:

MS (ESI, pos.ion) m/z: 452.3 [M+H]⁺; and
¹H NMR (400 MHz, CDCl₃) δ (ppm): 7.81-7.79 (d, 2H, J=8.04 Hz), 7.60 (br, 2H), 7.26 (s, 1H), 5.28-5.26 (d, 1H, J=8.0 Hz), 3.53 (br, 1H), 3.30-3.27 (br, 1H), 1.67-1.66 (m, 2H), 1.52 (s, 9H), 1.34 (s, 12H), 0.89-0.86 (m, 1H), 0.69-0.64 (m, 2H).

Step 13) The Preparation of Compound 18-14

To a solution of compound 18-13 (1.13 g, 2.5 mmol) in EtOAc (10 mL) was added a solution of HCl in EtOAc (10 mL, 4 M) dropwise. At the end of the addition, the mixture was stirred at rt for 8.0 hrs. After the reaction was completed, the mixture was concentrated in vacuo. The residue was purified by beating in EtOAc (10 mL) and filtered to give the title compound as a pale yellow solid (0.90 g, 85%). The compound was characterized by the following spectroscopic data:

MS (ESI, pos.ion) m/z: 352.5 [M+H]⁺.

Step 14) The Preparation of Compound 18-15

To a suspension of compound 18-14 (0.80 g, 1.88 mmol), compound 1-24-2 (0.49 g, 2.82 mmol) and EDCI (0.54 g, 2.82 mmol) in DCM (10 mL) was added DIPEA (1.87 mL, 11.28 mmol) dropwise at 0° C. At the end of the addition, the mixture was stirred at rt for 3.0 hrs. After the reaction was completed, the mixture was diluted with DCM (50 mL), washed with NH₄Cl aqueous solution and brine, dried over anhydrous Na₂SO₄ and concentrated in vacuo. The residue was purified by silica gel column chromatography (PE/EtOAc (v/v)=1/2) to give the title compound as a solid (0.81 g, 85%). The compound was characterized by the following spectroscopic data:

MS (ESI, pos.ion) m/z: 509.5 [M+H]⁺; and
¹H NMR (400 MHz, CDCl₃) δ (ppm): 7.64-7.57 (m, 4H), 7.29 (s, 1H), 5.56, 5.55 (d, d, 1H), 4.89-4.85 (m, 1H), 4.12-4.08 (m, 1H), 3.66 (s, 3H), 3.45-3.38 (m, 1H), 2.46-2.39 (m, 1H), 2.26-2.14 (m, 1H), 2.00-1.94 (m, 1H), 1.43-1.37 (m, 1H), 1.35, 1.32 (q, q, 12H), 1.02, 1.00 (m, m, 3H), 0.94, 0.91 (m, m, 3H), 0.50-0.46 (m, 2H).

Step 15) The Preparation of Compound 18-16

A mixture of compound 18-15 (0.27 g, 0.522 mmol), compound 1-11 (0.22 g, 0.522 mmol), Pd(PPh₃)₄ (60.29 mg, 0.0522 mmol) and K₂CO₃ (0.22 g, 1.566 mmol) in mixed solvents of DME and H₂O (8 mL, v/v=3/1) was stirred at 90° C. under N₂ for 3.0 hrs. After the reaction was completed, the mixture was cooled to rt and diluted with EtOAc (40 mL). The resulting mixture was washed with water (20 mL×3) and brine, dried over anhydrous Na₂SO₄ and concentrated in vacuo. The residue was purified by silica gel column chromatography (DCM/EtOH (v/v)=100/1) to give the title compound as a pale yellow solid (0.17 g, 50%). The compound was characterized by the following spectroscopic data:

MS (ESI, pos.ion) m/z: 673.5 [M+H]⁺; and
1H NMR (400 MHz, CDCl₃) δ (ppm): 7.62 (s, 1H), 7.59-7.56 (m, 2H), 7.52-7.49 (m, 2H), 7.26, 7.23 (s, s, 1H), 6.98, 6.96 (t, t, 1H), 5.32, 5.29 (d, d, 1H), 4.89-4.85 (m, 1H), 4.09-4.04 (m, 1H), 3.63 (s, 3H), 3.45-3.35 (m, 2H), 3.09-2.97 (m, 2H), 2.70-2.52 (m, 2H), 2.46-2.39 (m, 1H), 2.22-2.07 (m, 3H), 2.00-1.94 (m, 1H), 1.61-1.51 (m, 1H), 1.43-1.36 (m, 1H), 0.97, 0.95 (m, m, 3H), 0.91, 0.89 (m, m, 3H), 0.50-0.46 (m, 2H).

Step 16) The Preparation of Compound 18-17

A suspension of compound 18-16 (0.35 g, 0.522 mmol), compound 18-10 (0.25 g, 0.574 mmol), Pd(PPh₃)₄ (60.29 mg, 0.0522 mmol) and K₂CO₃ (0.22 g, 1.566 mmol) in mixed solvents of DME and H₂O (8 mL, v/v=3/1) was stirred at 90° C. under N₂ for 3.0 hrs. After the reaction was cooled to rt, the mixture was diluted with EtOAc (40 mL). The resulting mixture was washed with water (20 mL×3) and brine, dried over anhydrous Na₂SO₄ and concentrated in vacuo. The residue was purified by silica gel column chromatography (DCM/EtOH (v/v)=50/1) to give the title compound as a pale yellow solid (0.25 g, 55%). The compound was characterized by the following spectroscopic data:

MS (ESI, pos.ion) m/z: 440.5 [M+2H]²⁺; and
¹H NMR (400 MHz, CDCl₃) δ (ppm): 7.85, 7.83 (d, d, 1H), 7.62-7.50 (m, 8H), 7.44, 7.42 (t, t, 1H), 5.32, 5.29 (d, d, 2H), 5.14-5.10 (m, 1H), 4.89-4.85 (m, 1H), 4.13-4.04 (m, 2H), 3.75-3.67 (m, 1H), 3.63 (s, 6H), 3.45-3.36 (m, 2H), 3.13-3.03 (m, 1H), 2.68-2.54 (m, 3H), 2.46-2.39 (m, 1H), 2.22-2.08 (m, 6H), 2.00-1.94 (m, 1H), 1.62-1.36 (m, 3H), 0.97, 0.95 (m, m, 6H), 0.90, 0.89 (m, m, 6H), 0.50-0.46 (m, 4H).

Example 19
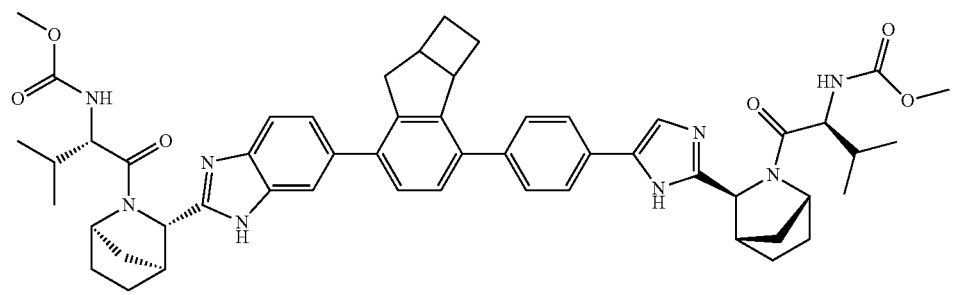
Synthetic Route:
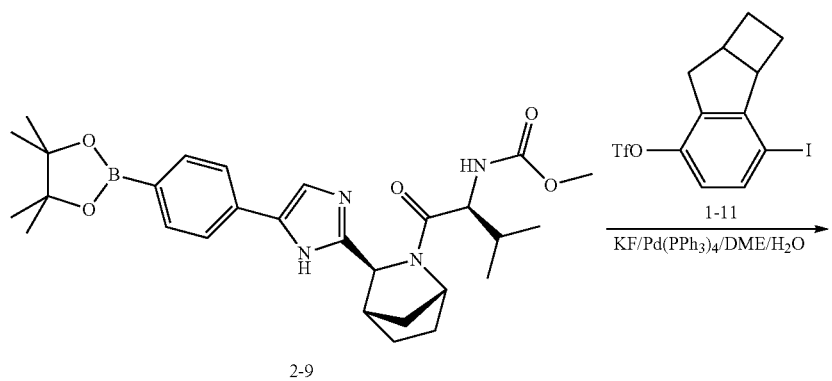
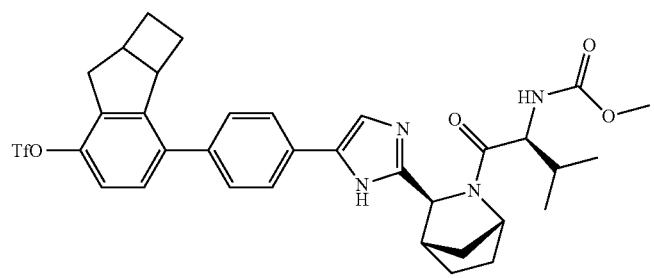
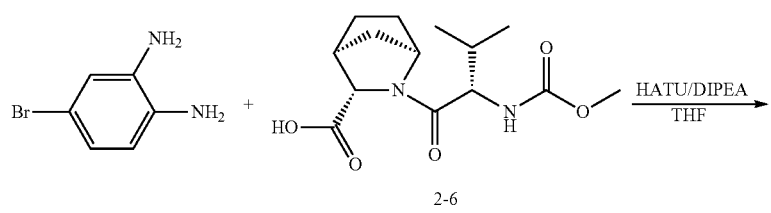

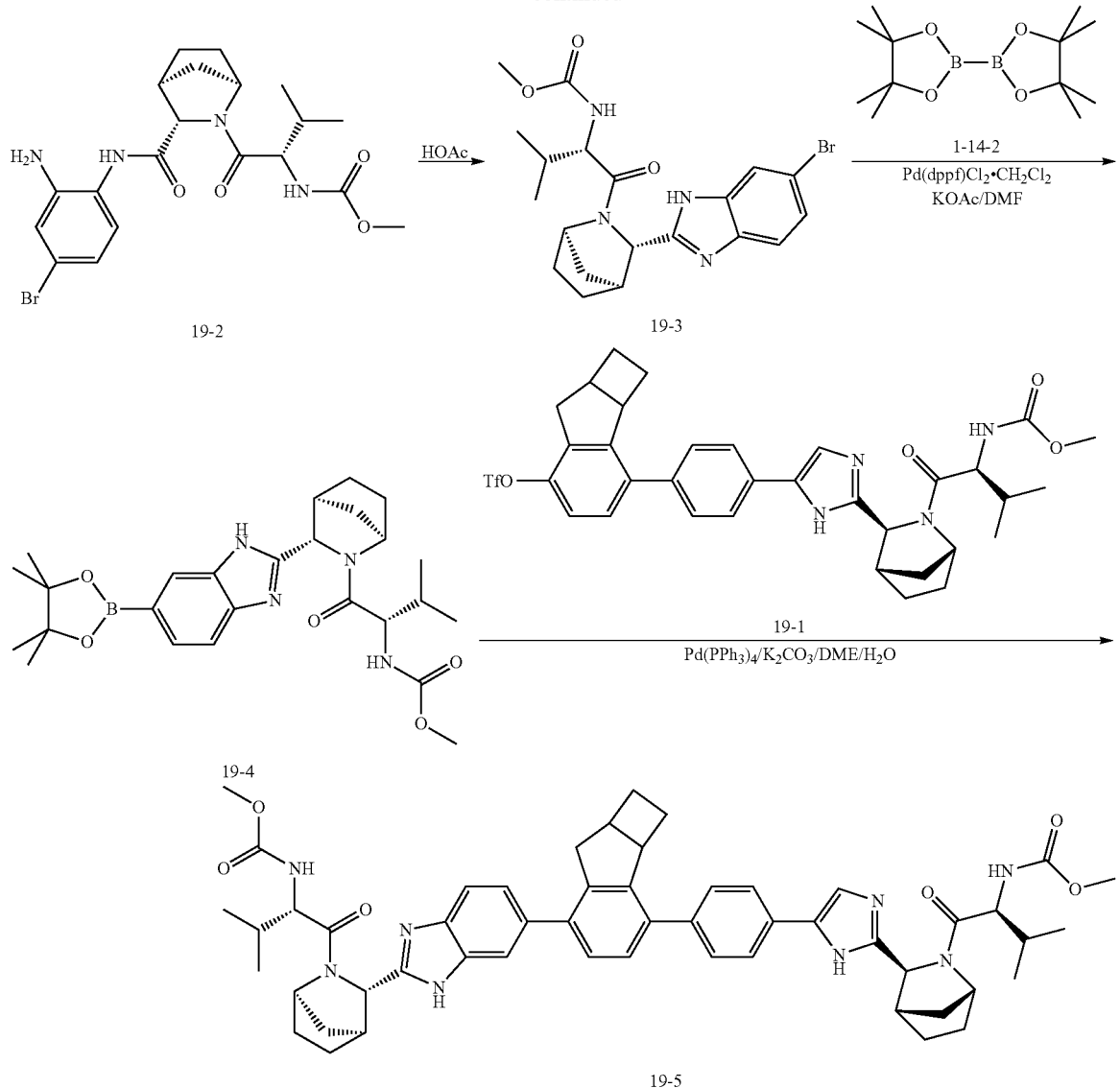

Step 1) The Preparation of Compound 19-1

A suspension of compound 2-9 (1.37 g, 2.62 mmol), compound 1-11 (1.10 g, 2.62 mmol), Pd(PPh$_3$)$_4$ (0.12 g, 0.1 mmol) and KF (0.30 g, 5.24 mmol) in mixed solvents of DME and H$_2$O (15 mL, v/v=4/1) was stirred at 90° C. under N$_2$ for 2.0 hrs. After the reaction was cooled to rt, the mixture was diluted with EtOAc (100 mL). The resulting mixture was washed with water (30 mL×3) and brine, dried over anhydrous Na$_2$SO$_4$ and concentrated in vacuo. The residue was purified by silica gel column chromatography (DCM/MeOH (v/v)=100/1) to give the title compound as a white solid (1.08 g, 60%). The compound was characterized by the following spectroscopic data:

MS (ESI, pos.ion) m/z: 687.5 [M+H]$^+$; and $^1$H NMR (400 MHz, CDCl$_3$) δ (ppm): 7.60 (s, 1H), 7.59-7.56 (m, 2H), 7.52-7.49 (m, 2H), 7.26, 7.23 (s, s, 1H), 6.98, 6.96 (t, t, 1H), 5.56, 5.55 (d, d, 1H), 5.06-5.02 (m, 1H), 4.80-4.75 (m, 1H), 4.21-4.17 (m, 1H), 3.66 (s, 3H), 3.44-3.35 (m, 1H), 3.09-2.97 (m, 2H), 2.70-2.50 (m, 3H), 2.26-2.00 (m, 4H), 1.83-1.78 (m, 1H), 1.67-1.51 (m, 4H), 1.47-1.36 (m, 1H), 1.02, 1.00 (m, m, 3H), 0.93, 0.91 (m, m, 3H).

Step 2) The Preparation of Compound 19-2

To a suspension of compound 2-6 (0.58 g, 1.9542 mmol) and HATU (0.78 g, 2.057 mmol) in THF (20 mL) was added DIPEA (0.41 mL, 2.481 mmol) dropwise at 0° C. After stirring at 0° C. for 0.5 hr, a solution of compound 2-10 (0.40 g, 2.152 mmol) in THF (10 mL) was added to the mixture. At the end of the addition, the mixture was stirred at rt for 2.0 hrs. After the reaction was completed, the THF solvent was removed and 20 mL of water was added. The resulting mixture was extracted with EtOAc (30 mL×3). The combined organic layers were washed with brine, dried over anhydrous Na$_2$SO$_4$ and concentrated in vacuo. The residue was purified by silica gel column chromatography (PE/EtOAc (v/v)=4/1) to give the title compound as brown oil (0.77 g, 85%).

Step 3) the Preparation of Compound 19-3

A solution of compound 19-2 (1.34 g, 2.87 mmol) in glacial acetic acid (40 mL) was stirred at 40° C. overnight. After the reaction was completed, AcOH was removed. The residue was dissolved in EtOAc (100 mL). The resulting mixture was washed with Na₂CO₃ aqueous solution (50 mL×3), dried over anhydrous Na₂SO₄ and concentrated in vacuo. The residue was purified by silica gel column chromatography (PE/EtOAc (v/v)=1/1) to give the title compound as a brown solid (0.87 g, 68%). The compound was characterized by the following spectroscopic data:

MS (ESI, pos.ion) m/z: 450.3 [M+H]⁺; and

¹H NMR (400 MHz, CDCl₃) δ (ppm): 7.59-7.52 (m, 1H), 7.32-7.21 (m, 2H), 5.41-5.38 (m, 2H), 4.35-4.32 (m, 1H), 3.87-3.76 (m, 1H), 3.70 (s, 3H), 3.66-3.62 (m, 1H), 2.67-2.65 (m, 1H), 2.20-2.13 (m, 1H), 1.85-1.73 (m, 4H), 1.46-1.43 (m, 2H), 0.88-0.84 (m, 6H).

Step 4) The Preparation of Compound 19-4

To a mixture of compound 19-3 (0.15 g, 0.327 mmol), bis(pinacolato)diboron (0.13 g, 0.4922 mmol), Pd(dppf)Cl₂·CH₂Cl₂ (27 mg, 0.0327 mmol) and KOAc (97 mg, 0.9884 mmol) was added DMF (5.0 mL) via syringe under N₂, and the mixture was stirred at 90° C. for 4.0 hrs. After the reaction was completed, the mixture was cooled to rt, diluted with EtOAc (40 mL) and filtered through a celite pad. The filtrate was washed with water (30 mL×3) and brine, dried over anhydrous Na₂SO₄ and concentrated in vacuo. The residue was purified by silica gel column chromatography (PE/EtOAc (v/v)=1/2) to give the title compound as a beige solid (0.09 g, 55.5%). The compound was characterized by the following spectroscopic data:

MS (ESI, pos.ion) m/z: 497.3 [M+H]⁺; and

¹H NMR (400 MHz, CDCl₃) δ (ppm): 7.85-7.80 (m, 1H), 7.72-7.68 (m, 2H), 5.45-5.41 (m, 2H), 4.56-4.48 (m, 1H), 4.33-4.30 (m, 1H), 3.86-3.84 (m, 1H), 3.70 (s, 3H), 3.64-3.62 (m, 1H), 3.04-2.98 (m, 1H), 2.25-2.20 (m, 1H), 2.20-2.13 (m, 2H), 1.87-1.76 (m, 1H), 1.46-1.49 (m, 2H), 1.35 (s, 12H), 0.88-0.84 (m, 6H).

Step 5) The Preparation of Compound 19-5

A suspension of compound 26-10 (48.04 mg, 0.06995 mmol), compound 19-4 (39.01 mg, 0.0786 mmol), Pd(PPh₃)₄ (8.0 mg, 0.007 mmol) and K₂CO₃ (30 mg, 0.21 mmol) in mixed solvents of DME and H₂O (6.0 mL, v/v=5/1) was stirred at 90° C. under N₂ for 3.0 hrs. After the reaction was completed, the mixture was cooled to rt and diluted with EtOAc (25 mL). The resulting mixture was washed with water (20 mL×3) and brine, dried over anhydrous Na₂SO₄ and concentrated in vacuo. The residue was purified by silica gel column chromatography (DCM/MeOH (v/v)=50/1) to give the title compound as a beige solid (31.73 mg, 50%). The compound was characterized by the following spectroscopic data:

MS (ESI, pos.ion) m/z: 454.5 [M+2H]²⁺; and

¹H NMR (400 MHz, CDCl₃) δ (ppm): 7.83-7.81 (m, 1H), 7.62-7.51 (m, 8H), 7.44, 7.42 (t, t, 1H), 5.56, 5.55 (d, d, 1H), 5.39-5.35 (m, 1H), 5.32, 5.29 (d, d, 1H), 5.06-5.02 (m, 1H), 4.80-4.75 (m, 1H), 4.73-4.69 (m, 1H), 4.44-4.40 (m, 1H), 4.21-4.17 (m, 1H), 3.75-3.67 (m, 1H), 3.66 (s, 3H), 3.63 (s, 3H), 3.13-3.03 (m, 1H), 2.68-2.50 (m, 4H), 2.26-2.00 (m, 6H), 1.83-1.69 (m, 3H), 1.67-1.52 (m, 6H), 1.47-1.36 (m, 2H), 1.31-1.24 (m, 1H), 1.02-0.89 (m, 12H).

Example 20

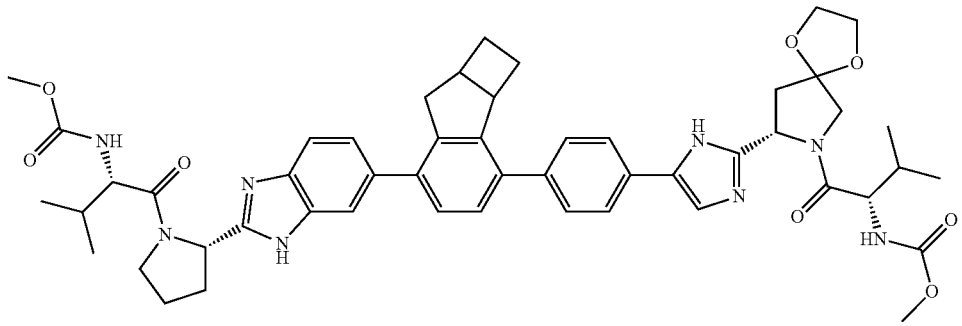 [SMILES: COC(=O)N[C@H](C(=O)N1CC2(C[C@H]1c1ncc(-c3ccc(-c4ccc(-c5ccc6nc([C@@H]7CCCN7C(=O)[C@@H](NC(=O)OC)C(C)C)[nH]c6c5)c5c4C4CCC4C5)cc3)[nH]1)OCCO2)C(C)C]

Synthetic Route:

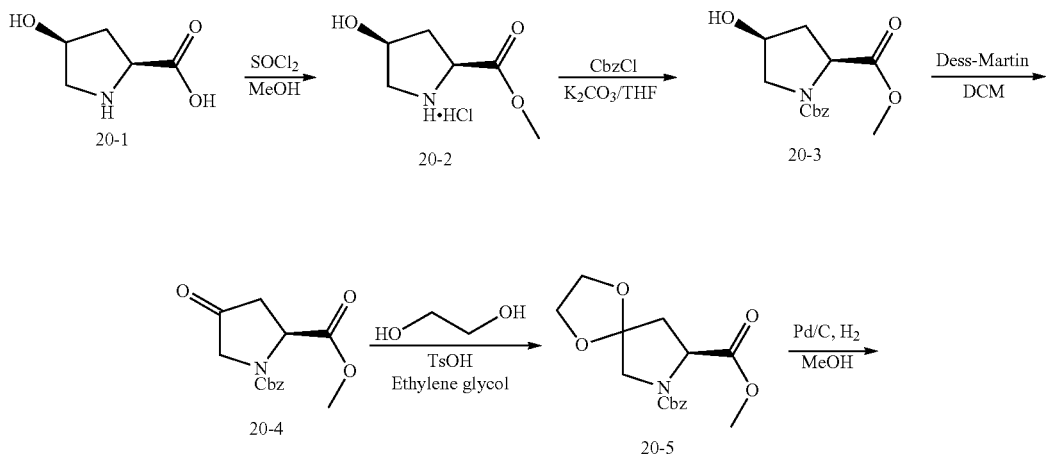

-continued
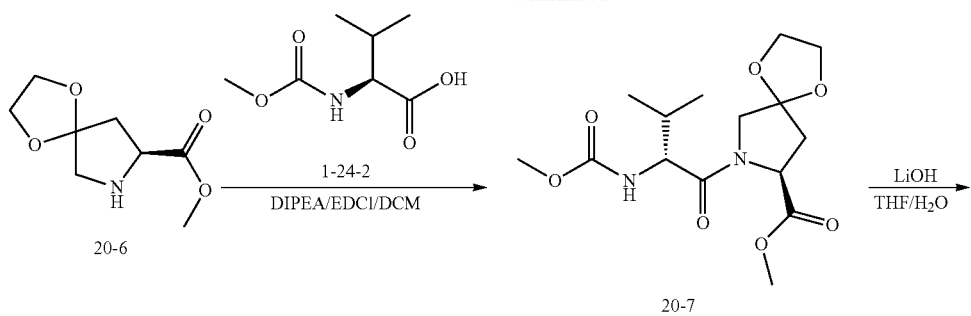
20-6     1-24-2, DIPEA/EDCl/DCM     20-7     LiOH, THF/H₂O
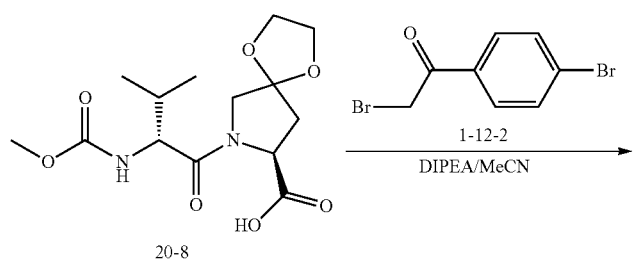
20-8     1-12-2, DIPEA/MeCN
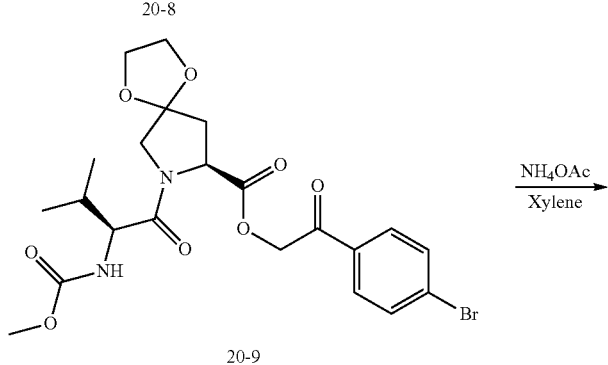
20-9     NH₄OAc/Xylene
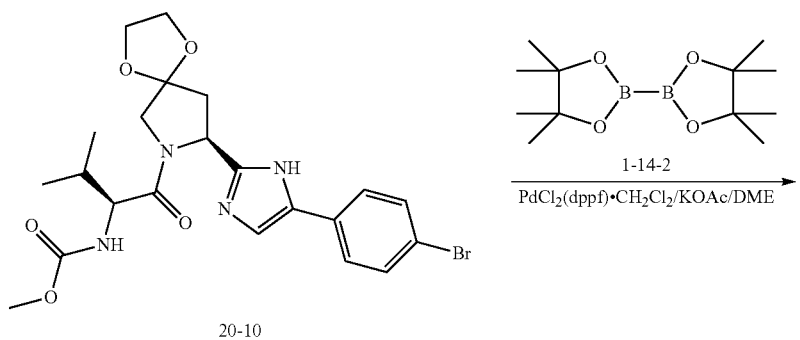
20-10     1-14-2, PdCl₂(dppf)·CH₂Cl₂/KOAc/DME
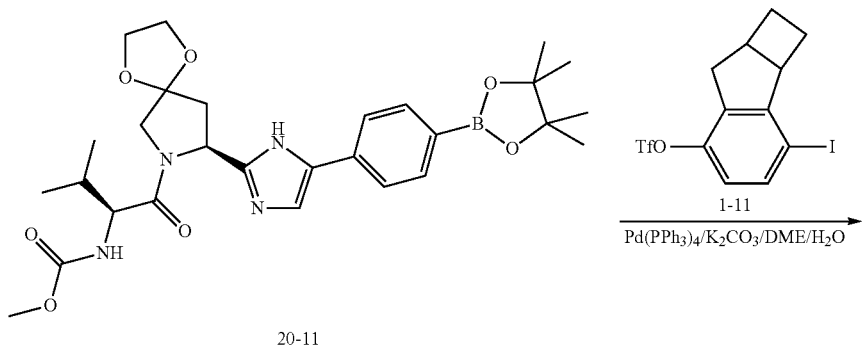
20-11     1-11, Pd(PPh₃)₄/K₂CO₃/DME/H₂O

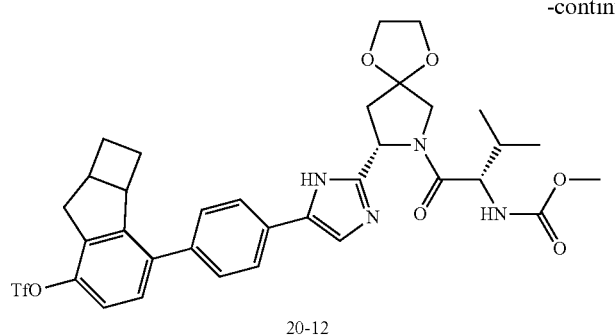

20-12

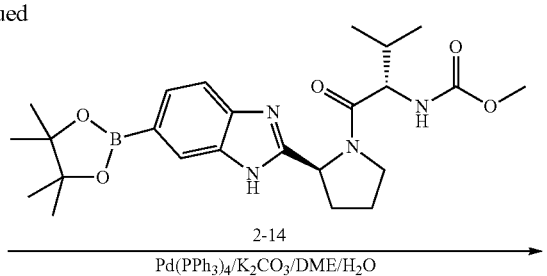

2-14

Pd(PPh₃)₄/K₂CO₃/DME/H₂O

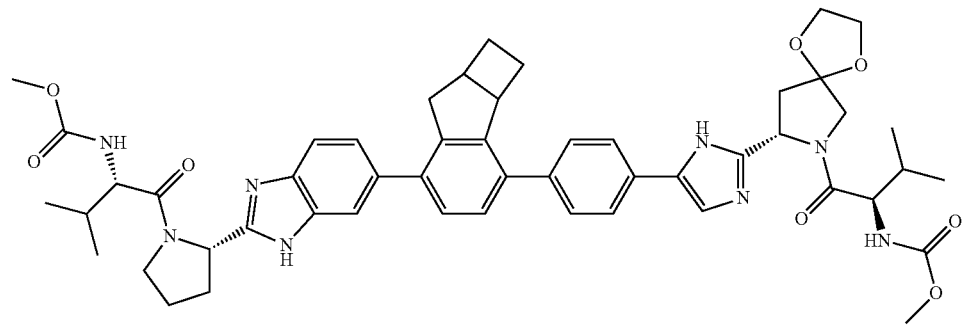

20-13

Step 1) The Preparation of Compound 20-2

To a solution of compound 20-1 (2.0 g, 15.3 mmol) in MeOH (20 mL) was added thionyl chloride (3.4 mL, 46.9 mmol) dropwise at 0° C. When the addition was completed complete, the mixture was stirred at 80° C. for 3.5 hrs. After the reaction was completed, the mixture was concentrated in vacuo to give the title compound as a white solid (2.76 g, 99.5%), which was used for the next step without further purification. The compound was characterized by the following spectroscopic data:

¹H NMR (400 Hz, CDCl₃) δ (ppm): 3.68 (s, 3H), 3.58 (t, 1H), 3.56 (s, 1H), 3.32 (m, 1H), 3.02 (m, 1H), 2.77 (m, 1H), 2.52 (s, 1H), 2.21 (m, 1H), 1.96 (m, 1H).

Step 2) The Preparation of Compound 20-3

To a vigorously stirred solution of benzyl chloroformate (3.7 mL, 26.3 mmol) and K₂CO₃ (10.6 g, 76.7 mmol) in a mixed solvent of THF (20 mL) and H₂O (10 mL) was added compound 20-2 (3.1 g, 17.1 mmol) in one portion. The reaction mixture was stirred at rt overnight. After the reaction was completed, the mixture was adjusted to pH 3 with diluted hydrochloric acid (1 M) and extracted with EtOAc (50 mL×3). The combined organic layers were washed with brine, dried over anhydrous Na₂SO₄ and concentrated in vacuo. The residue was purified by silica gel column chromatography (PE/EtOAc (v/v)=4/1) to give the title compound as pale yellow oil (3.0 g, 62.8%). The compound was characterized by the following spectroscopic data:

¹H NMR (400 Hz, CDCl₃) δ (ppm): 7.47 (d, 2H, J=8.24 Hz), 7.38 (d, 2H, J=8.24 Hz), 7.24 (m, 1H), 5.09 (s, 2H), 4.18 (t, 1H), 3.68 (s, 3H), 3.63 (m, 1H), 3.58 (s, 1H), 3.38 (m, 1H), 3.32 (m, 1H), 2.21 (m, 1H), 1.96 (m, 1H).

Step 3) The Preparation of Compound 20-4

To a solution of compound 20-3 (1.0 g, 3.6 mmol) in DCM (20 mL) was added Dess-Martin periodinane (3.0 g, 7.1 mmol) in a portionwise manner at 0° C. When the addition was completed, the mixture was stirred at rt for 1.0 hr. After the reaction was completed, the mixture was concentrated in vacuo. The residue was purified by silica gel column chromatography (PE/EtOAc (v/v)=5/1) to give the title compound as yellow oil (0.79 g, 79.5%). The compound was characterized by the following spectroscopic data:

¹H NMR (400 Hz, CDCl₃) δ (ppm): 7.47 (d, 2H, J=8.24 Hz), 7.38 (d, 2H, J=8.24 Hz), 7.24 (m, 1H), 5.09 (s, 2H), 4.18 (t, 1H), 3.68 (s, 3H), 3.38 (m, 1H), 3.32 (m, 1H), 2.21 (m, 1H), 1.96 (m, 1H).

Step 4) The Preparation of Compound 20-5

To a solution of compound 20-4 (1.0 g, 3.6 mmol) in toluene (20 mL) were added ethylene glycol (0.8 mL, 15.7 mmol) and TsOH (0.14 g, 0.8 mmol) separately. When the addition was completed, the mixture was refluxed overnight. After the reaction was completed, the mixture was diluted with EtOAc (50 mL), washed with saturated NaHCO₃ aqueous solution (30 mL) and brine (30 mL), dried over anhydrous Na₂SO₄ and concentrated in vacuo. The residue was purified by silica gel column chromatography (PE/EtOAc (v/v)=6/1) to give the title compound as colorless liquid (0.54 g, 46.7%). The compound was characterized by the following spectroscopic data:

¹H NMR (400 Hz, CDCl₃) δ (ppm): 7.47 (d, 2H, J=8.24 Hz), 7.38 (d, 2H, J=8.24 Hz), 7.24 (m, 1H), 5.09 (s, 2H), 4.18 (t, 1H), 4.05 (m, 2H), 3.95 (m, 2H), 3.68 (s, 3H), 3.38 (m, 1H), 3.32 (m, 1H), 2.21 (m, 1H), 1.96 (m, 1H).

Step 5) The Preparation of Compound 20-6

To a solution of compound 20-5 (0.59 g, 1.8 mmol) in MeOH (150 mL) was added a catalytic amount of Pd/C (0.2 g). When the addition was completed, the mixture was stirred at rt under H₂ overnight. After the reaction was completed, the mixture was filtered. The filtrate was concentrated in vacuo to give the title compound (0.34 g, 98.9%), which was used for the next step without further purification. The compound was characterized by the following spectroscopic data:

¹H NMR (400 Hz, CDCl₃) δ (ppm): 4.18 (t, 1H), 4.05 (m, 2H), 3.95 (m, 2H), 3.68 (s, 3H), 3.38 (m, 1H), 3.32 (m, 1H), 2.21 (m, 1H), 1.96 (m, 1H).

Step 6) The Preparation of Compound 20-7

To a suspension of compound 20-6 (3.48 g, 18.6 mmol), compound 1-24-2 (3.26 g, 18.6 mmol) and EDCI (7.1 g, 37 mmol) in DCM (50 mL) was added DIPEA (12.3 mL, 74.4 mmol) dropwise at 0° C. When the addition was completed, the mixture was stirred at rt overnight. After the reaction was completed, the mixture was washed with brine, dried over anhydrous $Na_2SO_4$ and concentrated in vacuo. The residue was purified by silica gel column chromatography (PE/EtOAc (v/v)=3/1) to give the title compound as pale yellow oil (2.5 g, 39.1%). The compound was characterized by the following spectroscopic data:

$^1$H NMR (400 Hz, $CDCl_3$) δ (ppm): 9.80 (s, 1H), 4.54 (d, 1H, J=7.25 Hz), 4.28 (m, 1H), 4.06 (m, 4H), 3.76 (m, 2H), 3.50 (s, 3H), 3.45 (s, 3H), 2.71 (m, 2H), 2.65 (m, 1H), 0.87 (m, 3H), 0.81 (m, 3H).

Step 7) The Preparation of Compound 20-8

To a solution of compound 20-7 (0.9 g, 2.6 mmol) in THF (5.0 mL) was added a solution of LiOH (0.12 g, 5.0 mmol) in water (5.0 mL). When the addition was completed, the mixture was stirred at rt overnight. After the reaction was completed, the mixture was adjusted to pH 2 with diluted hydrochloric acid (1 M), and extracted with EtOAc (50 mL×3). The combined organic layers were washed with brine, dried over anhydrous $Na_2SO_4$ and concentrated in vacuo to give the title compound as a white solid (0.85 g, 99.0%), which was used for the next step without further purification. The compound was characterized by the following spectroscopic data:

$^1$H NMR (400 Hz, $CD_3C_1$) δ (ppm): 9.80 (s, 1H), 4.54 (d, 1H, J=7.25 Hz), 4.28 (m, 1H), 4.06 (m, 4H), 3.76 (m, 2H), 3.50 (s, 3H), 2.71 (m, 2H), 2.65 (m, 1H), 0.87 (m, 3H), 0.81 (m, 3H).

Step 8) The Preparation of Compound 20-9

To a mixture of compound 1-12-2 (1.65 g, 5.9 mmol) and compound 20-8 (1.78 g, 5.4 mmol) in MeCN (30 mL) was added DIPEA (1.1 mL, 6.7 mmol) dropwise at 0° C. At the end of the addition, the mixture was stirred at rt for 3.0 hrs. After the reaction was completed, the mixture was concentrated in vacuo. The residue was purified by silica gel column chromatography (PE/EtOAc (v/v)=3/1) to give the title compound as a pale yellow solid (2.76 g, 97.3%). The compound was characterized by the following spectroscopic data:

$^1$H NMR (400 MHz, $CDCl_3$) δ (ppm): 7.82-7.78 (m, 2H), 7.67-7.64 (m, 2H), 5.32, 5.29 (d, d, 1H), 5.22 (s, 2H), 5.06-5.02 (m, 1H), 4.36-4.31 (m, 1H), 4.02-4.00 (m, 4H), 3.81-3.77 (m, 1H), 3.63 (s, 3H), 3.56-3.51 (m, 1H), 2.79-2.73 (m, 1H), 2.41-2.34 (m, 1H), 2.18-2.06 (m, 1H), 0.97-0.95 (m, 3H), 0.91-0.89 (m, 3H).

Step 9) The Preparation of Compound 20-10

A suspension of compound 20-9 (3.0 g, 5.7 mmol) and $NH_4OAc$ (4.4 g, 57.1 mmol) in xylene (20 mL) was stirred at 130° C. overnight. After the reaction was completed, the mixture was cooled to rt and diluted with EtOAc (150 mL). The resulting mixture was washed with brine, dried over anhydrous $Na_2SO_4$ and concentrated in vacuo. The residue was purified by silica gel column chromatography (PE/EtOAc (v/v)=3/1) to give the title compound as a yellow solid (2.6 g, 89.9%). The compound was characterized by the following spectroscopic data:

$^1$H NMR (400 MHz, $CDCl_3$) δ (ppm): 7.45-7.41 (m, 2H), 7.29-7.26 (m, 3H), 5.40-5.36 (m, 1H), 5.32, 5.29 (d, d, 1H), 4.42-4.38 (m, 1H), 3.98-3.92 (m, 5H), 3.71-3.69 (m, 1H), 3.63 (s, 3H), 2.83-2.77 (m, 1H), 2.45-2.39 (m, 1H), 2.24-2.11 (m, 1H), 0.97-0.95 (m, 3H), 0.91-0.89 (m, 3H).

Step 10) The Preparation of Compound 20-11

A suspension of compound 20-10 (4.0 g, 7.9 mmol), compound 1-14-2 (3.11 g, 12.2 mmol), $Pd(dppf)Cl_2 \cdot CH_2Cl_2$ (0.64 g, 0.8 mmol) and KOAc (1.94 g, 19.8 mmol) in DME (50 mL) was stirred at 90° C. under $N_2$ for 4.0 hrs. After the reaction was completed, the mixture was cooled to rt, diluted with EtOAc (200 mL) and filtered through a celite pad. The filtrate was washed with water (100 mL×3) and brine, dried over anhydrous $Na_2SO_4$ and concentrated in vacuo. The residue was purified by silica gel column chromatography (PE/DCM (v/v)=4/1) to give the title compound as a white solid (4.15 g, 94.7%). The compound was characterized by the following spectroscopic data:

$^1$H NMR (400 MHz, $CDCl_3$) δ (ppm): 7.64-7.57 (m, 4H), 7.22 (s, 1H), 5.40-5.36 (m, 1H), 5.32, 5.29 (d, d, 1H), 4.42-4.38 (m, 1H), 3.98-3.96 (m, 5H), 3.71-3.69, 3.67-3.66 (m, 1H), 3.63 (s, 3H), 2.83-2.77 (m, 1H), 2.45-2.39 (m, 1H), 2.24-2.11 (m, 1H), 1.35, 1.32 (m, m, 12H), 0.97-0.95 (m, 3H), 0.91-0.89 (m, 3H).

Step 11) The Preparation of Compound 20-12

A suspension of compound 20-11 (1.3 g, 2.34 mmol), compound 1-11 (1.00 g, 2.4 mmol), $Pd(PPh_3)_4$ (0.14 g, 0.12 mmol) and $K_2CO_3$ (0.8 g, 5.85 mmol) in mixed solvents of DME and $H_2O$ (16 mL, v/v=3/1) was stirred at 90° C. under $N_2$ for 3.0 hrs. After the reaction was completed, the mixture was diluted with EtOAc (50 mL), washed with brine, dried over anhydrous $Na_2SO_4$ and concentrated in vacuo. The residue was purified by recrystallization to give the title compound as a white solid (1.345 g, 80%). The compound was characterized by the following spectroscopic data:

MS (ESI, pos.ion) m/z: 719.5 [M+H]$^+$; and $^1$H NMR (400 MHz, $CDCl_3$) δ (ppm): 7.59-7.56 (m, 2H), 7.52-7.49 (m, 2H), 7.35 (s, 1H), 7.26, 7.23 (s, s, 1H), 6.98, 6.96 (t, t, 1H), 5.56, 5.55 (d, d, 1H), 5.40-5.36 (m, 1H), 4.35-4.31 (m, 1H), 3.99-3.92 (m, 5H), 3.71-3.69 (m, 1H), 3.66 (s, 3H), 3.44-3.35 (m, 1H), 3.09-2.97 (m, 2H), 2.83-2.77 (m, 1H), 2.70-2.52 (m, 2H), 2.45-2.39 (m, 1H), 2.28-2.07 (m, 3H), 1.61-1.51 (m, 1H), 1.02, 1.00 (m, m, 3H), 0.94, 0.91 (m, m, 3H).

Step 12) The Preparation of Compound 20-13

A suspension of compound 2-14 (32.9 mg, 0.06995 mmol), compound 20-12 (50.27 mg, 0.06995 mmol), $Pd(PPh_3)_4$ (8.0 mg, 0.007 mmol) and $K_2CO_3$ (30 mg, 0.21 mmol) in mixed solvents of DME and $H_2O$ (6.0 mL, v/v=5/1) was stirred at 90° C. under $N_2$ for 3.0 hrs. After the reaction was completed, the mixture was diluted with EtOAc (25 mL), washed with brine, dried over anhydrous $Na_2SO_4$ and concentrated in vacuo. The residue was purified by silica gel column chromatography (DCM/MeOH (v/v)=50/1) to give the title compound as a beige solid (31.93 mg, 50%). The compound was characterized by the following spectroscopic data:

MS (ESI, pos.ion) m/z: 457.5 [M+2H]$^{2+}$; and $^1$H NMR (400 MHz, $CDCl_3$) δ (ppm): 7.85, 7.83 (d, d, 1H), 7.62, 7.60 (s, s, 1H), 7.59-7.51 (m, 6H), 7.44, 7.42 (t, t, 1H), 7.35 (s, 1H), 6.08, 6.05 (d, d, 2H), 5.40-5.36 (m, 1H), 5.25-5.18 (m, 1H), 4.36-4.31 (m, 2H), 3.98-3.96 (m, 5H), 3.84-3.78 (m, 1H), 3.75-3.69 (m, 2H), 3.68-3.66 (m, 2H), 3.65 (s, 6H), 3.13-3.03 (m, 1H), 2.83-2.77 (m, 1H), 2.68-2.54 (m, 2H), 2.45-2.28 (m, 2H), 2.27-2.08 (m, 8H), 2.01-1.86 (m, 1H), 1.62-1.52 (m, 1H), 1.02, 1.00 (m, m, 6H), 0.94, 0.91 (m, m, 6H).

Example 21
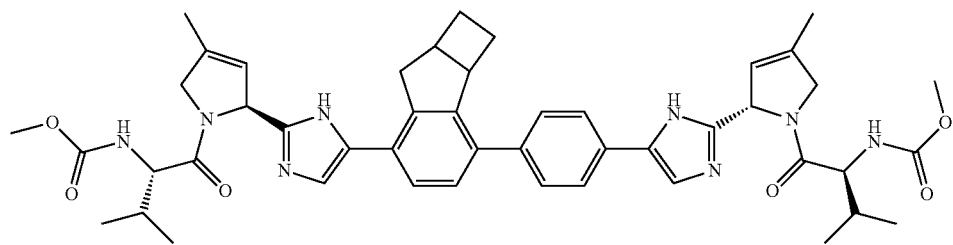 [SMILES: COC(=O)N[C@H](C(=O)N1CC(C)=C[C@H]1c1ncc(-c2ccc(-c3ccc(-c4cnc([C@@H]5C=C(C)CN5C(=O)[C@@H](NC(=O)OC)C(C)C)[nH]4)c4c3C3CCC3C4)cc2)[nH]1)C(C)C]
Synthetic Route:
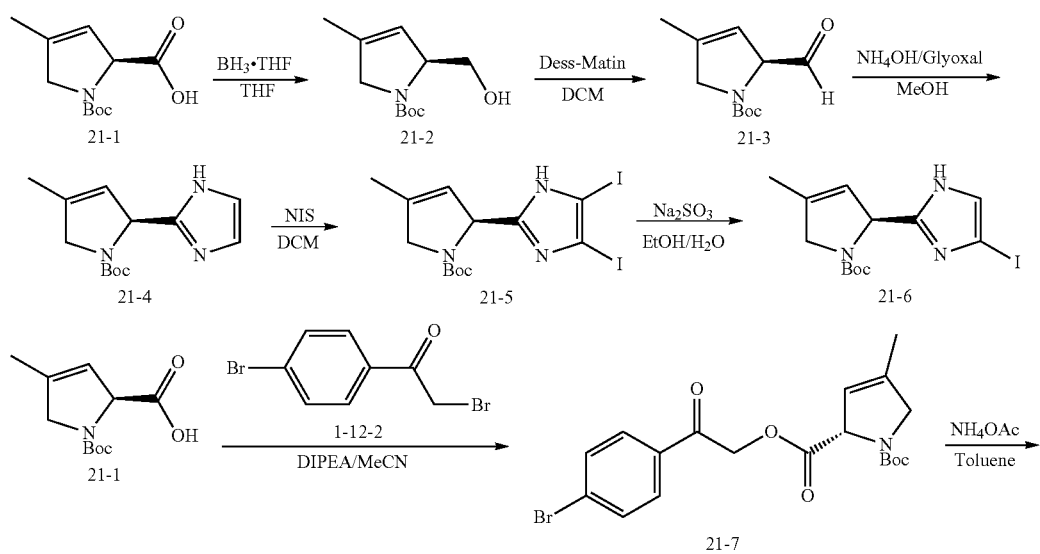
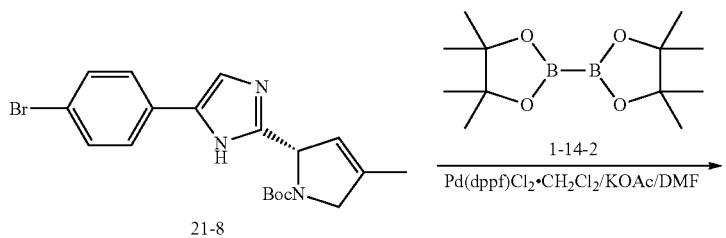
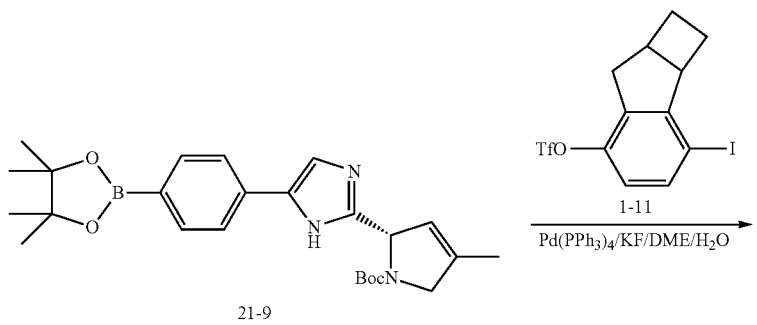

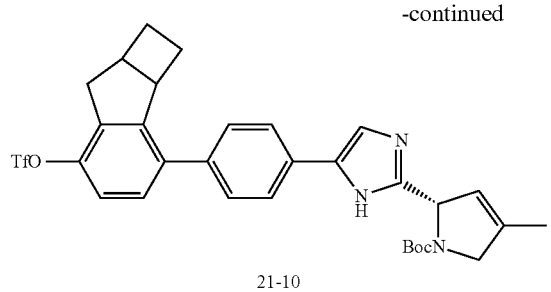

21-10

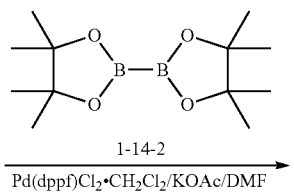

1-14-2
————————————→
Pd(dppf)Cl₂•CH₂Cl₂/KOAc/DMF

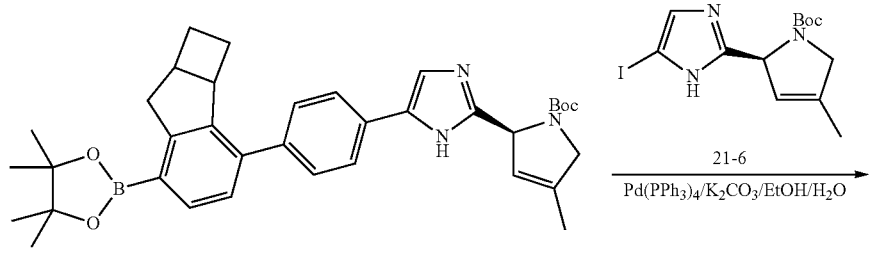

21-11

21-6
————————————→
Pd(PPh₃)₄/K₂CO₃/EtOH/H₂O

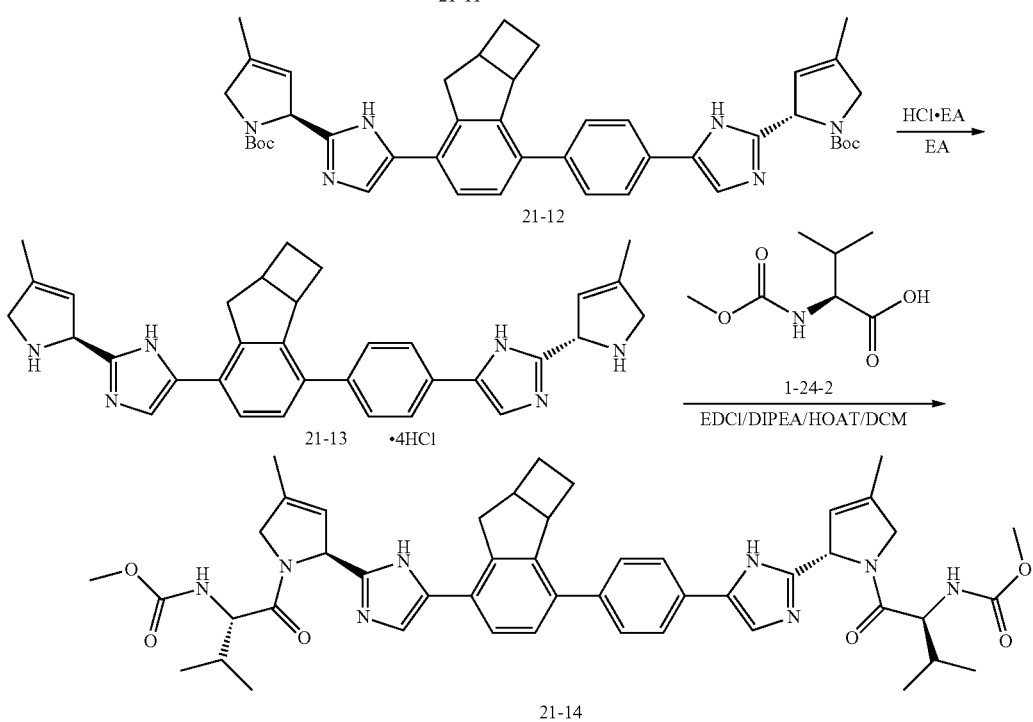

Step 1) The Preparation of Compound 21-2

To a solution of compound 21-1 (10.58 g, 46.6 mmol) in THF (100 mL) was added diborane (100 mL, 1M in THF) dropwise at 0° C. under $N_2$. At the end of the addition, the mixture was stirred at 0° C. for 3.0 hrs. After the reaction was completed, the mixture was quenched with MeOH (80 mL) and concentrated in vacuo. The residue was purified by silica gel column chromatography (PE/EtOAc (v/v)=3/2) to give the title compound as colorless oil (7.45 g, 75%). The compound was characterized by the following spectroscopic data:

$^1$H NMR (400 MHz, CDCl$_3$) δ (ppm): 5.32-5.29 (m, 1H), 4.63-4.54 (m, 1H), 4.16-4.09 (m, 1H), 3.97-3.92 (m, 1H), 3.88-3.82 (m, 1H), 3.80-3.79 (m, 1H), 3.22 (br, 1H), 1.62-1.61 (m, 3H), 1.43 (s, 9H).

Step 2) The Preparation of Compound 21-3

To a solution of compound 21-2 (7.42 g, 34.8 mmol) in DCM (250 mL) was added Dess-Martin periodinane (20.7 g, 48.8 mmol) in a portionwise manner at 0° C. At the end of the addition, the mixture was stirred at rt for 2.0 hrs. After the reaction was completed, the mixture was quenched with water (150 mL) and filtered. The filtrate was washed with brine, dried over anhydrous $Na_2SO_4$ and concentrated in vacuo. The residue was purified by silica gel column chromatography (PE/EtOAc (v/v)=3/1) to give the title compound as colorless oil (3.72 g, 50.7%). The compound was characterized by the following spectroscopic data:

$^1$H NMR (400 MHz, CDCl$_3$) δ (ppm): 9.77-9.75 (m, 1H), 5.41-5.38 (m, 1H), 4.64-4.59 (m, 1H), 4.24-4.17 (m, 1H), 3.96-3.89 (m, 1H), 1.65-1.64 (m, 3H), 1.44 (s, 9H).

Step 3) The Preparation of Compound 21-4

To a solution of compound 21-3 (3.71 g, 17.6 mmol) and ammonia (13 mL) in MeOH (30 mL) was added glyoxal (8.0 mL, 40% in water) dropwise at 0° C. At the end of the addition, the mixture was stirred at rt overnight. After the reaction was completed, the mixture was concentrated in vacuo. The residue was purified by silica gel column chromatography (PE/EtOAc (v/v)=4/1) to give the title compound as a white solid (2.08 g, 47.6%). The compound was characterized by the following spectroscopic data:

MS (ESI, pos.ion) m/z: 250.5 [M+H]$^+$; and $^1$H NMR (400 MHz, CDCl$_3$) δ (ppm): 7.05 (s, 2H), 6.32-6.28 (m, 1H), 5.38-5.35 (m, 1H), 4.23-4.17 (m, 1H), 3.86-3.80 (m, 1H), 1.68-1.67 (m, 3H), 1.40 (s, 9H).

Step 4) The Preparation of Compound 21-5

To a solution of compound 21-4 (2.09 g, 8.4 mmol) in DCM (60 mL) was added N-iodosuccinimide (3.8 g, 16.8 mmol) at 0° C. in a portionwise manner. At the end of the addition, the mixture was stirred at 0° C. for 1.5 hrs. After the reaction was completed, the mixture was washed with brine, dried over anhydrous Na$_2$SO$_4$ and concentrated in vacuo. The residue was purified by silica gel column chromatography (PE/EtOAc (v/v)=3/2) to give the title compound as a white solid (2.65 g, 63%). The compound was characterized by the following spectroscopic data:

MS (ESI, pos.ion) m/z: 501.5 [M+H]$^+$; and $^1$H NMR (400 MHz, CDCl$_3$) δ (ppm): 5.52-5.45 (m, 2H), 4.35-4.29 (m, 1H), 3.94-3.88 (m, 1H), 1.67-1.66 (m, 3H), 1.40 (s, 9H).

Step 5) The Preparation of Compound 21-6

To a suspension of compound 21-5 (1.64 g, 3.27 mmol) in mixed solvents of ethanol and water (50 mL, v/v=3/7) was added Na$_2$SO$_3$ (3.7 g, 29 mmol), and the mixture was refluxed for 17 hrs. After the reaction was completed, the ethanol solvent was removed, and to the mixture was added water (50 mL). The resulting mixture was extracted with EtOAc (50 mL×3). The combined organic layers were washed with brine, dried over anhydrous Na$_2$SO$_4$ and concentrated in vacuo. The residue was purified by silica gel column chromatography (PE/EtOAc (v/v)=3/2) to give the title compound as a white solid (1.03 g, 84%). The compound was characterized by the following spectroscopic data:

MS (ESI, pos.ion) m/z: 376.5 [M+H]$^+$; and $^1$H NMR (400 MHz, CDCl$_3$) δ (ppm): 7.18 (s, 1H), 5.35-5.32 (m, 1H), 5.28-5.24 (m, 1H), 4.29-4.23 (m, 1H), 3.91-3.85 (m, 1H), 1.67-1.66 (m, 3H), 1.40 (s, 9H).

Step 6) The Preparation of Compound 21-7

To a solution of compound 1-12-2 (2.98 g, 10.79 mmol) and compound 21-1 (2.69 g, 11.87 mmol) in MeCN (250 mL) was added DIPEA (2.14 mL, 12.95 mmol) dropwise at 0° C. At the end of the addition, the mixture was stirred at rt for 3.0 hrs. After the reaction was completed, the MeCN solvent was removed, and to the mixture was added water (100 mL). The resulting mixture was extracted with EtOAc (100 mL×3). The combined organic layers were washed with brine, dried over anhydrous Na$_2$SO$_4$ and concentrated in vacuo. The residue was purified by silica gel column chromatography (PE/EtOAc (v/v)=10/1) to give the title compound as a white solid (4.1 g, 90%). The compound was characterized by the following spectroscopic data:

MS (ESI, pos.ion) m/z: 424.5 [M+H]$^+$; and $^1$H NMR (400 MHz, CDCl$_3$) δ (ppm): 7.82-7.78 (m, 2H), 7.67-7.64 (m, 2H), 5.61-5.59 (m, 1H), 5.33 (s, 2H), 4.73-4.69 (m, 1H), 4.35-4.28 (m, 1H), 3.99-3.92 (m, 1H), 1.76-1.74 (m, 3H), 1.42 (s, 9H).

Step 7) The Preparation of Compound 21-8

A mixture of compound 21-7 (1.54 g, 3.64 mmol) and ammonium acetate (4.2 g, 5.46 mmol) in toluene (30 mL) was stirred at 110° C. for 5.0 hrs. After the reaction was completed, the mixture was cooled to rt and quenched with water (50 mL). The resulting mixture was extracted with EtOAc (50 mL×3). The combined organic layers were washed with brine, dried over anhydrous Na$_2$SO$_4$ and concentrated in vacuo. The residue was purified by silica gel column chromatography (PE/EtOAc (v/v)=6/1) to give the title compound as a pale yellow solid (1.25 g, 85%). The compound was characterized by the following spectroscopic data:

MS (ESI, pos.ion) m/z: 404.5 [M+H]$^+$; and $^1$H NMR (400 MHz, CDCl$_3$) δ (ppm): 7.64 (s, 1H), 7.45-7.41 (m, 2H), 7.35-7.32 (m, 2H), 5.78-5.75 (m, 1H), 5.55-5.52 (m, 1H), 4.24-4.17 (m, 1H), 3.77-3.69 (m, 1H), 1.78-1.77 (m, 3H), 1.39 (s, 9H).

Step 8) The Preparation of Compound 21-9

A mixture of compound 21-8 (4.12 g, 10.23 mmol), compound 1-14-2 (2.86 g, 11.25 mmol), Pd(dppf)Cl$_2$.CH$_2$Cl$_2$ (0.42 g, 0.51 mmol) and KOAc (2.51 g, 25.57 mmol) in DMF (40.0 mL) was stirred at 90° C. under N$_2$ for 3.0 hrs. After the reaction was completed, the mixture was cooled to rt, diluted with EtOAc (100 mL) and filtered through a celite pad. The filtrate was washed with water (80 mL×3) and brine, dried over anhydrous Na$_2$SO$_4$ and concentrated in vacuo. The residue was purified by silica gel column chromatography (PE/EtOAc (v/v)=2/1) to give the title compound (3.69 g, 80%). The compound was characterized by the following spectroscopic data:

$^1$H NMR (400 MHz, CDCl$_3$) δ (ppm): 7.75-7.72 (m, 2H), 7.61-7.58 (m, 2H), 7.28 (s, 1H), 5.78-5.75 (m, 1H), 5.55-5.52 (m, 1H), 4.24-4.17 (m, 1H), 3.77-3.69 (m, 1H), 1.78-1.77 (m, 3H), 1.39 (s, 9H).

Step 9) The Preparation of Compound 21-10

To a mixture of compound 21-9 (1.18 g, 2.62 mmol), compound 1-11 (1.10 g, 2.62 mmol), Pd(PPh$_3$)$_4$ (0.12 g, 0.10 mmol) and KF (0.30 g, 5.24 mmol) were added DME (12 mL) and pure water (3 mL) via syringe under N$_2$, and the mixture was stirred at 90° C. for 2.0 hrs. After the reaction was completed, the mixture was cooled to rt and diluted with EtOAc (80 mL). The resulting mixture was washed with water (20 mL×3) and brine, dried over anhydrous Na$_2$SO$_4$ and concentrated in vacuo. The residue was purified by silica gel column chromatography (DCM/MeOH (v/v)=100/1) to give the title compound as a white solid (0.97 g, 60%). The compound was characterized by the following spectroscopic data:

MS (ESI, pos.ion) m/z: 616.5 [M+H]$^+$; and $^1$H NMR (400 MHz, CDCl$_3$) δ (ppm): 7.60-7.57 (m, 2H), 7.52-7.49 (m, 2H), 7.39 (s, 1H), 7.26, 7.23 (s, s, 1H), 6.98, 6.96 (t, t, 1H), 5.43-5.39 (m, 1H), 5.36-5.33 (m, 1H), 4.28-4.26, 4.23-4.20 (m, m, 1H), 3.80-3.78, 3.74-3.72 (m, m, 1H), 3.45-3.35 (m, 1H), 3.09-2.97 (m, 2H), 2.70-2.52 (m, 2H), 2.20-2.07 (m, 2H), 1.67-1.66 (m, 3H), 1.61-1.51 (m, 1H), 1.41 (s, 9H).

Step 10) The Preparation of Compound 21-11

A mixture of compound 21-10 (0.99 g, 1.61 mmol), compound 1-14-2 (0.61 g, 2.415 mmol), Pd(dppf)Cl$_2$.CH$_2$Cl$_2$ (80 mg, 0.096 mmol) and KOAc (0.4 g, 4.02 mmol) in DMF (10.0 mL) was stirred at 120° C. under N$_2$ for 4.0 hrs. After the reaction was completed, the mixture was cooled to rt, diluted with EtOAc (100 mL) and filtered through a celite pad. The filtrate was washed with water (20 mL×3) and brine, dried over anhydrous Na$_2$SO$_4$ and concentrated in vacuo. The residue was purified by silica gel column chromatography (DCM/MeOH (v/v)=100/1) to give the title compound as a white solid (0.67 g, 70%). The compound was characterized by the following spectroscopic data:

MS (ESI, pos.ion) m/z: 594.5 [M+H]$^+$; and $^1$H NMR (400 MHz, CDCl$_3$) δ (ppm): 7.72, 7.70 (s, s, 1H), 7.60-7.53 (m, 4H), 7.39 (s, 1H), 7.31, 7.28 (t, t, 1H), 5.43-5.39 (m, 1H), 5.36-5.33 (m, 1H), 4.28-4.26, 4.23-4.20 (m, m, 1H), 3.80-3.78, 3.74-3.72 (m, m, 1H), 3.63-3.56 (m, 1H), 3.20-3.11 (m, 1H), 3.01-2.93 (m, 1H), 2.55-2.39 (m, 2H), 2.18-2.08 (m, 1H), 2.05-1.95 (m, 1H), 1.67-1.66 (m, 3H), 1.62-1.51 (m, 1H), 1.41 (s, 9H), 1.32, 1.29 (q, q, 12H).

Step 11) The Preparation of Compound 21-12

A suspension of compound 21-6 (0.17 g, 0.446 mmol), compound 21-11 (0.25 g, 0.42 mmol), Pd(PPh$_3$)$_4$ (25 mg, 0.02 mmol) and K$_2$CO$_3$ (0.17 g, 1.27 mmol) in mixed solvents of ethanol and water (8.0 mL, v/v=3/1) was stirred at 90° C. under N$_2$ for 2.0 hrs. After the reaction was completed, the mixture was concentrated in vacuo. The residue was dissolved in EtOAc (50 mL). The resulting mixture was washed with brine, dried over anhydrous Na$_2$SO$_4$ and concentrated in vacuo. The residue was purified by silica gel column chromatography (DCM/EtOH (v/v) =50/1) to give the title compound as a pale yellow solid (0.26 g, 85%). The compound was characterized by the following spectroscopic data:

MS (ESI, pos.ion) m/z: 715.5 [M+H]$^+$; and $^1$H NMR (400 MHz, CDCl$_3$) δ (ppm): 7.66 (s, 1H), 7.64, 7.62 (s, s, 1H), 7.60-7.53 (m, 4H), 7.47, 7.44 (t, t, 1H), 7.39 (s, 1H), 5.80-5.75 (m, 1H), 5.66-5.62 (m, 1H), 5.38-5.34 (m, 2H), 4.46-4.38 (m, 1H), 4.13-4.11 (m, 1H), 4.07-4.05 (m, 1H), 3.74-3.72 (m, 1H), 3.68-3.66 (m, 1H), 3.24-3.14 (m, 1H), 2.82-2.64 (m, 2H), 2.37-2.12 (m, 3H), 1.67-1.66 (m, 6H), 1.65-1.56 (m, 1H), 1.39 (s, 18H).

Step 12) The Preparation of Compound 21-13

To a solution of compound 21-12 (0.36 g, 0.51 mmol) in EtOAc (4.0 mL) was added a solution of HCl in EtOAc (3.0 mL, 4 M) dropwise. At the end of the addition, the mixture was stirred at rt for 8.0 hrs. After the reaction was completed, the mixture was concentrated in vacuo. The residue was purified by beating in EtOAc (20 mL) and filtered to give the title compound as a pale yellow solid (0.27 g, 80%). The compound was characterized by the following spectroscopic data:

MS (ESI, pos.ion) m/z: 515.5 [M+H]$^+$.

Step 13) The Preparation of Compound 21-14 To a suspension of compound 21-13 (0.19 g, 0.29 mmol), compound 1-24-2 (0.11 g, 0.65 mmol), EDCI (0.12 g, 0.65 mmol) and HOAT (80 mg, 0.59 mmol) in DCM (5.0 mL) was added DIPEA (0.6 mL, 3.63 mmol) dropwise. At the end of the addition, the mixture was stirred at rt for 3.0 hrs. After the reaction was completed, the mixture was diluted with DCM (20 mL). The resulting mixture was washed with NH$_4$Cl aqueous solution and brine, dried over Na$_2$SO$_4$ and concentrated in vacuo. The residue was purified by silica gel column chromatography (DCM/MeOH (v/v) =40/1) to give the title compound as a white solid (0.15 g, 65%). The compound was characterized by the following spectroscopic data:

MS (ESI, pos.ion) m/z: 415.5 [M+2H]$^{2+}$; and $^1$H NMR (400 MHz, CDCl$_3$) δ (ppm): 7.64, 7.62 (s, s, 1H), 7.60-7.57 (m, 3H), 7.56-7.53 (m, 2H), 7.47, 7.44 (t, t, 1H), 7.34 (s, 1H), 5.84-5.80 (m, 1H), 5.74-5.70 (m, 1H), 5.45-5.42 (m, 2H), 5.32, 5.30 (d, d, 2H), 4.70-4.67, 4.68-4.63 (m, m, 2H), 4.46-4.38 (m, 3H), 4.16-4.13, 4.12-4.09 (m, m, 2H), 3.63 (s, 6H), 3.24-3.14 (m, 1H), 2.82-2.64 (m, 2H), 2.37-2.12 (m, 5H), 1.66-1.56 (m, 7H), 0.97, 0.95 (m, m, 6H), 0.90, 0.89 (m, m, 6H).

Example 22

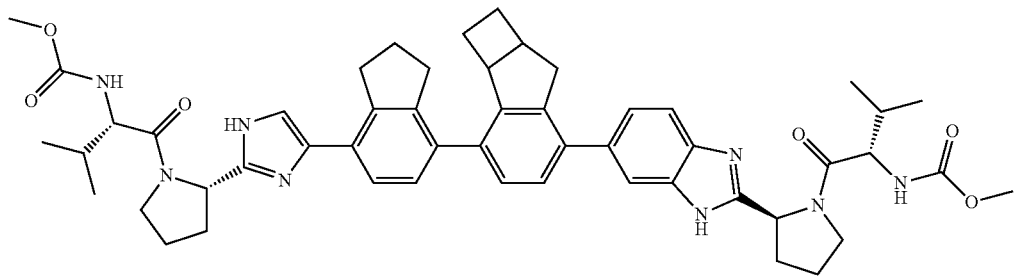

Synthetic Route:

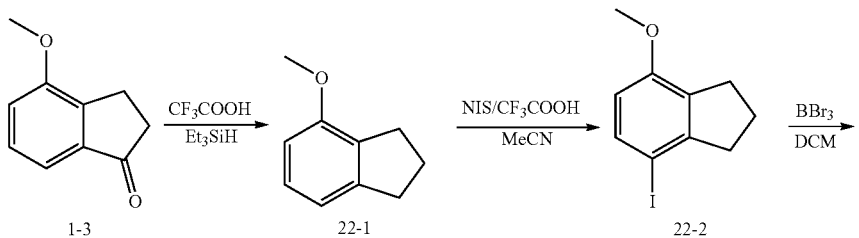

-continued
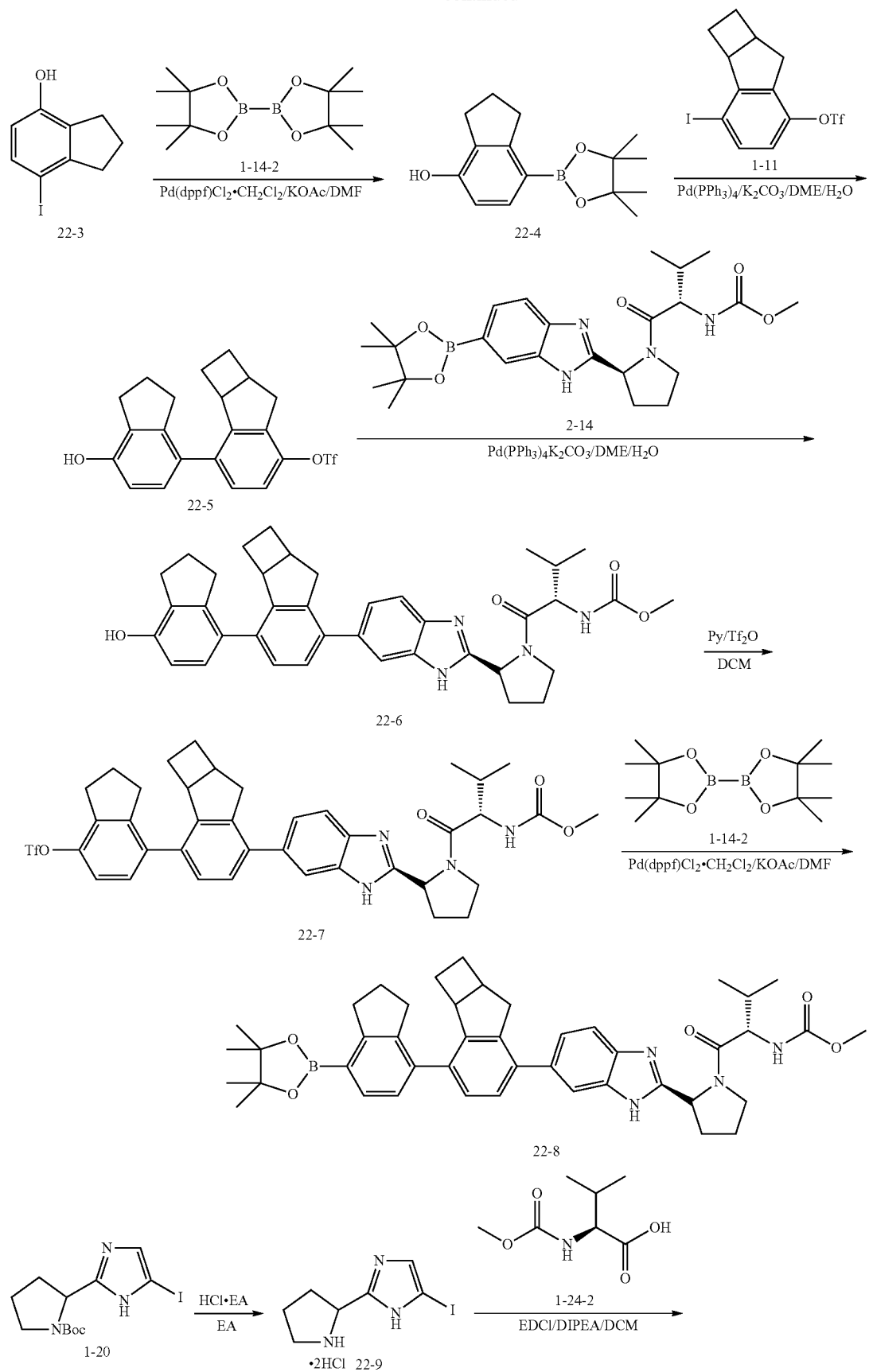

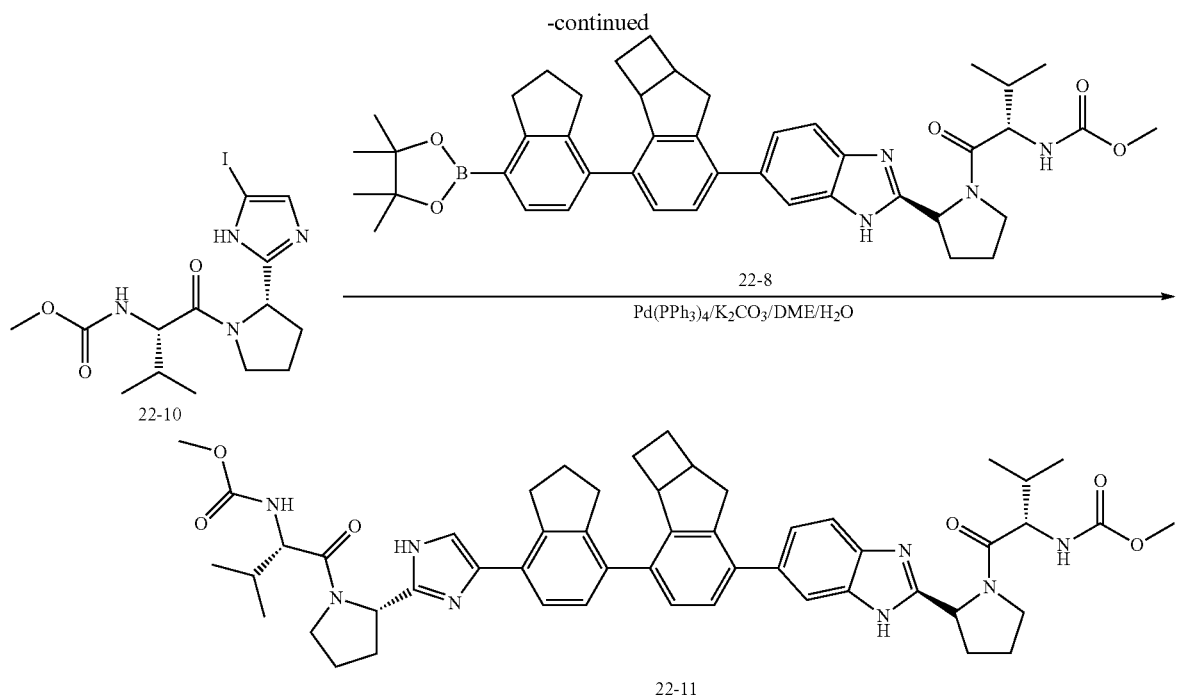

Step 1) The Preparation of Compound 22-1

To a mixture of compound 1-3 (7.29 g, 45 mmol) and triethylsilane (20.98 g, 180 mmol) was added TFA (30 mL) dropwise at 0° C. At the end of the addition, the mixture was stirred at 40° C. overnight. After the reaction was completed, the mixture was concentrated in vacuo. The residue was dissolved in EtOAc (150 mL). The resulting mixture was washed with brine (50 mL×2), dried over anhydrous $Na_2SO_4$ and concentrated in vacuo. The residue was purified by silica gel column chromatography (PE) to give the title compound (5.2 g, 78%). The compound was characterized by the following spectroscopic data:

MS (ESI, pos.ion) m/z: 149.5 [M+H]$^+$; and $^1$H NMR (400 MHz, CDCl$_3$) δ (ppm): 7.03-6.96 (m, 2H), 6.68-6.66 (m, 1H), 3.86 (s, 3H), 2.99-2.81 (m, 4H), 2.24-2.05 (m, 2H).

Step 2) The Preparation of Compound 22-2

To a suspension of compound 22-1 (10.34 g, 69.8 mmol) and NIS (17.2 g, 76.8 mmol) in MeCN (200 mL) was added TFA (0.52 mL, 6.98 mmol) dropwise at 0° C. At the end of the addition, the mixture was stirred at rt overnight. After the reaction was completed, the mixture was quenched with saturated NaHCO$_3$ aqueous solution (100 mL), and the MeCN solvent was removed. The aqueous layer was extracted with EtOAc (100 mL×3). The combined organic layers were washed with brine, dried over anhydrous Na$_2$SO$_4$ and concentrated in vacuo. The residue was purified by silica gel column chromatography (PE) to give the title compound (16.44 g, 86%). The compound was characterized by the following spectroscopic data:

MS (ESI, pos.ion) m/z: 275.5 [M+H]$^+$; and $^1$H NMR (400 MHz, CDCl$_3$) δ (ppm): 7.42, 7.40 (t, t, 1H), 6.41-6.40, 6.39-6.38 (m, m, 1H), 3.87 (s, 3H), 2.96-2.76 (m, 4H), 2.37-2.18 (m, 2H).

Step 3) The Preparation of Compound 22-3

To a solution of compound 22-2 (16.35 g, 59.7 mmol) in DCM (150 mL) was added boron tribromide (74.7 g, 298.8 mmol) dropwise at −78° C. At the end of the addition, the reaction mixture was stirred at rt for 1.0 hr.

After the reaction was completed, the mixture was quenched with ice water (200 mL) and the organic phase was separated. The aqueous layer was extracted with EtOAc (100 mL×3). The combined organic layers were washed with brine, dried over anhydrous Na$_2$SO$_4$ and concentrated in vacuo. The residue was purified by silica gel column chromatography (PE/EtOAc (v/v)=40/1) to give the title compound (14.28 g, 92%). The compound was characterized by the following spectroscopic data:

MS (ESI, pos.ion) m/z: 261.3 [M+H]$^+$; and $^1$H NMR (400 MHz, CDCl$_3$) δ (ppm): 7.32, 7.30 (t, t, 1H), 6.32, 6.30 (t, t, 1H), 4.81 (br, 1H), 2.90-2.74 (m, 4H), 2.36-2.18 (m, 2H).

Step 4) The Preparation of Compound 22-4

A mixture of compound 22-3 (0.42 g, 1.62 mmol), compound 1-14-2 (0.42 g, 1.7 mmol), Pd(dppf)Cl$_2$.CH$_2$Cl$_2$ (67 mg, 0.08 mmol) and KOAc (0.4 g, 4.05 mmol) in DMF (5 mL) was stirred at 90° C. under N$_2$ for 3.0 hrs. After the reaction was completed, the mixture was cooled to rt, diluted with EtOAc (50 mL) and filtered through a celite pad. The filtrate was washed with water (20 mL×3) and brine, dried over anhydrous Na$_2$SO$_4$ and concentrated in vacuo. The residue was purified by silica gel column chromatography (PE/EtOAc (v/v)=10/1) to give the title compound as a pale yellow solid (0.3 g, 70%). The compound was characterized by the following spectroscopic data:

MS (ESI, pos.ion) m/z: 261.5 [M+H]$^+$; and $^1$H NMR (400 MHz, CDCl$_3$) δ (ppm): 7.94, 7.92 (t, t, 1H), 6.71, 6.69 (t, t, 1H), 4.81 (br, 1H), 2.97-2.92 (m, 2H), 2.87-2.70 (m, 2H), 2.29-2.10 (m, 2H), 1.32, 1.29 (m, m, 12H).

Step 5) The Preparation of Compound 22-5

A mixture of compound 22-4 (0.88 g, 3.4 mmol), compound 1-11 (1.42 g, 3.4 mmol), Pd(PPh$_3$)$_4$ (0.2 g, 0.17 mmol) and K$_2$CO$_3$ (1.41 g, 10.22 mmol) in mixed solvents of DME/H$_2$O (15 mL, v/v=4/1) was stirred at 90° C. under N₂ for 4.0 hrs. After the reaction was completed, the mixture was cooled to rt and diluted with EtOAc (80 mL). The resulting mixture was washed with water (20 mL×3) and brine, dried over anhydrous $Na_2SO_4$ and concentrated in vacuo. The residue was purified by silica gel column chromatography (PE/EtOAc (v/v)=20/1) to give the title compound as a pale yellow solid (0.72 g, 50%). The compound was characterized by the following spectroscopic data:

MS (ESI, pos.ion) m/z: 425.5 [M+H]⁺; and
¹H NMR (400 MHz, CDCl₃) δ (ppm): 7.35, 7.33 (s, s, 1H), 7.00, 6.98 (t, t, 1H), 6.96, 6.94 (t, t, 1H), 6.68, 6.66 (t, t, 1H), 4.81 (brs, 1H), 4.01-3.94 (m, 1H), 3.08-2.84 (m, 4H), 2.74-2.69 (m, 2H), 2.63-2.48 (m, 2H), 2.34-2.08 (m, 4H), 1.31-1.52 (m, 1H).

Step 6) The Preparation of Compound 22-6

A mixture of compound 22-5 (0.19 g, 0.446 mmol), compound 2-14 (0.20 g, 0.42 mmol), Pd(PPh₃)₄ (25 mg, 0.02 mmol) and K₂CO₃ (0.17 g, 1.27 mmol) in mixed solvents of DME/H₂O (8.0 mL, v/v=3/1) was stirred at 90° C. under N₂ for 3.0 hrs. After the reaction was completed, the mixture was cooled to rt and diluted with EtOAc (50 mL). The resulting mixture was washed with water (20 mL×3) and brine, dried over anhydrous Na₂SO₄ and concentrated in vacuo. The residue was purified by silica gel column chromatography (DCM/EtOH (v/v)=100/1) to give the title compound as a pale yellow solid (0.22 g, 85%). The compound was characterized by the following spectroscopic data:

MS (ESI, pos.ion) m/z: 619.5 [M+H]⁺; and
¹H NMR (400 MHz, CDCl₃) δ (ppm): 7.85, 7.83 (d, d, 1H), 7.56-7.55 (m, 1H), 7.53 (s, 1H), 7.52, 7.51 (d, d, 1H), 7.46, 7.44 (d, d, 1H), 7.05, 7.02 (t, t, 1H), 6.68, 6.66 (t, t, 1H), 5.32, 5.29 (d, d, 1H), 5.24-5.20 (m, 1H), 4.40-4.35 (m, 1H), 4.16-4.09 (m, 1H), 3.84-3.78 (m, 1H), 3.68-3.65 (m, 1H), 3.63 (s, 3H), 3.12-2.84 (m, 3H), 2.74-2.69 (m, 2H), 2.65-2.54 (m, 1H), 2.51-2.44 (m, 1H), 2.39-2.09 (m, 8H), 2.06-1.86 (m, 2H), 1.62-1.52 (m, 1H), 0.97, 0.95 (m, m, 3H), 0.91, 0.89 (m, m, 3H).

Step 7) The Preparation of Compound 22-7

To a solution of compound 22-6 (3.10 g, 5.0 mmol) in DCM (20.0 mL) was added pyridine (2.4 mL, 30 mmol) dropwise at 0° C. After the mixture was stirred for 10 mins, trifluoromethanesulfonic anhydride (3.37 mL, 20.0 mmol) was added. At the end of the addition, the mixture was stirred at rt for 1.0 hr. After the reaction was completed, the mixture was quenched with ice water (25 mL). The aqueous layer was extracted with DCM (30 mL×3). The combined organic layers were washed with brine, dried over anhydrous Na₂SO₄ and concentrated in vacuo. The residue was purified by silica gel column chromatography (PE/EtOAc (v/v)=5/1) to give the title compound as white oil (3.38 g, 90%). The compound was characterized by the following spectroscopic data:

¹H NMR (400 MHz, CDCl₃) δ (ppm): 7.85, 7.83 (d, d, 1H), 7.56-7.53 (m, 2H), 7.53, 7.51 (d, d, 1H), 7.37, 7.34 (t, t, 1H), 7.17, 7.15 (t, t, 1H), 7.03, 7.00 (t, t, 1H), 5.32, 5.29 (d, d, 1H), 5.24-5.20 (m, 1H), 4.40-4.35 (m, 1H), 4.16-4.09 (m, 1H), 3.84-3.78 (m, 1H), 3.68-3.64 (m, 1H), 3.63 (s, 3H), 3.12-2.86 (m, 3H), 2.69-2.54 (m, 3H), 2.51-2.44 (m, 1H), 2.39-1.86 (m, 10H), 1.62-1.52 (m, 1H), 0.97, 0.95 (m, m, 3H), 0.90, 0.89 (m, m, 3H).

Step 8) The Preparation of Compound 22-8

A mixture of compound 22-7 (1.22 g, 1.62 mmol), compound 1-14-2 (0.42 g, 1.7 mmol), Pd(dppf)Cl₂·CH₂Cl₂ (67 mg, 0.08 mmol) and KOAc (0.4 g, 4.05 mmol) in DMF (5.0 mL) was stirred at 90° C. under N₂ for 3.0 hrs. After the reaction was completed, the mixture was cooled to rt, diluted with EtOAc (50 mL) and filtered through a celite pad. The filtrate was washed with water (20 mL×3) and brine, dried over anhydrous Na₂SO₄ and concentrated in vacuo. The residue was purified by silica gel column chromatography (PE/EtOAc (v/v)=1/3) to give the title compound as a pale yellow solid (0.83 g, 70%). The compound was characterized by the following spectroscopic data:

MS (ESI, pos.ion) m/z: 729.5 [M+H]⁺; and
¹H NMR (400 MHz, CDCl₃) δ (ppm): 7.88, 7.86 (t, t, 1H), 7.85, 7.83 (d, d, 1H), 7.56-7.54 (m, 2H), 7.53 (d, 1H), 7.50, 7.48 (t, t, 1H), 7.38, 7.35 (t, t, 1H), 5.32, 5.29 (d, d, 1H), 5.24-5.20 (m, 1H), 4.40-4.35 (m, 1H), 4.16-4.09 (m, 1H), 3.84-3.78 (m, 1H), 3.68-3.65 (m, 1H), 3.63 (s, 3H), 3.12-2.97 (m, 3H), 2.74-2.70 (m, 2H), 2.67-2.54 (m, 1H), 2.51-2.44 (m, 1H), 2.38-1.86 (m, 10H), 1.62-1.52 (m, 1H), 1.32, 1.29 (m, m, 12H), 0.97, 0.95 (m, m, 3H), 0.90, 0.89 (m, m, 3H).

Step 9) The Preparation of Compound 22-9

To a solution of compound 1-20 (1.50 g, 4.13 mmol) in EtOAc (10 mL) was added a solution of HCl in EtOAc (5.0 mL, 4 M) dropwise. At the end of the addition, the mixture was stirred at rt for 8.0 hrs. After the reaction was completed, the mixture was concentrated in vacuo. The residue was purified by beating in EtOAc (10 mL) and filtered to give the title compound as a solid (1.2 g, 86.45%), which was used for the next step without further purification. The compound was characterized by the following spectroscopic data:

MS (ESI, pos.ion) m/z: 264 [M+H]⁺.

Step 10) The Preparation of Compound 22-10

A suspension of compound 22-9 (1.2 g, 3.6 mmol), compound 1-24-2 (0.69 g, 3.9 mmol) and EDCI (0.75 g, 3.9 mmol) in DCM (20 mL) was stirred at 0° C. for 5 mins, then DIPEA (2.38 mL, 14.4 mmol) was added dropwise. At the end of the addition, the mixture was stirred at rt for 2.0 hrs. After the reaction was completed, the mixture was diluted with DCM (40 mL). The organic layer was washed with saturated NH₄Cl aqueous solution, dried over anhydrous Na₂SO₄ and concentrated in vacuo. The residue was purified by silica gel column chromatography (PE/EtOAc (v/v)=1/2) to give the title compound as a pale yellow solid (1.31 g, 86.8%). The compound was characterized by the following spectroscopic data:

MS (ESI, pos.ion) m/z: 421.1 [M+H]⁺; and
¹H NMR (400 MHz, CDCl₃) δ (ppm): 7.35 (s, 1H), 5.32, 5.29 (brs, brs, 1H), 5.20-5.15 (m, 1H), 4.41-4.37 (m, 1H), 3.85-3.78 (m, 1H), 3.69-3.65 (m, 1H), 3.63 (s, 3H), 2.28-2.17 (m, 3H), 2.11-1.96 (m, 2H), 0.97-0.95 (m, 3H), 0.91-0.89 (m, 3H).

Step 11) The Preparation of Compound 22-11

A mixture of compound 22-8 (2.48 g, 3.4 mmol), compound 22-10 (1.43 g, 3.4 mmol), Pd(PPh₃)₄ (0.20 g, 0.17 mmol) and K₂CO₃ (1.41 g, 10.22 mmol) in mixed solvents of DME/H₂O (30 mL, v/v=4/1) was stirred at 90° C. under N₂ for 4.0 hrs. After the reaction was completed, the mixture was cooled to rt and diluted with EtOAc (100 mL). The resulting mixture was washed with water (50 mL×3) and brine, dried over anhydrous Na₂SO₄ and concentrated in vacuo. The residue was purified by silica gel column chromatography (DCM/MeOH (v/v)=60/1) to give the title compound as a pale yellow solid (1.52 g, 50%). The compound was characterized by the following spectroscopic data:

MS (ESI, pos.ion) m/z: 448.5 [M+2H]²⁺; and
¹H NMR (400 MHz, CDCl₃) δ (ppm): 7.85, 7.83 (d, d, 1H), 7.56-7.53 (m, 3H), 7.53, 7.51 (d, d, 1H), 7.44, 7.41 (t, t, 1H), 7.36, 7.33 (t, t, 1H), 7.29, 7.27 (t, t, 1H), 5.32, 5.30 (d, d, 2H), 5.24-5.20 (m, 1H), 5.18-5.13 (m, 1H), 4.41-4.35 (m, 2H), 4.17-4.09 (m, 1H), 3.85-3.78 (m, 2H), 3.68-3.66 (m, 2H), 3.63 (s, 6H), 3.12-3.00 (m, 1H), 2.91-2.86 (m, 2H), 2.81-2.76 (m, 2H), 2.67-2.54 (m, 2H), 2.51-2.44 (m, 1H), 2.38-1.86 (m, 15H), 1.62-1.52 (m, 1H), 0.97, 0.95 (m, m, 6H), 0.90-0.89 (m, m, 6H).

Example 23
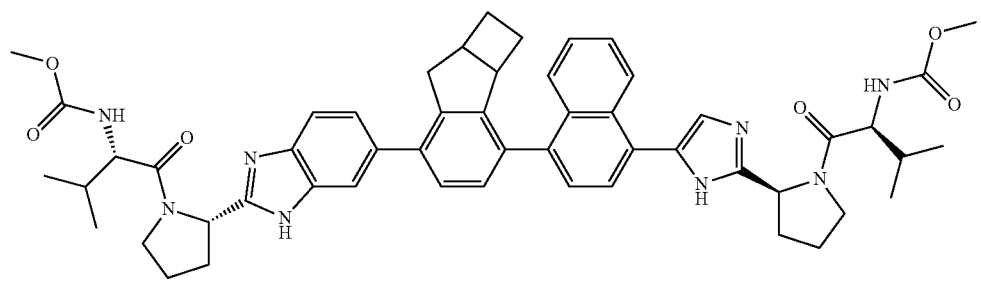
Synthetic Route:
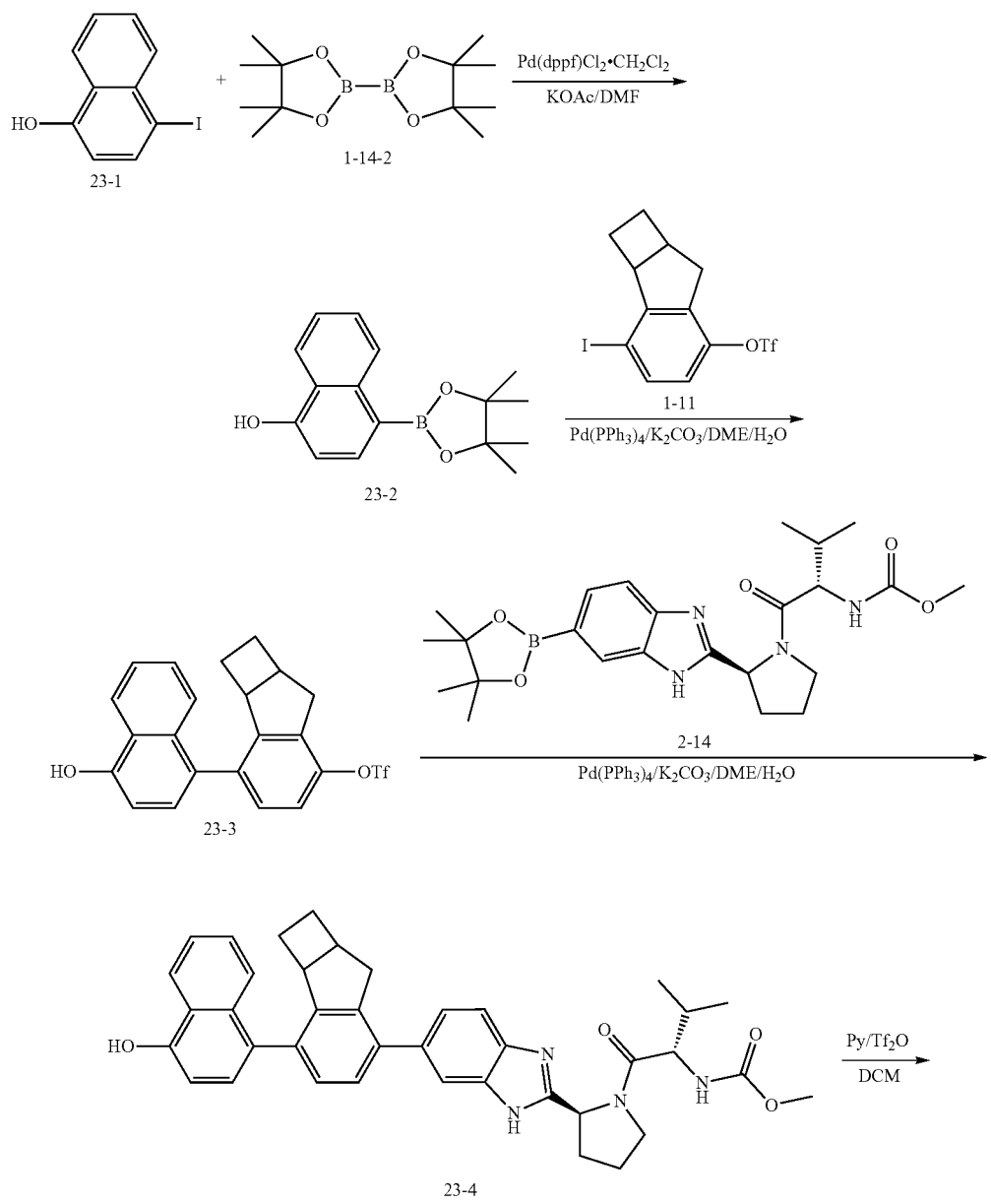

-continued

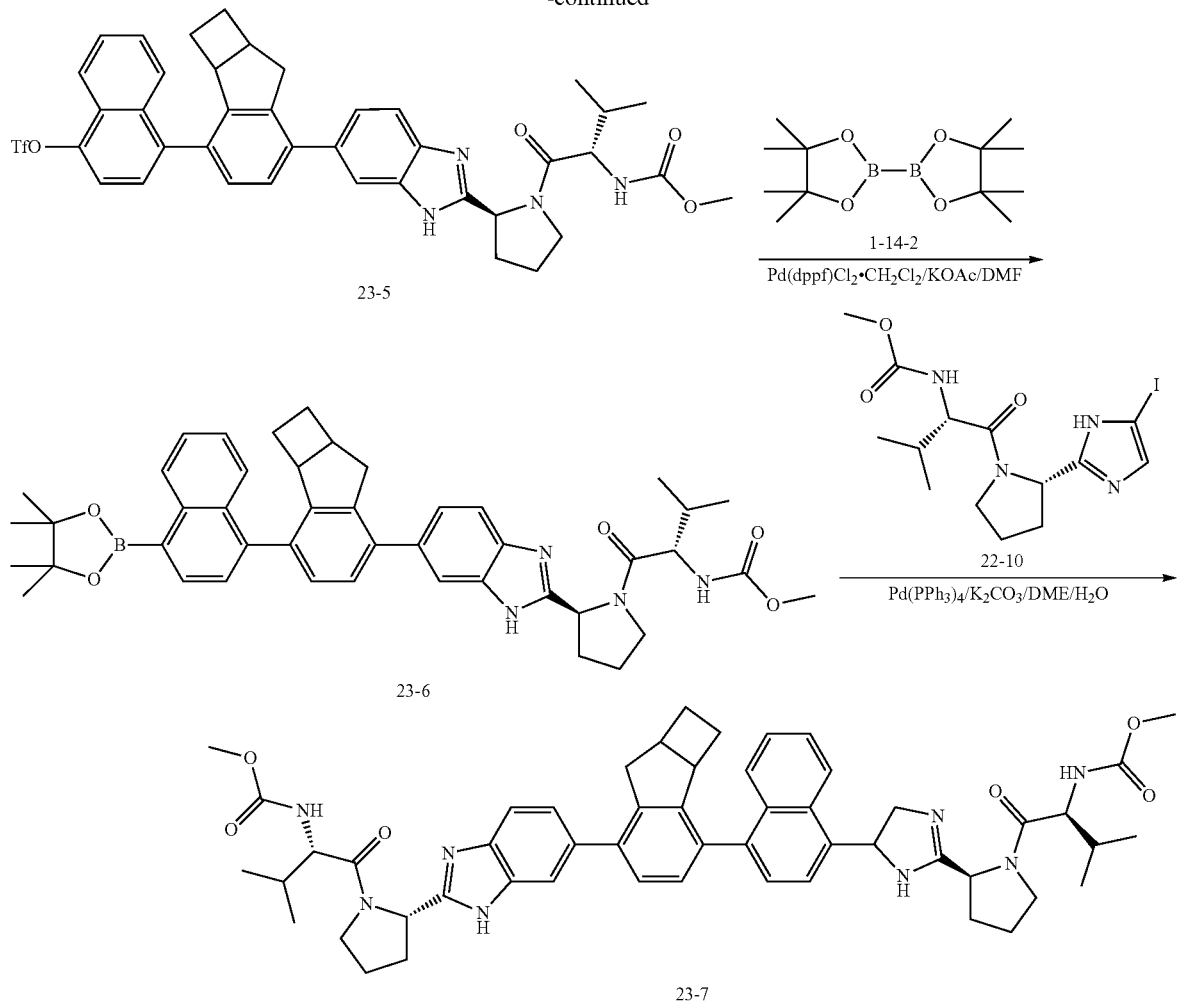

Step 1) The Preparation of Compound 23-2

A mixture of compound 23-1 (0.44 g, 1.62 mmol), compound 1-14-2 (0.42 g, 1.7 mmol), Pd(dppf)Cl$_2$CH$_2$Cl$_2$ (67 mg, 0.08 mmol) and KOAc (0.4 g, 4.05 mmol) in DMF (5.0 mL) was stirred at 90° C. under N$_2$ for 3.0 hrs. After the reaction was completed, the mixture was cooled to rt, diluted with EtOAc (50 mL) and filtered through a celite pad. The filtrate was washed with water (20 mL×3) and brine, dried over anhydrous Na$_2$SO$_4$ and concentrated in vacuo. The residue was purified by silica gel column chromatography (PE/EtOAc (v/v)=15/1) to give the title compound as a pale yellow solid (0.31 g, 70%). The compound was characterized by the following spectroscopic data:

MS (ESI, pos.ion) m/z: 271.5 [M+H]$^+$; and $^1$H NMR (400 MHz, CDCl$_3$) δ (ppm): 8.53-8.50 (m, 1H), 8.45-8.43 (m, 1H), 7.83, 7.81 (m, m, 1H), 7.62-7.58 (m, 1H), 7.52-7.48 (m, 1H), 7.06, 7.04 (br, br, 1H), 6.17 (br, 1H), 1.57 (m, 6H), 1.54 (m, 6H).

Step 2) The Preparation of Compound 23-3

A mixture of compound 23-2 (0.92 g, 3.4 mmol), compound 1-11 (1.42 g, 3.4 mmol), Pd(PPh$_3$)$_4$ (0.2 g, 0.17 mmol) and K$_2$CO$_3$ (1.41 g, 10.22 mmol) in mixed solvents of DME/H$_2$O (15.0 mL, v/v=4/1) was stirred at 90° C. under N$_2$ for 4.0 hrs. After the reaction was completed, the mixture was cooled to rt and diluted with EtOAc (60 mL). The resulting mixture was washed with water (20 mL×3) and brine, dried over anhydrous Na$_2$SO$_4$ and concentrated in vacuo. The residue was purified by silica gel column chromatography (PE/EtOAc (v/v)=20/1) to give the title compound as a pale yellow solid (0.66 g, 45%). The compound was characterized by the following spectroscopic data:

$^1$H NMR (400 MHz, CDCl$_3$) δ (ppm): 8.28-8.27, 8.26-8.25 (m, m, 1H), 7.48-7.44 (m, 2H), 7.40, 7.38 (m, m, 1H), 7.25-7.21 (m, 1H), 7.19, 7.17 (t, t, 1H), 7.15, 7.12 (s, s, 1H), 7.03, 7.01 (brs, brs, 1H), 6.17 (brs, 1H), 3.61-3.54 (m, 1H), 3.07-2.96 (m, 1H), 2.93-2.86 (m, 1H), 2.65-2.48 (m, 2H), 2.20-2.08 (m, 2H), 1.61-1.52 (m, 1H).

Step 3) The Preparation of Compound 23-4

A mixture of compound 23-3 (0.19 g, 0.446 mmol), compound 2-14 (0.20 g, 0.42 mmol), Pd(PPh$_3$)$_4$ (25 mg, 0.02 mmol) and K$_2$CO$_3$ (0.17 g, 1.27 mmol) in mixed solvents of DME/H$_2$O (8.0 mL, v/v=3/1) was stirred at 90° C. under N$_2$ for 3.0 hrs. After the reaction was completed, the mixture was concentrated in vacuo and the residue was dissolved in EtOAc (50 mL). The resulting mixture was washed with water (20 mL×3) and brine, dried over anhydrous Na$_2$SO$_4$ and concentrated in vacuo. The residue was purified by silica gel column chromatography (DCM/EtOH (v/v)=100/1) to give the title compound as a pale yellow solid (0.21 g, 80%). The compound was characterized by the following spectroscopic data:

MS (ESI, pos.ion) m/z: 629.5 [M+H]$^+$; and $^1$H NMR (400 MHz, CDCl$_3$) δ (ppm): 8.28-8.25 (m, 1H), 7.85, 7.83 (d, d, 1H), 7.64, 7.61 (s, s, 1H), 7.59, 7.57 (t, t, 1H), 7.56-7.55 (q, 1H), 7.53, 7.51 (d, d, 1H), 7.50-7.44 (m, 3H), 7.25-7.21 (m, 1H), 7.03, 7.01 (brs, brs, 1H), 5.32, 5.29 (d, d, 1H), 5.24-5.20 (m, 1H), 4.40-4.35 (m, 1H), 3.96-3.87 (m, 1H), 3.84-3.78 (m, 1H), 3.68-3.65 (m, 1H), 3.63 (s, 3H), 3.11-3.00 (m, 1H), 2.68-2.57 (m, 1H), 2.55-2.48 (m, 1H), 2.38-2.28 (m, 1H), 2.25-1.87 (m, 8H), 1.62-1.52 (m, 1H), 0.97, 0.95 (m, m, 3H), 0.90, 0.89 (m, m, 3H).

Step 4) The Preparation of Compound 23-5

To a solution of compound 23-4 (3.14 g, 5.0 mmol) in DCM (20 mL) was added pyridine (2.4 mL, 30.0 mmol) dropwise at 0° C. After the mixture was stirred for 10 mins, trifluoromethanesulfonic anhydride (3.37 mL, 20 mmol) was added. At the end of the addition, the mixture was stirred at rt for 1.0 hr. After the reaction was completed, the mixture was quenched with ice water (25 mL). The aqueous layer was extracted with DCM (30 mL×3). The combined organic layers were washed with brine, dried over anhydrous Na$_2$SO$_4$ and concentrated in vacuo. The residue was purified by silica gel column chromatography (PE/EtOAc (v/v)=5/1) to give the title compound as white oil (3.42 g, 90%). The compound was characterized by the following spectroscopic data:

$^1$H NMR (400 MHz, CDCl$_3$) δ (ppm): 8.41, 8.39 (m, m, 1H), 7.85, 7.83 (d, d, 1H), 7.77, 7.75 (m, m, 1H), 7.63-7.59 (m, 2H), 7.56-7.55 (q, 1H), 7.53-7.52, 7.51-7.50 (m, m, 2H), 7.49-7.48, 7.47-7.46 (m, 1H), 7.33-7.31 (brs, brs, 1H), 7.30-7.27 (m, 1H), 5.32, 5.29 (d, d, 1H), 5.24-5.20 (m, 1H), 4.40-4.35 (m, 1H), 3.96-3.89 (m, 1H), 3.84-3.78 (m, 1H), 3.68-3.66 (m, 1H), 3.63 (s, 3H), 3.11-3.00 (m, 1H), 2.68-2.48 (m, 2H), 2.39-2.27 (m, 1H), 2.25-1.87 (m, 7H), 1.62-1.52 (m, 1H), 0.97, 0.95 (m, m, 3H), 0.91, 0.89 (m, m, 3H).

Step 5) The Preparation of Compound 23-6

A mixture of compound 23-5 (1.23 g, 1.62 mmol), compound 1-14-2 (0.42 g, 1.7 mmol), Pd(dppf)Cl$_2$.CH$_2$Cl$_2$ (67 mg, 0.08 mmol) and KOAc (0.4 g, 4.05 mmol) in DMF (5.0 mL) was stirred at 90° C. under N$_2$ for 3.0 hrs. After the reaction was completed, the mixture was cooled to rt, diluted with EtOAc (50 mL) and filtered through a celite pad. The filtrate was washed with water (20 mL×3) and brine, dried over anhydrous Na$_2$SO$_4$ and concentrated in vacuo. The residue was purified by silica gel column chromatography (PE/EtOAc (v/v)=1/3) to give the title compound as a pale yellow solid (0.84 g, 70%). The compound was characterized by the following spectroscopic data:

MS (ESI, pos.ion) m/z: 739.5 [M+H]$^+$; and $^1$H NMR (400 MHz, CDCl$_3$) δ (ppm): 8.80, 8.78 (m, m, 1H), 8.05, 8.03 (brs, brs, 1H), 7.86-7.83 (m, 2H), 7.76, 7.74 (m, m, 1H), 7.67, 7.65 (t, t, 1H), 7.63, 7.61 (s, s, 1H), 7.60, 7.58, 7.56 (m, m, m, 1H), 7.56-7.55 (q, 1H), 7.53, 7.51 (d, d, 1H), 7.23, 7.21, 7.19 (m, m, m, 1H), 5.32, 5.30 (d, d, 1H), 5.24-5.20 (m, 1H), 4.40-4.35 (m, 1H), 3.96-3.89 (m, 1H), 3.84-3.78 (m, 1H), 3.68-3.64 (m, 1H), 3.63 (s, 3H), 3.11-3.00 (m, 1H), 2.67-2.48 (m, 2H), 2.38-2.28 (m, 1H), 2.25-1.86 (m, 7H), 1.62-1.57 (m, 1H), 1.57, 1.53 (q, q, 12H), 0.97, 0.95 (m, m, 3H), 0.91, 0.89 (m, m, 3H).

Step 6) The Preparation of Compound 23-7

A mixture of compound 23-6 (2.51 g, 3.4 mmol), compound 22-10 (1.43 g, 3.4 mmol), Pd(PPh$_3$)$_4$ (0.20 g, 0.17 mmol) and K$_2$CO$_3$ (1.41 g, 10.22 mmol) in mixed solvents of DME/H$_2$O (30 mL, v/v=4/1) was stirred at 90° C. under N$_2$ for 4.0 hrs. After the reaction was completed, the mixture was cooled to rt and diluted with EtOAc (100 mL). The resulting mixture was washed with water (50 mL×3) and brine, dried over anhydrous Na$_2$SO$_4$ and concentrated in vacuo. The residue was purified by silica gel column chromatography (DCM/MeOH (v/v)=80/1) to give the title compound as a pale yellow solid (1.54 g, 50%). The compound was characterized by the following spectroscopic data:

MS (ESI, pos.ion) m/z: 453.5 [M+2H]$^{2+}$; and $^1$H NMR (400 MHz, CDCl$_3$) δ (ppm): 8.06-8.05, 8.04-8.03 (m, m, 1H), 7.85, 7.83 (d, d, 1H), 7.75, 7.73 (brs, brs, 1H), 7.74 (s, 1H), 7.64, 7.61 (s, s, 1H), 7.60, 7.58 (t, t, 1H), 7.56-7.55 (q, 1H), 7.53, 7.51 (d, d, 1H), 7.43-7.38 (m, 1H), 7.29-7.26 (m, 2H), 7.12-7.08 (m, 1H), 6.08, 6.05 (d, d, 1H), 5.36-5.33 (m, 1H), 5.32, 5.30 (d, d, 1H), 5.25-5.20 (m, 1H), 4.41-4.32 (m, 2H), 3.96-3.89 (m, 1H), 3.85-3.77 (m, 2H), 3.69-3.66 (m, 2H), 3.65 (s, 3H), 3.63 (s, 3H), 3.10-3.01 (m, 1H), 2.67-2.47 (m, 2H), 2.37-1.88 (m, 13H), 1.63-1.52 (m, 1H), 1.02-0.89 (m, 12H).

Example 24

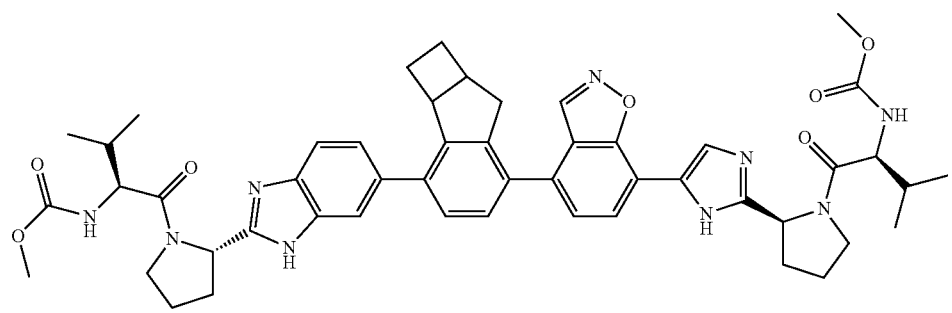 [SMILES: COC(=O)N[C@H](C(=O)N1CCC[C@H]1c1ncc(-c2ccc(-c3ccc(-c4ccc5nc([C@@H]6CCCN6C(=O)[C@@H](NC(=O)OC)C(C)C)[nH]c5c4)c4c3CC3CCC43)c3cnoc23)[nH]1)C(C)C]

Synthetic Route:

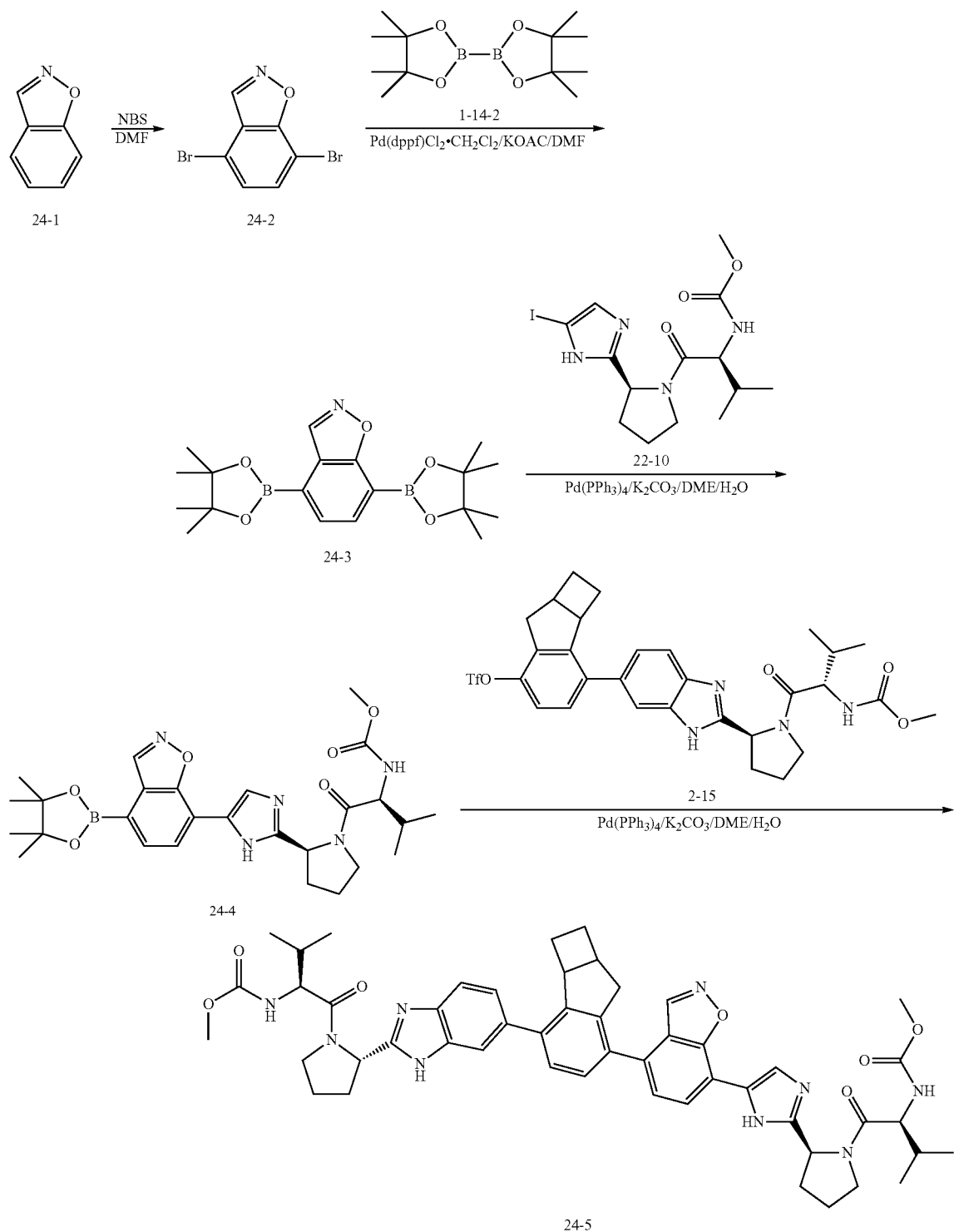

Step 1) The Preparation of Compound 24-2

To a solution of NBS (2.16 g, 12 mmol) in DMF (6.0 mL) was added a solution of compound 24-1 (0.71 g, 6.0 mmol) in DMF (6.0 mL) dropwise in the dark at −15° C. At the end of the addition, the mixture was stirred at rt for 1.0 hr and at 60° C. for another 5.0 hrs. After the reaction was completed, the mixture was poured into the mixed solvents of ice water (50 mL) and diethyl ether (60 mL). The organic layer was separated, washed several times with water to neutral pH, dried over anhydrous $Na_2SO_4$ and concentrated in vacuo to give the title compound (1.07 g, 65%). The compound was characterized by the following spectroscopic data:

MS (ESI, pos.ion) m/z: 275.5 [M+H]+; and

¹H NMR (400 MHz, CDCl₃) δ (ppm): 9.02 (d, 1H), 7.53, 7.51 (s, s, 1H), 7.34, 7.32 (d, d, 1H).

Step 2) The Preparation of Compound 24-3

A mixture of compound 24-2 (0.25 g, 0.91 mmol), compound 1-14-2 (0.53 g, 2.093 mmol), Pd(dppf)Cl₂·CH₂Cl₂ (71 mg, 0.09 mmol) and KOAc (0.27 g, 2.73 mmol) in DMF (10 mL) was stirred at 90° C. under N₂ for 3.0 hrs. After cooling to rt, the mixture was diluted with EtOAc (60 mL) and filtered through a celite pad. The filtrate was washed with water (30 mL×3) and brine, dried over anhydrous Na₂SO₄ and concentrated in vacuo. The residue was purified by silica gel column chromatography (PE/EtOAc (v/v)=5/2) to give the title compound (0.27 g, 80%). The compound was characterized by the following spectroscopic data:

MS (ESI, pos.ion) m/z: 372.5 [M+H]+; and

¹H NMR (400 MHz, CDCl₃) δ (ppm): 9.53 (d, 1H), 8.53, 8.51 (d, d, 1H), 7.94, 7.92 (d, d, 1H), 1.56, 1.54 (m, m, 12H), 1.32, 1.29 (m, m, 12H).

Step 3) The Preparation of Compound 24-4

To a mixture of compound 24-3 (0.27 g, 0.72 mmol), compound 22-10 (0.30 g, 0.72 mmol), Pd(PPh₃)₄ (83 mg, 0.07 mmol) and K₂CO₃ (0.30 g, 2.12 mmol) were added DME (4.0 mL) and water (1.0 mL) via syringe under N₂, and the mixture was stirred at 90° C. for 4.0 hrs. After the reaction was completed, the mixture was cooled to rt and quenched with water (10 mL). The aqueous layer was extracted with EtOAc (20 mL×3). The combined organic layers were washed with brine, dried over anhydrous Na₂SO₄ and concentrated in vacuo. The residue was purified by silica gel column chromatography (PE/EtOAc (v/v)=1/1) to give the title compound (0.23 g, 60%). The compound was characterized by the following spectroscopic data:

MS (ESI, pos.ion) m/z: 538.5 [M+H]+; and

¹H NMR (400 MHz, CDCl₃) δ (ppm): 9.37 (d, 1H), 7.66 (s, 1H), 7.54, 7.52 (d, d, 1H), 7.26, 7.24 (s, s, 1H), 5.38-5.34 (m, 1H), 5.32, 5.29 (d, d, 1H), 4.41-4.36 (m, 1H), 3.85-3.78 (m, 1H), 3.68-3.65 (m, 1H), 3.63 (s, 3H), 2.30-1.92 (m, 5H), 1.56, 1.53 (m, m, 12H), 0.97-0.89 (m, 6H).

Step 4) The Preparation of Compound 24-5

To a mixture of compound 24-4 (0.54 g, 1.0 mmol), compound 2-15 (0.63 g, 1.0 mmol), Pd(PPh₃)₄ (0.16 g, 0.1 mmol) and K₂CO₃ (0.35 g, 2.5 mmol) were added DME (4.0 mL) and water (1.0 mL) via syringe, and the mixture was stirred at 90° C. under N₂ for 4.0 hrs. After the reaction was completed, the mixture was cooled to rt and quenched with water (10.0 mL). The aqueous layer was extracted with EtOAc (20 mL×3). The combined organic layers were washed with brine, dried over anhydrous Na₂SO₄ and concentrated in vacuo. The residue was purified by silica gel column chromatography (DCM/MeOH (v/v)=50/1) to give the title compound (0.45 g, 50%). The compound was characterized by the following spectroscopic data:

MS (ESI, pos.ion) m/z: 448.5 [M+2H]²⁺; and

¹H NMR (400 MHz, CDCl₃) δ (ppm): 9.07 (d, 1H), 7.85, 7.83 (s, s, 1H), 7.63 (s, 1H), 7.62-7.60 (m, 3H), 7.48, 7.46 (d, d, 1H), 7.40, 7.38 (s, s, 1H), 7.24-7.22 (m, 1H), 5.38-5.34 (m, 1H), 5.32, 5.29 (d, d, 2H), 5.24-5.20 (m, 1H), 4.41-4.35 (m, 2H), 3.85-3.77 (m, 3H), 3.69-3.65 (m, 2H), 3.63 (s, 6H), 3.11-3.00 (m, 1H), 2.80-2.73 (m, 1H), 2.68-2.54 (m, 1H), 2.37-1.88 (m, 13H), 1.62-1.52 (m, 1H), 0.97, 0.95 (m, m, 6H), 0.91, 0.89 (m, m, 6H).

Example 25

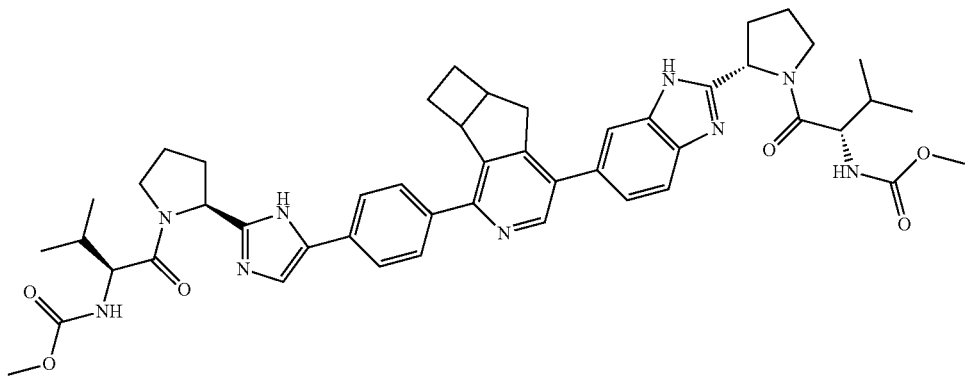

Synthetic Route:

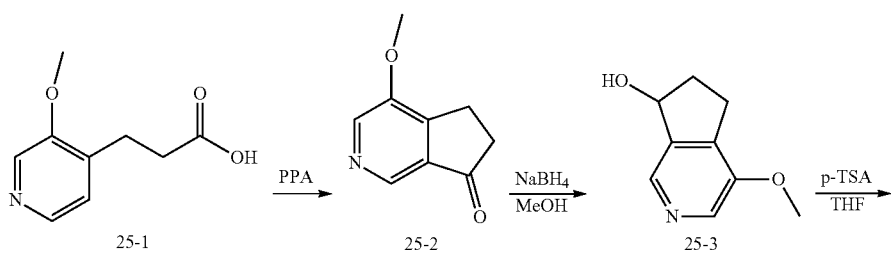

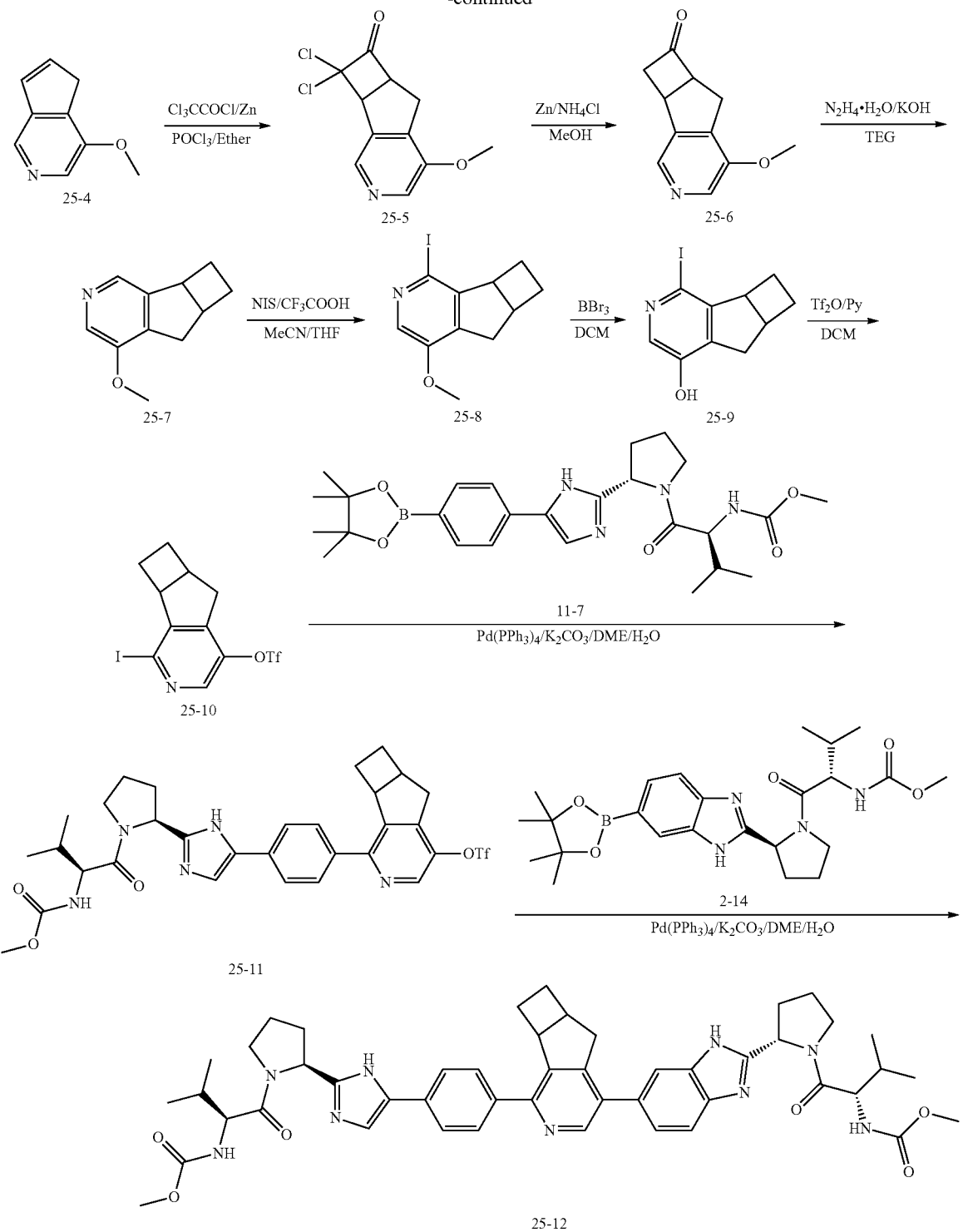

Step 1) The Preparation of Compound 25-2

A mixture of compound 25-1 (4.04 g, 22.3 mmol) and PPA (50.87 g, 24.8 mmol) was stirred at 80° C. for 4.0 hrs. After the reaction was completed, ice water (250 mL) was added to the mixture, and the resulting mixture was extracted with EtOAc (100 mL×5). The combined organic layers were washed with NaHCO₃ aqueous solution and brine, dried over anhydrous Na₂SO₄ and concentrated in vacuo. The residue was purified by silica gel column chromatography (PE/EtOAc (v/v)=3/1) to give the title compound as a pale yellow solid (2.18 g, 60%). The compound was characterized by the following spectroscopic data:

MS (ESI, pos.ion) m/z: 164.5 [M+H]$^+$; and $^1$H NMR (400 MHz, CDCl₃) δ (ppm): 8.48-8.46 (m, 2H), 3.87 (s, 3H), 3.13-3.09 (m, 2H), 2.78-2.74 (m, 2H).

Step 2) The Preparation of Compound 25-3

To a solution of compound 25-2 (9.78 g, 60 mmol) in MeOH (150 mL) was added NaBH$_4$ (1.3 g, 40 mmol) portionwise. At the end of the addition, the mixture was stirred at rt for 1.0 hr. After the reaction was completed, the mixture was quenched with water (50 mL), and the MeOH solvent was removed. The resulting mixture was extracted with EtOAc (50 mL×3). The combined organic layers were washed with brine, dried over anhydrous Na$_2$SO$_4$ and concentrated in vacuo. The residue was purified by silica gel column chromatography (PE/EtOAc (v/v)=4/1) to give the title compound (7.92 g, 80%). The compound was characterized by the following spectroscopic data:

MS (ESI, pos.ion) m/z: 166.5 [M+H]$^+$; and $^1$H NMR (400 MHz, CDCl$_3$) δ (ppm): 8.27-8.25 (m, 1H), 8.09 (m, 1H), 5.26-5.22 (m, 1H), 3.86 (s, 3H), 2.98-2.94 (m, 2H), 2.70 (brs, 1H), 2.57-2.48 (m, 1H), 2.03-1.96 (m, 1H).

Step 3) The Preparation of Compound 25-4

To a solution of compound 25-3 (2.7 g, 16.4 mmol) in THF (100 mL) was added p-TSA (1.4 g, 8.2 mmol) at 0° C. At the end of the addition, the mixture was refluxed for 2.0 hrs. After the reaction was completed, the THF solvent was removed. To the residue was added EtOAc (100 mL). The resulting mixture was washed with water (50 mL×3) and brine, dried over anhydrous Na$_2$SO$_4$ and concentrated in vacuo. The residue was purified by silica gel column chromatography (PE) to give the title compound as colorless oil (0.97 g, 40%). The compound was characterized by the following spectroscopic data:

MS (ESI, pos.ion) m/z: 148.5 [M+H]$^+$; and $^1$H NMR (400 MHz, CDCl$_3$) δ (ppm): 8.18-8.17 (m, 1H), 7.32-7.31 (m, 1H), 6.98-6.95 (m, 1H), 6.66-6.64 (m, 1H), 3.88 (s, 3H), 3.39-3.38 (m, 2H).

Step 4) The Preparation of Compound 25-5

To a solution of compound 25-4 (5.0 g, 34.2 mmol) in diethyl ether (35 mL) was added activated zinc powder (2.5 g, 37.6 mmol). After the mixture was stirred for 10 mins, a solution of trichloroacetyl chloride (4.0 mL, 35.9 mmol) and phosphorus oxychloride (3.3 mL, 35.9 mmol) in diethyl ether (35 mL) was added dropwise under N$_2$ to the reaction mixture. At the end of the addition, the mixture was refluxed overnight. After the reaction was completed, the mixture was filtered, and then to the filtrate was added water (50 mL). The resulting mixture was extracted with EtOAc (60 mL×3). The combined organic layers were washed with brine, dried over anhydrous Na$_2$SO$_4$ and concentrated in vacuo. The residue was purified by silica gel column chromatography (PE) to give the title compound as a pale yellow solid (6.53 g, 74%). The compound was characterized by the following spectroscopic data:

MS (ESI, pos.ion) m/z: 259.1 [M+H]$^+$; and $^1$H NMR (400 MHz, CDCl$_3$) δ (ppm): 8.17 (m, 1H), 8.15 (m, 1H), 4.14-4.09 (m, 1H), 3.98-3.97, 3.96-3.95 (m, m, 1H), 3.86 (s, 3H), 3.52-3.46 (m, 1H), 3.09-3.00 (m, 1H), 3.19-3.13 (m, 1H).

Step 5) The Preparation of Compound 25-6

To a solution of compound 25-5 (6.48 g, 25.2 mmol) in MeOH (80 mL) were added zinc powder (8.2 g, 126 mmol) and NH$_4$Cl (6.7 g, 126 mmol) in turn at rt. At the end of the addition, the mixture was stirred at 45° C. overnight. After the reaction was completed, the mixture was filtered through a celite pad. The filtrate was concentrated in vacuo, and then to the residue was added water (50 mL). The resulting mixture was extracted with EtOAc (60 mL×3). The combined organic layers were washed with brine, dried over anhydrous Na$_2$SO$_4$ and concentrated in vacuo. The residue was purified by silica gel column chromatography (PE/EtOAc (v/v)=60/1) to give the title compound as colorless liquid (3.72 g, 78%). The compound was characterized by the following spectroscopic data:

MS (ESI, pos.ion) m/z: 190.2 [M+H]$^+$; and $^1$H NMR (400 MHz, CDCl$_3$) δ (ppm): 8.11-8.09 (m, 2H), 4.03-3.99 (m, 1H), 3.86 (s, 3H), 3.79-3.67 (m, 2H), 3.54-3.47 (m, 1H), 3.21-3.14 (m, 1H), 2.95-2.93, 2.91-2.89 (m, m, 1H).

Step 6) The Preparation of Compound 25-7

To a solution of compound 25-6 (2.31 g, 12.2 mmol) in TEG (30 mL) were added KOH(2.1 g, 36.7 mmol) and hydrazine hydrate (4.8 mL, 97.8 mmol) in turn. After the mixture was stirred at 130° C. for 20 mins, the mixture was further stirred at 200° C. for 50 mins with a Dean-Stark trap. After the reaction was completed, the mixture was cooled to rt and 100 mL of water was added. The aqueous layer was extracted with PE (150 mL×3). The combined organic layers were washed with brine, dried over anhydrous Na$_2$SO$_4$ and concentrated in vacuo. The residue was purified by silica gel column chromatography (PE) to give the title compound as colorless oil (1.43 g, 67%). The compound was characterized by the following spectroscopic data:

MS (ESI, pos.ion) m/z: 176.1 [M+H]$^+$; and $^1$H NMR (400 MHz, CDCl$_3$) δ (ppm): 8.03 (m, 1H), 7.89-7.88 (m, 1H), 3.86 (s, 3H), 3.72-3.64 (m, 1H), 3.11-3.01 (m, 1H), 2.82-2.74 (m, 1H), 2.52-2.36 (m, 2H), 2.20-2.10 (m, 1H), 2.08-1.98 (m, 1H), 1.64-1.53 (m, 1H).

Step 7) The Preparation of Compound 25-8

To a solution of compound 25-7 (9.98 g, 57.0 mmol) in THF (80 mL) and MeCN (40 mL) was added NIS (14.2 g, 63.0 mmol). After the mixture was stirred for 10 mins, a catalytic amount of trifluoroacetic acid was added dropwise. At the end of the addition, the mixture was stirred at rt for 5.0 hrs. After the reaction was completed, the mixture was concentrated in vacuo. To the residue was added EtOAc (200 mL). The resulting mixture was washed with saturated sodium sulfite aqueous solution (50 mL×3), dried over anhydrous Na$_2$SO$_4$ and concentrated in vacuo. The residue was purified by silica gel column chromatography (PE) to give the title compound as colorless liquid (12.87 g, 75%). The compound was characterized by the following spectroscopic data:

MS (ESI, pos.ion) m/z: 302.1 [M+H]$^+$; and $^1$H NMR (400 MHz, CDCl$_3$) δ (ppm): 7.75 (m, 1H), 3.90 (s, 3H), 3.75-3.68 (m, 1H), 3.18-3.08 (m, 1H), 2.95-2.88 (m, 1H), 2.58-2.44 (m, 2H), 2.20-2.00 (m, 2H), 1.63-1.53 (m, 1H).

Step 8) The Preparation of Compound 25-9

To a solution of compound 25-8 (2.17 g, 7.2 mmo) in DCM (20 mL) was added boron tribromide (2.7 mL, 28.8 mmol) dropwise at −78° C. At the end of the addition, the mixture was stirred at −78° C. for 10 mins and at rt for another 4.0 hr. After the reaction was completed, the mixture was poured slowly into ice water (100 mL) and the organic phase was separated. The aqueous layer was extracted with DCM (50 mL×3). The combined organic layers were washed with brine, dried over anhydrous Na$_2$SO$_4$ and concentrated in vacuo. The residue was purified by silica gel column chromatography (PE/EtOAc (v/v)=20/1) to give the title compound as colorless liquid (1.86 g, 90%). The compound was characterized by the following spectroscopic data:

MS (ESI, pos.ion) m/z: 288.1 [M+H]$^+$; and $^1$H NMR (400 MHz, CDCl$_3$) δ (ppm): 8.00 (brs, 1H), 7.87 (s, 1H), 3.90-3.83 (s, 1H), 3.22-3.12 (m, 1H), 2.88-2.81 (m, 1H), 2.61-2.43 (m, 2H), 2.24-2.07 (m, 2H), 1.67-1.56 (m, 1H).

Step 9) The Preparation of Compound 25-10

To a solution of compound 25-9 (1.55 g, 5.4 mmol) in DCM (15 mL) was added pyridine (1.1 mL, 13.5 mmol) dropwise at 0° C. After the mixture was stirred for 10 mins, trifluoromethanesulfonic anhydride (1.4 mL, 8.1 mmol) was added dropwise. At the end of the addition, the mixture was stirred at rt for 1.0 hr. After the reaction was completed, the mixture was quenched with ice water (50 mL). The aqueous layer was extracted with DCM (50 mL×3). The combined organic layers were washed with brine, dried over anhydrous $Na_2SO_4$ and concentrated in vacuo. The residue was purified by silica gel column chromatography (PE) to give the title compound as colorless liquid (2.22 g, 98%). The compound was characterized by the following spectroscopic data:

MS (ESI, pos.ion) m/z: 420.0 $[M+H]^+$; and $^1$H NMR (400 MHz, $CDCl_3$) δ (ppm): 8.04 (s, 1H), 3.78-3.70 (m, 1H), 3.17-3.02 (m, 2H), 2.75-2.50 (m, 2H), 2.20-2.07 (m, 2H), 1.63-1.53 (m, 1H).

Step 10) The Preparation of Compound 25-11

To a mixture of compound 25-10 (0.30 g, 0.72 mmol), compound 11-7 (0.36 g, 0.72 mmol), $Pd(PPh_3)_4$ (83 mg, 0.07 mmol) and $K_2CO_3$ (0.30 g, 2.12 mmol) were added DME (4.0 mL) and water (1.0 mL) via syringe under $N_2$, and the mixture was stirred at 90° C. for 4.0 hrs. After the reaction was completed, the mixture was cooled to rt and quenched with water (10 mL). The aqueous layer was extracted with EtOAc (20 mL×3). The combined organic layers were washed with brine, dried over anhydrous $Na_2SO_4$ and concentrated in vacuo. The residue was purified by silica gel column chromatography (PE/EtOAc (v/v)=1/1) to give the title compound (0.29 g, 60%). The compound was characterized by the following spectroscopic data:

MS (ESI, pos.ion) m/z: 662.7 $[M+H]^+$; and $^1$H NMR (400 MHz, $CDCl_3$) δ (ppm): 8.78 (s, 1H), 7.91-7.86 (m, 2H), 7.74-7.71 (m, 2H), 7.59 (s, 1H), 5.32, 5.29 (d, d, 1H), 5.23-5.19 (m, 1H), 4.41-4.36 (m, 1H), 3.85-3.78 (m, 1H), 3.67-3.64 (m, 1H), 3.63 (s, 3H), 3.62-3.58 (m, 1H), 3.13-2.99 (m, 2H), 2.79-2.66 (m, 1H), 2.63-2.48 (m, 1H), 2.30-1.92 (m, 7H), 1.64-1.54 (m, 1H), 0.97, 0.95 (m, m, 3H), 0.90, 0.89 (m, m, 3H).

Step 11) The Preparation of Compound 25-12

To a mixture of compound 25-11 (0.66 g, 1.0 mmol), compound 2-14 (0.47 g, 1.0 mmol), $Pd(PPh_3)_4$ (0.16 g, 0.1 mmol) and $K_2CO_3$ (0.35 g, 2.5 mmol) were added DME (4.0 mL) and water (1.0 mL) via syringe, and the mixture was stirred at 90° C. under $N_2$ for 4.0 hrs. After the reaction was completed, the mixture was cooled to rt and quenched with water (10 mL). The aqueous layer was extracted with EtOAc (20 mL×3). The combined organic layers were washed with brine, dried over anhydrous $Na_2SO_4$ and concentrated in vacuo. The residue was purified by silica gel column chromatography (DCM/MeOH (v/v)=50/1) to give the title compound (0.43 g, 50%). The compound was characterized by the following spectroscopic data:

MS (ESI, pos.ion) m/z: 428.5 $[M+2H]^{2+}$; and $^1$H NMR (400 MHz, $CDCl_3$) δ (ppm): 8.59 (s, 1H), 7.95-7.92 (m, 3H), 7.74-7.73, 7.72-7.71 (m, m, 2H), 7.66-7.65 (q, 1H), 7.64, 7.62 (d, d, 1H), 7.59 (s, 1H), 5.56, 5.55 (d, d, 1H), 5.32, 5.29 (d, d, 1H), 5.24-5.19 (m, 2H), 4.41-4.32 (m, 2H), 3.93-3.86 (m, 1H), 3.85-3.78 (m, 2H), 3.68-3.67 (m, 2H), 3.66 (s, 3H), 3.63 (s, 3H), 3.15-3.03 (m, 1H), 2.74-2.67 (m, 1H), 2.65-2.51 (m, 1H), 2.37-1.88 (m, 13H), 1.65-1.55 (m, 1H), 1.02-0.89 (m, 12H).

Example 26

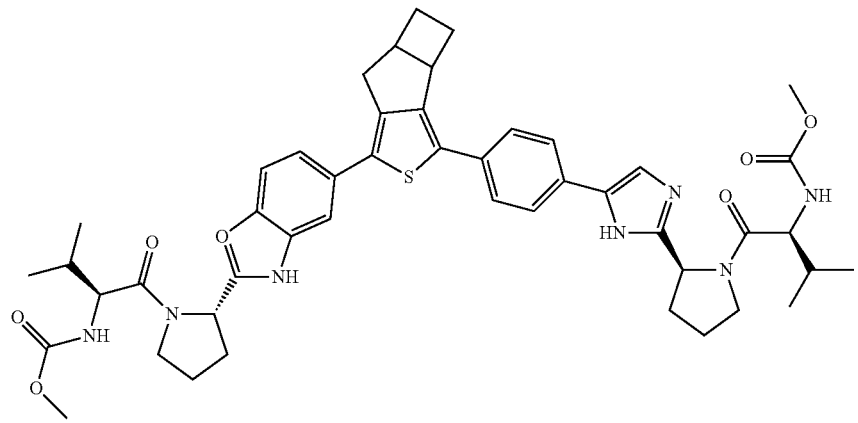

Synthetic Route:

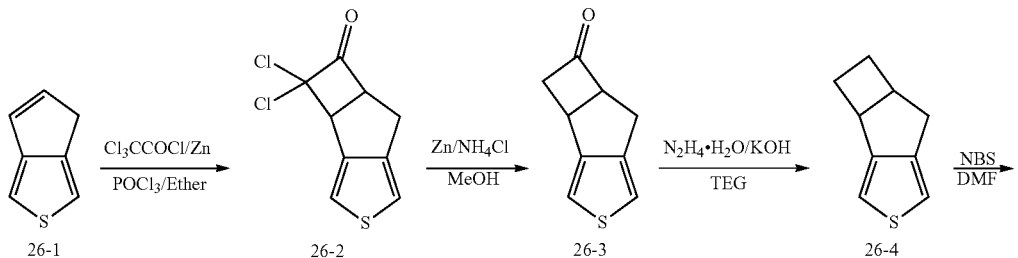

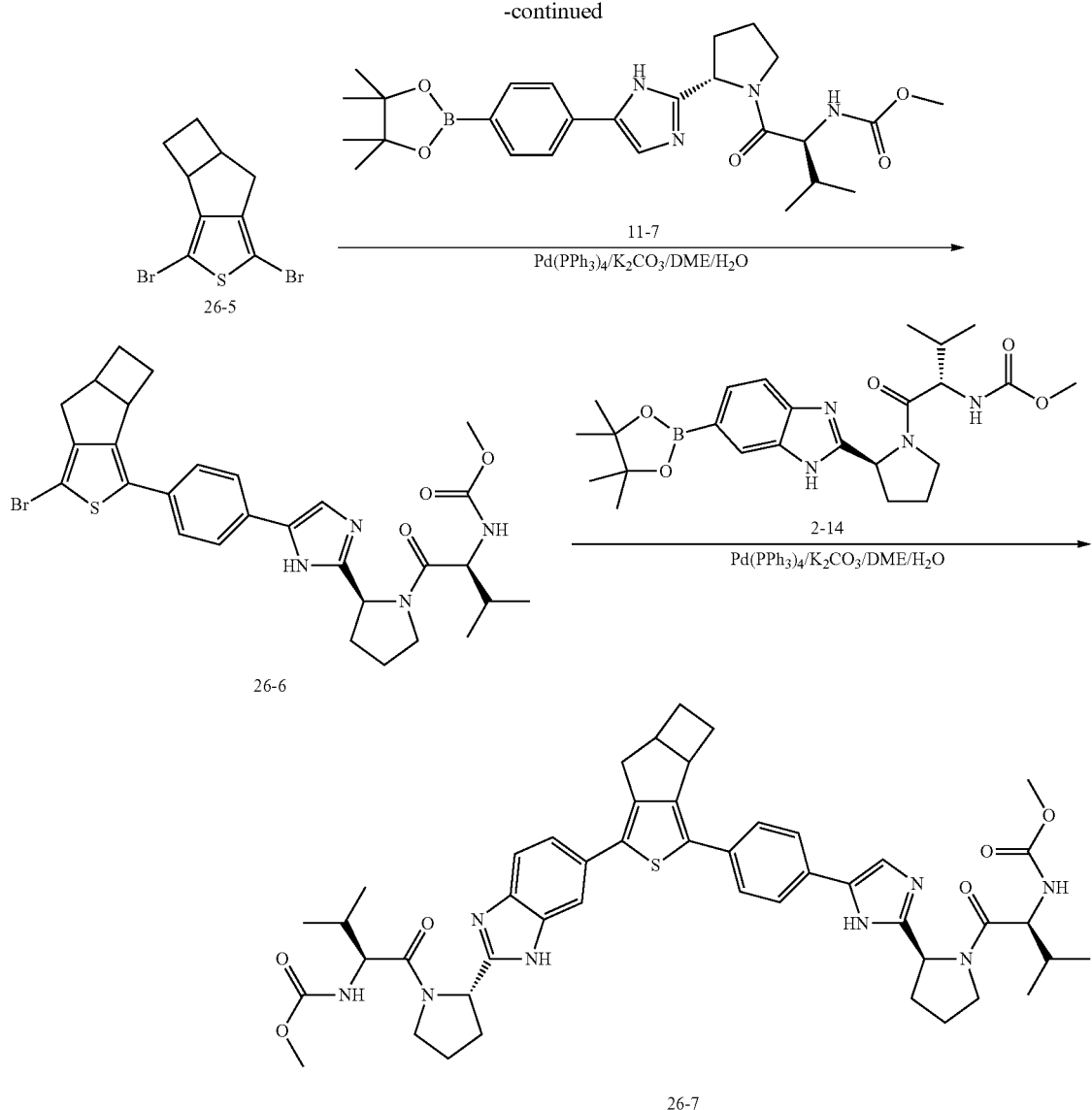

Step 1) The Preparation of Compound 26-2

To a solution of compound 26-1 (0.42 g, 3.42 mmol) in diethyl ether (35 mL) was added activated zinc powder (0.25 g, 3.76 mmol). After the mixture was stirred for 10 mins, a solution of trichloroacetyl chloride (0.4 mL, 3.59 mmol) and phosphorus oxychloride (0.33 mL, 3.59 mmol) in diethyl ether (5 mL) was added dropwise under $N_2$ to the reaction mixture. At the end of the addition, the mixture was refluxed overnight. After the reaction was completed, the mixture was filtered, and then to the filtrate was added water (20 mL). The resulting mixture was extracted with EtOAc (20 mL×3). The combined organic layers were washed with brine, dried over anhydrous $Na_2SO_4$ and concentrated in vacuo. The residue was purified by silica gel column chromatography (PE) to give the title compound as a pale yellow solid (0.59 g, 74%). The compound was characterized by the following spectroscopic data:

MS (ESI, pos.ion) m/z: 233.1 [M+H]$^+$; and $^1$H NMR (400 MHz, CDCl$_3$) δ (ppm): 7.32-7.31 (m, 1H), 7.06-7.04 (m, 1H), 4.53-4.52, 4.51-4.50 (m, m, 1H), 4.04-3.99 (m, 1H), 3.26-3.20 (m, 1H), 2.92-2.86 (m, 1H).

Step 2) The Preparation of Compound 26-3

To a solution of compound 26-2 (0.58 g, 2.52 mmol) in MeOH (80 mL) were added zinc powder (0.82 g, 12.6 mmol) and NH$_4$Cl (0.67 g, 12.6 mmol) in turn at rt. At the end of the addition, the mixture was stirred at 45° C. overnight under $N_2$. After the reaction was completed, the mixture was filtered through a celite pad. The filtrate was concentrated in vacuo, and then to the residue was added water (20 mL). The resulting mixture was extracted with EtOAc (20 mL×3). The combined organic layers were washed with brine, dried over anhydrous $Na_2SO_4$ and concentrated in vacuo. The residue was purified by silica gel column chromatography (PE/EtOAc (v/v)=60/1) to give the title compound as colorless liquid (0.32 g, 78%). The compound was characterized by the following spectroscopic data:

MS (ESI, pos.ion) m/z: 165.2 [M+H]$^+$; and $^1$H NMR (400 MHz, CDCl$_3$) δ (ppm): 7.32-7.31 (m, 1H), 7.06-7.04 (m, 1H), 4.53-4.52, 4.51-4.50 (m, m, 1H), 4.04-3.99 (m, 1H), 3.26-3.20 (m, 1H), 2.92-2.86 (m, 1H).

Step 3) The Preparation of Compound 26-4

To a solution of compound 26-3 (2.00 g, 12.2 mmol) in TEG (30 mL) were added KOH (2.1 g, 36.7 mmol) and hydrazine hydrate (4.8 mL, 97.8 mmol) in turn. After the mixture was stirred at 130° C. for 20 mins, and then the mixture was stirred at 200° C. to remove water by Dean-Stark trap for 50 mins. After the reaction was completed, the mixture was cooled to rt and 100 mL of water was added. The aqueous layer was extracted with PE (150 mL×3). The combined organic layers were washed with brine, dried over anhydrous $Na_2SO_4$ and concentrated in vacuo. The residue was purified by silica gel column chromatography (PE) to give the title compound as colorless oil (1.19 g, 65%). The compound was characterized by the following spectroscopic data:

MS (ESI, pos.ion) m/z: 151.1 [M+H]$^+$; and $^1$H NMR (400 MHz, CDCl$_3$) δ (ppm): 7.20-7.18 (m, 1H), 6.97-6.95 (m, 1H), 4.07-3.98 (m, 1H), 3.01-2.89 (m, 2H), 2.64-2.52 (m, 1H), 2.47-2.37 (m, 1H), 2.11-1.92 (m, 2H), 1.54-1.43 (m, 1H).

Step 4) The Preparation of Compound 26-5

To a solution of NBS (2.16 g, 12 mmol) in DMF (6.0 mL) was added a solution of compound 26-4 (0.90 g, 6.0 mmol) in DMF (6.0 mL) dropwise in the dark at −15° C. At the end of the addition, the mixture was stirred at rt for 0.5 hr and at 60 OC for another 5.0 hrs. After the reaction was completed, the mixture was poured into the mixed solvents of ice water (50 mL) and diethyl ether (60 mL). The organic layer was separated, washed several times with water to neutral pH, dried over anhydrous $Na_2SO_4$ and concentrated in vacuo to give the title compound (1.47 g, 80%). The compound was characterized by the following spectroscopic data:

MS (ESI, pos.ion) m/z: 309.5 [M+H]$^+$; and $^1$H NMR (400 MHz, CDCl$_3$) δ (ppm): 3.95-3.87 (m, 1H), 3.15-3.05 (m, 1H), 2.98-2.91 (m, 1H), 2.63-2.55 (m, 1H), 2.34-2.23 (m, 1H), 2.20-2.09 (m, 1H), 1.93-1.82 (m, 1H), 1.63-1.53 (m, 1H).

Step 5) The Preparation of Compound 26-6

To a mixture of compound 26-5 (0.56 g, 1.83 mmol), compound 11-7 (0.90 g, 1.83 mmol), Pd(PPh$_3$)$_4$ (0.10 g, 0.0915 mmol) and K$_2$CO$_3$ (0.63 g, 4.575 mmol) were added DME (10 mL) and water (2.0 mL) via syringe under N$_2$, and the mixture was stirred at 90° C. for 4.0 hrs. After the reaction was completed, the mixture was quenched with water (20 mL). The aqueous layer was extracted with EtOAc (20 mL×3). The combined organic layers were washed with brine, dried over anhydrous Na$_2$SO$_4$ and concentrated in vacuo. The residue was purified by silica gel column chromatography (PE/EtOAc (v/v)=1/2) to give the title compound (0.76 g, 70%). The compound was characterized by the following spectroscopic data:

MS (ESI, pos.ion) m/z: 598.5 [M+H]$^+$; and $^1$H NMR (400 MHz, CDCl$_3$) δ (ppm): 7.66-7.62 (m, 2H), 7.59 (s, 1H), 7.55-7.52 (m, 2H), 5.32, 5.29 (d, d, 1H), 5.23-5.19 (m, 1H), 4.41-4.36 (m, 1H), 3.85-3.78 (m, 1H), 3.73-3.65 (m, 2H), 3.63 (s, 3H), 3.08-2.93 (m, 2H), 2.68-2.53 (m, 2H), 2.30-1.97 (m, 7H), 1.60-1.49 (m, 1H), 0.97, 0.95 (m, m, 3H), 0.90, 0.89 (m, m, 3H).

Step 6) The Preparation of Compound 26-7

To a mixture of compound 26-6 (0.60 g, 1.0 mmol), compound 2-14 (0.48 g, 1.02 mmol), Pd(PPh$_3$)$_4$ (0.17 g, 0.10 mmol) and K$_2$CO$_3$ (0.35 g, 2.5 mmol) were added DME (10 mL) and water (2.0 mL) via syringe, and the mixture was stirred at 90° C. under N$_2$ for 5.0 hrs. After the reaction was completed, the mixture was cooled to rt and quenched with water (20 mL). The aqueous layer was extracted with EtOAc (20 mL×3). The combined organic layers were washed with brine, dried over anhydrous Na$_2$SO$_4$ and concentrated in vacuo. The residue was purified by silica gel column chromatography (DCM/MeOH (v/v)=50/1) to give the title compound (0.52 g, 60%). The compound was characterized by the following spectroscopic data:

MS (ESI, pos.ion) m/z: 431.5 [M+2H]$^{2+}$; and $^1$H NMR (400 MHz, CDCl$_3$) δ (ppm): 7.87, 7.84 (d, d, 1H), 7.71-7.70 (q, 1H), 7.65-7.61 (m, 2H), 7.59 (s, 1H), 7.58, 7.57 (d, d, 1H), 7.52-7.49 (m, 2H), 5.32, 5.30 (d, d, 2H), 5.24-5.19 (m, 2H), 4.41-4.35 (m, 2H), 3.89-3.77 (m, 3H), 3.69-3.65 (m, 2H), 3.63 (s, 6H), 3.24-3.16 (m, 1H), 3.00-2.80 (m, 2H), 2.37-1.78 (m, 13H), 1.56-1.46 (m, 1H), 0.97, 0.95 (m, m, 6H), 0.90, 0.89 (m, m, 6H).

Example 27

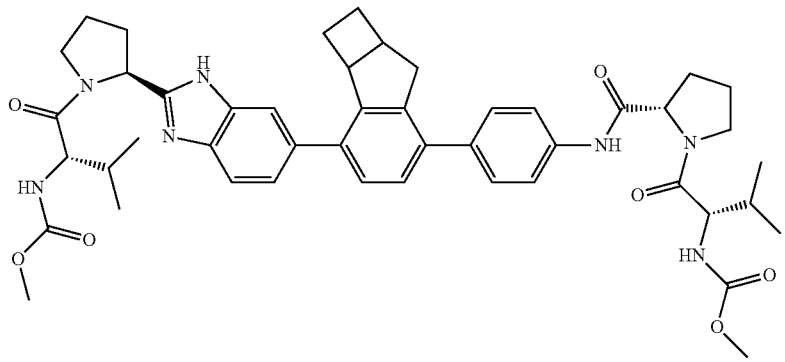 [SMILES: COC(=O)N[C@H](C(=O)N1CCC[C@H]1C(=O)Nc1ccc(-c2ccc(-c3ccc4nc([C@@H]5CCCN5C(=O)[C@@H](NC(=O)OC)C(C)C)[nH]c4c3)c3c2CC2CCC32)cc1)C(C)C]

Synthetic Route:
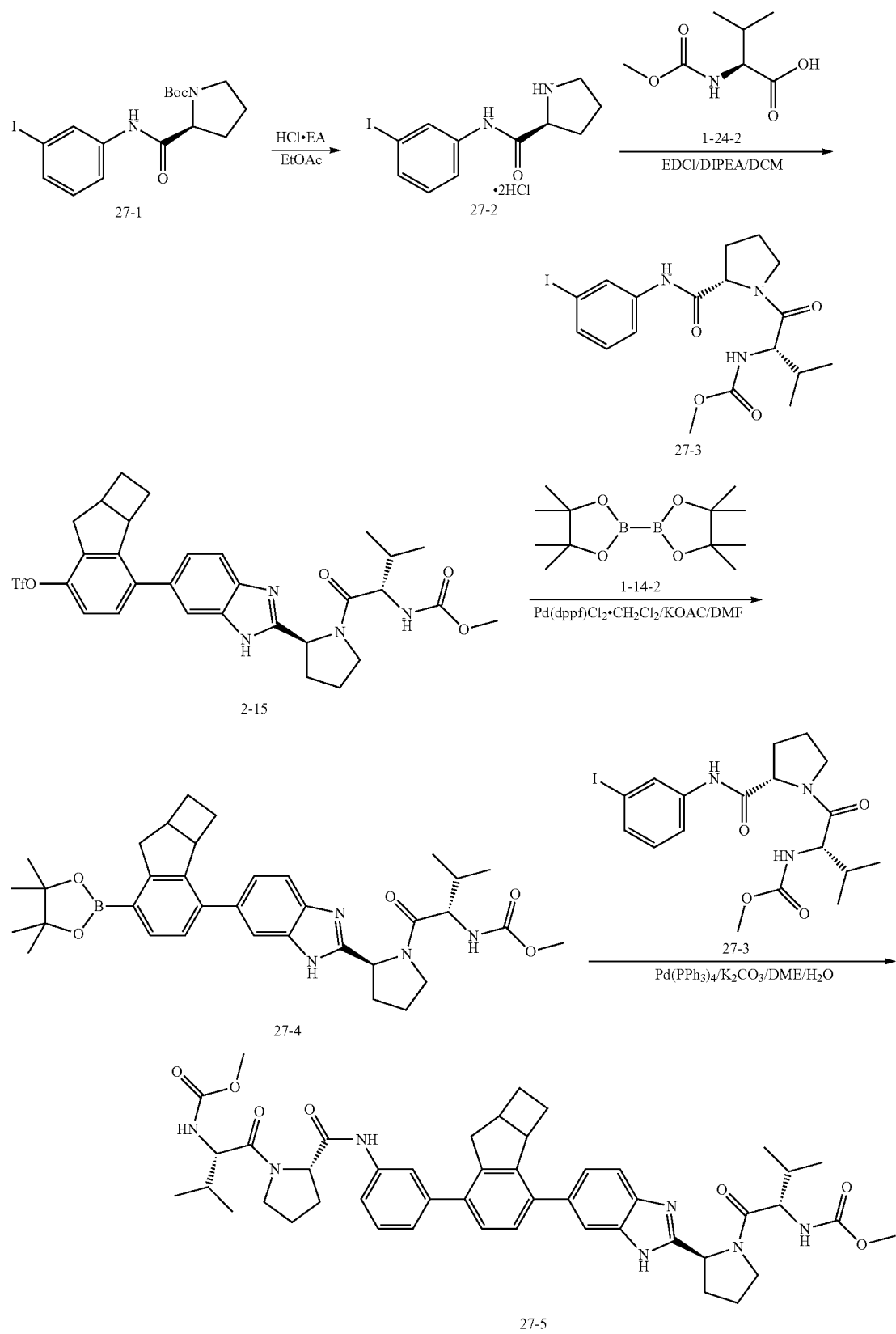

Step 1) The Preparation of Compound 27-1

To a solution of compound 27-1 (1.72 g, 4.13 mmol) in EtOAc (10 mL) was added a solution of HCl in EtOAc (5.0 mL, 4 M) dropwise. At the end of the addition, the mixture was stirred at rt for 8.0 hrs. After the reaction was completed, the mixture was concentrated in vacuo. The residue was purified by beating in EtOAc (5.0 mL) and filtered to give the title compound as a solid (1.37 g, 85%). The compound was characterized by the following spectroscopic data:

MS (ESI, pos.ion) m/z: 317.5 [M+H]$^+$.

Step 2) The Preparation of Compound 27-3

To a suspension of compound 27-2 (1.4 g, 3.6 mmol), compound 1-24-2 (0.69 g, 3.9 mmol) and EDCI (0.75 g, 3.9 mmol) in DCM (10 mL) was added DIPEA (2.38 mL, 14.4 mmol) dropwise at 0° C. At the end of the addition, the mixture was stirred at rt for 2.0 hrs. After the reaction was completed, the mixture was diluted with DCM (40 mL), washed with NH$_4$Cl aqueous solution and brine, dried over anhydrous Na$_2$SO$_4$ and concentrated in vacuo. The residue was purified by silica gel column chromatography (PE/EtOAc (v/v)=1/2) to give the title compound as a pale yellow solid (1.45 g, 85%). The compound was characterized by the following spectroscopic data:

MS (ESI, pos.ion) m/z: 474.5 [M+H]$^+$; and $^1$H NMR (400 MHz, CDCl$_3$) δ (ppm): 8.96 (brs, 1H), 7.68-7.67 (m, 1H), 7.55-7.52 (m, 1H), 7.35-7.32 (m, 1H), 7.14-7.10 (m, 1H), 5.32, 5.29 (d, d, 1H), 4.55-4.51 (m, 1H), 4.31-4.26 (m, 1H), 3.63 (s, 3H), 3.62-3.55 (m, 1H), 3.47-3.40 (m, 1H), 2.27-1.99 (m, 4H), 1.94-1.82 (m, 1H), 0.97, 0.95 (m, m, 3H), 0.90, 0.89 (m, m, 3H).

Step 3) The Preparation of Compound 27-4

A mixture of compound 2-15 (1.03 g, 1.62 mmol), compound 1-14-2 (0.42 g, 1.7 mmol), Pd(dppf)Cl$_2$.CH$_2$Cl$_2$ (67 mg, 0.08 mmol) and KOAc (0.4 g, 4.05 mmol) in DMF (5 mL) was stirred at 90° C. under N$_2$ for 3.0 hrs. After cooling to rt, the mixture was diluted with EtOAc (50 mL) and filtered through a celite pad. The filtrate was washed with water (20 mL×3) and brine, dried over anhydrous Na$_2$SO$_4$ and concentrated in vacuo. The residue was purified by silica gel column chromatography (PE/EtOAc (v/v)=1/3) to give the title compound as a pale yellow solid (0.7 g, 70%). The compound was characterized by the following spectroscopic data:

MS (ESI, pos.ion) m/z: 613.5 [M+H]$^+$; and $^1$H NMR (400 MHz, CDCl$_3$) δ (ppm): 7.77, 7.75 (s, s, 1H), 7.73-7.70 (m, 2H), 7.63, 7.60 (d, d, 1H), 7.24, 7.22 (d, d, 1H), 5.32, 5.29 (d, d, 1H), 5.24-5.20 (m, 1H), 4.40-4.35 (m, 1H), 3.84-3.78 (m, 1H), 3.68-3.64 (m, 1H), 3.63 (s, 3H), 3.60-3.54 (m, 1H), 3.19-3.09 (m, 1H), 2.99-2.91 (m, 1H), 2.53-2.27 (m, 3H), 2.25-1.87 (m, 6H), 1.62-1.54 (m, 1H), 1.32, 1.29 (q, q, 12H), 0.97, 0.95 (m, m, 3H), 0.90, 0.89 (m, m, 3H).

Step 4) The Preparation of Compound 27-5

To a mixture of compound 27-4 (2.08 g, 3.4 mmol), compound 27-3 (1.61 g, 3.4 mmol), Pd(PPh$_3$)$_4$ (0.20 g, 0.17 mmol) and K$_2$CO$_3$ (1.41 g, 10.22 mmol) were added DME (24 mL) and water (6 mL) via syringe under N$_2$, and the mixture was stirred at 90° C. for 4.0 hrs. After the reaction was completed, the mixture was cooled to rt and diluted with EtOAc (100 mL). The resulting mixture was washed with water (50 mL×3) and brine, dried over anhydrous Na$_2$SO$_4$ and concentrated in vacuo. The residue was purified by silica gel column chromatography (DCM/MeOH (v/v)=60/1) to give the title compound as a pale yellow solid (1.41 g, 50%). The compound was characterized by the following spectroscopic data:

MS (ESI, pos.ion) m/z: 416.5 [M+2H]$^2$; and $^1$H NMR (400 MHz, CDCl$_3$) δ (ppm): 8.90 (brs, 1H), 7.83-7.82 (m, 1H), 7.74, 7.72 (s, s, 1H), 762-7.60 (m, 2H), 7.55-7.52 (m, 1H), 7.48-7.45 (t, t, 1H), 7.34, 7.32 (m, m, 1H), 7.24-7.22 (m, 1H), 7.19-7.15 (m, 1H), 5.56, 5.55 (d, d, 1H), 5.32-5.29 (d, d, 1H), 5.24-5.20 (m, 1H), 4.40-4.35 (m, 1H), 4.33-4.29 (m, 1H), 4.28-4.23 (m, 1H), 3.84-3.73 (m, 2H), 3.66 (s, 3H), 3.65-3.64 (m, 1H), 3.63 (s, 3H), 3.62-3.55 (m, 1H), 3.44-3.36 (m, 1H), 3.11-3.01 (m, 1H), 2.72-2.54 (m, 2H), 2.38-1.87 (m, 11H), 1.74-1.52 (m, 3H), 1.02-0.89 (m, 12H).

Example 28

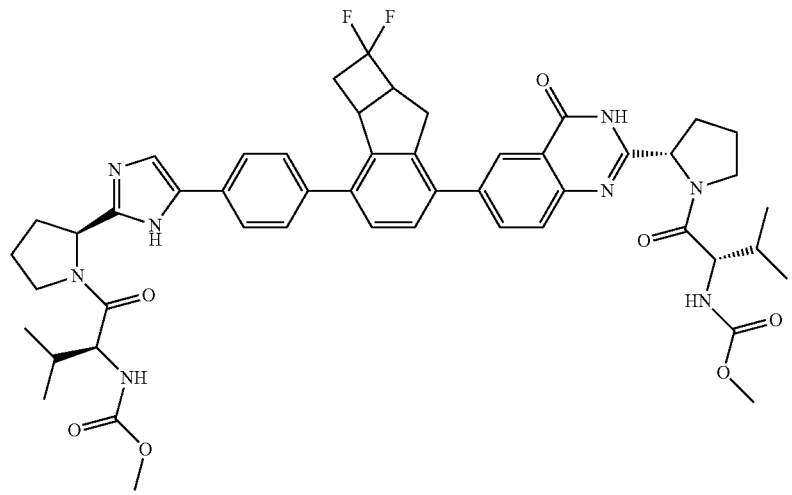 [SMILES: COC(=O)N[C@H](C(=O)N1CCC[C@H]1c1ncc(-c2ccc(-c3ccc(-c4ccc5nc([C@@H]6CCCN6C(=O)[C@@H](NC(=O)OC)C(C)C)[nH]c(=O)c5c4)c4c3C3CC(F)(F)C3C4)cc2)[nH]1)C(C)C]

Synthetic Route:
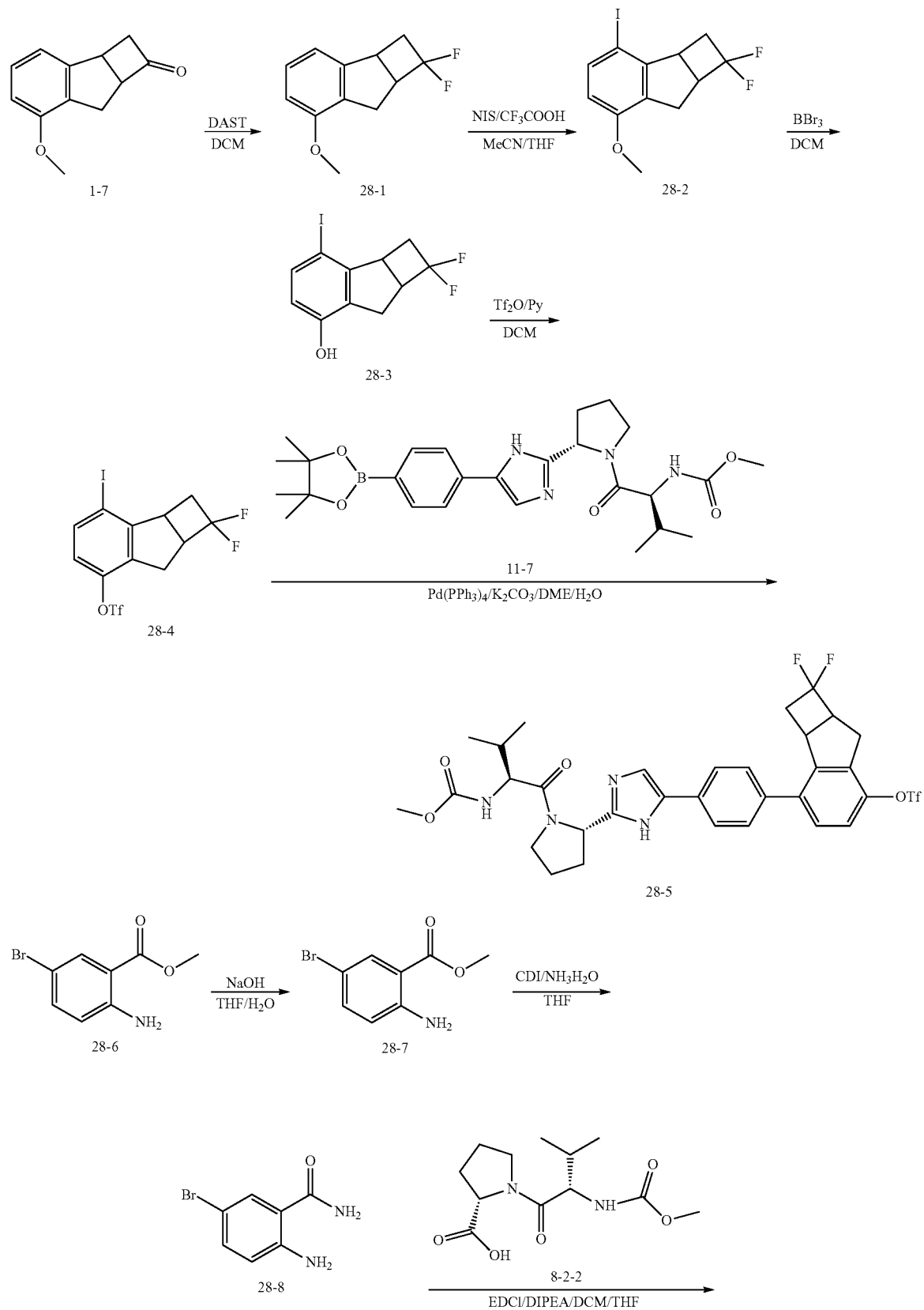

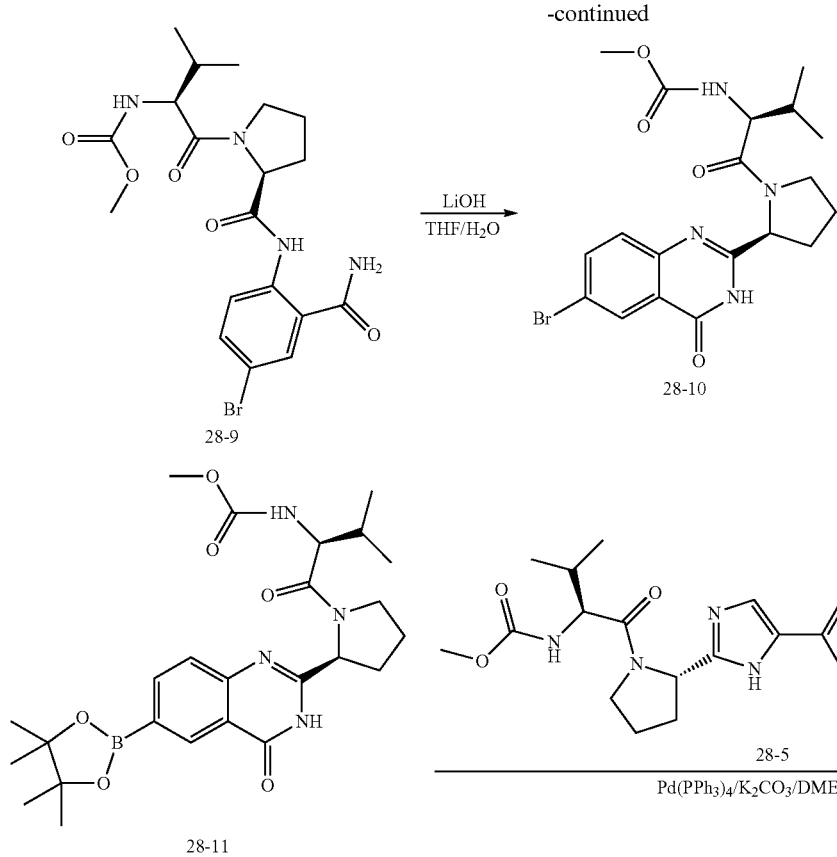
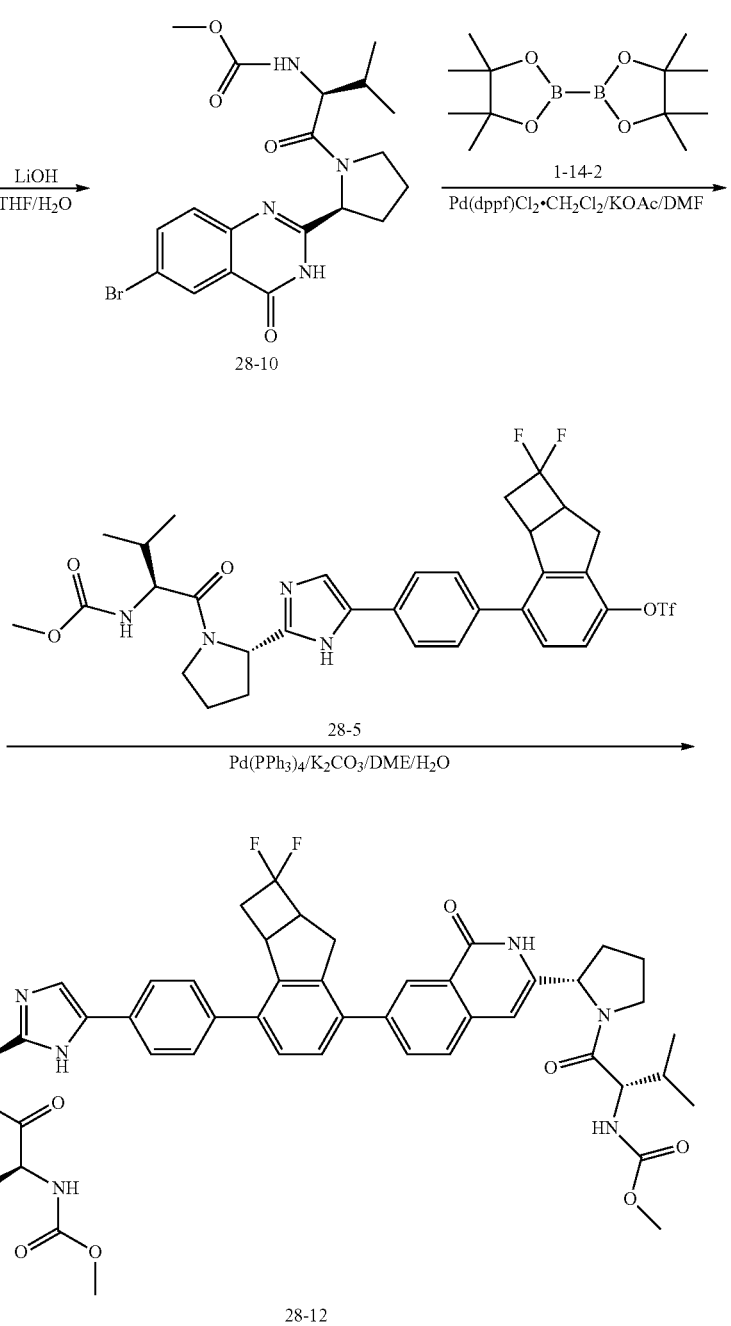

Step 1) The Preparation of Compound 28-1

To a solution of compound 1-7 (4.50 g, 23.9 mmol) in DCM (70 mL) was added Et$_2$NSF$_3$ (4.85 mL, 35.9 mmol) dropwise at −78° C. At the end of the addition, the mixture was stirred at −78° C. for 2.0 hrs and at rt for another 19 hrs. After the reaction was completed, the mixture was quenched with NH$_4$Cl aqueous solution (50 mL). The resulting mixture was extracted with DCM (100 mL×3). The combined organic layers were washed with brine, dried over anhydrous Na$_2$SO$_4$ and concentrated in vacuo. The residue was purified by silica gel column chromatography (PE/EtOAc (v/v)=20/1) to give the title compound as pale yellow liquid (3.97 g, 70%). The compound was characterized by the following spectroscopic data:

MS (ESI, pos.ion) m/z: 211.1 [M+H]$^+$; and $^1$H NMR (400 MHz, CDCl$_3$) δ (ppm): 7.06, 7.04, 7.02 (m, m, m, 1H), 6.84-6.83, 6.82-6.81 (m, m, 1H), 6.73-6.72, 6.71-6.70 (m, m, 1H), 3.91 (s, 3H), 3.83-3.69 (m, 1H), 3.50-3.43 (m, 1H), 3.07-3.00 (m, 1H), 2.70-2.56 (m, 2H), 2.33-2.21 (m, 1H).

Step 2) The Preparation of Compound 28-2

To a solution of compound 28-1 (1.20 g, 5.7 mmol) in THF (10 mL) and MeCN (10 mL) was added NIS (1.42 g, 6.3 mmol). After the mixture was stirred for 10 mins, a catalytic amount of trifluoroacetic acid was added dropwise. At the end of the addition, the mixture was stirred at rt for 5.0 hrs. After the reaction was completed, the mixture was concentrated in vacuo. To the residue was added EtOAc (100 mL). The resulting mixture was washed with saturated sodium sulfite aqueous solution (20 mL×3), dried over anhydrous $Na_2SO_4$ and concentrated in vacuo. The residue was purified by silica gel column chromatography (PE) to give the title compound as colorless liquid (1.44 g, 75%). The compound was characterized by the following spectroscopic data:

MS (ESI, pos.ion) m/z: 336.1 [M+H]$^+$; and
$^1$H NMR (400 MHz, CDCl$_3$) δ (ppm): 7.29, 7.27 (t, t, 1H), 6.57, 6.55 (q, q, 1H), 4.26-4.20 (m, 1H), 3.90 (s, 3H), 3.88-3.81 (m, 1H), 3.15-3.07 (m, 1H), 2.94-2.82 (m, 1H), 2.78-2.71 (m, 1H), 2.60-2.48 (m, 1H).

Step 3) The Preparation of Compound 28-3

To a solution of compound 28-2 (2.42 g, 7.2 mmo) in DCM (20 mL) was added boron tribromide (2.7 mL, 28.8 mmol) dropwise at −78° C. At the end of the addition, the mixture was stirred at −78° C. for 10 mins and at rt for another 4.0 hr. After the reaction was completed, the mixture was poured slowly into ice water (100 mL) and the organic phase was separated. The aqueous layer was extracted with DCM (50 mL×3). The combined organic layers were washed with brine, dried over anhydrous $Na_2SO_4$ and concentrated in vacuo. The residue was purified by silica gel column chromatography (PE/EtOAc (v/v)=20/1) to give the title compound as colorless liquid (2.09 g, 90%). The compound was characterized by the following spectroscopic data:

MS (ESI, pos.ion) m/z: 323.1 [M+H]$^+$; and
$^1$H NMR (400 MHz, CDCl$_3$) δ (ppm): 7.20, 7.18 (m, m, 1H), 6.51, 6.49 (s, s, 1H), 4.81 (brs, 1H), 4.26-4.20 (m, 1H), 3.95-3.81 (m, 1H), 3.13-3.06 (m, 1H), 3.03-2.91 (m, 1H), 2.76-2.67 (m, 1H), 2.66-2.56 (m, 1H).

Step 4) The Preparation of Compound 28-4

To a solution of compound 28-3 (1.74 g, 5.4 mmol) in DCM (15 mL) was added pyridine (1.1 mL, 13.5 mmol) dropwise at 0° C. After the mixture was stirred for 10 mins, trifluoromethanesulfonic anhydride (1.4 mL, 8.1 mmol) was added dropwise. At the end of the addition, the mixture was stirred at rt for 1.0 hr. After the reaction was completed, the mixture was quenched with ice water (50 mL). The aqueous layer was extracted with DCM (50 mL×3). The combined organic layers were washed with brine, dried over anhydrous $Na_2SO_4$ and concentrated in vacuo. The residue was purified by silica gel column chromatography (PE) to give the title compound as colorless liquid (2.40 g, 98%). The compound was characterized by the following spectroscopic data:

MS (ESI, pos.ion) m/z: 454.5 [M+H]$^+$; and
$^1$H NMR (400 MHz, CDCl$_3$) δ (ppm): 7.41, 7.39 (t, t, 1H), 6.92, 6.90 (s, s, 1H), 4.18-4.12 (m, 1H), 3.86-3.74 (m, 1H), 3.27-3.20 (m, 1H), 3.06-2.94 (m, 1H), 2.91-2.83 (m, 1H), 2.71-2.60 (m, 1H).

Step 5) The Preparation of Compound 28-5

To a mixture of compound 28-4 (0.43 g, 0.957 mmol), compound 11-7 (0.48 g, 0.957 mmol), Pd(PPh$_3$)$_4$ (0.11 g, 0.0957 mmol) and $K_2CO_3$ (0.40 g, 2.87 mmol) were added DME (10 mL) and water (2.5 mL) via syringe under $N_2$, and the mixture was stirred at 90° C. for 5.0 hrs. After the reaction was completed, the mixture was cooled to rt and diluted with EtOAc (50 mL). The resulting mixture was washed with water (20 mL×3) and brine, dried over anhydrous $Na_2SO_4$ and concentrated in vacuo. The residue was purified by silica gel column chromatography (DCM/EtOH (v/v)=100/1) to give the title compound as a pale yellow solid (0.37 g, 55%). The compound was characterized by the following spectroscopic data:

MS (ESI, pos.ion) m/z: 697.7 [M+H]$^+$; and
$^1$H NMR (400 MHz, CDCl$_3$) δ (ppm): 7.59 (s, 1H), 7.58-7.56 (m, 2H), 7.53-7.50 (m, 2H), 7.29, 7.27 (s, s, 1H), 7.03, 7.00 (t, t, 1H), 5.32, 5.29 (d, d, 1H), 5.23-5.19 (m, 1H), 4.41-4.36 (m, 1H), 4.29-4.23 (m, 1H), 3.85-3.78 (m, 1H), 3.69-3.64 (m, 1H), 3.63 (s, 3H), 3.43-3.30 (m, 1H), 3.20-3.12 (m, 1H), 2.97-2.76 (m, 2H), 2.62-2.51 (m, 1H), 2.30-1.92 (m, 5H), 0.97, 0.95 (m, m, 3H), 0.91, 0.89 (m, m, 3H).

Step 6) The Preparation of Compound 28-7

To a solution of compound 28-6 (2.1 g, 9.17 mmol) in THF (20 mL) was added a aqueous solution of NaOH (2.1 g, 20 mL). At the end of the addition, the mixture was stirred at 60° C. overnight. After the reaction was completed, the THF solvent was removed. The residue was dissolved in EtOAc (50 mL) and washed with water (50 mL×3). The combined aqueous phase was adjusted to pH 4 with hydrochloric acid (1 M) and the solid was precipitated. The resulting mixture was filtered to give the title compound as a pale yellow solid (1.42 g, 72%). The compound was characterized by the following spectroscopic data:

MS (ESI, pos.ion) m/z: 217 [M+H]$^+$; and
$^1$H NMR (400 MHz, CDCl$_3$) δ (ppm): 7.59 (d, 1H, J=8.0 Hz), 6.96 (d, 1H, J=1.6 Hz), 6.64 (dd, 1H, J=8.0 Hz, 2.0 Hz).

Step 7) The Preparation of Compound 28-8

To a suspension of compound 28-7 (1.52 g, 7.00 mmol) in dry THF (5.0 mL) was added CDI (0.83 g, 5.12 mmol) dropwise. At the end of the addition, the mixture was stirred at rt for 2.0 hrs, and then $NH_3.H_2O$ (20 mL) was added dropwise at 0° C. At the end of the addition, the mixture was stirred at rt overnight. After the reaction was completed, the THF solvent was removed. The residue was dissolved in EtOAc (100 mL). The resulting mixture was washed with brine, dried over anhydrous $Na_2SO_4$ and concentrated in vacuo to give the title compound as a pale yellow solid (1.2 g, 80%). The compound was characterized by the following spectroscopic data:

MS (ESI, pos.ion) m/z: 215 [M+H]$^+$; and
$^1$H NMR (400 MHz, CDCl$_3$) δ (ppm): 7.78 (s, 1H), 7.45 (d, 1H, J=8.0 Hz), 7.15 (s, 1H), 6.89 (d, 1H, J=2.0 Hz), 6.79 (s, 1H), 6.61 (dd, 1H, J=8.0 Hz, 2.0 Hz).

Step 8) The Preparation of Compound 28-9

To a suspension of compound 28-8 (1.5 g, 7.00 mmol), compound 8-2-2 (2.85 g, 10.47 mmol) and EDCI (2.67 g, 13.93 mmol) in DCM (15 mL) and THF (10 mL) was added DIPEA (5.8 mL, 35 mmol) at 0° C. At the end of the addition, the mixture was stirred at rt for 8.0 hrs. After the reaction was completed, the solvent was removed. The residue was dissolved in EtOAc (100 mL), washed with water and brine, dried over $Na_2SO_4$ and concentrated in vacuo. The residue was purified by a silica gel column chromatography (PE/EtOAc (v/v)=1/3) to give the title compound as colorless slurry (0.65 g, 20%). The compound was characterized by the following spectroscopic data:

MS (ESI, pos.ion) m/z: 469.5 [M+H]$^+$; and
$^1$H NMR (400 MHz, CDCl$_3$) δ (ppm): 11.92 (s, 1H), 8.63 (s, 1H), 7.39 (d, 1H, J=8.0 Hz), 7.05 (d, 1H, J=8.0 Hz), 5.57 (d, 1H, J=8.0 Hz), 4.49-4.52 (m, 1H), 4.36-4.40 (m, 1H), 3.86-3.89 (m, 2H), 3.68 (s, 3H), 2.15-2.24 (m, 2H), 2.00-2.09 (m, 2H), 1.09 (d, 3H, J=6.0 Hz), 0.97 (d, 3H, J=6.0 Hz).

Step 9) The Preparation of Compound 28-10

To a solution of compound 28-9 (0.6 g, 1.28 mmol) in THF (10 mL) was added lithium hydroxide aqueous solution (0.27 g, 6.0 mL) at 0° C. At the end of addition, the mixture was stirred at rt for 5.0 hrs. After the reaction was completed, the THF solvent was removed, and the residue was dissolved in EtOAc (50 mL). The resulting mixture was washed with water and brine, dried over $Na_2SO_4$ and concentrated in vacuo. The residue was purified by a silica gel column chromatography (PE/EtOAc (v/v)=1/3) to give the title compound as a white solid (0.55 g, 96%). The compound was characterized by the following spectroscopic data:

MS (ESI, pos.ion) m/z: 452.3 [M+H]$^+$; and $^1$H NMR (400 MHz, CDCl$_3$) δ (ppm): 11.31 (s, 1H), 8.07 (d, 1H, J=8.0 Hz), 7.79 (d, 1H, J=2.0 Hz), 7.53 (dd, 1H, J=8.0 Hz, 2.0 Hz), 5.78 (d, 1H, J=8.0 Hz), 5.10 (dd, 1H, J=8.0 Hz, 2.0 Hz), 4.33 (t, 1H, J=8.0 Hz), 4.09-4.14 (m, 1H), 3.86-3.90 (m, 1H), 3.66 (s, 3H), 2.51-2.53 (m, 1H), 2.29-2.31 (m, 1H), 2.16-2.18 (m, 1H), 1.79-2.04 (m, 2H), 0.93 (d, 1H, J=2.0 Hz), 0.93 (d, 1H, J=2.0 Hz).

Step 10) The Preparation of Compound 28-11

A suspension of compound 28-10 (0.2 g, 0.444 mmol), compound 1-14-2 (0.13 g, 0.51 mmol), Pd(dppf)Cl$_2$·CH$_2$Cl$_2$ (0.04 g, 0.049 mmol) and KOAc (0.11 g, 1.12 mmol) in DMF (5.0 mL) was stirred at 80° C. under N$_2$ for 3.0 hrs. After the reaction was completed, the mixture was cooled to rt, diluted with EtOAc (20 mL) and filtered through a celite pad. The filtrate was washed with water (20 mL×3) and brine, dried over anhydrous Na$_2$SO$_4$ and concentrated in vacuo. The residue was purified by a silica gel column chromatography (PE/EtOAc (v/v)=2/1) to give the title compound as a yellow solid (0.15 g, 70%). The compound was characterized by the following spectroscopic data:

MS (ESI, pos.ion) m/z: 499.2 [M+H]$^+$; and $^1$H NMR (400 MHz, CDCl$_3$) δ (ppm): 11.08 (s, 1H), 8.22 (d, 1H, J=8.0 Hz), 8.11 (s, 1H), 7.83 (d, 1H, J=8.0 Hz), 5.71 (d, 1H, J=8.0 Hz), 5.17 (d, 1H, J=6.0 Hz), 4.35 (t, 1H, J=8.0 Hz), 4.10-4.15 (m, 1H), 3.86-3.88 (m, 1H), 3.67 (s, 3H), 2.67-2.71 (m, 1H), 2.32-2.34 (m, 1H), 1.99-2.09 (m, 2H), 1.37-2.04 (s, 12H), 0.89-0.94 (m, 6H).

Step 11) The Preparation of Compound 28-12

A mixture of compound 28-11 (0.11 g, 0.23 mmol), compound 28-5 (0.11 g, 0.164 mmol), Pd(PPh$_3$)$_4$ (30 mg, 0.026 mmol) and K$_2$CO$_3$ (60 mg, 0.435 mmol) in the mixed solvent of DME/H$_2$O (v/v=3/1, 4.0 mL) was stirred at 90° C. under N$_2$ for 3.0 hrs. After the reaction was completed, the mixture was cooled to rt, diluted with EtOAc (50 mL), and washed with water (20 mL×3) and brine. The combined organic layers were dried over anhydrous Na$_2$SO$_4$ and concentrated in vacuo. The residue was purified by a silica gel column chromatography (MeOH/DCM (v/v)=1/25) to give the title compound as a pale yellow solid (75.36 mg, 50%). The compound was characterized by the following spectroscopic data:

MS (ESI, pos.ion) m/z: 460.5 [M+2H]; and $^1$H NMR (400 MHz, CDCl$_3$) δ (ppm): 7.91, 7.89 (s, s, 1H), 7.83, 7.80 (d, d, 1H), 7.62-7.54 (m, 6H), 7.52, 7.50 (t, t, 1H), 6.82-6.81 (q, 1H), 5.32, 5.30 (d, d, 2H), 5.23-5.19 (m, 1H), 5.10-5.05 (m, 1H), 4.44-4.37 (m, 2H), 4.30-4.25 (m, 1H), 3.90-3.76 (m, 2H), 3.68-3.65 (m, 1H), 3.63 (s, 6H), 3.60-3.54 (m, 1H), 3.24-3.16 (m, 1H), 3.06-2.99 (m, 1H), 2.90-2.77 (m, 1H), 2.61-2.38 (m, 3H), 2.30-1.72 (m, 9H), 0.97, 0.95 (m, m, 6H), 0.90, 0.89 (m, m, 6H).

Example 29

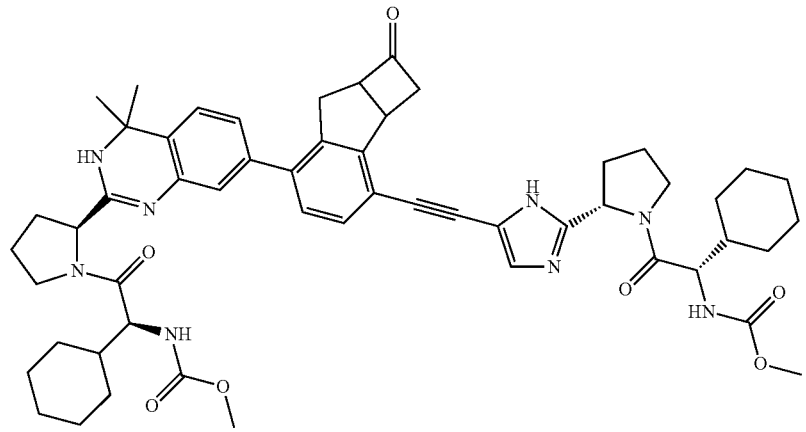 [SMILES: COC(=O)N[C@H](C(=O)N1CCC[C@H]1C1=Nc2cc(-c3ccc(C#Cc4cnc([C@@H]5CCCN5C(=O)[C@@H](NC(=O)OC)C5CCCCC5)[nH]4)c4c3CC3C(=O)CC43)ccc2C(C)(C)N1)C1CCCCC1]

Synthetic Route:

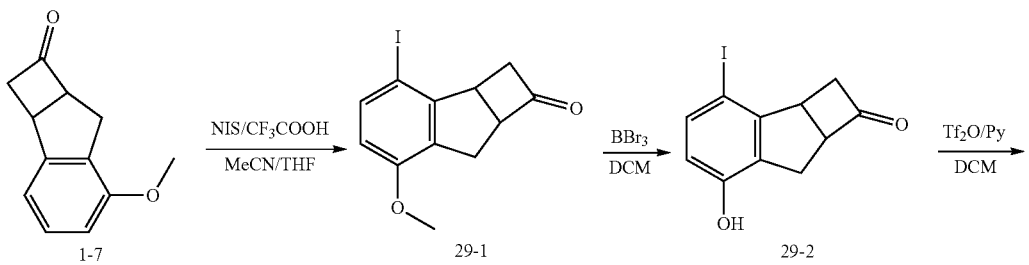

-continued
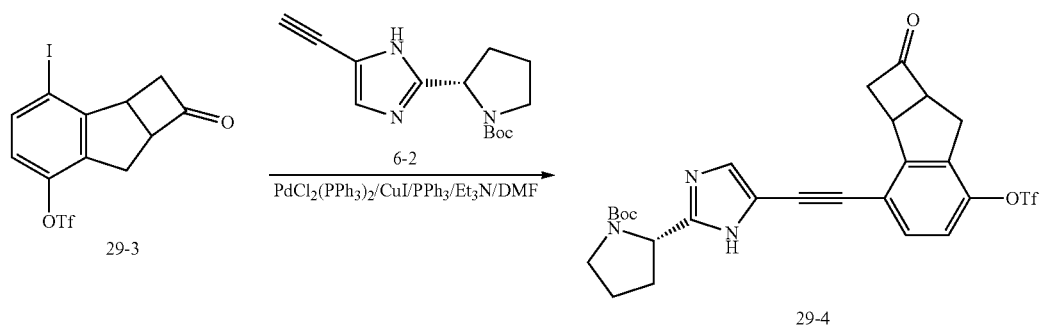
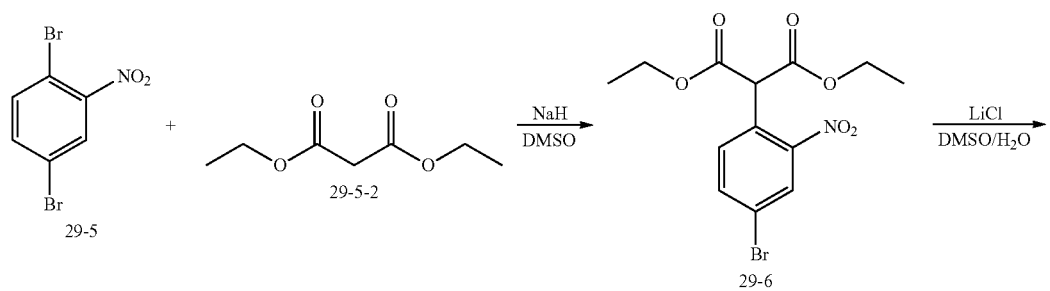
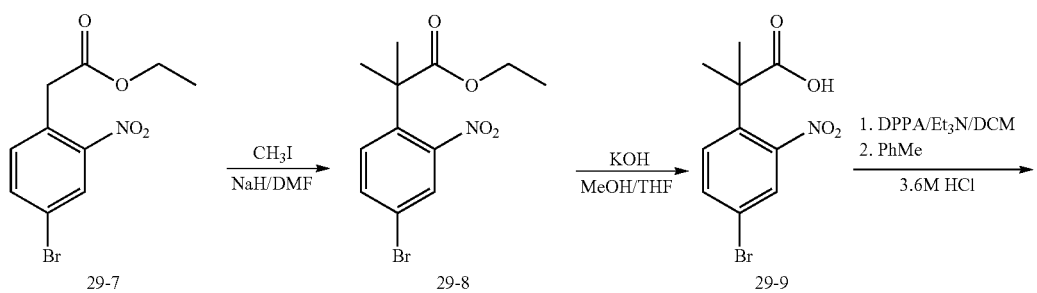
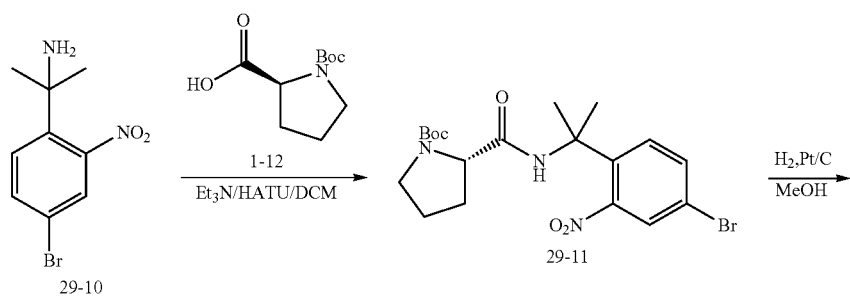
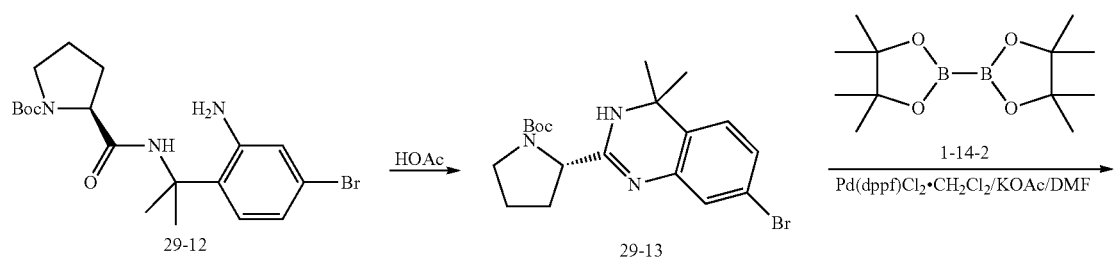

-continued
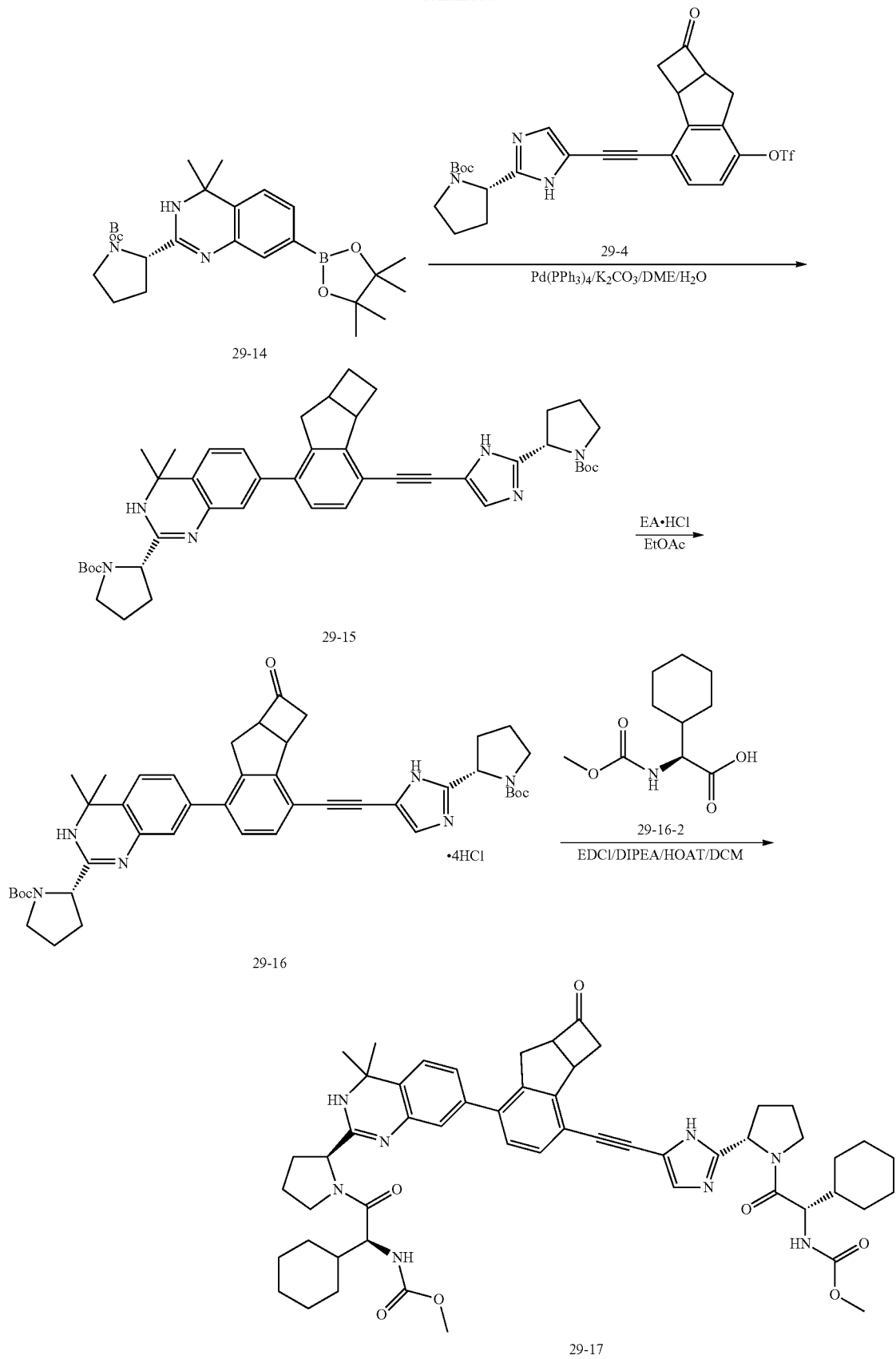

Step 1) The Preparation of Compound 29-1

To a solution of compound 1-7 (1.07 g, 5.7 mmol) in THF (10 mL) and MeCN (10 mL) was added NIS (1.42 g, 6.3 mmol). After the mixture was stirred for 10 mins, a catalytic amount of trifluoroacetic acid was added dropwise. At the end of the addition, the mixture was stirred at rt for 5.0 hrs. After the reaction was completed, the mixture was concentrated in vacuo. To the residue was added EtOAc (100 mL). The resulting mixture was washed with saturated sodium sulfite aqueous solution (20 mL×3), dried over anhydrous $Na_2SO_4$ and concentrated in vacuo. The residue was purified by silica gel column chromatography (PE) to give the title compound as colorless liquid (1.34 g, 75%). The compound was characterized by the following spectroscopic data:

MS (ESI, pos.ion) m/z: 315.1 $[M+H]^+$; and $^1$H NMR (400 MHz, $CDCl_3$) δ (ppm): 7.35, 7.33 (t, t, 1H), 6.51, 6.49 (m, m, 1H), 3.99-3.95 (m, 1H), 3.91 (s, 3H), 3.85-3.78 (m, 1H), 3.74-3.66 (m, 1H), 3.20-3.14 (m, 1H), 3.00, 2.94 (m, m, 1H), 2.88-2.85, 2.83-2.81 (m, m, 1H).

Step 2) The Preparation of Compound 29-2

To a solution of compound 29-1 (2.26 g, 7.2 mmo) in DCM (20 mL) was added boron tribromide (2.7 mL, 28.8 mmol) dropwise at −78° C. At the end of the addition, the mixture was stirred at −78° C. for 10 mins and at rt for another 4.0 hr. After the reaction was completed, the mixture was poured slowly into ice water (100 mL) and the organic phase was separated. The aqueous layer was extracted with DCM (50 mL×3). The combined organic layers were washed with brine, dried over anhydrous $Na_2SO_4$ and concentrated in vacuo. The residue was purified by silica gel column chromatography (PE/EtOAc (v/v)=20/1) to give the title compound as colorless liquid (1.94 g, 90%). The compound was characterized by the following spectroscopic data:

MS (ESI, pos.ion) m/z: 301.1 $[M+H]^+$; and $^1$H NMR (400 MHz, $CDCl_3$) δ (ppm): 7.26, 7.24 (t, t, 1H), 6.45, 6.42 (s, s, 1H), 4.81 (brs, 1H), 4.36-4.32 (m, 1H), 3.88-3.81 (m, 1H), 3.74-3.66 (m, 1H), 3.19, 3.13 (m, 1H), 3.00, 2.96 (m, m, 1H), 2.87-2.80 (m, 1H).

Step 3) The Preparation of Compound 29-3

To a solution of compound 29-2 (1.62 g, 5.4 mmol) in DCM (15 mL) was added pyridine (1.1 mL, 13.5 mmol) dropwise at 0° C. After the mixture was stirred for 10 mins, trifluoromethanesulfonic anhydride (1.4 mL, 8.1 mmol) was added dropwise. At the end of the addition, the mixture was stirred at rt for 1.0 hr. After the reaction was completed, the mixture was quenched with ice water (50 mL). The aqueous layer was extracted with DCM (50 mL×3). The combined organic layers were washed with brine, dried over anhydrous $Na_2SO_4$ and concentrated in vacuo. The residue was purified by silica gel column chromatography (PE) to give the title compound as colorless liquid (2.29 g, 98%). The compound was characterized by the following spectroscopic data:

MS (ESI, pos.ion) m/z: 432.5 $[M+H]^+$; and $^1$H NMR (400 MHz, $CDCl_3$) δ (ppm): 7.47, 7.45 (t, t, 1H), 6.83, 6.81 (s, s, 1H), 4.33-4.29 (s, 1H), 3.83-3.76 (m, 1H), 3.70-3.63 (m, 2H), 3.28-3.21 (m, 1H), 2.96-2.89 (m, 1H).

Step 4) The Preparation of Compound 29-4

To a mixture of compound 29-3 (0.17 g, 0.39 mmol), compound 6-2 (0.11 g, 0.43 mmol), CuI (33 mg, 0.172 mmol), $Pd(PPh_3)_2Cl_2$ (27.37 mg, 0.039 mmol) and $PPh_3$ (0.23 g, 0.86 mmol) were added anhydrous DMF (5 mL) and $Et_3N$ (5 mL) separately under $N_2$. At the end of the addition, the mixture was stirred at rt for 10 mins and at 90° C. for another 6.0 hrs. After the reaction was completed, the mixture was diluted with EtOAc (50 mL) and filtered through a celite pad. The filtrate was washed with water (20 mL×3) and brine, dried over anhydrous $Na_2SO_4$ and concentrated in vacuo. The residue was purified by silica gel column chromatography (PE/EtOAc (v/v)=1/2) to give the title compound (0.12 g, 55%). The compound was characterized by the following spectroscopic data:

$^1$H NMR (400 MHz, $CDCl_3$) δ (ppm): 7.54, 7.52 (t, t, 1H), 7.48 (s, 1H), 7.11, 7.09 (s, s, 1H), 5.18-5.14 (m, 1H), 3.72-3.57 (m, 4H), 3.38-3.30 (m, 1H), 3.28-3.21 (m, 1H), 2.95-2.84 (m, 2H), 2.56-2.48 (m, 1H), 2.40-2.30 (m, 1H), 2.28-2.19 (m, 1H), 2.07-1.97 (m, 1H), 1.41 (s, 9H).

Step 5) The Preparation of Compound 29-6

NaH (60%, 3.13 g, 78 mmol) was added to DMSO (100 mL) followed by dropwise addition of diethyl malonate (12.54 g, 78 mmol). At the end of addition, the mixture was heated to 100° C. for 40 mins. The mixture was cooled to rt followed by addition of compound 3-1 (10 g, 35.60 mmol). The reaction mixture was stirred for another 30 mins at rt, and then heated to 100° C. for 1.0 hr. After the reaction was completed, the reaction was quenched with aqueous saturated $NH_4Cl$ solution (50 mL), and then EtOAc (150 mL) was added to the mixture. The combined organic layer were washed with brine, dried over anhydrous $Na_2SO_4$ and concentrated in vacuo to give the title compound 15 g, which was used for the next step. The compound was characterized by the following spectroscopic data:

$^1$H NMR (400 MHz, $CDCl_3$) δ (ppm): 8.36-8.35 (m, 1H), 7.73, 7.70 (dd, dd, 1H), 7.60, 7.58 (t, t, 1H), 5.24-5.23 (m, 1H), 4.32-4.26 (m, 4H), 1.29-1.25 (t, 6H, J=8.0 Hz).

Step 6) The Preparation of Compound 29-7

To a solution of compound 29-6 (15 g) in DMSO (100 mL) was added LiCl (3.0 g, 70 mmol) and water (0.64 g, 35.6 mmol) dropwise at rt. At the end of the addition, the mixture was stirred at 100° C. for 3.0 hrs. After the reaction was completed, the mixture was cooled to rt and diluted with 200 mL of EtOAc. The combined organic layers were washed with brine, dried over anhydrous $Na_2SO_4$ and concentrated in vacuo. The residue was purified by silica gel column chromatography (PE/EtOAc (v/v)=50/1) to give the title compound (9.0 g). The compound was characterized by the following spectroscopic data:

MS (ESI, pos.ion) m/z: 287.5 $[M+H]^+$; and $^1$H NMR (400 MHz, $CDCl_3$) δ (ppm): 8.32 (m, 1H), 7.77, 7.75 (m, m, 1H), 7.22, 7.20 (m, m, 1H), 4.50 (m, 2H), 4.42-4.36 (m, 2H), 1.42-1.38 (t, 3H, J=8.0 Hz).

Step 7) The Preparation of Compound 29-8

NaH (60%, 3.75 g, 93 mmol) was added to a stirred suspension of compound 29-7 (8.0 g, 27.8 mmol) in DMF (90 mL) at rt. After 15 mins, $CH_3I$ (22.2 g, 156 mmol) was added. At the end of the addition, the mixture was stirred at rt overnight. After the reaction was completed, the mixture was poured into ice water (200 mL) and EtOAc (200 mL). The organic layers were washed with water (200 mL×3) and brine (50 mL), dried over anhydrous $Na_2SO_4$ and concentrated in vacuo. The residue was purified by silica gel column chromatography (PE/EtOAc (v/v)=200/1) to give the title compound as a solid (7.0 g, 80%). The compound was characterized by the following spectroscopic data:

$^1$H NMR (400 MHz, $CDCl_3$) δ (ppm): 8.11-8.10 (m, 1H), 7.58 (m, 2H), 4.08-3.94 (m, 2H), 1.62 (s, 6H), 1.08-1.04 (t, 3H, J=8.0 Hz).

Step 8) The Preparation of Compound 29-9

To a solution of compound 29-8 (7.0 g, 22.1 mmol) in MeOH (80 mL) and THF (40 mL) was added KOH (2 M, 80 mL, 160 mmol). At the end of addition, the mixture was stirred at 80° C. for 5.0 hrs. After the reaction was completed, the mixture was concentrated in vacuo. The residue was diluted with water (50 mL), and washed with MTBE (50 mL). The aqueous layer was acidified to pH 2 by addition of hydrochloric acid (6 M), and then extracted with EtOAc (200 mL×3). The combined organic layers were washed with brine, dried over anhydrous $Na_2SO_4$ and concentrated in vacuo to give the title compound (5.0 g, 79%). The compound was characterized by the following spectroscopic data:

$^1$H NMR (400 MHz, $CDCl_3$) δ (ppm): 8.15 (m, 1H), 7.65, 7.62 (d, d, 1H), 7.59, 7.57 (d, d, 1H), 1.64 (s, 6H).

Step 9) The preparation of compound 29-10

Compound 29-9 (8.8 g, 30.5 mmol) was dissolved in DCM (200 mL) under $N_2$. After addition of triethylamine (4.01 g, 39.6 mmol), the mixture was stirred at rt for 15 mins. Diphenylphosphoryl azide (11 g, 40.0 mmol) was added and the reaction mixture was stirred at rt for 3.0 hrs. After removal of the volatiles in vacuo, the obtained residue was diluted with toluene (200 mL) and the mixture was refluxed for 2.0 hrs. The mixture was cooled to rt and hydrochloric acid (6 M, 100 mL) was added. The resulting solution was refluxed for 3.0 hrs. The crude mixture was concentrated in vacuo, diluted with ice water and basified with NaOH aqueous solution (5 M), extracted with EtOAc (150 mL×3). The combined organic layers were washed with brine, dried over anhydrous $Na_2SO_4$ and concentrated in vacuo. The residue was purified by silica gel column chromatography (PE/EtOAc (v/v)=10/1) to give the title compound (7.1 g, 89%). The compound was characterized by the following spectroscopic data:

$^1$H NMR (400 MHz, $CDCl_3$) δ (ppm): 7.90-7.89 (m, 1H), 7.57, 7.54 (d, d, 1H), 7.46, 7.44 (d, d, 1H), 1.84 (brs, 2H), 1.58 (s, 6H).

Step 10) The Preparation of Compound 29-11

To a solution of compound 1-12 (6.42 g, 29.8 mmol) in DCM (150 mL) were added HATU (20.6 g, 54.2 mmol) and triethylamine (8.22 g, 81.4 mmol) dropwise at rt in turn, the mixture was stirred at rt for 15 mins. Compound 29-10 (7.1 g, 27.4 mmol) was added. At the end of the addition, the mixture was stirred at rt for 1.0 hrs. After the reaction was completed, the mixture was diluted with 150 mL of water. The combined organic layers were washed with brine, dried over anhydrous $Na_2SO_4$ and concentrated in vacuo. The residue was purified by silica gel column chromatography (PE/EtOAc (v/v)=20/1) to give the title compound (8.98 g, 72%). The compound was characterized by the following spectroscopic data:

MS (ESI, pos.ion) m/z: 456.5 [M+H]$^+$; and $^1$H NMR (400 MHz, $CDCl_3$) δ (ppm): 8.08-8.07 (m, 1H), 7.65 (m, 2H), 6.40 (m, 1H), 4.19-4.15 (m, 1H), 3.52-3.46 (m, 1H), 3.35-3.28 (m, 1H), 2.28-2.09 (m, 2H), 1.93-1.72 (m, 2H), 1.68 (d, 6H), 1.40 (s, 9H).

Step 11) The Preparation of Compound 29-12

To a solution of compound 29-11 (8.9 g, 19.5 mmol) in MeOH (50 mL) was added Pt/C (1.0 g). The mixture was stirred at rt under 20 atm of $H_2$ gas overnight. After the reaction was completed, the mixture was filtered. The filtrate was concentrated in vacuo to give the title compound (8.29 g, 100%). The compound was characterized by the following spectroscopic data:

$^1$H NMR (400 MHz, $CDCl_3$) δ (ppm): 7.07, 7.05 (dd, dd, 1H), 7.04, 7.02 (dd, dd, 1H), 6.77 (q, 1H), 6.40 (m, 1H), 4.11-4.07 (m, 1H), 3.98 (brs, 2H), 3.52-3.46 (m, 1H), 3.35-3.28 (m, 1H), 2.28-2.09 (m, 2H), 1.93-1.73 (m, 2H), 1.69 (d, 6H), 1.40 (s, 9H).

Step 12) The Preparation of Compound 29-13

A solution of compound 29-12 (8.29 g, 19.5 mmol) in acetic acid glacial (100 mL) was stirred at 50° C. for 1.0 hrs. After the reaction was completed, the mixture was concentrated in vacuo. The residue was purified by silica gel column chromatography (PE/EtOAc (v/v)=7/1) to give the title compound (1.5 g, 19%). The compound was characterized by the following spectroscopic data:

MS (ESI, pos.ion) m/z: 408.1 [M+H]$^+$; and $^1$H NMR (400 MHz, $CDCl_3$) δ (ppm): 7.30-7.29, 7.27-7.26 (d, d, 1H), 7.24-7.22 (m, 1H), 6.84, 6.81 (d, d, 1H), 5.14 (brs, 1H), 4.81-4.77 (m, 1H), 3.52-3.46 (m, 1H), 3.41-3.34 (m, 1H), 2.52-2.45 (m, 1H), 2.18-2.09 (m, 1H), 1.95-1.86 (m, 1H), 1.85-1.75 (m, 1H), 1.65-1.64 (m, 3H), 1.62-1.61 (m, 3H), 1.42 (s, 9H).

Step 13) The Preparation of Compound 29-14

To a mixture of compound 29-13 (0.37 g, 0.91 mmol), compound 1-14-2 (0.46 g, 1.82 mmol), Pd(dppf)$Cl_2 \cdot CH_2Cl_2$ (71.0 mg, 0.09 mmol) and KOAc (0.27 g, 2.73 mmol) was added DMF (5.0 mL) via syringe under $N_2$, and the mixture was stirred at 90° C. for 3.0 hrs. After the reaction was completed, the mixture was diluted with EtOAc (60 mL). The resulting mixture was filtered through a celite pad. The filtrate was washed with water (20 mL×3) and brine, dried over anhydrous $Na_2SO_4$ and concentrated in vacuo. The residue was purified by silica gel column chromatography (PE/EtOAc (v/v)=1/1) to give the title compound (0.33 g, 80%). The compound was characterized by the following spectroscopic data:

MS (ESI, pos.ion) m/z: 456.5 [M+H]$^+$; and $^1$H NMR (400 MHz, $CDCl_3$) δ (ppm): 7.67, 7.65 (d, d, 1H), 7.48-7.47 (m, 1H), 7.26, 7.24 (d, d, 1H), 4.81-4.76 (m, 1H), 3.62-3.55 (m, 1H), 3.47-3.40 (m, 1H), 2.21-2.13 (m, 1H), 2.08-1.93 (m, 2H), 1.91-1.81 (m, 1H), 1.65-1.64 (m, 3H), 1.62-1.61 (m, 3H), 1.43 (s, 9H), 1.25-1.21 (m, m, 12H).

Step 14) The Preparation of Compound 29-15

To a mixture of compound 29-14 (0.28 g, 0.61 mmol), compound 29-4 (0.35 g, 0.61 mmol), Pd(PPh$_3$)$_4$ (35.26 mg, 0.03 mmol) and $K_2CO_3$ (0.25 g, 1.83 mmol) were added DME (5.0 mL) and $H_2O$ (1.0 mL) via syringe. The mixture was stirred at 90° C. under $N_2$ for 4.0 hrs. After the reaction was completed, the mixture was diluted with EtOAc (50 mL). The resulting mixture was washed with water (20 mL×3) and brine, dried over anhydrous $Na_2SO_4$ and concentrated in vacuo. The residue was purified by silica gel column chromatography (DCM/EtOAc (v/v)=80/1) to give the title compound (0.27 g, 60%). The compound was characterized by the following spectroscopic data:

MS (ESI, pos.ion) m/z: 745.5 [M+2H]; and $^1$H NMR (400 MHz, $CDCl_3$) δ (ppm): 7.63-7.62 (m, 1H), 7.56, 7.54 (d, d, 1H), 7.51, 7.49 (s, s, 1H), 7.48 (s, 1H), 7.30, 7.28 (t, t, 1H), 7.13, 7.11 (d, d, 1H), 5.18-5.14 (m, 1H), 4.81-4.76 (m, 1H), 4.58-4.54 (m, 1H), 3.82-3.66 (m, 4H), 3.62-3.55 (m, 1H), 3.47-3.40 (m, 1H), 3.38-3.30 (m, 1H), 3.23-3.16 (m, 1H), 3.08-3.06, 3.04-3.02 (m, m, H), 2.83-2.76 (m, 1H), 2.56-2.48 (m, 1H), 2.40-2.30 (m, 1H), 2.28-2.13 (m, 2H), 2.08-1.81 (m, 3H), 1.65-1.64 (m, 3H), 1.62-1.61 (m, 3H), 1.43 (s, 9H), 1.41 (s, 9H).

Step 15) The Preparation of Compound 29-16

To a solution of compound 29-15 (0.38 g, 0.51 mmol) in EtOAc (4 mL) was added a solution of HCl in EtOAc (3.0 mL, 4 M) dropwise. At the end of the addition, the mixture was stirred at rt for 8.0 hrs. After the reaction was completed, the mixture was concentrated in vacuo. The residue was purified by beating in EtOAc (10 mL) and filtered to give the title compound as pale yellow powder (0.28 g, 80%). The compound was characterized by the following spectroscopic data:

MS (ESI, pos.ion) m/z: 545.5 [M+H]$^+$.

Step 16) The Preparation of Compound 29-17

To a mixture of compound 29-16 (0.20 g, 0.29 mmol), compound 29-16-2 (0.14 g, 0.65 mmol), EDCI (0.12 g, 0.65 mmol) and HOAT (80 mg, 0.59 mmol) in DCM (5 mL) was added DIPEA (0.6 mL, 3.63 mmol) dropwise at 0° C. At the end of the addition, the mixture was stirred at rt for 3.0 hrs. After the reaction was completed, the mixture was diluted with DCM (20 mL). The organic layer was washed with saturated NH$_4$Cl aqueous solution and brine, dried over anhydrous Na$_2$SO$_4$ and concentrated in vacuo. The residue was purified by silica gel column chromatography (DCM/MeOH (v/v)=40/1) to give the title compound as white powder (0.18 g, 65%). The compound was characterized by the following spectroscopic data:

MS (ESI, pos.ion) m/z: 470.5 [M+2H]$^{2+}$; and $^1$H NMR (400 MHz, CDCl$_3$) δ (ppm): 7.63-7.62 (m, 1H), 7.51, 7.49 (s, s, 1H), 7.47, 7.45 (d, d, 1H), 7.46 (s, 1H), 7.30, 7.28 (t, t, 1H), 7.13, 7.11 (d, d, 1H), 5.28-5.24 (m, 1H), 5.21, 5.19 (d, d, 2H), 4.79-4.74 (m, 1H), 4.58-4.54 (m, 1H), 4.47-4.41 (m, 1H), 4.38-4.32 (m, 1H), 3.91-3.84 (m, 1H), 3.82-3.67 (m, 2H), 3.63 (s, 6H), 3.48-3.41 (m, 1H), 3.39-3.32 (m, 1H), 3.23-3.20, 3.18-3.16 (m, m, 1H), 3.08-3.06, 3.04-3.02 (m, 2H), 2.83-2.76 (m, 1H), 2.34-1.79 (m, 10H), 1.72-1.51 (m, 16H), 1.40-1.03 (m, 10H).

Example 30

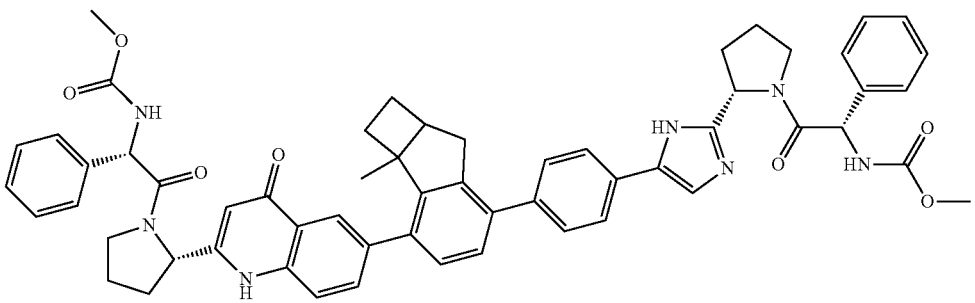 [SMILES: COC(=O)N[C@H](C(=O)N1CCC[C@H]1c1cc(=O)c2cc(-c3ccc(-c4ccc(-c5cnc([C@@H]6CCCN6C(=O)[C@@H](NC(=O)OC)c6ccccc6)[nH]5)cc4)c4c3C3(C)CCC3C4)ccc2[nH]1)c1ccccc1]

Synthetic Route:

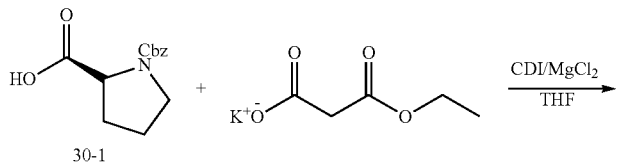

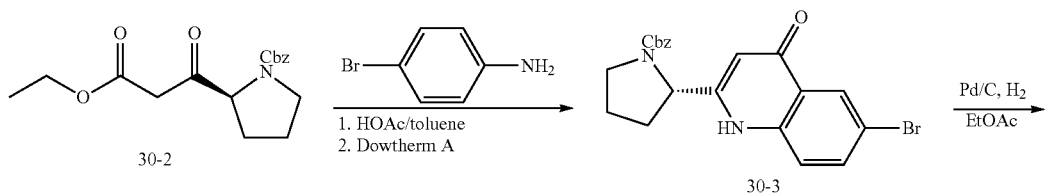

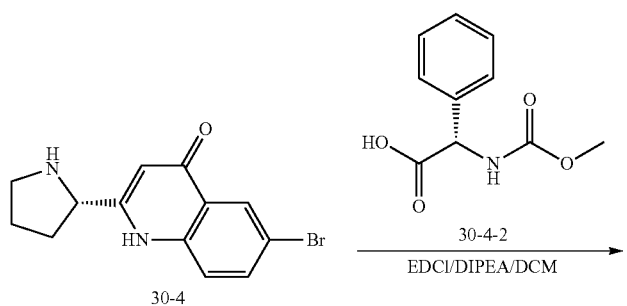

-continued
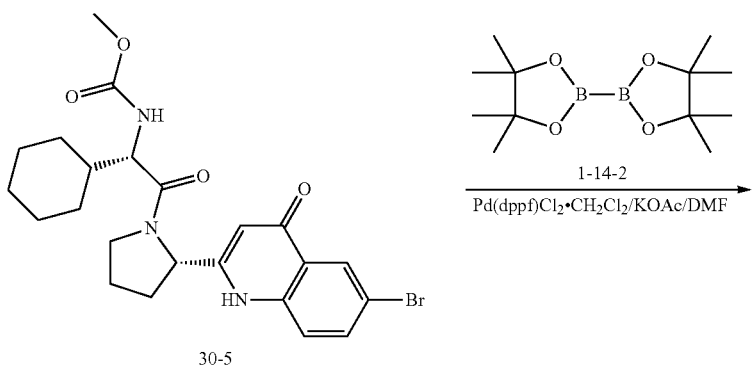
30-5
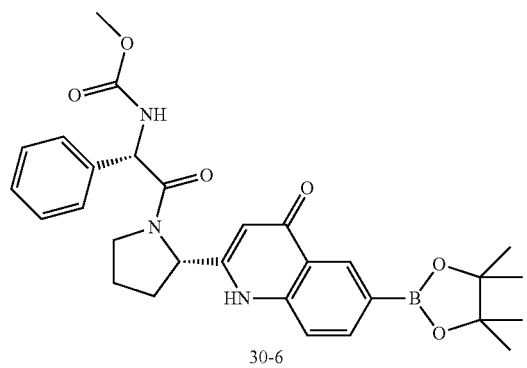
30-6
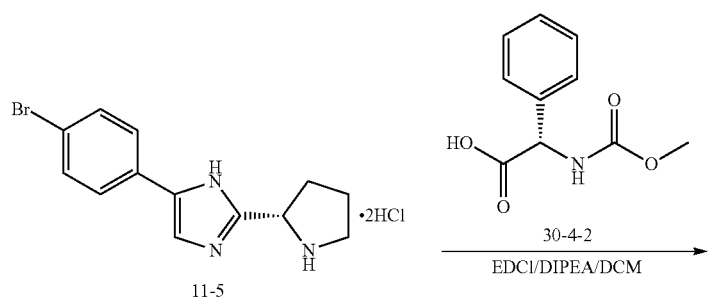
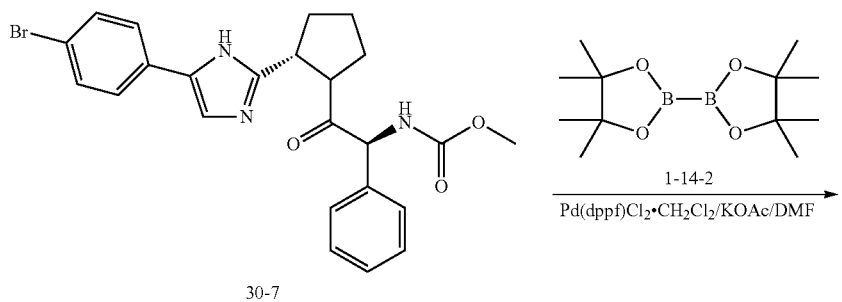
30-7
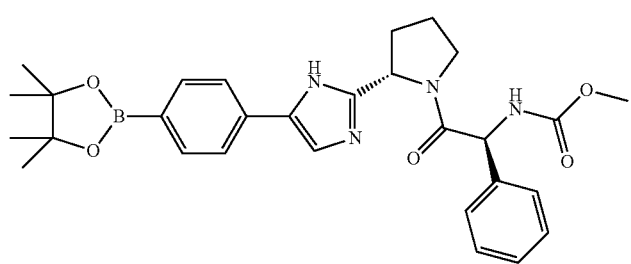
30-8

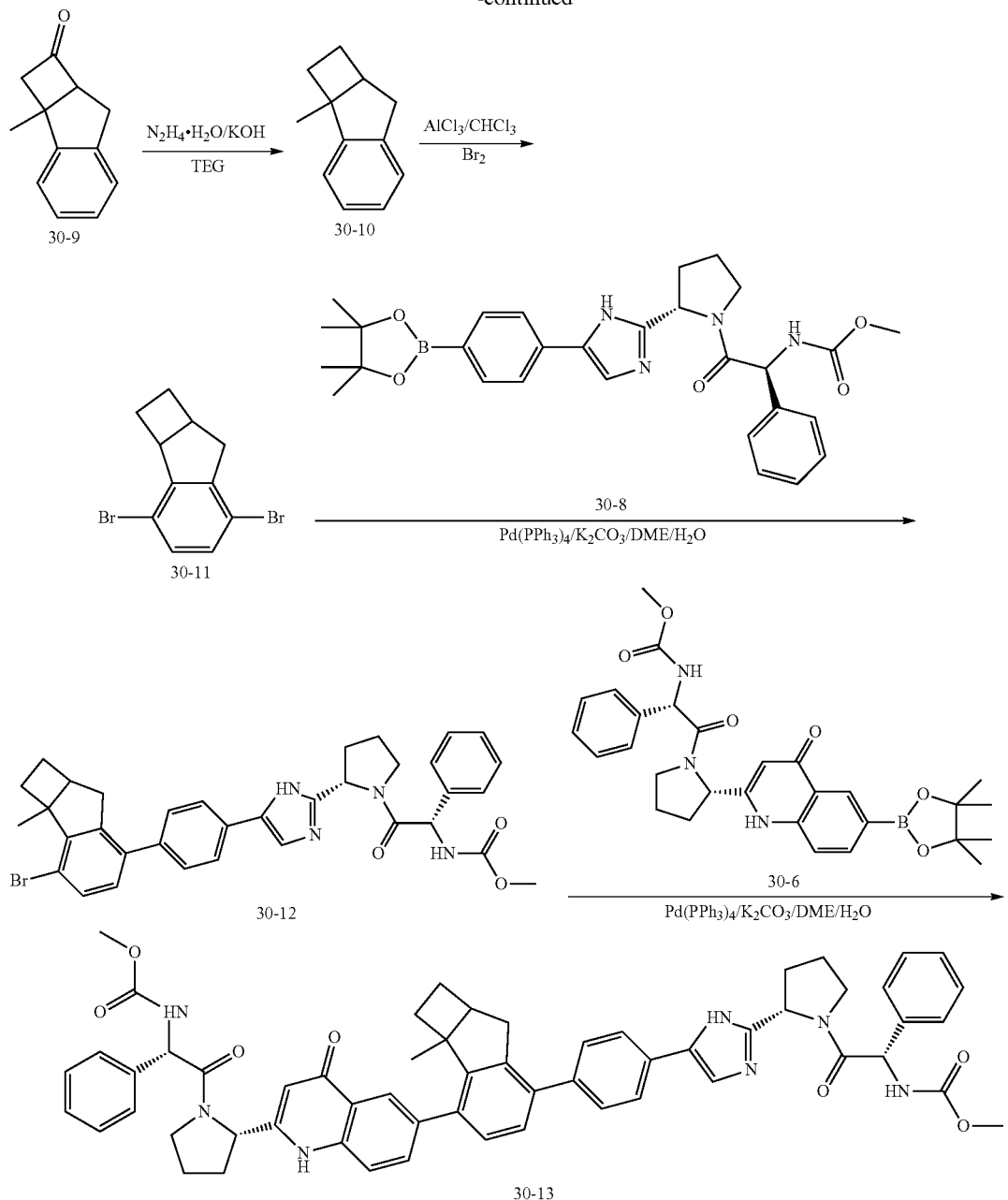

Step 1) The Preparation of Compound 30-2

MgCl$_2$ (1.53 g, 16.4 mmol) was added in one portion to a solution of ethyl potassium malonate (3.55 g, 20.85 mmol) in THF (25 mL). The reaction mixture was stirred at 70° C. for 7.0 hrs and then further stirred at 30° C. overnight. A solution of compound 30-1 (4.0 g, 16.06 mmol) in THF (10 mL) was slowly added to a mixture of CDI (3.12 g, 19.248 mmol) in THF (15 mL) and the mixture was stirred at 30° C. for 2.0 hrs. The solution was added to the ethyl potassium malonate at 30° C. At the end of the addition, the mixture was stirred overnight at 30° C. The mixture was cooled to 20° C. and neutralized with diluted hydrochloric acid (4 M). The solution was concentrated and the product was dissolved in EtOAc (50 mL) and washed with 5% aqueous sodium bicarbonate and brine. The organic layer was concentrated and the residue was purified by silica gel column chromatography (PE/EtOAc (v/v)=20/1) to give the title compound (4.6 g, 90%). The compound was characterized by the following spectroscopic data:

MS (ESI, pos.ion) m/z: 320.5 [M+H]$^+$; and $^1$H NMR (400 MHz, CDCl$_3$) δ (ppm): 7.19-7.18 (m, 5H), 5.13-5.12 (m, 2H), 4.23, 4.21, 4.19, 4.18 (s, s, s, s, 2H), 4.03-3.97 (m, 1H), 3.59, 3.58 (s, s, 2H), 3.50-3.43 (m, 1H), 3.32-3.23 (m, 1H), 2.08-1.93 (m, 2H), 1.82-1.70 (m, 2H), 1.29-1.25 (t, 3H, J=8.0 Hz).

Step 2) The Preparation of Compound 30-3

To a solution of compound 30-2 (1.0 g, 3.13 mmol) and acetic acid glacial (0.17 mL, 3.13 mmol) in toluene (10 mL) was added 4-bromoaniline (0.4 g, 2.35 mmol). At the end of the addition, the mixture was refluxed for 6.0 hrs. After the reaction was completed, the solvent was removed. The residue was dissolved in DOWTHERM A (5.0 mL) and then stirred at 235° C. for 1.5 hrs. After the reaction was completed, the mixture was cooled to rt, and diethyl ether (8.0 mL) followed by heptane (5.0 mL) was added. An oily residue precipitated and the solvent was decanted. The residue was purified by silica gel column chromatography (DCM/EtOAc (v/v)=1/1) to give the title compound (0.15 g, 11%). The compound was characterized by the following spectroscopic data:

MS (ESI, pos.ion) m/z: 427.5 [M+H]$^+$; and $^1$H NMR (400 MHz, CDCl$_3$) δ (ppm): 8.13-8.12 (m, 1H), 7.60, 7.58 (dd, dd, 1H), 7.45, 7.43 (dd, dd, 1H), 7.28-7.22 (m, 5H), 6.58 (t, 1H), 5.14-5.13 (m, 2H), 4.98-4.94 (m, 1H), 3.64-3.57 (m, 1H), 3.43-3.36 (m, 1H), 2.26-2.17 (m, 1H), 2.09-1.83 (m, 3H).

Step 3) The Preparation of Compound 30-4

To a solution of compound 30-3 (2.13 g, 5.0 mmol) in EtOAc (40 mL) was added Pd/C (0.2 g). The mixture was stirred at 40° C. under 10 atm of H$_2$ gas for 5.0 hrs. After the reaction was completed, the mixture was filtered. The filtrate was concentrated in vacuo to give the title compound (1.24 g, 85%). The compound was characterized by the following spectroscopic data:

MS (ESI, pos.ion) m/z: 293.5 [M+H]$^+$.

Step 4) The Preparation of Compound 30-5

To a solution of compound 30-4 (2.92 g, 10.0 mmol), compound 30-4-2 (2.3 g, 11.0 mmol) and EDCI (2.10 g, 11.0 mmol) in DCM (30 mL) was added DIPEA (6.6 mL, 39.9 mmol) dropwise at 0° C. At the end of the addition, the mixture was stirred at rt for 3.0 hrs. After the reaction was completed, the mixture was diluted with DCM (100 mL). The combined organic layers were washed with NH$_4$Cl aqueous solution and brine, dried over anhydrous Na$_2$SO$_4$ and concentrated in vacuo. The residue was purified by silica gel column chromatography (PE/EtOAc (v/v)=2/1) to give the title compound (2.91 g, 60%). The compound was characterized by the following spectroscopic data:

MS (ESI, pos.ion) m/z: 484.5 [M+H]$^+$; and $^1$H NMR (400 MHz, CDCl$_3$) δ (ppm): 8.13-8.12 (m, 1H), 7.60, 7.58 (d, d, 1H), 7.45, 7.43 (d, d, 1H), 7.35-7.27 (m, 3H), 7.19-7.13 (m, 2H), 6.61 (m, 1H), 5.91, 5.89 (s, s, 1H), 5.26-5.18 (m, 2H), 3.67-3.65 (m, 1H), 3.64 (s, 3H), 3.43-3.36 (m, 1H), 2.29-2.22 (m, 1H), 2.03-1.76 (m, 3H).

Step 5) The Preparation of Compound 30-6

To a mixture of compound 30-5 (0.44 g, 0.91 mmol), compound 1-14-2 (0.46 g, 1.82 mmol), Pd(dppf)Cl$_2$·CH$_2$Cl$_2$ (71.0 mg, 0.09 mmol) and KOAc (0.27 g, 2.73 mmol) was added DMF (5.0 mL) via syringe under N$_2$, and the mixture was stirred at 90° C. for 3.0 hrs. After the reaction was completed, the mixture was diluted with EtOAc (60 mL), and filtered through a celite pad. The filtrate was washed with water (20 mL×3) and brine, dried over anhydrous Na$_2$SO$_4$ and concentrated in vacuo. The residue was purified by silica gel column chromatography (PE/EtOAc (v/v)=1/1) to give the title compound (0.41 g, 85%). The compound was characterized by the following spectroscopic data:

MS (ESI, pos.ion) m/z: 532.5 [M+H]$^+$; and $^1$H NMR (400 MHz, CDCl$_3$) δ (ppm): 8.48, 8.47 (m, m, 1H), 7.99, 7.97 (d, d, 1H), 7.47, 7.45 (d, d, 1H), 7.35-7.27 (m, 3H), 7.19-7.14 (m, 2H), 6.73-6.72 (m, 1H), 5.91, 5.89 (s, s, 1H), 5.26-5.18 (m, 2H), 3.67-3.65 (m, 1H), 3.64 (s, 3H), 3.43-3.36 (m, 1H), 2.29-2.22 (m, 1H), 2.03-1.76 (m, 3H), 1.24, 1.20 (m, m, 12H).

Step 6) The Preparation of Compound 30-7

To a solution of compound 11-5 (7.03 g, 19.26 mmol), compound 30-4-2 (6.04 g, 28.88 mmol) and EDCI (5.56 g, 28.88 mmol) in DCM (100 mL) was added DIPEA (21 mL, 127 mmol) dropwise at 0° C. At the end of the addition, the mixture was stirred at rt for 3.0 hrs. After the reaction was completed, the mixture was diluted with water (100 mL) and extracted with DCM (100 mL×3). The combined organic layers were washed with brine, dried over anhydrous Na$_2$SO$_4$ and concentrated in vacuo. The residue was purified by silica gel column chromatography (PE/EtOAc (v/v)=1/2) to give the title compound as a solid (7.44 g, 80%). The compound was characterized by the following spectroscopic data:

MS (ESI, pos.ion) m/z: 483.5 [M+H]$^+$; and $^1$H NMR (400 MHz, CDCl$_3$) δ (ppm): 7.45-7.41 (m, 2H), 7.35-7.26 (m, 6H), 7.20-7.15 (m, 2H), 5.91, 5.89 (s, s, 1H), 5.35-5.34, 5.33-5.32 (m, m, 1H), 5.18-5.13 (m, 1H), 3.91-3.84 (m, 1H), 3.75-3.67 (m, 1H), 3.64 (s, 3H), 2.34-2.08 (m, 3H), 2.03-1.93 (m, 1H).

Step 7) The Preparation of Compound 30-8

To a mixture of compound 30-7 (5.38 g, 11.13 mmol), compound 1-14-2 (4.3 g, 16.7 mmol), Pd(dppf)Cl$_2$·CH$_2$Cl$_2$ (0.91 g, 1.11 mmol) and KOAc (3.3 g, 33.4 mmol) was added DMF (50 mL) via syringe under N$_2$, and the mixture was stirred at 90° C. for 3.0 hrs. After the reaction was completed, the mixture was cooled to rt, diluted with EtOAc (200 mL) and filtered through a celite pad. The filtrate was washed with water (100 mL×3) and brine, dried over anhydrous Na$_2$SO$_4$ and concentrated in vacuo. The residue was purified by silica gel column chromatography (PE/EtOAc (v/v)=1/2) to give the title compound as a beige solid (4.13 g, 70%). The compound was characterized by the following spectroscopic data:

$^1$H NMR (400 MHz, CDCl$_3$) δ (ppm): 7.64-7.57 (m, 4H), 7.35-7.27 (m, 3H), 7.23 (s, 1H), 7.20-7.15 (m, 2H), 5.91, 5.89 (s, s, 1H), 5.35-5.34, 5.33-5.32 (m, m, 1H), 5.18-5.13 (m, 1H), 3.91-3.84 (m, 1H), 3.75-3.67 (m, 1H), 3.64 (s, 3H), 2.34-2.08 (m, 3H), 2.03-1.93 (m, 1H), 1.35, 1.32 (m, m, 12H).

Step 8) The Preparation of Compound 30-10

To a solution of compound 30-9 (2.1 g, 12.2 mmol) in TEG (30 mL) were added KOH (2.1 g, 36.7 mmol) and hydrazine hydrate (4.8 mL, 97.8 mmol) in turn. After the mixture was stirred at 130° C. for 20 mins, a Dean-Stark trap was added, and then the mixture was stirred at 200° C. for 50 mins. After the reaction was completed, the mixture was cooled to rt and 100 mL of water was added. The aqueous layer was extracted with PE (150 mL×3). The combined organic layers were washed with brine, dried over anhydrous Na$_2$SO$_4$ and concentrated in vacuo. The residue was purified by silica gel column chromatography (PE) to give the title compound as colorless oil (1.16 g, 60%). The compound was characterized by the following spectroscopic data:

MS (ESI, pos.ion) m/z: 159.5 [M+H]$^+$; and $^1$H NMR (400 MHz, CDCl$_3$) δ (ppm): 7.27, 7.24 (m, m, 1H), 7.22, 7.20 (m, m, 1H), 7.13, 7.10, 7.08 (m, m, m, 1H), 7.07-7.03 (m, 1H), 3.08-3.02 (m, 1H), 2.74-2.64 (m, 1H), 2.62-2.55 (m, 1H), 2.34-2.17 (m, 2H), 2.12-2.03 (m, 1H), 1.59-1.50 (m, 1H), 1.31-1.30 (q, 3H).

Step 9) The Preparation of Compound 30-11

To a suspension of AlCl$_3$ (3.02 g, 22.6 mmol) in CHCl$_3$ (30 mL) was added a solution of compound 30-10 (1.58 g, 10 mmol) in CHCl$_3$ (20 mL) dropwise at 0 OC. After the mixture was stirred at rt for 1.0 hr, Br$_2$ (1.03 mL, 20 mmol) in CHCl$_3$ (10 mL) was added dropwise. At the end of the addition, the mixture was stirred at rt overnight. After the reaction was completed, the mixture was poured slowly into ice water (100 mL). The aqueous layer was extracted with DCM (50 mL×3). The combined organic layers were washed with NaHCO₃ aqueous solution and brine, dried over anhydrous Na₂SO₄ and concentrated in vacuo. The compound was characterized by the following spectroscopic data:

MS (ESI, pos.ion) m/z: 315.5 [M+H]⁺; and

¹H NMR (400 MHz, CDCl₃) δ (ppm): 7.28, 7.26 (s, s, 1H), 7.04, 7.02 (t, t, 1H), 2.96-2.89 (m, 1H), 2.82-2.72 (m, 1H), 2.49-2.30 (m, 3H), 2.21-2.12 (m, 1H), 1.68-1.59 (m, 1H), 1.40 (q, 3H).

Step 10) The Preparation of Compound 30-12

A mixture of compound 30-11 (0.16 g, 0.522 mmol), compound 30-8 (0.28 g, 0.522 mmol), Pd(PPh₃)₄ (60.29 mg, 0.0522 mmol) and K₂CO₃ (0.22 g, 1.566 mmol) in mixed solvents of DME and H₂O (8 mL, v/v=3/1) was stirred at 90° C. under N₂ for 3.0 hrs. After the reaction was completed, the mixture was cooled to rt and diluted with EtOAc (40 mL). The resulting mixture was washed with water (20 mL×3) and brine, dried over anhydrous Na₂SO₄ and concentrated in vacuo. The residue was purified by silica gel column chromatography (DCM/EtOH (v/v)=150/1) to give the title compound as a pale yellow solid (0.16 g, 50%). The compound was characterized by the following spectroscopic data:

MS (ESI, pos.ion) m/z: 639.5 [M+H]⁺; and

¹H NMR (400 MHz, CDCl₃) δ (ppm): 7.66-7.63 (m, 2H), 7.59 (s, 1H), 7.52-7.48 (m, 3H), 7.43, 7.41 (s, s, 1H), 7.35-7.27 (m, 3H), 7.20-7.15 (m, 2H), 5.91, 5.89 (s, s, 1H), 5.35-5.34, 5.33-5.32 (m, m, 1H), 5.18-5.13 (m, 1H), 3.91-3.84 (m, 1H), 3.75-3.67 (m, 1H), 3.64 (s, 3H), 2.85-2.79 (m, 1H), 2.78-2.68 (m, 1H), 2.49-2.08 (m, 7H), 2.01-1.93 (m, 1H), 1.64-1.55 (m, 1H), 1.38-1.37 (q, 3H).

Step 11) The Preparation of Compound 30-13

A suspension of compound 30-12 (0.33 g, 0.522 mmol), compound 30-6 (0.28 g, 0.522 mmol), Pd(PPh₃)₄ (60.29 mg, 0.0522 mmol) and K₂CO₃ (0.22 g, 1.566 mmol) in mixed solvents of DME and H₂O (8 mL, v/v=3/1) was stirred at 90° C. under N₂ for 3.0 hrs. After the reaction cooling to rt, the mixture was diluted with EtOAc (40 mL). The resulting mixture was washed with water (20 mL×3) and brine, dried over anhydrous Na₂SO₄ and concentrated in vacuo. The residue was purified by silica gel column chromatography (DCM/EtOH (v/v)=50/1) to give the title compound as a pale yellow solid (0.28 g, 55%). The compound was characterized by the following spectroscopic data:

MS (ESI, pos.ion) m/z: 482.7 [M+2H]²⁺; and

¹H NMR (400 MHz, CDCl₃) δ (ppm): 8.05-8.04 (m, 1H), 7.71, 7.69 (d, d, 1H), 7.66-7.58 (m, 5H), 7.51-7.46 (m, 3H), 7.35-7.27 (m, 6H), 7.19-7.14 (m, 4H), 6.97-6.96 (m, 1H), 5.91, 5.89 (s, s, 2H), 5.35-5.34, 5.33-5.32 (m, m, 1H), 5.26-5.13 (m, 3H), 3.91-3.84 (m, 1H), 3.75-3.67 (m, 2H), 3.64 (s, 6H), 3.43-3.36 (m, 1H), 2.92-2.81 (m, 2H), 2.44-1.76 (m, 11H), 1.60-1.52 (m, 2H), 1.37-1.36 (m, 3H).

Example 31

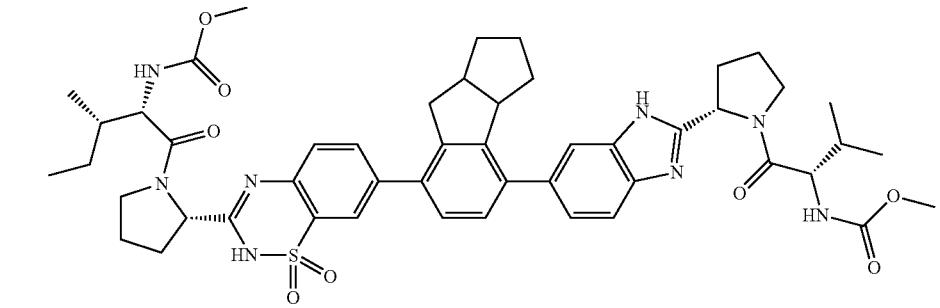 [SMILES: CC[C@H](C)[C@H](NC(=O)OC)C(=O)N1CCC[C@H]1C1=Nc2ccc(-c3ccc(-c4ccc5nc([C@@H]6CCCN6C(=O)[C@@H](NC(=O)OC)C(C)C)[nH]c5c4)c4c3CC3CCCC43)cc2S(=O)(=O)N1]

Synthetic Route:

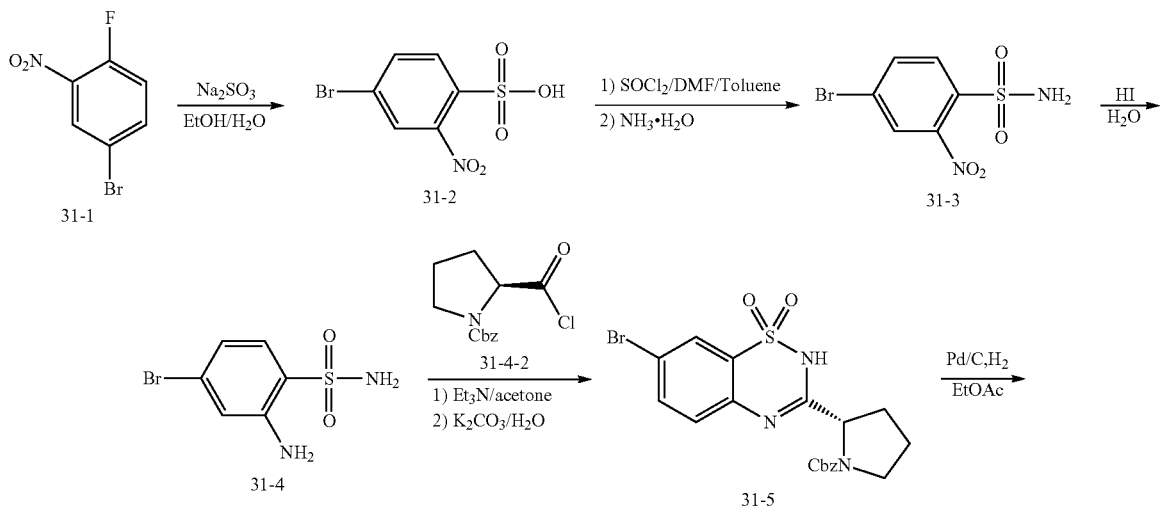

-continued
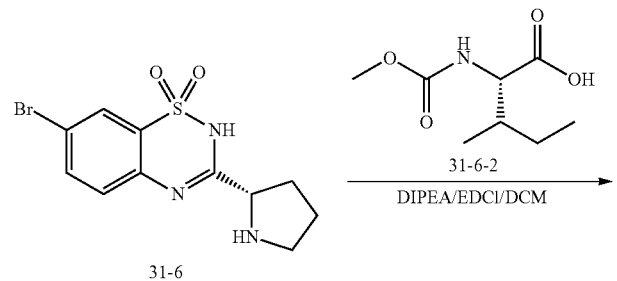
31-6
31-6-2
DIPEA/EDCl/DCM
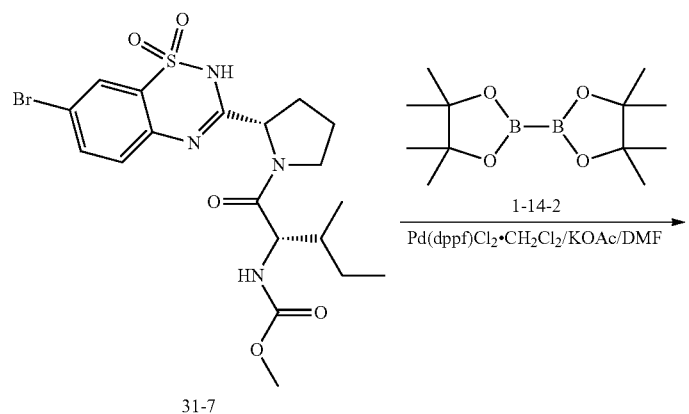
31-7
1-14-2
Pd(dppf)Cl$_2$·CH$_2$Cl$_2$/KOAc/DMF
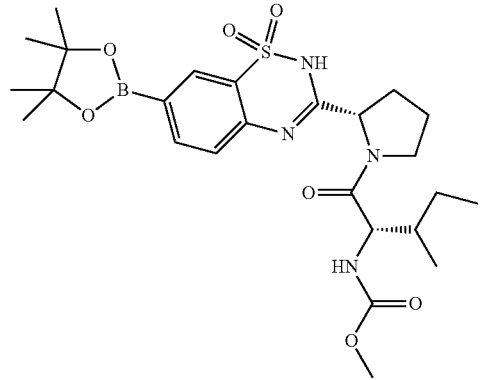
31-8
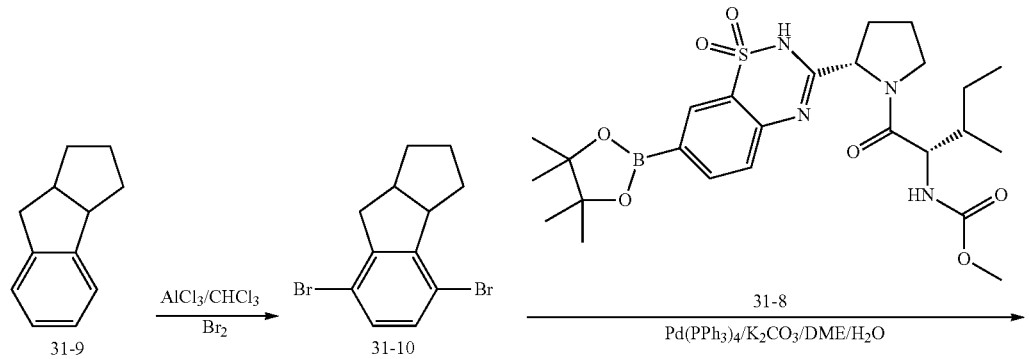
31-9
AlCl$_3$/CHCl$_3$
Br$_2$
31-10
31-8
Pd(PPh$_3$)$_4$/K$_2$CO$_3$/DME/H$_2$O

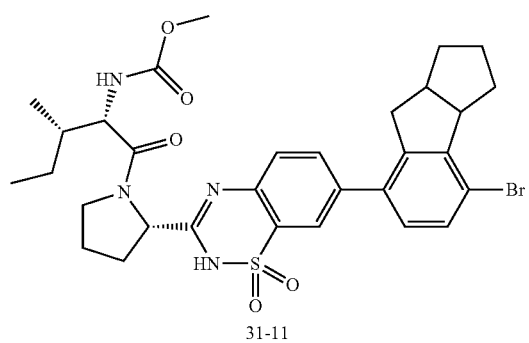

31-11

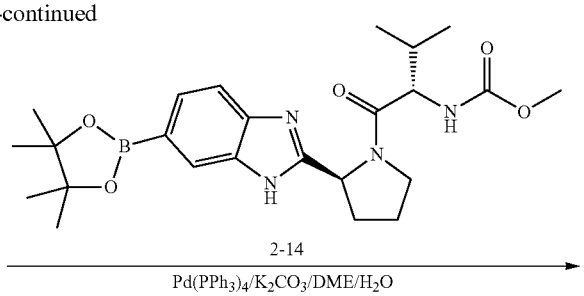

2-14

Pd(PPh₃)₄/K₂CO₃/DME/H₂O

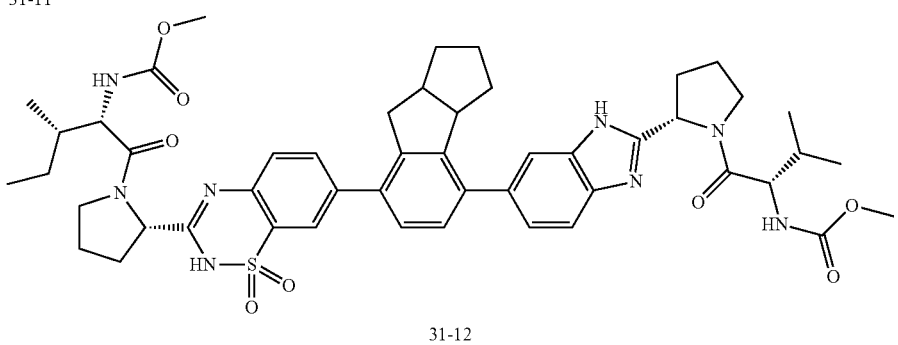

31-12

Step 1) The Preparation of Compound 31-2

To a solution of compound 31-1 (5.0 g, 22.7 mmol) in EtOH (60 mL) were added a suspension of Na₂SO₃ (7.16 g, 56.8 mmol) in EtOH (100 mL) and water (125 mL). At the end of the addition, the suspension was stirred at 70° C. for 15.0 hrs. After the reaction was completed, the mixture was cooled to rt, and the reaction was acidified with hydrochloric acid (2 M) to pH=2, and then concentrated in vacuo. The residue was dissolved under reflux in brine (100 mL). Subsequently, water (10 mL) was added and the solution was cooled in an ice bath. The precipitate was collected by filtration resulting in compound 31-2 (5.70 g, 89%). The compound was characterized by the following spectroscopic data:

MS (ESI, pos.ion) m/z: 282.5 [M+H]⁺; and

¹H NMR (400 MHz, CDCl₃) δ (ppm): 8.75 (br, 1H), 8.31 (m, 1H), 8.07 (m, 2H).

Step 2) The Preparation of Compound 31-3

To a solution of compound 31-2 (3.0 g, 10.6 mmol) in toluene (50 mL) and DMF (1 drop) was added thionyl chloride (5.0 mL). At the end of the addition, the reaction was refluxed for 4.0 hrs. After the reaction was completed, the mixture was cooled and concentrated in vacuo. The residue was dissolved in toluene (4 mL), and then to the resulting mixture was added a mixture of concentrated aqueous ammonium hydroxide solution (1 mL) and THF (10 mL) at −10° C. After stirring for 2.0 hrs, the reaction was quenched by adding a solution of hydrochloric acid (6 M) until pH=4. The organic layers were separated and then dried over anhydrous Na₂SO₄ and concentrated in vacuo. PE (15.0 mL) was added to the resulting slurry and the product was collected by vacuum filtration to afford compound 31-3. The compound was characterized by the following spectroscopic data:

MS (ESI, pos.ion) m/z: 281.5 [M+H]⁺; and

¹H NMR (400 MHz, CDCl₃) δ (ppm): 8.18, 8.17 (d, d, 1H), 8.03, 8.00 (d, d, 1H), 7.84, 7.81 (d, d, 1H), 5.47 (br, 2H).

Step 3) The Preparation of Compound 31-4

A suspension of compound 31-3 (2.12 g, 7.5 mmol) in HI (25 mL, 57% in water) was stirred at 90° C. for 4.0 hrs. After cooling to rt, the dark purple mixture was diluted with EtOAc (50 mL) and washed successively with saturated Na₂S₂O₃ aqueous solution, saturated NaHCO₃ aqueous solution and brine. The colorless organic layers were dried over anhydrous Na₂SO₄ and concentrated in vacuo. The crude product was purified by high-performance liquid chromatography (eluent: CH₃CN/H₂O from 22/78 to 52/48 with 0.01% NH₃·H₂O as buffer) resulting in compound 31-4 (1.86 g). The compound was characterized by the following spectroscopic data:

MS (ESI, pos.ion) m/z: 251.5 [M+H]⁺; and

¹H NMR (400 MHz, CDCl₃) δ (ppm): 7.62-7.60 (m, 1H), 7.18-7.15 (m, 2H), 4.85 (brs, 4H).

Step 4) The Preparation of Compound 31-5

To a solution of compound 31-4 (1.86 g, 7.4 mmol) in acetone (20 mL) was added triethylamine (4.05 mL, 29.6 mmol). Compound 31-4-2 (1.28 g, 4.8 mmol) was added to the reaction at 0° C. After stirring for 5.0 hrs, the mixture was diluted with water (10 mL) and acidified by hydrochloric acid (2 M) to pH 4. The resulting precipitate was collected by filtration and then transferred to another flask. A solution of K₂CO₃ (1.5 g, 10.87 mmol) in water (10.0 mL) was added, and the mixture was refluxed for 2.0 hrs until the reaction became homogeneous. The reaction was acidified by hydrochloric acid (2 M) until pH=4. The precipitate was filtered off and washed with water. The crude product was purified by high-performance liquid chromatography (eluent: CH₃CN/H₂O from 35/65 to 65/35 with 0.75% CF₃COOH as buffer) resulting in compound (1.00 g, 45%). The compound was characterized by the following spectroscopic data:

MS (ESI, pos.ion) m/z: 464.5 [M+H]⁺; and

¹H NMR (400 MHz, CDCl₃) δ (ppm): 7.93, 7.90 (d, d, 1H), 7.77-7.76 (m, 1H), 7.43, 7.41 (d, d, 1H), 7.28-7.22 (m, 5H), 6.30 (brs, 1H), 5.14-5.13 (m, 2H), 4.86-4.80 (m, 1H), 3.68-3.62 (m, 1H), 3.50-3.43 (m, 1H), 2.22-1.98 (m, 4H).

Step 5) The Preparation of Compound 31-6

To a solution of compound 31-5 (3.73 g, 8.03 mmol) in EtOAc (40 mL) was added a catalytic amount of Pd/C (0.35 g), and the mixture was stirred at 40° C. under 10 atm of $H_2$ gas for 5.0 hrs. After the reaction was completed, the mixture was filtered, and the filtrate was concentrated in vacuo to give the title compound (2.27 g, 86%). The compound was characterized by the following spectroscopic data:

MS (ESI, pos.ion) m/z: 330.5 $[M+H]^+$.

Step 6) The Preparation of Compound 31-7

To a suspension of compound 31-6 (3.29 g, 10.0 mmol), compound 31-6-2 (2.08 g, 11.0 mmol) and EDCI (2.10 g, 11.0 mmol) in DCM (30.0 mL) was added DIPEA (6.6 mL, 39.9 mmol) dropwise at 0° C. At the end of the addition, the mixture was stirred at rt for 3.0 hrs. After the reaction was completed, the mixture was diluted with DCM (50 mL). The resulting mixture was washed successively with water (30 mL×3), saturated $NH_4Cl$ aqueous solution and brine, dried over $Na_2SO_4$ and concentrated in vacuo. The residue was purified by silica gel column chromatography (PE/EtOAc (v/v)=2/1) to give the title compound (2.50 g, 50%). The compound was characterized by the following spectroscopic data:

MS (ESI, pos.ion) m/z: 501.5 $[M+H]^+$; and $^1$H NMR (400 MHz, $CDCl_3$) δ (ppm): 7.92, 7.90 (d, d, 1H), 7.77-7.76 (m, 1H), 7.43, 7.41 (d, d, 1H), 5.31, 5.28 (d, d, 1H), 5.00-4.96 (m, 1H), 4.37-4.31 (m, 1H), 3.63 (s, 3H), 3.62-3.56 (m, 1H), 3.24-3.17 (m, 1H), 2.36-2.29 (m, 1H), 2.06-1.97 (m, 1H), 1.92-1.72 (m, 3H), 1.61-1.50 (m, 1H), 1.26-1.12 (m, 1H), 0.94-0.90 (m, 3H), 0.88-0.86 (m, 3H).

Step 7) The Preparation of Compound 31-8

A mixture of compound 31-7 (0.46 g, 0.91 mmol), compound 1-14-2 (0.46 g, 1.82 mmol), $Pd(dppf)Cl_2 \cdot CH_2Cl_2$ (71.0 mg, 0.09 mmol) and KOAc (0.27 g, 2.73 mmol) in DMF (5.0 mL) was stirred at 90° C. under $N_2$ for 3.0 hrs. After cooling to room temperature, the mixture was diluted with EtOAc (50.0 mL) and filtered through a celite pad. The filtrate was washed with water (20.0 mL×3) and brine, dried over anhydrous $Na_2SO_4$ and concentrated in vacuo. The residue was purified by silica gel column chromatography (PE/EtOAc (v/v)=2/1) to give the title compound (0.44 g, 88%). The compound was characterized by the following spectroscopic data:

MS (ESI, pos.ion) m/z: 549.5 $[M+H]^+$; and $^1$H NMR (400 MHz, $CDCl_3$) δ (ppm): 8.02 (q, 1H), 7.79, 7.77 (d, d, 1H), 7.46, 7.44 (d, d, 1H), 5.39, 5.36 (d, d, 1H), 5.00-4.96 (m, 1H), 4.35-4.31 (m, 1H), 3.63 (s, 3H), 3.62-3.56 (m, 1H), 3.24-3.17 (m, 1H), 2.36-2.29 (m, 1H), 2.10-1.97 (m, 2H), 1.92-1.84 (m, 1H), 1.82-1.72 (m, 1H), 1.61-1.51 (m, 1H), 1.32, 1.29 (t, t, 12H), 1.25-1.12 (m, 1H), 1.00-0.98 (m, 3H), 0.92-0.88 (m, 3H).

Step 8) The Preparation of Compound 31-10

To a suspension of $AlCl_3$ (3.02 g, 22.6 mmol) in $CHCl_3$ (30 mL) was added a solution of compound 31-9 (1.58 g, 10 mmol) in $CHCl_3$ (20 mL) dropwise at 0 OC. After the mixture was stirred at rt for 1.0 hr, a solution of $Br_2$ (1.03 mL, 20 mmol) in $CHCl_3$ (10 mL) was added dropwise. At the end of the addition, the mixture was stirred at rt overnight. After the reaction was completed, the mixture was poured slowly into ice water (100 mL). The aqueous layer was extracted with DCM (50 mL×3). The combined organic layers were washed with $NaHCO_3$ aqueous solution and brine, dried over anhydrous $Na_2SO_4$ and concentrated in vacuo. The compound was characterized by the following spectroscopic data:

MS (ESI, pos.ion) m/z: 315.5 $[M+H]^+$; and $^1$H NMR (400 MHz, $CDCl_3$) δ (ppm): 7.26, 7.24 (s, s, 1H), 7.17, 7.14 (t, t, 1H), 3.62-3.53 (m, 1H), 3.04-2.96 (m, 1H), 2.74-2.61 (m, 1H), 2.58-2.50 (m, 1H), 2.10-2.01 (m, 1H), 1.94-1.83 (m, 2H), 1.75-1.57 (m, 2H), 1.52-1.40 (m, 1H).

Step 9) The Preparation of Compound 31-11

A mixture of compound 31-10 (0.16 g, 0.522 mmol), compound 31-8 (0.29 g, 0.522 mmol), $Pd(PPh_3)_4$ (60.29 mg, 0.0522 mmol) and $K_2CO_3$ (0.22 g, 1.566 mmol) in mixed solvents of DME and $H_2O$ (8 mL, v/v=3/1) was stirred at 90° C. under $N_2$ for 3.0 hrs. After the reaction was completed, the mixture was cooled to rt and diluted with EtOAc (40 mL). The resulting mixture was washed with water (20 mL×3) and brine, dried over anhydrous $Na_2SO_4$ and concentrated in vacuo. The residue was purified by silica gel column chromatography (DCM/EtOH (v/v)=150/1) to give the title compound as a pale yellow solid (0.17 g, 50%). The compound was characterized by the following spectroscopic data:

MS (ESI, pos.ion) m/z: 657.5 $[M+H]^+$; and $^1$H NMR (400 MHz, $CDCl_3$) δ (ppm): 7.86-7.85 (q, 1H), 7.80, 7.78 (d, d, 1H), 7.59, 7.57 (t, t, 1H), 7.51, 7.49 (s, s, 1H), 7.41, 7.38 (d, d, 1H), 6.51, 6.49 (d, d, 1H), 5.00-4.96 (m, 1H), 4.28-4.23 (m, 1H), 3.76-3.68 (m, 1H), 3.65 (s, 3H), 3.62-3.56 (m, 1H), 3.24-3.17 (m, 1H), 2.91-2.82 (m, 1H), 2.73-2.61 (m, 1H), 2.45-2.37 (m, 1H), 2.36-2.29 (m, 1H), 2.20-2.09 (m, 2H), 2.06-1.97 (m, 2H), 1.92-1.55 (m, 5H), 1.52-1.37 (m, 2H), 1.22-1.09 (m, 1H), 0.93-0.90 (m, 3H), 0.87-0.83 (m, 3H).

Step 10) The Preparation of Compound 31-12

To a mixture of compound 31-11 (0.34 g, 0.522 mmol), compound 2-14 (0.25 g, 0.522 mmol), $Pd(PPh_3)_4$ (60.29 mg, 0.0522 mmol) and $K_2CO_3$ (0.22 g, 1.566 mmol) were added DME (6.0 mL) and $H_2O$ (2.0 mL) via syringe. The mixture was stirred at 90° C. under $N_2$ for 3.0 hrs. After the reaction was completed, the mixture was diluted with EtOAc (40 mL). The resulting mixture was washed with water (20 mL×3) and brine, dried over anhydrous $Na_2SO_4$ and concentrated in vacuo. The residue was purified by silica gel column chromatography (DCM/EtOH (v/v)=50/1) to give the title compound (0.26 g, 55%). The compound was characterized by the following spectroscopic data:

MS (ESI, pos.ion) m/z: 461.2 $[M+2H]^2$; and $^1$H NMR (400 MHz, $CDCl_3$) δ (ppm): 8.02-8.01 (q, 1H), 7.86, 7.83 (d, d, 1H), 7.81, 7.79 (d, d, 1H), 7.70, 7.68 (t, t, 1H), 7.57-7.56 (m, 1H), 7.55, 7.53 (s, s, 1H), 7.49, 7.46 (d, d, 1H), 7.41, 7.39 (d, d, 1H), 6.51, 6.49 (d, d, 1H), 5.56, 5.55 (d, d, 1H), 5.25-5.20 (m, 1H), 5.00-4.96 (m, 1H), 4.36-4.32 (m, 1H), 4.28-4.23 (m, 1H), 3.84-3.77 (m, 1H), 3.66 (s, 3H), 3.65 (s, 3H), 3.63-3.56 (m, 3H), 3.24-3.17 (m, 1H), 2.87-2.66 (m, 2H), 2.42-2.28 (m, 3H), 2.27-2.09 (m, 3H), 2.06-1.72 (m, 8H), 1.69-1.34 (m, 4H), 1.21-1.09 (m, 1H), 1.02, 1.00 (m, m, 3H), 0.94-0.90 (m, 6H), 0.87-0.83 (m, 3H).

Example 32

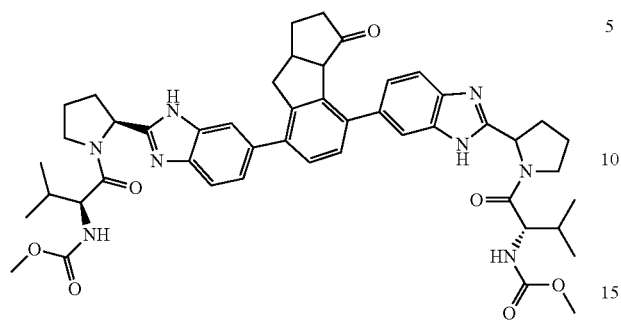

Synthetic Route:

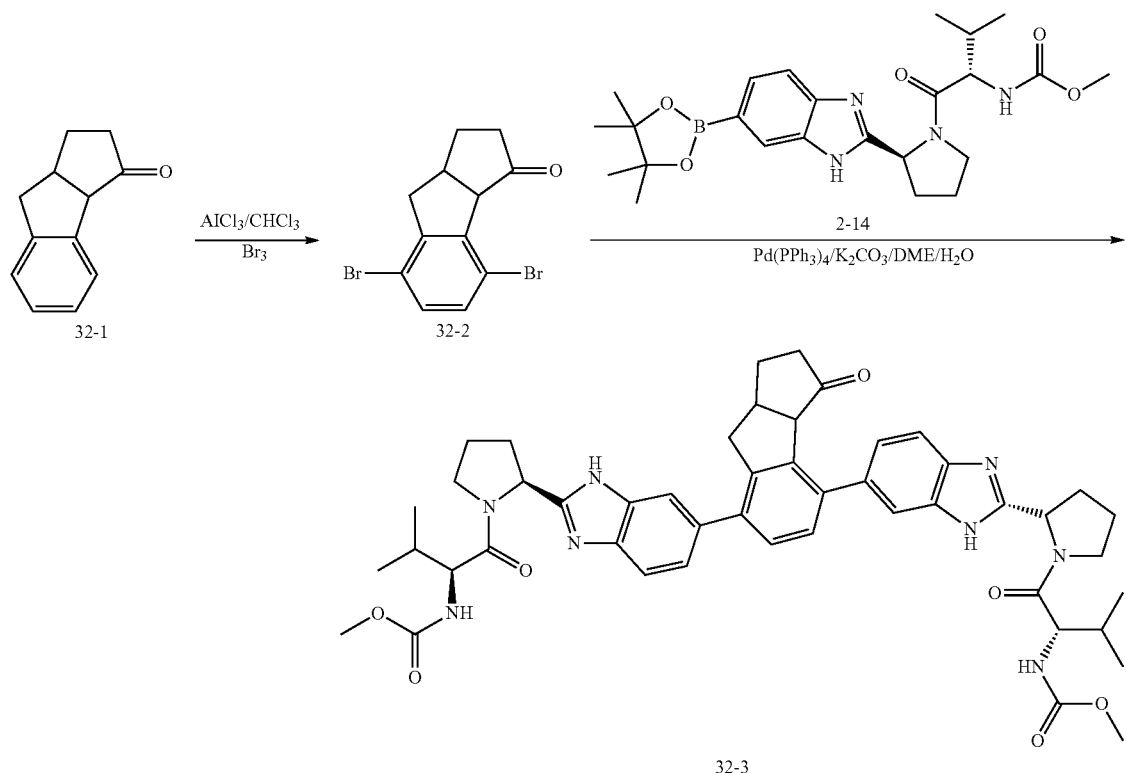

Step 1) The Preparation of Compound 32-2

To a suspension of $AlCl_3$ (3.02 g, 22.6 mmol) in $CHCl_3$ (30 mL) was added a solution of compound 32-1 (1.72 g, 10 mmol) in $CHCl_3$ (20 mL) dropwise at 0 OC. After the mixture was stirred at rt for 1.0 hr, a solution of $Br_2$ (1.03 mL, 20 mmol) in $CHCl_3$ (10 mL) was added dropwise. At the end of the addition, the mixture was stirred at rt overnight. After the reaction was completed, the mixture was poured slowly into ice water (100 mL). The aqueous layer was extracted with DCM (50 mL×3). The combined organic layers were washed with $NaHCO_3$ aqueous solution and brine, dried over anhydrous $Na_2SO_4$ and concentrated in vacuo. The compound was characterized by the following spectroscopic data:

MS (ESI, pos.ion) m/z: 329.5 [M+H]$^+$; and
$^1$H NMR (400 MHz, $CDCl_3$) δ (ppm): 7.37, 7.35 (t, t, 1H), 7.34, 7.32 (s, s, 1H), 3.47-3.42 (m, 1H), 3.13-3.06 (m, 1H), 3.02-2.91 (m, 3H), 2.66-2.58 (m, 1H), 2.49-2.40 (m, 1H), 2.20-2.12 (m, 2H), 1.84-1.73 (m, 1H).

Step 2) The Preparation of Compound 32-3

A mixture of compound 32-2 (0.17 g, 0.522 mmol), compound 2-14 (0.52 g, 1.0962 mmol), Pd(PPh$_3$)$_4$ (60.29 mg, 0.0522 mmol) and $K_2CO_3$ (0.22 g, 1.566 mmol) in mixed solvents of DME and $H_2O$ (8 mL, v/v=3/1) was stirred at 90° C. under $N_2$ for 3.0 hrs. After the reaction was completed, the mixture was cooled to rt and diluted with EtOAc (40 mL). The resulting mixture was washed with water (20 mL×3) and brine, dried over anhydrous $Na_2SO_4$ and concentrated in vacuo. The residue was purified by silica gel column chromatography (DCM/EtOH (v/v)=50/1) to give the title compound as a pale yellow solid (0.22 g, 50%). The compound was characterized by the following spectroscopic data:
MS (ESI, pos.ion) m/z: 429.5 [M+2H]$^{2+}$; and
$^1$H NMR (400 MHz, CDCl$_3$) δ (ppm): 7.79, 7.77 (d, d, 1H), 7.71, 7.69 (t, t, 1H), 7.62-7.59 (m, 2H), 7.54 (m, 1H), 7.53-7.51 (m, 1H), 7.50, 7.48 (s, s, 1H), 7.19, 7.17 (d, d, 1H), 5.56, 5.55 (d, d, 1H), 5.46, 5.44 (d, d, 1H), 5.25-5.18 (m, 2H), 4.40-4.32 (m, 2H), 3.84-3.78 (m, 2H), 3.66 (s, 6H), 3.65-3.60 (m, 2H), 3.53-3.48 (m, 1H), 3.42-3.34 (m, 1H), 2.96-2.78 (m, 2H), 2.56-2.48 (m, 1H), 2.38-2.05 (m, 10H), 2.01-1.86 (m, 2H), 1.78-1.67 (m, 1H), 1.02-0.89 (m, 12H).
Example 33
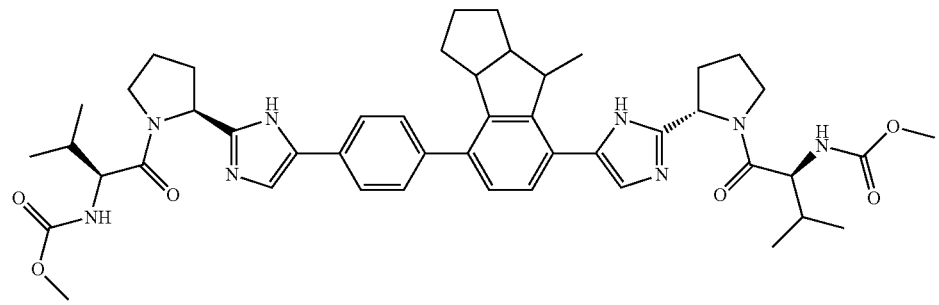 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)c4c3C3CCCC3C4C)cc2)[nH]1)C(C)C]
Synthetic Route:
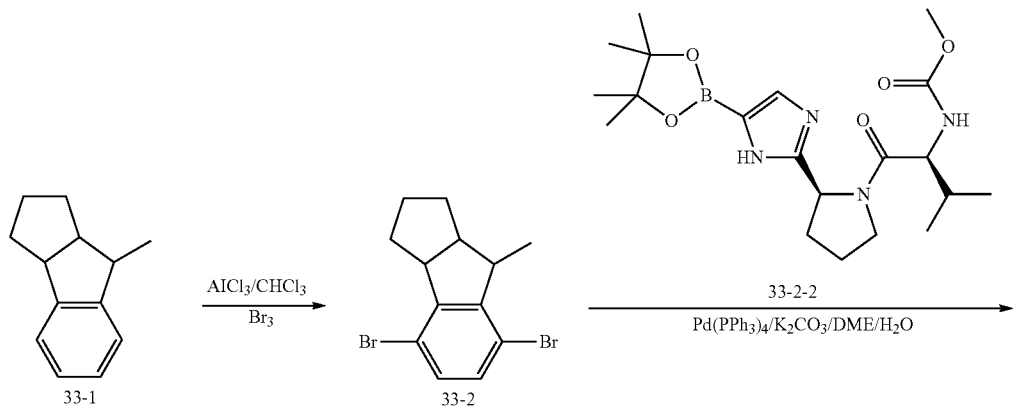
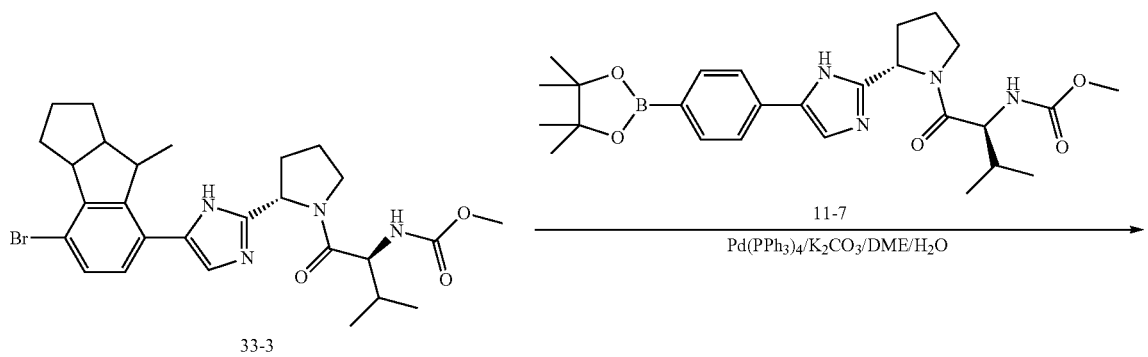

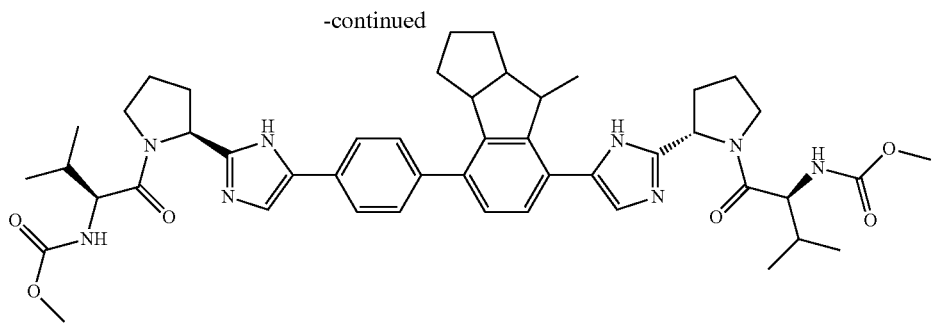

33-4

Step 1) The Preparation of Compound 33-2

To a suspension of $AlCl_3$ (3.02 g, 22.6 mmol) in $CHCl_3$ (30 mL) was added a solution of compound 33-1 (1.72 g, 10 mmol) in $CHCl_3$ (20 mL) dropwise at 0 OC. After the mixture was stirred at rt for 1.0 hr, $Br_2$ (1.03 mL, 20 mmol) in $CHCl_3$ (10 mL) was added dropwise. At the end of the addition, the mixture was stirred at rt overnight. After the reaction was completed, the mixture was poured slowly into ice water (100 mL). The aqueous layer was extracted with DCM (50 mL×3). The combined organic layers were washed with $NaHCO_3$ aqueous solution and brine, dried over anhydrous $Na_2SO_4$ and concentrated in vacuo. The compound was characterized by the following spectroscopic data:

MS (ESI, pos.ion) m/z: 329.5 [M+H]$^+$; and $^1$H NMR (400 MHz, $CDCl_3$) δ (ppm): 7.27, 7.24 (s, s, 1H), 7.21, 7.18 (d, d, 1H), 3.58-3.50 (m, 1H), 3.11-3.03 (m, 1H), 2.37-2.27 (m, 1H), 2.07-1.81 (m, 3H), 1.74-1.48 (m, 3H), 1.34, 1.32 (d, d, 3H).

Step 2) The Preparation of Compound 33-3

A mixture of compound 33-2 (0.17 g, 0.522 mmol), compound 33-2-2 (0.22 g, 0.522 mmol), Pd(PPh$_3$)$_4$ (60.29 mg, 0.0522 mmol) and $K_2CO_3$ (0.22 g, 1.566 mmol) in mixed solvents of DME and $H_2O$ (8 mL, v/v=3/1) was stirred at 90° C. under $N_2$ for 3.0 hrs. After the reaction was completed, the mixture was cooled to rt and diluted with EtOAc (40 mL). The resulting mixture was washed with water (20 mL×3) and brine, dried over anhydrous $Na_2SO_4$ and concentrated in vacuo. The residue was purified by silica gel column chromatography (DCM/EtOH (v/v)=100/1) to give the title compound as a pale yellow solid (0.14 g, 50%). The compound was characterized by the following spectroscopic data:

MS (ESI, pos.ion) m/z: 544.5 [M+H]$^+$; and $^1$H NMR (400 MHz, $CDCl_3$) δ (ppm): 7.63 (s, 1H), 7.30, 7.28 (d, d, 1H), 7.06, 7.04 (s, s, 1H), 5.32, 5.30 (d, d, 1H), 5.29-5.25 (m, 1H), 4.41-4.36 (m, 1H), 3.91-3.78 (m, 2H), 3.68-3.65 (m, 1H), 3.63 (s, 3H), 3.00-2.92 (m, 1H), 2.30-1.81 (m, 9H), 1.72-1.43 (m, 3H), 1.30, 1.29 (d, d, 3H), 0.97, 0.95 (m, m, 3H), 0.91, 0.89 (m, m, 3H).

Step 3) The Preparation of Compound 33-4

A mixture of compound 33-3 (0.28 g, 0.522 mmol), compound 11-7 (0.26 g, 0.522 mmol), Pd(PPh$_3$)$_4$ (60.29 mg, 0.0522 mmol) and $K_2CO_3$ (0.22 g, 1.566 mmol) in mixed solvents of DME and $H_2O$ (8 mL, v/v=3/1) was stirred at 90° C. under $N_2$ for 3.0 hrs. After the reaction was completed, the mixture was cooled to rt and diluted with EtOAc (40 mL). The resulting mixture was washed with water (20 mL×3) and brine, dried over anhydrous $Na_2SO_4$ and concentrated in vacuo. The residue was purified by silica gel column chromatography (DCM/EtOH (v/v)=80/1) to give the title compound as a pale yellow solid (0.22 g, 50%). The compound was characterized by the following spectroscopic data:

MS (ESI, pos.ion) m/z: 417.5 [M+H]$^+$; and $^1$H NMR (400 MHz, $CDCl_3$) δ (ppm): 7.75 (s, 1H), 7.62-7.59 (m, 3H), 7.53-7.50 (m, 2H), 7.46, 7.44 (d, d, 1H), 7.36, 7.34 (s, s, 1H), 5.32, 5.30 (d, d, 2H), 5.29-5.25 (m, 1H), 5.23-5.19 (m, 1H), 4.41-4.36 (m, 2H), 3.85-3.78 (m, 2H), 3.68-3.64 (m, 2H), 3.63 (s, 6H), 3.53-3.45 (m, 1H), 3.23-3.16 (m, 1H), 2.32-1.81 (m, 14H), 1.68-1.40 (m, 3H), 1.26, 1.24 (d, d, 3H), 0.97, 0.95 (m, m, 6H), 0.90, 0.89 (m, m, 6H).

Example 34

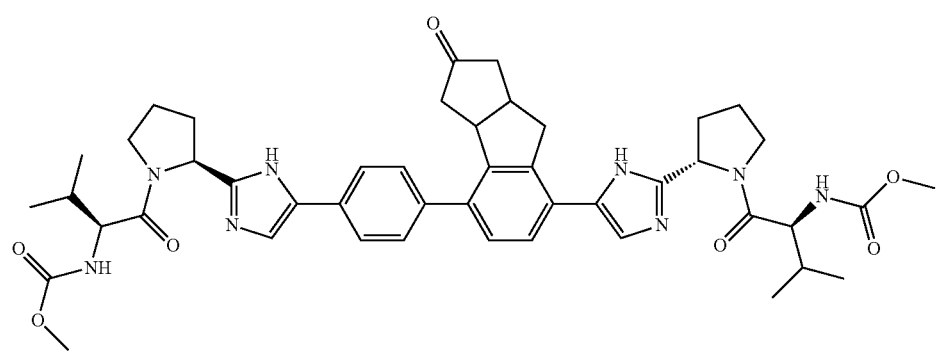 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)c4c3C3CC(=O)CC3C4)cc2)[nH]1)C(C)C]

Synthetic Route:

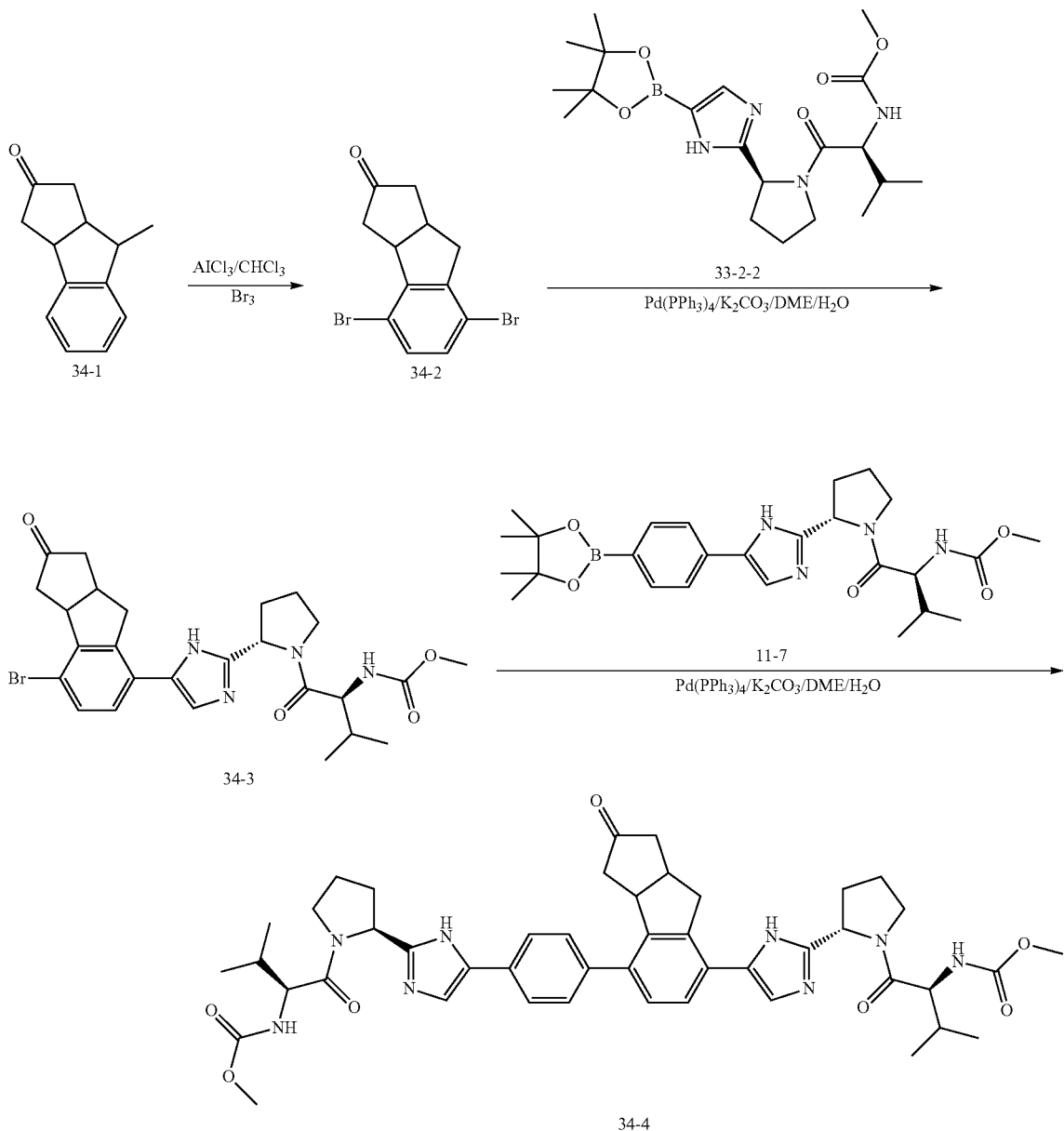

Compounds disclosed herein can be synthesized through the procedure depicted in Example 33:

Compound 34-2 was characterized by the following spectroscopic data:

MS (ESI, pos.ion) m/z: 329.5 [M+H]$^+$; and $^1$H NMR (400 MHz, CDCl$_3$) δ (ppm): 7.28, 7.26 (t, t, 1H), 7.25, 7.23 (s, s, 1H), 4.00-3.93 (m, 1H), 3.41-3.30 (m, 1H), 3.15-3.07 (m, 1H), 2.81-2.57 (m, 4H), 2.30-2.27, 2.25-2.22 (m, m, 1H).

Compound 34-3 was characterized by the following spectroscopic data:

MS (ESI, pos.ion) m/z: 544.5 [M+H]$^+$; and $^1$H NMR (400 MHz, CDCl$_3$) δ (ppm): 7.46 (s, 1H), 7.41, 7.39 (t, t, 1H), 7.19, 7.17 (s, s, 1H), 5.32-5.28 (m, 2H), 4.41-4.36 (m, 1H), 4.27-4.19 (m, 1H), 3.85-3.78 (m, 1H), 3.68-3.64 (m, 1H), 3.63 (s, 3H), 3.61-3.54 (m, 1H), 2.99-2.91 (m, 1H), 2.82-2.71 (m, 2H), 2.62-2.60, 2.57-2.55 (m, m, 1H), 2.53-2.44 (m, 1H), 2.34-1.92 (m, 6H), 0.97, 0.95 (m, m, 3H), 0.90, 0.89 (m, m, 3H).

Compound 34-4 was characterized by the following spectroscopic data:

MS (ESI, pos.ion) m/z: 834.5 [M+H]$^+$; and $^1$H NMR (400 MHz, CDCl$_3$) δ (ppm): 7.59 (s, 1H), 7.58-7.52 (m, 6H), 7.47, 7.45 (t, t, 1H), 5.32-5.28 (m, 3H), 5.23-5.19 (m, 1H), 4.41-4.36 (m, 2H), 4.15-4.07 (m, 1H), 3.84-3.78 (m, 2H), 3.68-3.65 (m, 2H), 3.63 (s, 6H), 3.55-3.44 (m, 1H), 2.96-2.88 (m, 1H), 2.82-2.70 (m, 2H), 2.60-2.54 (m, 1H), 2.50-2.41 (m, 1H), 2.35-1.92 (m, 11H), 0.97, 0.95 (m, m, 6H), 0.91, 0.89 (m, m, 6H).

Example 35
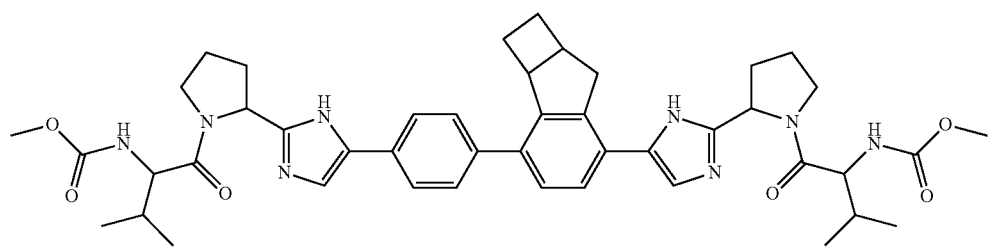
Synthetic Route:
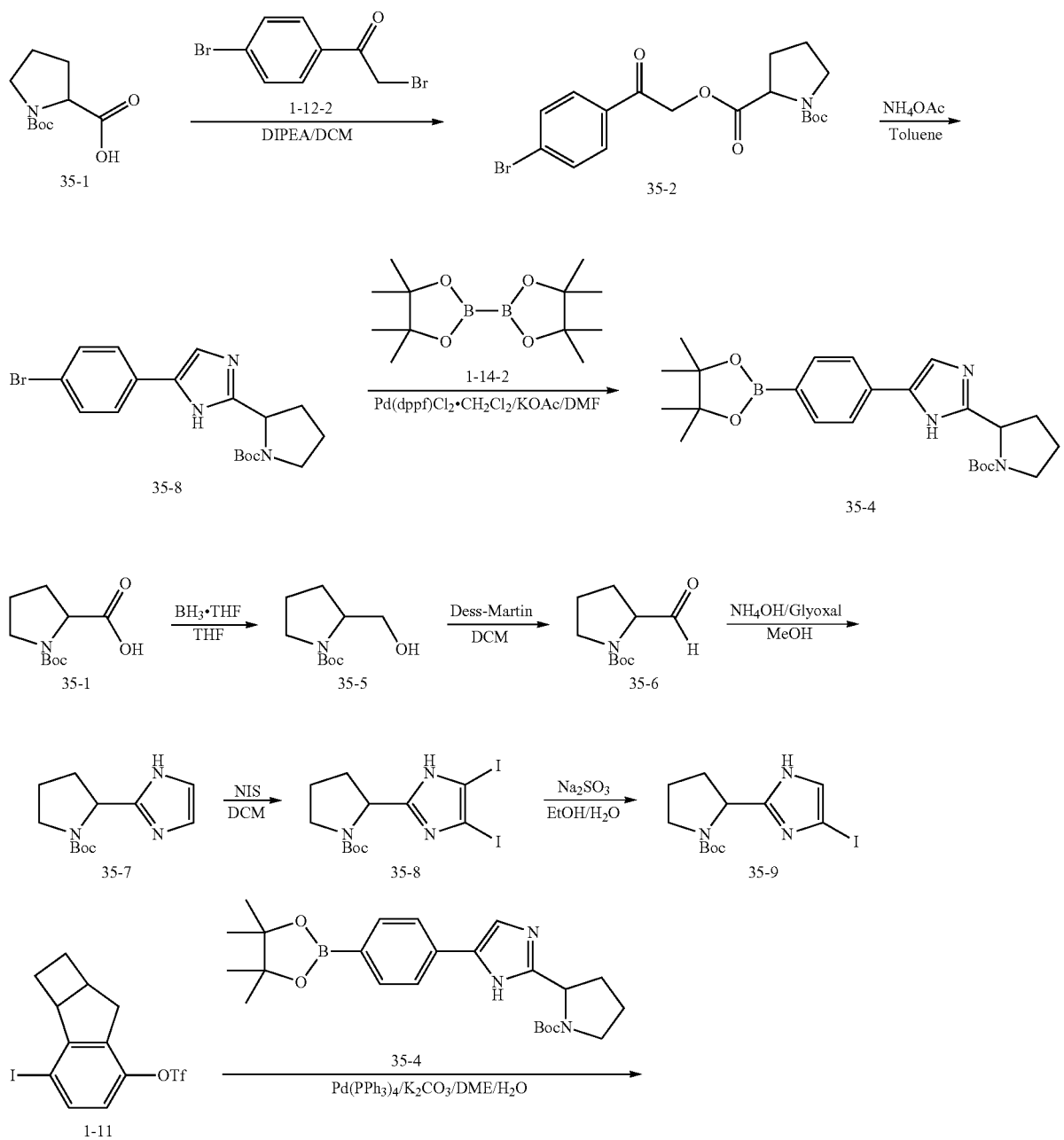

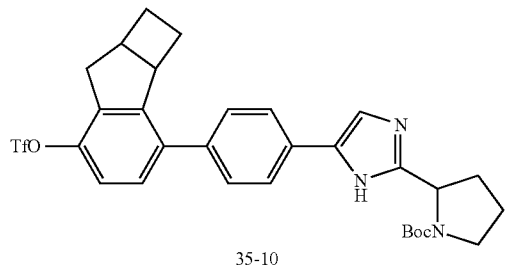
35-10

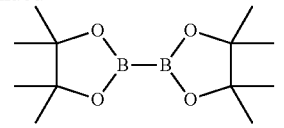
1-14-2
Pd(dppf)₂Cl₂·CH₂Cl₂/KOAc/DMF

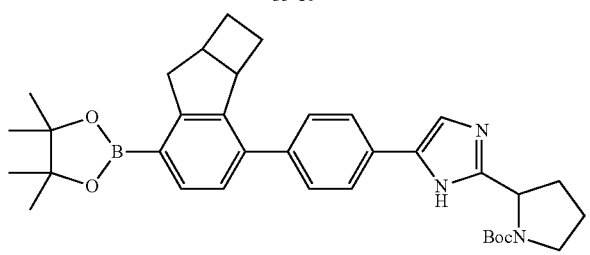
35-11

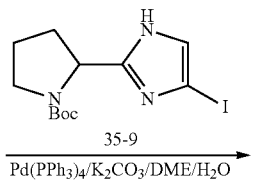
35-9
Pd(PPh₃)₄/K₂CO₃/DME/H₂O

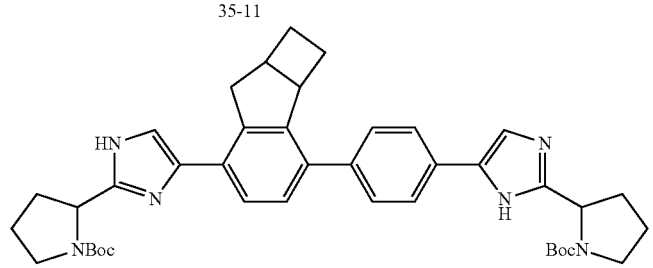
35-12

EA·HCl / EA

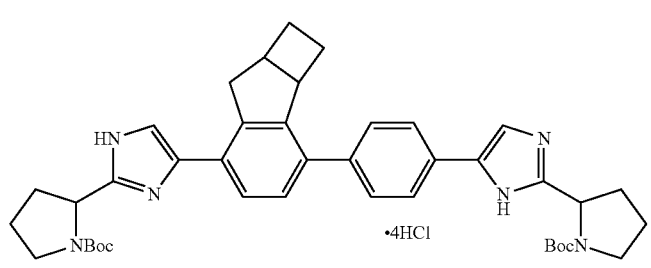
35-13

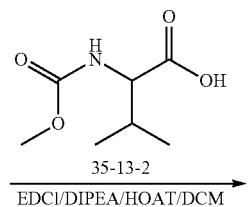
35-13-2
EDCl/DIPEA/HOAT/DCM

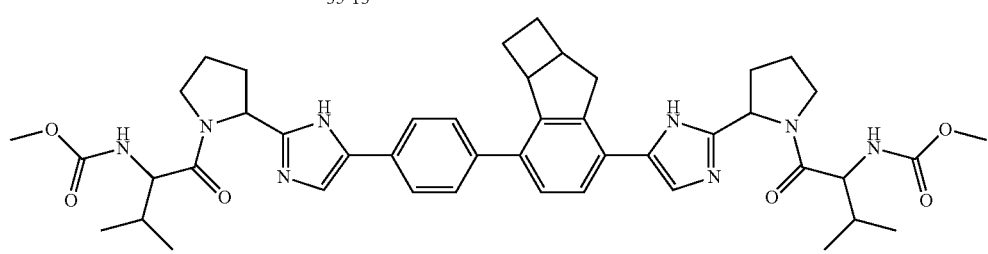
35-14

Compounds disclosed herein can be synthesized through the procedure depicted in Example 1:

Compound 35-2 was characterized by the following spectroscopic data:

MS (ESI, pos.ion) m/z: 412.7 [M+H]⁺; and

¹H NMR (400 MHz, CDCl₃) δ (ppm): 7.78-7.75 (m, 2H), 7.65-7.63 (m, 2H), 5.53-5.15 (m, 2H), 4.49-4.39 (m, 1H), 3.59-3.54 (m, 1H), 3.48-3.38 (m, 1H), 2.31-2.21 (m, 2H), 2.12-2.01 (m, 1H), 1.98-1.85 (m, 1H), 1.45 (d, 9H).

Compound 35-3 was characterized by the following spectroscopic data:

MS (ESI, pos.ion) m/z: 392.2 [M+H]⁺; and

¹H NMR (400 MHz, CDCl₃) δ (ppm): 7.78-7.75 (m, 2H), 7.65-7.63 (m, 2H), 7.21-7.20 (m, 1H), 5.53-5.15 (m, 2H), 4.49-4.39 (m, 1H), 3.59-3.54 (m, 1H), 3.48-3.38 (m, 1H), 2.31-2.21 (m, 2H), 2.12-2.01 (m, 1H), 1.98-1.85 (m, 1H), 1.45 (d, 9H).

Compound 35-4 was characterized by the following spectroscopic data:

$^1$H NMR (400 MHz, CDCl$_3$) δ (ppm): 7.35 (m, 4H), 7.10 (s, 1H), 4.93 (t, 1H, J=8.2 Hz), 3.88-3.66 (m, 2H), 2.90 (t, 1H, J=8.0 Hz), 2.50-2.47 (m, 2H), 2.27-2.25 (m, 1H), 1.48 (s, 9H), 1.26 (s, 12H).

Compound 35-5 was characterized by the following spectroscopic data:

$^1$H NMR (400 MHz, CDCl$_3$) δ (ppm): 3.99-3.87 (br, 1H), 3.68-3.51 (m, 2H), 3.48-3.39 (m, 1H), 3.34-3.25 (m, 1H), 2.05-1.92 (m, 2H), 1.88-1.71 (m, 2H), 1.45 (s, 9H).

Compound 35-6 was characterized by the following spectroscopic data:

$^1$H NMR (400 MHz, CDCl$_3$) δ (ppm): 9.46 (d, 1H, J=2.8 Hz), 4.08-4.03 (m, 1H), 3.51-3.42 (m, 2H), 2.01-1.93 (m, 2H), 1.91-1.84 (m, 2H), 1.43 (s, 9H).

Compound 35-7 was characterized by the following spectroscopic data:

MS (ESI, pos.ion) m/z: 238.2 [M+H]$^+$; and $^1$H NMR (400 MHz, CDCl$_3$) δ (ppm): 6.96 (s, 1H), 4.94 (dd, 1H, J=7.68 Hz, 2.40 Hz), 3.38 (t, 2H, J=6.24 Hz), 2.17-2.03 (m, 2H), 1.99-1.91 (m, 2H), 1.48 (s, 9H).

Compound 35-8 was characterized by the following spectroscopic data:

MS (ESI, pos.ion) m/z: 490.0 [M+H]$^+$; and $^1$H NMR (400 MHz, CDCl$_3$) δ (ppm): 4.89 (dd, 1H, J=7.64 Hz, 2.52 Hz), 3.36 (t, 2H), 2.14-2.02 (m, 2H), 1.97-1.85 (m, 2H), 1.49 (s, 9H).

Compound 35-9 was characterized by the following spectroscopic data:

MS (ESI, pos.ion) m/z: 364.1 [M+H]$^+$; and $^1$H NMR (400 MHz, CDCl$_3$) δ (ppm): 7.04 (d, 1H, J=1.84 Hz), 4.89 (dd, 1H, J=7.72 Hz, 2.56 Hz), 3.36 (t, 2H), 2.18-2.03 (m, 2H), 1.97-1.82 (m, 2H), 1.47 (s, 9H).

Compound 35-10 was characterized by the following spectroscopic data:

MS (ESI, pos.ion) m/z: 604.3 [M+H]$^+$; and $^1$H NMR (400 MHz, CDCl$_3$) δ (ppm): 7.90-7.70 (m, 1H), 7.60-7.30 (m, 2H), 7.30-7.20 (m, 2H), 7.18 (d, 1H, J=8.4 Hz), 5.03-4.94 (m, 1H), 4.05-3.97 (m, 1H), 3.48-3.35 (m, 2H), 3.31-3.22 (m, 2H), 3.22-3.12 (m, 1H), 3.05-2.93 (m, 1H), 2.41-2.29 (m, 1H), 2.29-2.10 (m, 3H), 2.10-1.90 (m, 2H), 1.80-1.60 (m, 2H), 1.50 (s, 9H).

Compound 35-11 was characterized by the following spectroscopic data:

MS (ESI, pos.ion) m/z: 582.5 [M+H]$^+$; and $^1$H NMR (400 MHz, CDCl$_3$) δ (ppm): 7.78 (d, 1H, J=7.5 Hz), 7.72-7.58 (m, 2H), 7.45-7.38 (m, 2H), 7.30-7.22 (m, 2H), 5.07-4.98 (m, 1H), 4.02-3.93 (m, 1H), 3.55-3.37 (m, 3H), 3.25-3.16 (m, 1H), 3.15-3.04 (m, 1H), 2.96-2.83 (m, 1H), 2.45-2.33 (m, 1H), 2.28-2.13 (m, 3H), 2.03-1.91 (m, 1H), 1.80-1.70 (m, 2H), 1.52 (s, 9H), 1.37 (d, 12H, J=3.0 Hz).

Compound 35-12 was characterized by the following spectroscopic data:

MS (ESI, pos.ion) m/z: 691.5 [M+H]$^+$; and $^1$H NMR (400 MHz, CDCl$_3$) δ (ppm): 7.75-7.56 (m, 3H), 7.42-7.35 (m, 2H), 7.30-7.25 (m, 1H), 7.23 (s, 1H), 7.20-7.17 (m, 1H), 5.06-4.97 (m, 2H), 4.05-3.98 (m, 1H), 3.50-3.40 (m, 4H), 3.18-3.09 (m, 1H), 2.98-2.82 (m, 4H), 2.44-2.27 (m, 2H), 2.26-2.10 (m, 4H), 2.03-1.90 (m, 2H), 1.79-1.67 (m, 2H), 1.55-1.31 (m, 20H).

Compound 35-13 was characterized by the following spectroscopic data:

MS (ESI, pos.ion) m/z: 491.5 [M+H]$^+$.

Compound 35-14 was characterized by the following spectroscopic data:

MS (ESI, pos.ion) m/z: 805.3 [M+H]$^+$; and $^1$H NMR (400 MHz, CDCl$_3$) δ (ppm): 11.00 (brs, 1H), 10.63 (brs, 1H), 7.98-7.64 (m, 2H), 7.46-7.27 (m, 3H), 7.25-7.10 (m, 3H), 6.14-5.88 (m, 2H), 5.38-5.19 (m, 2H), 4.33 (t, 2H, J=8.0 Hz), 3.98-3.78 (m, 2H), 3.79-3.58 (m, 8H), 3.31-3.20 (m, 1H), 3.16-3.00 (m, 1H), 3.00-2.80 (m, 3H), 2.44-2.26 (m, 3H), 2.23-2.13 (m, 3H), 2.13-2.03 (m, 3H), 2.01-1.89 (m, 2H), 1.75-1.55 (m, 2H), 0.94-0.76 (m, 12H).

Example 36

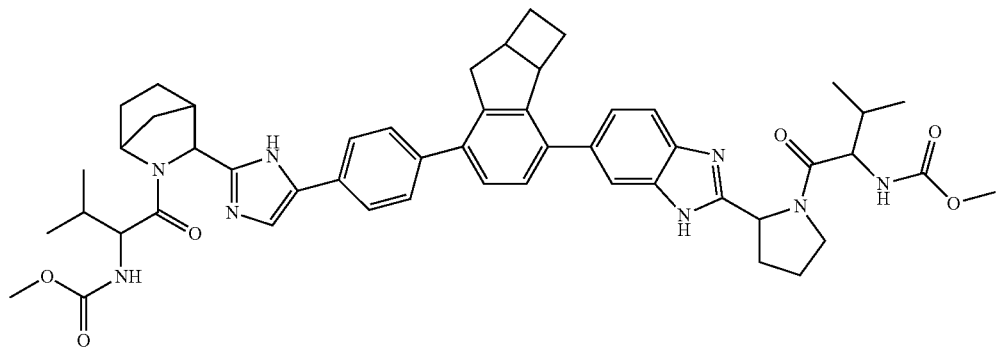

Synthetic Route:
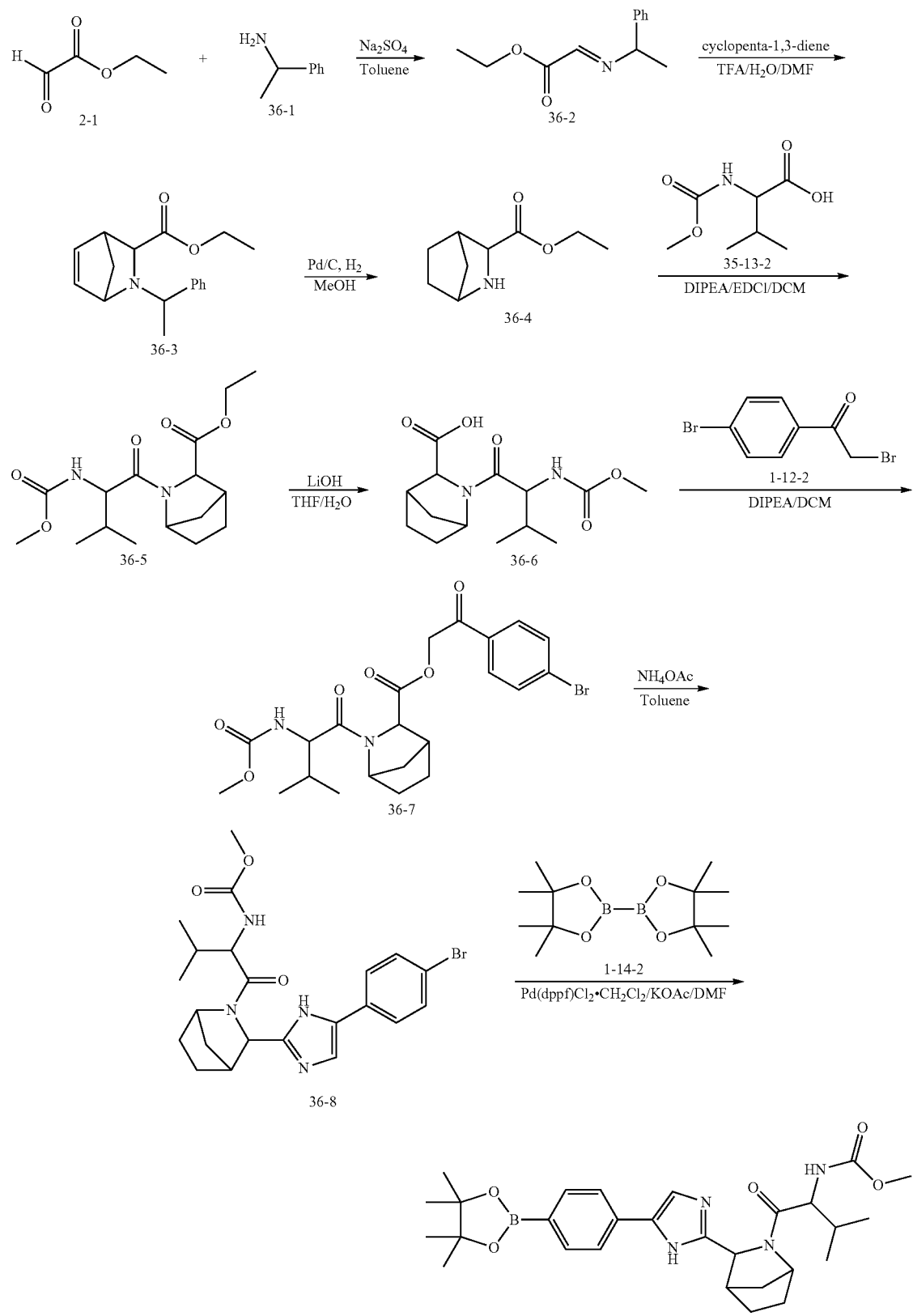

429 430
-continued
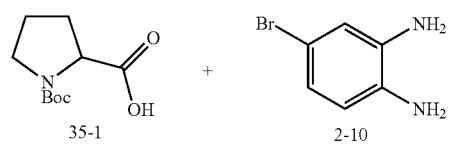
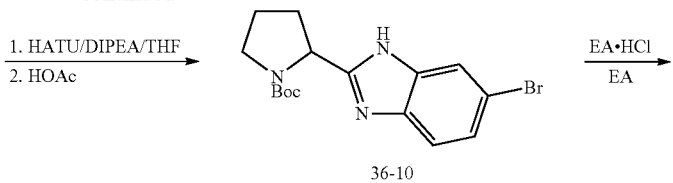
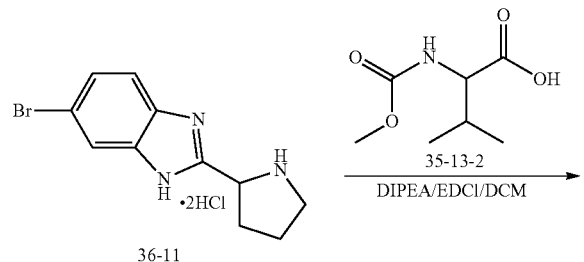
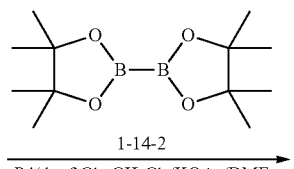
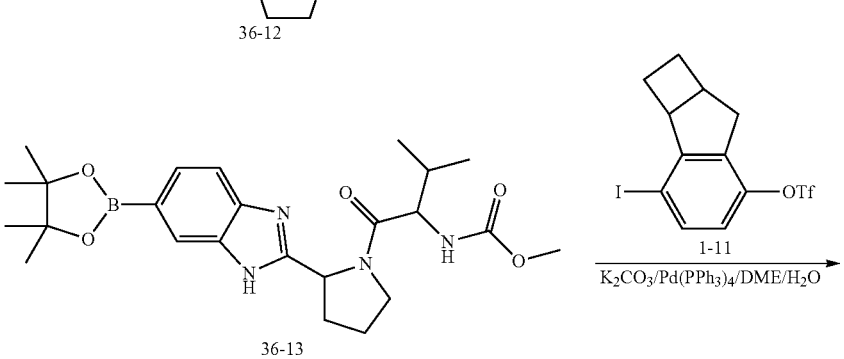
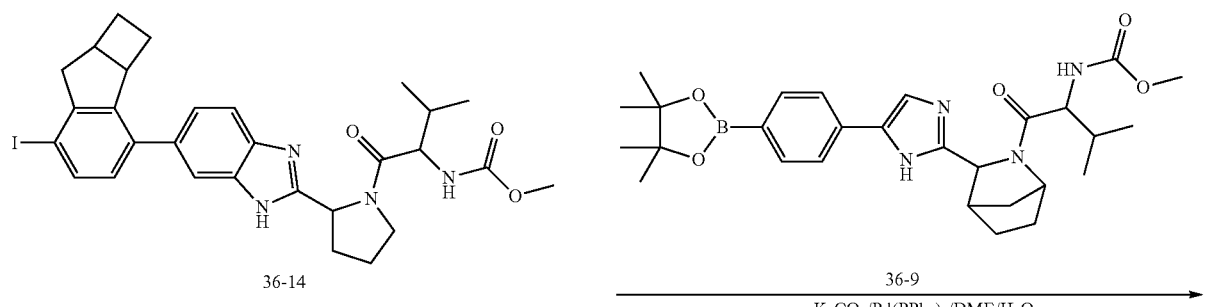
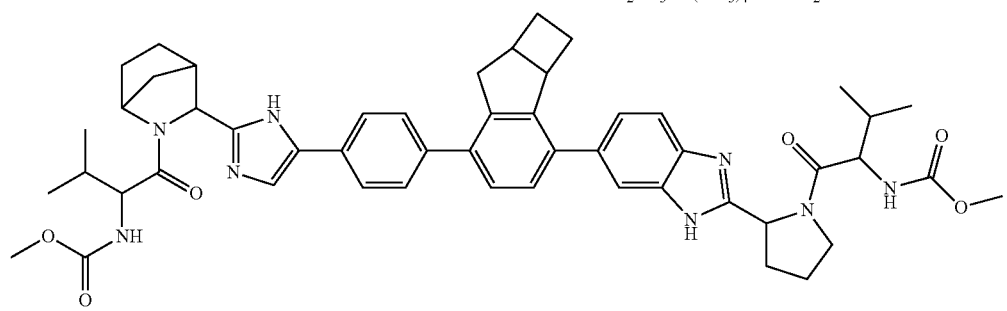

Compounds disclosed herein can be synthesized through the procedure depicted in Example 2:

Compound 36-3 was characterized by the following spectroscopic data:
$^1$H NMR (400 MHz, CDCl$_3$) δ (ppm): 7.35-7.17 (m, 5H), 6.42 (br, 1H), 6.28-6.26 (br, 1H), 4.34-4.30 (m, 2H), 3.82-3.78 (m, 2H), 3.04-3.02 (m, 1H), 2.90 (br, 1H), 2.20 (br, 1H), 2.13 (m, 1H), 1.41 (d, 3H, J=6.6 Hz), 0.95 (t, 3H, J=7.2 Hz).

Compound 36-4 was characterized by the following spectroscopic data:
MS (ESI, pos.ion) m/z: 170.2 [M+H]$^+$; and
$^1$H NMR (400 MHz, CDCl$_3$) δ (ppm): 4.21-4.15 (m, 2H), 3.55 (br, 1H), 3.33 (br, 1H), 2.63 (br, 1H), 2.32 (br, 1H), 1.64-1.60 (m), 2H), 1.53-1.47 (m, 2H), 1.42-1.36 (m, 2H), 1.28 (t, 3H, J=7.1 Hz).

Compound 36-5 was characterized by the following spectroscopic data:
MS (ESI, pos.ion) m/z: 327.5 [M+H]$^+$; and
$^1$H NMR (400 MHz, CDCl$_3$) δ (ppm): 5.44 (br, 1H), 4.40 (br, 1H), 4.33-4.30 (m, 1H), 4.19-4.14 (m, 2H), 4.02 (br, 1H), 3.66 (s, 3H), 2.74 (br, 1H), 2.04 (br, 1H), 1.91-1.88 (m, 2H), 1.80-1.74 (m, 2H), 1.56-1.54 (m, 1H), 1.43-1.38 (m, 1H), 1.26 (t, 3H, J=7.1 Hz), 1.07 (d, 3H, J=6.8 Hz), 0.97 (d, 3H, J=6.8 Hz).

Compound 36-6 was characterized by the following spectroscopic data:
MS (ESI, pos.ion) m/z: 299.2 [M+H]$^+$; and
$^1$H NMR (400 MHz, CDCl$_3$) δ (ppm): 4.52 (br, 1H), 4.20 (d, 1H, J=7.8 Hz), 3.93 (br, 1H), 3.63 (s, 3H), 2.73 (br, 1H), 2.01-1.98 (m, 4H), 1.85-1.75 (m, 2H), 1.54-1.46 (m, 2H), 1.05 (d, 3H, J=6.8 Hz), 0.98 (d, 3H, J=6.8 Hz).

Compound 36-7 was characterized by the following spectroscopic data:
MS (ESI, pos.ion) m/z: 495.3 [M+H]$^+$; and
$^1$H NMR (400 MHz, CDCl$_3$) δ (ppm): 7.75 (d, 2H, J=8.52 Hz), 7.68 (d, 2H, J=8.56 Hz), 5.45 (d, 1H, J=9.4 Hz), 5.24 (d, 1H, J=16.56 Hz), 4.55-4.59 (m, 1H), 3.67 (s, 3H), 3.57 (m, 1H), 2.73-2.65 (m, 2H), 2.27-2.19 (m, 1H), 2.04 (s, 1H), 1.84-1.77 (m, 2H), 1.49-1.46 (m, 1H), 1.27-1.24 (m, 1H), 1.08-1.07 (br, 1H), 1.05-1.03 (m, 1H), 0.91-0.89 (m, 6H).

Compound 36-8 was characterized by the following spectroscopic data:
MS (ESI, pos.ion) m/z: 476.3 [M+H]$^+$; and
$^1$H NMR (400 MHz, CDCl$_3$) δ (ppm): 10.35 (s, 1H), 7.64-7.62 (d, 2H, J=8.52 Hz,), 7.55-7.45 (d, 2H, J=1.84 Hz), 7.16 (s, 1H), 5.54-5.46 (br, 2H), 4.57-4.53 (m, 1H), 3.70 (s, 3H), 3.58 (m, 1H), 2.69 (m, 1H), 2.54-2.48 (m, 1H), 1.87-1.76 (m, 4H), 1.47-1.45 (m, 2H), 0.85-0.81 (m, 6H).

Compound 36-9 was characterized by the following spectroscopic data:
MS (ESI, pos.ion) m/z: 523.3 [M+H]$^+$; and
$^1$H NMR (400 MHz, CDCl$_3$) δ (ppm): 10.48 (s, 1H), 7.81-7.75 (m, 4H), 7.43-7.41 (d, 1H, J=8.0 Hz), 5.49-5.39 (m, 2H), 4.58-4.53 (m, 2H), 3.67 (s, 3H), 3.57 (m, 1H), 2.65 (m, 1H), 2.54-2.47 (m, 1H), 2.10-2.04 (m, 2H), 1.83-1.79 (m, 1H), 1.49-1.46 (m, 2H), 1.38 (s, 12H), 0.85-0.81 (m, 6H).

Compound 36-10 was characterized by the following spectroscopic data:
MS (ESI, pos.ion) m/z: 367.3 [M+H]$^+$; and
$^1$H NMR (400 MHz, CDCl$_3$) δ (ppm): 7.68 (s, 1H), 7.42-7.40 (m, 1H), 7.30-7.28 (m, 1H), 5.11-5.09 (m, 1H), 3.45-3.43 (m, 2H), 2.94-2.93 (m, 1H), 2.21-2.18 (m, 2H), 2.01-1.91 (m, 1H), 1.49 (s, 9H).

Compound 36-11 was characterized by the following spectroscopic data:
MS (ESI, pos.ion) m/z: 313.2 [M+H]$^+$; and
$^1$H NMR (400 MHz, CDCl$_3$) δ (ppm): 8.01 (s, 1H), 7.70-7.76 (m, 2H), 5.27-5.25 (m, 1H), 3.31-3.30 (m, 2H), 2.77-2.74 (m, 1H), 2.54-2.52 (m, 1H), 2.40-2.37 (m, 1H), 2.30-2.10 (m, 1H).

Compound 36-12 was characterized by the following spectroscopic data:
MS (ESI, pos.ion) m/z: 423.3 [M+H]$^+$; and
$^1$H NMR (400 MHz, CDCl$_3$) δ (ppm): 7.59-7.51 (m, 1H), 7.34-7.21 (m, 2H), 5.42-5.38 (m, 2H), 4.34-4.30 (m, 1H), 3.87-3.76 (m, 1H), 3.70 (s, 3H), 3.66-3.62 (m, 1H), 3.04-2.98 (m, 1H), 2.25-2.21 (m, 1H), 2.20-2.13 (m, 2H), 1.96-1.94 (m, 1H), 0.88-0.84 (m, 6H).

Compound 36-13 was characterized by the following spectroscopic data:
MS (ESI, pos.ion) m/z: 471.3 [M+H]$^+$; and
$^1$H NMR (400 MHz, CDCl$_3$) δ (ppm): 7.87-7.80 (m, 1H), 7.71-7.66 (m, 2H), 5.47-5.42 (m, 2H), 4.34-4.30 (m, 1H), 3.86-3.84 (m, 1H), 3.70 (s, 3H), 3.64-3.62 (m, 1H), 3.04-2.98 (m, 1H), 2.25-2.21 (m, 1H), 2.20-2.13 (m, 2H), 1.96-1.94 (m, 1H), 1.35 (s, 12H), 0.88-0.84 (m, 6H).

Compound 36-14 was characterized by the following spectroscopic data:
MS (ESI, pos.ion) m/z: 635.3 [M+H]$^+$; and
$^1$H NMR (400 MHz, CDCl$_3$) δ (ppm): 7.85-7.79 (m, 2H), 7.42-7.41 (m, 2H), 7.27 (s, 1H), 5.12-4.95 (m, 1H), 4.83-4.68 (m, 1H), 3.72 (s, 3H), 3.63-3.59 (m, 2H), 3.35-3.32 (m, 2H), 3.12-3.02 (m, 2H), 2.94-2.89 (m, 1H), 2.02-1.98 (m, 2H), 1.87-1.75 (m, 6H), 1.02-0.91 (m, 6H).

Compound 36-15 was characterized by the following spectroscopic data:
MS (ESI, pos.ion) m/z: 441.3 [M+2H]$^{2+}$; and
$^1$H NMR (400 MHz, CDCl$_3$) δ (ppm): 7.91-7.89 (m, 2H), 7.74-7.71 (m, 2H), 7.59-7.52 (m, 4H), 7.33-7.31 (m, 2H), 5.44-5.40 (m, 2H), 4.71-4.69 (m, 1H), 4.30-4.21 (br, 1H), 3.73 (s, 6H), 3.54-3.49 (m, 2H), 3.02-3.00 (d, 4H, J=8.0 Hz), 2.60-2.51 (br, 1H), 2.41-2.32 (br, 1H), 2.20-2.17 (br, 2H), 2.10 (s, 1H), 2.04 (s, 1H), 1.96-1.91 (br, 2H), 1.66-1.58 (m, 2H), 1.27-1.24 (m, 2H), 1.14 (s, 6H), 0.85-0.81 (m, 12H).

Example 37

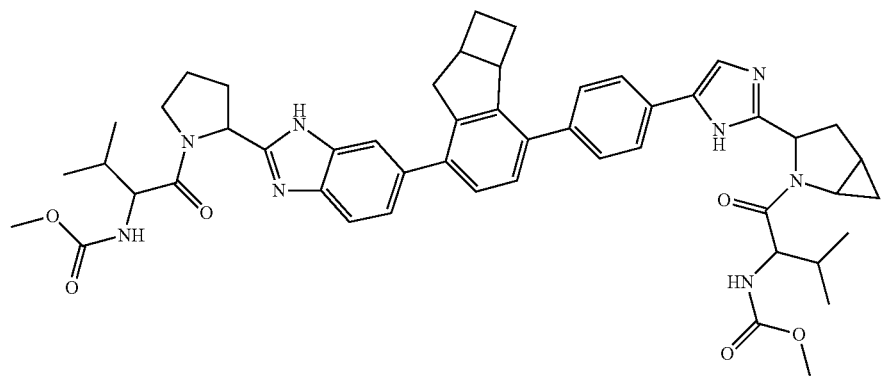 [SMILES: COC(=O)NC(C(=O)N1CCCC1c1nc2ccc(-c3ccc(-c4ccc(-c5cnc(C6CC7CC7N6C(=O)C(NC(=O)OC)C(C)C)[nH]5)cc4)c4c3CC3CCC43)cc2[nH]1)C(C)C]

Synthetic Route:
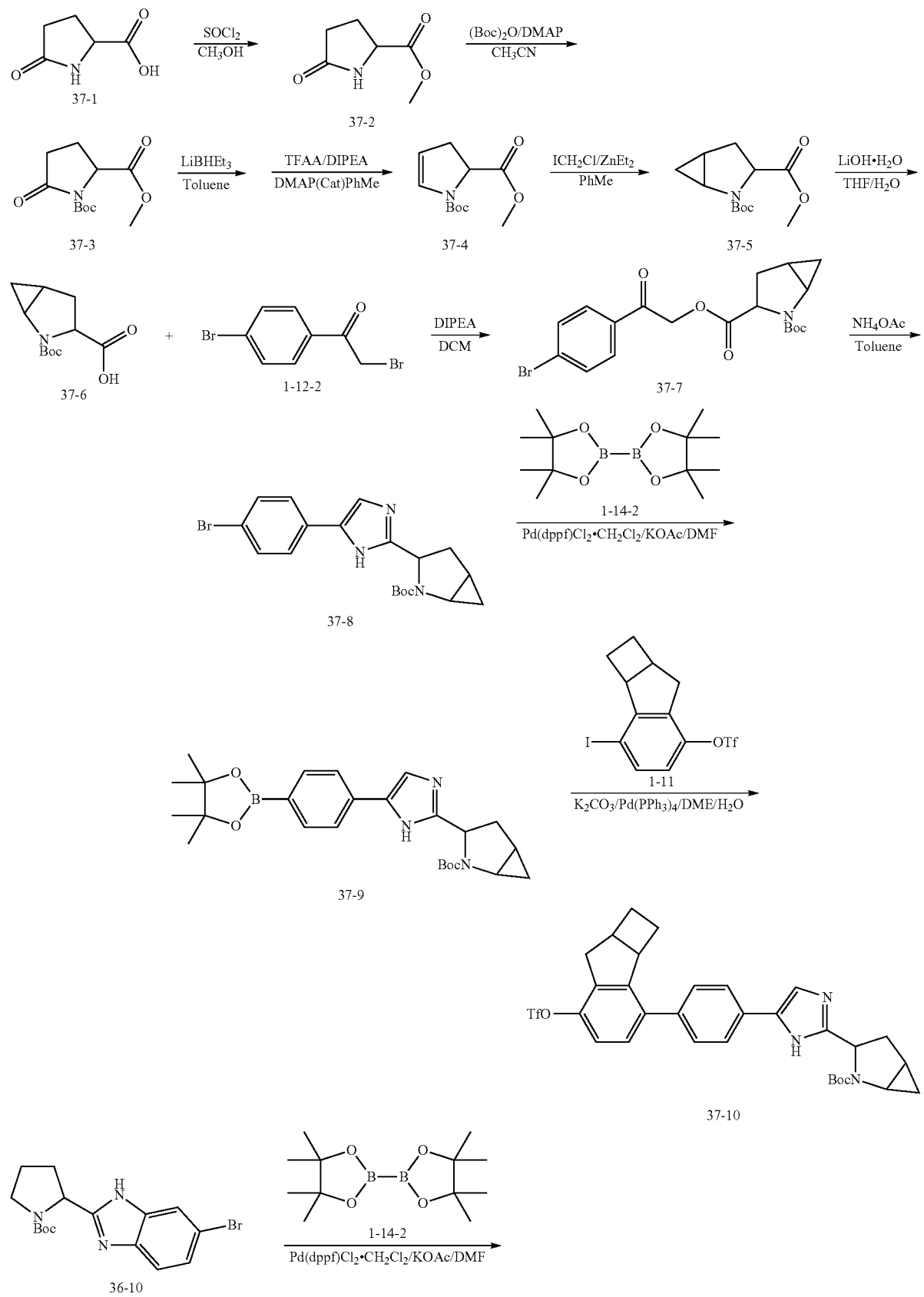

-continued
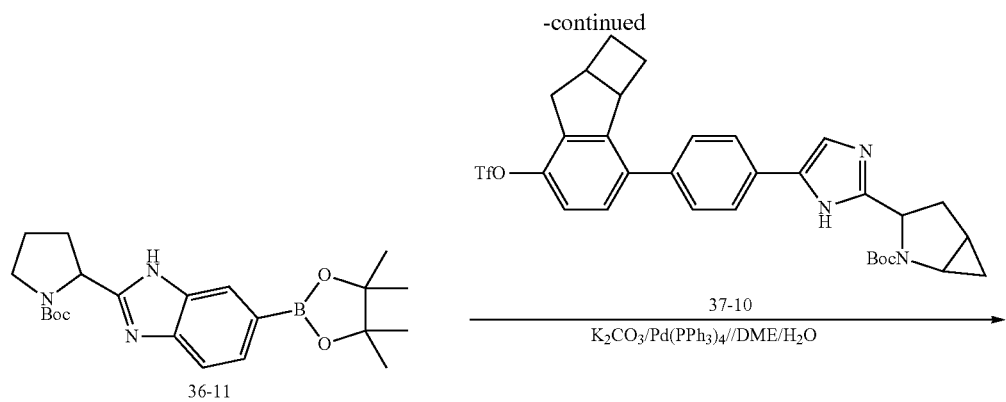
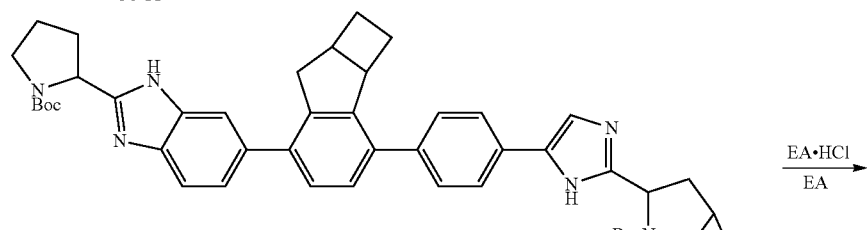
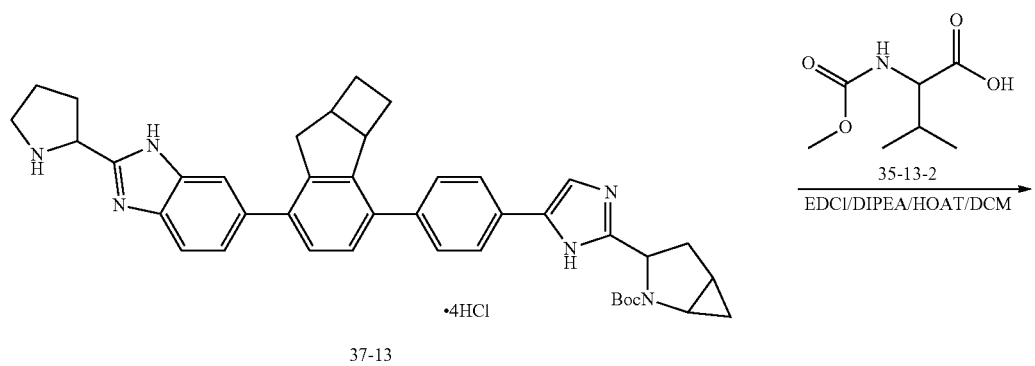
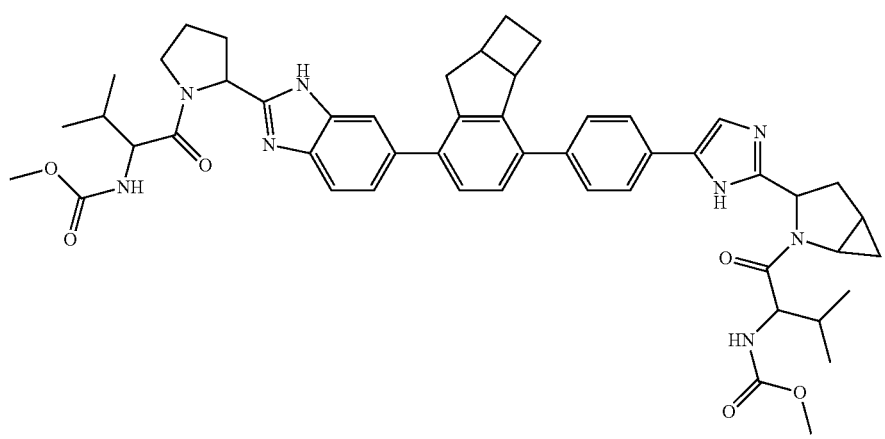

Compounds disclosed herein can be synthesized through the procedure depicted in Example 3:

Compound 37-2 was characterized by the following spectroscopic data:

MS (ESI, pos.ion) m/z: 144.2 [M+H]⁺; and
¹H NMR (400 MHz, CDCl₃) δ (ppm): 7.38 (br, 1H), 4.20-4.16 (m, 1H), 3.67 (s, 3H), 2.39-2.23 (m, 3H), 2.14-2.07 (m, 1H).

Compound 37-3 was characterized by the following spectroscopic data:

MS (ESI, pos.ion) m/z: 144.2 [M-Boc]⁺; and
¹H NMR (400 MHz, CDCl₃) δ (ppm): 4.60-4.57 (m, 1H), 3.75 (s, 3H), 2.65-2.55 (m, 1H), 2.50-2.42 (m, 1H), 2.36-2.24 (m, 1H), 2.04-1.96 (m, 1H), 1.45 (s, 9H).

Compound 37-4 was characterized by the following spectroscopic data:

MS (ESI, pos.ion) m/z: 128.2 [M-Boc]⁺; and
¹H NMR (400 MHz, CDCl₃) δ (ppm): 6.65-6.52 (br, 1H), 4.96-4.91 (br, 1H), 4.68-4.57 (m, 1H), 3.76 (s, 3H), 3.12-3.00 (m, 1H), 2.71-2.61 (m, 1H), 1.49-1.44 (br, 9H).

Compound 37-5 was characterized by the following spectroscopic data:

MS (ESI, pos.ion) m/z: 142.2 [M-Boc]⁺; and
¹H NMR (400 MHz, CDCl₃) δ (ppm): 4.64-4.51 (m, 1H), 3.70 (s, 3H), 3.56-3.45 (m, 1H), 2.64-2.54 (m, 1H), 2.05-2.01 (m, 1H), 1.50, 1.41 (s, s, 9H), 0.75-0.65 (m, 3H).

Compound 37-6 was characterized by the following spectroscopic data:

MS (ESI, neg.ion) m/z: 226.2 [M–H]⁻; and
¹H NMR (400 MHz, CD₃OD) δ (ppm): 4.53-4.46 (m, 1H), 3.48-3.42 (m, 1H), 2.70-2.57 (m, 1H), 2.05-2.01 (m, 1H), 1.60-1.54 (m, 1H), 1.48, 1.41 (s, s, 9H), 0.89-0.80 (m, 1H), 0.73-0.66 (m, 1H).

Compound 37-7 was characterized by the following spectroscopic data:

MS (ESI, pos.ion) m/z: 424.3 [M+H]⁺; and
¹H NMR (400 MHz, CDCl₃) δ (ppm): 7.77-7.73 (m, 2H), 7.64-7.62 (m, 2H), 5.53-5.09 (m, 2H), 4.78-4.67 (m, 1H), 3.59-3.46 (m, 1H), 2.69-2.62 (m, 1H), 2.43-2.40 (m, 1H), 1.42 (s, 9H), 1.00-0.96 (m, 1H), 0.76-0.69 (m, 2H).

Compound 37-8 was characterized by the following spectroscopic data:

MS (ESI, pos.ion) m/z: 404.3 [M+H]⁺; and
¹H NMR (400 MHz, CDCl₃) δ (ppm): 7.62-7.52 (br, 2H), 7.49-7.46 (d, 2H, J=12 Hz), 7.21 (s, 1H), 5.27-5.24 (d, 1H, J=10.0 Hz), 3.31-3.27 (m, 1H), 1.71-1.67 (m, 2H), 1.52 (s, 9H), 0.89-0.86 (m, 1H), 0.64-0.69 (m, 2H).

Compound 37-9 was characterized by the following spectroscopic data:

MS (ESI, pos.ion) m/z: 452.3 [M+H]⁺; and
¹H NMR (400 MHz, CDCl₃) δ (ppm): 7.81-7.79 (d, 2H, J=8.04 Hz), 7.60 (br, 2H), 7.26 (s, 1H), 5.28-5.26 (d, 1H, J=8.0 Hz), 3.53 (br, 1H), 3.30-3.27 (br, 1H), 1.67-1.66 (m, 2H), 1.52 (s, 9H), 1.34 (s, 12H), 0.89-0.86 (m, 1H), 0.69-0.64 (m, 2H).

Compound 37-10 was characterized by the following spectroscopic data:

MS (ESI, pos.ion) m/z: 616.3 [M+H]⁺; and
¹H NMR (400 MHz, CDCl₃) δ (ppm): 7.72 (br, 2H), 7.52-7.42 (m, 1H), 7.41-7.38 (s, 2H), 7.31-7.28 (m, 1H), 7.13-7.11 (m, 1H), 5.31-5.28 (m, 1H), 3.25-3.17 (m, 3H), 2.54-2.50 (br, 2H), 2.40-2.33 (m, 2H), 2.23-2.03 (m, 2H), 1.80-1.71 (m, 2H), 1.56 (s, 9H), 0.92-0.84 (m, 1H), 0.67-0.65 (m, 2H).

Compound 37-11 was characterized by the following spectroscopic data:

MS (ESI, pos.ion) m/z: 414.3 [M+H]⁺; and
¹H NMR (400 MHz, CDCl₃) δ (ppm): 7.69 (s, 1H), 7.45-7.43 (m, 1H), 7.32-7.30 (m, 1H), 5.12-5.10 (m, 1H), 3.45-3.43 (m, 2H), 2.95-2.94 (m, 1H), 2.25-2.22 (m, 2H), 2.01-1.91 (m, 1H), 1.49 (s, 9H), 1.35 (s, 12H).

Compound 37-12 was characterized by the following spectroscopic data:

MS (ESI, pos.ion) m/z: 753.3 [M+H]⁺; and
¹H NMR (400 MHz, CDCl₃) δ (ppm): 7.68-7.65 (m, 2H), 7.55-7.50 (m, 2H), 7.47-7.43 (m, 4H), 7.32 (s, 1H), 7.23 (s, 1H), 5.30-5.27 (m, 1H), 5.18-5.17 (m, 1H), 3.56 (br, 1H), 3.47-3.46 (br, 1H), 3.23-3.21 (br, 1H), 3.08-3.06 (br, 1H), 2.93-2.89 (br, 2H), 2.23-2.19 (m, 2H), 2.21-1.93 (m, 4H), 1.83-1.62 (m, 5H), 1.51 (s, 18H), 0.80-0.85 (m, 1H), 0.63-0.61 (m, 2H).

Compound 37-13 was characterized by the following spectroscopic data:

MS (ESI, pos.ion) m/z: 553.3[M+H]⁺.

Compound 37-14 was characterized by the following spectroscopic data:

MS (ESI, pos.ion) m/z: 434.3 [M+2H]²⁺; and
¹H NMR (400 MHz, CDCl₃) δ (ppm): 7.73-7.69 (m, 3H), 7.52-7.49 (m, 1H), 7.44-7.42 (d, 1H, J=8.0 Hz), 7.31 (s, 2H), 7.20 (s, 1H), 5.60-5.56 (m, 2H), 5.53-5.50 (m, 1H), 5.44-5.43 (m, 1H), 3.71 (s, 6H), 3.09-3.07 (m, 1H), 2.93-2.89 (m, 1H), 2.54-2.53 (m, 1H), 2.37-2.28 (m, 2H), 2.25-2.16 (m, 2H), 2.14-2.04 (m, 4H), 1.92-1.88 (m, 2H), 1.72-1.65 (m, 6H), 1.23 (s, 12H), 0.85-0.80 (m, 1H), 0.63-0.61 (m, 2H).

Example 38

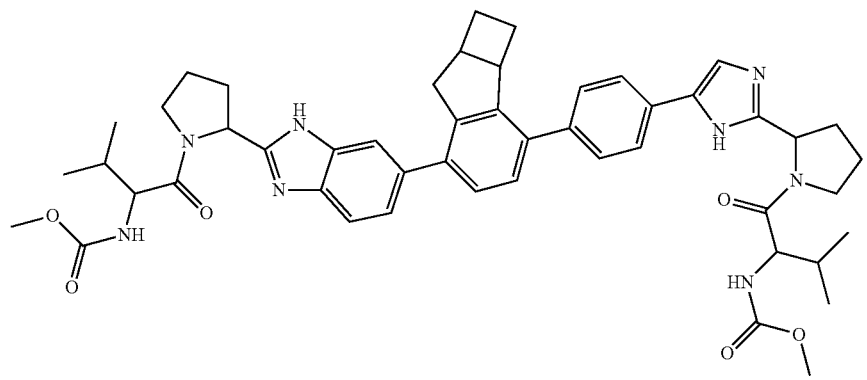 [SMILES: COC(=O)NC(C(=O)N1CCCC1c1ncc(-c2ccc(-c3ccc(-c4ccc5nc(C6CCCN6C(=O)C(NC(=O)OC)C(C)C)[nH]c5c4)c4c3C3CCC3C4)cc2)[nH]1)C(C)C]

Synthetic Route:
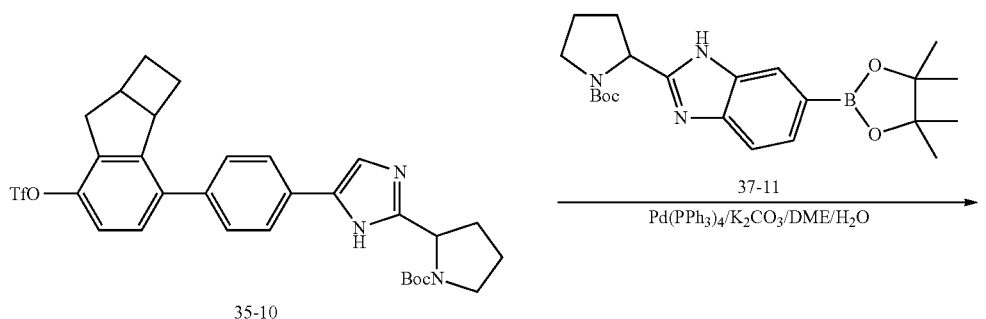
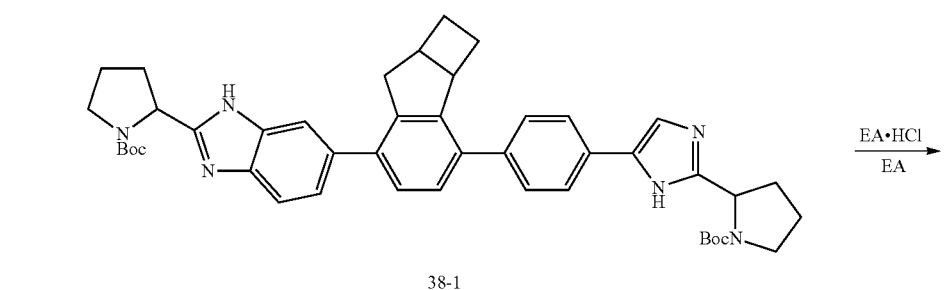
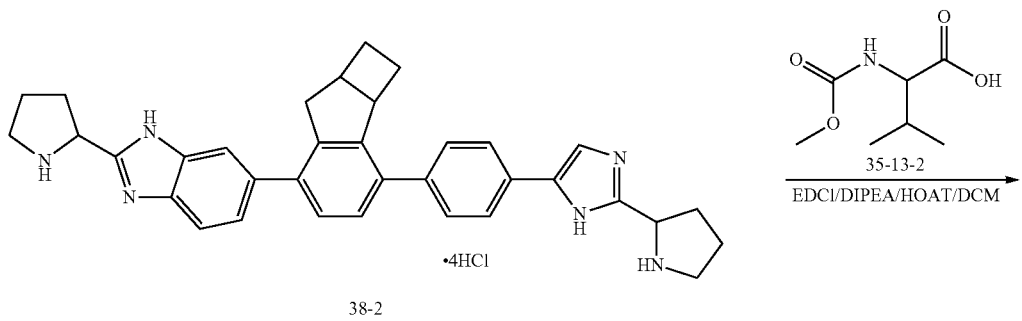
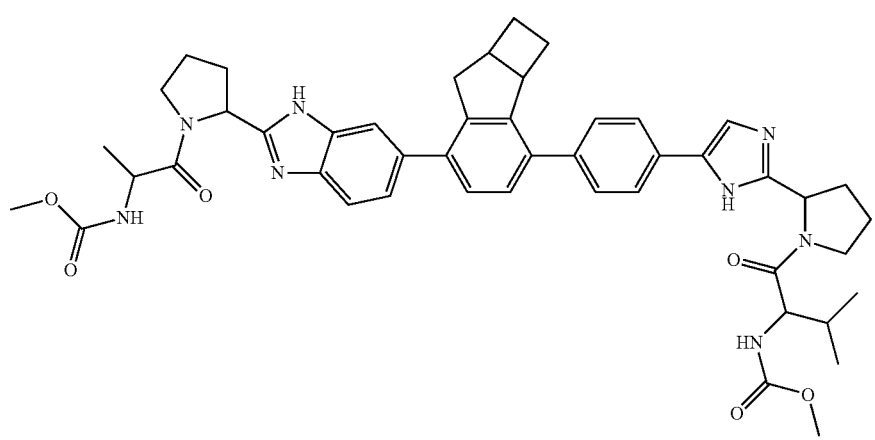

Compounds disclosed herein can be synthesized through the procedure depicted in Example 4:

Compound 38-1 was characterized by the following spectroscopic data:

MS (ESI, pos.ion) m/z: 741.3 [M+H]$^+$; and $^1$H NMR (400 MHz, CDCl$_3$) δ (ppm): 7.85, 7.83 (d, d, 1H), 7.62, 7.60 (s, s, 1H), 7.59 (s, 1H), 7.58-7.51 (m, 6H), 7.44, 7.42 (t, t, 1H), 5.04-4.99 (m, 1H), 4.97-4.93 (m, 1H), 3.82-3.76 (m, 1H), 3.75-3.67 (m, 1H), 3.64-3.57 (m, 2H), 3.31-3.23 (m, 1H), 3.13-3.03 (m, 1H), 2.68-2.54 (m, 3H), 2.47-2.36 (m, 2H), 2.29-1.94 (m, 8H), 1.62-1.56 (m, 1H), 1.53 (s, 9H), 1.41 (s, 9H).

Compound 38-2 was characterized by the following spectroscopic data:

MS (ESI, pos.ion) m/z: 541.3 [M+H]$^+$.

Compound 38-3 was characterized by the following spectroscopic data:

MS (ESI, pos.ion) m/z: 855.5 [M+H]$^+$; and $^1$H NMR (400 MHz, CDCl$_3$) δ (ppm): 7.85, 7.83 (d, d, 1H), 7.62, 7.60 (s, s, 1H), 7.59 (s, 1H), 7.58-7.51 (m, 6H), 7.44, 7.42 (t, t, 1H), 5.56, 5.55 (d, d, 1H), 5.46-5.44 (d, d, 1H), 5.25-5.19 (m, 2H), 4.40-4.30 (m, 2H), 3.85-3.78 (m, 2H), 3.75-3.68 (m, 2H), 3.66 (s, 6H), 3.65-3.60 (m, 1H), 3.13-3.03 (m, 1H), 2.68-2.54 (m, 2H), 2.37-1.88 (m, 13H), 1.62-1.52 (m, 1H), 1.02-0.89 (m, 12H).

Biological Activity

HCV Replicon System was utilized as a screening model in the present disclosure to evaluate the antivirus effects of the compounds disclosed herein against HCV. HCV Replicon assay was first described in *Science*, 1999, 285 (5424), 110-3. HCV Replicon System is one of the most important tools for research on HCV RNA replication, pathogenicity and persistent of virus, for example, 5'-NCR minimum areas is necessary for HCV RNA replication that was proved by using replicon, and HCV Replicon System was utilized successfully as an evaluation model of antiviral drugs. To determine the potential anti-HCV effects of the test compounds, luciferase assay and antibiotic Neomycin resistance gene were tested according to the method described in *Science*. 1999 Jul. 2; 285 (5424), 110-3 and *J. Virol.* 2003 March; 77 (5), 3007-19.

In a word, the compounds disclosed herein were tested by using human hepatic carcinoma cell line Huh-7 which is transfected stably with HCV GT1a, GT1b or GT2a replicon respectively, and resistant cells of Y93H, L31F, P32L or I302V and wild-type cells HCV 1b. HCV Replicon System disclosed herein contains G418 resistance gene NEO and Luciferase Reporter Gene, and the level of HCV replication in host cells is detected and characterized by the expression level of the NEO gene or Luciferase Reporter Gene, so the effects of the compounds herein inhibit HCV replication can be evaluated in this system. In this article, a real-time quantitative polymerase chain reaction (qPCR) method was used to detect NEO gene expression level, and chemiluminescence method was used to test Luciferase Reporter Gene expression level.

Operating Procedure:

1. Test Method for Measuring EC$_{50}$ of the Compounds Based on Luciferase Assay.

The Huh-7 cells transfected with HCV replicons system were seeded into 96-well plates (8,000 cells in 125 μL/well) respectively; each test compound was diluted to desired concentration using 5-fold serial dilutions protocol, 10 doses in duplicate, and added to wells with POD™ 810 Plate Assembler. The plates were incubated in a CO$_2$ incubator for 72 hours; after that, 40 μL of Luciferase assay substrate (Promega Bright-Glo) was added to each well, and detected by a chemiluminescence detection system (Topcount Microplate Scintillation and Luminescence Counter) 5 minutes later; the EC$_{50}$ (half-maximal effective concentration, concentration for 50% of maximal effect) values of test compounds were analyzed by GraphPad Prism software. In this paper, experiments were repeated twice and set the wells without compounds as negative control.

2. Test Method for Measuring EC$_{50}$ of the Compounds by Detecting Antibiotic G418 Resistance Gene NEO Gene.

The Huh-7 cells transfected with HCV replicons system were seeded into 96-well plates (8,000 cells in 125 μL/well) respectively; each test compound was diluted to desired concentration using 5-fold serial dilutions protocol, 10 doses in duplicate, and added to each well with POD™ 810 Plate Assembler; the cells were incubated in a CO$_2$ incubator for 72 hours; and detected the expression level of the NEO gene expression with real-time quantitative PCR later; the EC$_{50}$ (half-maximal effective concentration, concentration for 50% of maximal effect) values of test compounds were analyzed by GraphPad Prism software, respectively. In this paper, experiments were repeated twice and set the wells without compounds as negative control.

3. Results

The test compounds of the present disclosure can be effective against the HCV 1a, 1b, 2a, 2b, 3a, 3b, 4a, 5a and 6a genotypes according to the experiment data, and EC$_{50}$ ranges of the test compounds against HCV 1b are 1 pM-99 nM; Table 2 shows the EC$_{50}$ values of representative compounds of the present disclosure against the HCV 1a and HCV 1b genotypes.

TABLE 2

| Example | 1a (nM) | 1b (nM) |
|---|---|---|
| 1 | 0.605 | 0.005 |
| 2 | 0.071 | 0.021 |
| 3 | 0.088 | 0.018 |
| 4 | 0.060 | 0.020 |
| 5 | 1.045 | 0.119 |
| 6 | 0.243 | 0.106 |
| 7 | 0.093 | 0.053 |
| 8 | 0.066 | 0.028 |
| 9 | 0.035 | 0.014 |
| 10 | 4.328 | 0.927 |
| 11 | 0.051 | 0.033 |
| 12 | 0.080 | 0.027 |
| 13 | 0.418 | 0.206 |
| 14 | 0.003 | 0.001 |
| 15 | 0.381 | 0.105 |
| 16 | 2.548 | 0.879 |
| 17 | 0.062 | 0.078 |
| 18 | 0.083 | 0.030 |
| 19 | 0.217 | 0.044 |
| 20 | 0.429 | 0.036 |
| 21 | 0.068 | 0.015 |
| 22 | 0.233 | 0.082 |
| 23 | 0.449 | 0.050 |
| 24 | 0.207 | 0.118 |
| 25 | 0.065 | 0.032 |
| 26 | 0.832 | 0.048 |
| 27 | 1.639 | 0.672 |
| 28 | 0.022 | 0.008 |
| 29 | 7.552 | 0.309 |
| 30 | 0.211 | 0.092 |
| 31 | 0.083 | 0.035 |
| 32 | 0.063 | 0.026 |
| 33 | 0.082 | 0.030 |
| 34 | 0.075 | 0.022 |
| 35 | 0.548 | 0.007 |
| 36 | 0.935 | 0.010 |
| 37 | 0.063 | 0.016 |
| 38 | 0.058 | 0.013 |

The experiment results of HCV 1b wild-type and Y93H, L31F, P32L, I302V resistance cells and the simulation results of molecular modeling and docking show that the present disclosure plays an excellent anti-HCV role, which suggest a novel anti-HCV mechanism by interfering with HCV NS5A protein.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A. The compounds of the present disclosure may inhibit multiple genotypes of HCV.

In the description of the invention, the reference term "one embodiment," "some embodiments," "example", "a specific example", or "some examples" and means in connection with the embodiment described in or example described in Example particular feature, structure, material, or characteristic be included in the present invention, at least one embodiment or example. In the present specification, the term of the above schematic representation is not necessarily referring to the same embodiment or example. Moreover, describe a particular feature, structure, material, or characteristics can be in any one or more embodiments or examples in combination in an appropriate manner.

Although embodiments of the present invention has been shown and described above, the above embodiments are illustrative embodiments that can be understood, and cannot be understood as a limit for the invention, the skills in the art without departing from the principles of the invention and purpose, can change modify, substitute, and vary these embodiments within the scope of the present invention.

What is claimed is:

1. A Compound having one of the following structures:

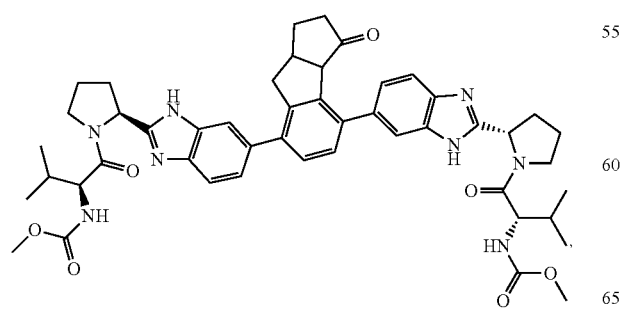

(6)

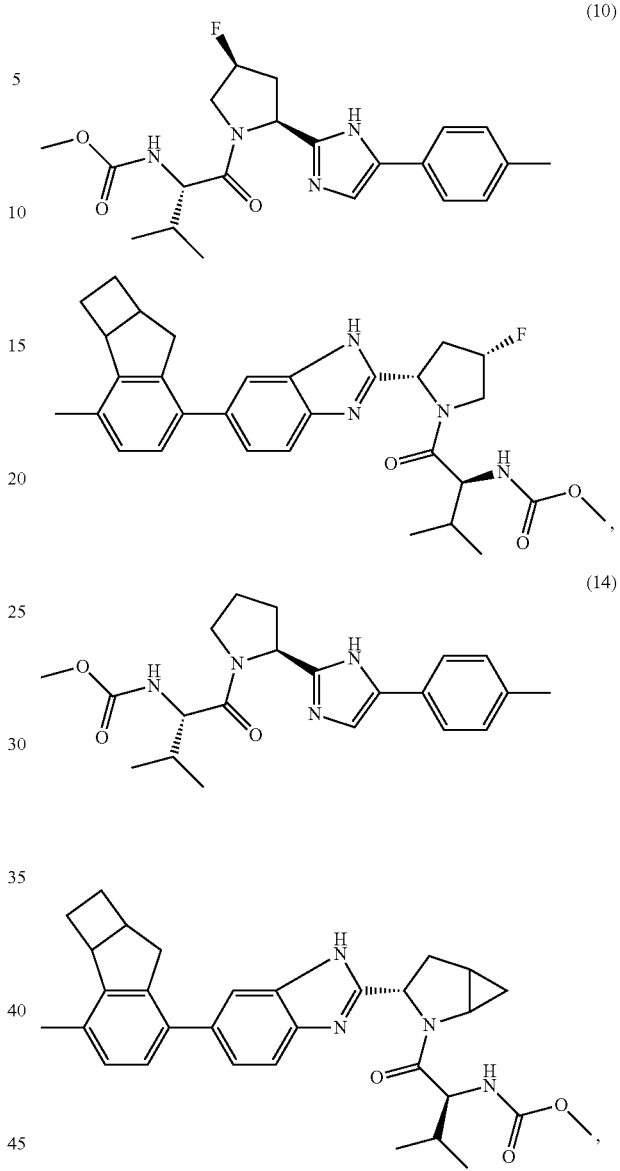

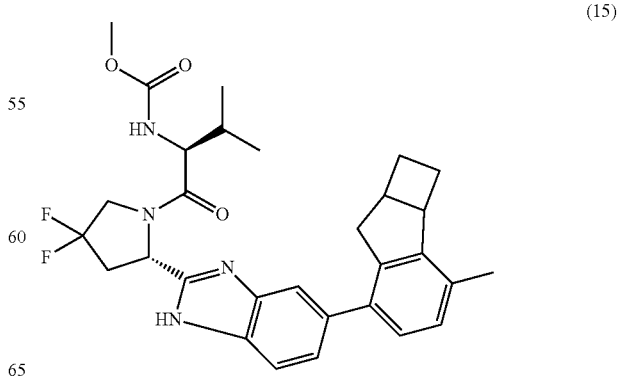

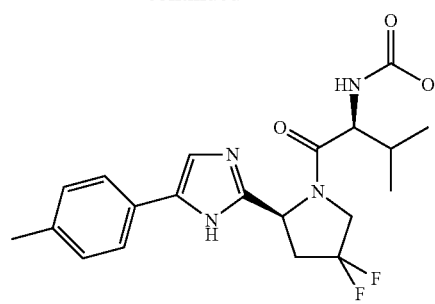
(16)
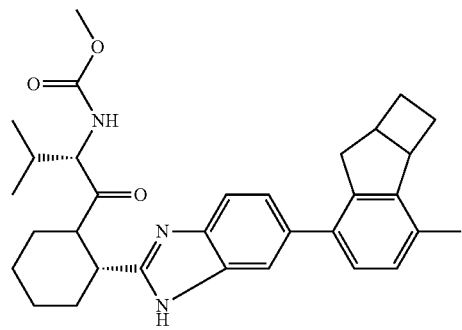
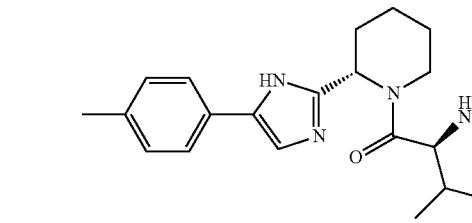
(17)
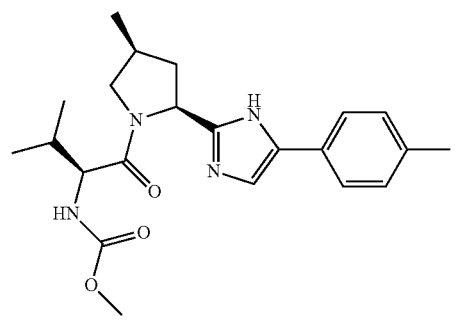
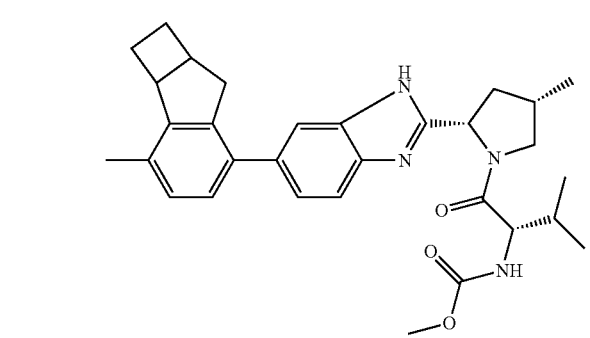
(18)
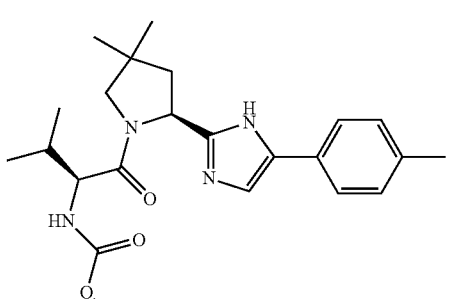
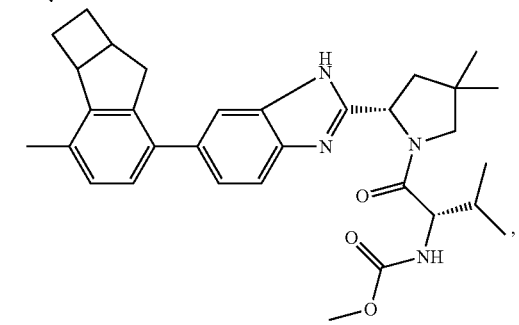
(19)
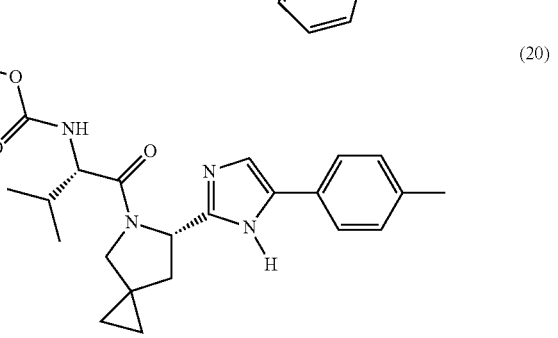
(20)

447
-continued
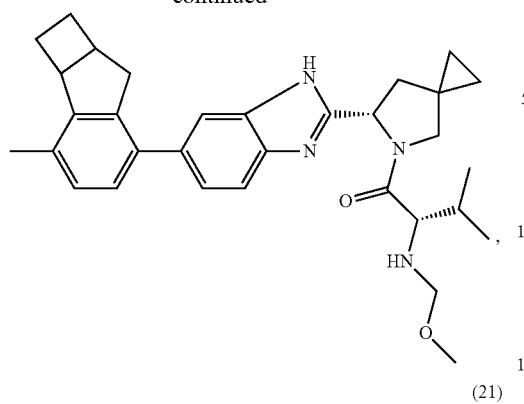
(21)
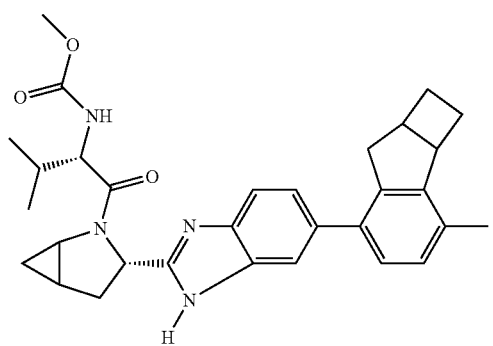
(22)
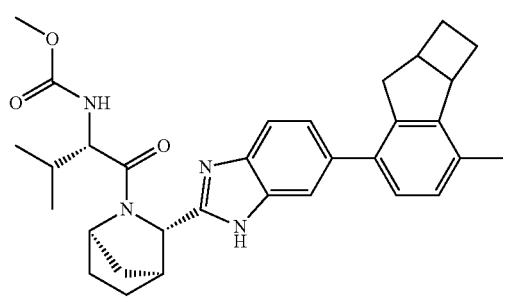
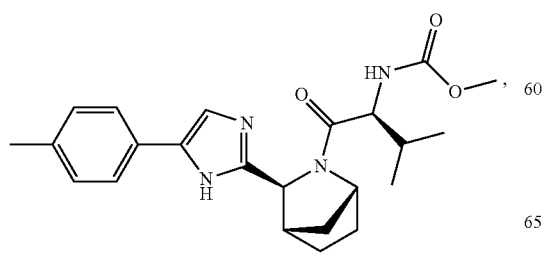
448
-continued
(23)
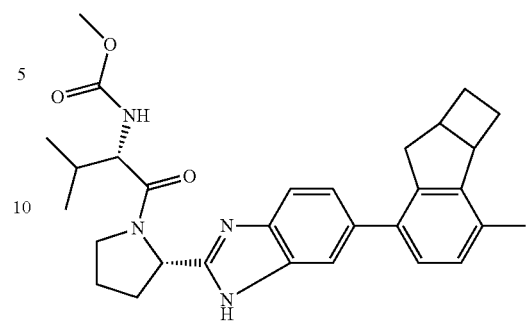
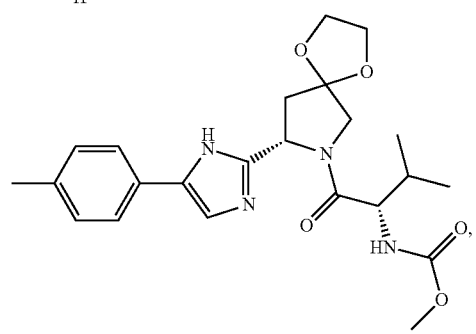
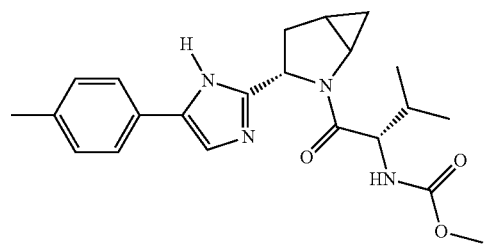
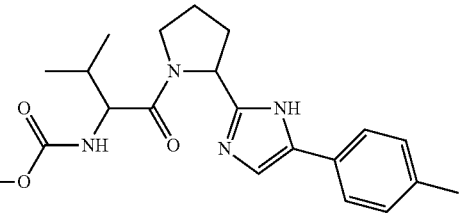
(28)
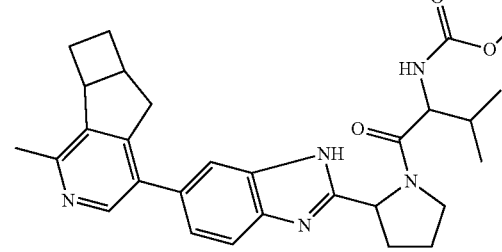
(32)
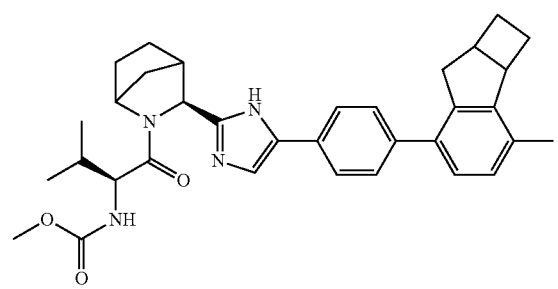
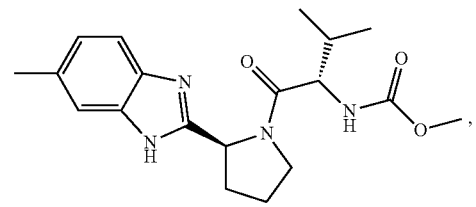

(33)
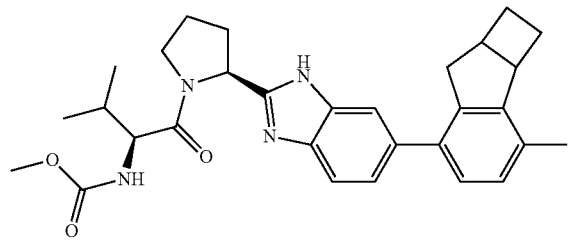
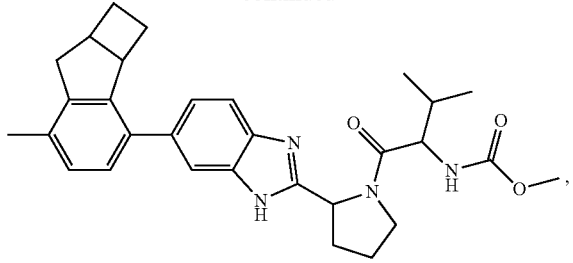
(43)
(34)
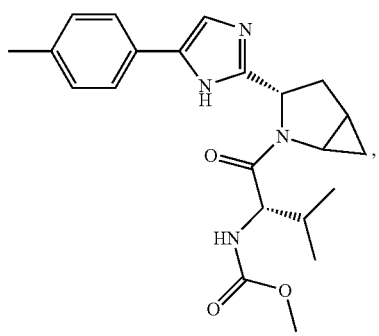
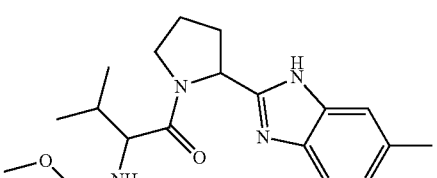
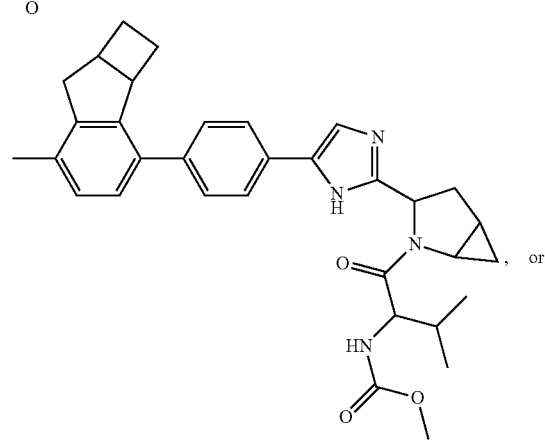
, or
(44)
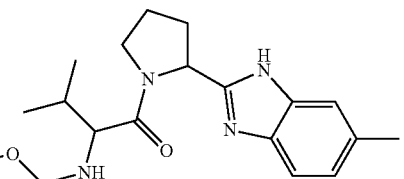
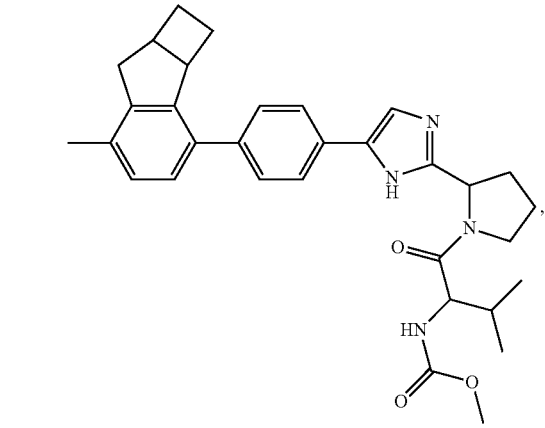
,
(42)
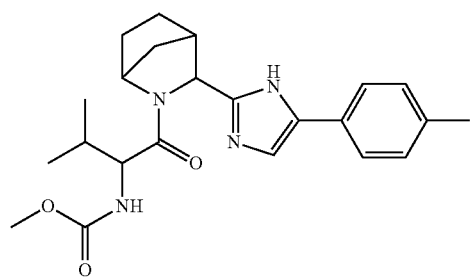
or a stereoisomer, a geometric isomer, a tautomer, an N-oxide, a hydrate, or a pharmaceutically acceptable salt thereof.
2. A pharmaceutical composition comprising the compound according to claim 1; and a pharmaceutically acceptable carrier, excipient, diluent, adjuvant, vehicle or a combination thereof; an anti-HCV agent, and at least one HCV inhibitor;

wherein the anti-HCV agent is an interferon, ribavirin, IL-2, IL-6, IL-12, a compound that enhances the development of a type 1 helper T cell response, interfering RNA, anti-sense RNA, imiquimod, an inosine5'-monophosphate dehydrogenase inhibitor, amantadine, rimantadine, bavituximab, human hepatitis C immune globulin (CIVACIR™), boceprevir, telaprevir, erlotinib, daclatasvir, simeprevir, asunaprevir, vaniprevir, faldaprevir, ABT-450, danoprevir, sovaprevir, MK-5172, vedroprevir, BZF-961, GS-9256, narlaprevir, ANA975, ABT-267, EDP239, PPI-668, GS-5816, samatasvir (IDX-719), MK-8742, MK-8325, GSK-2336805, PPI-461, TMC-435, MK-7009, BI-2013335, ciluprevir, BMS-650032, ACH-1625, ACH-1095, VX-985, IDX-375, VX-500, VX-813, PHX-1766, PHX-2054, IDX-136, IDX-316, EP-013420, VBY-376, TMC-649128, R-7128, PSI-7977, INX-189, IDX-184, IDX102, R1479, UNX-08189, PSI-6130, PSI-938, PSI-879, HCV-796, HCV-371, VCH-916, VCH-222, ANA-598, MK-3281, ABT-333, ABT-072, PF-00868554, BI-207127, GS-9190, A-837093, JKT-109, Gl-59728, GL-60667, AZD-2795, TMC647055 or a combination thereof;

wherein the interferon is interferon α-2b, pegylated interferon α, interferon α-2a, pegylated interferon α-2a, consensus interferon-α, interferon γ or a combination thereof; and wherein the at least one HCV inhibitor inhibits at least one of HCV replication process and HCV viral protein function, wherein the HCV replication process is a whole viral cycle consisting of HCV entry, uncoating, translation, replication, assembly and egress; and wherein the HCV viral protein is metalloproteinase, NS2, NS3, NS4A, NS4B, NS5A or NS5B, or an internal ribosome entry site (IRES) and inosine-5'-monophosphate dehydrogenase (IMPDH) required in HCV viral replication.

3. A method of treating HCV infection or a HCV disorder in a patient comprising administering to the patient in need of such treatment a therapeutically effective amount of the compound according to claim 1.

4. A method of treating HCV infection or a HCV disorder in a patient comprising administering to the patient in need of such treatment a therapeutically effective amount of the pharmaceutical composition according to claim 2.

* * * * *

UNITED STATES PATENT AND TRADEMARK OFFICE
CERTIFICATE OF CORRECTION

PATENT NO. : 9,802,949 B2
APPLICATION NO. : 14/647449
DATED : May 26, 2015
INVENTOR(S) : Yingjun Zhang et al.

It is certified that error appears in the above-identified patent and that said Letters Patent is hereby corrected as shown below:

Column 443, approx. Line 53 - Column 450, approx. Line 62 should read:

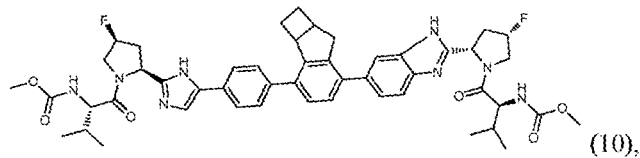
(10),

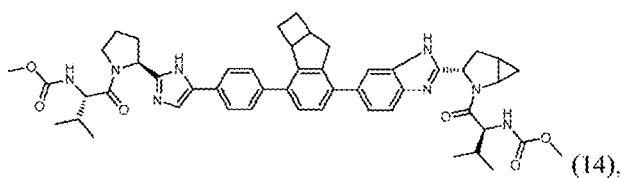
(14),

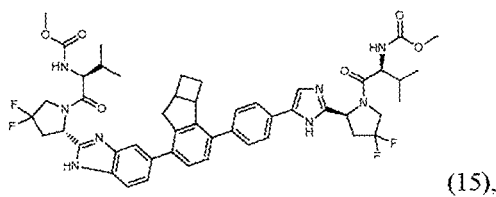
(15),

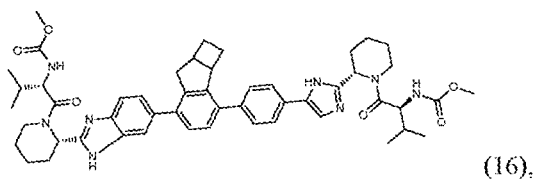
(16),

Signed and Sealed this
Ninth Day of January, 2018

Joseph Matal
*Performing the Functions and Duties of the
Under Secretary of Commerce for Intellectual Property and
Director of the United States Patent and Trademark Office*

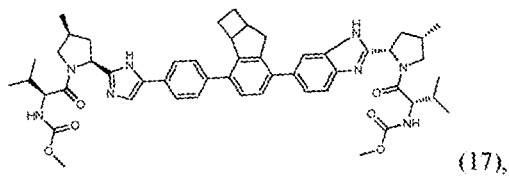
(17),
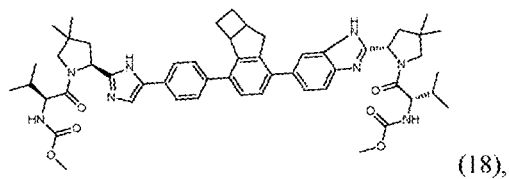
(18),
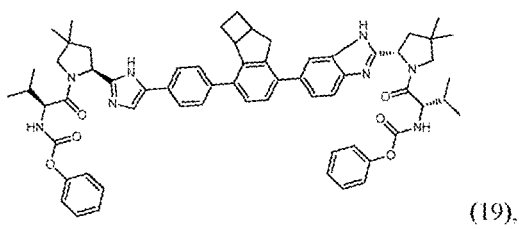
(19),
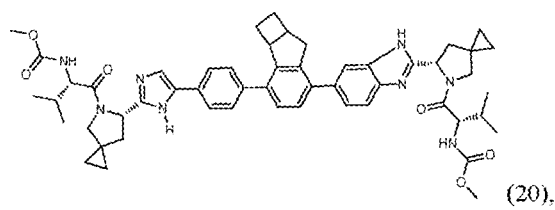
(20),
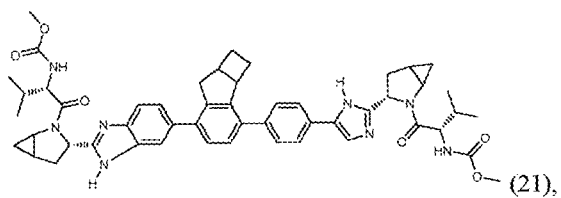
(21),
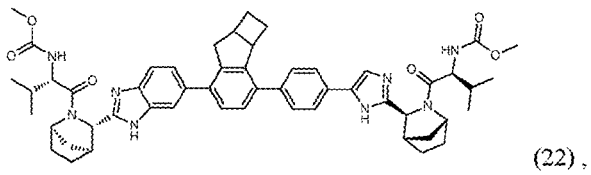
(22),
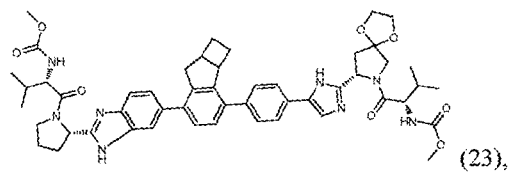
(23),

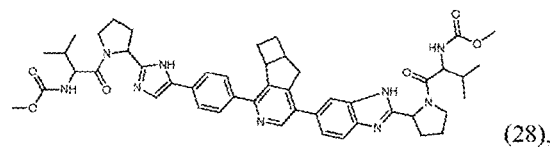
(28),
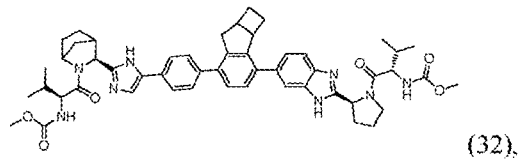
(32),
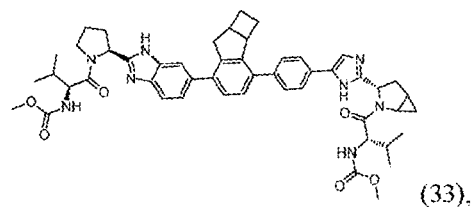
(33),
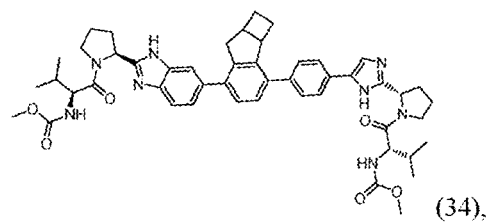
(34),
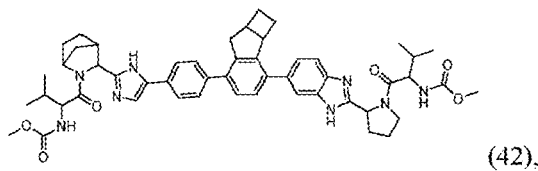
(42),
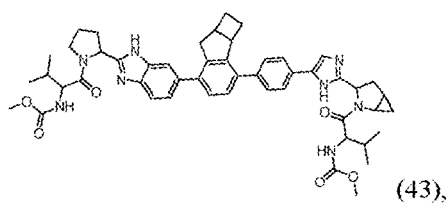
(43),
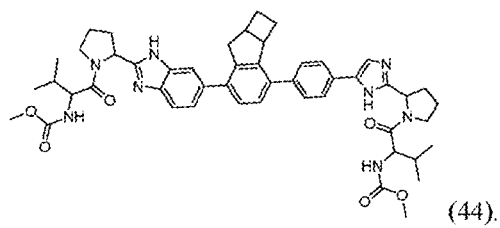
(44).